United States Patent
Yeung et al.

(10) Patent No.: US 8,309,558 B2
(45) Date of Patent: Nov. 13, 2012

(54) COMPOUNDS FOR THE TREATMENT OF HEPATITIS C

(75) Inventors: Kap-Sun Yeung, Madison, CT (US);
Kyle E. Parcella, Wallingford, CT (US);
John A. Bender, Middletown, CT (US);
Brett R. Beno, Cromwell, CT (US);
Katharine A. Grant-Young, Madison, CT (US); Ying Han, Cheshire, CT (US);
Piyasena Hewawasam, Middletown, CT (US); John F. Kadow, Wallingford, CT (US); Andrew Nickel, San Marino, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/371,786

(22) Filed: Feb. 13, 2012

(65) Prior Publication Data

US 2012/0201783 A1    Aug. 9, 2012

Related U.S. Application Data

(63) Continuation of application No. 13/166,926, filed on Jun. 23, 2011, now Pat. No. 8,148,382, which is a continuation of application No. 12/721,423, filed on Mar. 10, 2010, now Pat. No. 7,994,171, which is a continuation-in-part of application No. 12/554,193, filed on Sep. 4, 2009, now Pat. No. 8,048,887.

(60) Provisional application No. 61/096,005, filed on Sep. 11, 2008.

(51) Int. Cl.
*A61K 31/506* (2006.01)
*C07D 405/02* (2006.01)

(52) U.S. Cl. .................................. 514/256; 544/333
(58) Field of Classification Search ............ 514/256; 544/333

See application file for complete search history.

(56) References Cited

U.S. PATENT DOCUMENTS

| 7,265,152 B2 | 9/2007 | Saha et al. |
| 7,868,037 B2 | 1/2011 | Karp et al. |
| 2009/0281336 A1 | 11/2009 | Saha et al. |

FOREIGN PATENT DOCUMENTS

| JP | 57-123181 | 7/1982 |
| WO | WO 02/16359 | 2/2002 |
| WO | WO 02/078701 | 10/2002 |
| WO | WO 2004/041201 | 5/2004 |
| WO | WO 2004041201 A2 * | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |

OTHER PUBLICATIONS

Database Caplus [Online], Chemical Abstracts Service, Columbus, OH, US, Grinev, A.N. et al., "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.

Cheung, M., "The identification of pyrazolo[1,5-*a*]pyridines as potent p38 kinase inhibitors", Bioorganic & Medicinal Chemistry Letters, vol. 18, pp. 5428-5430 (2008).

Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).

Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).

Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).

Kakehi, A. et al., "Preparation of New Nitrogen-Bridged Heterocycles. XIV. Further Investigation of the Desulfurization and the Rearrangement of Pyrido[1,2-*d*]-1,3,4-thiadiazine Intermediates", Chem. Pharm. Bull., vol. 35, No. 1, pp. 156-169 (1987).

Miki, Y. et al., "Acid-Catalyzed Reactions of 3-(Hydroxymethyl)- and 3-(1-Hydroxyethyl)pyrazolo[1,5-*a*]pyridines", J. Heterocyclic Chem., vol. 26, pp. 1739-1745 (1989).

* cited by examiner

Primary Examiner — Kristin Bianchi
(74) Attorney, Agent, or Firm — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

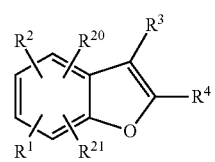

2 Claims, No Drawings

COMPOUNDS FOR THE TREATMENT OF HEPATITIS C

CROSS REFERENCE TO RELATED APPLICATIONS

This application is a Continuation of U.S. Continuation Application U.S. Ser. No. 13/166,926 filed Jun. 23, 2011, now U.S. Pat. No. 8,148,382 now allowed, which is a Continuation of U.S. Continuation-in-Part Application U.S. Ser. No. 12/721,423 filed Mar. 10, 2010, now U.S. Pat. No. 7,994,171, which is a Continuation-in-Part of U.S. Non-Provisional Application U.S. Ser. No. 12/554,193 filed Sep. 4, 2009, now U.S. Pat. No. 8,048,887, which claims the benefit of U.S. Provisional Application U.S. Ser. No. 61/096,005 filed Sep. 11, 2008.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides" (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during exteneded dosing of the combination regimens. U.S. Pat. No. 7,265,152 and the corresponding PCT patent application WO2004/041201A2 describe compounds of the HCV-796 class.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

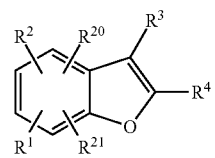

I $R^1$ is $R^5R^6N$; alkoxy; (alkoxycarbonylamino)alkoxy; (alkylphenyl)alkoxy; (carboxy)alkenyl; (alkoxycarbonyl)alkenyl; (benzyloxycarbonyl)alkenyl; ((N-dimethylbenzyl)aminocarbonyl)alkenyl; or phenyl where said phenyl is substituted with 1-2 substituents selected from the group consisting of halo, cyano, alkyl, haloalkyl, hydroxyalkyl, alkoxyalkyl, (carboxy)alkyl, alkoxy, hydroxyalkyloxy, alkoxyalkyloxy, benzyloxy, tetrahydropyranyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, $Ar^5$, $SO_2NR^{15}R^{16}$, and $CONR^7R^8$; and where said phenyl is also substituted with 0-2 substituents selected from the group consisting of halo; nitro; alkyl; cycloalkyl; haloalkyl; aminoalkyl; hydroxyalkyl; alkoxyalkyl; hydroxy; alkoxy; $OR^{17}$; cycloalkoxy; amino; alkylamino; dialkylamino; alkylcarboxamido; alkoxycarboxamido; alkoxyalkylcarboxamido; furanyl, thienyl, or pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; or phenyl substituted with 0-2 substituents selected from halo, alkyl, cyanoalkyl, hydroxyalkyl, alkoxyalkyl, hydroxy, alkoxy, amino, carboxy, alkoxycarbonyl, aminocarbonyl, alkylaminocarbonyl, dialkylaminocarbonyl, alkylcarboxamido, carboxyalkenyl, and phenyl;

$R^2$ is hydrogen, halo, nitro, amino, phenyl, or $R^5R^6N$;

$R^3$ is cyano, alkoxycarbonyl, (cycloalkyl)oxycarbonyl, (alkylsulfonyl)aminocarbonyl, $CONR^{11}R^{12}$, $(R^{11})(R^{12})NCONH$, triazolyl, thiazolyl, or tetrazolyl;

$R^4$ is phenyl substituted with 0-2 halo substituents;

$R^5$ is hydrogen, alkyl, or alkylsulfonyl;

$R^6$ is hydrogen, alkyl, hydroxyalkyl, alkoxyalkyl, or alkylsulfonyl;

$R^7$ is hydrogen, alkyl, alkenyl, alkynyl, cyanoalkyl, haloalkyl, hydroxyalkyl, dihydroxyalkyl, alkoxyalkyl, oxoalkyl, aminoalkyl, (alkylamino)alkyl, (dialkylamino)alkyl, (cycloalkyl)alkyl, cycloalkyl, (alkyl)cycloalkyl, (hydroxyalkyl)cycloalkyl, (tetrahydrofuranyl)alkyl, (tetrahydropyranyl)alkyl, (carboxy)alkyl, (alkoxycarbonyl)alkyl, (alkenyloxycarbonyl)alkyl, (alkoxycarbonyl)hydroxyalkyl, $(CONR^{13}R^{14})$alkyl, $(CONR^{13}R^{14})$(hydroxyalkyl)alkyl, $(CONR^{13}R^{14})$cylcoalkyl, (alkylcarbonyl)aminoalkyl, (phenyl)alkyl, (pyridinyl)alkyl, alkylsulfonyl, phenylsulfonyl, $Ar^2$, $Ar^3$,

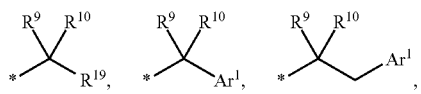

or

$R^8$ is hydrogen, alkyl, hydroxyalkyl, or alkoxyalkyl;

or $R^7R^8N$ taken together is azetidinyl, pyrrolidinyl, piperidinyl, piperazinyl, morpholinyl, dihydroindolyl, or isoindolinyl, and is substituted with 0-2 substituents selected from alkyl, hydroxyalkyl, alkoxyalkyl, hydroxy, alkoxy, carboxy, alkoxycarbonyl, dialkylcarboxamido, alkylcarbonylamino, alkoxycarbonylamino, pyridinyl, and phenyl where said phenyl is substituted with 0-2 halo or alkyl substituents;

or where $R^7R^8N$ taken together is

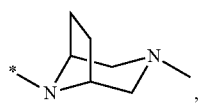

(quinuclidinyl)amino, (quinuclidinyl)(alkyl)amino, (methylpyrrolidinyl)(alkyl)amino, ((imidazolyl)alkyl)(hydroxyalkyl)amino, (alkylthiazolyl)amino, ((carboxamido)cyclopentanyl)amino, ((halophenyl)cyclopentanyl)amino, 3H-spiro(isobenzofuranyl)piperidinyl, (hydroxyindanyl)amino, or

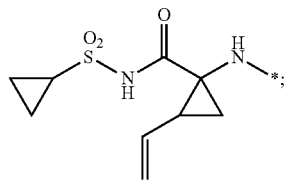

$R^9$ is hydrogen, alkyl, hydroxyalkyl, or alkoxyalkyl;

$R^{10}$ is hydrogen, alkyl, hydroxyalkyl, or alkoxyalkyl; or $R^9$ and $R^{10}$ taken together is ethylene, propylene, butylene, pentylene, or hexylene;

$R^{11}$ is hydrogen, alkyl, or cycloalkyl;

$R^{12}$ is hydrogen, alkyl, or cycloalkyl;

or $R^{11}$ and $R^{12}$ taken together with the nitrogen to which they are attached is azetidinyl, pyrrolidinyl, piperidinyl, piperazinyl, or morpholinyl;

$R^{13}$ is hydrogen, alkyl, cyanoalkyl, haloalkyl, alkenyl, alkynyl, or thiazolyl;

$R^{14}$ is hydrogen or alkyl;

$R^{15}$ is hydrogen, alkyl, hydroxyalkyl, cycloalkyl, or benzyl;

$R^{16}$ is hydrogen or alkyl;

or $R^{15}$ and $R^{16}$ taken together with the nitrogen to which they are attached is azetidinyl, pyrrolidinyl, piperidinyl, piperazinyl, or morpholinyl;

$R^{17}$ is haloalkyl, cyanoalkyl, (cycloalkyl)alkyl, hydroxyalkyl, alkoxyalkyl, aminoalkyl, $(R^{18})$alkyl, $(Ar^4)$alkyl, alkynyl, or aminocycloalkyl;

$R^{18}$ is $CONH_2$, $H_2NCONH$, dibenzylamino, phthalimido, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents;

$R^{19}$ is cyano, hydroxyalkyl, morpholinylalkyl, carboxy, alkoxycarbonyl, cycloalkylsulfoxamido, ((alkyl)pyrazolyl)amino, ((alkyl)isoxazolyl)amino, (thiadiazolyl)amino, (triazinyl)amino, or alkynylaminocarbonyl;

$R^{20}$ is hydrogen, halo, alkyl, or alkoxy;

$R^{21}$ is hydrogen, halo, alkyl, or alkoxy;

$Ar^1$ is phenyl, naphthalenyl, pyridinyl, furanyl, thienyl, pyrrolyl, pyrazolyl, isoxazolyl, isothiazolyl, imidazolyl, oxazolyl, thiazolyl, oxadiazolyl, oxadiathiazolyl, triazolyl, tetrazolyl, pyrazinyl, pyrimidinyl, or benzothiazolyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl;

$Ar^2$ is phenyl, biphenyl, or pyridinyl and is substituted witlh 0-2 substituents selected from halo, alkyl, cyano, hydroxy, alkoxy, and carboxy;

$Ar^3$ is pyrazolyl, isoxazolyl, isothiazolyl, imidazolyl, oxazolyl, thiazolyl, triazolyl, oxadiazolyl, oxathiadiazolyl, pyrimidinyl, or pyrizinyl and is substituted witlh 0-2 substituents selected from hydroxy, alkyl, hydroxyalkyl, and $CONR^{13R14}$;

$Ar^4$ is furanyl, thienyl, pyrrolyl, pyrazolyl, isoxazolyl, isothiazolyl, imidazolyl, oxadiazolyl, thiadiazolyl, triazolyl, pyridinyl, indolyl, or phenyl and is substituted with 0-2 substituents selected from halo, alkyl, haloalkyl, hydroxyl, and alkoxy; and $Ar^5$ is pyrrozolyl, imidazolyl, or oxadiazolyl and is substituted with 0-2 substituents selected from alkyl, carboxy, alkoxycarbonyl, benzyl, and phenyl;

or a pharmaceutically acceptable salt thereof.

Another aspect of the inventon is a compound of formula I where $R^{20}$ and $R^{21}$ are hydrogen.

Another aspect of the invention is a compound of formula I where
$R^1$ is $R^5R^6N$; (carboxy)alkenyl; (alkoxycarbonyl)alkenyl; (benzyloxycarbonyl)alkenyl; or phenyl where said phenyl is substituted with 1-2 substituents selected from the group consisting of cyano, alkyl, alkoxy, hydroxyalkyl, alkoxyalkyl, hydroxyalkyloxy, alkoxyalkyloxy, haloalkyl, benzyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, tetrahydropyranyloxy, $Ar^5$, $SO_2NR^{15}R^{16}$, and $CONR^7R^8$; and where said phenyl is also substituted with 0-1 substituents selected from the group consisting of halo; alkyl; hydroxyalkyl; alkoxyalkyl; hydroxyl; alkoxy; $OR^{17}$; cycloalkoxy; amino; alkylamino; dialkylamino; alkylcarboxamido; alkoxyalkylcarboxamido; furanyl; indolyl; isoquinolinyl; pyridinyl substituted with 0-2 halo, alkyl, hydroxy, or alkoxy substituents; pyrazolyl substituted with 0-2 alkyl substituents; and phenyl substituted with 0-2 halo, alkyl, cyanoalkyl, hydroxyalkyl, alkoxyalkyl, hydroxy, alkoxy, carboxy, alkoxycarbonyl, aminocarbonyl, alkylaminocarbonyl, dialkylaminocarbonyl, alkylcarboxamido, carboxyalkenyl, or phenyl substituents;
$R^2$ is hydrogen, nitro, or $R^5R^6N$;
$R^3$ is cyano, alkoxycarbonyl, (cycloalkyl)oxycarbonyl, (alkylsulfonyl)aminocarbonyl, $CONR^{11}R^{12}$, $(R^{11})(R^{12})$NCONH, triazolyl, thiazolyl, or tetrazolyl;
$R^4$ is phenyl substituted with 0-2 halo substituents;
$R^5$ is hydrogen, alkyl, or alkylsulfonyl;
$R^6$ is hydrogen, alkyl, hydroxyalkyl, alkoxyalkyl, or alkylsulfonyl;
$R^7$ is hydrogen, alkyl, alkenyl, alkynyl, cyanoalkyl, haloalkyl, hydroxyalkyl, alkoxyalkyl, oxoalkyl, aminoalkyl, (alkylamino)alkyl, (dialkylamino)alkyl, (cycloalkyl)alkyl, cycloalkyl, (alkyl)cycloalkyl, (hydroxyalkyl)cycloalkyl, (tetrahydrofuranyl)alkyl, (tetrahydropyranyl)alkyl, (carboxy)alkyl, (alkoxycarbonyl)alkyl, (alkoxycarbonyl)hydroxyalkyl, $(CONR^{13}R^{14})$alkyl, (alkylcarbonyl)aminoalkyl, (phenyl)alkyl, (pyridinyl)alkyl, alkylsulfonyl, phenylsulfonyl, $Ar^2$, $Ar^3$,

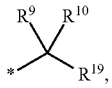 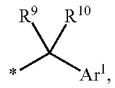 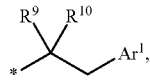

or

$R^8$ is hydrogen, alkyl, hydroxyalkyl, or alkoxyalkyl;
or $R^7R^8N$ taken together is azetidinyl, pyrrolidinyl, piperidinyl, piperazinyl, morpholinyl, or dihydroindolyl, and is substituted with 0-2 substituents selected from alkyl, hydroxyalkyl, alkoxyalkyl, hydroxy, alkoxy, carboxy, alkoxycarbonyl, dimethylcarboxamido, alkylcarbonylamino, alkoxycarbonylamino, pyridinyl, and phenyl where phenyl is substituted with 0-2 substituents selected from halo and alkyl; or where $R^7R^8N$ taken together is

(quinuclidinyl)(alkyl)amino, (methylpyrrolidinyl)(alkyl)amino, (alkylthiazolyl)amino, ((carboxamido)cyclopentanyl)amino, ((halophenyl)cyclopentanyl)amino, or (hydroxyindanyl)amino;
$R^9$ is hydrogen, alkyl, hydroxyalkyl, or alkoxyalkyl;
$R^{10}$ is hydrogen, alkyl, hydroxyalkyl, or alkoxyalkyl;
or $R^9$ and $R^{10}$ taken together is ethylene, propylene, butylene, or pentylene;
$R^{11}$ is hydrogen, alkyl, or cycloalkyl;
$R^{12}$ is hydrogen, alkyl, or cycloalkyl;
or $R^{11}$ and $R^{12}$ taken together with the nitrogen to which they are attached is azetidinyl, pyrrolidinyl, piperidinyl, piperazinyl, or morpholinyl;
$R^{13}$ is hydrogen, alkyl, cyanoalkyl, alkenyl, or alkynyl;
$R^{14}$ is hydrogen or alkyl;
$R^{15}$ is hydrogen or alkyl;
$R^{16}$ is hydrogen or alkyl;
$R^{17}$ is haloalkyl, hydroxyalkyl, alkoxyalkyl, alkynyl, $(R^{18})$alkyl or $(Ar^4)$alkyl;
$R^{18}$ is $CONH_2$, dibenzylamino, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl, and is substituted with 0-3 substituents selected from alkyl and alkoxycarbonyl;
$R^{19}$ is cyano, ((alkyl)pyrazolyl)amino, ((alkyl)isoxazolyl)amino(thiadiazolyl)amino, or (triazinyl)amino;
$R^{20}$ and $R^{21}$ are hydrogen;
$Ar^1$ is phenyl, naphthalenyl, pyridinyl, thienyl, thiazolyl, or pyrazinyl and is substituted with 0-2 substituents selected from alkyl, halo, hydroxy, alkoxy, amino, alkylamino, and dialkylamino;
$Ar^2$ is phenyl, biphenyl, or pyridinyl and is substituted witlh 0-2 substituents selected from halo, alkyl, cyano, hydroxy, and alkoxy;
$Ar^3$ is pyrazolyl isoxazolyl, thiazolyl, pyrimidinyl, or pyrizinyl and is substituted witlh 0-2 substituents selected from alkyl and hydroxyalkyl;
$Ar^4$ is pyrrolyl, imidazolyl, pyridinyl, indolyl, or phenyl and is substituted with 0-2 substituents selected from halo, alkyl, hydroxyl, and alkoxy; and
$Ar^5$ is pyrrozolyl, imidazolyl, or oxadiazolyl and is substituted with 0-2 substituents selected from alkyl, carboxy, alkoxycarbonyl, benzyl, and phenyl;
or a pharmaceutically acceptable salt thereof.

Another aspect of the invention is a compound of formula I where $R^1$ is alkoxy; (alkoxycarbonylamino)alkoxy; (alkylphenyl)alkoxy; (carboxy)alkenyl; ((N-dimethylbenzyl)aminocarbonyl)alkenyl; or phenyl where said phenyl is substituted with 1-2 substituents selected from the group consisting of halo, cyano, alkyl, haloalkyl, hydroxyalkyl, (carboxy)alkyl, alkoxy, hydroxyalkyloxy, tetrahydropyranyloxy, carboxy, alkoxycarbonyl, (carboxy)alkenyl, alkylcarboxamido, alkoxycarboxamido, (alkylsulfamido)alkyl, $Ar^y$, $SO_2NR^{15}R^{16}$, and $CONR^7R^8$; and where said phenyl is also substituted with 0-2 substituents selected from the group consisting of halo; nitro; alkyl; cycloalkyl; haloalkyl; aminoalkyl; hydroxy; alkoxy; $OR^{17}$; cycloalkoxy; amino; alkoxycarboxamido; furanyl, thienyl, or pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from halo, cyanoalkyl, hydroxyalkyl, alkoxyalkyl, alkoxy, amino, carboxy, aminocarbonyl, alkylaminocarbonyl, alkylcarboxamido, and carboxyalkenyl;

$R^2$ is hydrogen, halo, nitro, amino, phenyl, or $R^5R^6N$;
$R^3$ is $CONR^{11}R^{12}$;
$R^4$ is phenyl substituted with 0-2 halo substituents;
$R^5$ is hydrogen or alkylsulfonyl;
$R^6$ is hydrogen, alkyl, hydroxyalkyl, or alkylsulfonyl;
$R^7$ is hydrogen, alkyl, alkynyl, cyanoalkyl, haloalkyl, hydroxyalkyl, dihydroxyalkyl, alkoxyalkyl, oxoalkyl, (dialkylamino)alkyl, (cycloalkyl)alkyl, cycloalkyl, (alkyl)cycloalkyl, (hydroxyalkyl)cycloalkyl, (tetrahydrofuranyl)alkyl, (tetrahydropyranyl)alkyl, (carboxy)alkyl, (alkoxycarbonyl)alkyl, (alkenyloxycarbonyl)alkyl, (alkoxycarbonyl)hydroxyalkyl, $(CONR^{13}R^{14})$alkyl, $(CONR^{13}R^{14})$(hydroxyalkyl)alkyl, $(CONR^{13}R^{14})$cylcoalkyl, (alkylcarbonyl)aminoalkyl, (phenyl)alkyl, alkylsulfonyl, phenylsulfonyl, $Ar^2$, $Ar^3$,

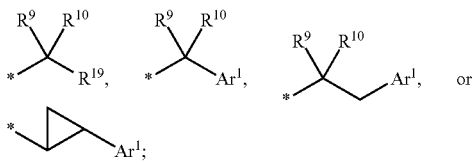

$R^8$ is hydrogen, alkyl, or alkoxyalkyl;
or $R^7R^8N$ taken together is azetidinyl, pyrrolidinyl, piperidinyl, piperazinyl, morpholinyl, dihydroindolyl, or isoindolinyl, and is substituted with 0-2 substituents selected from alkyl, hydroxyalkyl, alkoxyalkyl, hydroxy, alkoxycarbonyl, dialkylcarboxamido, alkylcarbonylamino, pyridinyl, and phenyl where said phenyl is substituted with 0-2 halo or alkyl substituents;
or where $R^7R^8N$ taken together is

(quinuclidinyl)amino, (quinuclidinyl)(alkyl)amino, (methylpyrrolidinyl)(alkyl)amino, ((imidazolyl)alkyl)(hydroxyalkyl)amino, (alkylthiazolyl)amino, ((carboxamido)cyclopentanyl)amino, ((halophenyl)cyclopentanyl)amino, 3H-spiro(isobenzofuranyl)piperidinyl, (hydroxyindanyl)amino, or

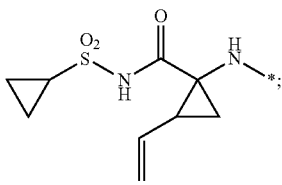

$R^9$ is hydrogen, alkyl, or hydroxyalkyl;
$R^{10}$ is hydrogen or alkyl;
or $R^9$ and $R^{10}$ taken together is ethylene or propylene;
$R^{11}$ is alkyl;
$R^{12}$ is hydrogen;
$R^{13}$ is hydrogen, alkyl, cyanoalkyl, haloalkyl, alkenyl, or thiazolyl;
$R^{14}$ is hydrogen or alkyl;
$R^{15}$ is alkyl, hydroxyalkyl, cycloalkyl, or benzyl;
$R^{16}$ is hydrogen;
or $R^{15}$ and $R^{16}$ taken together with the nitrogen to which they are attached is azetidinyl, pyrrolidinyl, piperidinyl, piperazinyl, or morpholinyl;
$R^{12}$ is haloalkyl, cyanoalkyl, (cycloalkyl)alkyl, hydroxyalkyl, alkoxyalkyl, aminoalkyl, $(R^{18})$alkyl, $(Ar^4)$alkyl, alkynyl, or aminocycloalkyl;

$R^{18}$ is $CONH_2$, $H_2NCONH$, dibenzylamino, phthalimido, amino, dialkylamino, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents;
$R^{19}$ is cyano, hydroxyalkyl, morpholinylalkyl, carboxy, alkoxycarbonyl, cycloalkylsulfoxamido, ((alkyl)pyrazolyl)amino, ((alkyl)isoxazolyl)amino, (thiadiazolyl)amino, (triazinyl)amino, or alkynylaminocarbonyl;
$R^{20}$ and $R^{21}$ are hydrogen;
$Ar^1$ is phenyl, naphthalenyl, pyridinyl, furanyl, pyrazolyl, isoxazolyl, imidazolyl, oxazolyl, thiazolyl, oxadiazolyl, triazolyl, tetrazolyl, pyrazinyl, pyrimidinyl, or benzothiazolyl, and is substituted with 0-2 substituents selected from halo, alkyl, cycloalkyl, haloalkyl, alkoxyalkyl, hydroxy, alkoxy, amino, aminocarbonyl, pyridinyl, phenyl, halophenyl, alkylphenyl, and alkoxyphenyl;
$Ar^2$ is phenyl, biphenyl, or pyridinyl and is substituted with 0-2 substituents selected from halo, alkyl, cyano, hydroxy, alkoxy, and carboxy;
$Ar^3$ is pyrazolyl, isoxazolyl, thiazolyl, triazolyl, pyrimidinyl, or pyrizinyl and is substituted witlh 0-2 substituents selected from hydroxy, alkyl, and $CONR^{13R14}$;
$Ar^4$ is furanyl, pyrrolyl, pyrazolyl, isoxazolyl, imidazolyl, oxadiazolyl, triazolyl, pyridinyl, indolyl, or phenyl and is substituted with 0-2 substituents selected from halo, alkyl, haloalkyl, and hydroxy; and
$Ar^5$ is pyrrozolyl, imidazolyl, or oxadiazolyl and is substituted with 0-2 substituents selected from alkyl, alkoxycarbonyl, benzyl, and phenyl;
or a pharmaceutically acceptable salt thereof.

Another aspect of the invention is a compound of formula I where $R^1$ is phenyl substituted with 1 $CONR^7R^8$ substituent and also substituted with 0-2 halo, alkyl, or alkoxy substituents; $R^2$ is hydrogen, halo, or $R^5R^6N$; $R^3 CONR^{11}R^{12}$; $R^4$ is monofluorophenyl; $R^5$ is alkylsulfonyl; $R^6$ is hydroxyalkyl; $R^7$ is

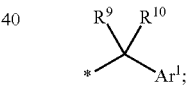

$R^8$ is hydrogen; $R^9$ is alkyl; $R^{10}$ is alkyl or $R^9$ and $R^{10}$ taken together is ethylene or propylene; $R^{11}$ is alkyl; $R^{12}$ is hydrogen; $R^{20}$ and $R^{21}$ are hydrogen; $Ar^1$ is phenyl, pyridinyl, pyrimidinyl, isoxazolyl, oxazolyl, or oxadiazolyl, and is substituted with 0-1 halo or alkyl substituents; or a pharmaceutically acceptable salt thereof.

Another aspect of the invention is a compound of formula I where $R^1$ is phenyl substituted with 1-2 substituents selected from the group consisting of halo, cyano, alkyl, haloalkyl, hydroxyalkyl, (carboxy)alkyl, alkoxy, hydroxyalkyloxy, tetrahydropyranyloxy, carboxy, alkoxycarbonyl, (carboxy)alkenyl, alkylcarboxamido, alkoxycarboxamido, (alkylsulfamido)alkyl, $Ar^5$, $SO_2NR^{15}R^{16}$, and $CONR^7R^8$; and where said phenyl is also substituted with 0-2 substituents selected from the group consisting of halo; nitro; alkyl; cycloalkyl; haloalkyl; aminoalkyl; hydroxy; alkoxy; $OR^{17}$; cycloalkoxy; amino; alkoxycarboxamido; furanyl, thienyl, or pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from halo, cyanoalkyl, hydroxyalkyl, alkoxyalkyl, alkoxy, amino, carboxy, aminocarbonyl, alkylaminocarbonyl, alkylcarboxamido, and carboxyalkenyl.

Another aspect of the invention is a compound of formula I where $R^1$ is phenyl substituted with 1 $CONR^7R^8$ substituent and also substituted with 0-2 halo, alkyl, or alkoxy substituents.

Another aspect of the invention is compound of formula I where $R^7$ is

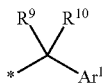

and at least one of $R^9$ and $R^{10}$ is not hydrogen.

Another aspect of the invention is compound of formula I where $R^2$ is $R^5R^6N$.

Another aspect of the invention is compound of formula I where $R^3$ is $CONR^{11}R^{12}$.

Another aspect of the invention is compound of formula I where $R^4$ is phenyl or monofluorophenyl.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. For example, substituents $R^1$ and $R^2$ of formula I are intended to bond to the benzene ring of formula I and not to the furan ring.

Ethylene means ethanediyl or $-CH_2CH_2-$; propylene means propanediyl or $-CH_2CH_2CH_2-$; butylene means butanediyl or $-CH_2CH_2CH_2CH_2-$; pentylene means pentanediyl or $-CH_2CH_2CH_2CH_2CH_2-$.

Dioxothiazinyl means

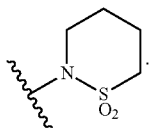

Any scope of any variable, including $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, Ar^1, Ar^2, Ar^3, Ar^4,$ or $Ar^5$ can be used independently with the scope of any other instance of a variable.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2-$; and "TMOF" for trimethylorthoformate.

As shown in Scheme 1, some compounds of the invention may be prepared by coupling a benzofuran triflate or halide to a substituted phenyl boronic acid that in some examples contains a carboxylic acid or carboxylic acid ester. Other coupling techniques and conditions are also known in the art as are other carbon-carbon bond forming reactions. Acids and esters may be converted to amides by methods known in the art.

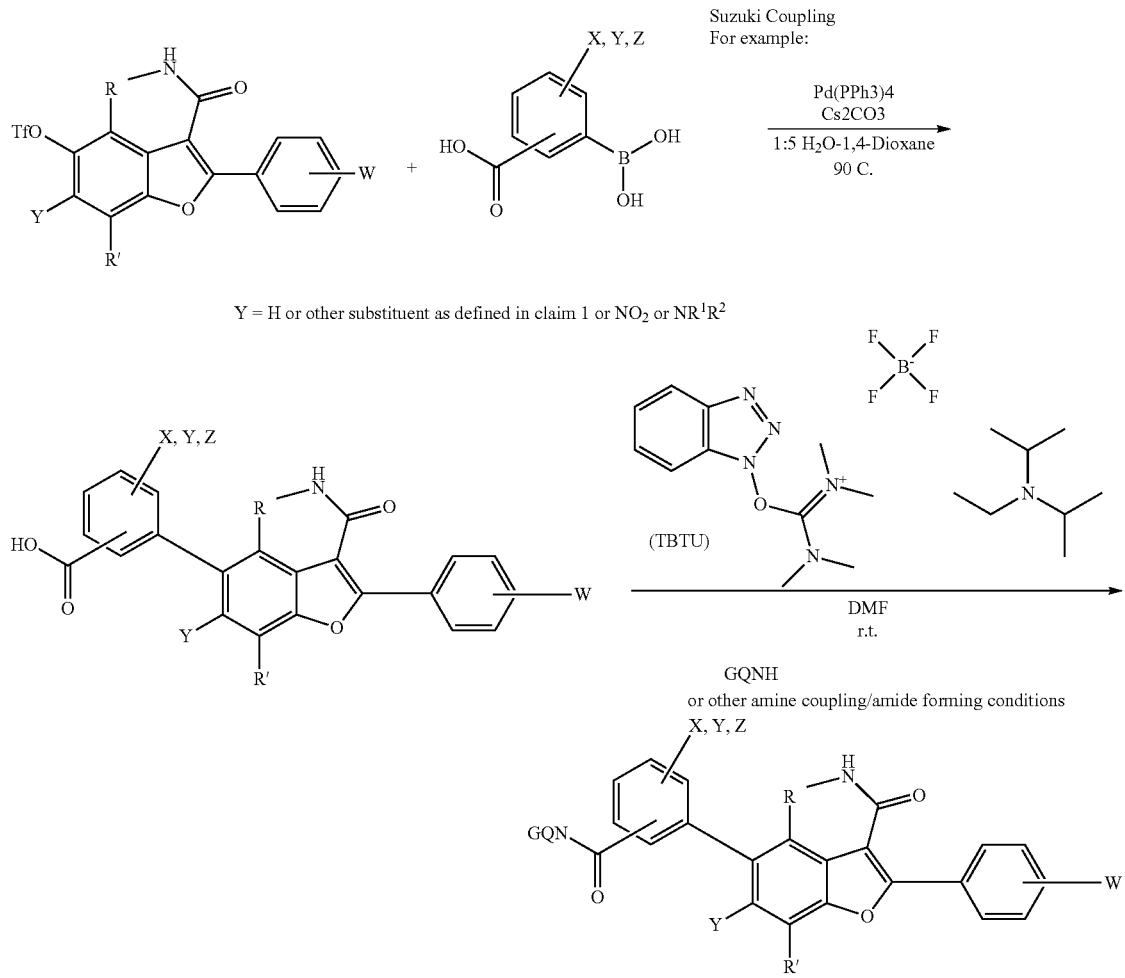

Scheme 2 depicts one specific example of Scheme 1.

As shown in Scheme 2, a nitro group on the benzofuran ring may be reduced and the resulting amino group may be functionalized using known chemistry. For example, the amine may be converted to a monosulfonamide via reaction with a sulfonyl chloride or by preparation of a bis sulfonamide followed by selective hydrolysis. The monosulfonamide may be alkylated again with either a simple or functionalized alkyl. In Scheme 3, the hydroxyethyl group is unmasked via acidic removal of the silyl protecting group.

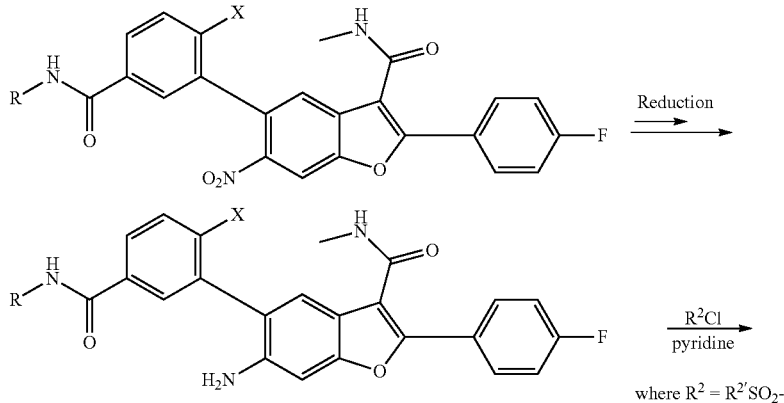

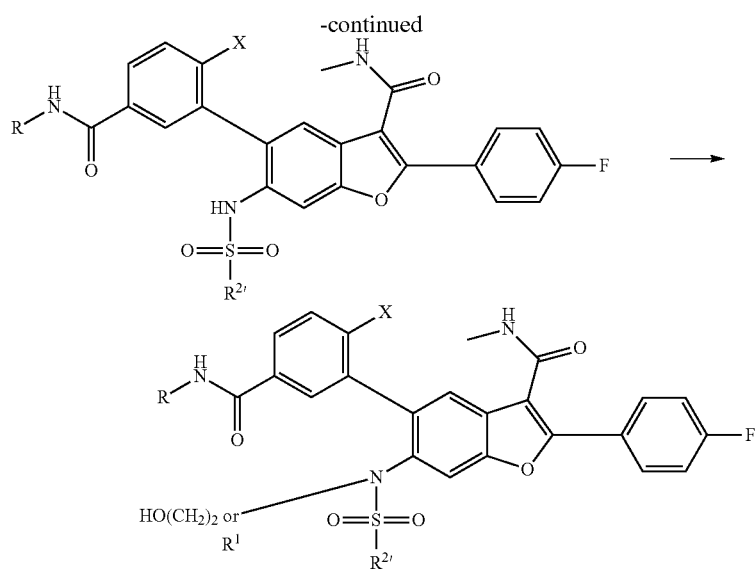

Scheme 3 depicts the preparation of two intermediates labelled as common intermediate 1 and 2 which can be used to prepare some compounds of the invention. The isopropyl group is used to temporarily mask the C5 hydroxy group so the methyl amide can be constructed from the ethyl ester. The more advanced common intermediate 2 allows functionalization of the sulfonamide, acid deprotection and formation of some amide compounds after coupling of amines to the acid as described earlier.

Scheme 3.

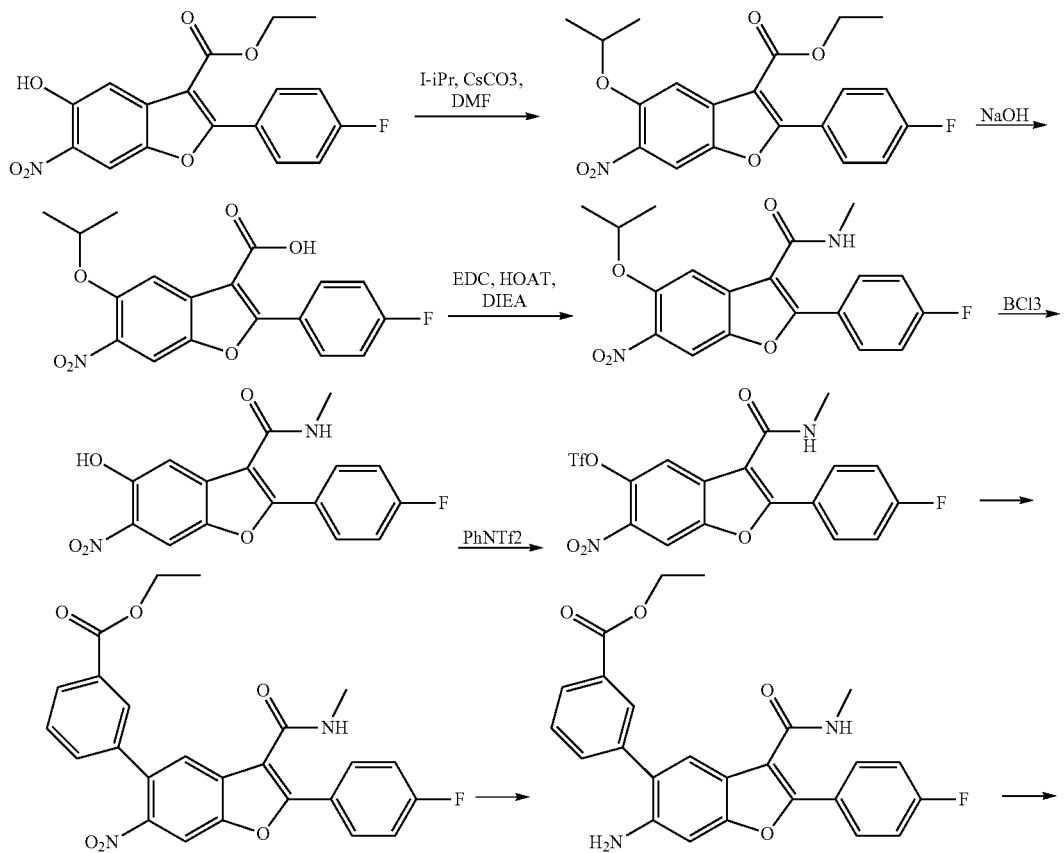

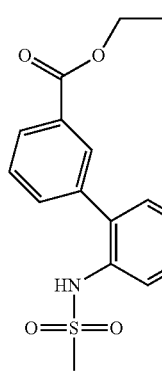
-continued
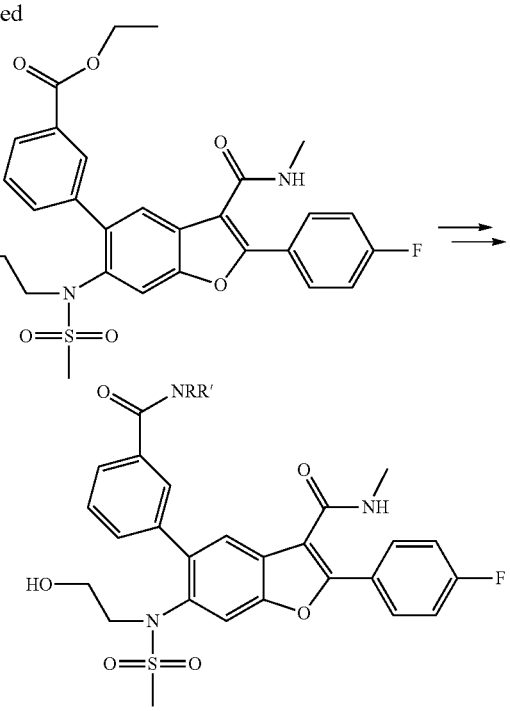
Scheme 4 depicts some conditions for preparing some of the compounds described and for accessing an alternate common intermediate 3 which allows amide formation prior to nitro reduction and amine functionalization.
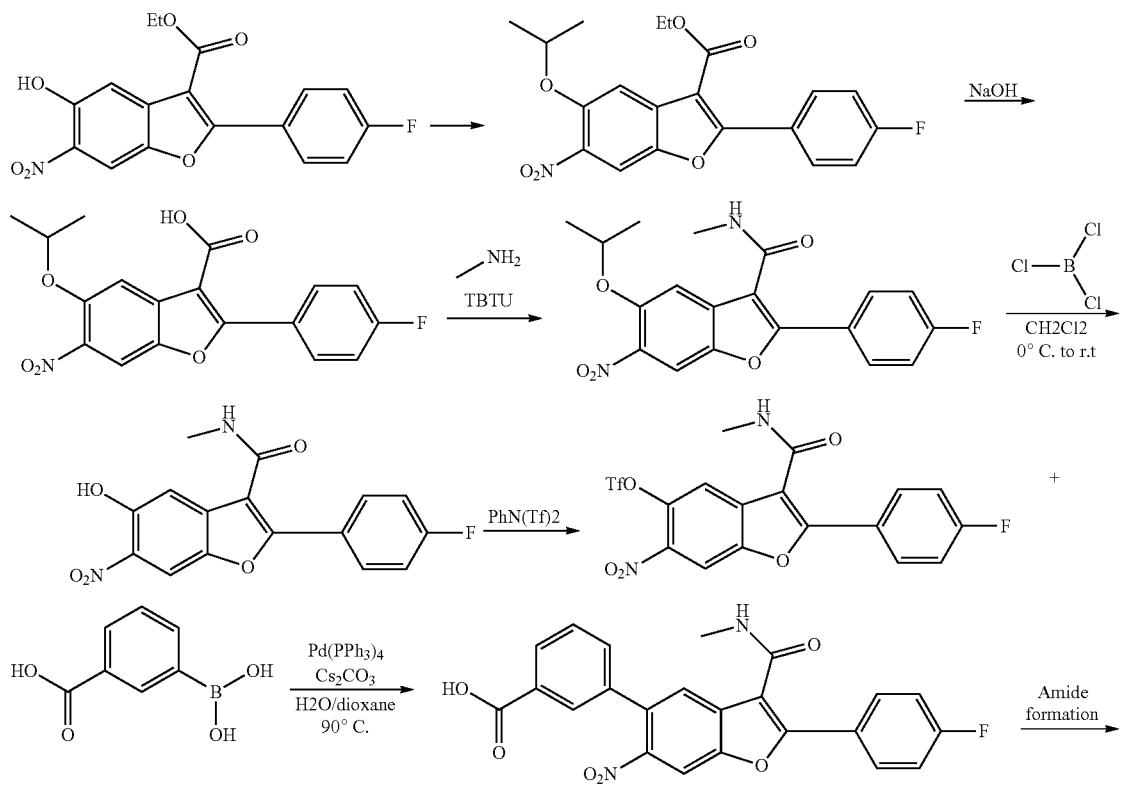

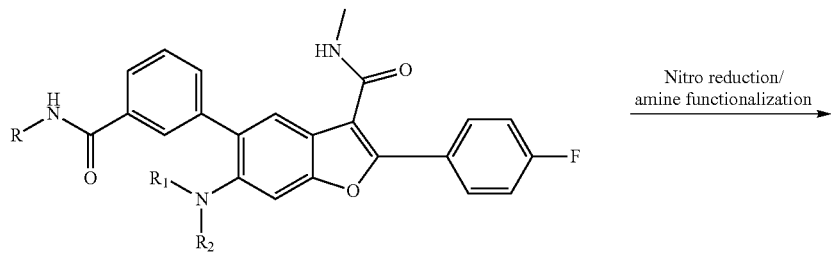
Scheme 5 illustrates a method for preparing some compounds by preparing 2-(4-fluorophenyl)-N-methyl-5-(4,4,5,5-tetramethyl-1,3,2-dioxaborolan-2-yl)benzofuran-3-carboxamide in which the boron is attached to the benozfuran and then coupling to triflates or halogen containing aryl moieties.
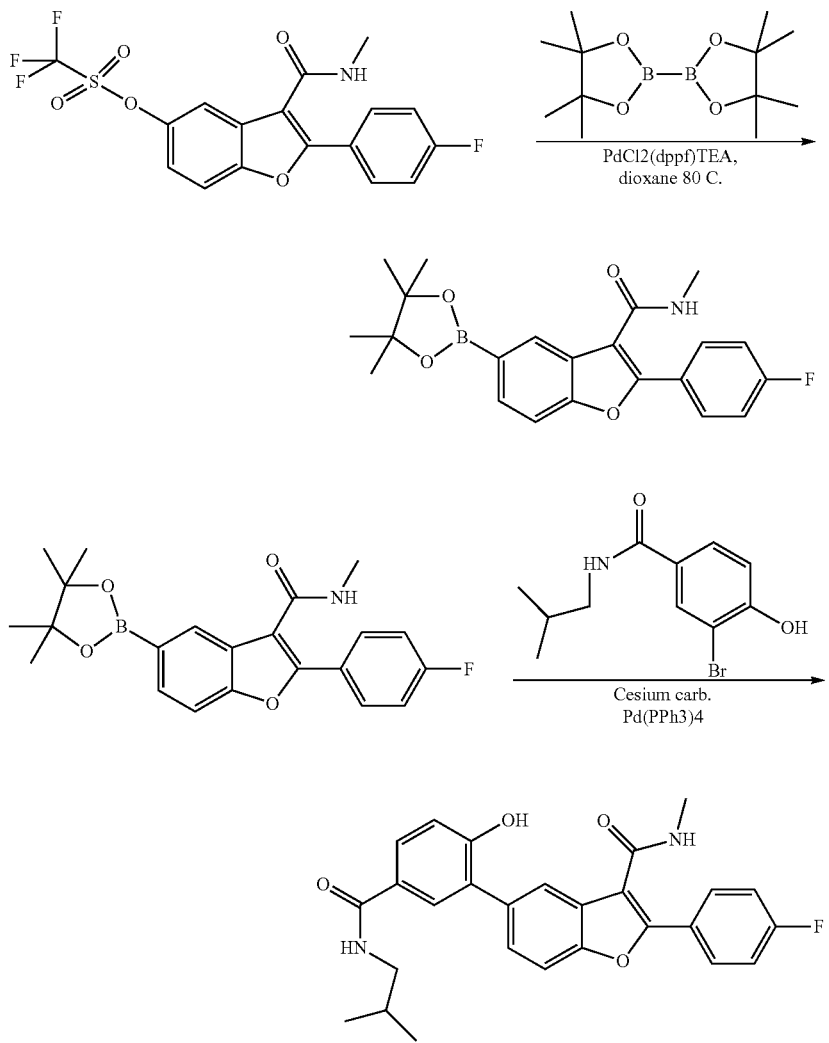

Scheme 6 shows a preparation of the functionalized benzofuran and Scheme 7 shows one method for installation of nitrogen functionality which can then functionalized as described in the previous schemes.

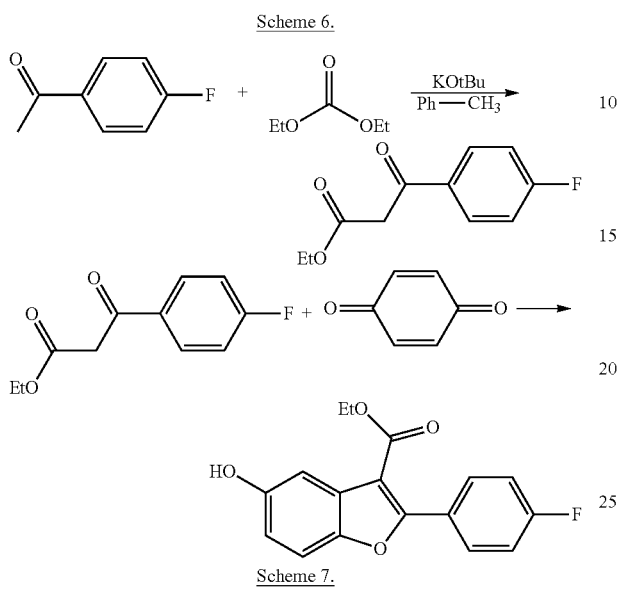

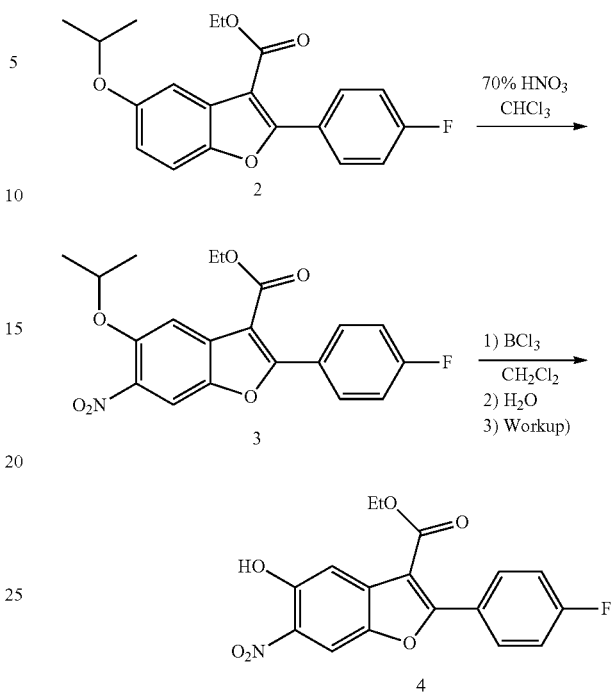

Scheme 8 illustrates that a free phenolic OH group can be used to form some ether compounds. Scheme 9 provides an alkylation for forming ethers under mild or more extreme contions depending on the reactivity of the alkylating reagent.

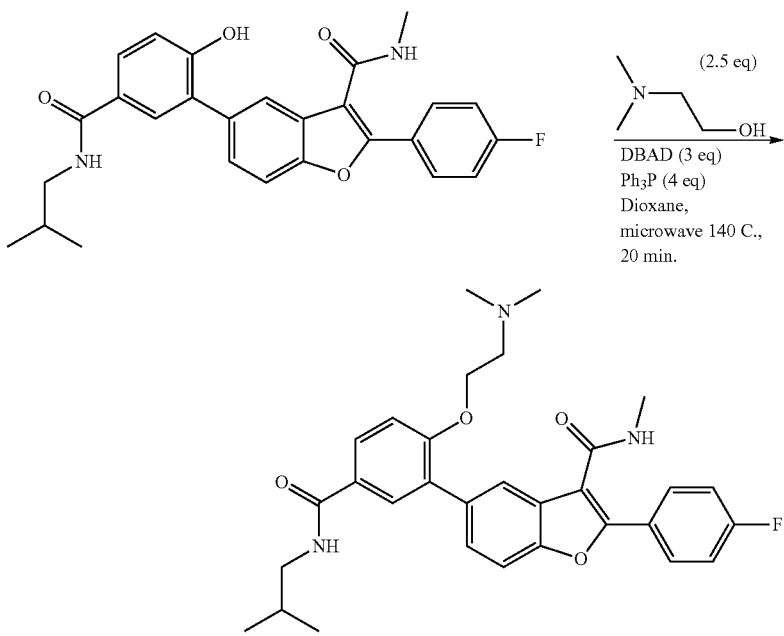

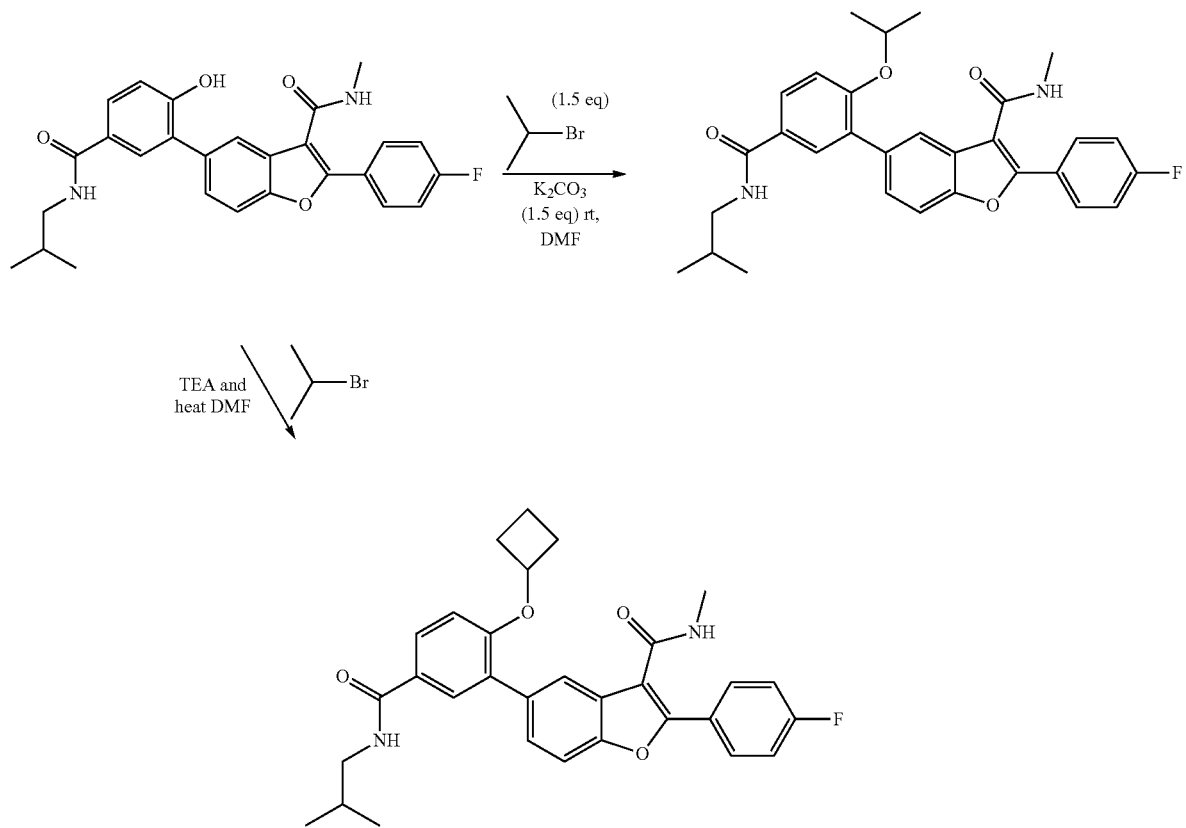
Scheme 9.
Scheme 10 shows how an ether with a protected amine can be attached, and after subsequent deprotection of the pthalimide, a free amine is liberated which can be either incorporated into compounds of the invention or derivatized further via standard chemistry to provide secondary or tertiary amines or amides or sulfonamides.
Scheme 10.
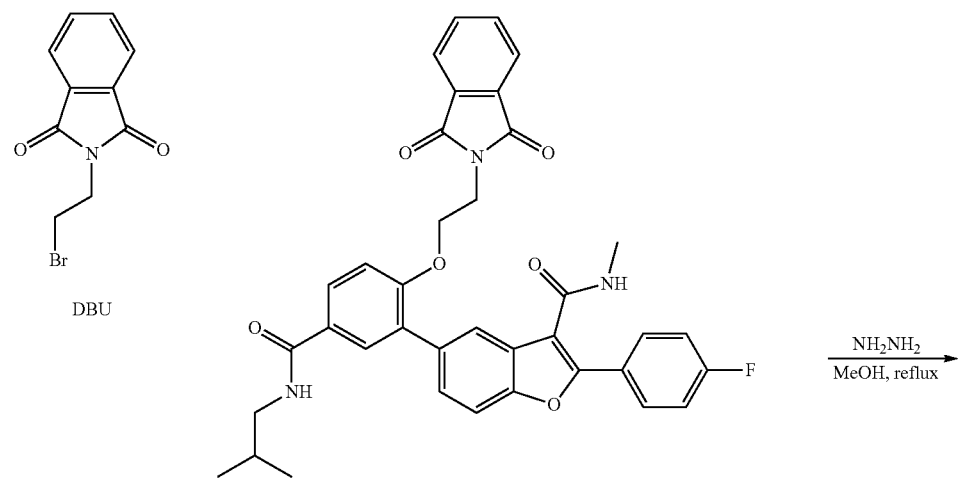

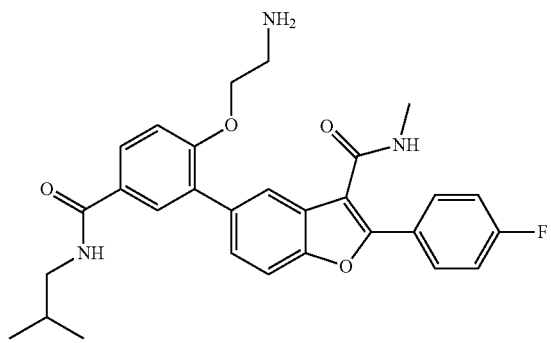

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM $MgCl_2$, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 μM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, *J. Virol.* 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µl of cells at a density of $3.0 \times 10^3$ cells/well in DMEM containing 4% FCS (final DMSO concentration at 0.5%). After 3 days incubation at 37° C., cells were analyzed for *Renilla* Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). 3 µl of Cell-Titer Blue was added to each well and incubated for 8 hrs at 37° C. The fluorescence signal from each well was read, with an excitation wavelength at 525/10 nm and an emission wavelength of 598/10 nm, using the Viewlux Imager.

Representative data for compounds are reported in Tables 1a, 1b, 1c, 1d, and 1e.

TABLE 1a

| Structure | $IC_{50}$ | $EC_{50}$ |
|---|---|---|
|  | A | A |
|  | A | A |

TABLE 1a-continued
| Structure | IC$_{50}$ | EC$_{50}$ |
|---|---|---|
| 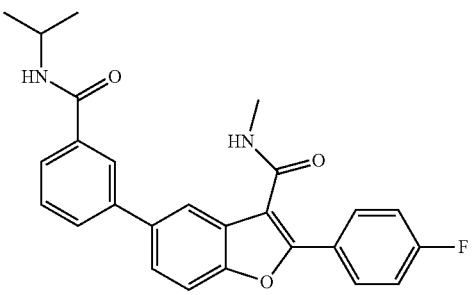 | A | A |
| 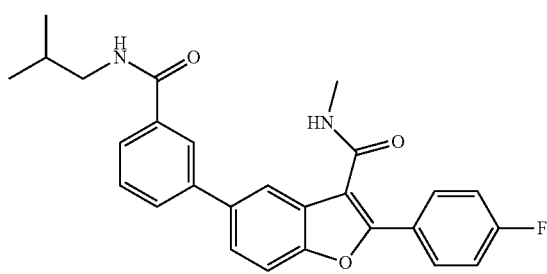 | A | A |
| 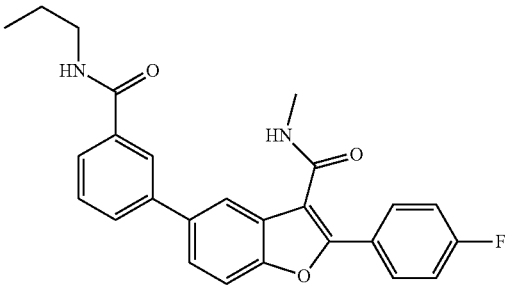 | A | A |
| 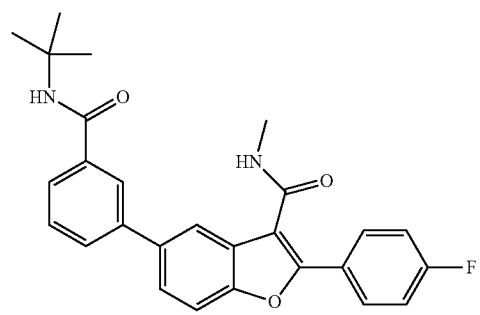 | A | A |
| 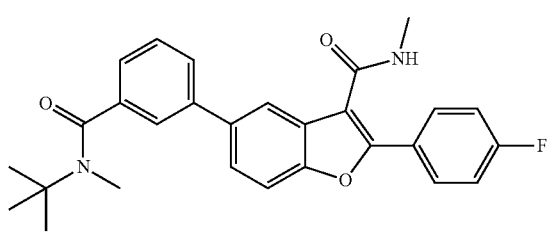 | A | A |

TABLE 1a-continued

| Structure | IC$_{50}$ | EC$_{50}$ |
|---|---|---|
| (structure) | A | A |
| (structure) | B | A |
| (structure) | A | A |
| (structure) | A | A |
| (structure) | A | A |
| (structure) | A | A |

TABLE 1a-continued
| Structure | IC$_{50}$ | EC$_{50}$ |
|---|---|---|
| 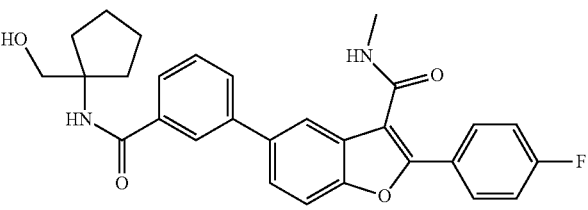 | A | A |
| 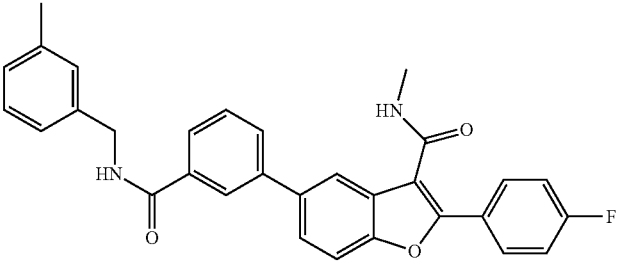 | A | A |
| 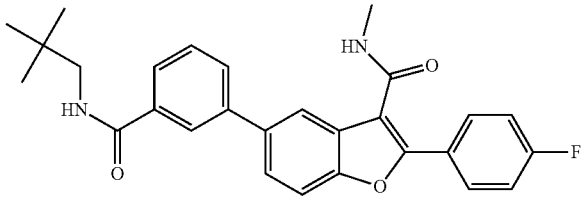 | A | A |
| 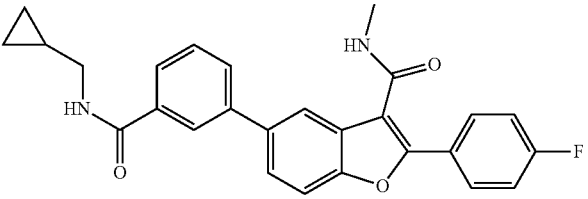 | A | A |
| 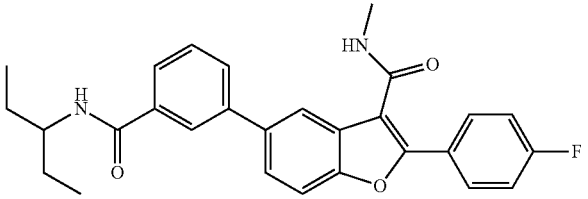 | A | A |
| 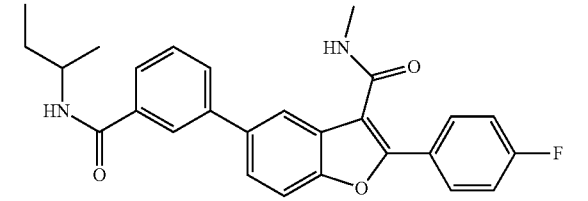 | A | A |
| 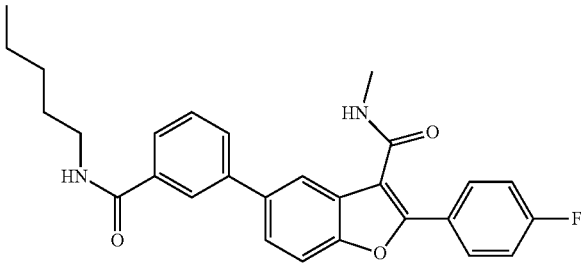 | A | A |

TABLE 1a-continued

| Structure | IC$_{50}$ | EC$_{50}$ |
|---|---|---|
| (structure) | A | A |
| (structure) | B | A |
| (structure) | A | A |
| (structure) | B | A |
| (structure) | A | A |
| (structure) | A | A |

TABLE 1a-continued

| Structure | IC$_{50}$ | EC$_{50}$ |
|---|---|---|
| | A | A |
| | A | A |
| 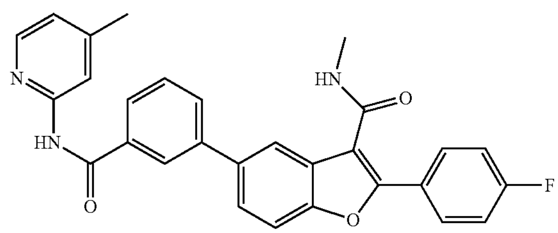 | B | A |
| | A | A |
| | A | A |
| | A | A |

TABLE 1a-continued

| Structure | IC$_{50}$ | EC$_{50}$ |
|---|---|---|
| | A | A |
| | A | A |
| Chiral | A | A |
| Chiral | A | A |
| | A | A |
| | A | A |

TABLE 1a-continued

| Structure | IC$_{50}$ | EC$_{50}$ |
|---|---|---|
| | A | A |
| | A | A |
| | A | A |
| | A | A |
| 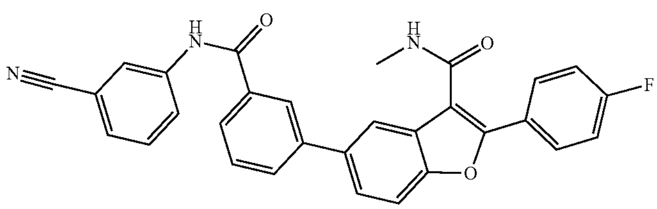 | B | A |
| | A | A |

TABLE 1a-continued

| Structure | IC$_{50}$ | EC$_{50}$ |
|---|---|---|
| | A | A |
| | A | A |
| | A | A |
| | A | A |
| | A | A |
| Chiral | F | A |

TABLE 1a-continued
| Structure | IC$_{50}$ | EC$_{50}$ |
|---|---|---|
| 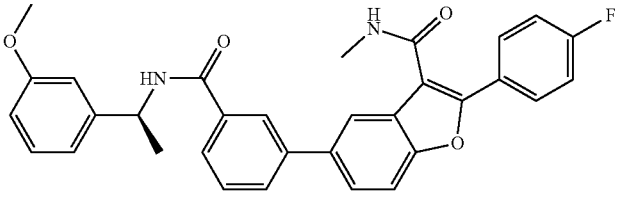 Chiral | A | A |
| 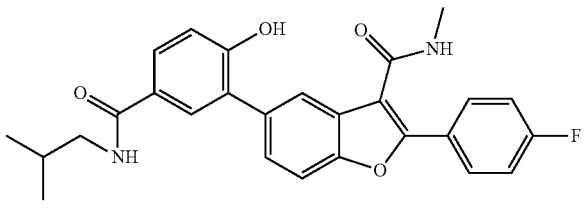 | A | A |
| 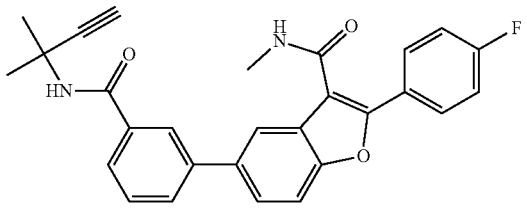 | A | A |
| 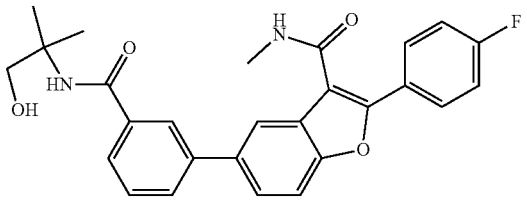 | A | A |
| 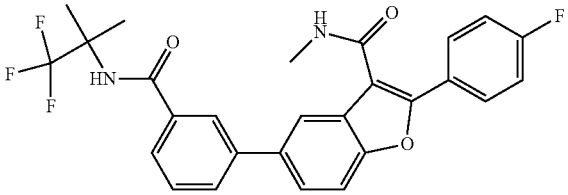 | A | A |
| 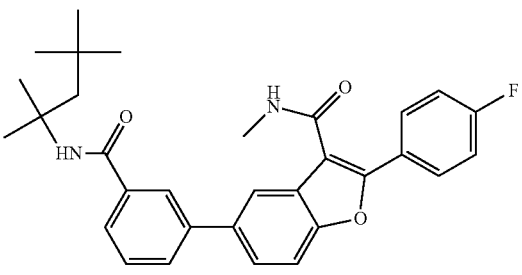 | B | A |
| 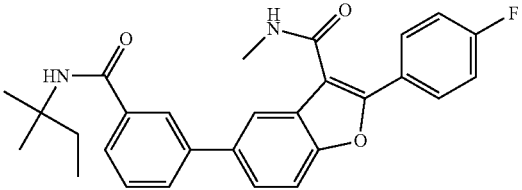 | A | A |

TABLE 1a-continued
| Structure | IC$_{50}$ | EC$_{50}$ |
|---|---|---|
|  | A | A |
| 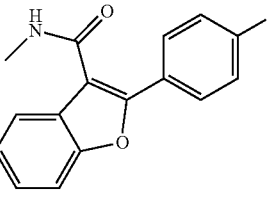 | A | A |
| 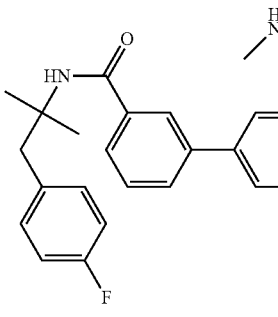 | B | A |
| 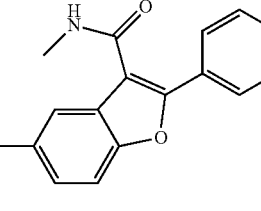 | A | A |
| 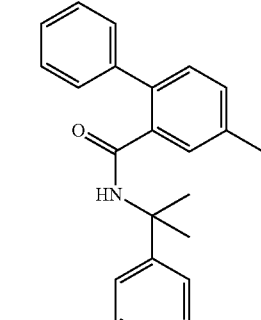 | A | A |

TABLE 1a-continued

| Structure | IC$_{50}$ | EC$_{50}$ |
|---|---|---|
| *(structure)* | A | A |
| *(structure)* | A | A |
| *(structure)* | A | A |
| *(structure)* | A | A |
| *(structure)* | A | A |

TABLE 1a-continued

| Structure | IC$_{50}$ | EC$_{50}$ |
|---|---|---|
| | A | A |
| 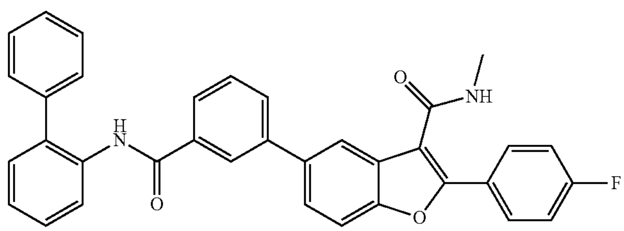 | C | A |
| | A | A |
| | A | A |
| | A | A |

TABLE 1a-continued

| Structure | IC$_{50}$ | EC$_{50}$ |
|---|---|---|
| (structure) | A | A |
| (structure) | A | A |
| (structure) | A | A |
| (structure) | A | A |
| (structure) | A | A |

TABLE 1a-continued

| Structure | IC$_{50}$ | EC$_{50}$ |
|---|---|---|
| *(structure)* | A | A |
| *(structure)* | A | A |
| *(structure)* | E | B |
| *(structure)* | E | F |
| *(structure)* | E | H |

TABLE 1a-continued

| Structure | IC$_{50}$ | EC$_{50}$ |
|---|---|---|
| | E | F |
| | E | B |
| 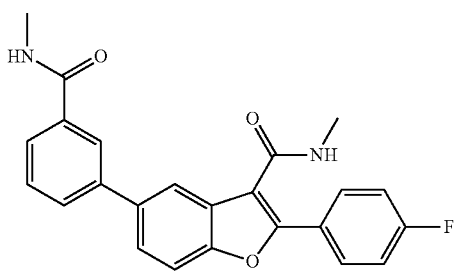 | C | B |
| 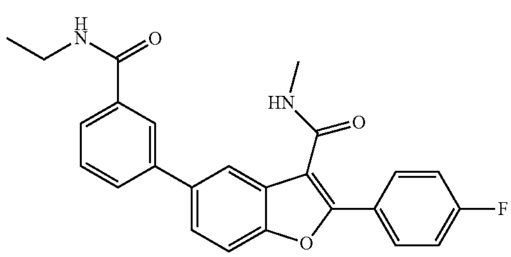 | B | B |
| 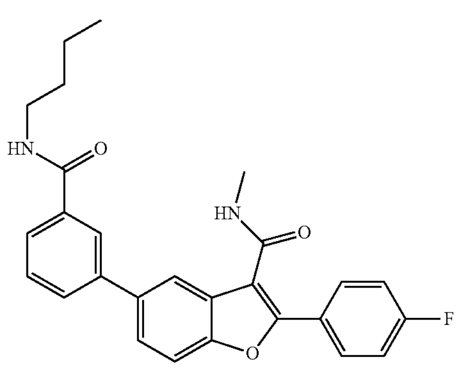 | A | A |

TABLE 1a-continued

| Structure | IC$_{50}$ | EC$_{50}$ |
|---|---|---|
| (structure) | B | B |
| (structure) | A | B |
| (structure) | B | B |
| (structure) | B | B |
| (structure) | B | B |
| (structure) | A | B |

TABLE 1a-continued
| Structure | IC$_{50}$ | EC$_{50}$ |
|---|---|---|
| 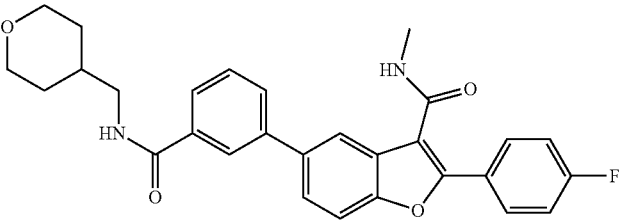 | A | B |
| 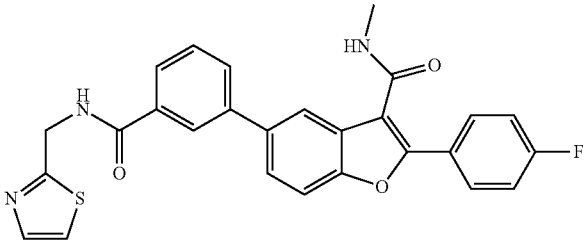 | B | B |
| 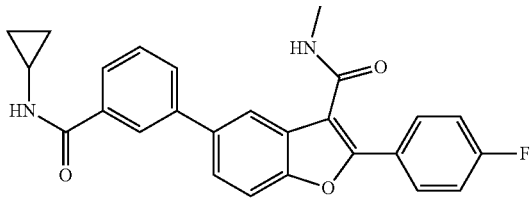 | B | B |
| 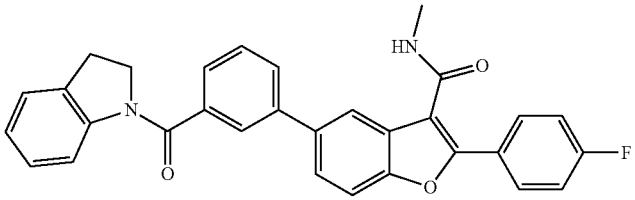 | C | B |
| 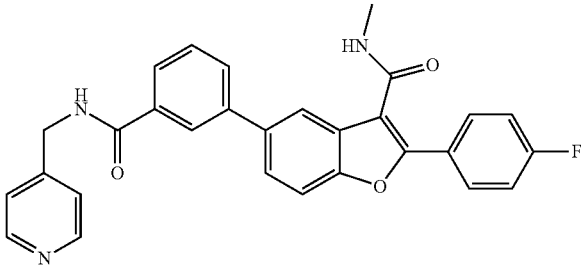 | A | B |
| 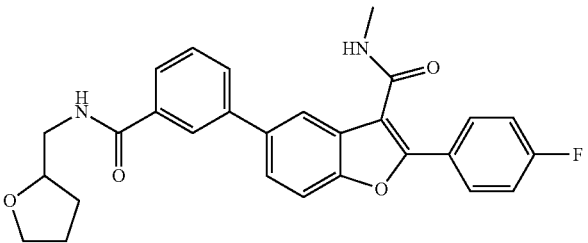 | A | B |

TABLE 1a-continued

| Structure | IC$_{50}$ | EC$_{50}$ |
|---|---|---|
| (pyrrolidine-carbonyl-phenyl benzofuran with 4-fluorophenyl and N-methylcarboxamide) | B | B |
| (cyclohexylmethylaminocarbonyl-phenyl benzofuran with 4-fluorophenyl and N-methylcarboxamide) | A | B |
| (azetidine-carbonyl-phenyl benzofuran with 4-fluorophenyl and N-methylcarboxamide) | B | B |
| (pyridin-2-ylmethylaminocarbonyl-phenyl benzofuran with 4-fluorophenyl and N-methylcarboxamide) | A | B |
| (pyridin-3-ylmethylaminocarbonyl-phenyl benzofuran with 4-fluorophenyl and N-methylcarboxamide) | A | B |
| (4-methylthiazol-2-ylaminocarbonyl-phenyl benzofuran with 4-fluorophenyl and N-methylcarboxamide) | A | B |

TABLE 1a-continued

| Structure | IC$_{50}$ | EC$_{50}$ |
|---|---|---|
| 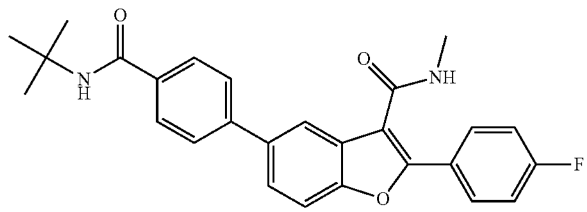 | C | B |
| 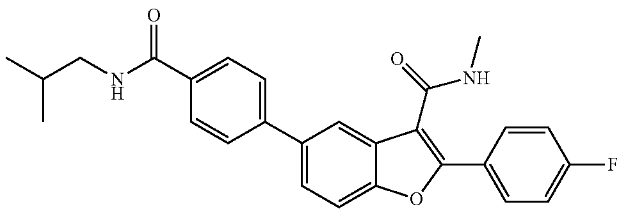 | E | B |
| | A | A |
| | B | B |
| | B | B |
| | A | B |
| | B | B |

TABLE 1a-continued

| Structure | IC$_{50}$ | EC$_{50}$ |
|---|---|---|
| | B | B |
| | B | B |
| | B | B |
| | A | B |
| 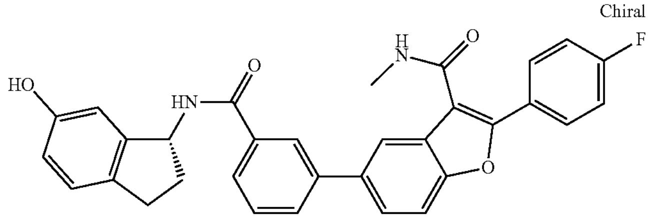 | G | B |
| 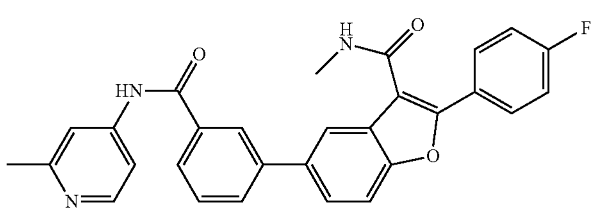 | C | B |
| | A | B |

TABLE 1a-continued
| Structure | IC$_{50}$ | EC$_{50}$ |
| --- | --- | --- |
| 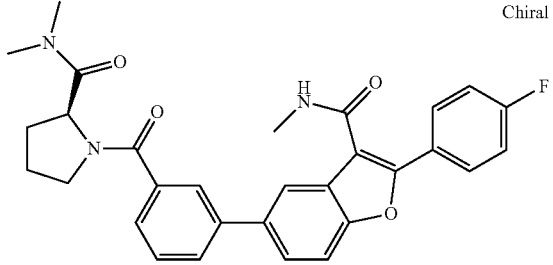 Chiral | B | B |
| 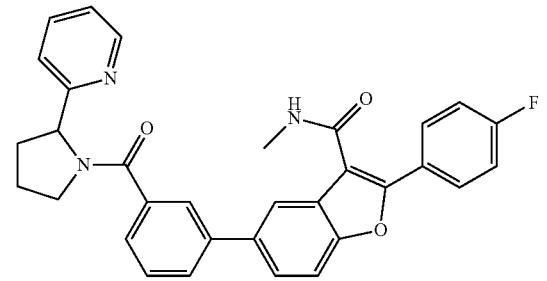 | B | B |
| 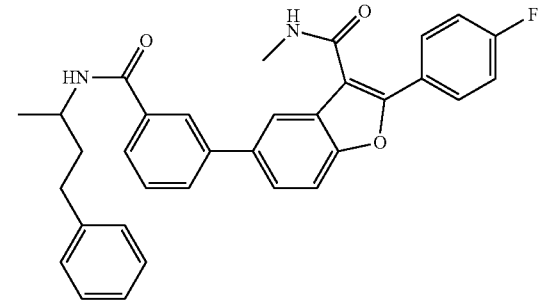 | B | B |
| 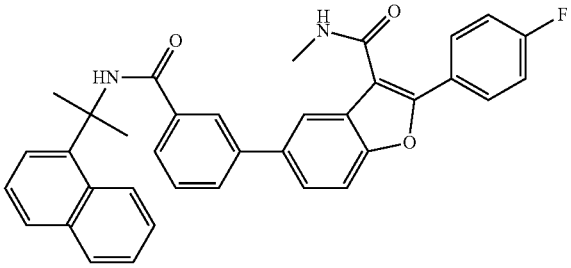 | B | B |
| 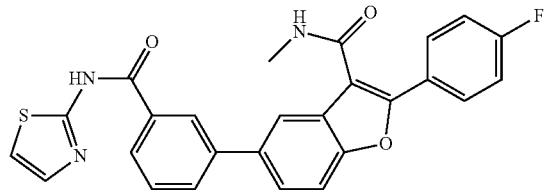 | A | B |
| 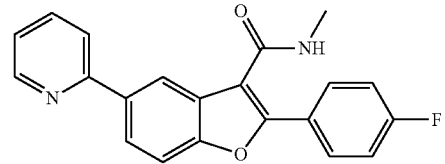 | C | B |

TABLE 1a-continued

| Structure | IC$_{50}$ | EC$_{50}$ |
|---|---|---|
| (3-cyanophenyl-substituted 2-(4-fluorophenyl)-N-methylbenzofuran-3-carboxamide) | E | B |
| (1H-indol-4-yl-substituted 2-(4-fluorophenyl)-N-methylbenzofuran-3-carboxamide) | E | B |
| (3-(N-benzyl-N-methylcarbamoyl)phenyl-substituted 2-(4-fluorophenyl)-N-methylbenzofuran-3-carboxamide) | B | B |
| (3-(2-phenylpyrrolidine-1-carbonyl)phenyl-substituted 2-(4-fluorophenyl)-N-methylbenzofuran-3-carboxamide) | B | B |
| (3-(3-(4-fluorophenyl)pyrrolidine-1-carbonyl)phenyl-substituted 2-(4-fluorophenyl)-N-methylbenzofuran-3-carboxamide) | B | B |

TABLE 1a-continued

| Structure | IC$_{50}$ | EC$_{50}$ |
|---|---|---|
| (structure) | B | B |
| (structure) | A | B |
| (structure) | B | B |
| (structure) | B | B |
| (structure) | B | B |

TABLE 1a-continued
| Structure | IC$_{50}$ | EC$_{50}$ |
|---|---|---|
| 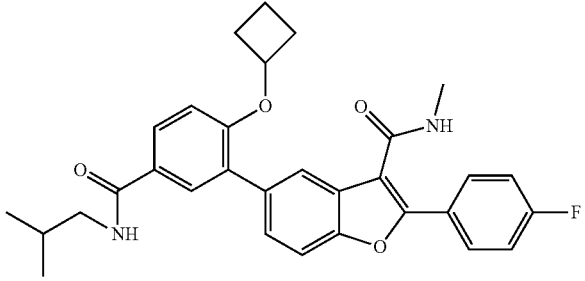 | G | B |
| 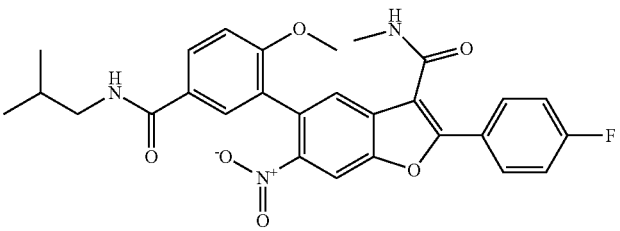 | B | B |
| 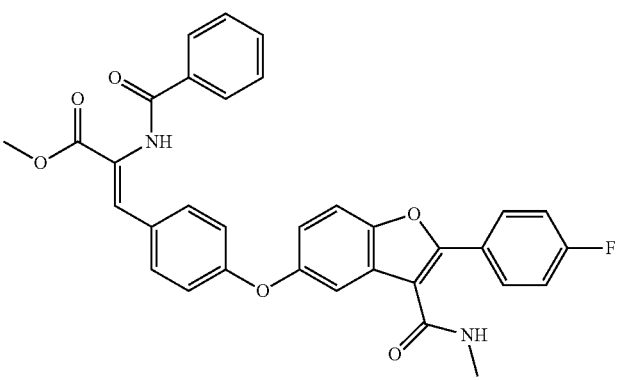 | C | C |
| 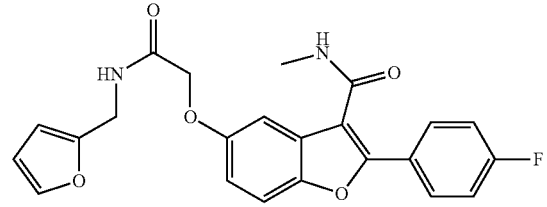 | | C |
| 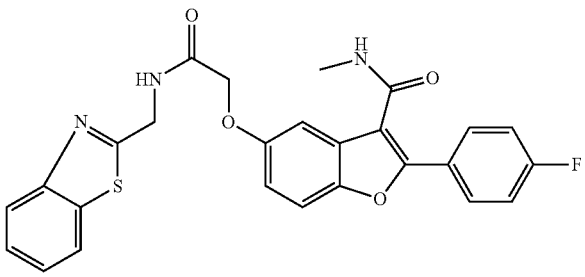 | | C |
|  | C | C |

TABLE 1a-continued

| Structure | IC$_{50}$ | EC$_{50}$ |
|---|---|---|
| 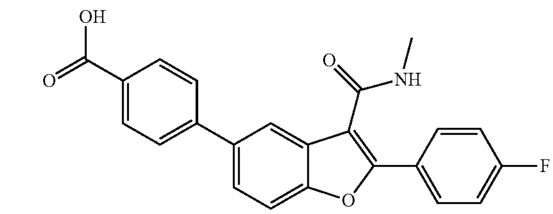 | B | C |
| | C | C |
| | C | C |
| | C | C |
| 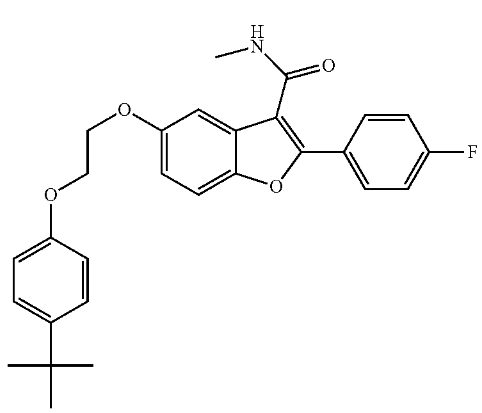 | E | C |

TABLE 1a-continued

| Structure | IC$_{50}$ | EC$_{50}$ |
|---|---|---|
| 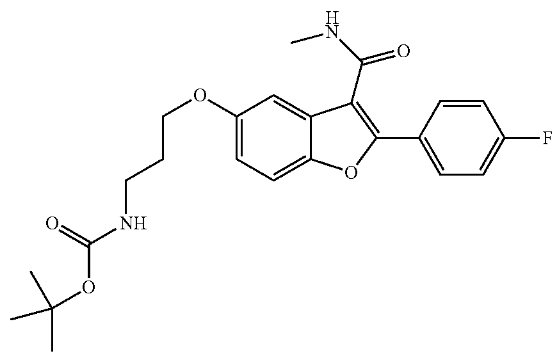 | C | C |
| | E | C |
| | E | C |
| | E | C |
| | E | C |

TABLE 1a-continued

| Structure | IC$_{50}$ | EC$_{50}$ |
|---|---|---|
| (5-chloro-2-fluoropyridin-3-yl substituted 2-(4-fluorophenyl)-N-methylbenzofuran-3-carboxamide) | E | C |
| (4-(pyrrolidine-1-carbonyl)phenyl substituted 2-(4-fluorophenyl)-N-methylbenzofuran-3-carboxamide) | C | C |
| (2-chloro-5-(hydroxymethyl)phenyl substituted 2-(4-fluorophenyl)-N-methylbenzofuran-3-carboxamide) | E | C |
| (5-isopropoxy-6-(N-methylmethanesulfonamido)-2-(4-fluorophenyl)-3-(1H-1,2,4-triazol-3-yl)benzofuran) | B | C |
| (3-(2-methoxyethylcarbamoyl)phenyl substituted 2-(4-fluorophenyl)-N-methylbenzofuran-3-carboxamide) | C | C |

TABLE 1a-continued
| Structure | IC$_{50}$ | EC$_{50}$ |
|---|---|---|
| 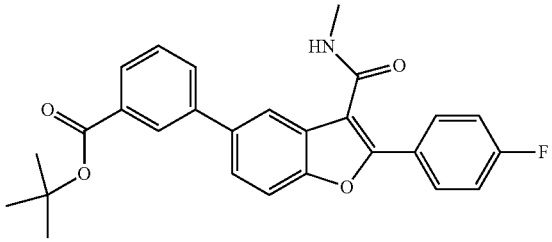 | C | C |
| 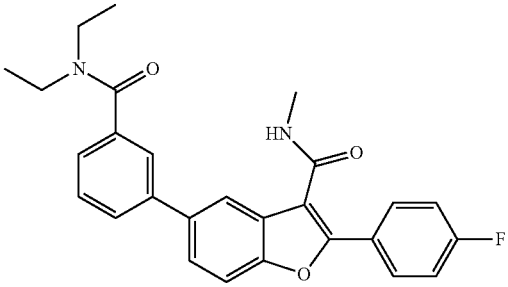 | C | C |
| 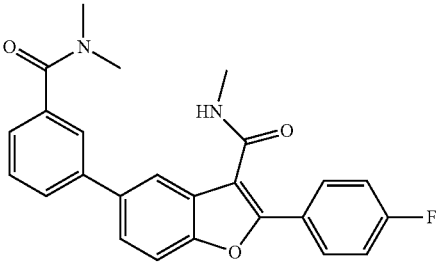 | C | C |
| 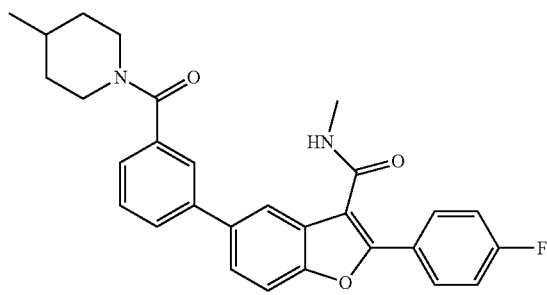 | B | C |
| | C | C |

TABLE 1a-continued

| Structure | IC$_{50}$ | EC$_{50}$ |
|---|---|---|
| | B | C |
| | C | C |
| | B | C |
| | C | C |
| | C | C |
| | C | C |

TABLE 1a-continued
| Structure | IC$_{50}$ | EC$_{50}$ |
|---|---|---|
| 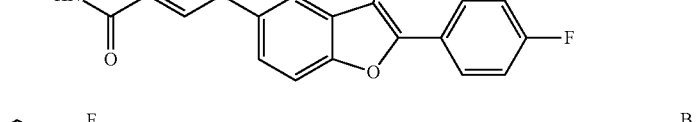 | B | C |
| 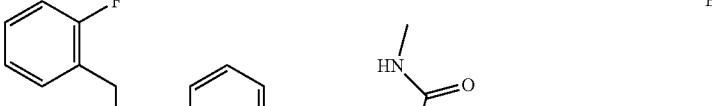 | B | C |
| 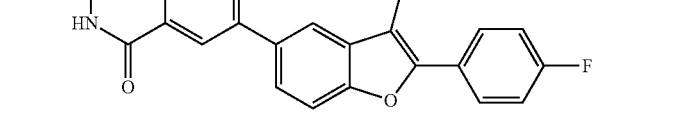 | B | C |
| 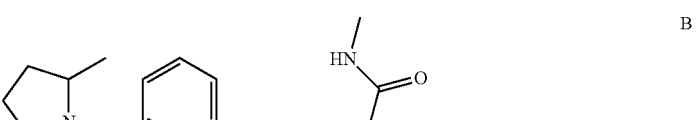 Chiral | C | C |
| 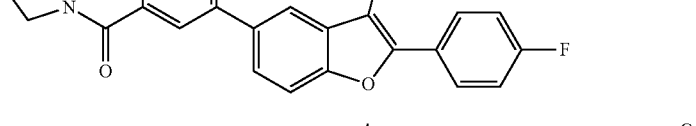 | C | C |
| 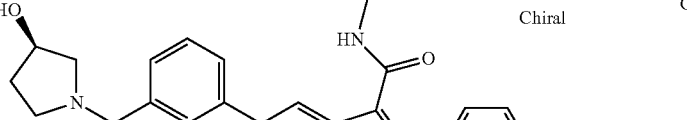 | C | C |
| 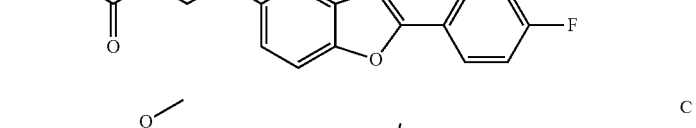 | C | C |

TABLE 1a-continued

| Structure | IC$_{50}$ | EC$_{50}$ |
|---|---|---|
| (structure) | E | C |
| (structure) | C | C |
| (structure) | C | C |
| (structure) | B | C |
| (structure) | C | C |
| (structure) Chiral | B | C |

TABLE 1a-continued
| Structure | IC$_{50}$ | EC$_{50}$ |
|---|---|---|
| 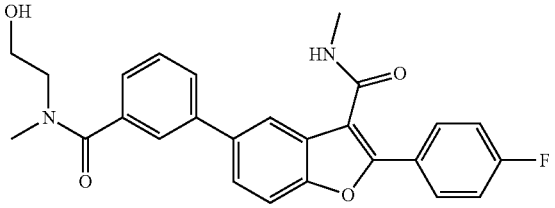 | C | C |
| 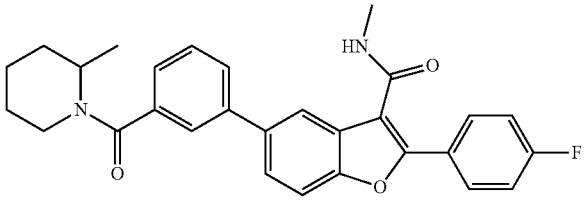 | B | C |
| 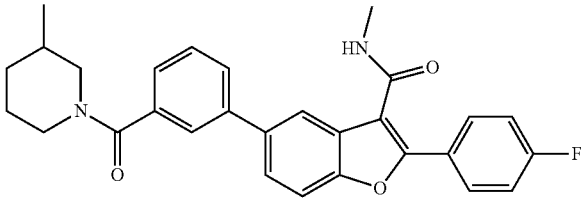 | C | C |
| 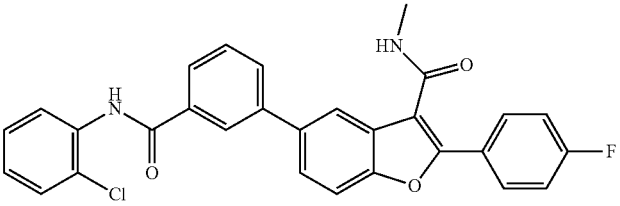 | C | C |
| 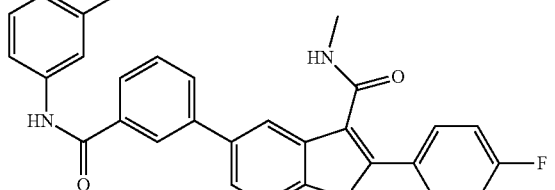 | C | C |
| 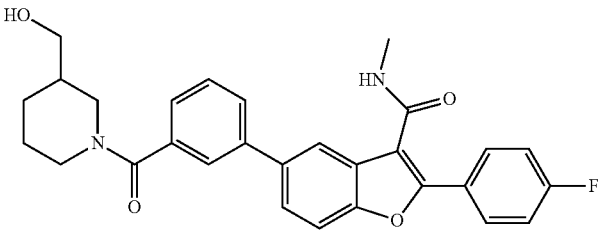 | C | C |
| 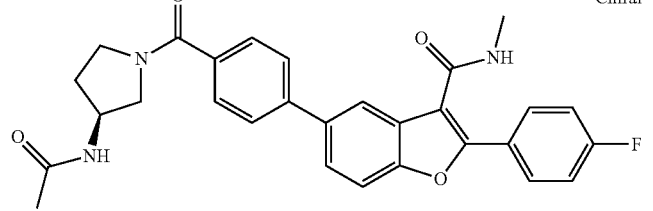 Chiral | C | C |

TABLE 1a-continued
| Structure | IC$_{50}$ | EC$_{50}$ |
|---|---|---|
| 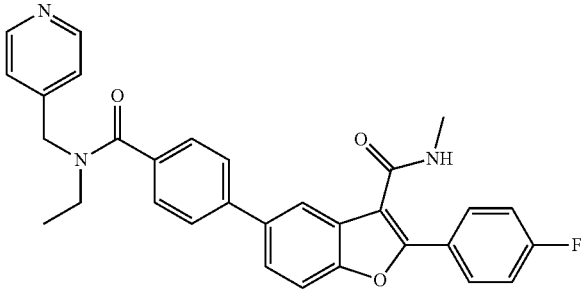 | E | C |
| 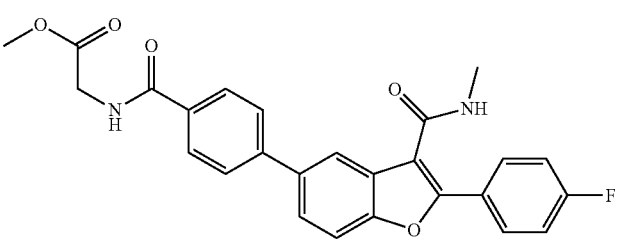 | E | C |
| 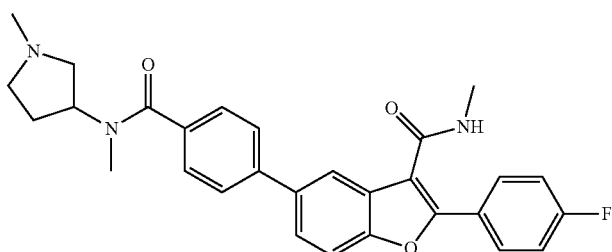 | E | C |
| 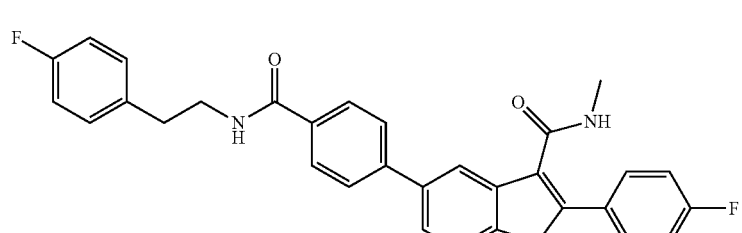 | E | C |
| 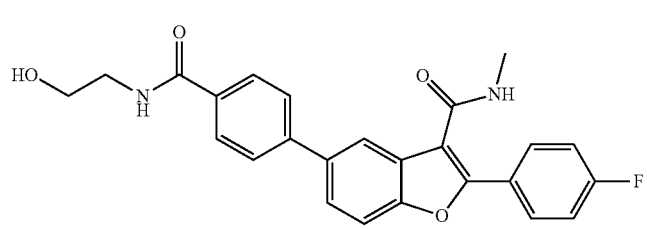 | E | C |
| 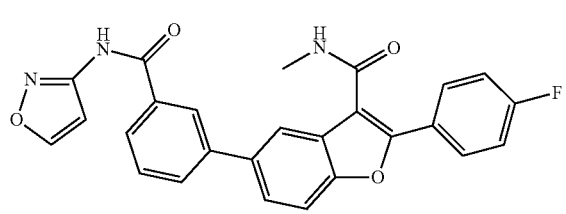 | B | C |

TABLE 1a-continued

| Structure | IC$_{50}$ | EC$_{50}$ |
|---|---|---|
| | C | C |
| | C | C |
| | C | C |
| Chiral | A | C |
| Chiral | C | C |
| Chiral | A | C |

TABLE 1a-continued

| Structure | IC$_{50}$ | EC$_{50}$ |
|---|---|---|
| (Chiral structure) | B | C |
| (Structure) | B | C |
| (Chiral structure) | C | C |
| (Structure) | C | C |
| (Chiral structure) | B | C |
| (Chiral structure) | B | C |

TABLE 1a-continued

| Structure | IC$_{50}$ | EC$_{50}$ |
|---|---|---|
| (Chiral) | B | C |
| | B | C |
| (Chiral) | B | C |
| (Chiral) | B | C |
| (Chiral) | C | C |
| (Chiral) | C | C |

TABLE 1a-continued

| Structure | IC$_{50}$ | EC$_{50}$ |
|---|---|---|
| 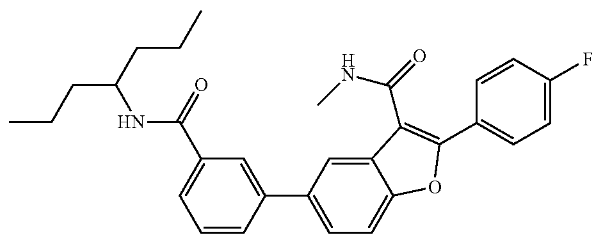 | F | C |
| | A | C |
| | A | C |
| 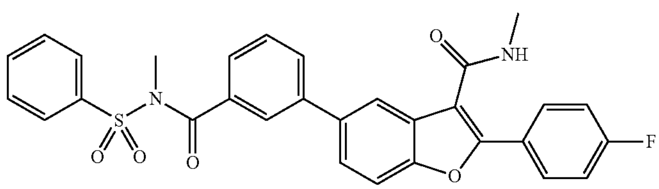 | G | C |
| 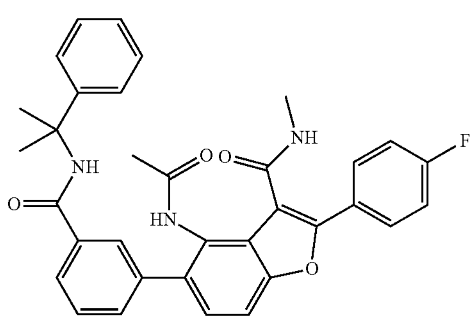 | C | C |
| 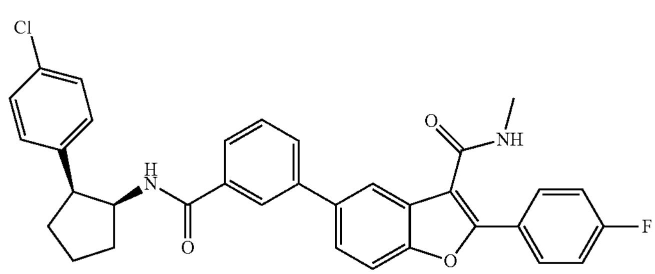 | E | C |

TABLE 1a-continued

| Structure | IC$_{50}$ | EC$_{50}$ |
|---|---|---|
| | E | C |
| | E | J |
| | E | K |
| | E | J |
| | E | K |
| | E | K |

TABLE 1a-continued

| Structure | IC$_{50}$ | EC$_{50}$ |
|---|---|---|
| | E | K |
| | E | K |
| | E | K |
| | E | H |
| 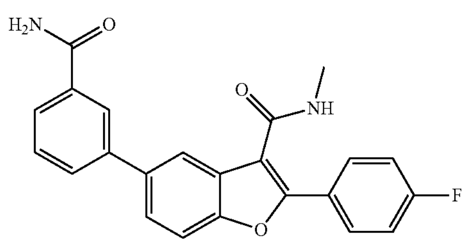 | C | J |
| | E | J |
| | E | J |

TABLE 1a-continued

| Structure | IC$_{50}$ | EC$_{50}$ |
|---|---|---|
| *(structure)* | E | J |
| *(structure)* | C | E |
| *(structure)* | C | E |
| *(structure)* | E | E |
| *(structure)* | C | E |
| *(structure)* | E | E |

TABLE 1a-continued

| Structure | IC$_{50}$ | EC$_{50}$ |
|---|---|---|
| | C | E |
| | C | E |
| | E | E |
| | E | E |
| | E | E |
| | C | E |

TABLE 1a-continued

| Structure | IC$_{50}$ | EC$_{50}$ |
|---|---|---|
| | E | E |
| | C | E |
| | C | E |
| | E | E |
| | E | E |
| | C | E |

TABLE 1a-continued

| Structure | IC$_{50}$ | EC$_{50}$ |
|---|---|---|
| 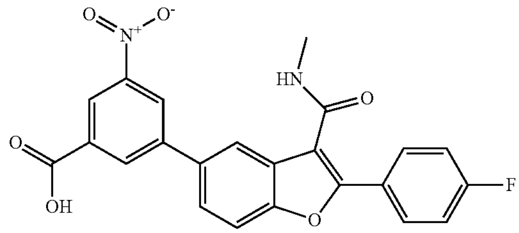 | B | E |
| | C | E |
| Chiral | C | E |
| | E | E |
| | E | E |
| | E | E |

TABLE 1a-continued
| Structure | IC$_{50}$ | EC$_{50}$ |
|---|---|---|
| 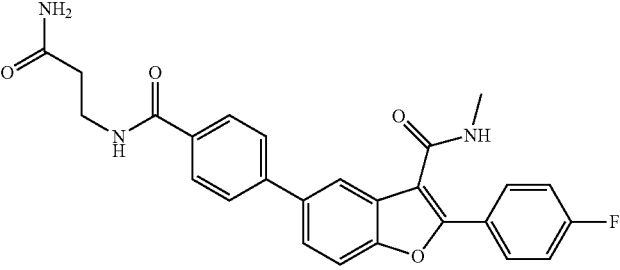 | E | E |
| 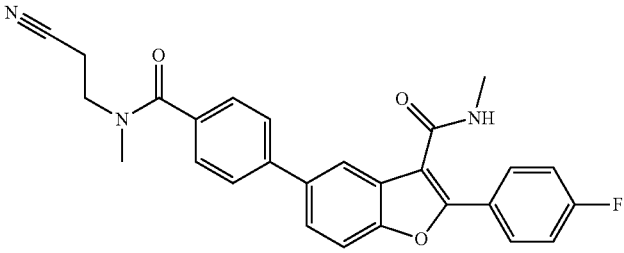 | C | E |
| 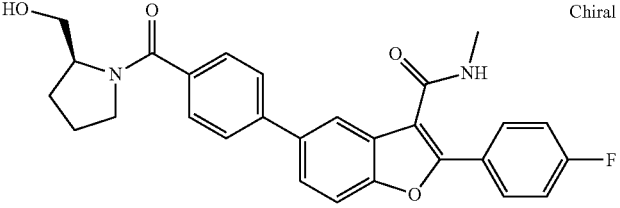 Chiral | E | E |
| 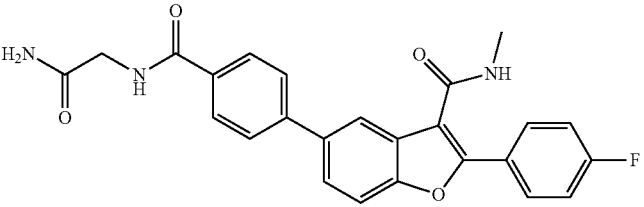 | E | E |
| 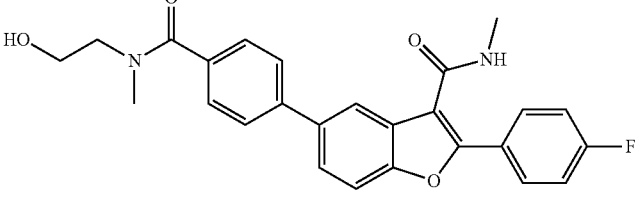 | C | E |
| 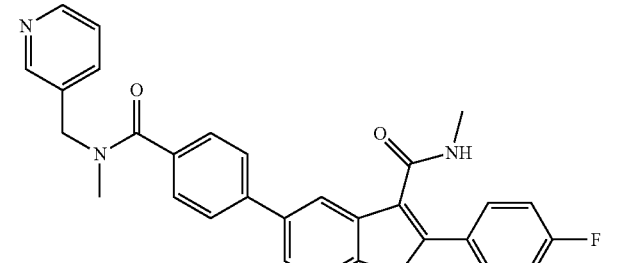 | C | E |

TABLE 1a-continued

| Structure | IC$_{50}$ | EC$_{50}$ |
|---|---|---|
| (structure) | E | E |
| (structure) Chiral | E | E |
| (structure) | E | E |
| (structure) | E | E |
| (structure) | E | E |
| (structure) | E | E |

TABLE 1a-continued
| Structure | IC$_{50}$ | EC$_{50}$ |
|---|---|---|
| 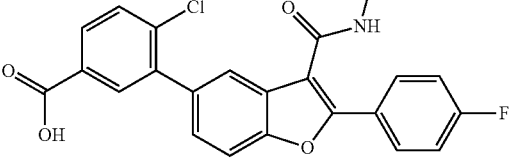 | C | E |
| 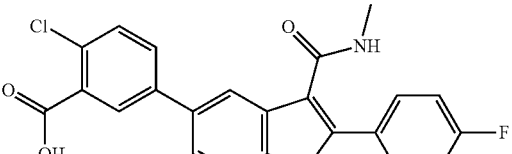 | C | E |
| 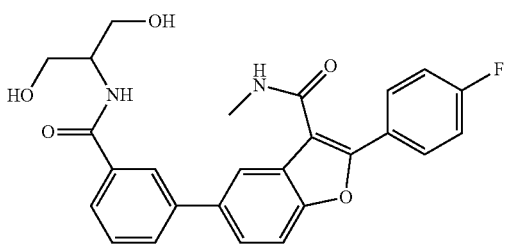 | C | E |
| 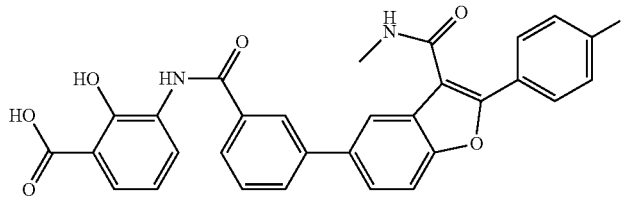 | B | E |
| 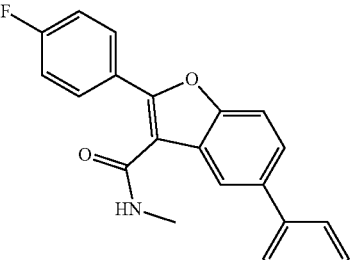 | B | E |
| 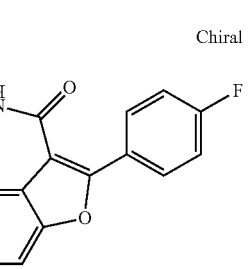 Chiral | C | E |

TABLE 1a-continued
| Structure | IC$_{50}$ | EC$_{50}$ |
|---|---|---|
| 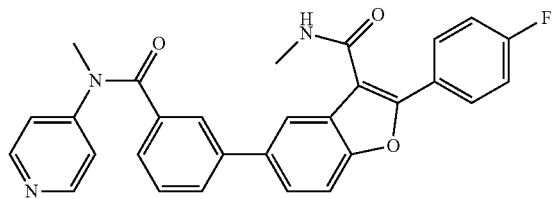 | C | E |
| 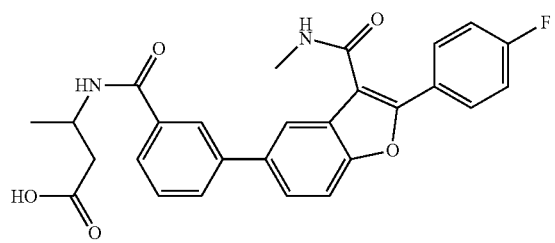 | B | E |
| 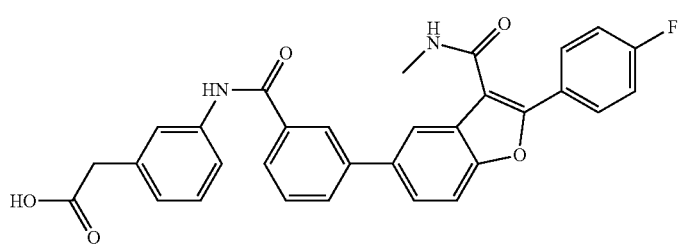 | A | E |
| 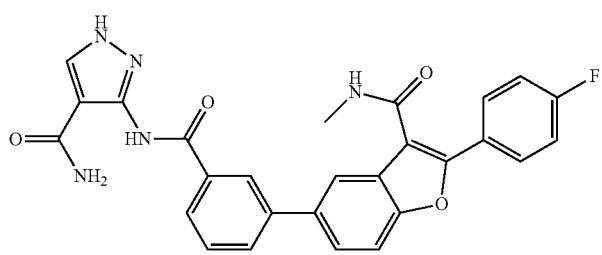 | C | E |
| Chiral 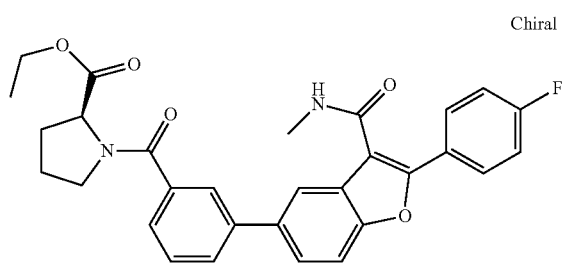 | C | E |

TABLE 1a-continued

| Structure | IC$_{50}$ | EC$_{50}$ |
|---|---|---|
| (structure) | B | E |
| (structure) | B | E |
| (structure, Chiral) | A | E |
| (structure) | C | E |
| (structure) | A | E |

TABLE 1a-continued

| Structure | IC$_{50}$ | EC$_{50}$ |
|---|---|---|
| (Chiral) | B | E |
| | B | E |
| | B | E |
| | E | E |
| | I | E |
| | E | E |

TABLE 1a-continued

| Structure | IC$_{50}$ | EC$_{50}$ |
|---|---|---|
| | E | E |
| | E | E |
| | E | E |
| 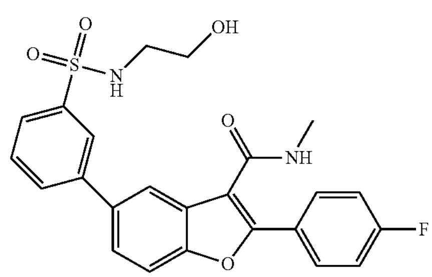 | C | E |
| | E | E |

TABLE 1a-continued
| Structure | IC$_{50}$ | EC$_{50}$ |
|---|---|---|
| 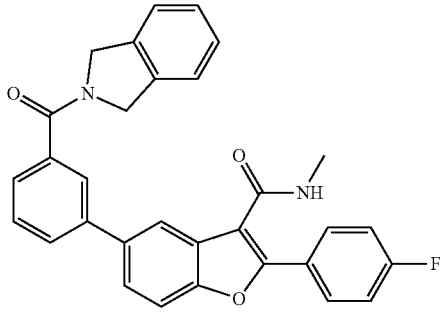 | F | E |
TABLE 1b
| Structure | IC$_{50}$ | EC$_{50}$ |
|---|---|---|
| 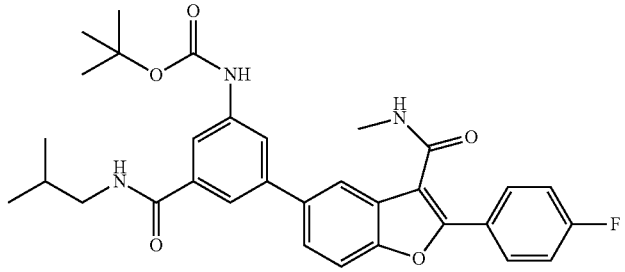 | B | A |
| 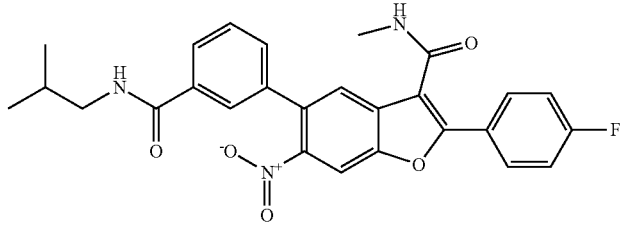 | A | A |
| 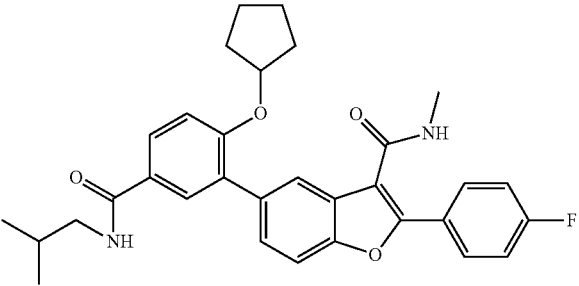 | E | C |
| 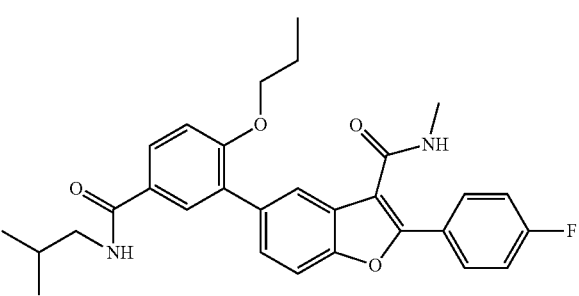 | C | B |

TABLE 1b-continued

| Structure | IC$_{50}$ | EC$_{50}$ |
|---|---|---|
| 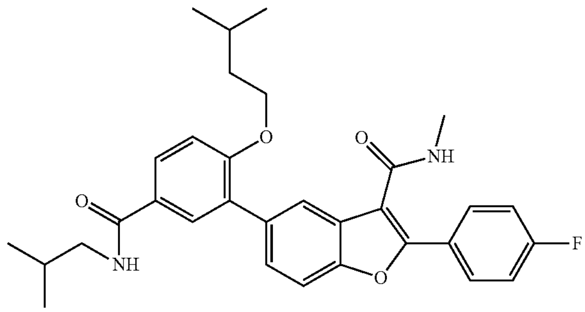 | E | C |
| | | A |
| | A | A |
| | A | A |
| | A | A |

TABLE 1b-continued
| Structure | IC$_{50}$ | EC$_{50}$ |
|---|---|---|
| 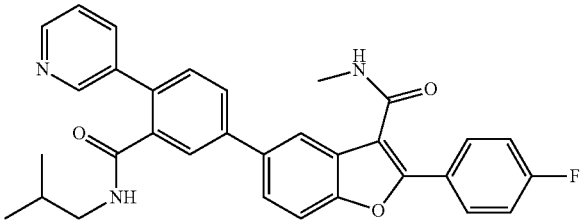 | A | |
| 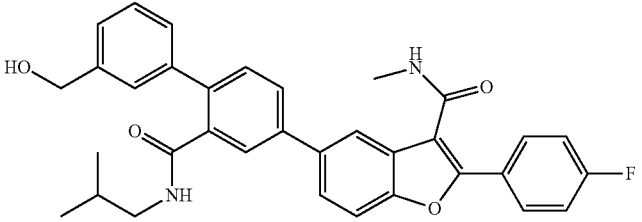 | A | A |
| 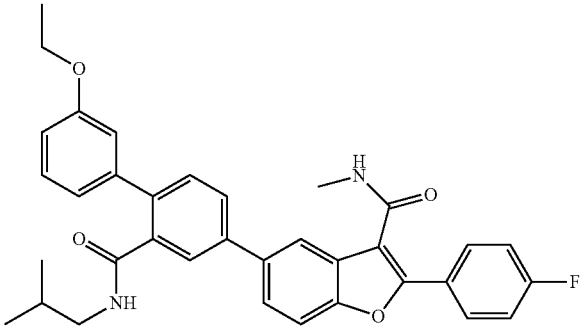 | A | |
| 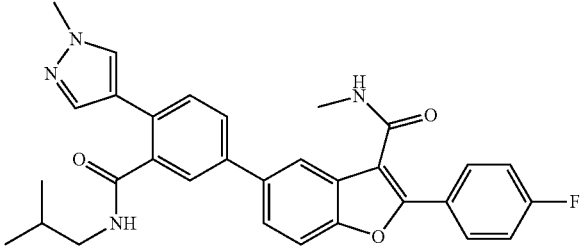 | A | A |
| 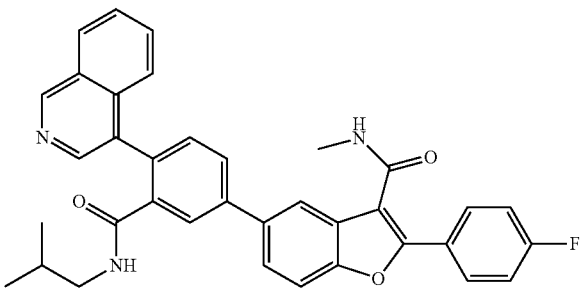 | B | A |
| 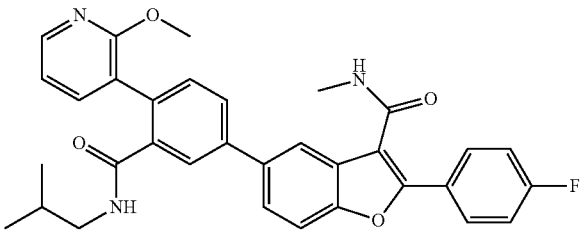 | A | A |

TABLE 1b-continued
| Structure | IC$_{50}$ | EC$_{50}$ |
|---|---|---|
| 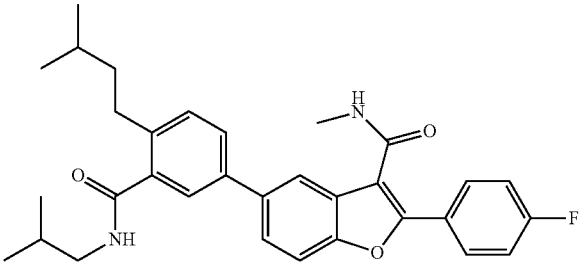 | E | |
| 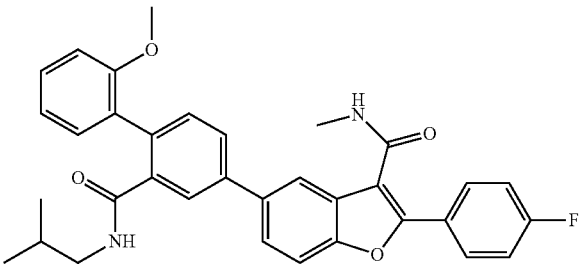 | A | A |
| 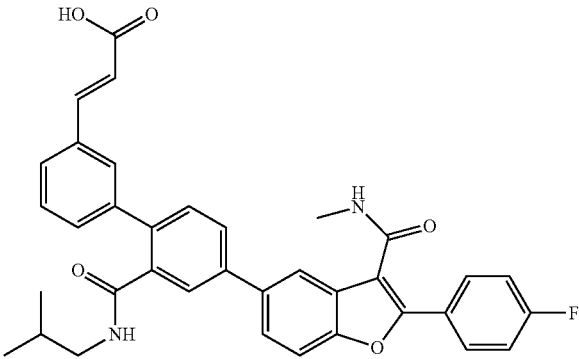 | A | B |
| 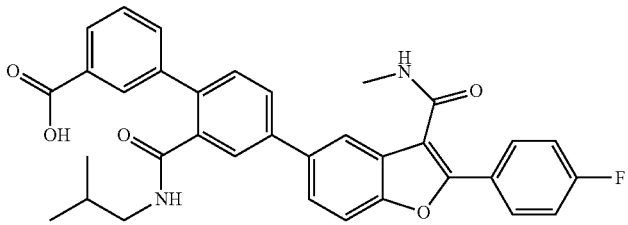 | C | |
| 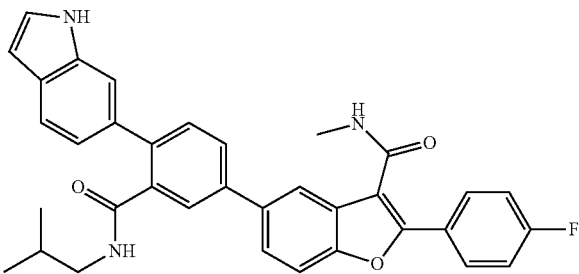 | B | A |

TABLE 1b-continued

| Structure | IC$_{50}$ | EC$_{50}$ |
|---|---|---|
| | A | |
| | A | A |
| | A | A |
| 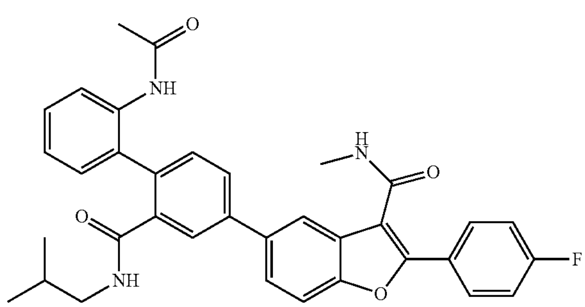 | B | C |
| | A | |

TABLE 1b-continued

| Structure | IC$_{50}$ | EC$_{50}$ |
|---|---|---|
| 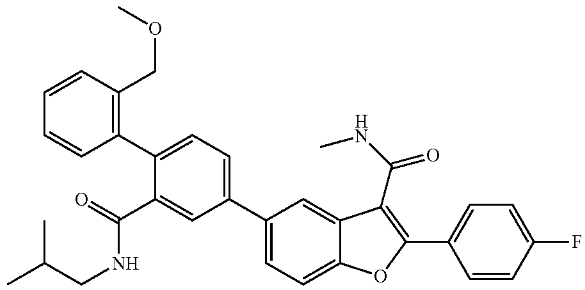 | B | A |
| | A | A |
| | A | A |
| | | A |
| 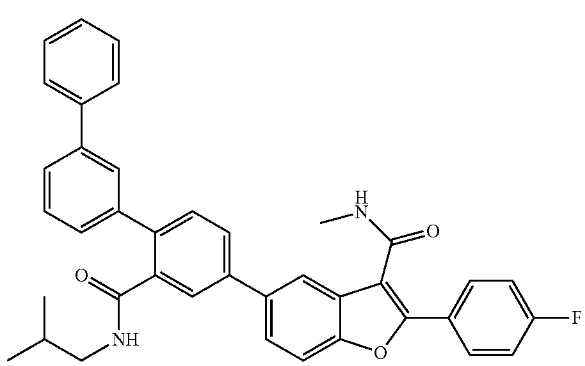 | E | B |

TABLE 1b-continued

| Structure | IC$_{50}$ | EC$_{50}$ |
|---|---|---|
| 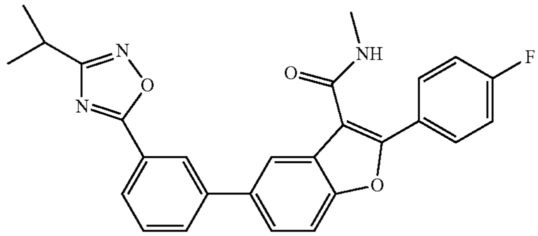 | G | B |
| 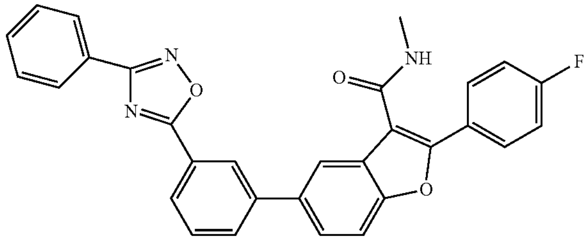 | E | A |
| | A | A |
| | A | A |
| | A | A |

TABLE 1b-continued
| Structure | IC$_{50}$ | EC$_{50}$ |
|---|---|---|
| 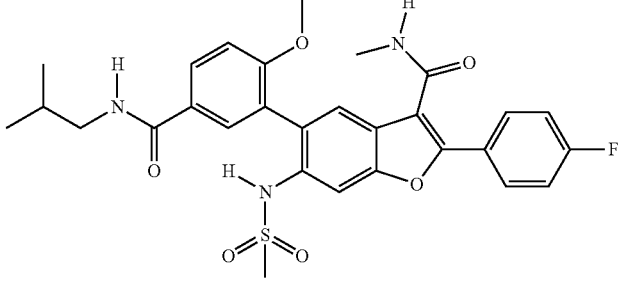 | A | A |
| 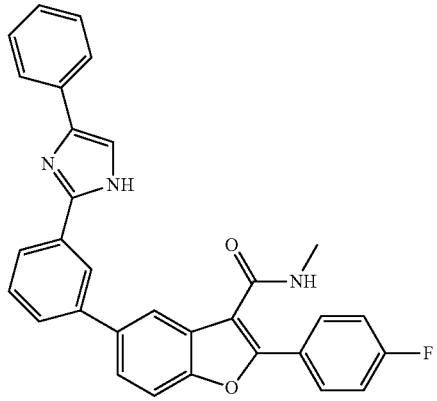 | B | A |
| 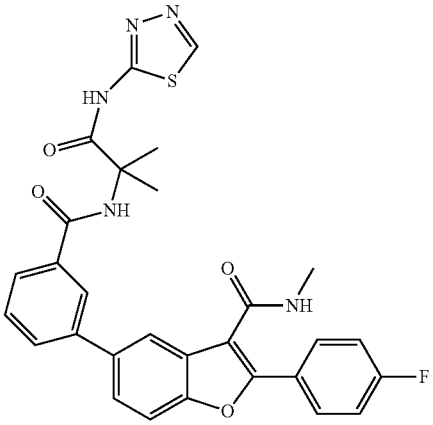 | A | A |
| 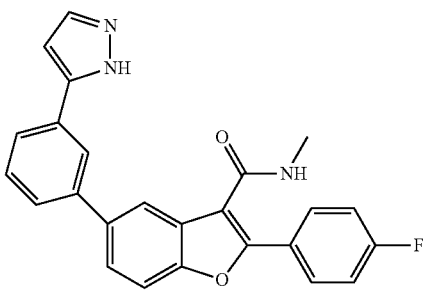 | C | C |

TABLE 1b-continued
| Structure | IC$_{50}$ | EC$_{50}$ |
|---|---|---|
| 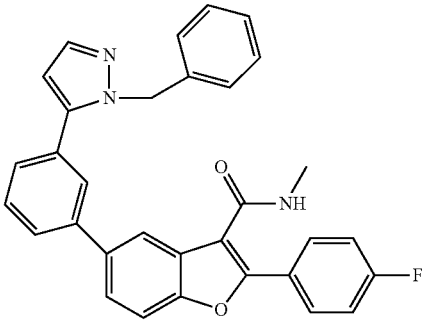 | A | A |
| 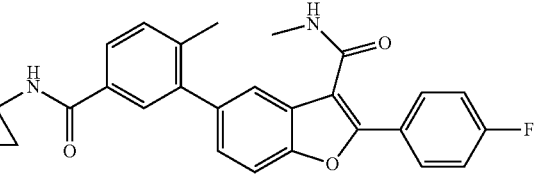 | A | A |
| 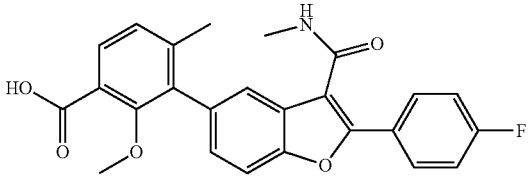 | C | E |
| 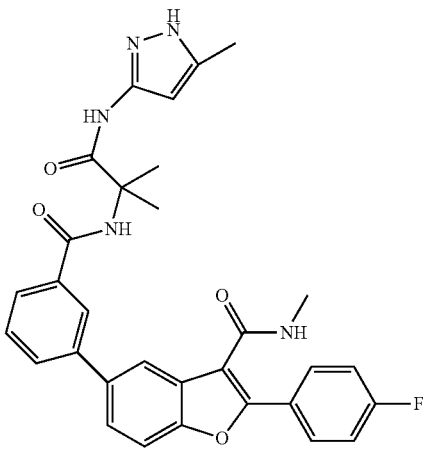 | A | A |
| 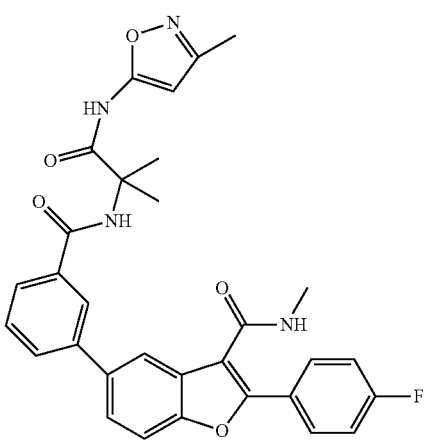 | A | A |

TABLE 1b-continued

| Structure | IC$_{50}$ | EC$_{50}$ |
|---|---|---|
| | A | A |
| | A | A |
| | A | A |
| | A | A |

TABLE 1b-continued

| Structure | IC$_{50}$ | EC$_{50}$ |
|---|---|---|
| (structure) | A | A |
| (structure) | E | E |
| (structure) | B | A |
| (structure) | A | A |
| (structure) | A | A |
| (structure) | A | A |

TABLE 1b-continued

| Structure | IC$_{50}$ | EC$_{50}$ |
|---|---|---|
| 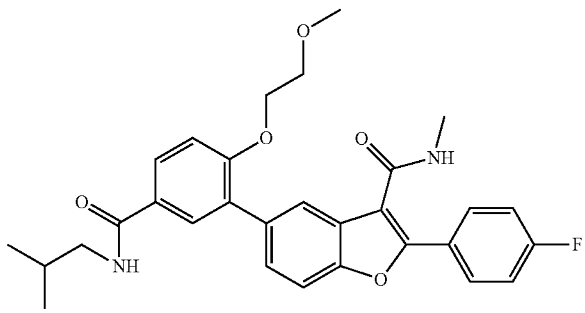 | B | A |
| | A | A |
| | A | |
| | A | A |

TABLE 1b-continued
| Structure | IC50 | EC50 |
|---|---|---|
| 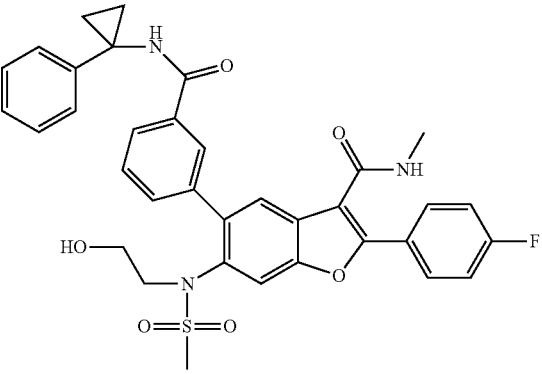 | A | A |
| 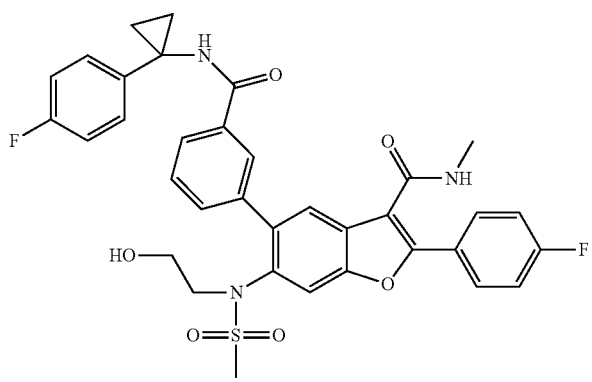 | A | A |
| 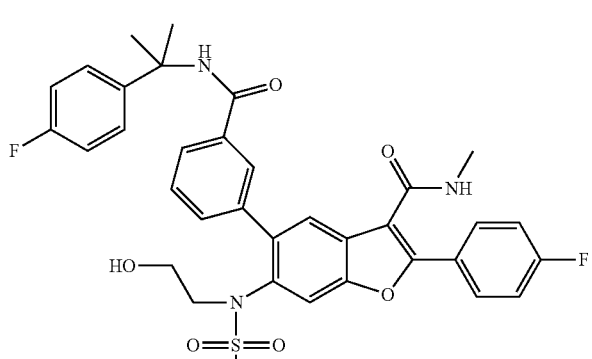 | A | A |
| 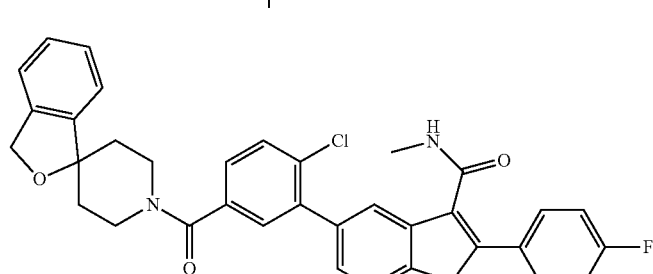 | C | C |
| 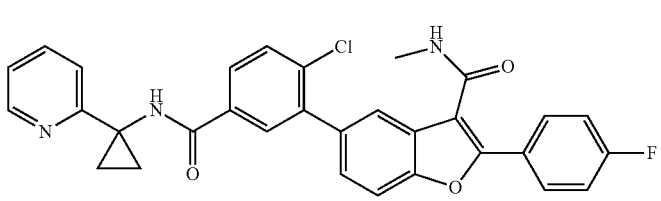 | A | A |

TABLE 1b-continued

| Structure | IC$_{50}$ | EC$_{50}$ |
|---|---|---|
| | A | A |
| | A | A |
| | A | A |
| 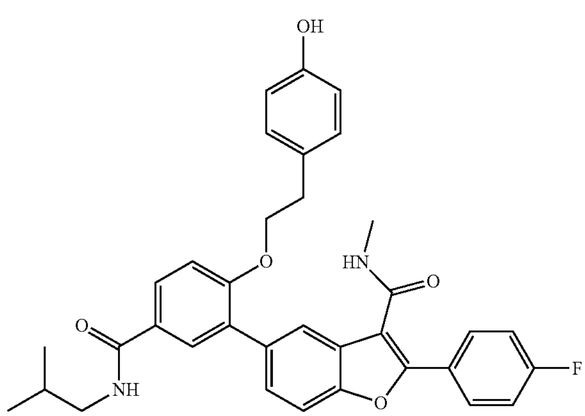 | B | B |

TABLE 1b-continued
| Structure | IC$_{50}$ | EC$_{50}$ |
|---|---|---|
| 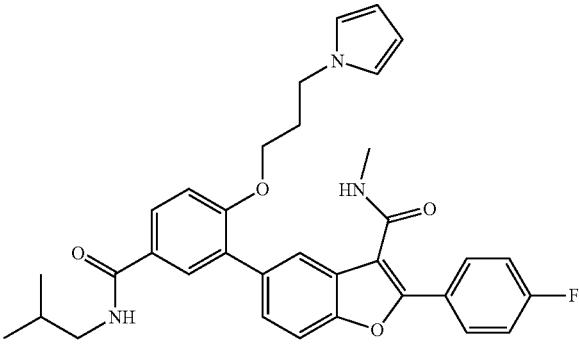 | C | B |
| 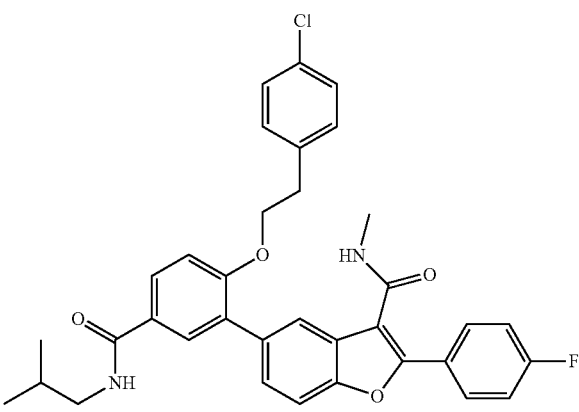 | E | E |
| 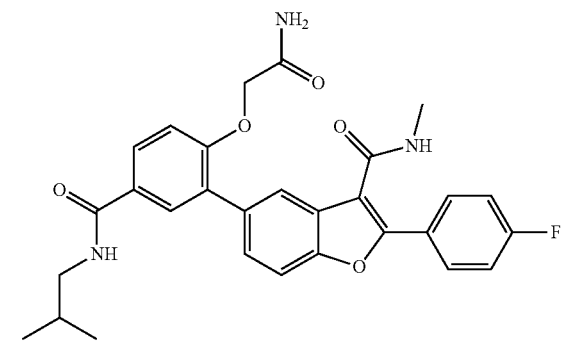 | A | A |
| 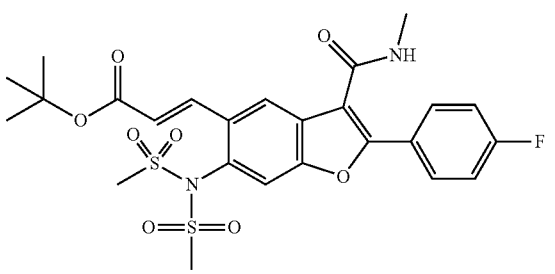 | | |

TABLE 1b-continued

| Structure | IC$_{50}$ | EC$_{50}$ |
|---|---|---|
| | A | A |
| | A | A |
| | A | A |
| | A | A |

TABLE 1b-continued
| Structure | IC$_{50}$ | EC$_{50}$ |
|---|---|---|
| 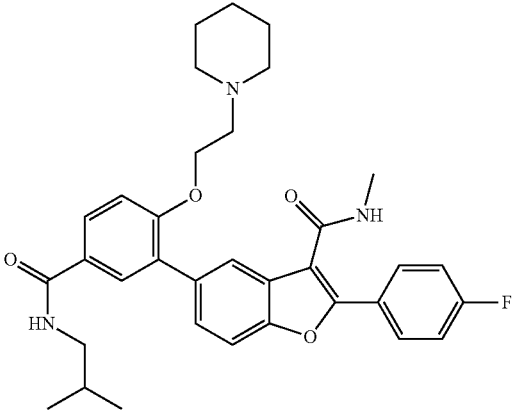 | B | A |
| 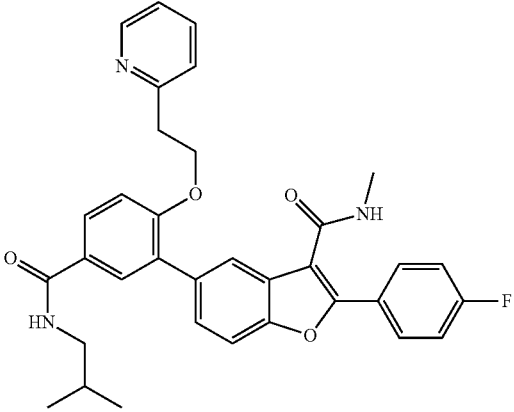 | B | A |
| 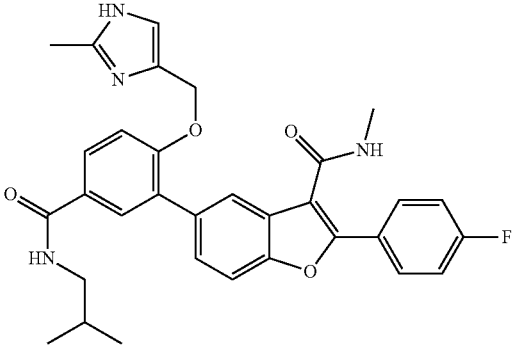 | A | A |
| 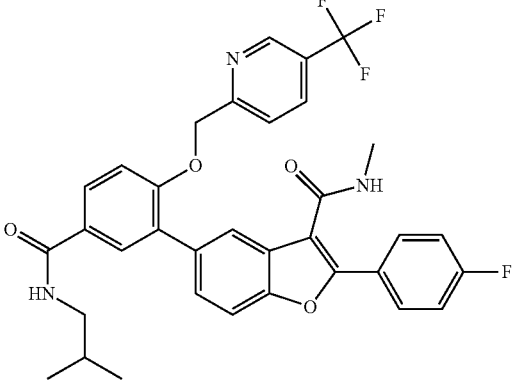 | E | E |

TABLE 1b-continued

| Structure | IC$_{50}$ | EC$_{50}$ |
|---|---|---|
| (structure) | A | A |
| (structure) | C | B |
| (structure) | C | C |
| (structure) | B | A |

TABLE 1b-continued

| Structure | IC$_{50}$ | EC$_{50}$ |
|---|---|---|
| (structure) | B | B |
| (structure) | A | A |
| (structure) | C | |
| (structure) | A | |

TABLE 1b-continued
| Structure | IC$_{50}$ | EC$_{50}$ |
|---|---|---|
| 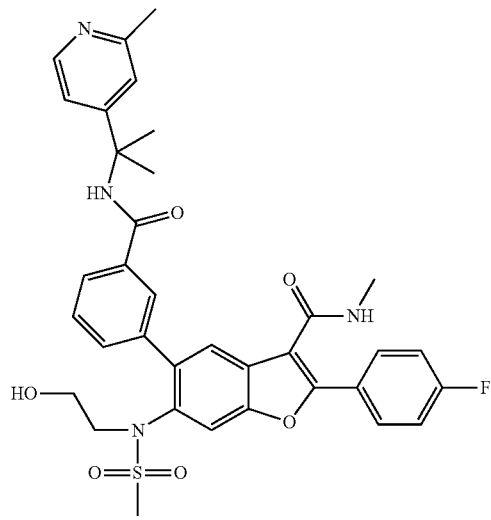 | A | |
| 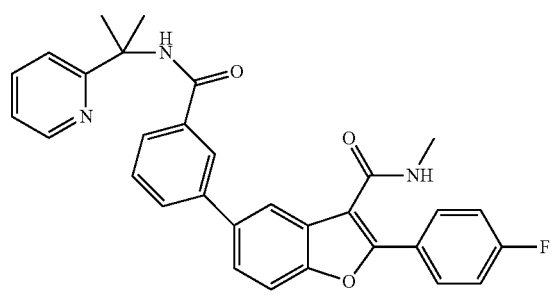 | A | |
| 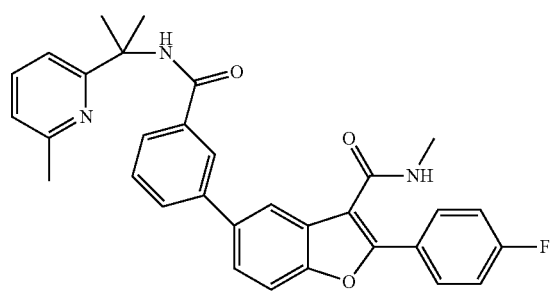 | B | |
| 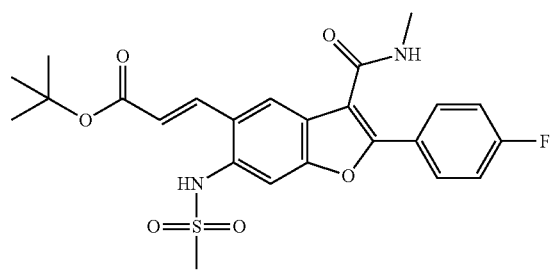 | C | |

TABLE 1b-continued

| Structure | IC$_{50}$ | EC$_{50}$ |
|---|---|---|
| *(structure)* | | |
| *(structure)* | A | A |
| *(structure)* | A | A |
| *(structure)* | A | A |

TABLE 1b-continued
| Structure | IC$_{50}$ | EC$_{50}$ |
|---|---|---|
| 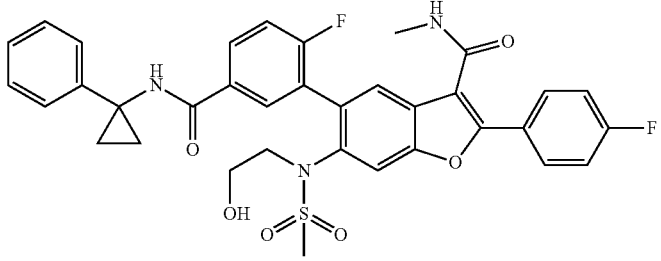 | A | A |
| 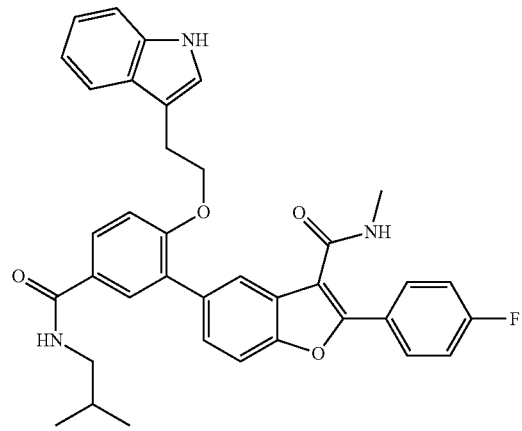 | C | C |
| 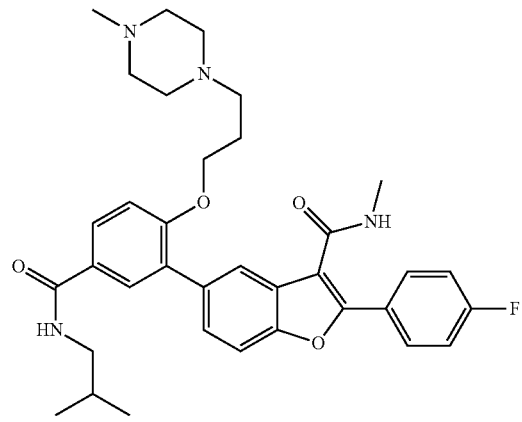 | A | A |
| 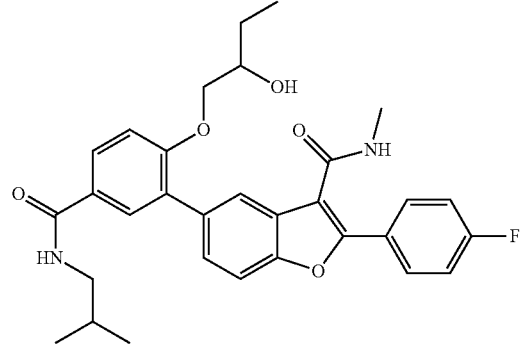 | B | B |

TABLE 1b-continued
| Structure | IC$_{50}$ | EC$_{50}$ |
|---|---|---|
| 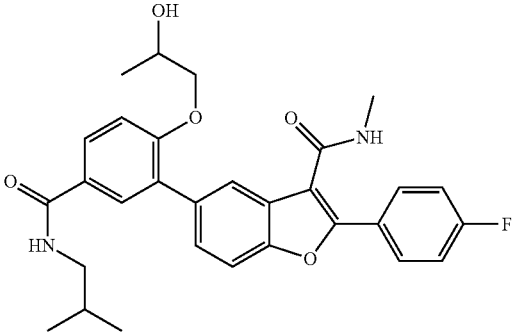 | A | A |
| 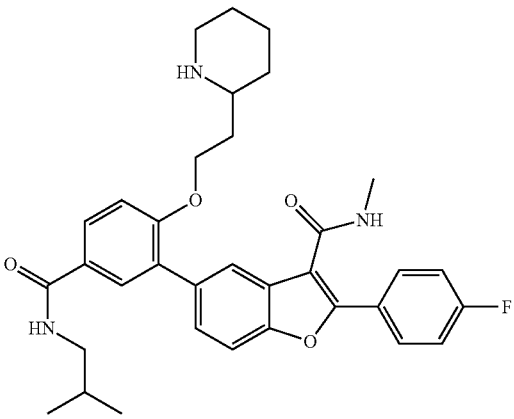 | A | A |
| 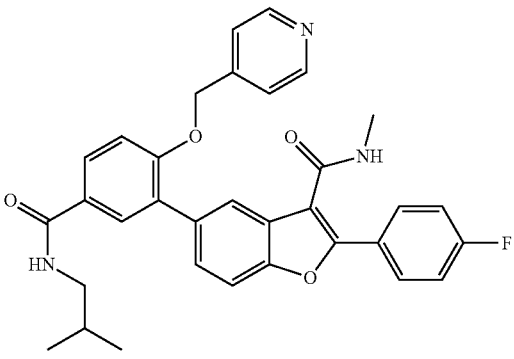 | A | A |
| 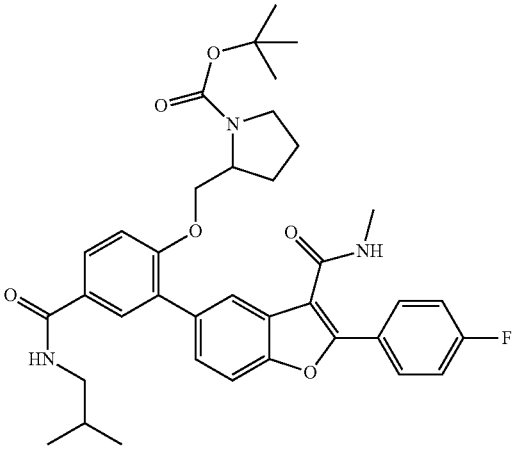 | E | C |

TABLE 1b-continued
| Structure | IC$_{50}$ | EC$_{50}$ |
|---|---|---|
| 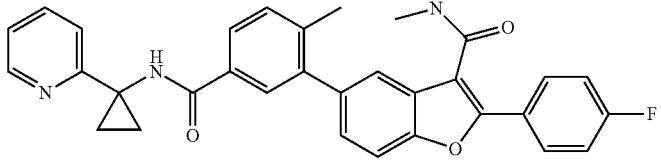 | A | A |
| 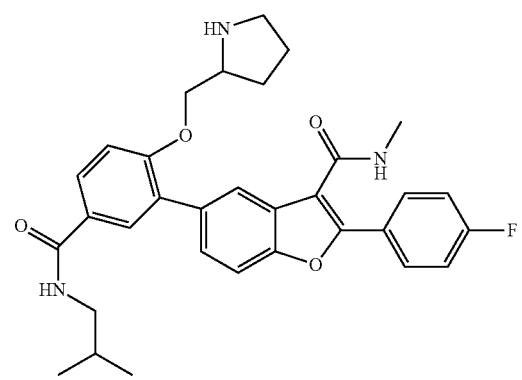 | A | B |
| 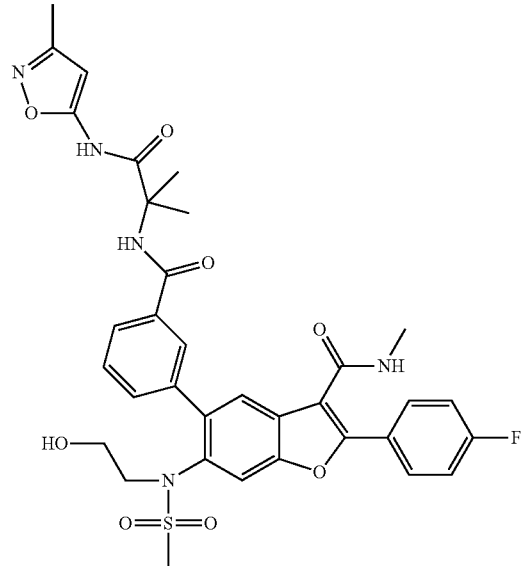 | A | A |
| 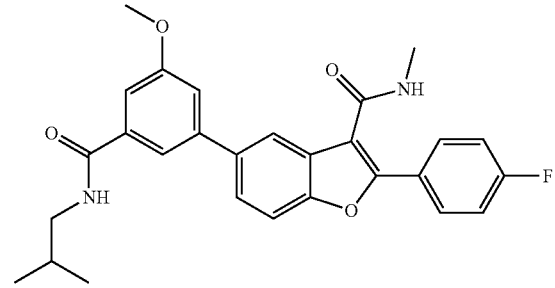 | B | B |

TABLE 1b-continued
| Structure | IC$_{50}$ | EC$_{50}$ |
|---|---|---|
| 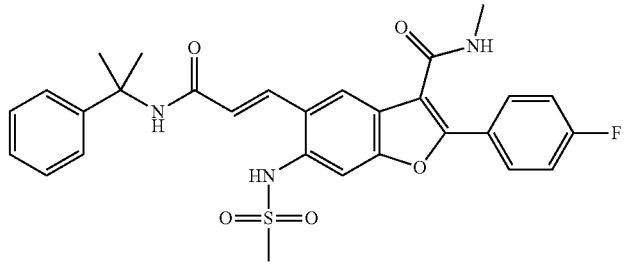 | C | |
| 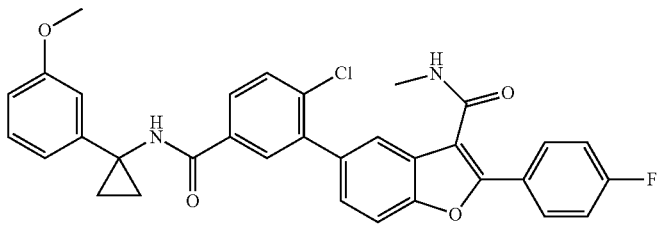 | | |
| 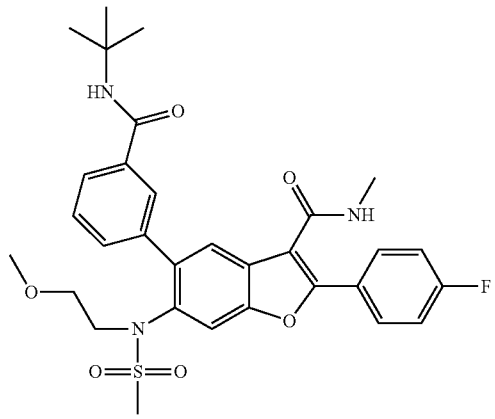 | | |
| 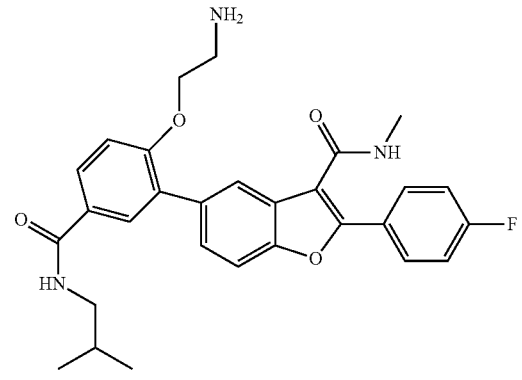 | A | A |
| 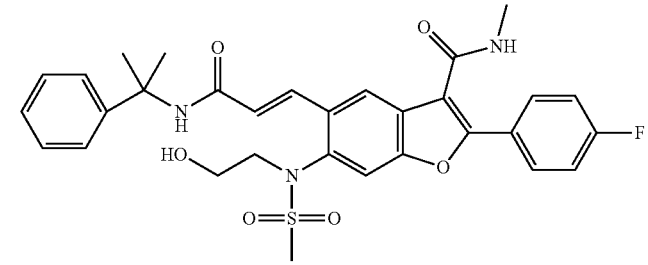 | A | |

TABLE 1b-continued
| Structure | IC$_{50}$ | EC$_{50}$ |
|---|---|---|
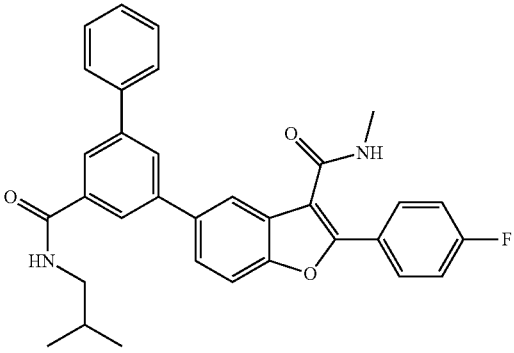
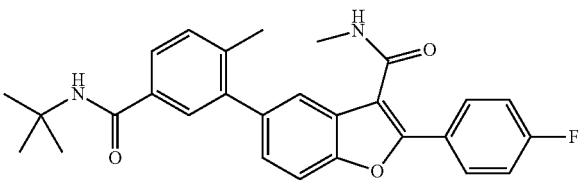
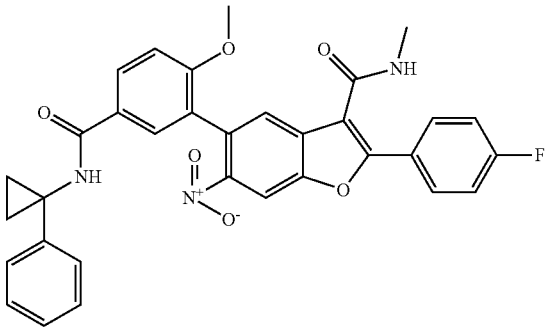
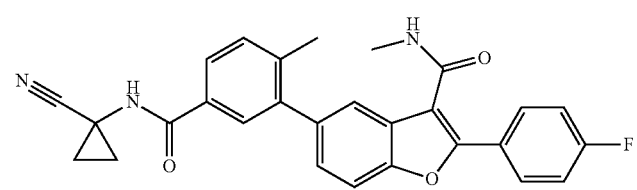
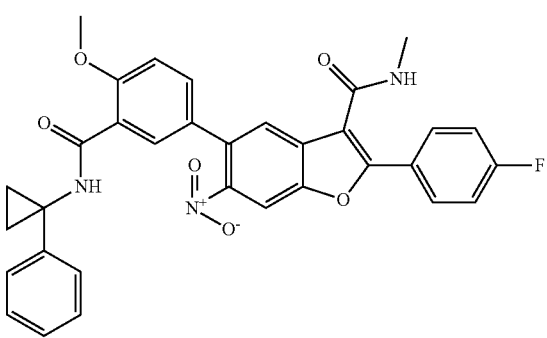

TABLE 1b-continued

| Structure | IC$_{50}$ | EC$_{50}$ |
|---|---|---|
| 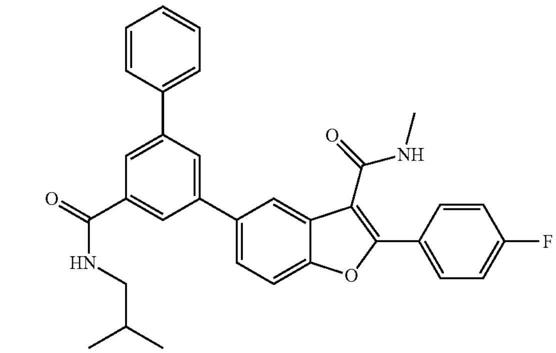 | E | E |
| | A | A |
| | A | B |
| | A | A |
| | A | A |
| 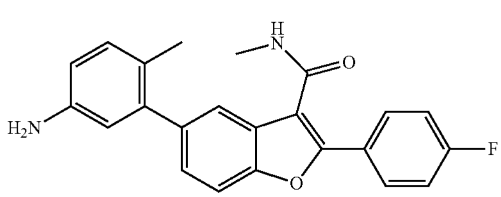 | C | C |

TABLE 1b-continued

| Structure | IC$_{50}$ | EC$_{50}$ |
|---|---|---|
| | A | A |
| 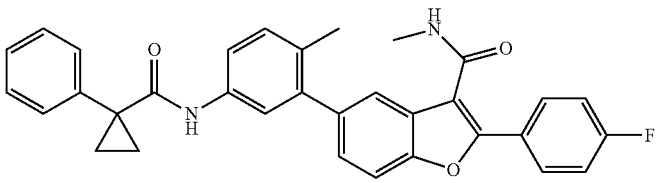 | C | B |
| | A | A |
| | A | A |
| | A | A |
| | A | A |
| | A | C |

| Structure | IC$_{50}$ | EC$_{50}$ |
|---|---|---|
| 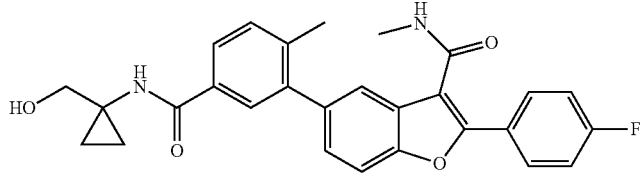 | C | C |
| 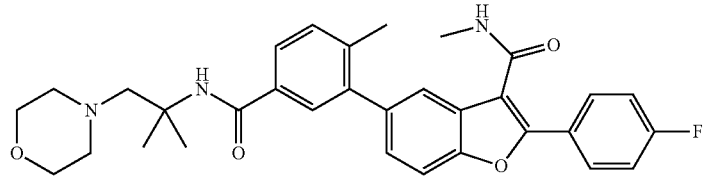 | A | A |
| 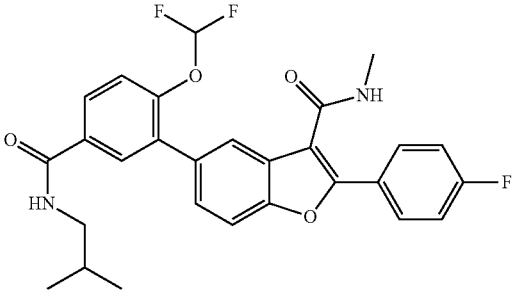 | A | A |
| 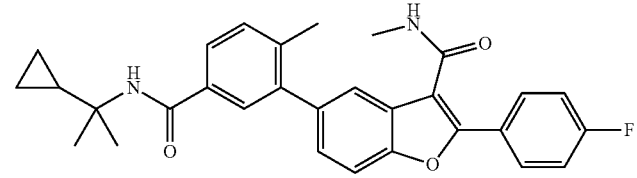 | A | A |
| 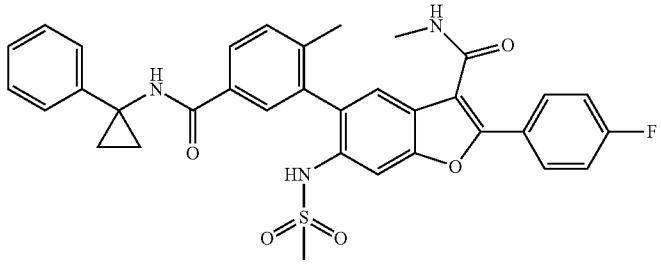 | A | A |
| 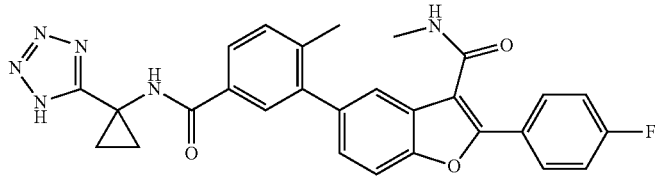 | A | C |
| 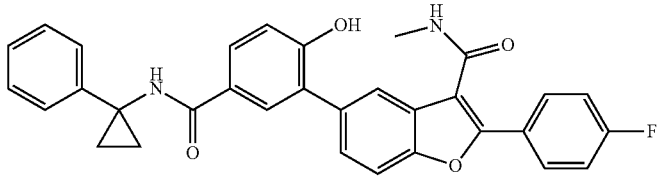 | A | A |

TABLE 1b-continued
| Structure | IC$_{50}$ | EC$_{50}$ |
|---|---|---|
| 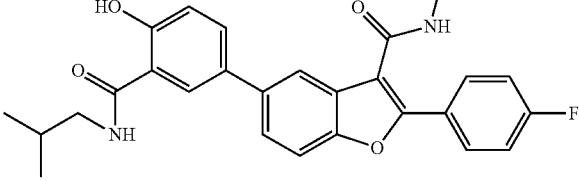 | C | E |
| 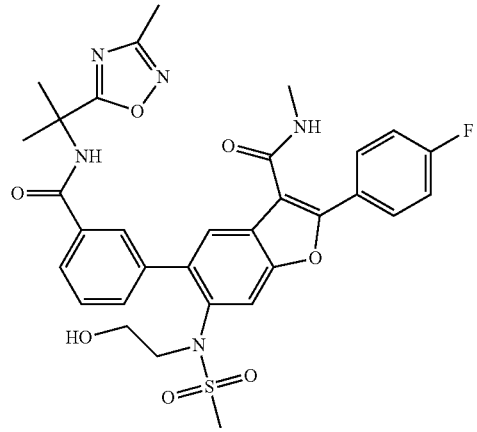 | A | A |
| 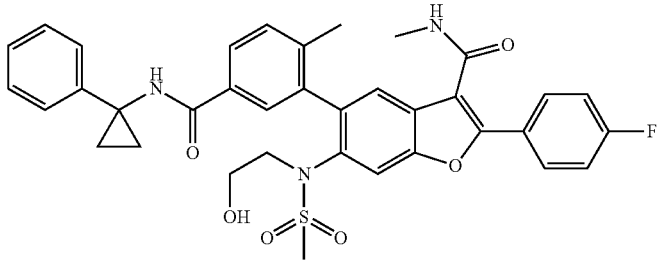 | A | A |
| 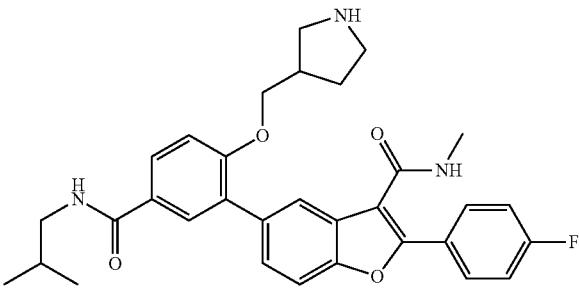 | A | A |
| 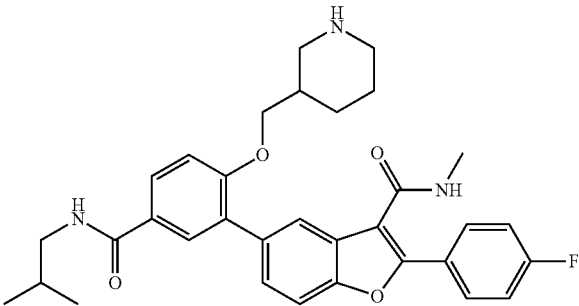 | A | A |

TABLE 1b-continued
| Structure | IC$_{50}$ | EC$_{50}$ |
|---|---|---|
| 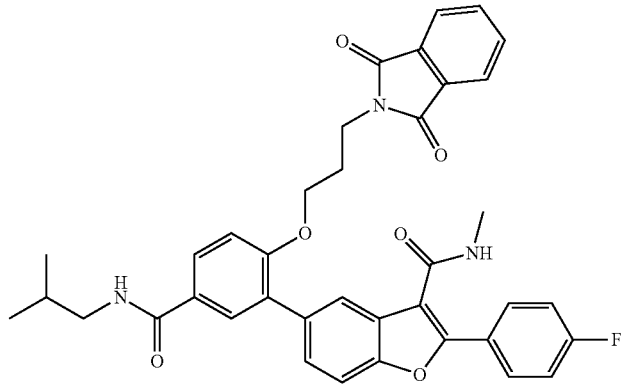 | E | |
| 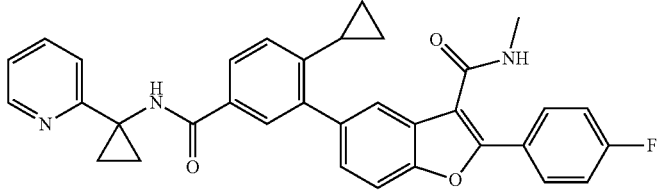 | E | |
| 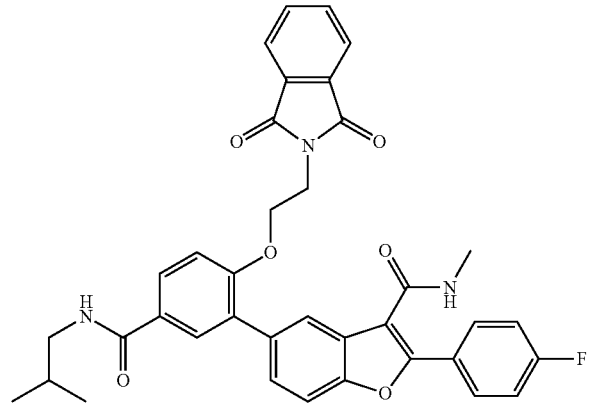 | | |
| 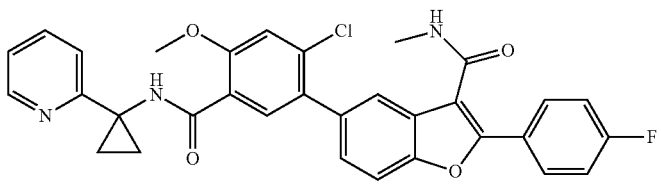 | A | A |
| 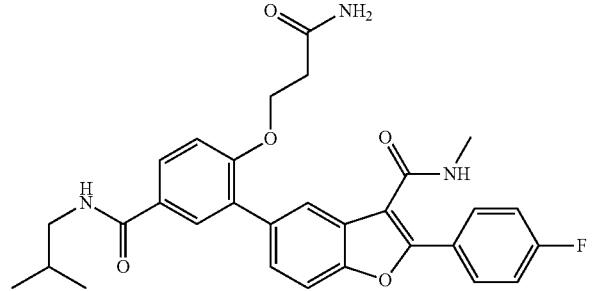 | E | E |

TABLE 1b-continued
| Structure | IC$_{50}$ | EC$_{50}$ |
|---|---|---|
| 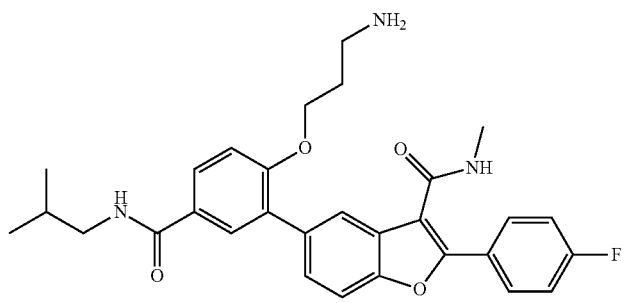 | A | A |
| 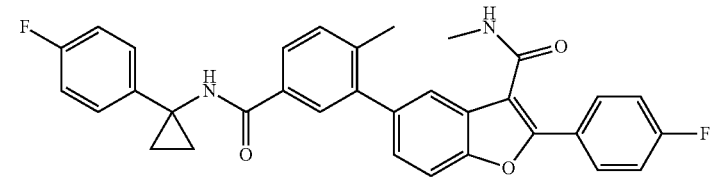 | A | A |
| 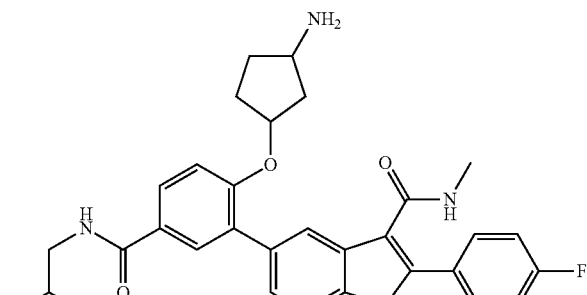 | A | A |
| 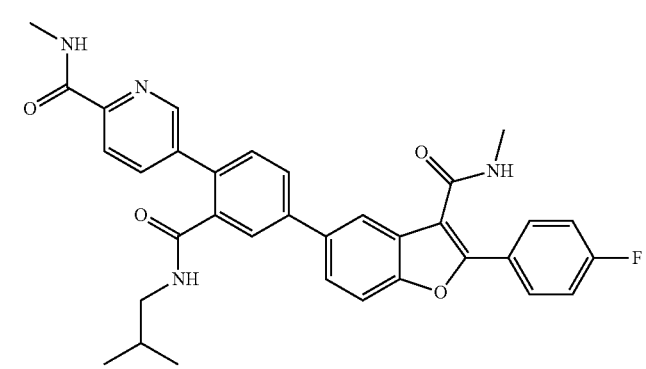 | E | E |
| 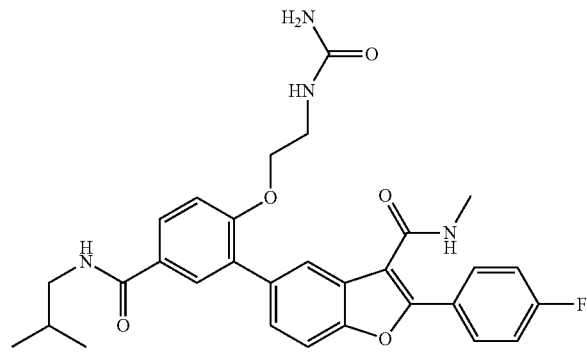 | A | A |

TABLE 1b-continued

| Structure | IC$_{50}$ | EC$_{50}$ |
|---|---|---|
| | A | E |
| | A | B |
| | A | A |
| | A | A |
| | | A |
| | A | A |
| | A | A |

TABLE 1b-continued

| Structure | IC$_{50}$ | EC$_{50}$ |
|---|---|---|
| | A | A |
| 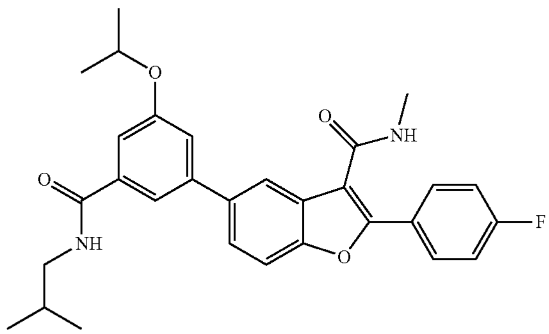 | C | E |
| 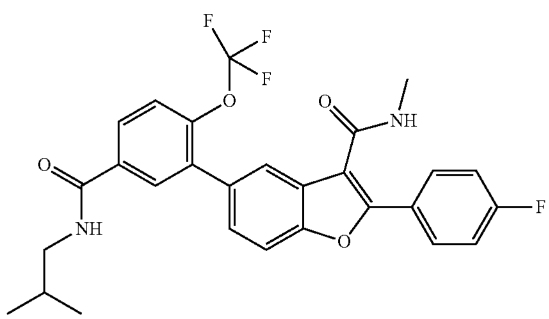 | B | E |
| | A | B |
| | A | A |
| | | E |

TABLE 1b-continued

| Structure | IC$_{50}$ | EC$_{50}$ |
|---|---|---|
| | B | A |
| | B | A |
| | A | A |
| | A | A |
| | A | A |

TABLE 1b-continued

| Structure | IC$_{50}$ | EC$_{50}$ |
|---|---|---|
| 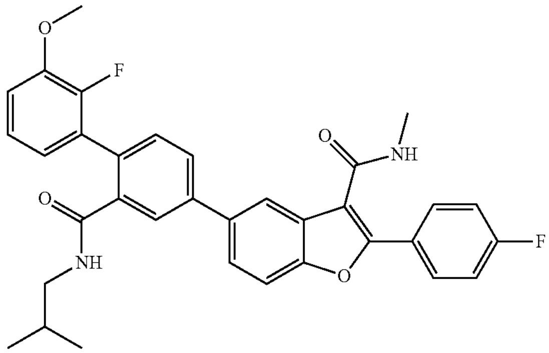 | E | B |
| | A | |
| | A | |
| 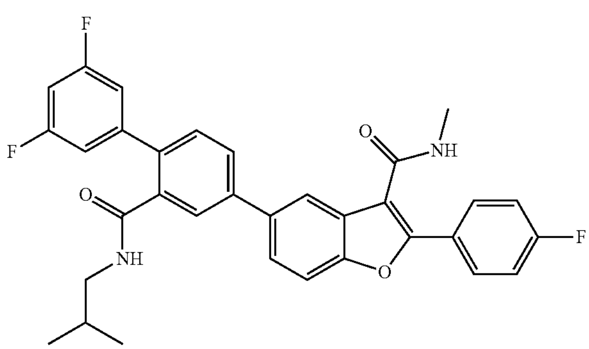 | B | A |
| | A | A |

TABLE 1b-continued

| Structure | IC$_{50}$ | EC$_{50}$ |
|---|---|---|
| | A | A |
| 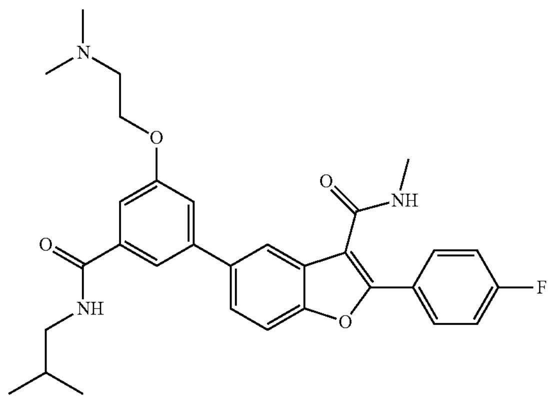 | B | B |
| 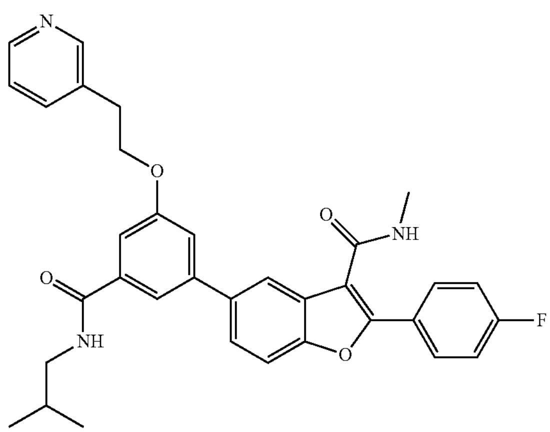 | E | C |
| | A | A |
| | A | A |
| | A | A |

TABLE 1b-continued

| Structure | IC₅₀ | EC₅₀ |
|---|---|---|
| (structure) | L | A |
| (structure) |  | A |
| (structure) | A | A |
| (structure) | A | B |
| (structure) |  | A |

TABLE 1b-continued
| Structure | IC$_{50}$ | EC$_{50}$ |
|---|---|---|
| 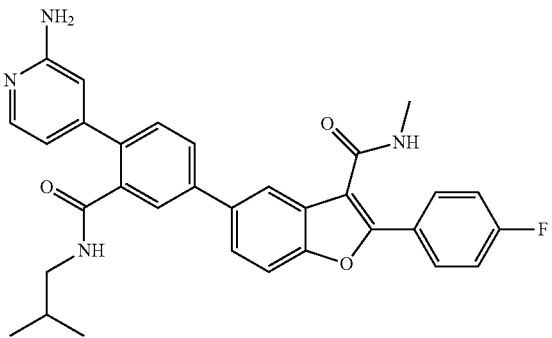 | L | A |
| 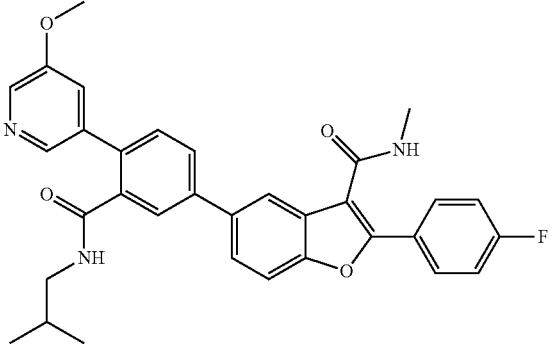 | B | |
| 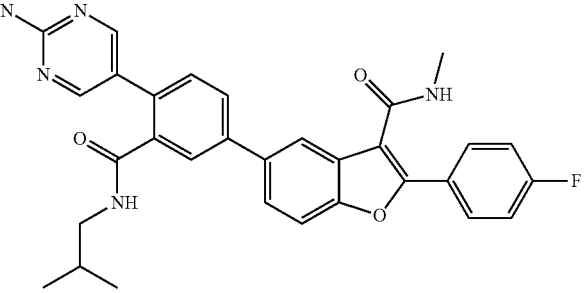 | A | |
| 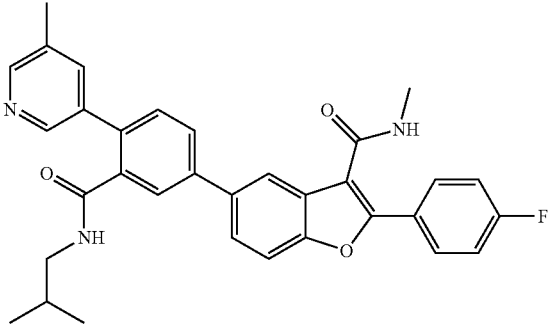 | B | |
| 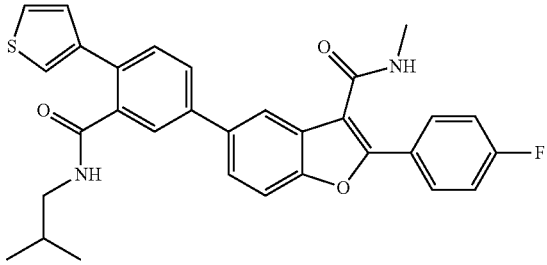 | A | |

TABLE 1b-continued

| Structure | IC$_{50}$ | EC$_{50}$ |
|---|---|---|
| | A | B |
| 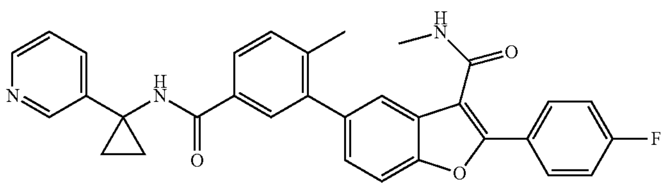 | L | A |
| | B | |
| | B | |
| | A | B |
| | A | C |

TABLE 1b-continued
| Structure | IC$_{50}$ | EC$_{50}$ |
|---|---|---|
| 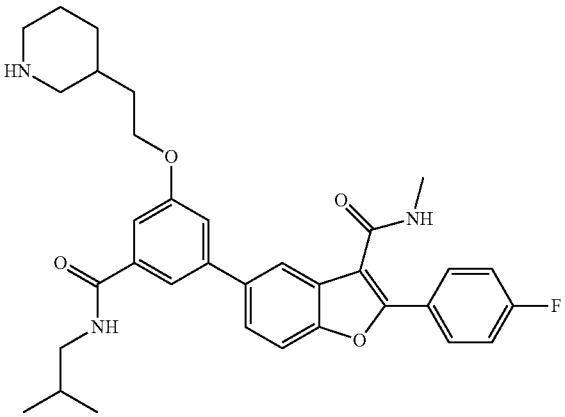 | A | A |
| 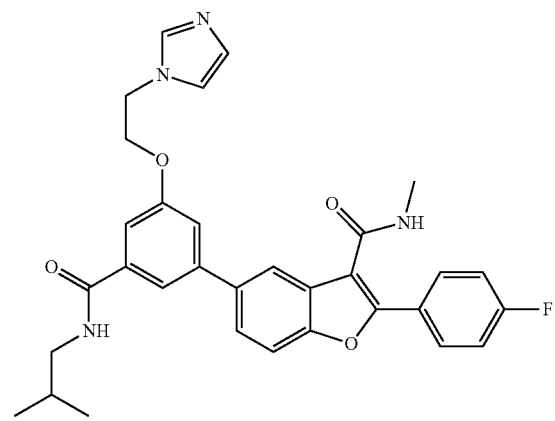 | C | C |
| 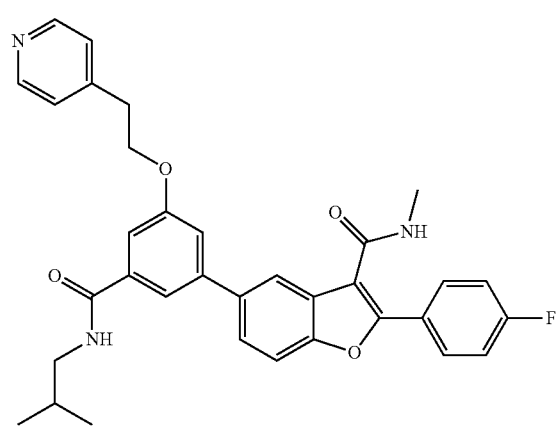 | A | M |
| 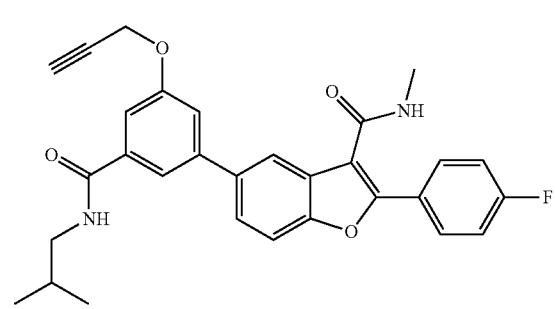 | C | C |

TABLE 1b-continued
| Structure | IC$_{50}$ | EC$_{50}$ |
|---|---|---|
| 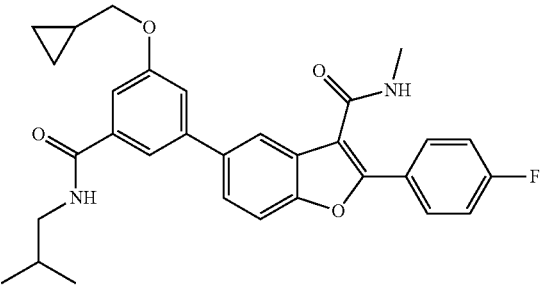 | E | B |
| 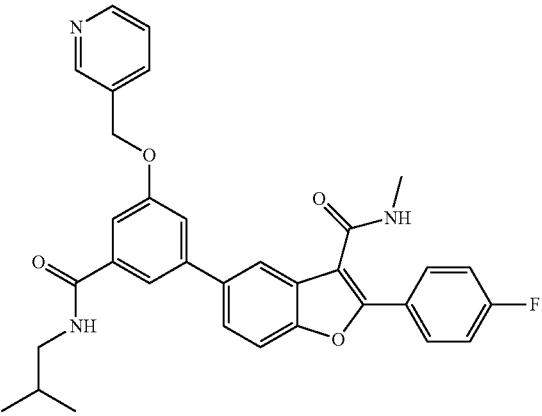 | C | C |
| 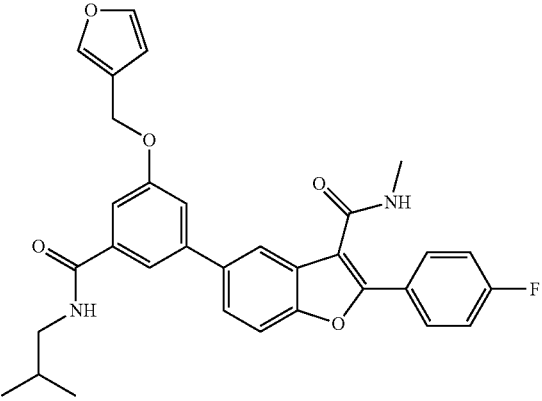 | C | C |
| 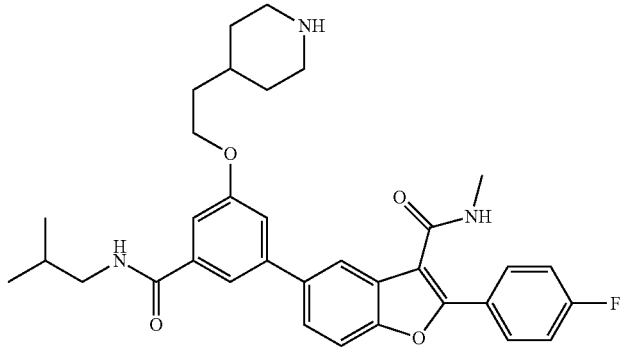 | A | C |

TABLE 1b-continued

| Structure | IC$_{50}$ | EC$_{50}$ |
|---|---|---|
| (structure) | E | C |
| (structure) | M | C |
| (structure) | M | C |
| (structure) | C | C |

TABLE 1b-continued

| Structure | | IC$_{50}$ | EC$_{50}$ |
|---|---|---|---|
| (structure) | Chiral | C | C |
| (structure) | | G | C |
| (structure) | | C | C |
| (structure) | | E | C |

TABLE 1b-continued

| Structure | IC$_{50}$ | EC$_{50}$ |
|---|---|---|
| | A | C |
| 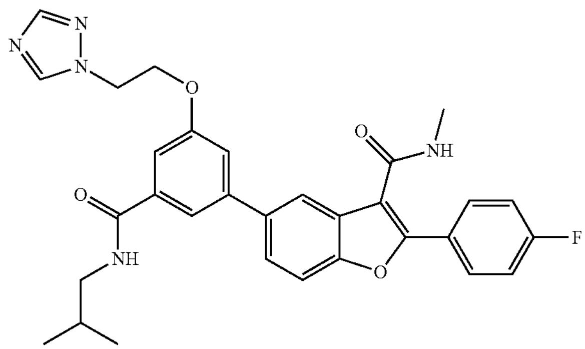 | B | C |
| | A | A |
| | A | A |
| | A | A |

TABLE 1b-continued
| Structure | IC$_{50}$ | EC$_{50}$ |
| --- | --- | --- |
| 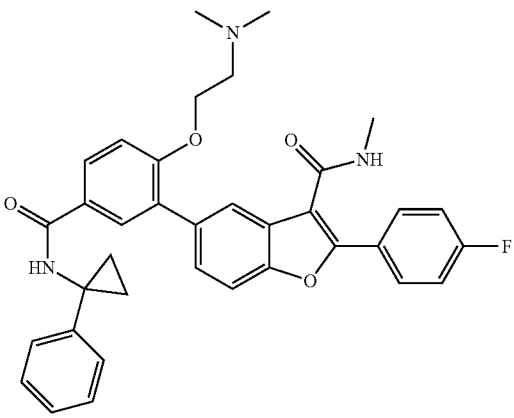 | A | A |
| 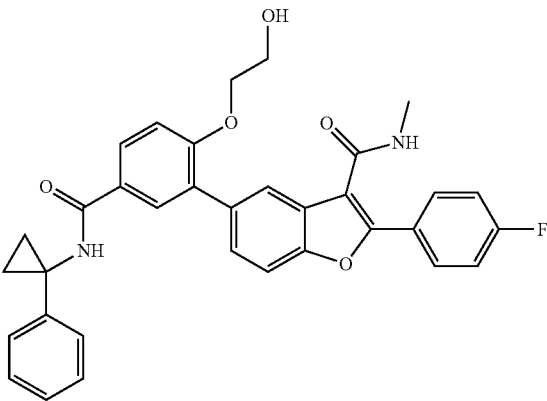 | A | A |
| 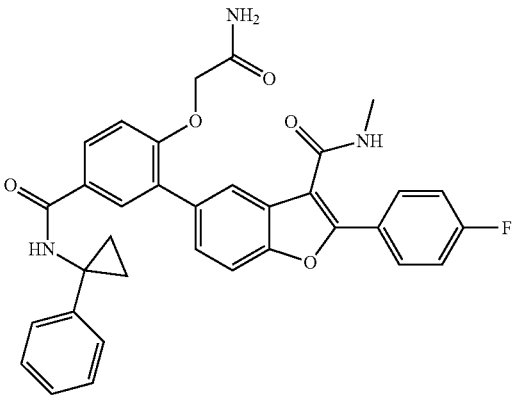 | A | A |
| 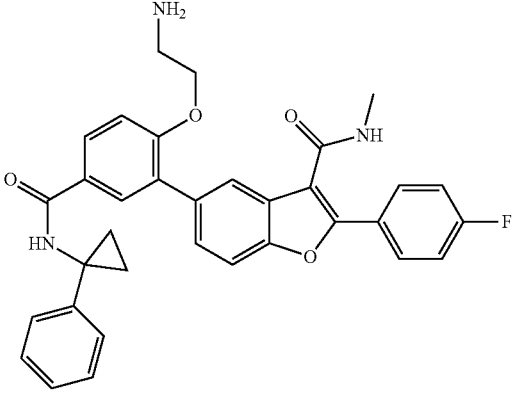 | A | A |

TABLE 1b-continued

| Structure | IC$_{50}$ | EC$_{50}$ |
|---|---|---|
| | A | A |
| | A | A |
| | A | A |
| 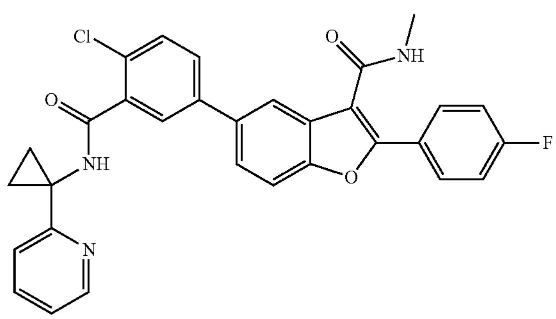 | B | E |
| | | A |
| | | A |

TABLE 1b-continued

| Structure | IC$_{50}$ | EC$_{50}$ |
|---|---|---|
| | A | A |
| | A | A |
| | | A |
| | A | A |
| | A | A |
| | A | A |

TABLE 1b-continued

| Structure | IC$_{50}$ | EC$_{50}$ |
|---|---|---|
| | A | A |
| | A | A |
| | A | A |
| 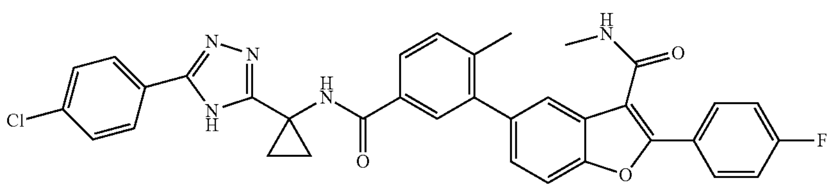 | B | A |
| | A | B |
| | | A |
| | A | A |
| | A | A |

TABLE 1b-continued

| Structure | IC$_{50}$ | EC$_{50}$ |
|---|---|---|
| (structure) | A | |
| (structure) | A | A |
| (structure) | A | A |
| (structure) | A | |
| (structure) | A | |
| (structure) | A | |

TABLE 1b-continued

| Structure | IC$_{50}$ | EC$_{50}$ |
|---|---|---|
| | A | A |
| | A | A |
| 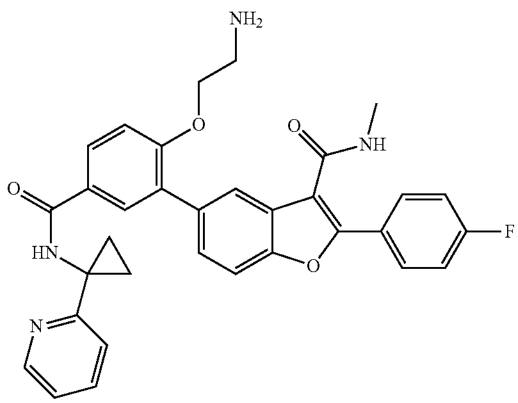 | N | A |
| | A | A |
| | A | A |

TABLE 1b-continued
| Structure | IC$_{50}$ | EC$_{50}$ |
|---|---|---|
| 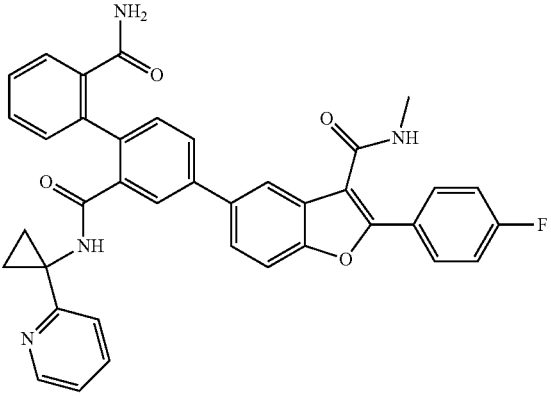 | A | A |
| 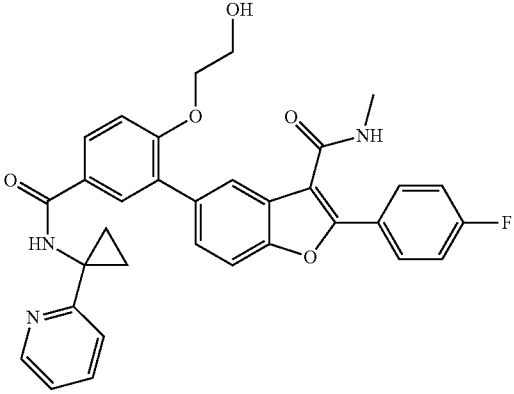 | A | A |
| 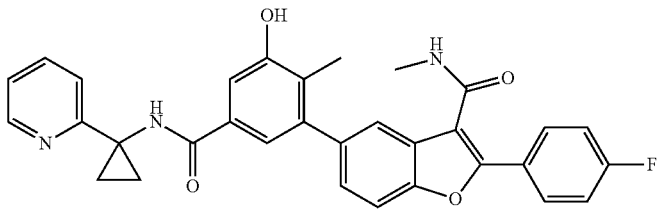 | A | A |
| 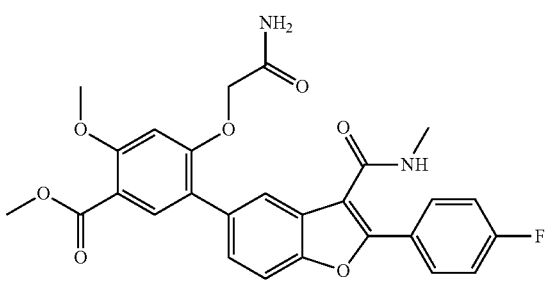 | | C |
| 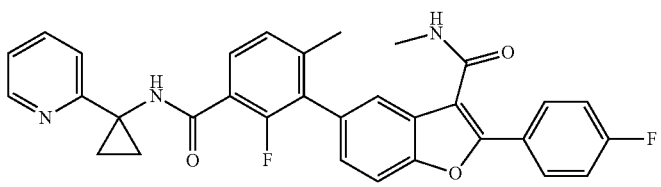 | N | A |

TABLE 1b-continued
| Structure | IC$_{50}$ | EC$_{50}$ |
|---|---|---|
| 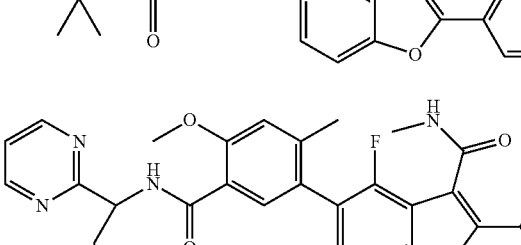 | A | A |
| 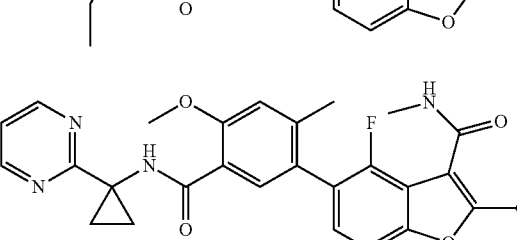 | A | A |
| 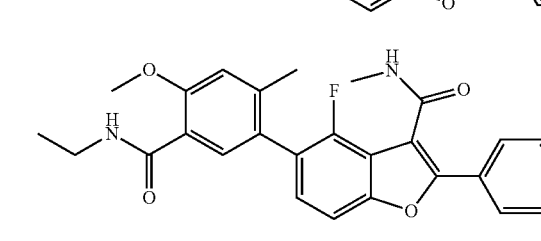 | A | A |
| 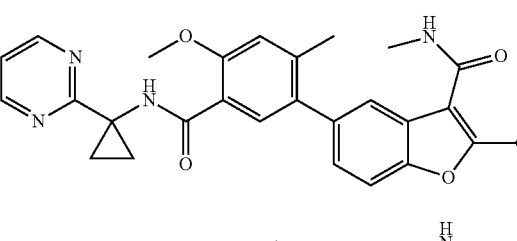 |  | A |
| 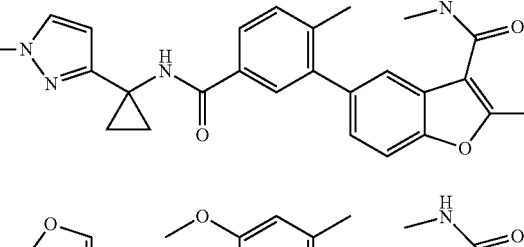 | A | A |
| 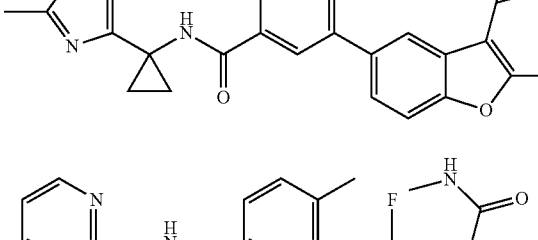 | N | A |
| 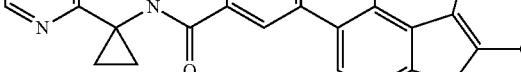 | A | A |
|  | A | A |

TABLE 1b-continued

| Structure | IC$_{50}$ | EC$_{50}$ |
|---|---|---|
| | A | A |
| | A | A |
| | A | A |
| 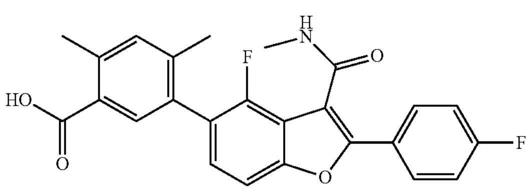 | C | E |
| 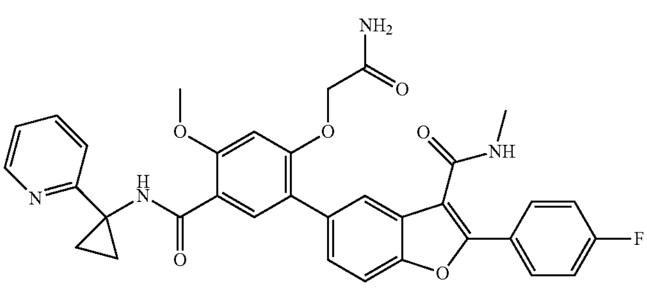 | N | A |
| 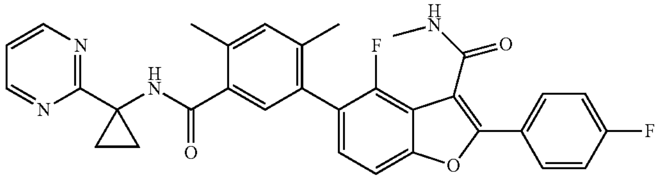 | B | A |

TABLE 1b-continued

| Structure | IC$_{50}$ | EC$_{50}$ |
|---|---|---|
| 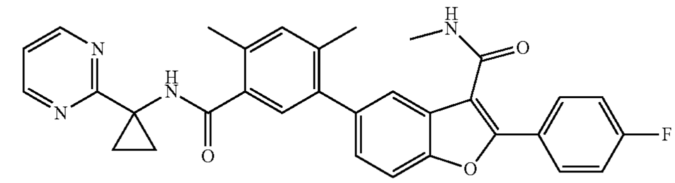 | A | A |
| | | A |
| | | A |
| | | A |

A 0.002 or less to 0.25 µM; B>0.25 µM-<1.0 µM; C 1.0 µM-10.0 µM; D>0.67 µM but an exact value was not determined; E>10.0 µM; F>0.4 µM; but an exact value was not determined; G>1.39 µM but an exact value was not determined; H>0.62 µM but an exact value was not determined; I>4 µM but an exact value was not determined; J>3.7 µM but an exact value was not determined; K>1.23 µM but an exact value was not determined; L<0.02 µM but an exact value was not determined; M>0.50 but an exact value was not determined N<0.02 but an exact value was not determined

| Structure | IC$_{50}$ (µM) | EC$_{50}$ (µM) |
|---|---|---|
| 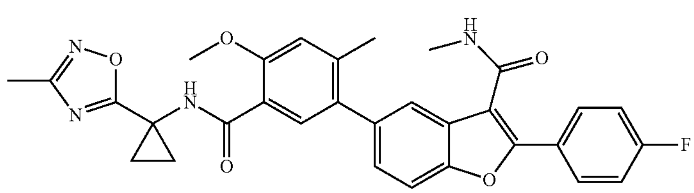 | 0.02 | 1.60E−03* |
| 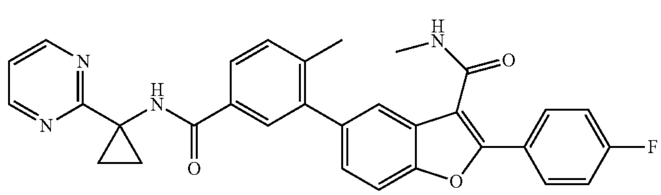 | <0.02 | 3.04E−04* |

-continued
| Structure | IC$_{50}$ (μM) | EC$_{50}$ (μM) |
|---|---|---|
| 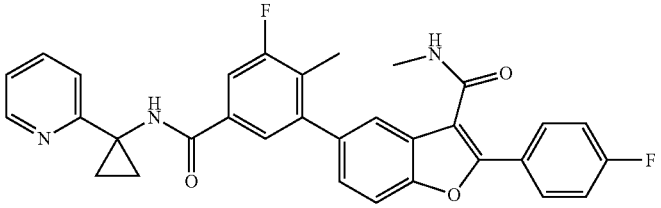 | 0.01 | 4.25E−04* |
| 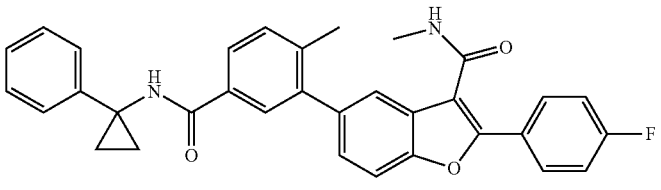 | 0.02 | 7.86E−04* |
| 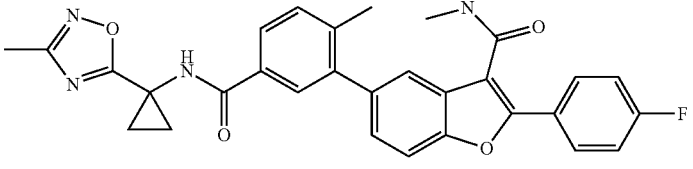 | 7.20E−03 | 8.05E−04* |
| 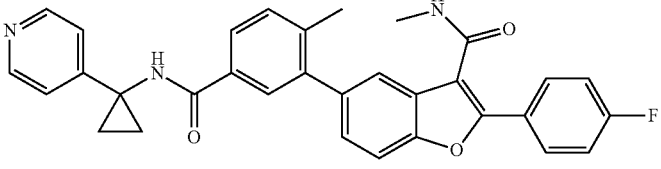 | 3.95E−03 | 8.30E−04* |
| 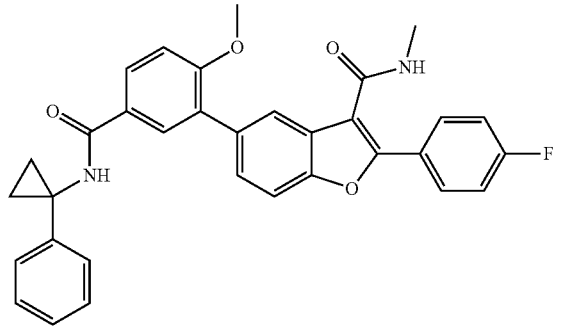 | 9.95E−03 | 1.78E−03 |
| 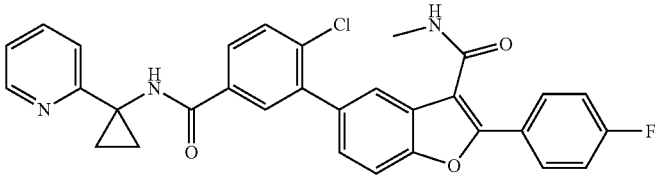 | 0.01 | 1.83E−03 |
| 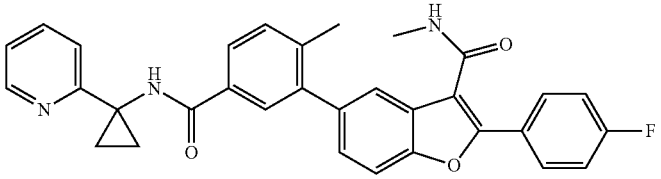 | 8.60E−03 | 1.95E−03 |

| Structure | IC$_{50}$ (μM) | EC$_{50}$ (μM) |
|---|---|---|
| 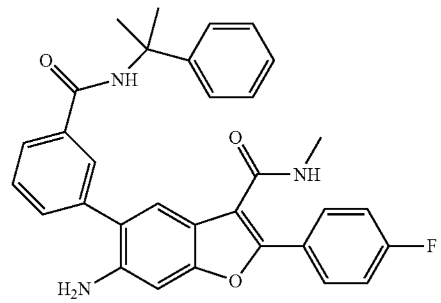 | 5.45E−03 | 2.47E−03 |
| 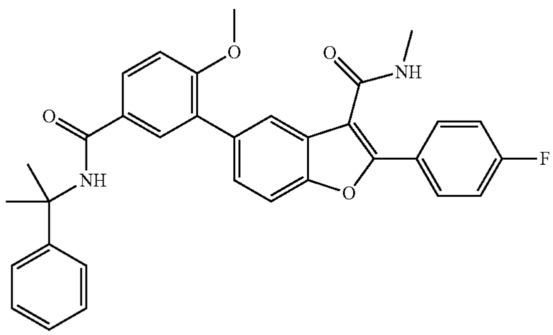 | 9.65E−03 | 3.04E−03 |
| 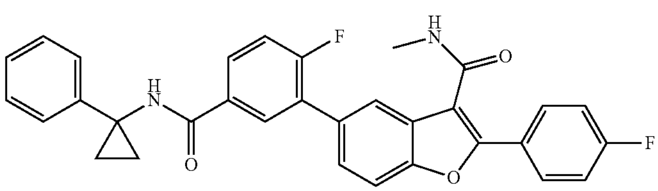 | 0.02 | 3.57E−03 |
| 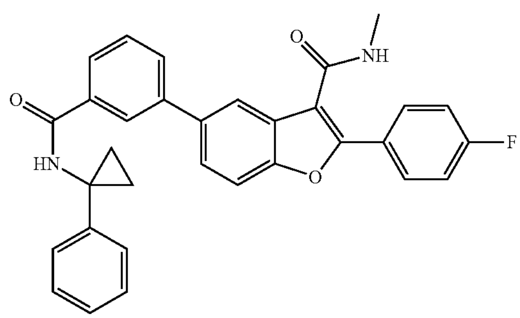 | 5.90E−03 | 3.58E−03 |
| 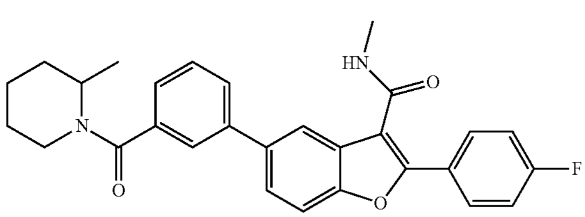 | 0.29 | 1.13 |

| Structure | IC$_{50}$ (μM) | EC$_{50}$ (μM) |
|---|---|---|
| 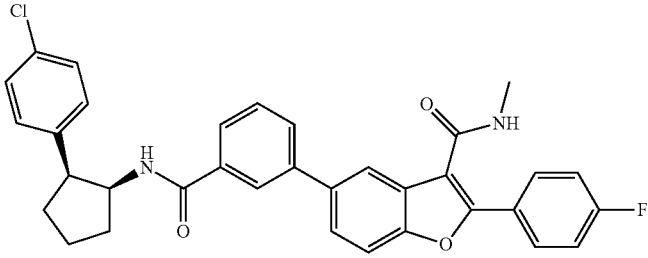 | >12.50 | 1.13 |
| Chiral<br>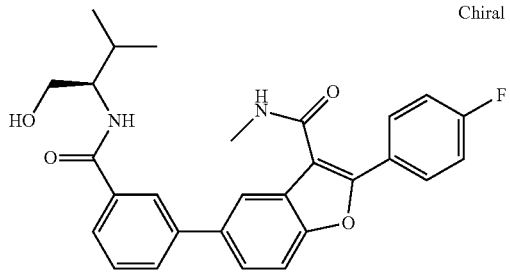 | 0.80 | 1.25 |
| Chiral<br>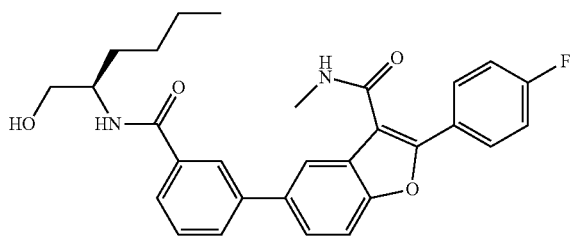 | 0.60 | 1.26 |
| 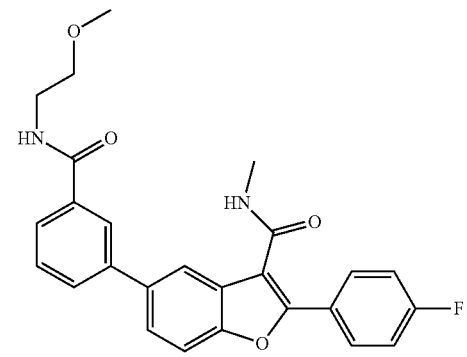 | 1.71 | 1.34 |
|  | 0.80 | 1.38 |

-continued
| Structure | IC$_{50}$ (μM) | EC$_{50}$ (μM) |
|---|---|---|
| Chiral  | 1.15 | 1.39 |
| 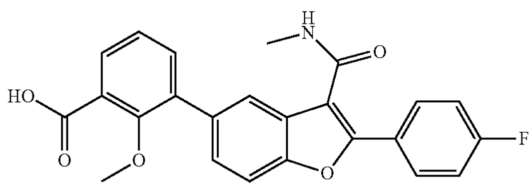 | 4.75 | 13.26 |
| 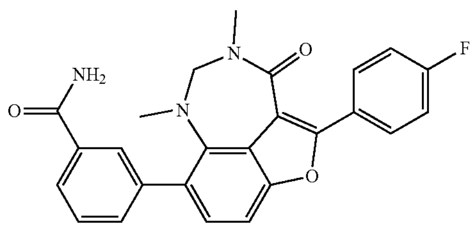 | >12.50 | 13.66 |
| 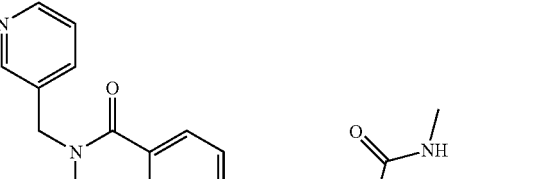 | 9.92 | 15.11 |
| Chiral 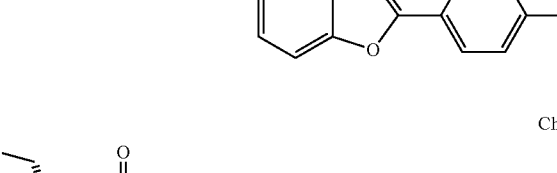 | 10.39 | 15.39 |
| Chiral 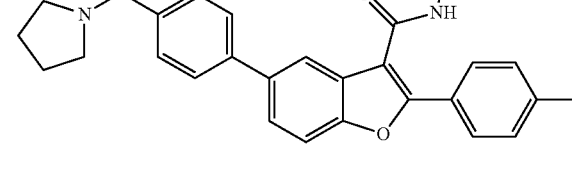 | 7.13 | 16.08 |

| Structure | IC$_{50}$ (μM) | EC$_{50}$ (μM) |
|---|---|---|
|  | | 5.68E−03* |
*EC$_{50}$ determined using 384 well plate method
TABLE 1d
| Structure | IC$_{50}$ | EC$_{50}$ |
|---|---|---|
| 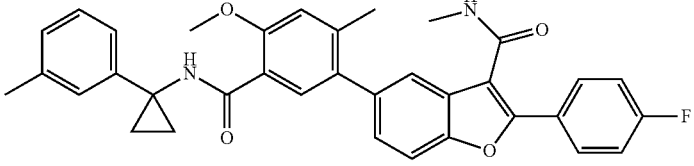 | A | A |
| 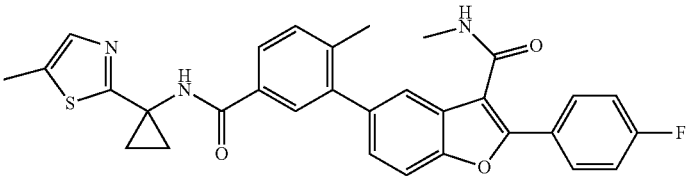 | N | A |
| 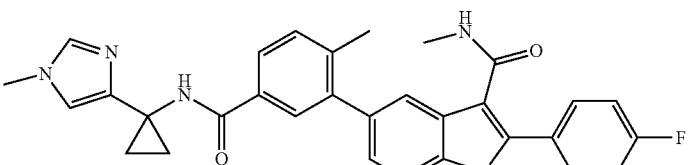 | N | A |
| 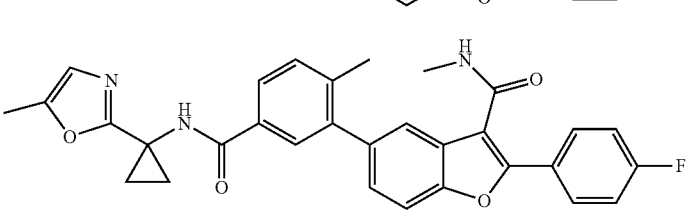 | N | A |
| 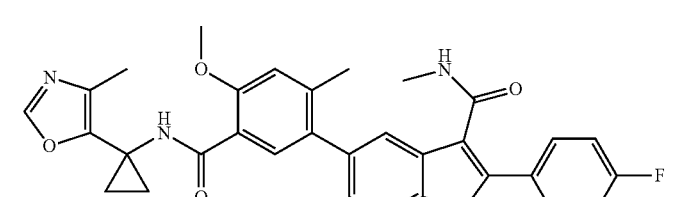 | A | A |
| 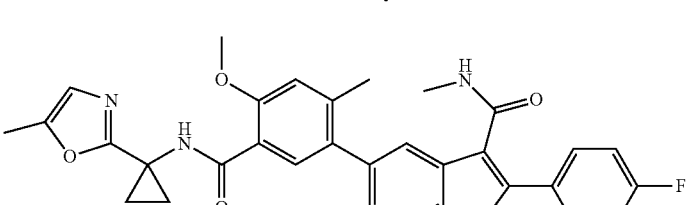 | N | A |

TABLE 1d-continued
| Structure | IC$_{50}$ | EC$_{50}$ |
|---|---|---|
| 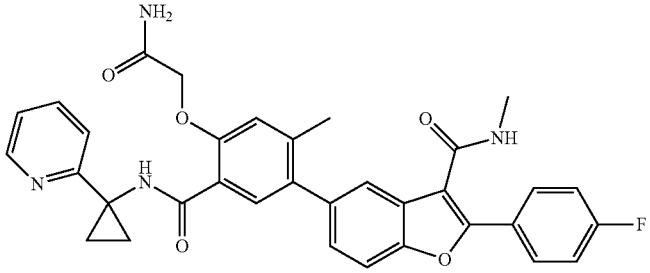 | N | A |
| 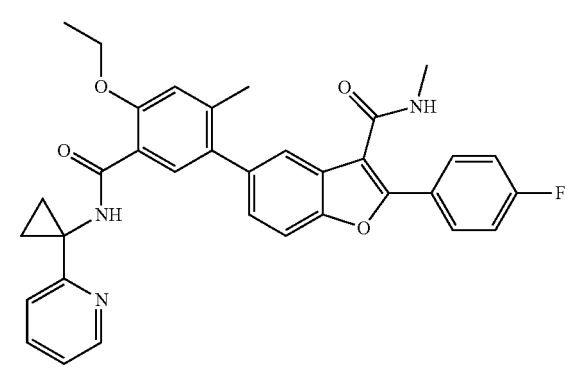 | A | A |
| 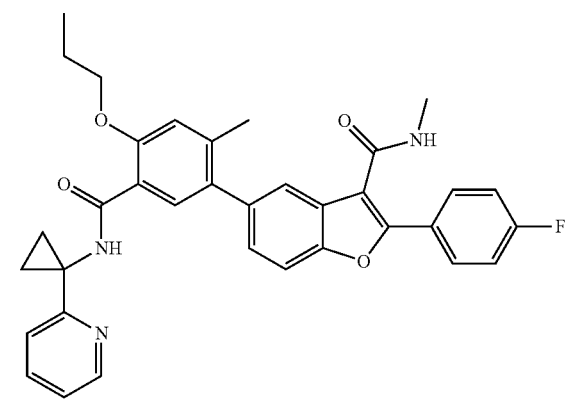 | A | A |
| 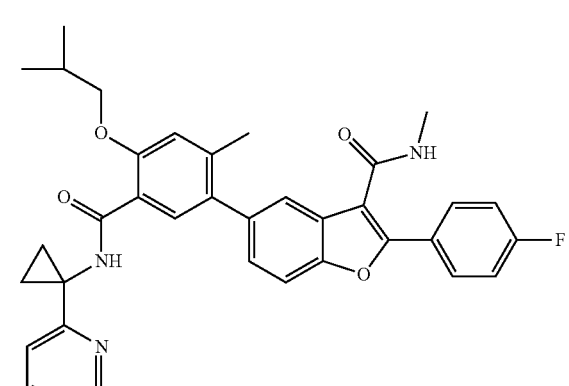 | A | A |

TABLE 1d-continued
| Structure | IC$_{50}$ | EC$_{50}$ |
| --- | --- | --- |
| 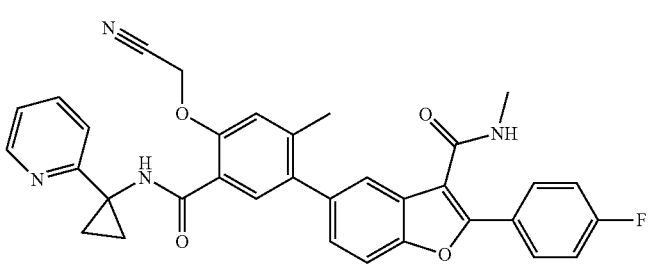 | A | |
| 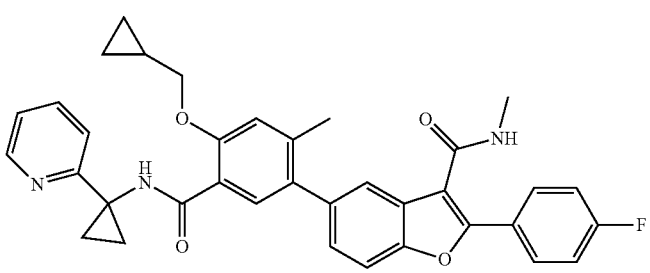 | A | A |
| 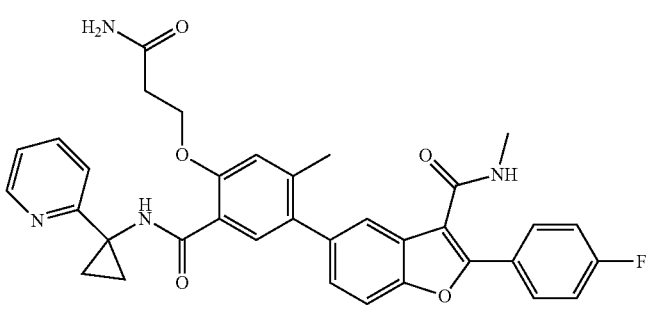 | N | A |
| 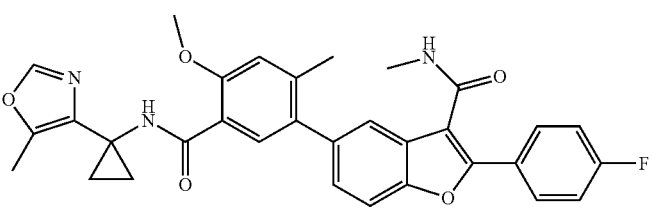 | | A |
| 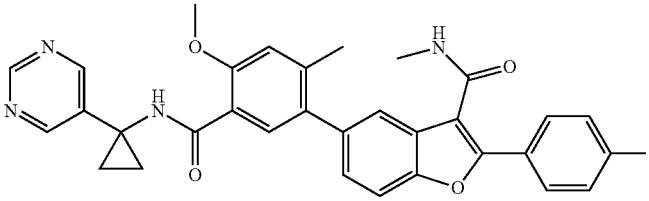 | | A |
| 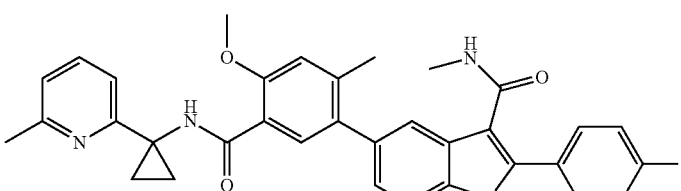 | | A |

TABLE 1d-continued

| Structure | IC$_{50}$ | EC$_{50}$ |
|---|---|---|
| | A | |
| | A | |
| | B | |
| | A | A |

TABLE 1d-continued
| Structure | IC$_{50}$ | EC$_{50}$ |
|---|---|---|
| 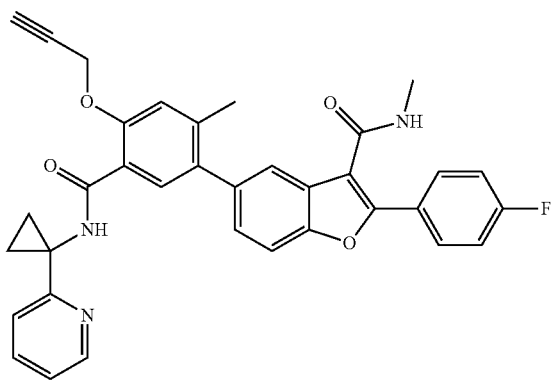 | A | A |
| 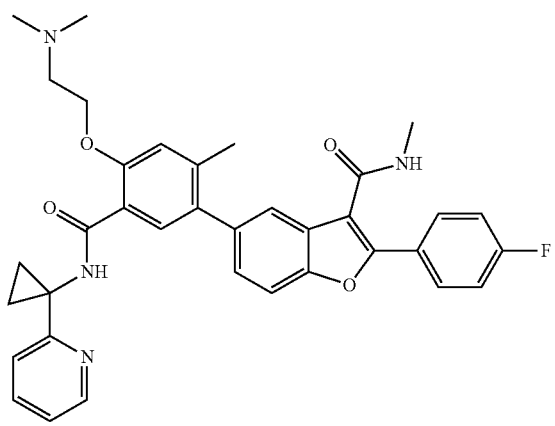 | A | |
| 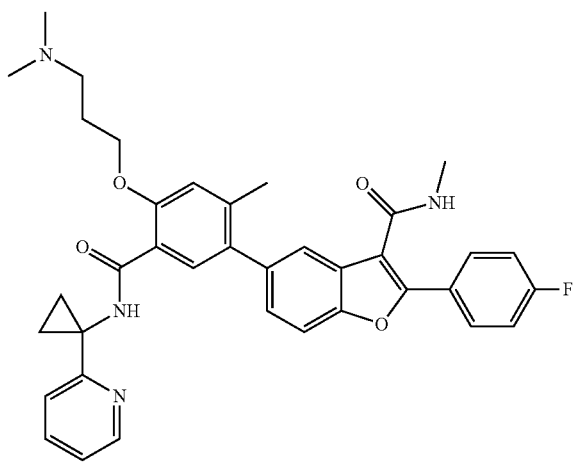 | A | |

TABLE 1d-continued
| Structure | IC$_{50}$ | EC$_{50}$ |
|---|---|---|
| 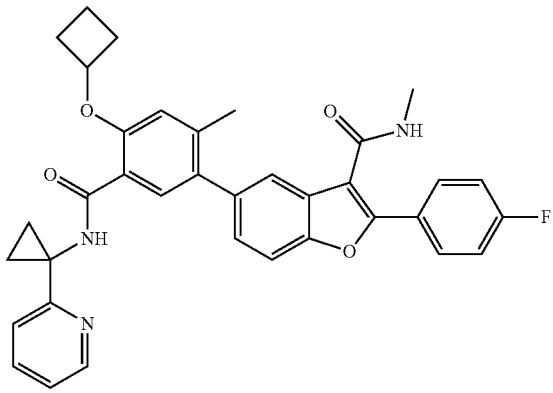 | | A |
| 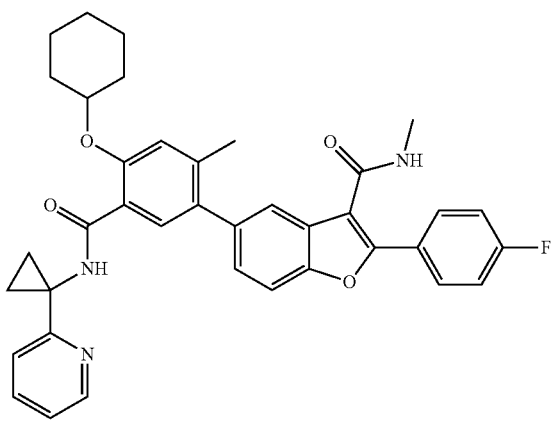 | | A |
| 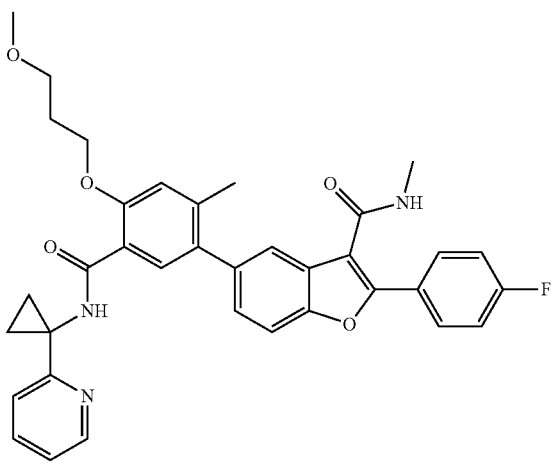 | | A |

TABLE 1d-continued
| Structure | IC$_{50}$ | EC$_{50}$ |
|---|---|---|
|  | A | |
| | A | |
| | A | |

TABLE 1d-continued
| Structure | IC$_{50}$ | EC$_{50}$ |
|---|---|---|
| 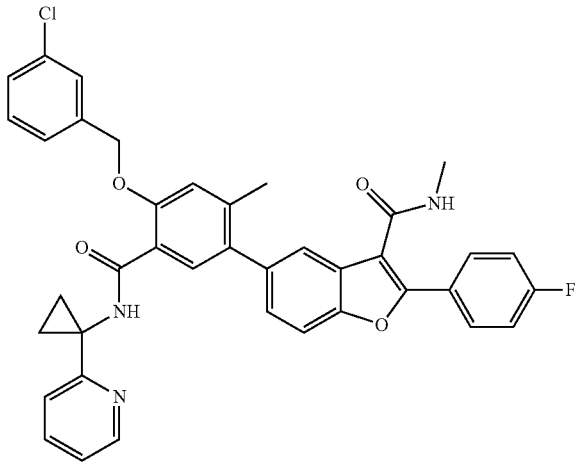 | A | |
| 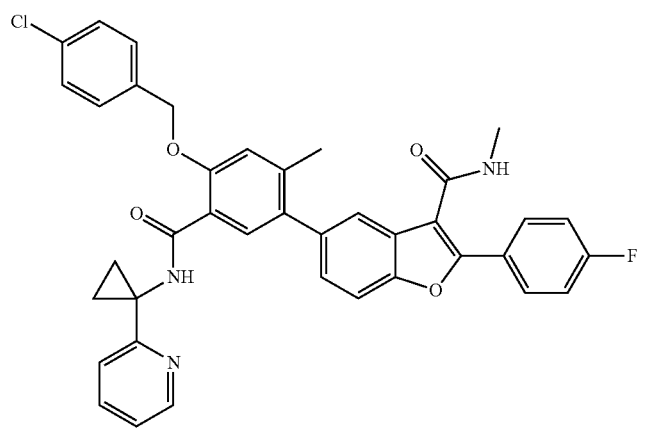 | A | |
| 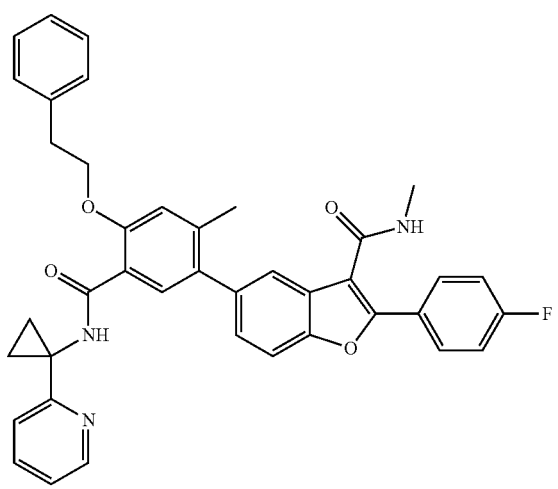 | A | |

TABLE 1d-continued

| Structure | IC$_{50}$ | EC$_{50}$ |
|---|---|---|
| *(structure)* | A | |
| *(structure)* | A | |
| *(structure)* | A | |

TABLE 1d-continued
| Structure | IC$_{50}$ | EC$_{50}$ |
|---|---|---|
| 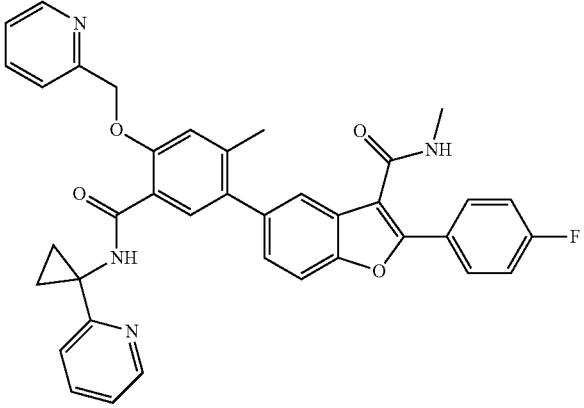 | A | |
| 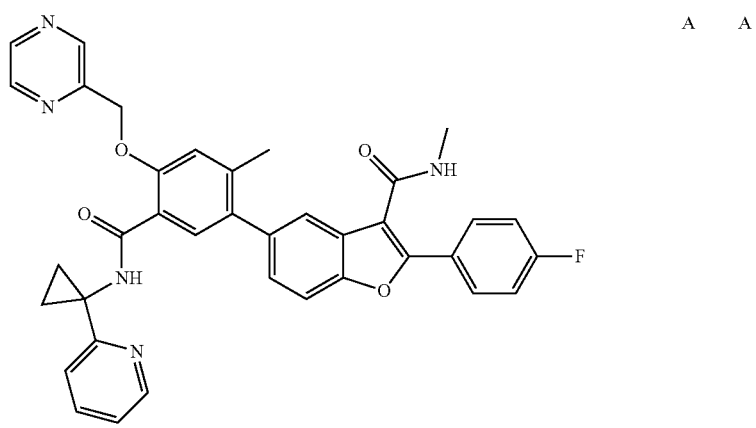 | A | A |
| 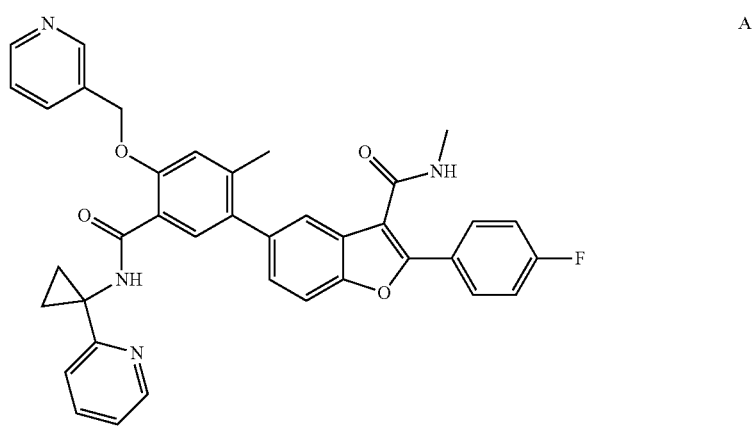 | A | |

TABLE 1d-continued

| Structure | IC$_{50}$ | EC$_{50}$ |
|---|---|---|
| | A | |
| | A | |
| | A | |

TABLE 1d-continued
| Structure | IC$_{50}$ | EC$_{50}$ |
|---|---|---|
| 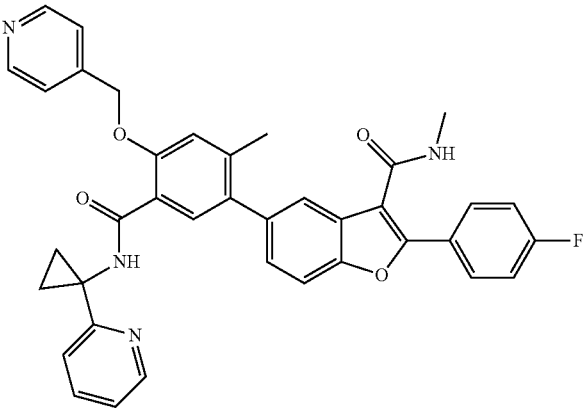 | A | |
| 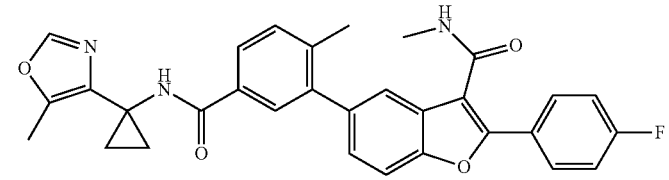 | A | |
| 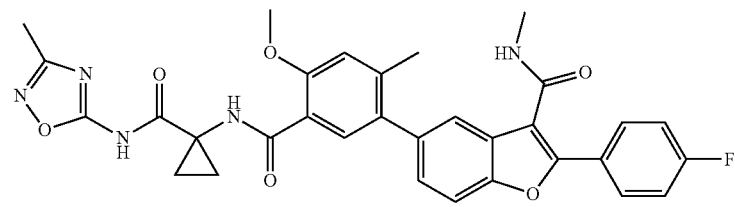 | A | |
| 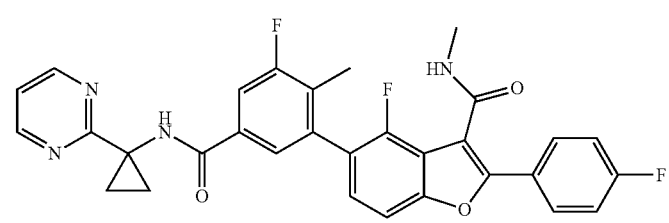 | A | A |
| 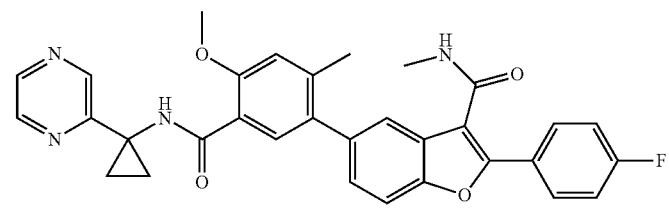 | A | A |

TABLE 1d-continued
| Structure | IC$_{50}$ | EC$_{50}$ |
|---|---|---|
| 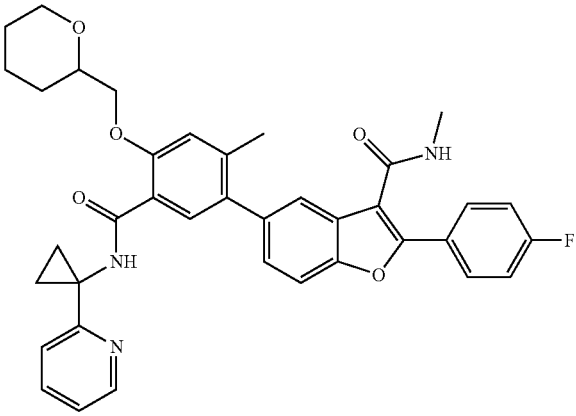 | A | |
| 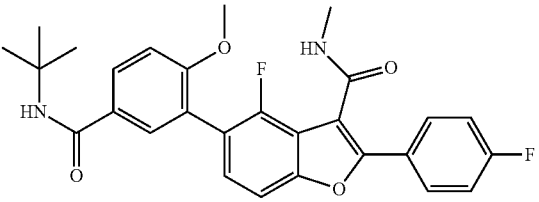 | A | |
| 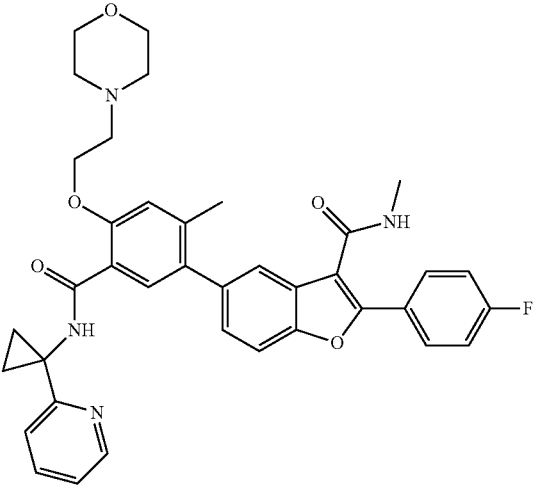 | A | |
| 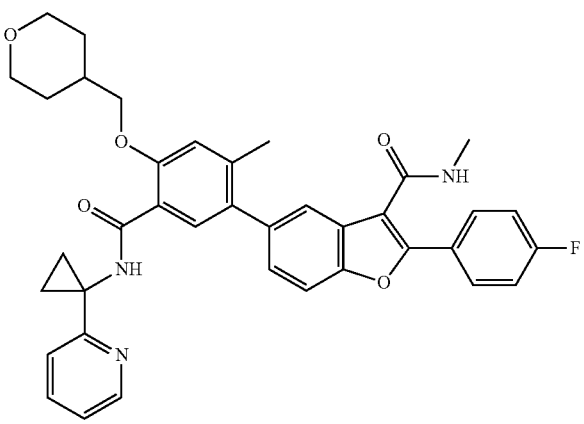 | A | |

TABLE 1d-continued
| Structure | IC$_{50}$ | EC$_{50}$ |
|---|---|---|
| 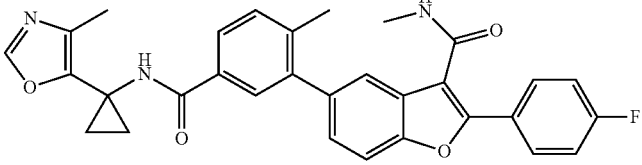 | | A |
| 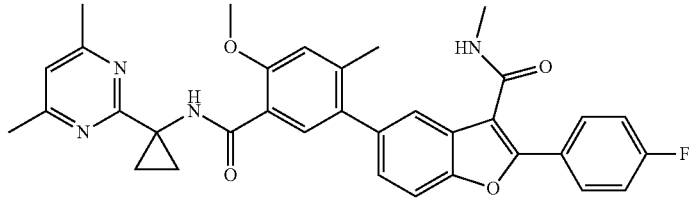 | | A |
| 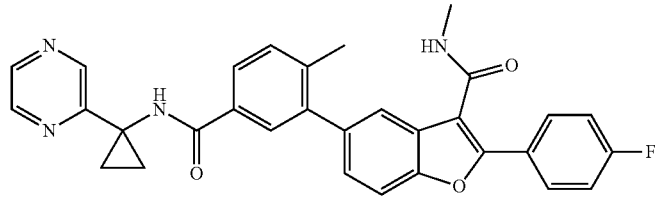 | | A |
| 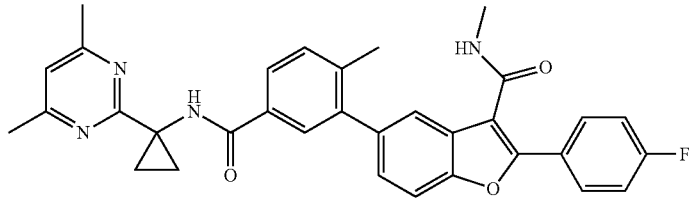 | | A |
| 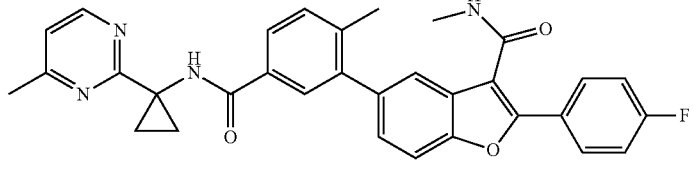 | | A |
| 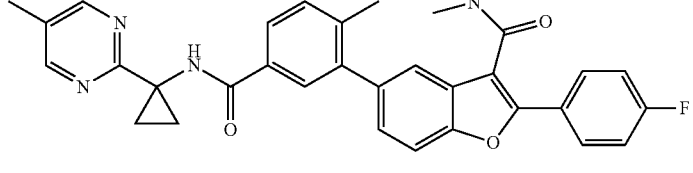 | | A |
| 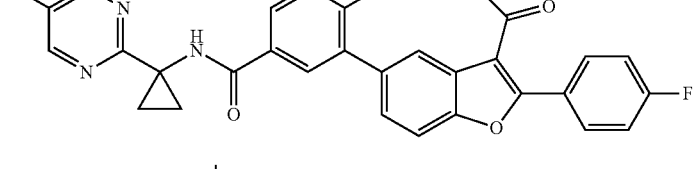 | | A |
| 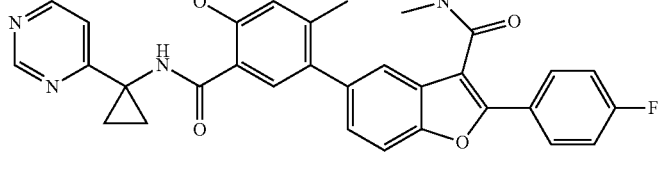 | | A |

TABLE 1d-continued

| Structure | IC$_{50}$ | EC$_{50}$ |
|---|---|---|
| | | A |
| | | A |
| | | A |
| | | A |
| | | A |
| | | A |
| | | A |

TABLE 1d-continued
| Structure | IC$_{50}$ | EC$_{50}$ |
|---|---|---|
| 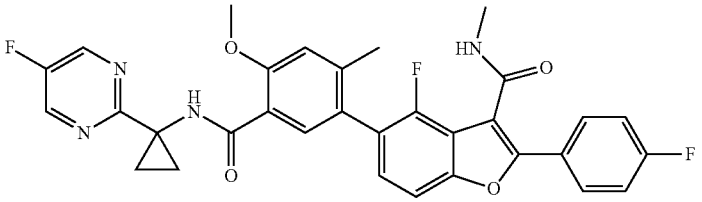 | | A |
| 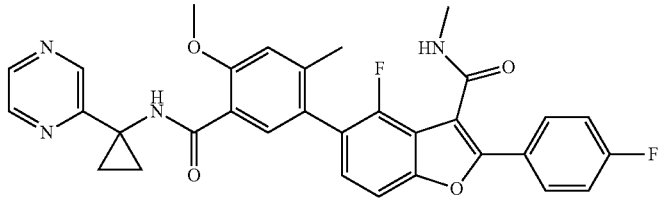 | | A |
| 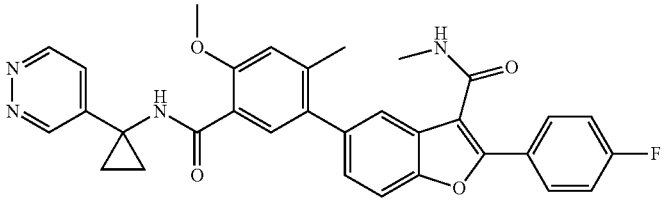 | | A |
| 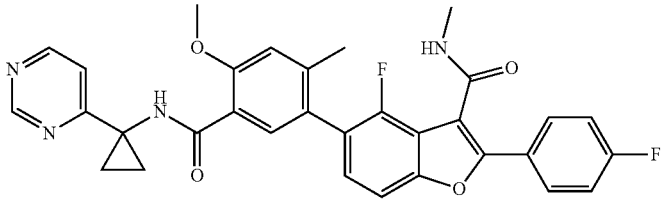 | | A |
| 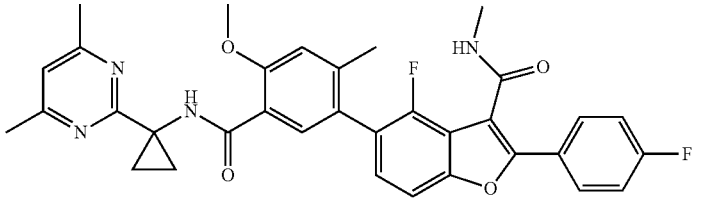 | | A |
| 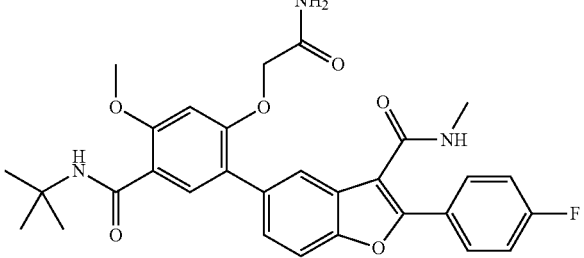 | | A |
| 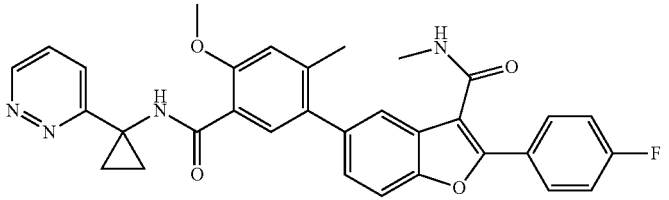 | | A |

TABLE 1d-continued

| Structure | IC$_{50}$ | EC$_{50}$ |
|---|---|---|
| | | A |
| | | A |
| | | A |
| | | A |
| | | A |
| | | A |
| | | A |

TABLE 1d-continued

| Structure | IC$_{50}$ | EC$_{50}$ |
|---|---|---|
| 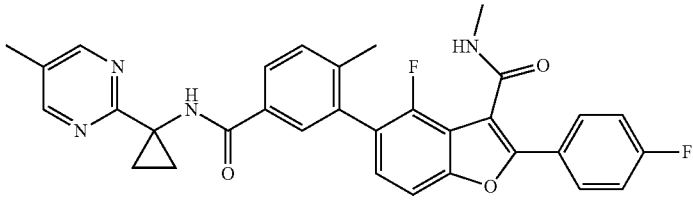 | A | |
| 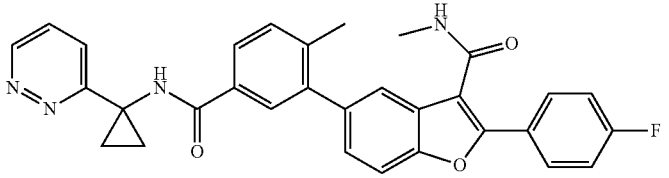 | A | |
| 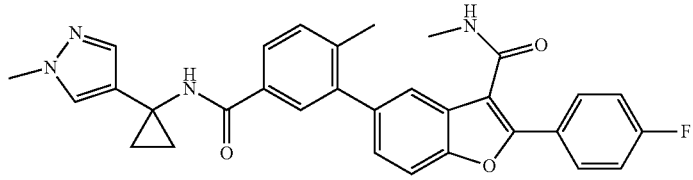 | A | |
| 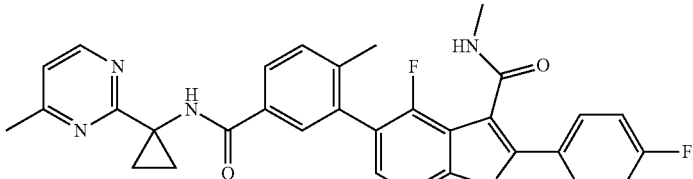 | A | |
| 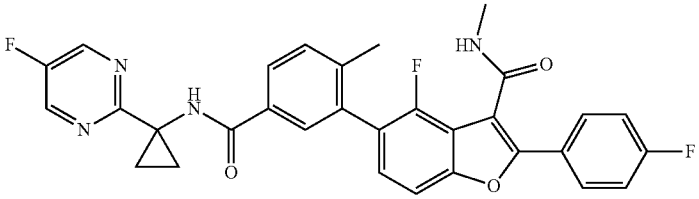 | A | |

A 0.001 to 0.25 µM; B>0.25 µM-<1.0 µM; C 1.0 µM-10.0 µM; D>0.67 µM but an exact value was not determined; E>10.0 µM; F>0.4 µM; but an exact value was not determined; G>1.39 µM but an exact value was not determined; H>0.62 µM but an exact value was not determined; I>4 µM but an exact value was not determined; J>3.7 µM but an exact value was not determined; K>1.23 µM but an exact value was not determined; L<0.02 µM but an exact value was not determined; M>0.50 but an exact value was not determined N<0.02 but an exact value was not determined

TABLE 1d

| Structure | IC$_{50}$ (µM) | EC$_{50}$ (µM) |
|---|---|---|
| 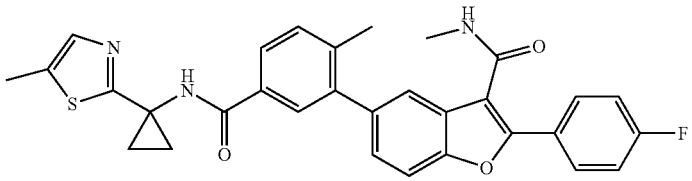 | <0.017 | 0.0019 |

TABLE 1d-continued
| Structure | IC$_{50}$ (μM) | EC$_{50}$ (μM) |
|---|---|---|
| 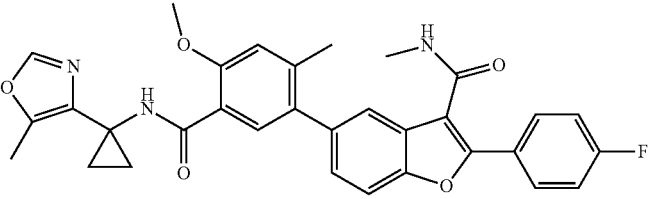 | | 0.002 |
| 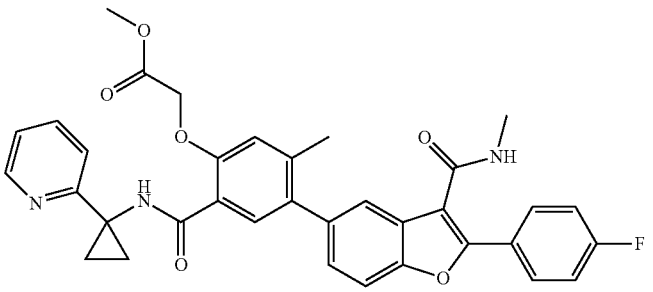 | | 0.21 |
| 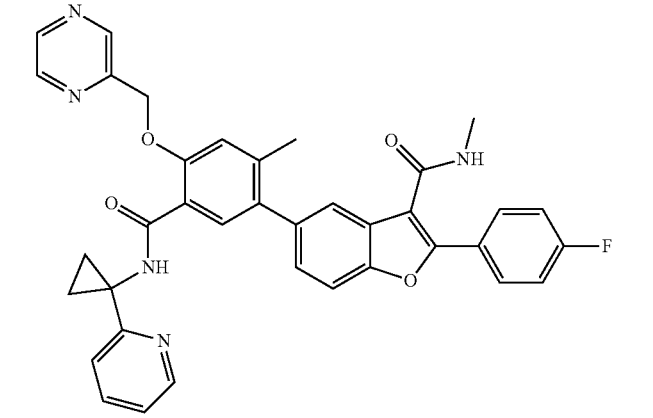 | 0.0021 | 0.001 |
| 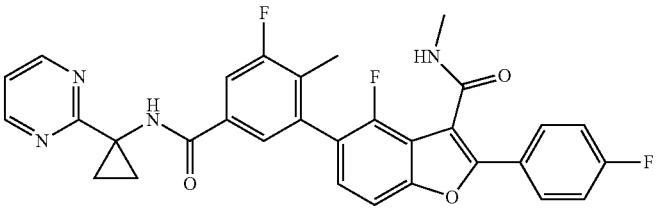 | 0.0081 | 0.0024 |
| 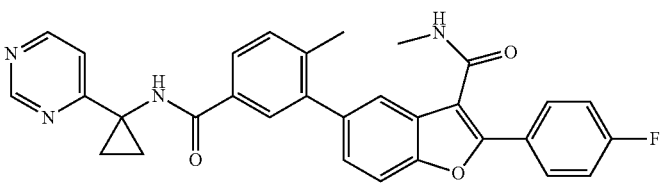 | | 0.002 |
| 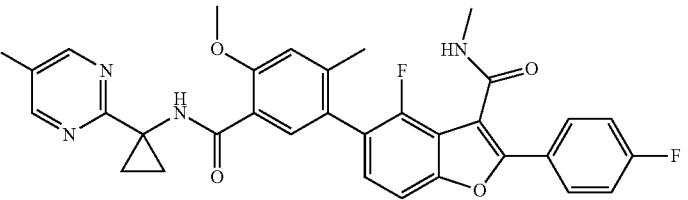 | | 0.010 |

TABLE 1d-continued

| Structure | IC$_{50}$ (μM) | EC$_{50}$ (μM) |
|---|---|---|
| | | 0.056 |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound or a pharmaceutically acceptable salt thereof. Another aspect of the invention is a method of inhibiting the function of the HCV replicon. Another aspect of the invention is a method of inhibiting the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |

TABLE 2-continued

| Brand Name | Type of Inhibitor or Target | Source Company |
|---|---|---|
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO 2005047288 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

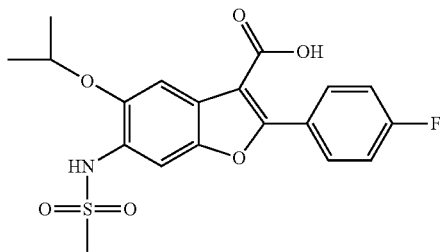

2-(4-fluorophenyl)-5-isopropoxy-6-(methylsulfonamido) benzofuran-3-carboxylic acid. Excess NaOH (10 mL, 1N aq) was added to a stirring solution of methyl 2-(4-fluorophenyl)-5-isopropoxy-6-(methylsulfonamido)benzofuran-3-carboxylate (3.0 g, 6.89 mmol) in EtOH (34 mL) and THF (34 mL). It was allowed to stir at 60° C. overnight. The mixture was then heated to 67° C. and allowed to stir for 4 more hours. The mixture was concentrated then diluted with EtOAc and washed with 1M HCl, and sat NaCl. The organic phase was dried over Na2SO4, filtered and concentrated to give the titled compound (2.7 g, 96%). 1H NMR (300 MHz, DMSO-D6) δ ppm 1.31-1.38 (m, 6H) 2.99 (s, 3H) 4.63-4.73 (m, 1H) 7.32-7.41 (m, 2H) 8.00-8.08 (m, 2H) 8.88 (s, 2H) 13.05 (s, 1H). LC-MS retention time: 1.03 min; m/z (MH−): 406. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

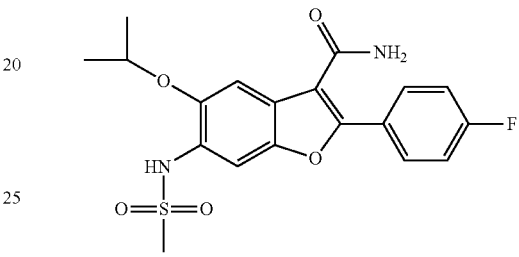

2-(4-fluorophenyl)-5-isopropoxy-6-(methylsulfonamido) benzofuran-3-carboxamide. Ammonia (6.1 ml, 12.2 mmol, 2M in MeOH) was added to a stirring solution of HATU (1.1 g, 2.95 mmol) and 2-(4-fluorophenyl)-5-isopropoxy-6-(methylsulfonamido)benzofuran-3-carboxylic acid (1.0 g, 2.46 mmol) in DMF (20 ml) at 0° C. It was allowed to warm to rt and stir for 1 hr. The mixture was diluted with EtOAc and washed with sat NaHCO3, and sat NaCl. The organic phase was dried over Na2SO4, filtered and concentrated to give the title compound (925 mg, 93%). $^1$H NMR (300 MHz, DMSO-D6) δ ppm 1.30-1.37 (m, 6H) 2.98 (s, 3H) 4.64-4.77 (m, 1H) 7.19 (s, 1H) 7.30-7.41 (m, 2H) 7.54 (s, 1H) 7.63-7.71 (m, 1H) 7.89 (s, 1H) 7.93-8.02 (m, 2H) 8.85 (s, 1H). LC-MS retention time: 1.26 min; m/z (MH+) 407. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

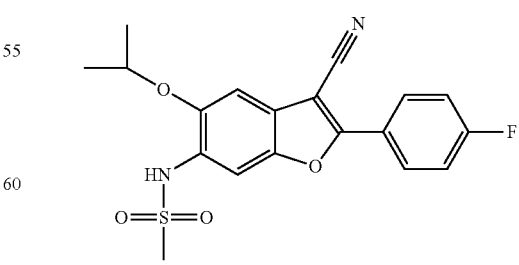

N-(3-cyano-2-(4-fluorophenyl)-5-isopropoxybenzofuran-6-yl)methanesulfonamide. Trifluoroacetic anhydride (375 μL, 2.66 mmol) was added to a stirring solution of DIEA (928

μL, 5.31 mmol), 2-(4-fluorophenyl)-5-isopropoxy-6 (methylsulfonamido) benzofuran-3-carboxamide (300 mg, 0.738 mmol) in CH2Cl2 (4 mL) and THF (4 mL) at 0° C. for 1 hour. The mixture was diluted with EtOAc and washed with sat NaHCO3, and sat NaCl. The organic phase was dried over Na2SO4, filtered and concentrated. The crude residue was purified by on silica gel (Biotage, gradient EtOAc/hexanes, fraction collection at λ=254 nm) to give the title compound (143 mg, 50%). $^1$H NMR (300 MHz, DMSO-D6) δ ppm 1.28-1.41 (m, 6H) 3.01 (s, 3H) 4.77-4.95 (m, 1H) 7.35 (s, 1H) 7.44-7.57 (m, 2H) 7.68 (s, 1H) 8.04-8.20 (m, 2H) 9.01 (s, 1H). LC-MS retention time: 1.65 min; m/z (MH−): 387. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

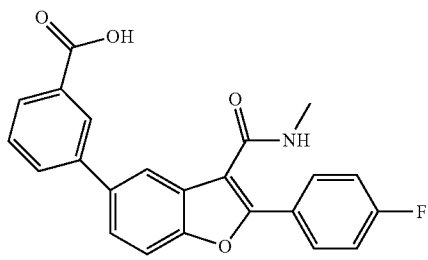

3-(2-(4-fluorophenyl)-3-(methylcarbamoyl)benzofuran-5-yl)benzoic acid. Cesium carbonate (3.5 g, 10.7 mmol) was added to Pd(Ph3P)4 (108 mg, 0.093 mmol), 2-(4-fluorophenyl)-3-(methylcarbamoyl)benzofuran-5-yltrifluoromethanesulfonate (3.0 g, 7.19 mmol), 3-boronobenzoic acid (1.97 g, 11.86 mmol). Dioxane (60 ml) and water (12 ml) was added at rt. The reaction was degassed 3× and then heated to 95° C. and allowed to stir overnight. It was allowed to cool to rt. The mixture was diluted with EtOAc and washed with 1M HCl, and sat NaCl. The precipitate that formed was filtered and dried overnight at 55° C. under vacuum. The remaining organic phase was concentrated and triturated with DCM, followed by hot DCE and finally hot MeOH to afford the titled compound which was combined with the previously collected precipitate (2.4 g, 87%). LC-MS retention time: 1.19 min; m/z (MH+): 390. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

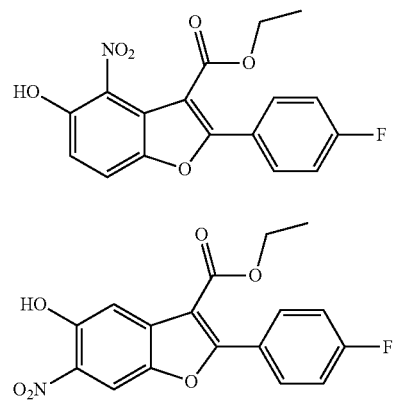

Ethyl 2-(4-fluorophenyl)-5-hydroxy-4-nitrobenzofuran-3-carboxylate and ethyl 2-(4-fluorophenyl)-5-hydroxy-6-nitrobenzofuran-3-carboxylate. Nitric acid (21 μL, 0.33 mmol) was added to a stirring solution of ethyl 2-(4-fluorophenyl)-5-hydroxybenzofuran-3-carboxylate (100 mg, 0.33 mmol) in chloroform (3.3 mL) at −20° C. It was allowed to stir for 10 min. A 9:2 ratio of ethyl 2-(4-fluorophenyl)-5-hydroxy-4-nitrobenzofuran-3-carboxylate to ethyl 2-(4-fluorophenyl)-5-hydroxy-6-nitrobenzofuran-3-carboxylate was observed. The crude reaction was purified on silica gel (Biotage, EtOAc/hexanes gradient, fraction collection at λ=254 nm) to give the titled compounds:

Ethyl 2-(4-fluorophenyl)-5-hydroxy-6-nitrobenzofuran-3-carboxylate. 1H NMR (500 MHz, DMSO-$d_6$) δ ppm 10.92 (1H, s), 8.33 (1H, s), 8.03-8.11 (2H, m), 7.69 (1H, s), 7.43 (2H, t, J=8.85 Hz), 4.34 (2H, q, J=7.22 Hz), 1.33 (3H, t, J=7.17 Hz). LC-MS retention time: 1.79 min; m/z (MH−): 344. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Ethyl 2-(4-fluorophenyl)-5-hydroxy-4-nitrobenzofuran-3-carboxylate. $^1$H NMR (500 MHz, DMSO-$d_6$) δ ppm 11.03 (1H, s), 7.92-8.01 (2H, m), 7.86 (1H, d, J=9.16 Hz), 7.42 (2H, t, J=8.85 Hz), 7.17 (1H, d, J=8.85 Hz), 4.20 (2H, q, J=7.12 Hz), 1.21 (3H, t, J=7.17 Hz). LC-MS retention time: 1.56 min; m/z (MH−): 344. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

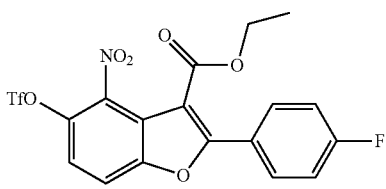

Ethyl 2-(4-fluorophenyl)-4-nitro-5-(trifluoromethylsulfonyloxy)benzofuran-3-carboxylate. Triethylamine (91 μL, 0.652 mmol) was added to a stirring solution of 1,1,1-trifluoro-N-phenyl-N-(trifluoromethylsulfonyl)methanesulfonamide (116 mg, 0.326 mmol) and ethyl 2-(4-fluorophenyl)-5-hydroxy-4-nitrobenzofuran-3-carboxylate (75 mg, 0.217 mmol) in DCM (2.2 mL). The crude reaction was purified on silica gel (Biotage, EtOAc/hexanes gradient, fraction collection at λ=254 nm) to give titled compound (78 mg, 75%). $^1$H NMR (500 MHz, DMSO-$d_6$) δ ppm 11.03 (1H, s), 7.92-8.01 (2H, m), 7.86 (1H, d, J=9.16 Hz), 7.42 (2H, t, J=8.85 Hz), 7.17 (1H, d, J=8.85 Hz), 4.20 (2H, q, J=7.12 Hz), 1.21 (3H, t, J=7.17 Hz). LC-MS retention time: 1.91 min; m/z (MH+): no ion detected. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

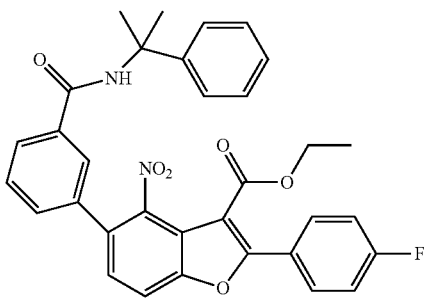

Ethyl 2-(4-fluorophenyl)-4-nitro-5-(3-(2-phenylpropan-2-ylcarbamoyl)phenyl)benzofuran-3-carboxylate. Step 1: Cesium carbonate (333 mg, 1.021 mmol) was added to Pd(Ph3P)$_4$ (39 mg, 0.034 mmol), ethyl 2-(4-fluorophenyl)-4-nitro-5-(trifluoromethylsulfonyloxy)benzofuran-3-carboxylate (325 mg, 0.681 mmol), 3-boronobenzoic acid (169 mg, 1.021 mmol). Dioxane (5.6 mL) and water (1.1 mL) was added at rt. The reaction was degassed 3× and heated to 90° C. overnight. It was allowed to cool. The mixture was diluted with EtOAc and washed with 1M HCl, and sat NaCl. The organic phase was dried over Na2SO4, filtered and concentrated to give the m-acid.

Step 2: The crude m-acid was diluted with DMF (5 mL) and treated with HATU (388 mg, 1.021 mmol), 2-phenylpropan-2-amine (138 mg, 1.021 mmol), and DIEA (357 μL, 2.043 mmol) and allowed to stir at rt for 1 hr. The mixture was diluted with EtOAc and washed with sat NaHCO3, and sat NaCl. The organic phase was dried over Na2SO4, filtered and concentrated to give the titled compound which was purified on silica gel (Biotage 25+M column, EtOAc/hexanes gradient; Rf ~0.2 for 20% EtOAc/hexanes; fraction collection at λ=254 nm) to give a light yellow solid (294 mg, 76%). LC-MS retention time: 1.97 min; m/z (MH+): 567. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

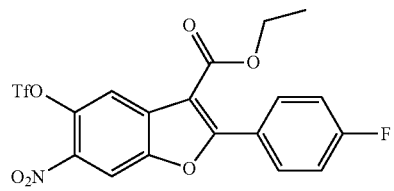

Ethyl 2-(4-fluorophenyl)-6-nitro-5-(trifluoromethylsulfonyloxy)benzofuran-3-carboxylate. Triethylamine (121 μL, 0.869 mmol) was added to a stirring solution of 1,1,1-trifluoro-N-phenyl-N-(trifluoromethylsulfonyl)methanesulfonamide (155 mg, 0.434 mmol) and ethyl 2-(4-fluorophenyl)-5-hydroxy-6-nitrobenzofuran-3-carboxylate (100 mg, 0.290 mmol) in DCM (3 mL). It was allowed to stir overnight. The mixture concentrated and was purified on silica gel (Biotage, EtOAc/hexanes gradient, fraction collection at λ=254 nm) to give the titled compound (140 mg, 100%). $^1$H NMR (300 MHz, DMSO-$d_6$) δ ppm 8.91 (1H, s), 8.10-8.19 (3H, m), 7.48 (2H, t, J=8.97 Hz), 4.37 (2H, q, J=7.07 Hz), 1.34 (3H, t, J=6.95 Hz). LC-MS retention time: 1.91 min; m/z (MH+): no ion detected. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

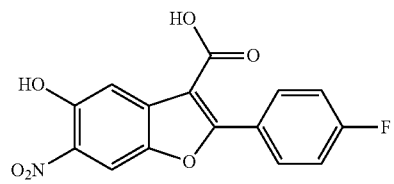

2-(4-fluorophenyl)-5-hydroxy-6-nitrobenzofuran-3-carboxylic acid. Excess NaOH (11 ml, 11.00 mmol, 1M aq) was added to a stirring solution of ethyl 2-(4-fluorophenyl)-5-hydroxy-6-nitrobenzofuran-3-carboxylate (1.9 g, 5.50 mmol) in EtOH (55 ml) and THF (55 ml) and was allowed to stir at 64° C. overnight. The mixture was concentrated and diluted with EtOAc and washed with 1M HCl, and sat NaCl. The organic phase was dried over Na2SO4, filtered and concentrated to give the titled compound (1.7 g, quant.). $^1$H NMR (300 MHz, DMSO-D6) δ ppm 7.31-7.48 (m, 2H) 7.71 (s, 1H) 8.00-8.14 (m, 2H) 8.29 (s, 1H) 10.80 (s, 1H) 13.35 (s, 1H). LC-MS retention time: 0.99 min; m/z (MH−): 416. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

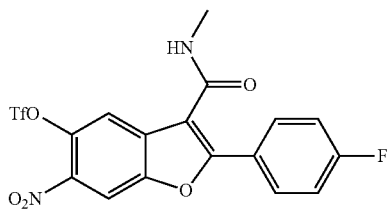

2-(4-fluorophenyl)-3-(methylcarbamoyl)-6-nitrobenzofuran-5-yl trifluoromethanesulfonate. Step 1: Methanamine (4.4 ml, 8.83 mmol) was added to a stirring solution of DIEA (3 ml, 17.65 mmol), BOP (2.9 g, 6.62 mmol), and 2-(4-fluorophenyl)-5-hydroxy-6-nitrobenzofuran-3-carboxylic acid (1.4 g, 4.41 mmol) in DMF (44 ml) at 0° C. It was allowed to warm to rt and stir for 1 hr. The mixture was concentrated and diluted with EtOAc and washed with 1M HCl, and sat NaCl. The organic phase was dried over Na2SO4, filtered and concentrated to give a crude product which was triturated with MeOH to give the methyl amide, nitro phenol-hmpa adduct (1.7 g, 78%). Step 2: The hmpa-adduct (100 mg, 0.203 mmol) was taken up in EtOH and treated with 1M NaOH (609 μL, 0.609 mmol) at 70° C. It was allowed to stir overnight. The mixture was diluted with EtOAc and washed with 1M HCl, and sat NaCl. The organic phase was dried over Na2SO4, filtered and concentrated to give the nitro phenol (50 mg, 75%) as a brown solid. LC-MS retention time: 1.34 min; m/z (MH+): 331. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Step 3: Triethylamine (422 μL, 3.03 mmol) was added to a stirring solution of N-Phenylbis(trifluoromethane)sulfonimide (649 mg, 1.817 mmol) and 2-(4-fluorophenyl)-5-hydroxy-N-methyl-6-nitrobenzofuran-3-carboxamide (400 mg, 1.211 mmol) in DCM (24 mL) at rt. The slurry was allowed to stir overnight. The mixture was diluted with EtOAc and washed with sat NaHCO3, and sat NaCl. The organic phase was dried over Na2SO4, filtered and concentrated to give a crude residue which was purified on silica gel (Biotage, EtOAc/hexanes gradient, Rf ~0.2 in 30% EtOAc/hexanes, fraction collection at λ=254 nm) to give the titled compound (375 mg, 67%). $^1$H NMR (500 MHz, DMSO-d6) δ ppm 8.83 (1H, s), 8.55-8.65 (1H, m), 7.98-8.05 (2H, m), 7.95 (1H, s), 7.47 (2H, t, J=8.85 Hz), 2.84 (3H, d, J=4.58 Hz). LC-MS retention time: 1.96 min; m/z (MH−): 461. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

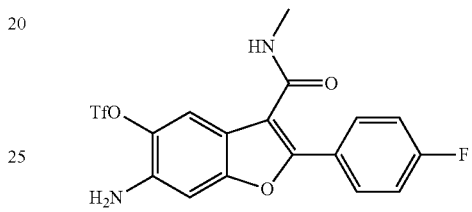

6-amino-2-(4-fluorophenyl)-3-(methylcarbamoyl)benzofuran-5-yl trifluoromethanesulfonate. Iron (211 mg, 3.79 mmol) was added to a stirring solution of 2-(4-fluorophenyl)-3-(methylcarbamoyl)-6-nitrobenzofuran-5-yl trifluoromethanesulfonate (350 mg, 0.757 mmol) in EtOH (8.4 mL) and AcOH (8.4 mL) at rt and then was heated to 100° C. for 10 min. The mixture was diluted with EtOAc and washed with 1M HCl, and sat NaCl followed by 1M NaOH and brine. The organic phase was dried over Na2SO4, filtered and concentrated to give a white solid which was 1:1 starting material: product. It was resubjected to the reaction conditions for 15 min and re-worked up to give the titled compound (275 mg, 84%). LC-MS retention time: 1.47 min; m/z (MH+): 433. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

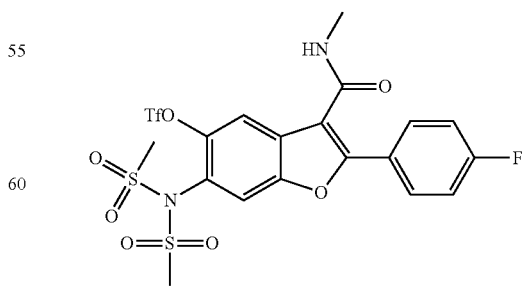

2-(4-fluorophenyl)-3-(methylcarbamoyl)-6-(N-(methylsulfonyl)methylsulfonamido)benzofuran-5-yl trifluoromethanesulfonate. Methanesulfonyl chloride (146 μL, 1.873 mmol) was added to a stirring solution of 6-amino-2-(4-fluorophenyl)-3-(methylcarbamoyl)benzofuran-5-yl trifluoromethanesulfonate (270 mg, 0.624 mmol) and DIEA (500 μL, 2.86 mmol) in DCM (6.3 mL) at 25° C. It was allowed to stir for 1 hour and then diluted with EtOAc and washed with sat NaHCO3, and sat NaCl. The organic phase was dried over Na2SO4, filtered and concentrated. It was purified on silica gel (Biotage, EtOAc/hexanes gradient, fraction collection at λ=254 nm) to give the titled compound (300 mg, 82%). LC-MS retention time: 1.49 min; m/z (MH+): 589. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

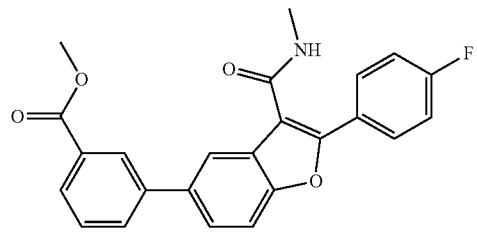

Methyl 3-(2-(4-fluorophenyl)-3-(methylcarbamoyl)benzofuran-5-yl)benzoate. Trimethylsilyldiazomethane (500 μL, 1.00 mmol, 2M in diethyl ether) was added to a stirring solution of 3-(2-(4-fluorophenyl)-3-(methylcarbamoyl)benzofuran-5-yl)benzoic acid (100 mg, 0.257 mmol) in diethyl ether (2.5 mL) at 25° C. It was allowed to stir for 2 hours. The mixture was concentrated to afford the titled compound (100 mg, 97%). LC-MS retention time: 2.46 min; m/z (MH+): 404. LC data was recorded on a Shimadzu LC-10AS liquid chromatograph equipped with a Waters SunFire 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

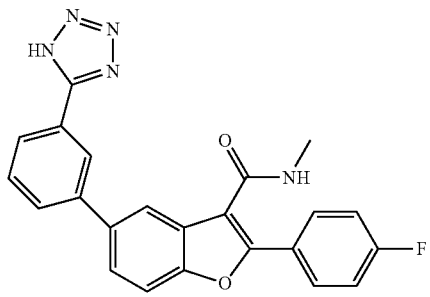

5-(3-(1H-tetrazol-5-yl)phenyl)-2-(4-fluorophenyl)-N-methylbenzofuran-3-carboxamide. Azidotrimethylsilane (161 μL, 1.215 mmol) was added to a stirring solution of 5-(3-cyanophenyl)-2-(4-fluorophenyl)-N-methylbenzofuran-3-carboxamide (225 mg, 0.607 mmol) and dibutylstannanone (30 mg, 0.121 mmol) in toluene (6 mL) at rt. It was heated to 105° C. and allowed to stir overnight. The reaction, which remained a slurry, resulted in ~70% conversion. Additonal equiv of reagents and solvents were added and the mixture was allowed to stir overnight at 105° C. The reaction was allowed to cool and filtered to give the titled compound (205 mg, 82%). LC-MS retention time: 1.03 min; m/z (MH+): 414. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

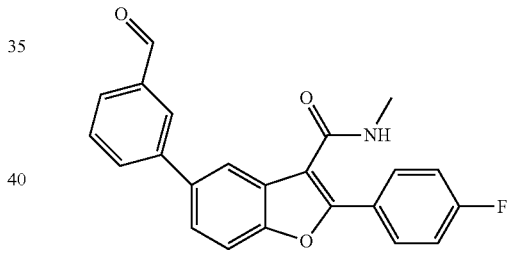

2-(4-fluorophenyl)-5-(3-formylphenyl)-N-methylbenzofuran-3-carboxamide. Cesium carbonate (176 mg, 0.539 mmol) was added to Pd(Ph3P)4 (20 mg, 0.018 mmol), 2-(4-fluorophenyl)-3-(methylcarbamoyl)benzofuran-5-yl trifluoromethanesulfonate (150 mg, 0.359 mmol), 3-formylphenylboronic acid (59 mg, 0.395 mmol). Dioxane (3 mL) and water (600 μL) was added at rt. The reaction was heated to 90° C. overnight. The mixture was diluted with ethyl acetate and washed with sat NaHCO3, and sat NaCl. The organic phase was dried over Na2SO4, filtered and concentrated and triturated with DCM to give the titled compound (55 mg, 41%). LC-MS retention time: 1.49 min; m/z (MH+): 374. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

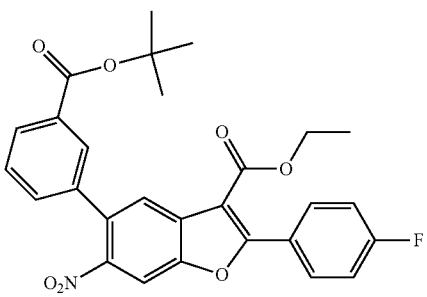

Ethyl 5-(3-(tert-butoxycarbonyl)phenyl)-2-(4-fluorophenyl)-6-nitrobenzofuran-3-carboxylate. Cesium carbonate (1.54 g, 4.71 mmol) was added to Pd(Ph3P)₄ (182 mg, 0.157 mmol), ethyl 2-(4-fluorophenyl)-6-nitro-5-(trifluoromethylsulfonyloxy)benzofuran-3-carboxylate (1500 mg, 3.14 mmol), 3-(tert-butoxycarbonyl)phenylboronic acid (768 mg, 3.46 mmol). Dioxane (26 mL) and water (5 mL) was added at rt. The reaction was heated to 90° C. overnight. The reaction was allowed to cool was diluted with EtOAc and washed with sat NaHCO3, and sat NaCl. The organic phase was dried over Na2SO4, filtered and concentrated and purified on silica gel (Biotage, EtOAc/hexanes gradient, fraction collection at λ=254 nm) to give to give the titled compound (1.10 g, 69%). ¹H NMR (300 MHz, DMSO-d₆) δ ppm 8.60 (1H, s), 8.08-8.18 (2H, m), 8.02 (1H, s), 7.95-8.01 (1H, m), 7.88 (1H, s), 7.58-7.70 (2H, m), 7.46 (2H, t, J=8.78 Hz), 4.34 (2H, q, J=7.20 Hz), 1.56 (9H, s), 1.27 (3H, t, J=7.14 Hz). LC-MS retention time: 2.13 min; m/z (MH+): parent does not ionize. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

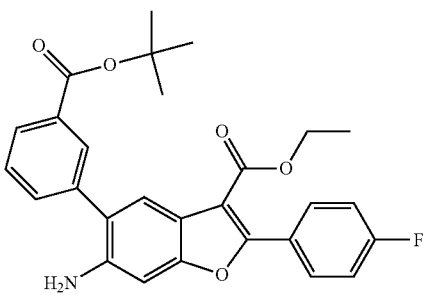

Ethyl 6-amino-5-(3-(tert-butoxycarbonyl)phenyl)-2-(4-fluorophenyl)benzofuran-3-carboxylate. Iron (28 mg, 0.495 mmol) was added to a stirring solution of ethyl 5-(3-(tert-butoxycarbonyl)phenyl)-2-(4-fluorophenyl)-6-nitrobenzofuran-3-carboxylate (50 mg, 0.099 mmol) in EtOH (495 μL) and AcOH (495 μL) at 100° C. It was allowed to stir for 1 hr. The mixture was diluted with EtOAc and washed with 1M HCl, and sat NaCl. The organic phase was dried over Na2SO4, filtered and concentrated to give the titled compound (45 mg, 96%). 1H NMR (400 MHz, DMSO-d₆) d ppm 7.99-8.06 (2H, m), 7.89-7.96 (2H, m), 7.65-7.72 (1H, m), 7.61 (1H, t, J=7.65 Hz), 7.55 (1H, s), 7.31-7.40 (2H, m), 7.00 (1H, s), 5.10 (2H, br. s.), 4.29 (2H, q, J=7.03 Hz), 1.56 (9H, s), 1.26 (3H, t, J=7.15 Hz). LC-MS retention time: 2.03 min; m/z (MH+): parent does not ionize. 420 (-tBu) was observed. LC data was recorded on a Shimadzu LC-10AS liquid chromatograph equipped with a Waters XBridge 5 u C18 4.6×50 mm column using a SPD-10AV UV-V is detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

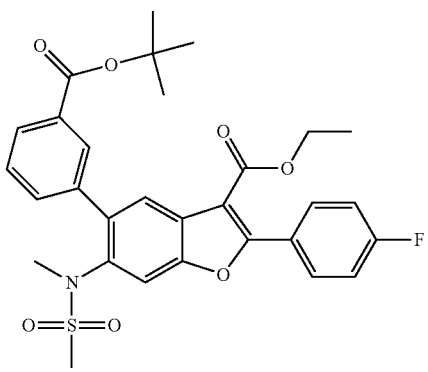

Ethyl 5-(3-(tert-butoxycarbonyl)phenyl)-2-(4-fluorophenyl)-6-(N-methylmethylsulfonamido)benzofuran-3-carboxylate. Step 1: Methanesulfonyl chloride (16 μL, 0.208 mmol) was added to a stirring solution of ethyl 6-amino-5-(3-(tert-butoxycarbonyl)phenyl)-2-(4-fluorophenyl)benzofuran-3-carboxylate (90 mg, 0.189 mmol) in pyridine (2 mL) at rt. It was allowed to stir for 6 hrs, then 8 uL of MsCl was added and the reaction was allowed to stir overnight. The reaction was concentrated and diluted with ethyl acetate and washed with sat NaHCO3, and sat NaCl. The organic phase was dried over Na2SO4, filtered and concentrated to give the NH sulfonamide intermediate. LC-MS retention time: 1.93 min; m/z (MH−): 552. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 mM where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Step 2: The crude residue was diluted with DMF (2 mL) and treated with DIEA (99 μL, 0.568 mmol) and Iodomethane (18 μL, 0.284 mmol) followed by Na2CO3 (20 mg). The reaction was allowed to stir for 3 days. The mixture was diluted with EtOAc and washed with sat NaHCO3, and sat NaCl. The organic phase was dried over Na2SO4, filtered and concentrated to give the titled compound (100 mg, 93%). LC-MS retention time: 1.96 min; m/z (MH+): the parent does not ionize. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

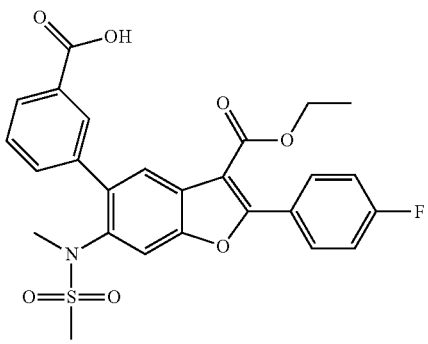

3-(3-(ethoxycarbonyl)-2-(4-fluorophenyl)-6-(N-methylmethylsulfonamido)benzofuran-5-yl)benzoic acid. TFA (2 mL, 26.0 mmol) was added to a stirring solution of ethyl 5-(3-(tert-butoxycarbonyl)phenyl)-2-(4-fluorophenyl)-6-(N-methylmethylsulfonamido)benzofuran-3-carboxylate (100 mg, 0.176 mmol) in DCE (9 mL) at 25° C. It was allowed to stir for several hours then concentrated to give the titled compound (92 mg, quant). $^1$H NMR (400 MHz, DMSO-$d_6$) δ ppm 8.05-8.12 (3H, m), 7.92-8.03 (3H, m), 7.65-7.75 (1H, m), 7.53-7.64 (1H, m), 7.44 (2H, t, J=8.91 Hz), 4.33 (2H, q, J=7.03 Hz), 3.12 (3H, s), 2.93 (3H, s), 1.26 (3H, t, J=7.15 Hz). LC-MS retention time: 1.17 min; m/z (MH−): 510. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

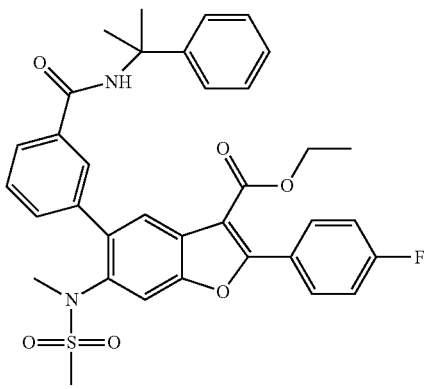

Ethyl 2-(4-fluorophenyl)-6-(N-methylmethylsulfonamido)-5-(3-(2-phenylpropan-2-ylcarbamoyl)phenyl)benzofuran-3-carboxylate. DIEA (51 μL, 0.293 mmol) was added to a stirring solution of 3-(3-(ethoxycarbonyl)-2-(4-fluorophenyl)-6-(N-methylmethylsulfonamido)benzofuran-5-yl)benzoic acid (50 mg, 0.098 mmol), 2-phenylpropan-2-amine (26 mg, 0.195 mmol), HATU (56 mg, 0.147 mmol) in DMF (1 mL) at 25° C. It was allowed to stir for 1 hour. The mixture was diluted with EtOAc and washed with 1M HCl, and sat NaCl. The organic phase was dried over Na2SO4, filtered and concentrated to give the titled compound (50 mg, 81%). LC-MS retention time: 1.82 min; m/z (MH+): 629. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

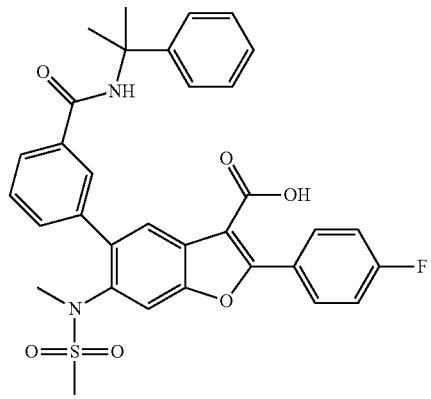

2-(4-fluorophenyl)-6-(N-methylmethylsulfonamido)-5-(3-(2-phenylpropan-2-ylcarbamoyl)phenyl)benzofuran-3-carboxylic acid. NaOH (500 μL, 0.500 mmol, 1M aq.) was added to a stirring solution of ethyl 2-(4-fluorophenyl)-6-(N-methylmethylsulfonamido)-5-(3-(2-phenylpropan-2-ylcarbamoyl)phenyl)benzofuran-3-carboxylate (50 mg, 0.080 mmol) in Ethanol (795 μL) at 60° C. The slurry was allowed to stir overnight. DMF (2 mL) was added along with additional portion of NaOH and the mixture was warmed to 70° C. and allowed to stir overnight. The mixture was diluted with EtOAc and washed with 1M HCl, and sat NaCl. The organic phase was dried over Na2SO4, filtered and concentrated to give the titled compound (49 mg, quant). LC-MS retention time: 2.36 min; m/z (MH+): 601. LC data was recorded on a Shimadzu LC-10AS liquid chromatograph equipped with a Waters SunFire 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

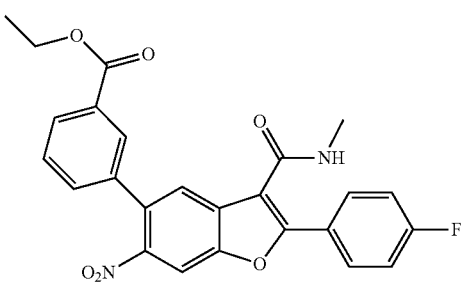

Ethyl 3-(2-(4-fluorophenyl)-3-(methylcarbamoyl)-6-nitrobenzofuran-5-yl)benzoate. Cesium carbonate (1.69 g, 5.19 mmol) was added to Pd(Ph3P)$_4$ (250 mg, 0.216 mmol), 2-(4-fluorophenyl)-3-(methylcarbamoyl)-6-nitrobenzofuran-5-yl trifluoromethanesulfonate (2.00 g, 4.33 mmol), 3-(ethoxycarbonyl)phenylboronic acid (1.01 g, 5.19 mmol). Dioxane (36 mL) and water (7 mL) was added at rt and the mixture was degassed 3×. The reaction was heated to 90° C. overnight. It was allowed to cool. The mixture was diluted with EtOAc and washed with 1M HCl, and sat NaCl. The organic phase was dried over Na2SO4, Tilt and concentrated. The crude solid was triturated with DCM to give the titled compound (1.70 g, 85%). 1H NMR (400 MHz, DMSO-d$_6$) δδ ppm 8.55-8.61 (1H, m), 8.54 (1H, s), 8.00-8.09 (3H, m), 7.95 (1H, s), 7.73 (1H, s), 7.61-7.70 (2H, m), 7.45 (2H, t, J=8.91 Hz), 4.35 (2H, q, J=7.19 Hz), 2.83 (3H, d, J=4.52 Hz), 1.34 (3H, t, J=7.03 Hz). LC-MS retention time: 1.62 min; m/z (MH+): 463. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

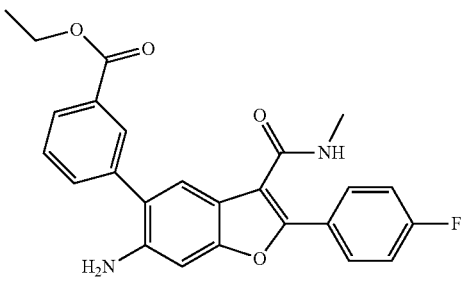

Ethyl 3-(6-amino-2-(4-fluorophenyl)-3-(methylcarbamoyl)benzofuran-5-yl)benzoate. Iron (1.03 g, 18.4 mmol) was added to a stirring solution of ethyl 3-(2-(4-fluorophenyl)-3-(methylcarbamoyl)-6-nitrobenzofuran-5-yl)benzoate (1.70 g, 3.68 mmol) in EtOH (37 mL) and AcOH (37 mL) at 90° C. The slurry was allowed to stir for 1 hour. The mixture was diluted with EtOAc and washed with 1M HCl, and sat NaCl followed by 1M NaOH and sat. NaCl. The organic phase was dried over Na2SO4, filtered and concentrated to give the titled compound (1.40 g 88%). $^1$H NMR (400 MHz, DMSO-d$_6$) δ ppm 8.25-8.34 (1H, m), 8.00-8.03 (1H, m), 7.87-7.99 (3H, m), 7.69-7.75 (1H, m), 7.63 (1H, t, J=7.65 Hz), 7.26-7.37 (2H, m), 7.20 (1H, s), 6.98 (1H, s), 5.07 (2H, s), 4.35 (2H, q, J=7.03 Hz), 2.78 (3H, d, J=4.52 Hz), 1.34 (3H, t, J=7.03 Hz). LC-MS retention time: 1.46 min; m/z (MH+): 433. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

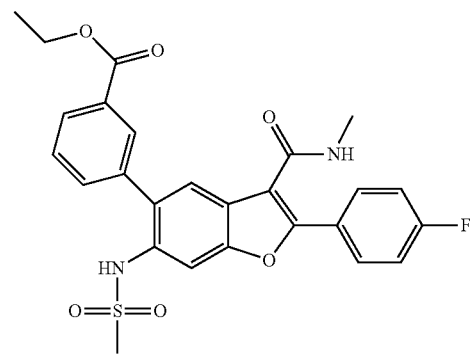

Ethyl 3-(2-(4-fluorophenyl)-3-(methylcarbamoyl)-6-(methylsulfonamido)benzofuran-5-yl)benzoate. Methanesulfonyl chloride (303 μL, 3.88 mmol) was added to a stirring solution of ethyl 3-(6-amino-2-(4-fluorophenyl)-3-(methylcarbamoyl)benzofuran-5-yl)benzoate (1.40 g, 3.24 mmol) in pyridine (32 mL) at 25° C. It was allowed to stir overnight at rt. The reaction was concentrated and was purified on silica gel (Biotage, EtOAc/hexanes gradient, fraction collection at λ=254 nm) to give the titled compound (1.01 g, 61%). LC-MS retention time: 1.53 min; m/z (MH+): 511. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

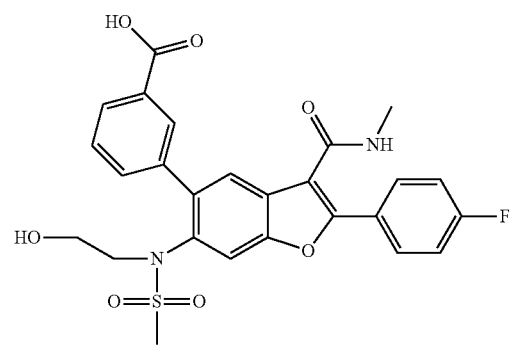

3-(2-(4-fluorophenyl)-6-(N-(2-hydroxyethyl)methylsulfonamido)-3-(methylcarbamoyl)benzofuran-5-yl)benzoic acid. Step 1: (2-bromoethoxy)(tert-butyl)dimethylsilane (189

μL, 0.881 mmol) was added to a stirring suspension of Na2CO3 (311 mg, 2.94 mmol) and ethyl 3-(6-(N-(2-(tert-butyldimethylsilyloxy)ethyl)methylsulfonamido)-2-(4-fluorophenyl)-3-(methylcarbamoyl)benzofuran-5-yl)benzoate in DMF (6 mL) at 100° C. It was allowed to stir for 5 hrs, and then allowed to cool to rt and stir overnight. The mixture was diluted with EtOAc and washed with sat NaHCO3, and sat NaCl. The organic phase was dried over Na2SO4, filtered and concentrated. LC-MS retention time: 2.12 min; m/z (MH+): 669. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Step 2: The residue was diluted with EtOH (10 mL) and treated with NaOH (2938 μL, 2.94 mmol) and allowed to stir at 60° C. for 4 hours. The mixture was diluted with EtOAc and washed with 1M HCl, and sat NaCl. The organic phase was dried over Na2SO4, filtered and concentrated. Step 3: The crude residue was taken up in THF and treated with 1M HCl (making it 30% in THF). The reaction was allowed to stir for 1 hour. The mixture was diluted with EtOAc and washed with 1M HCl, and sat NaCl. The organic phase was dried over Na2SO4, filtered and concentrated to give the titled compound (300 mg, 97%). LC-MS retention time: 1.09 min; m/z (MH+): 527. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

N-(2-(4-fluorophenyl)-5-isopropoxy-3-(1H-1,2,4-triazol-5-yl)benzofuran-6-yl)methanesulfonamide and N-(2-(4-fluorophenyl)-5-isopropoxy-3-(1H-1,2,4-triazol-5-yl)benzofuran-6-yl)-N-methylmethanesulfonamide. N,N-Dimethylformamide dimethyl acetal (500 μL, 3.76 mmol) and 2-(4-fluorophenyl)-5-isopropoxy-6-(methylsulfonamido)benzofuran-3-carboxamide (100 mg, 0.246 mmol) were combined and heated to 85° C. DMF (1 mL) was added. It was allowed to stir for 1 hr. The mixture was concentrated and diluted with dioxane (200 μl), acetic acid (1 ml) and treated with hydrazine (154 μL, 4.92 mmol) and heated at 85° C. for several hours. The mixture was diluted with EtOAc and washed with sat NaHCO3, and sat NaCl. The organic phase was dried over Na2SO4, filtered and concentrated. The crude residue was purified by preparative reverse phase HPLC on a C18 column using a suitably buffered gradient, and concentrated to give to give N-(2-(4-fluorophenyl)-5-isopropoxy-3-(1H-1,2,4-triazol-5-yl)benzofuran-6-yl)methanesulfonamide (25 mg, 0.058 mmol) and N-(2-(4-fluorophenyl)-5-isopropoxy-3-(1H-1,2,4-triazol-5-yl)benzofuran-6-yl)-N-methylmethanesulfonamide (11 mg, 0.025 mmol). N-(2-(4-fluorophenyl)-5-isopropoxy-3-(1H-1,2,4-triazol-5-yl) benzofuran-6-yl)methanesulfonamide. 1H NMR (300 MHz, DMSO-D6) δ ppm 1.30-1.42 (m, 6H) 2.99 (s, 3H) 4.57-4.73 (m, 1H) 7.24-7.40 (m, 2H) 7.57 (s, 1H) 7.67 (s, 1H) 8.06-8.22 (m, 2H) 8.68 (s, 1H). LC-MS retention time: 1.30 min; m/z (MH+): 431. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC were performed using a Shimadzu-VP instrument with UV detection at 220 nm and 254 nm. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, $R_t$=10.71 min, purity=94%; Column: Waters Xbridge Phenyl column 4.6×150 mm, 3.5 μm, $R_t$=9.74 min, purity=97%. N-(2-(4-fluorophenyl)-5-isopropoxy-3-(1H-1,2,4-triazol-5-yl)benzofuran-6-yl)-N-methylmethanesulfonamide. 1H NMR (300 MHz, DMSO-D6) δ ppm 1.29-1.41 (m, 6H) 3.04 (s, 3H) 3.19-3.24 (m, 3H) 4.61-4.80 (m, 1H) 7.28-7.39 (m, 2H) 7.61 (s, 1H) 7.76 (s, 1H) 8.08-8.27 (m, 2 H) 8.78 (s, 1H) 14.34 (s, 1H). LC-MS retention time: 1.36 min; m/z (MH+) 345. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters

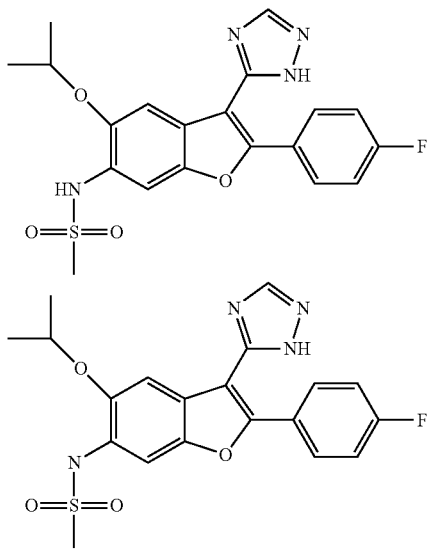

Sunfire C-18, 4.6×150 mm, 3.5 μm, $R_t$=11.30 min, purity=>95%; Column: Waters Xbridge Phenyl column 4.6×150 mm, 3.5 μm, $R_t$=10.21 min, purity=>95%.

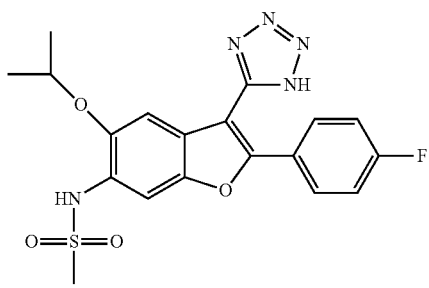

N-(2-(4-fluorophenyl)-5-isoprop oxy-3-(1H-1,2,4-triazol-5-yl)benzofuran-6-yl)methanesulfonamide. Azidotrimethylsilane (34.2 μL, 0.257 mmol) was added to a stirring solution of dibutyltin oxide (6.41 mg, 0.026 mmol) and N-(3-cyano-2-(4-fluorophenyl)-5-isopropoxybenzofuran-6-yl)methanesulfonamide (50 mg, 0.129 mmol) in dioxane (1.3 mL) at rt. It was subjected to microwave irradiation for 15 min at 150° C. It was treated with additional equivalents of reagents and re-subjected for 30 min followed by 60 min. The mixture was concentrated and purified by preparative reverse phase HPLC on a C18 column using a suitably buffered gradient, and concentrated to give the titled compound (12 mg, 22%). $^1$H NMR (300 MHz, DMSO-D6) δ ppm 1.29-1.39 (m, 6H) 3.01 (s, 3H) 4.62-4.81 (m, 1H) 7.28-7.45 (m, 3H) 7.65 (s, 1H) 7.84-7.98 (m, 2H) 8.92 (s, 1H). LC-MS retention time: 1.04 min; m/z (MH+): 432. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, $R_t$=11.56 min, purity=94%; Column: Waters Xbridge Phenyl column 4.6×150 mm, 3.5 μm, $R_t$=10.55 min, purity=96%.

General Procedure: m-Amide Coupling. DIEA (36 μL, 0.205 mmol) was added to a stirring solution of HATU (59 mg, 0.154 mmol), the appropriate amine (0.164 mmol), and 3-(2-(4-fluorophenyl)-3-(methylcarbamoyl)benzofuran-5-yl)benzoic acid (40 mg, 0.103 mmol) in DMF (1 mL) at room temperature. It was allowed to stir overnight. The reaction was concentrated and purified by preparative reverse phase HPLC on a C18 column using a suitably buffered H$_2$O/CH$_3$CN gradient, and concentrated to give the expected product. This general procedure was applied to Examples KP4 through KP14.

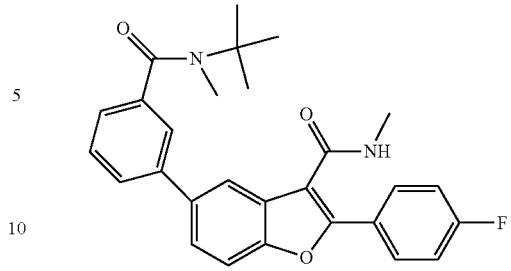

5-(3-(tert-butylmethyl)carbamoyl)phenyl)-2-(4-fluorophenyl)-N-methylbenzofuran-3-carboxamide. 1H NMR (500 MHz, CD$_3$OD) δ ppm 1.54-1.57 (m, 9H) 2.94-2.99 (m, 6H) 7.25 (t, 2H) 7.35-7.40 (m, 1H) 7.53 (t, 1H) 7.64-7.67 (m, 2H) 7.67-7.68 (m, 1H) 7.72-7.77 (m, 1H) 7.88-7.90 (m, 1H) 7.92-7.97 (m, 2H). LC-MS retention time: 1.71 min; m/z (MH+): 459. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

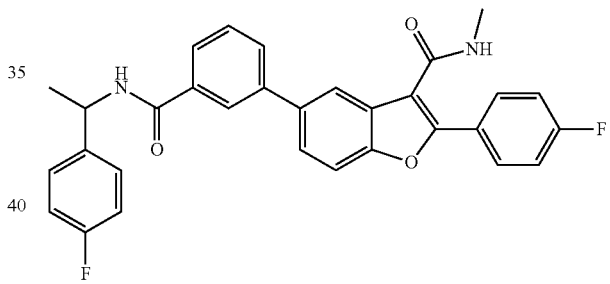

2-(4-fluorophenyl)-5-(3-(1-(4-fluorophenyl)ethylcarbamoyl)phenyl)-N-methylbenzofuran-3-carboxamide. 1H NMR (500 MHz, CD$_3$OD) δ ppm 8.10-8.15 (1H, m), 7.90-7.99 (3H, m), 7.84 (2H, t, J=9.61 Hz), 7.63-7.72 (2H, m), 7.56 (1H, t, J=7.78 Hz), 7.40-7.47 (2H, m), 7.22-7.29 (2H, m), 7.03-7.10 (2H, m), 5.24-5.30 (1H, m), 2.97 (3H, s), 1.59 (3H, d, J=7.02 Hz). LC-MS retention time: 1.67 min; m/z (MH−): 509. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18,

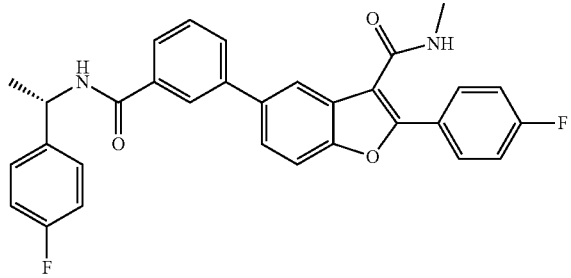

(S)-2-(4-fluorophenyl)-5-(3-(1-(4-fluorophenyl)ethylcarbamoyl)phenyl)-N-methylbenzofuran-3-carboxamide. 1H NMR (500 MHz, CD$_3$OD) δ ppm 8.13 (1H, s), 7.91-7.99 (3H, m), 7.84 (2H, t, J=9.31 Hz), 7.64-7.72 (2H, m), 7.56 (1H, t, J=7.78 Hz), 7.41-7.48 (2H, m), 7.26 (2H, t, J=8.85 Hz), 7.02-7.10 (2H, m), 5.28 (1H, q, J=7.22 Hz), 2.97 (3H, s), 1.59 (3H, d, J=7.02 Hz). LC-MS retention time: 1.67 min; m/z (MH−): 509. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18, 4.6×150 mm, 3 μm, R$_t$=15.55 min, purity=99%; Column: Waters Xbridge Phenyl column 4.6×150 mm, 3.5 μm, R$_t$=15.34 min, purity=98%.

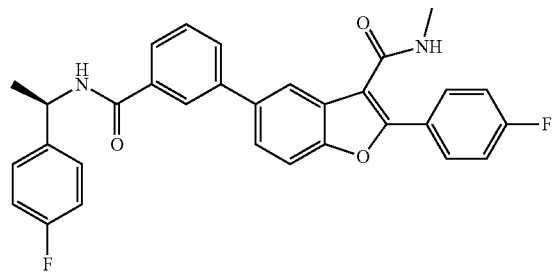

(R)-2-(4-fluorophenyl)-5-(3-(1-(4-fluorophenyl)ethylcarbamoyl)phenyl)-N-methylbenzofuran-3-carboxamide. 1H NMR (500 MHz, CD$_3$OD) δ ppm 8.14 (1H, s), 7.92-7.99 (3H, m), 7.81-7.87 (2H, m), 7.65-7.72 (2H, m), 7.57 (1H, t, J=7.63 Hz), 7.42-7.47 (2H, m), 7.23-7.29 (2H, m), 7.04-7.10 (2H, m), 5.28 (1H, q, J=7.02 Hz), 2.97 (3H, s), 1.59 (3H, d, J=7.02 Hz). LC-MS retention time: 1.66 min; m/z (MH−): 509. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18, 4.6×150 mm, 3 μm, R$_t$=15.56 min, purity=99%; Column: Waters Xbridge Phenyl column 4.6×150 mm, 3.5 μm, R$_t$=15.33 min, purity=97%.

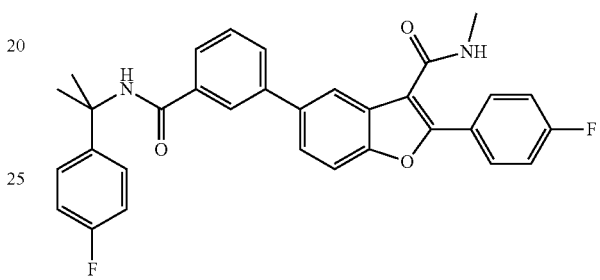

2-(4-fluorophenyl)-5-(3-(2-(4-fluorophenyl)propan-2-ylcarbamoyl)phenyl)-N-methylbenzofuran-3-carboxamide.
1H NMR (500 MHz, CD$_3$OD) δ ppm 8.04-8.10 (1H, m), 7.89-7.99 (3H, m), 7.76-7.86 (2H, m), 7.63-7.73 (2H, m), 7.56 (1 H, t, J=7.78 Hz), 7.42-7.51 (2H, m), 7.26 (2H, t, J=8.70 Hz), 6.98-7.06 (2H, m), 2.98 (3H, s), 1.78 (6H, s). LC-MS retention time: 1.72 min; m/z (MH−): 523. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18, 4.6×150 mm, 3 μm, R$_t$=15.73 min, purity=99%; Column: Waters Xbridge Phenyl column 4.6×150 mm, 3.5 μm, R$_t$=15.53 min, purity=99%.

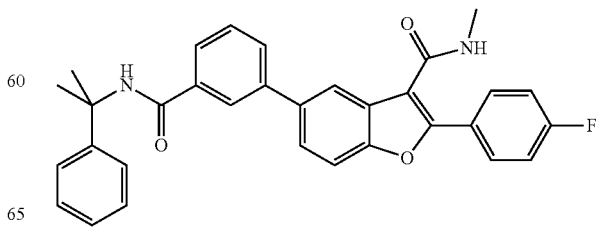

2-(4-fluorophenyl)-N-methyl-5-(3-(2-phenylpropan-2-yl-carbamoyl)phenyl)benzofuran-3-carboxamide. 1H NMR (500 MHz, CD$_3$OD) δ ppm 8.09 (1H, s), 7.90-7.99 (3H, m), 7.74-7.89 (1H, m), 7.63-7.72 (2H, m), 7.55 (1H, t, J=7.63 Hz), 7.47 (2H, d, J=7.32 Hz), 7.31 (2H, t, J=7.78 Hz), 7.22-7.28 (2H, m), 7.19 (1H, t, J=7.32 Hz), 2.97 (3H, s), 1.79 (6H, s). LC-MS retention time: 1.71 min; m/z (MH−): 505. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18, 4.6×150 mm, 3 μm, R$_t$=15.79 min, purity=99%; Column: Waters Xbridge Phenyl column 4.6×150 mm, 3.5 μm, R$_t$=15.53 min, purity=98%.

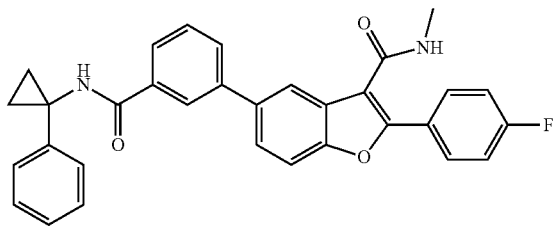

2-(4-fluorophenyl)-N-methyl-5-(3-(1-phenylcyclopropyl-carbamoyl)phenyl)benzofuran-3-carboxamide. 1H NMR (500 MHz, DMSO-d$_6$) δ ppm 9.35 (1H, s), 8.48-8.56 (1H, m), 8.24 (1H, s), 7.96-8.04 (2H, m), 7.87-7.96 (3H, m), 7.75-7.82 (2H, m), 7.59 (1H, t, J=7.63 Hz), 7.40 (2H, t, J=8.70 Hz), 7.21-7.29 (4H, m), 7.16 (1H, t, J=7.17 Hz), 2.86 (3H, d, J=4.58 Hz), 1.25-1.35 (4H, m). LC-MS retention time: 1.63 min; m/z (MH−): 503. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1-C-18, 4.6×150 mm, 3 μm, R$_t$=15.91 min, purity=96%; Column: Waters Xbridge Phenyl column 4.6×150 mm, 3.5 μm, R$_t$=15.79 min, purity=95%.

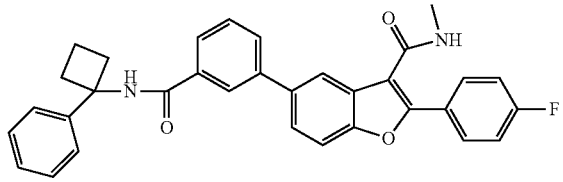

2-(4-fluorophenyl)-N-methyl-5-(3-(1-phenylcyclobutyl-carbamoyl)phenyl)benzofuran-3-carboxamide. 1H NMR (500 MHz, DMSO-d$_6$) δ ppm 9.18 (1H, s), 8.53 (1H, q, J=4.48 Hz), 8.20 (1H, s), 8.01 (2H, dd, J=8.85, 5.49 Hz), 7.92 (1H, d, J=1.22 Hz), 7.87 (2H, dd, J=7.63, 1.53 Hz), 7.73-7.83 (2H, m), 7.57 (1H, t, J=7.78 Hz), 7.52 (2H, d, J=7.32 Hz), 7.40 (2H, t, J=9.00 Hz), 7.33 (2H, t, J=7.78 Hz), 7.20 (1H, t, J=7.32 Hz), 2.87 (3H, d), 2.61-2.71 (2H, m), 2.54-2.58 (2H, m), 2.01-2.11 (1H, m), 1.82-1.92 (1H, m). LC-MS retention time 2.42 min; m/z (MH+): 519. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=14.66 min, purity=97%; Column: Waters Xbridge Phenyl column 4.6×150 mm, 3.5 μm, R$_t$=13.13 min, purity=97%.

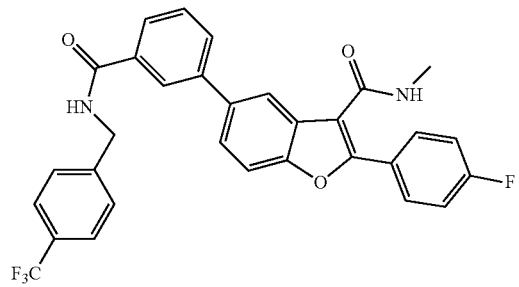

N-(2-(4-fluorophenyl)-5-isopropoxy-3-(1H-1,2,4-triazol-5-yl)benzofuran-6-yl)methanesulfonamide. $^1$H NMR (500 MHz, DMSO-d$_6$) δ ppm 11.03 (1H, s), 7.92-8.01 (2H, m), 7.86 (1H, d, J=9.16 Hz), 7.42 (2H, t, J=8.85 Hz), 7.17 (1H, d, J=8.85 Hz), 4.20 (2H, q, J=7.12 Hz), 1.21 (3H, t, J=7.17 Hz).). LC-MS retention time: 1.70 min; m/z (MH+): 547. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, $R_t$=14.86 min, purity=99%. Additional HPLC method 2: Solvent A=5% MeOH/95% H₂O/10 mM ammonium bicarbonate, Solvent B=95% MeOH/5% H₂O/10 mM ammonium bicarbonate, Start % B=10, Final % B=100, Gradient time=15 min, Stop time=18 min, Flow Rate=1 ml/min. Column: Phenomenex Gemini C-18, 4.6×150 mm, 3 µm, $R_t$=17.53 min, purity=99%.

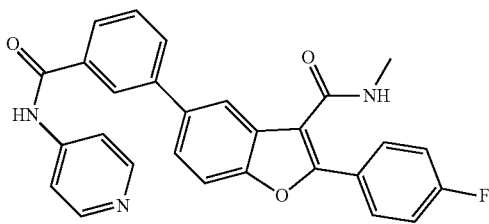

2-(4-fluorophenyl)-N-methyl-5-(3-(pyridin-4-ylcarbamoyl)phenyl)benzofuran-3-carboxamide. 1H NMR (500 MHz, DMSO-d₆) δ ppm 11.15 (1H, s), 8.64 (2H, d, J=6.41 Hz), 8.48-8.55 (1H, m), 8.30 (1H, s), 8.05-8.08 (2H, m), 7.97-8.03 (6H, m), 7.76-7.85 (2H, m), 7.71 (1H, t, J=7.78 Hz), 7.41 (2H, t, J=8.70 Hz), 2.83-2.92 (3H, m). LC-MS retention time: 1.45 min; m/z (MH+): 466. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H₂O/10 mM ammonium bicarbonate, Solvent B=95% MeOH/5% H₂O/10 mM ammonium bicarbonate, Start % B=10, Final % B=100, Gradient time=15 min, Stop time=18 min, Flow Rate=1 ml/min. Column: Phenomenex Gemini C-18, 4.6×150 mm, 3 µm, $R_t$=15.11 min, purity=97%; Column: Waters Xbridge Phenyl column 4.6× 150 mm, 3.5 µm, $R_t$=14.81 min, purity=96%.

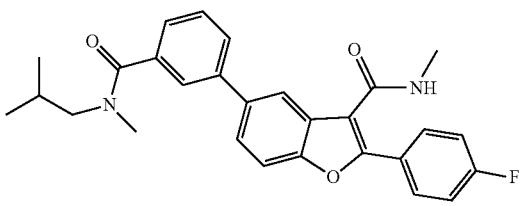

2-(4-fluorophenyl)-5-(3-(isobutyl(methyl)carbamoyl) phenyl)-N-methylbenzofuran-3-carboxamide. ¹H NMR (500 MHz, CD₃OD) δ ppm 7.93-7.98 (2H, m), 7.88-7.91 (1H, m), 7.74-7.81 (1H, m), 7.63-7.70 (3H, m), 7.51-7.60 (1H, m), 7.32-7.41 (1H, m), 7.25 (2H, t), 3.43 (1H, d), 3.21 (1H, d), 3.10 (2 H, s), 3.03 (2H, s), 2.96 (3H, s), 2.10-2.21 (1H, m), 1.92-2.07 (1H, m), 1.01 (3 H, d), 0.78 (3H, d). LC-MS retention time: 1.65 min; m/z (MH+): 459. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

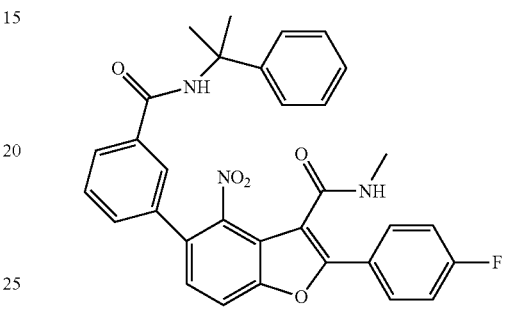

2-(4-fluorophenyl)-N-methyl-4-nitro-5-(3-(2-phenylpropan-2-ylcarbamoyl)phenyl)benzofuran-3-carboxamide. Step 1: ethyl 2-(4-fluorophenyl)-4-nitro-5-(3-(2-phenylpropan-2-ylcarbamoyl)phenyl)benzofuran-3-carboxylate (300 mg, 0.529 mmol) was diluted with EtOH (10 mL) and treated with NaOH (2.1 mL, 2.12 mmol, 1N aq.) and the mixture, which became a slurry, was allowed to stir overnight at 60° C. The reaction was diluted with EtOAc and washed with 1M HCl, and sat NaCl. The organic phase was dried over Na2SO4, filtered and concentrated. Step 2: EDC (128 mg, 0.668 mmol) was added to a stirring solution of the crude 2-(4-fluorophenyl)-4-nitro-5-(3-(2-phenylpropan-2-ylcarbamoyl)phenyl) benzofuran-3-carboxylic acid (300 mg, 0.557 mmol), methanamine (306 µL, 0.613 mmol), 1-hydroxy-7-azabenzotriazole (83 mg, 0.613 mmol), DIEA (204 µL, 1.170 mmol) in DCM (5.5 mL) at rt. It was allowed to stir for 3 days. The slurry had gone into solution over that period of time. The mixture was concentrated and purified on silica gel (Biotage, EtOAc/hexanes gradient, fraction collection at λ=254 nm) to give the titled compound (220 mg, 95%). 1H NMR (500 MHz, CD₃OD) δ ppm 7.90-7.99 (3H, m), 7.85-7.90 (1H, m), 7.82-7.84 (1H, m), 7.49-7.56 (3H, m), 7.45 (2 H, d, J=7.32 Hz), 7.27-7.34 (4H, m), 7.19 (1H, t, J=7.32 Hz), 2.87 (3H, s), 1.76 (6 H, s). LC-MS retention time: 1.62 min; m/z (MH+): 552. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, $R_t$=13.60 min,

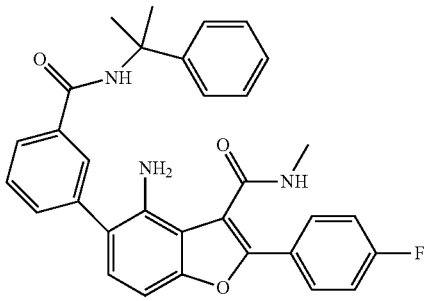

4-amino-2-(4-fluorophenyl)-N-methyl-5-(3-(2-phenyl-propan-2-ylcarbamoyl)phenyl)benzofuran-3-carboxamide. Iron (25 mg, 0.453 mmol) was added to a stirring solution of 2-(4-fluorophenyl)-N-methyl-4-nitro-5-(3-(2-phenylpropan-2-ylcarbamoyl)phenyl)benzofuran-3-carboxamide (50 mg, 0.091 mmol) in ethanol (1 mL) and AcOH (1 mL) at rt. It was placed in a reaction block set to 100° C. It was allowed to stir for 1 hr. The mixture was allowed to cool and was diluted with EtOAc and washed with 1M HCl, followed by 1N NaOH and sat NaCl. The organic phase was dried over Na2SO4, filtered and concentrated and triturated with Et2O to give the titled compound (28 mg, 56%). $^1$H NMR (300 MHz, CD$_3$OD) δ ppm 7.83-7.89 (1H, m), 7.73-7.81 (3H, m), 7.52-7.64 (2H, m), 7.42-7.49 (2H, m), 7.10-7.35 (6H, m), 6.98 (1H, d, J=8.42 Hz), 2.87 (3H, s), 1.76 (6H, s). LC-MS retention time: 2.33 min; m/z (MH+): 522. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=14.17 min, purity=97%; Column: Waters Xbridge Phenyl column 4.6×150 mm, 3.5 μm, R$_t$=12.84 min, purity=98%.

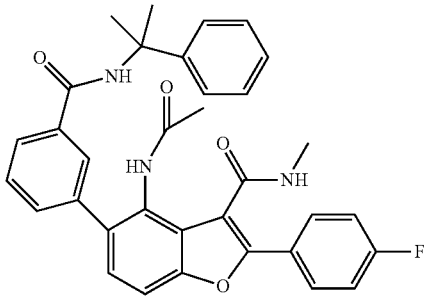

4-acetamido-2-(4-fluorophenyl)-N-methyl-5-(3-(2-phenylpropan-2-ylcarbamoyl)phenyl)benzofuran-3-carboxamide. 4-amino-2-(4-fluorophenyl)-N-methyl-5-(3-(2-phenylpropan-2-ylcarbamoyl)phenyl)benzofuran-3-carboxamide (20 mg, 0.038 mmol) was diluted in pyridine (1 mL) and treated with excess acetyl chloride (10 μL). The reaction was allowed to stir for 2 hours. The mixture was concentrated and diluted with MeOH (1 mL). The product began to crash out, it was sonicated and filtered and washed with MeOH to afford the titled compound (8 mg, 34%). 1H NMR (500 MHz, DMSO-d$_6$) δ ppm 9.41 (1H, s), 8.43 (1H, s), 8.31-8.38 (1H, m), 7.88-7.92 (1H, m), 7.82-7.87 (2H, m), 7.80 (1H, d, J=7.63 Hz), 7.71 (1H, d, J=8.55 Hz), 7.54-7.60 (1H, m), 7.43-7.49 (2H, m), 7.36-7.43 (5H, m), 7.28 (2H, t, J=7.78 Hz), 7.17 (1H, t, J=7.32 Hz), 2.76 (3H, d), 1.79 (3H, s), 1.69 (6H, s). LC-MS retention time 1.42 min; m/z 564 (MH+). LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=12.00 min, purity=96%; Column: Waters Xbridge Phenyl column 4.6×150 mm, 3.5 μm, R$_t$=11.26 min, purity=95%.

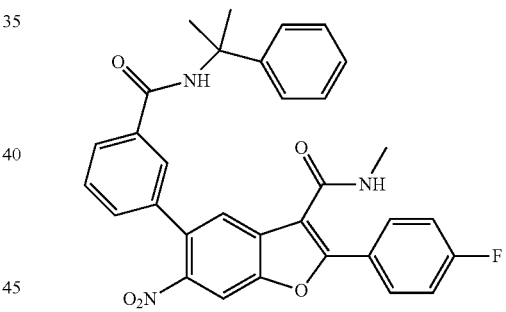

2-(4-fluorophenyl)-N-methyl-6-nitro-5-(3-(2-phenylpropan-2-ylcarbamoyl)phenyl)benzofuran-3-carboxamide. Step 1: cesium carbonate (143 mg, 0.440 mmol) was added to Pd(Ph3P)4 (17 mg, 0.015 mmol), ethyl 2-(4-fluorophenyl)-6-nitro-5-(trifluoromethylsulfonyloxy)benzofuran-3-carboxylate (140 mg, 0.293 mmol), 3-boronobenzoic acid (73 mg, 0.440 mmol). Dioxane (2.5 mL) and water (500 μL) was added at rt. The reaction was degassed 3× and heated to 90° C. overnight. It was allowed to cool. The mixture was diluted with EtOAc and washed with 1M HCl, and sat NaCl. The organic phase was dried over Na2SO4, filtered and concentrated. Step 2: The residue was diluted with DMF and treated with HATU (167 mg, 0.440 mmol), 2-phenylpropan-2-amine (60 mg, 0.440 mmol), and DIEA (154 μL, 0.880 mmol) and allowed to stir at rt overnight. The mixture was diluted with EtOAc and washed with sat NaHCO3, and sat NaCl. The organic phase was dried over Na2SO4, filtered and concentrated and purified on silica gel (Biotage, EtOAc/hexanes gradient, fraction collection at λ=254 nm) to give ethyl 2-(4-fluorophenyl)-6-nitro-5-(3-(2-phenylpropan-2-ylcarbamoyl)phenyl)benzofuran-3-carboxylate. (LC-MS retention time: 1.97 min; m/z (MH+): 567. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode) Step 3: This material was treated with NaOH (1 mL, 1.000 mmol) in ethanol (2.93 mL) at 60° C. for 2 hr then allowed to stir overnight while cooling to rt. The reaction was heated to 60° C. for 3 hrs. The mixture was diluted with EtOAc and washed with 1M HCl, and sat NaCl. The organic phase was dried over Na2SO4, filtered and concentrated. Step 4: EDC (58 mg, 0.301 mmol), methanamine (1 mL, 2.000 mmol), 1-hydroxy-7-azabenzotriazole (38 mg, 0.276 mmol), DIEA (92 µL, 0.526 mmol) was added to the residue in DCE (2.5 mL) at rt. It was allowed to stir for 3 days. The slurry had gone into solution over that period of time. The crude reaction was purified on silica gel (Biotage, EtOAc/hexanes gradient, fraction collection at λ=254 nm) to give the titled compound (112 mg, 81%). 1H NMR (500 MHz, CD3OD) δ ppm 8.32 (1H, s), 7.97-8.06 (2H, m), 7.82-7.90 (2H, m), 7.75 (1H, s), 7.47-7.56 (2H, m), 7.45 (2H, d, J=7.32 Hz), 7.31 (4H, t, J=8.09 Hz), 7.18 (1H, t, J=7.32 Hz), 2.94 (3H, s), 1.77 (6H, s). LC-MS retention time: 3.10 min; m/z (MH+): 552. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R_t=14.12 min, purity=96%; Column: Waters Xbridge Phenyl column 4.6×150 mm, 3.5 µm, R_t=12.98 min, purity=97%.

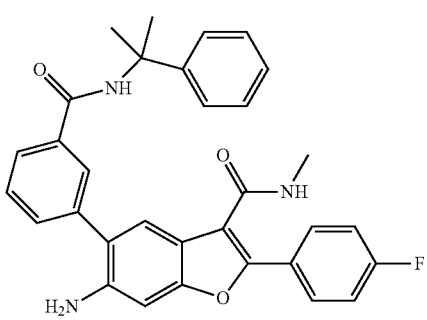

6-amino-2-(4-fluorophenyl)-N-methyl-5-(3-(2-phenyl-propan-2-ylcarbamoyl)phenyl)benzofuran-3-carboxamide. Iron (68 mg, 1.22 mmol) was added to a stirring solution of 2-(4-fluorophenyl)-N-methyl-6-nitro-5-(3-(2-phenylpropan-2-ylcarbamoyl)phenyl)benzofuran-3-carboxamide (112 mg, 0.203 mmol) in ethanol (2.3 mL) and AcOH (2.3 mL) at rt. It was placed in a reaction block set to 100° C. and allowed to stir for 1 hr. The mixture was allowed to cool and was diluted with EtOAc and washed with 1M HCl, followed by 1N NaOH and sat NaCl. The organic phase was dried over Na2SO4, filtered and concentrated and triturated with Et2O to give the titled compound (52 mg, 47%). 1H NMR (500 MHz, CD3OD) δ ppm 6.58-6.65 (3H, m), 6.52 (1H, d, J=7.63 Hz), 6.37 (1H, d, J=7.93 Hz), 6.30 (1H, t, J=7.63 Hz), 6.18 (2H, d, J=7.32 Hz), 6.08 (1H, s), 6.03 (2H, t, J=7.78 Hz), 5.88-5.97 (3H, m), 5.73 (1H, s), 1.65 (3H, s), 0.50 (6H, s). LC-MS retention time 1.54 min; m/z (MH−): 520. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R_t=15.11 min, purity=95%; Column: Waters Xbridge Phenyl column 4.6×150 mm, 3.5 µm, R_t=11.11 min, purity=94%.

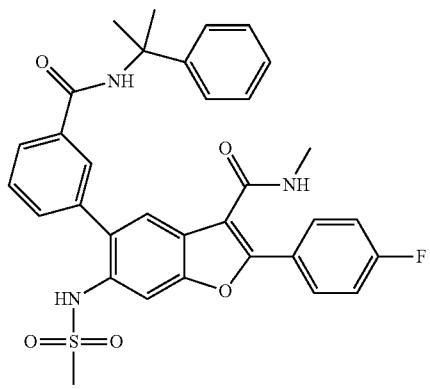

2-(4-fluorophenyl)-N-methyl-6-(methylsulfonamido)-5-(3-(2-phenylpropan-2-ylcarbamoyl)phenyl)benzofuran-3-carboxamide. Step 1: DIEA (134 µL, 0.765 mmol) was added to Pd(Ph3P)4 (30 mg, 0.025 mmol), 2-(4-fluorophenyl)-3-(methylcarbamoyl)-6-(N-(methylsulfonyl)methylsulfonamido)benzofuran-5-yl trifluoromethanesulfonate (150 mg, 0.255 mmol), 3-(ethoxycarbonyl)phenylboronic acid (74 mg, 0.382 mmol). Dioxane (5 mL) and water (1 mL) was added at rt. The reaction was degassed 3× and heated to 90° C. overnight. It was allowed to cool and left to stir for 3 days at rt. Step 2: The mixture was concentrated and diluted with EtOH (5 mL) and treated with excess 1N NaOH (~1 mL) and allowed to stir at rt overnight to give the meta-acid. The mixture was diluted with EtOAc and washed with 1M HCl, and 1M HCl. The organic phase was dried over Na2SO4, filtered and concentrated. Step 3: The crude residue was diluted with DMF (5 mL) and treated with HATU (145 mg, 0.382 mmol), 2-phenylpropan-2-amine (52 mg, 0.382 mmol)

and DIEA (134 μL, 0.765 mmol) and allowed to stir at rt overnight. The mixture was concentrated and purified by preparative reverse phase HPLC on a C18 column using a suitably buffered gradient, and concentrated. The isolated titled compound was re-purified on silica gel (Biotage, EtOAc/hexanes gradient, Rf ~0.2 50% EtOAc/hexanes, fraction collection at λ=254 nm) to give the titled compound (7 mg, 4%). 1H NMR (500 MHz, CD$_3$OD) δ ppm 7.94-8.01 (2H, m), 7.92 (1H, s), 7.83 (1H, d, J=7.63 Hz), 7.77 (1H, s), 7.63-7.68 (2H, m), 7.59 (1H, t, J=7.63 Hz), 7.46 (2H, d, J=7.32 Hz), 7.24-7.32 (4H, m), 7.18 (1H, t, J=7.32 Hz), 2.94 (3H, s), 2.88 (3H, s), 1.77 (6H, s). LC-MS retention time: 2.25 min; m/z (MH+): 600. LC data was recorded on a Shimadzu LC-10AS liquid chromatograph equipped with a Waters SunFire 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/0.1% TFA and solvent B was 5% H2O/95% acetonitrile/0.1% TFA. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=12.87 min, purity=96%; Column: Waters Xbridge Phenyl column 4.6×150 mm, 3.5 μm, R$_t$=11.97 min, purity=98%.

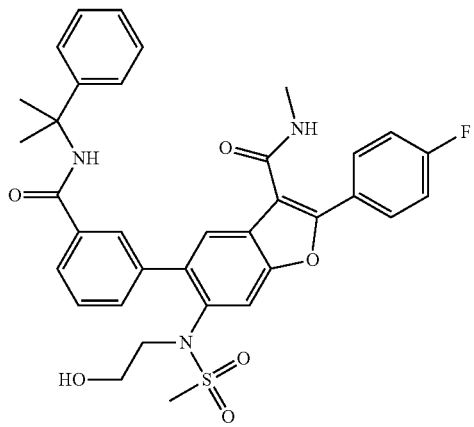

2-(4-fluorophenyl)-6-(N-(2-hydroxyethyl)methylsulfonamido)-N-methyl-5-(3-(2-phenylpropan-2-ylcarbamoyl)phenyl)benzofuran-3-carboxamide. Step 1: methanesulfonyl chloride (10 μL, 0.128 mmol) was added to a stirring solution of 6-amino-2-(4-fluorophenyl)-N-methyl-5-(3-(2-phenylpropan-2-ylcarbamoyl)phenyl)benzofuran-3-carboxamide (50 mg, 0.096 mmol) in pyridine (1 mL) at rt. It was allowed to stir for 2 hours and then concentrated and diluted with EtOAc and washed with sat NaHCO3, and sat NaCl. The organic phase was dried over Na2SO4, filtered and concentrated. Step 2: The crude residue was dissolved in DMF (1 mL) and treated with (2-bromoethoxy)(tert-butyl)dimethylsilane (102 μL, 0.479 mmol) and Na2CO3 (31 mg, 0.288 mmol) at rt. It was heated to 100° C. for 4 hours and then diluted with EtOAc and washed with sat NaHCO3, and sat NaCl. The organic phase was dried over Na2SO4, filtered and concentrated. Step 3: The crude residue was taken up in THF (2 mL) and treated with 2 mL of 1N HCl. and allowed to stir at rt for 1 hr. The mixture was diluted with EtOAc and washed with sat NaHCO3, and sat NaCl. The organic phase was dried over Na2SO4, filtered and concentrated and triturated with Et2O to give the titled compound (25 mg, 39%). 1H NMR (500 MHz, CD$_3$OD) δ ppm 8.14-8.21 (1H, m), 7.95-8.04 (2H, m), 7.83-7.87 (1H, m), 7.76-7.81 (1H, m), 7.66-7.74 (2H, m), 7.56 (1H, t, J=7.63 Hz), 7.41-7.49 (2H, m), 7.24-7.33 (4H, m), 7.17 (1H, t, J=7.32 Hz), 2.94 (3H, s), 1.76 (6H, s). LC-MS retention time 1.42 min; m/z (MH+): 644. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=12.26 min, purity=96%; Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C-18, 4.6×150 mm, 3 μm, R$_t$=13.61 min, purity=94%.

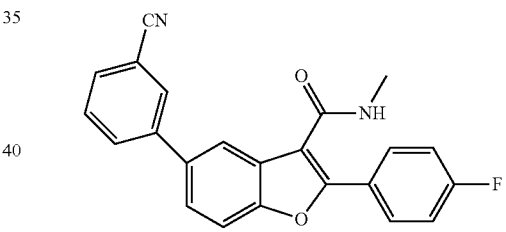

5-(3-cyanophenyl)-2-(4-fluorophenyl)-N-methylbenzofuran-3-carboxamide. Cesium carbonate (187 mg, 0.575 mmol) was added to Pd(Ph3P)$_4$ (22 mg, 0.019 mmol), 2-(4-fluorophenyl)-3-(methylcarbamoyl)benzofuran-5-yl trifluoromethanesulfonate (160 mg, 0.383 mmol), 3-cyanophenylboronic acid (85 mg, 0.575 mmol). Dioxane (3 mL) and water (600 μL) was added at rt. The reaction was degassed 3× and heated to 90° C. overnight. It was allowed to cool. The mixture was diluted with EtOAc and washed with 1M HCl, and sat NaCl. The organic phase was dried over Na$_2$SO$_4$, filtered and concentrated. The crude residue was taken up in DCM. A white precipitate formed which was filtered to give the titled compound. The filtrate was purified on silica gel (Biotage, EtOAc/hexanes gradient, Rf ~0.4:50% EtOAc/Hex, fraction collection at λ=254 nm) to give the titled compound which was combined with the previously collected precipitate (85 mg, 60%). $^1$H NMR (500 MHz, DMSO-d$_6$) δ ppm 8.46-8.53 (1H, m), 8.24 (1H, s), 8.09 (1H, d, J=7.93 Hz), 7.99-8.05 (2H, m), 7.96 (1H, d, J=1.53 Hz), 7.85 (1H, d, J=7.63 Hz), 7.74-7.82 (2H, m), 7.70 (1H, t, J=7.78 Hz), 7.40 (2H, t, J=8.85 Hz), 2.87 (3H, d, J=4.58 Hz). LC-MS retention time: 2.17 min; m/z (MH+): 371. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=13.59 min, purity=99%; Column: Waters Xbridge Phenyl column 4.6×150 mm, 3.5 µm, R$_t$=12.29 min, purity=99%.

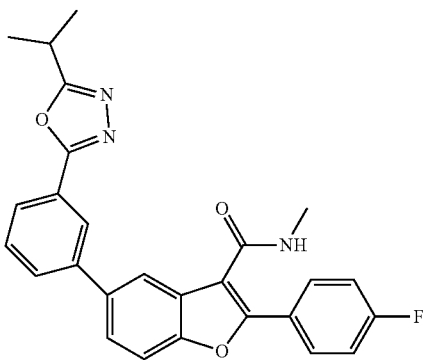

2-(4-fluorophenyl)-5-(3-(5-isopropyl-1,3,4-oxadiazol-2-yl)phenyl)-N-methylbenzofuran-3-carboxamide. Isobutyryl chloride (90 mg, 0.847 mmol) was added to a stirring solution of 5-(3-(1H-tetrazol-5-yl)phenyl)-2-(4-fluorophenyl)-N-methylbenzofuran-3-carboxamide (50 mg, 0.085 mmol) in pyridine (1 mL) at 100° C. It was allowed to stir overnight. The reaction was concentrated and diluted with EtOH (3 mL) and treated with excess 1N NaOH (500 µL) and stirred at 60° C. for 2 hours to hydrolyze the acylated amide. The mixture was filtered and the filtrate was diluted with EtOAc and washed with sat NaHCO3, and sat NaCl. The organic phase was dried over Na2SO4, filtered and concentrated and purified on silica gel (Biotage, EtOAc/hexanes gradient, fraction collection at λ=254 nm) to give the titled compound (8 mg, 20%). 1H NMR (500 MHz, CD$_3$OD) δ ppm 8.31-8.35 (1H, m), 8.03 (1H, d, J=7.94 Hz), 7.95-8.00 (3H, m), 7.93 (1H, d, J=7.93 Hz), 7.67-7.74 (3H, m), 7.25-7.30 (2H, m), 3.37-3.40 (1H, m), 2.99 (3H, s), 1.49 (6H, d, J=7.02 Hz). LC-MS retention time: 2.28 min; m/z (MH+): 456. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=14.30 min, purity=94%; Column: Waters Xbridge Phenyl column 4.6×150 mm, 3.5 µm, R$_t$=12.50 min, purity=93%.

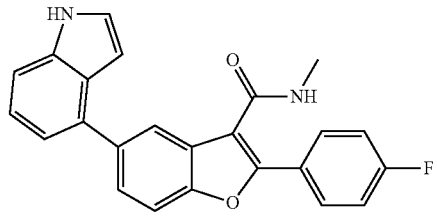

2-(4-fluorophenyl)-5-(1H-indol-4-yl)-N-methylbenzofuran-3-carboxamide. Cesium carbonate (176 mg, 0.539 mmol) was added to Pd(Ph3P)4 (20.77 mg, 0.018 mmol), 2-(4-fluorophenyl)-3-(methylcarbamoyl)benzofuran-5-yl trifluoromethanesulfonate (150 mg, 0.359 mmol), 1H-indol-4-yl-boronic acid (87 mg, 0.539 mmol). Dioxane (3 mL) and water (600 µL) was added at rt. The reaction was degassed 3× and then heated to 90° C. overnight. It was allowed to cool. The mixture was diluted with ethyl acetate and washed with sat NaHCO3, and sat NaCl. The organic phase was dried over Na2SO4, filtered and concentrated and purified on silica gel (Biotage, EtOAc/hexanes gradient, fraction collection at λ=254 nm) to give the titled compound (66 mg, 46%). 1H NMR (500 MHz, DMSO-d$_6$) δ ppm 11.28 (1H, br. s.), 8.48-8.57 (1H, m), 7.98-8.07 (2H, m), 7.86 (1H, br. s.), 7.79 (1H, d, J=8.24 Hz), 7.69 (1H, d, J=7.93 Hz), 7.37-7.47 (4H, m), 7.21 (1H, t, J=7.63 Hz), 7.14 (1H, d, J=7.02 Hz), 6.60 (1H, br. s.), 2.84 (3H, d, J=4.27 Hz). LC-MS retention time: 1.53 min; m/z (MH+): 385. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=13.46 min, purity=99%; Column: Waters Xbridge Phenyl column 4.6×150 mm, 3.5 µm, R$_t$=12.27 min, purity=97%.

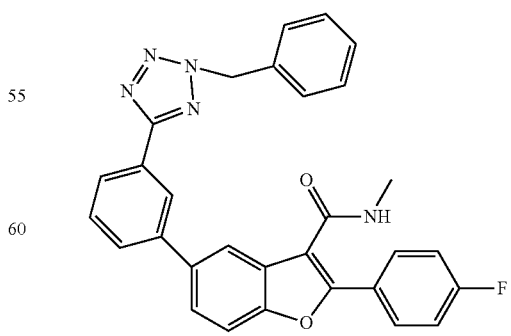

5-(3-(2-benzyl-2H-tetrazol-5-yl)phenyl)-2-(4-fluorophenyl)-N-methylbenzofuran-3-carboxamide. Benzyl bromide (29 µL, 0.242 mmol) was added to a stirring solution of 5-(3-(1H-tetrazol-5-yl)phenyl)-2-(4-fluorophenyl)-N-methylbenzofuran-3-carboxamide (50 mg, 0.121 mmol) and Na2CO3 (26 mg, 0.242 mmol) in DMF (1.2 mL) at 100° C. It was allowed to stir overnight. The mixture was concentrated and purified by preparative reverse phase HPLC on a C18 column using a suitably buffered H$_2$O/CH$_3$CN gradient, and concentrated to give the titled compound (12 mg, 19%). 1H NMR (500 MHz, DMSO-d$_6$) δ ppm 8.48-8.56 (1H, m), 8.30-8.35 (1H, m), 8.06 (1H, d, J=7.63 Hz), 7.98-8.03 (2H, m), 7.90-7.93 (2H, m), 7.78-7.83 (1H, m), 7.72-7.77 (1H, m), 7.69 (1H, t, J=7.78 Hz), 7.36-7.46 (7H, m), 6.04 (2H, s), 2.86 (3H, d, J=4.58 Hz). LC-MS retention time: 1.78 min; m/z (MH+): 504. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=15.69 min, purity=97%; Column: Waters Xbridge Phenyl column 4.6× 150 mm, 3.5 µm, R$_t$=13.95 min, purity=98%.

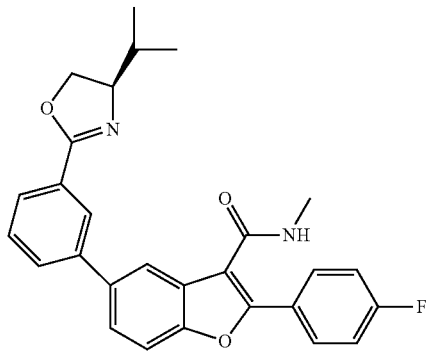

(R)-2-(4-fluorophenyl)-5-(3-(4-isopropyl-4,5-dihydrooxazol-2-yl)phenyl)-N-methylbenzofuran-3-carboxamide.

Zinc chloride (8 mg, 0.054 mmol) was added to a stirring solution of 5-(3-cyanophenyl)-2-(4-fluorophenyl)-N-methylbenzofuran-3-carboxamide (40 mg, 0.108 mmol) and (R)-2-amino-3-methylbutan-1-ol (111 mg, 1.08 mmol) in PhCl (3 mL) at rt. It was subjected for two interations to microwave irradiation for 1 hr at 200° C. The mixture was concentrated and purified by preparative reverse phase HPLC on a C18 column using a suitably buffered H$_2$O/CH$_3$CN gradient, and concentrated to give the titled compound (13 mg, 25%). 1H NMR (500 MHz, CD$_3$OD) δ ppm 8.24 (1H, s), 7.93-7.99 (2H, m), 7.89-7.93 (2H, m), 7.86 (1H, d, J=7.63 Hz), 7.63-7.69 (2H, m), 7.56 (1H, t, J=7.78 Hz), 7.26 (2H, t, J=8.55 Hz), 4.52 (1H, t, J=9.31 Hz), 4.30 (1H, t, J=8.09 Hz), 4.14-4.22 (1H, m), 2.98 (3H, s), 1.87-1.97 (1H, m), 1.04 (3H, d, J=7.02 Hz), 0.97 (3H, d, J=6.71 Hz). LC-MS retention time 1.64 min; m/z (MH+): 457. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=10.13 min, purity=95%; Column: Waters Xbridge Phenyl column 4.6× 150 mm, 3.5 µm, R$_t$=10.58 min, purity=94%.

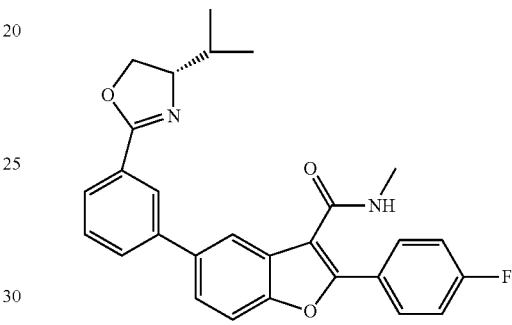

(S)-2-(4-fluorophenyl)-5-(3-(4-isopropyl-4,5-dihydrooxazol-2-yl)phenyl)-N-methylbenzofuran-3-carboxamide.

Zinc chloride (8 mg, 0.054 mmol) was added to a stirring solution of 5-(3-cyanophenyl)-2-(4-fluorophenyl)-N-methylbenzofuran-3-carboxamide (40 mg, 0.108 mmol) and (S)-2-amino-3-methylbutan-1-ol (111 mg, 1.080 mmol) in PhCl (3 mL) at rt. It was subjected for two 1 hr iterations to microwave irradiation at 200° C. The reaction was concentrated and purified by preparative reverse phase HPLC on a C18 column using a suitably buffered H$_2$O/CH$_3$CN gradient, and concentrated to give the titled compound (9 mg, 17%). 1H NMR (500 MHz, CD$_3$OD) δ ppm 8.24 (1H, s), 7.93-7.99 (2H, m), 7.89-7.93 (2H, m), 7.86 (1H, d, J=7.63 Hz), 7.63-7.69 (2H, m), 7.56 (1H, t, J=7.78 Hz), 7.26 (2H, t, J=8.70 Hz), 4.52 (1H, t, J=9.31 Hz), 4.30 (1H, t, J=8.09 Hz), 4.15-4.22 (1H, m), 2.98 (3H, s), 1.86-1.96 (1H, m), 1.04 (3H, d, J=6.71 Hz), 0.97 (3H, d, J=6.71 Hz). LC-MS retention time: 1.63 min; m/z (MH+): 457. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=10.06 min, purity=95%; Column: Waters Xbridge Phenyl column 4.6×150 mm, 3.5 µm, R$_t$=10.53 min, purity=95%.

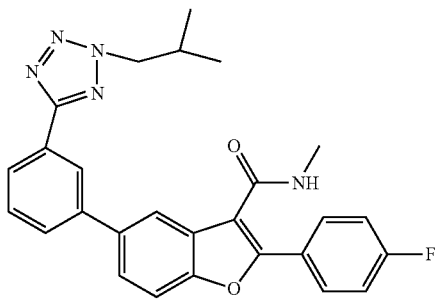

2-(4-fluorophenyl)-5-(3-(2-isobutyl-2H-tetrazol-5-yl)phenyl)-N-methylbenzofuran-3-carboxamide. 1-bromo-2-methylpropane (23 mg, 0.169 mmol) was added to a stirring solution of 5-(3-(1H-tetrazol-5-yl)phenyl)-2-(4-fluorophenyl)-N-methylbenzofuran-3-carboxamide (35 mg, 0.085 mmol) and Na$_2$CO$_3$ (18 mg, 0.169 mmol) in DMF (1 mL) at 100° C. It was allowed to stir overnight. The mixture was concentrated and purified by preparative reverse phase HPLC on a C18 column using a suitably buffered H$_2$O/CH$_3$CN gradient, and concentrated to give the titled compound (15 mg, 38%). 1H NMR (500 MHz, DMSO-d$_6$) δ ppm 8.49-8.56 (1H, m), 8.34 (1H, s), 8.08 (1H, d, J=7.63 Hz), 7.99-8.04 (2H, m), 7.87-7.94 (2H, m), 7.79-7.84 (1H, m), 7.73-7.78 (1H, m), 7.70 (1H, t, J=7.63 Hz), 7.41 (2H, t, J=8.70 Hz), 4.62 (2H, d, J=7.32 Hz), 2.87 (3H, d, J=4.27 Hz), 2.31-2.39 (1H, m), 0.95 (6H, d, J=6.71 Hz). LC-MS retention time: 2.09 min; m/z (MH+): 470. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=16.08 min, purity=99%; Column: Waters Xbridge Phenyl column 4.6×150 mm, 3.5 µm, R$_t$=13.89 min, purity=99%.

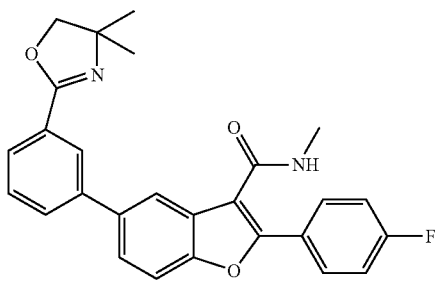

5-(3-(4,4-dimethyl-4,5-dihydrooxazol-2-yl)phenyl)-2-(4-fluorophenyl)-N-methylbenzofuran-3-carboxamide. Zinc chloride (1 mg) was added to a stirring solution of 5-(3-cyanophenyl)-2-(4-fluorophenyl)-N-methylbenzofuran-3-carboxamide (40 mg, 0.108 mmol) and 2-amino-2-methylpropan-1-ol (10 mg, 0.108 mmol) in PhCl (3 mL) at 130° C. It was allowed to stir for 7 days. ~20% conversion was observed. Additional amounts of ZnCl (8 mg) and 2-amino-2-methylpropan-1-ol (50 mg) were added and the reaction was heated in the microwave for 1 hr at 200° C. The reaction had progressed ~50%. The mixture was concentrated and purified on silica gel (Biotage, EtOAc/hexanes gradient, Rf ~0.2 in 50% EtOAc/hexanes; fraction collection at λ=254 nm) followed by preparative reverse phase HPLC on a C18 column using a suitably buffered H$_2$O/CH$_3$CN gradient, and concentrated to give the titled compound (7 mg, 14%). 1H NMR (500 MHz, CD$_3$OD) δ ppm 8.24 (1H, s), 7.97 (2H, dd, J=8.09, 5.65 Hz), 7.93 (1H, s), 7.88 (2H, dd, J=11.44, 8.39 Hz), 7.68 (2H, s), 7.57 (1H, t, J=7.78 Hz), 7.27 (2H, t, J=8.55 Hz), 4.25 (2H, s), 2.99 (3H, s), 1.42 (6H, s). LC-MS retention time 1.60 min; m/z (MH+): 443. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 µm, R$_t$=12.24 min, purity=95%; Column: Waters Xbridge Phenyl column 4.6×150 mm, 3.5 µm, R$_t$=10.02 min, purity=95%.

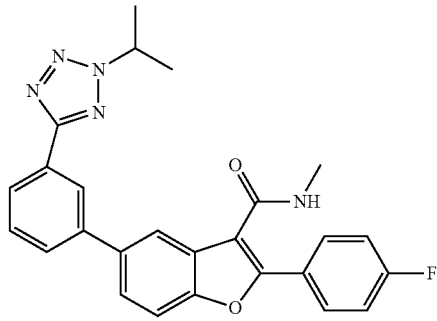

2-(4-fluorophenyl)-5-(3-(2-isopropyl-2H-tetrazol-5-yl)phenyl)-N-methylbenzofuran-3-carboxamide. 2-iodopropane (29 mg, 0.169 mmol) was added to a stirring solution of 5-(3-(1H-tetrazol-5-yl)phenyl)-2-(4-fluorophenyl)-N-methylbenzofuran-3-carboxamide (35 mg, 0.085 mmol) and Na2CO3 (18 mg, 0.169 mmol) in DMF (1 mL) at 100° C. It was allowed to stir overnight. The mixture was concentrated and purified by preparative reverse phase HPLC on a C18 column using a suitably buffered H$_2$O/CH$_3$CN gradient, and concentrated to give the titled compound (12 mg, 30%). 1H NMR (500 MHz, DMSO-d$_6$) δ ppm 8.49-8.57 (1H, m), 8.34 (1H, s), 8.08 (1H, d, J=7.32 Hz), 7.99-8.05 (2H, m), 7.87-7.94 (2H, m), 7.79-7.83 (1H, m), 7.72-7.78 (1H, m), 7.70 (1H, t, J=7.78 Hz), 7.41 (2H, t, J=8.70 Hz), 5.17-5.27 (1H, m), 2.87 (3H, d, J=4.58 Hz), 1.66 (6H, d, J=6.71 Hz). LC-MS retention time: 2.02 min; m/z (MH+): 456. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 μm, R$_t$=15.35 min, purity=96%; Column: Waters Xbridge Phenyl column 4.6×150 mm, 3.5 μm, R$_t$=13.39 min, purity=97%.

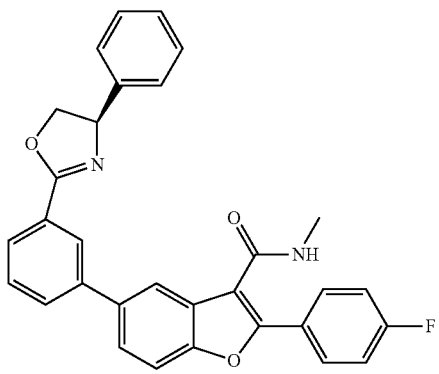

(R)-2-(4-fluorophenyl)-N-methyl-5-(3-(4-phenyl-4,5-dihydrooxazol-2-yl)phenyl)benzofuran-3-carboxamide. Zinc chloride (8 mg, 0.054 mmol) was added to a stirring solution of 5-(3-cyanophenyl)-2-(4-fluorophenyl)-N-methylbenzofuran-3-carboxamide (40 mg, 0.108 mmol) and (R)-2-amino-2-phenylethanol (148 mg, 1.080 mmol) in PhCl (3 mL) at rt. It was subjected to two interations of microwave irradiation at 200° C. for 1 hr. The material was concentrated and purified by preparative reverse phase HPLC on a C18 column using a suitably buffered H$_2$O/CH$_3$CN gradient, and concentrated to give the titled compound (7 mg, 13%). 1H NMR (500 MHz, CD$_3$OD) δ ppm 8.33 (1H, s), 7.94-8.00 (4H, m), 7.91 (1H, d, J=7.94 Hz), 7.64-7.73 (2H, m), 7.61 (1H, t, J=7.78 Hz), 7.32-7.42 (6H, m), 7.26 (2H, t, J=8.55 Hz), 5.45 (1H, t, J=9.16 Hz), 4.94 (1H, t, J=9.31 Hz), 4.36 (1H, t, J=8.24 Hz), 2.97 (3H, s). LC-MS retention time 1.75 min; m/z (MH+): 491. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C-18, 4.6×150 mm, 3 μm, R$_t$=18.32 min, purity=97%; Column: Waters Xbridge Phenyl column 4.6×150 mm, 3.5 μm, R$_t$=18.11 min, purity=97%.

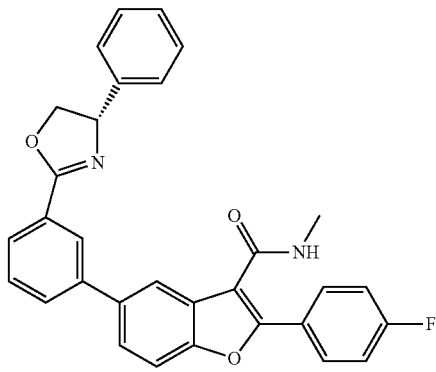

(S)-2-(4-fluorophenyl)-N-methyl-5-(3-(4-phenyl-4,5-dihydrooxazol-2-yl)phenyl)benzofuran-3-carboxamide. Zinc chloride (9 mg, 0.067 mmol) was added to a stirring solution of 5-(3-cyanophenyl)-2-(4-fluorophenyl)-N-methylbenzofuran-3-carboxamide (50 mg, 0.135 mmol) and (S)-2-amino-2-phenylethanol (93 mg, 0.675 mmol) in PhCl (3 mL) rt. It was subjected to two interations of microwave irradiation at 200° C. for 1 hr. The material was concentrated and purified by preparative reverse phase HPLC on a C18 column using a suitably buffered H$_2$O/CH$_3$CN gradient, and concentrated to give the titled compound (16 mg, 23%). 1H NMR (500 MHz, CD$_3$OD) δ ppm 8.33 (1H, s), 7.94-8.00 (4H, m), 7.91 (1H, d, J=7.94 Hz), 7.64-7.73 (2H, m), 7.61 (1H, t, J=7.78 Hz), 7.32-7.42 (6H, m), 7.26 (2H, t, J=8.55 Hz), 5.45 (1H, t, J=9.16 Hz), 4.94 (1H, t, J=9.31 Hz), 4.36 (1H, t, J=8.24 Hz), 2.97 (3H, s). LC-MS retention time 1.76 min; m/z (MH+): 491. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C-18, 4.6×150 mm, 3 μm, R$_t$=18.32 min, purity=99%; Column: Waters Xbridge Phenyl column 4.6×150 mm, 3.5 μm, R$_t$=18.10 min, purity=99%.

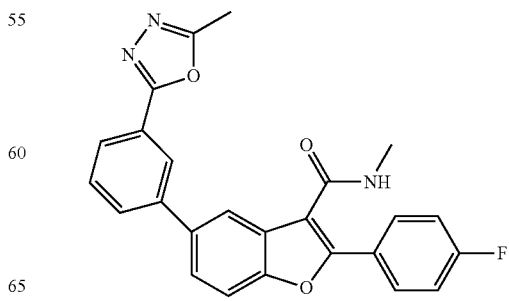

2-(4-fluorophenyl)-N-methyl-5-(3-(5-methyl-1,3,4-oxadiazol-2-yl)phenyl)benzofuran-3-carboxamide. DIEA (50 µL, 0.288 mmol) was added to Pd(Ph3P)$_4$ (6 mg, 4.79 µmol), -(4-fluorophenyl)-3-(methylcarbamoyl)benzofuran-5-yl trifluoromethanesulfonate (40 mg, 0.096 mmol), 3-(5-methyl-1,3,4-oxadiazol-2-yl)phenylboronic acid (29 mg, 0.144 mmol). Dioxane (1 mL) and water (200 µL) was added at rt. The reaction was heated to 90° C. overnight. The mixture was cooled and purified by preparative reverse phase HPLC on a C18 column using a suitably buffered H$_2$O/CH$_3$CN gradient, and concentrated to give the titled compound (16 mg, 37%). 1H NMR (500 MHz, DMSO-d6) δ ppm 8.49-8.56 (1H, m), 8.24 (1H, s), 7.98-8.05 (4H, m), 7.93 (1H, s), 7.79-7.83 (1H, m), 7.68-7.76 (2H, m), 7.41 (2H, t, J=8.70 Hz), 2.87 (3H, d, J=4.58 Hz), 2.62 (3H, s). LC-MS retention time: 1.41 min; m/z (MH−): 426. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additonal HPLC method: Solvent A=5% CH3CN/95% H2O/0.1% TFA, Solvent B=95% CH3CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, Rt=12.96 min, purity=95%; Column: Waters Xbridge Phenyl column 4.6×150 mm, 3.5 mm, Rt=11.53 min, purity=94%.

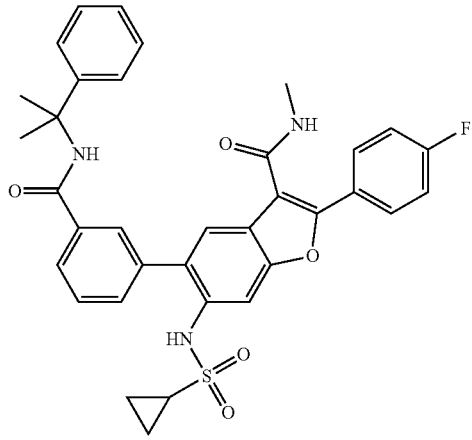

6-(cyclopropanesulfonamido)-2-(4-fluorophenyl)-N-methyl-5-(3-(2-phenylpropan-2-ylcarbamoyl)phenyl)benzofuran-3-carboxamide. Cyclopropanesulfonyl chloride (8 µL, 0.058 mmol) was added to a stirring solution of 6-amino-2-(4-fluorophenyl)-N-methyl-5-(3-(2-phenylpropan-2-ylcarbamoyl)phenyl)benzofuran-3-carboxamide (20 mg, 0.038 mmol) in Pyridine (0.5 mL) at rt. It was allowed to stir for 2 hours. The mixture was concentrated purified by preparative reverse phase HPLC on a C18 column using a suitably buffered H$_2$O/CH$_3$CN gradient, and concentrated to give the titled compound (17 mg, 70%). 1H NMR (500 MHz, CD$_3$OD) δ ppm 8.41 (1H, br. s.), 7.91-8.01 (3H, m), 7.78-7.86 (2H, m), 7.61-7.71 (2H, m), 7.58 (1H, t, J=7.63 Hz), 7.41-7.49 (2H, m), 7.24-7.33 (4H, m), 7.18 (1H, t, J=6.87 Hz), 2.94 (3H, s), 2.34-2.43 (1H, m), 1.77 (6H, s), 0.80-1.03 (4H, m). LC-MS retention time: 1.53 min; m/z (MH+): 626. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, Rt=15.40 min, purity=99%; Column: Waters Xbridge Phenyl column 4.6×150 mm, 3.5 mm, Rt=12.65 min, purity=99%.

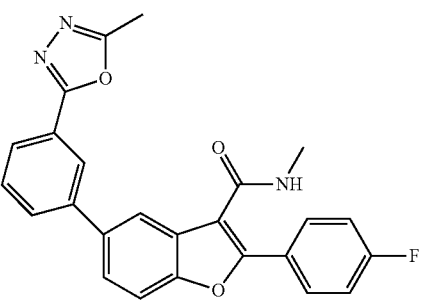

2-(4-fluorophenyl)-N-methyl-5-(3-(5-methyl-1,3,4-oxadiazol-2-yl)phenyl)benzofuran-3-carboxamide. DIEA (50 µL, 0.288 mmol) was added to Pd(Ph3P)4 (6 mg, 4.79 µmol), 2-(4-fluorophenyl)-3-(methylcarbamoyl)benzofuran-5-yl trifluoromethanesulfonate (40 mg, 0.096 mmol), 3-(5-methyl-1,3,4-oxadiazol-2-yl)phenylboronic acid (29 mg, 0.144 mmol). Dioxane (799 µL) and water (160 µL) was added at rt. The reaction was heated to 90° C. overnight. The mixture was cooled and purified by prep HPLC to give the titled compound (16 mg, 37%). 1H NMR (500 MHz, DMSO-d$_6$) ppm 8.49-8.56 (1H, m), 8.24 (1H, s), 7.98-8.05 (4H, m), 7.93 (1H, s), 7.79-7.83 (1H, m), 7.68-7.76 (2H, m), 7.41 (2H, t, J=8.70 Hz), 2.87 (3H, d, J=4.58 Hz), 2.62 (3H, s). LC-MS retention time: 1.41 min; m/z (MH−): 426. LC data was recorded on a Shimadzu LC-10AS liquid chromatograph equipped with a Waters XBridge 5 u C18 4.6×50 mm column using a SPD-10AV UV-V is detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Analytical HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 m, R$_f$=12.96 min, purity=95%; Column: Waters Xbridge Phenyl column 4.6×150 mm, 3.5 m, R$_f$=11.53 min, purity=94%.

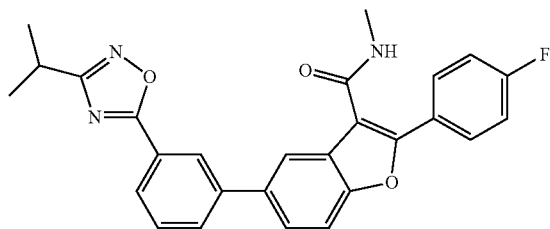

2-(4-fluorophenyl)-5-(3-(3-isopropyl-1,2,4-oxadiazol-5-yl)phenyl)-N-methylbenzofuran-3-carboxamide. Sodium methoxide (33 mg, 0.620 mmol) was added to a stirring slurry of methyl 3-(2-(4-fluorophenyl)-3-(methylcarbamoyl)benzofuran-5-yl)benzoate (50 mg, 0.124 mmol) and (Z)-N'-hydroxyisobutyrimidamide (38 mg, 0.372 mmol) in EtOH (2.5 mL) at rt. The mixture was subjected to microwave irradiation for 5 min at 160° C. The mixture was concentrated and purified by preparative reverse phase HPLC on a C18 column using a suitably buffered $H_2O/CH_3CN$ gradient, and concentrated to give the titled compound (11 mg, 20%). 1H NMR (400 MHz, DMSO-$d_6$) d ppm 8.46-8.54 (1H, m), 8.35 (1H, s), 8.11 (1H, d, J=7.78 Hz), 7.97-8.08 (3H, m), 7.92-7.97 (1H, m), 7.73-7.84 (3H, m), 7.40 (2H, t, J=8.91 Hz), 3.12-3.23 (1H, m), 2.87 (3H, d, J=4.52 Hz), 1.36 (6H, d, J=7.03 Hz). LC-MS retention time: 1.80 min; m/z (MH+): 456. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% $CH_3CN$/95% $H_2O$/0.1% TFA, Solvent B=95% $CH_3CN$/5% $H_2O$/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=16.33 min, purity=99%; Column: Waters Xbridge Phenyl column 4.6×150 mm, 3.5 mm, $R_t$=13.72 min, purity=99%.

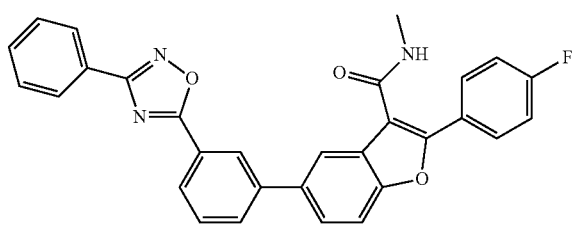

2-(4-fluorophenyl)-N-methyl-5-(3-(3-phenyl-1,2,4-oxadiazol-5-yl)phenyl)benzofuran-3-carboxamide. Sodium methoxide (33 mg, 0.620 mmol) was added to a stirring slurry of methyl 3-(2-(4-fluorophenyl)-3-(methylcarbamoyl)benzofuran-5-yl)benzoate (50 mg, 0.124 mmol) and (Z)—N'-hydroxybenzimidamide (51 mg, 0.372 mmol) in EtOH (2.5 mL) at rt. The mixture was subjected to microwave irradiation for 5 min at 160° C. The mixture was concentrated and purified by preparative reverse phase HPLC on a C18 column using a suitably buffered $H_2O/CH_3CN$ gradient, and concentrated to give the titled compound (8.7 mg, 14%). 1H NMR (400 MHz, DMSO-$d_6$) d ppm 8.49-8.56 (1H, m), 8.44-8.49 (1H, m), 8.19-8.25 (1H, m), 8.13-8.18 (2H, m), 8.07-8.12 (1H, m), 8.00-8.07 (2H, m), 7.98 (1H, s), 7.76-7.86 (3H, m), 7.59-7.68 (3H, m), 7.41 (2H, t, J=8.91 Hz), 2.88 (3H, d, J=4.77 Hz). LC-MS retention time: 1.94 min; m/z (MH+): 490. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% $CH_3CN$/95% $H_2O$/0.1% TFA, Solvent B=95% $CH_3CN$/5% $H_2O$/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=17.39 min, purity=99%; Column: Waters Xbridge Phenyl column 4.6×150 mm, 3.5 mm, $R_t$=14.58 min, purity=98%.

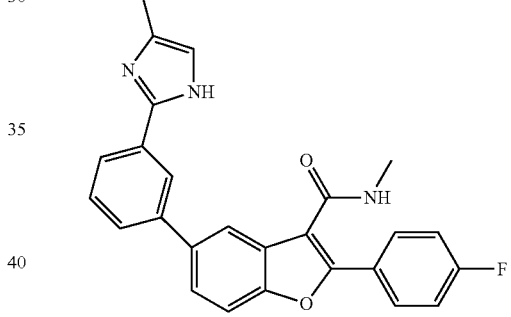

2-(4-fluorophenyl)-N-methyl-5-(3-(4-phenyl-1H-imidazol-2-yl)phenyl)benzofuran-3-carboxamide. 2-oxo-2-phenylacetaldehyde hydrate (10 mg, 0.066 mmol) in MeOH (1 mL) was added to a stirring solution of 2-(4-fluorophenyl)-5-(3-formylphenyl)-N-methylbenzofuran-3-carboxamide (20 mg, 0.054 mmol) and ammonium acetate (25 mg, 0.324 mmol) in MeOH (1 mL) at rt. It was allowed to stir overnight. The reaction was purified by preparative reverse phase HPLC on a C18 column using a suitably buffered $H_2O/CH_3CN$ gradient, and concentrated to give the titled compound (6.5 mg, 24%). 1H NMR (500 MHz, DMSO-$d_6$) ppm 12.82 (1H, br. s.), 8.51-8.58 (1H, m), 8.35 (1H, br. s.), 7.98-8.07 (3H, m), 7.93-7.97 (1H, m), 7.76-7.90 (4H, m), 7.72 (1H, d, J=7.63 Hz), 7.60 (1H, t, J=7.78 Hz), 7.36-7.45 (4H, m), 7.19-7.29 (1H, m), 2.88 (3H, d, J=4.58 Hz). LC-MS retention time: 1.57 min; m/z (MH+): 488. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10%

H2O/90% MeOH/0.1% trifluoroacetic acid. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_f$=9.54 min, purity=96%; Column: Waters Xbridge Phenyl column 4.6×150 mm, 3.5 mm, $R_f$=10.41 min, purity=97%.

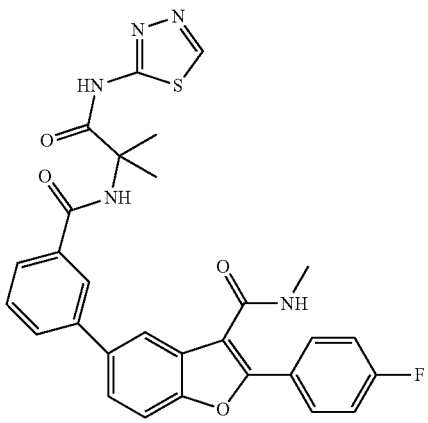

5-(3-(1-(1,3,4-thiadiazol-2-ylamino)-2-methyl-1-oxopropan-2-ylcarbamoyl)phenyl)-2-(4-fluorophenyl)-N-methylbenzofuran-3-carboxamide. DIEA (44 µL, 0.253 mmol) was added to a stirring solution of 2-(3-(2-(4-fluorophenyl)-3-(methylcarbamoyl)benzofuran-5-yl)benzamido)-2-methylpropanoic acid (40 mg, 0.084 mmol), 1,3,4-thiadiazol-2-amine (17.05 mg, 0.169 mmol) in DMF (843 µL) at rt. NaH (17 mg, 0.422 mmol) was added, and the slurry became a clear solution after 10 min. It was allowed to stir overnight. The reaction was purified by preparative reverse phase HPLC on a C18 column using a suitably buffered H₂O/CH₃CN gradient, and concentrated to give the titled compound (22 mg, 45%). 1H NMR (500 MHz, DMSO-d₆) δ ppm 12.44 (1H, br. s.), 9.14 (1H, br. s.), 8.78 (1H, br. s.), 8.47-8.57 (1H, m), 8.30 (1H, s), 7.97-8.04 (2H, m), 7.88-7.95 (3H, m), 7.75-7.84 (2H, m), 7.61 (1H, t, J=7.78 Hz), 7.41 (2H, t), 2.86 (3H, d, J=4.88 Hz), 1.57 (6H, s). LC-MS retention time: 1.57 min; m/z (MH+): 488. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_f$=11.23 min, purity=97%; Column: Waters Xbridge Phenyl column 4.6×150 mm, 3.5 mm, $R_f$=10.56 min, purity=96%.

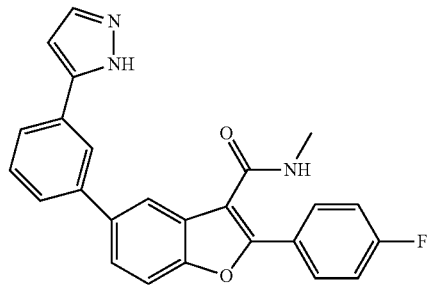

5-(3-(1H-pyrazol-5-yl)phenyl)-2-(4-fluorophenyl)-N-methylbenzofuran-3-carboxamide. Cesium carbonate (234 mg, 0.719 mmol) was added to Pd(Ph3P)4 (20.77 mg, 0.018 mmol), 2-(4-fluorophenyl)-3-(methylcarbamoyl)benzofuran-5-yl trifluoromethanesulfonate (150 mg, 0.359 mmol), 5-(3-(4,4,5,5-tetramethyl-1,3,2-dioxaborolan-2-yl)phenyl)-1H-pyrazole (146 mg, 0.539 mmol). Dioxane (3 mL) and water (599 µL) was added at rt. The reaction was heated to 90° C. overnight. The mixture was diluted with EtOAc and washed with sat NaHCO3, and sat NaCl. The organic phase was dried over Na2SO4, filtered and concentrated and purified by trituration with Et2O to give the titled compound (140 mg, 92%). 1H NMR (400 MHz, DMSO-d₆) d ppm 13.40 (1H, br. s.), 12.91 (1H, br. s.), 8.45-8.55 (1H, m), 8.13 (1H, s), 7.97-8.08 (2H, m), 7.85-7.95 (1H, m), 7.73-7.85 (4H, m), 7.59-7.67 (1H, m), 7.49-7.58 (1H, m), 7.35-7.45 (2H, m), 6.84 (1H, br. s.), 2.87 (3H, d, J=4.52 Hz). LC-MS retention time: 1.41 min; m/z (MH+): 412. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_f$=11.86 min, purity=97%; Column: Waters Xbridge Phenyl column 4.6×150 mm, 3.5 mm, $R_f$=10.97 min, purity=99%.

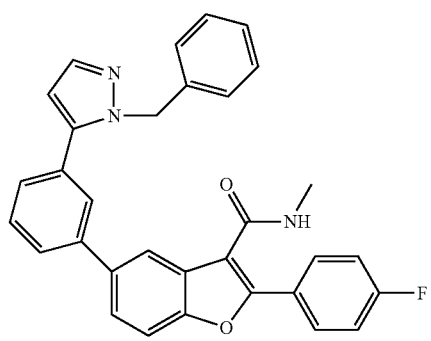

5-(3-(1-benzyl-1H-pyrazol-5-yl)phenyl)-2-(4-fluorophenyl)-N-methylbenzofuran-3-carboxamide. (Bromomethyl)benzene (17 mg, 0.097 mmol) was added to a stirring solution of Na2CO3 (11 mg, 0.097 mmol) and 5-(3-(1H-pyrazol-5-yl)phenyl)-2-(4-fluorophenyl)-N-methylbenzofuran-3-carboxamide (20 mg, 0.049 mmol) in DMF (486 μL) at 100° C. It was allowed to stir overnight, filtered and purified by preparative reverse phase HPLC on a C18 column using a suitably buffered H$_2$O/CH$_3$CN gradient, and concentrated to give the titled compound (8.6 mg, 35%). 1H NMR (500 MHz, DMSO-d$_6$) δ ppm 8.49-8.57 (1H, m), 8.06-8.11 (1 H, m), 7.98-8.04 (2H, m), 7.92 (1H, d, J=2.44 Hz), 7.86-7.89 (1H, m), 7.75-7.83 (2H, m), 7.69-7.75 (1H, m), 7.63 (1H, d, J=8.24 Hz), 7.51 (1H, t, J=7.63 Hz), 7.34-7.43 (4H, m), 7.27-7.32 (3H, m), 6.89 (1H, d, J=2.44 Hz), 5.41 (2H, s), 2.86 (3H, d, J=4.58 Hz). LC-MS retention time: 2.00 min; m/z (MH+): 502. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=15.47 min, purity=99%; Column: Waters Xbridge Phenyl column 4.6×150 mm, 3.5 mm, R$_t$=13.77 min, purity=100%.

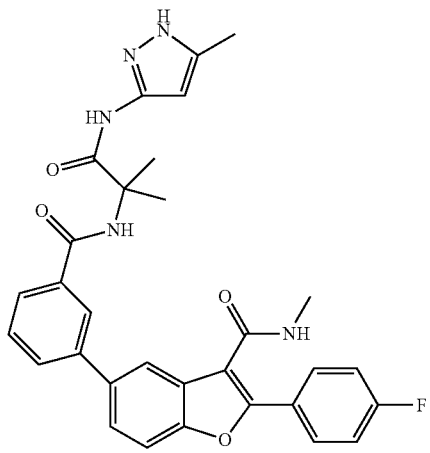

2-(4-fluorophenyl)-N-methyl-5-(3-(2-methyl-1-(5-methyl-1H-pyrazol-3-ylamino)-1-oxopropan-2-ylcarbamoyl)phenyl)benzofuran-3-carboxamide. DIEA (28 μL, 0.158 mmol) was added to a stirring solution of 2-(3-(2-(4-fluorophenyl)-3-(methylcarbamoyl)benzofuran-5-yl)benzamido)-2-methylpropanoic acid (25 mg, 0.053 mmol), 5-methyl-1H-pyrazol-3-amine (11 mg, 0.105 mmol) in DMF (527 μL) at rt. It was allowed to stir for 30 min. NaH (11 mg, 0.263 mmol) was added and the reaction was allowed to stir overnight. The mixture was treated with a drop of MeOH and was purified by preparative reverse phase HPLC on a C18 column using a suitably buffered H$_2$O/CH$_3$CN gradient, and concentrated to give the titled compound (6.4 mg, 21%). $^1$H NMR (500 MHz, DMSO-d$_6$) d ppm 11.90 (1H, br. s.), 9.84 (1H, br. s.), 8.51-8.56 (1H, m), 8.41 (1H, br. s.), 8.23-8.28 (1H, m), 7.98-8.03 (2H, m), 7.86-7.93 (3H, m), 7.76-7.83 (2H, m), 7.59 (1H, t, J=7.63 Hz), 7.37-7.43 (2H, m), 6.28 (1H, br. s.), 2.87 (3H, d, J=4.88 Hz), 2.17 (3H, s), 1.54 (6H, s). LC-MS retention time: 1.56 min; m/z (MH+): 554. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=10.47 min, purity=97%; Column: Waters Xbridge Phenyl column 4.6×150 mm, 3.5 mm, R$_t$=9.58 min, purity=96%.

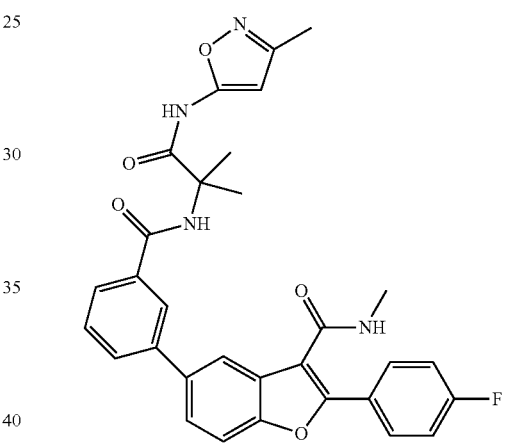

2-(4-fluorophenyl)-N-methyl-5-(3-(2-methyl-1-(3-methylisoxazol-5-ylamino)-1-oxopropan-2-ylcarbamoyl)phenyl)benzofuran-3-carboxamide. DIEA (28 μL, 0.158 mmol) was added to a stirring solution of 2-(3-(2-(4-fluorophenyl)-3-(methylcarbamoyl)benzofuran-5-yl)benzamido)-2-methylpropanoic acid (25 mg, 0.053 mmol), 3-methylisoxazol-5-amine (11 mg, 0.105 mmol) in DMF (527 μL) at rt. It was allowed to stir for 30 min. NaH (11 mg, 0.263 mmol) was added and the reaction was allowed to stir overnight. The mixture was treated with a drop of MeOH and was purified by preparative reverse phase HPLC on a C18 column using a suitably buffered H$_2$O/CH$_3$CN gradient, and concentrated to give the titled compound (3.3 mg, 11%). 1H NMR (500 MHz, CD$_3$OD) δ ppm 8.18-8.24 (1H, m), 7.93-8.00 (3H, m), 7.84-7.91 (2H, m), 7.65-7.74 (2H, m), 7.58 (1H, t, J=7.78 Hz), 7.23-7.31 (2H, m), 2.98 (3H, s), 2.24 (3H, s), 1.65 (6H, s). LC-MS retention time: 1.69 min; m/z (MH+): 555. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_f$=12.09 min, purity=100%; Column: Waters Xbridge Phenyl column 4.6×150 mm, 3.5 mm, R$_f$=11.18 min, purity=99%.

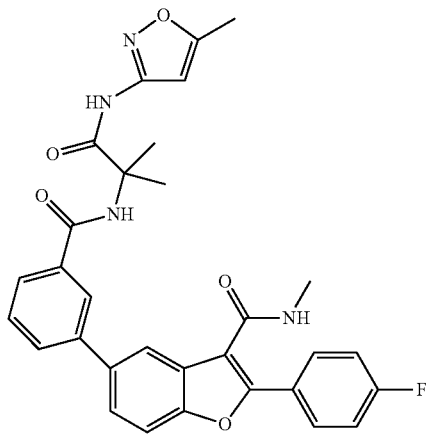

2-(4-fluorophenyl)-N-methyl-5-(3-(2-methyl-1-(5-methylisoxazol-3-ylamino)-1-oxopropan-2-ylcarbamoyl)phenyl) benzofuran-3-carboxamide. DIEA (28 μL, 0.158 mmol) was added to a stirring solution of 2-(3-(2-(4-fluorophenyl)-3-(methylcarbamoyl)benzofuran-5-yl)benzamido)-2-methylpropanoic acid (25 mg, 0.053 mmol), 5-methylisoxazol-3-amine (11 mg, 0.105 mmol) in DMF (527 μL) at rt. It was allowed to stir for 30 min. NaH (11 mg, 0.263 mmol) was added and the reaction was allowed to stir overnight. The mixture was treated with a drop of MeOH and was purified by preparative reverse phase HPLC on a C18 column using a suitably buffered H₂O/CH₃CN gradient, and concentrated to give the titled compound (2.8 mg, 9%). 1H NMR (500 MHz, CD₃OD) δ ppm 8.17-8.25 (1H, m), 7.92-8.00 (3H, m), 7.83-7.91 (2H, m), 7.66-7.76 (2H, m), 7.58 (1H, t, J=7.78 Hz), 7.27 (2H, t, J=8.85 Hz), 6.63 (1H, s), 2.98 (3H, s), 2.39 (3H, s), 1.65 (6H, s). LC-MS retention time: 1.69 min; m/z (MH+): 555. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_f$=12.20 min, purity=95%; Column: Waters Xbridge Phenyl column 4.6×150 mm, 3.5 mm, R$_f$=11.30 min, purity=90%.

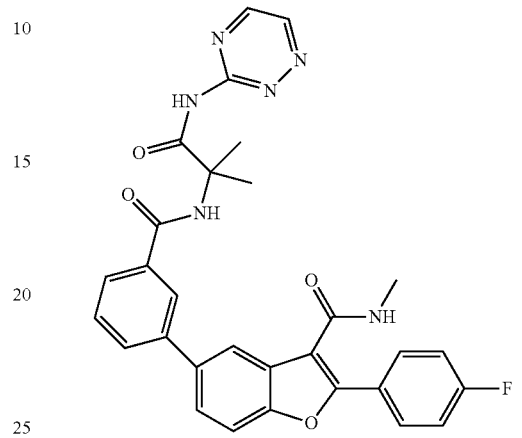

5-(3-(1-(1,2,4-triazin-3-ylamino)-2-methyl-1-oxopropan-2-ylcarbamoyl)phenyl)-2-(4-fluorophenyl)-N-methylbenzofuran-3-carboxamide. DIEA (28 μL, 0.158 mmol) was added to a stirring solution of 2-(3-(2-(4-fluorophenyl)-3-(methylcarbamoyl)benzofuran-5-yl)benzamido)-2-methylpropanoic acid (25 mg, 0.053 mmol), 1,2,4-triazin-3-amine (11 mg, 0.105 mmol) in DMF (527 μL) at rt. It was allowed to stir for 30 min. NaH (11 mg, 0.263 mmol) was added and the reaction was allowed to stir overnight. The mixture was treated with a drop of MeOH and was purified by preparative reverse phase HPLC on a C18 column using a suitably buffered H₂O/CH₃CN gradient, and concentrated to give the titled compound (7.4 mg, 25%). 1H NMR (500 MHz, CD₃OD) δ ppm 8.58-8.63 (1H, m), 8.22-8.26 (1 H, m), 7.93-8.00 (3H, m), 7.85-7.93 (2H, m), 7.66-7.75 (2H, m), 7.59 (1H, t, J=7.63 Hz), 7.27 (2H, t, J=8.85 Hz), 2.98 (3H, s), 1.72 (6H, s). LC-MS retention time: 1.56 min; m/z (MH+): 553. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_f$=9.65 min, purity=97%; Column: Waters Xbridge Phenyl column 4.6×150 mm, 3.5 mm, R$_f$=9.58 min, purity=97%.

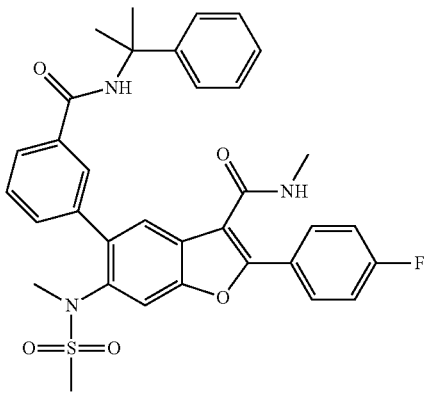

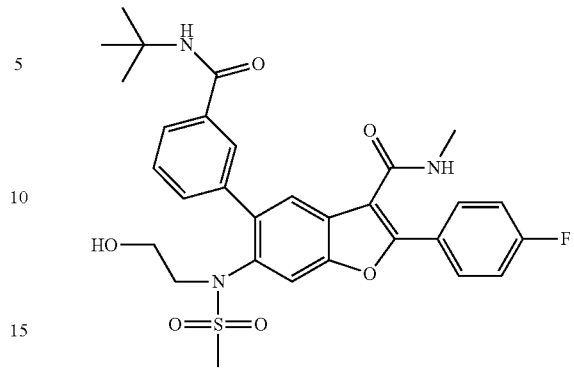

2-(4-fluorophenyl)-N-methyl-6-(N-methylmethylsulfonamido)-5-(3-(2-phenylpropan-2-ylcarbamoyl)phenyl)benzofuran-3-carboxamide. Oxalyl chloride (22 µL, 0.250 mmol) was added to a stirring solution of 2-(4-fluorophenyl)-6-(N-methylmethylsulfonamido)-5-(3-(2-phenylpropan-2-ylcarbamoyl)phenyl)benzofuran-3-carboxylic acid (50 mg, 0.083 mmol) in DCE (832 µL) at rt. DMF (3 µL, 0.042 mmol) was added. The mixture was allowed to stir for 30 min, concentrated and diluted with THF. DIEA (59 µL, 0.333 mmol) and methanamine (208 µL, 0.416 mmol, 2M in THF) was added. It was allowed to stir overnight. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (11 mg, 20%). 1H NMR (400 MHz, DMSO-d$_6$) d ppm 8.46-8.56 (1H, m), 8.36 (1H, s), 7.97-8.05 (3H, m), 7.94 (1H, s), 7.86 (1H, d, J=7.78 Hz), 7.59-7.67 (2H, m), 7.53 (1H, t, J=7.65 Hz), 7.35-7.42 (4H, m), 7.29 (2H, t, J=7.78 Hz), 7.17 (1H, t, J=7.28 Hz), 3.06 (3H, s), 3.01 (3H, s), 2.82 (3H, d, J=4.52 Hz), 1.69 (6H, s). LC-MS retention time: 1.51 min; m/z (MH+): 614. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=12.89 min, purity=92%; Column: Waters Xbridge Phenyl column 4.6×150 mm, 3.5 mm, R$_t$=12.11 min, purity=91%.

5-(3-(tert-butylcarbamoyl)phenyl)-2-(4-fluorophenyl)-6-(N-(2-hydroxyethyl)methylsulfonamido)-N-methylbenzofuran-3-carboxamide. Tert-butylamine (21 µL, 0.195 mmol) was added to a stirring solution of HATU (45 mg, 0.117 mmol), DIEA (41 µL, 0.234 mmol), and 3-(6-(N-(2-(tert-butyldimethylsilyloxy)ethyl)methylsulfonamido)-2-(4-fluorophenyl)-3-(methylcarbamoyl)benzofuran-5-yl)benzoic acid (50 mg, 0.078 mmol) in DMF (780 µL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (11 mg, 23%). 1H NMR (500 MHz, CD$_3$OD) d ppm 8.04 (1H, br. s.), 7.94-8.02 (2H, m), 7.77-7.86 (2H, m), 7.66-7.73 (2H, m), 7.49-7.59 (2H, m), 7.24-7.34 (2H, m), 3.56-3.66 (1H, m), 3.35-3.43 (2H, m), 3.27 (3H, s), 2.94 (3H, s), 2.78-2.87 (1H, m), 1.47 (9H, s). LC-MS retention time: 1.57 min; m/z (MH+): 582. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=10.88 min, purity=97%; Column: Waters Xbridge Phenyl column 4.6×150 mm, 3.5 mm, R$_t$=10.27 min, purity=96%.

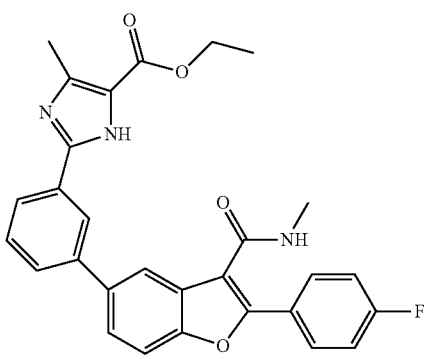

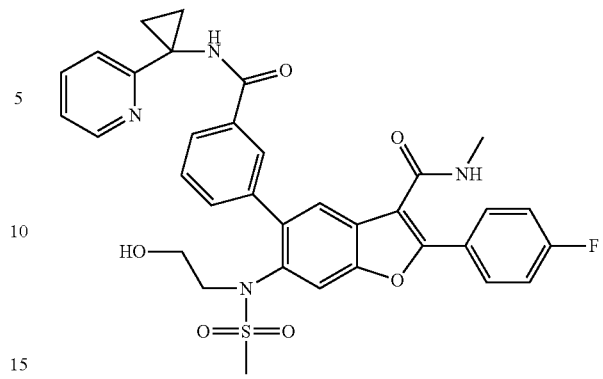

ethyl 2-(3-(2-(4-fluorophenyl)-3-(methylcarbamoyl)benzofuran-5-yl)phenyl)-4-methyl-1H-imidazole-5-carboxylate. Cesium carbonate (234 mg, 0.719 mmol) was added to Pd(Ph3P)4 (27.7 mg, 0.024 mmol), 2-(4-fluorophenyl)-3-(methylcarbamoyl)benzofuran-5-yl trifluoromethanesulfonate (200 mg, 0.479 mmol), ethyl 4-methyl-2-(3-(4,4,5,5-tetramethyl-1,3,2-dioxaborolan-2-yl)phenyl)-1H-imidazole-5-carboxylate (171 mg, 0.479 mmol). Dioxane (4 mL) and water (800 µL) was added at rt. The reaction was heated to 90° C. overnight. The mixture was diluted with ethyl acetate and washed with sat NaHCO3, and sat NaCl. The organic phase was dried over Na2SO4, filtered and concentrated and was purified on silica gel (Biotage, EtOAc/hexanes gradient, fraction collection at λ=254 nm) to give the titled compound (6.8 mg, 3%). 1H NMR (500 MHz, DMSO-$d_6$) d ppm 13.16 (0.34H, s), 12.96 (0.66H, s), 8.54 (1H, q, J=4.48 Hz), 8.50 (0.32H, s), 8.24 (0.68H, s), 8.10 (0.31H, d, J=7.93 Hz), 7.97-8.04 (2H, m), 7.89-7.97 (2H, m), 7.79-7.84 (1.35H, m), 7.70-7.79 (2H, m), 7.54-7.63 (1H, m), 7.37-7.44 (2H, m), 4.33 (0.65H, q, J=7.22 Hz), 4.25 (1.42H, q, J=7.22 Hz), 2.87 (3H, d, J=4.88 Hz), 2.55 (2H, s), 2.45 (1H, s), 1.34 (1H, t, J=7.02 Hz), 1.31 (2H, t, J=7.17 Hz). LC-MS retention time: 1.46 min; m/z (MH+): 498. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Xbridge Phenyl column 4.6×150 mm, 3.5 mm, $R_t$=9.90 min, purity=99%.

2-(4-fluorophenyl)-6-(N-(2-hydroxyethyl)methylsulfonamido)-N-methyl-5-(3-(1-(pyridin-2-yl)cyclopropylcarbamoyl)phenyl)benzofuran-3-carboxamide. 1-(pyridin-2-yl)cyclopropanamine dihydrochloride (24 mg, 0.114 mmol) was added to a stirring solution of HATU (54 mg, 0.142 mmol), DIEA (50 µL, 0.285 mmol), and 3-(2-(4-fluorophenyl)-6-(N-(2-hydroxyethyl)methylsulfonamido)-3-(methylcarbamoyl)benzofuran-5-yl)benzoic acid (50 mg, 0.095 mmol) in DMF (950 µL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H2O/CH3CN gradient, and concentrated to give the titled compound (20 mg, 32%). 1H NMR (500 MHz, DMSO-$d_6$) d ppm 9.20 (1H, s), 8.49-8.57 (1H, m), 8.45 (1H, d, J=3.97 Hz), 7.97-8.05 (3H, m), 7.96 (1H, s), 7.94 (1H, d, J=7.93 Hz), 7.80 (1H, d, J=7.93 Hz), 7.64-7.69 (1H, m), 7.63 (1H, s), 7.56 (1H, t, J=7.63 Hz), 7.37-7.47 (3H, m), 7.15 (1H, dd, J=6.41, 4.88 Hz), 4.91 (1H, br. s.), 3.51-3.60 (1H, m), 3.22 (3H, s), 2.89-2.98 (3H, m), 2.81 (3H, d), 1.50-1.60 (2H, m), 1.23-1.33 (2H, m). LC-MS retention time: 1.37 min; m/z (MH+): 643. LC data was recorded on a Shimadzu LC-10AS liquid chromatograph equipped with a Waters XBridge 5 u C18 4.6×50 mm column using a SPD-10AV UV-V is detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=7.17 min, purity=98%; Column: Waters Xbridge Phenyl column 4.6×150 mm, 3.5 mm, $R_t$=7.89 min, purity=99%.

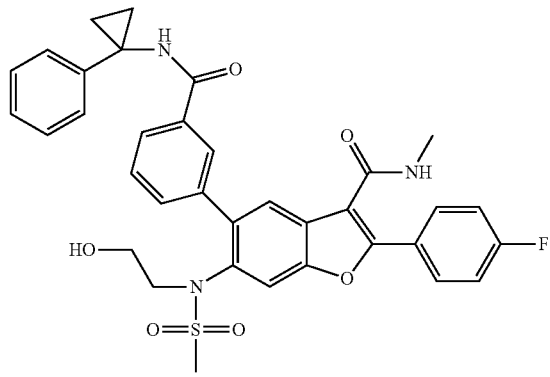
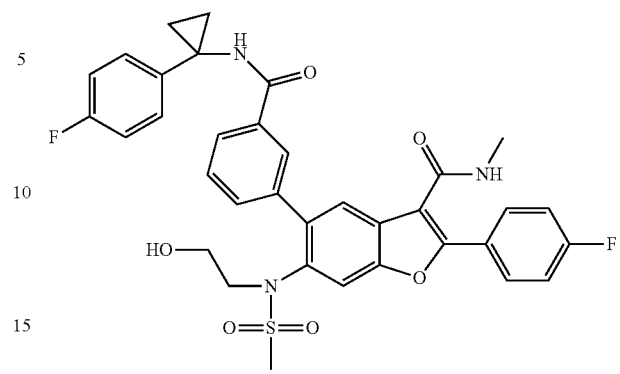

2-(4-fluorophenyl)-6-(N-(2-hydroxyethyl)methylsulfonamido)-N-methyl-5-(3-(1-phenylcyclopropylcarbamoyl)phenyl)benzofuran-3-carboxamide. 1-phenylcyclopropanamine hydrochloride (16 mg, 0.091 mmol) was added to a stirring solution of HATU (43 mg, 0.114 mmol), DIEA (40 μL, 0.228 mmol), and 3-(2-(4-fluorophenyl)-6-(N-(2-hydroxyethyl)methylsulfonamido)-3-(methylcarbamoyl)benzofuran-5-yl)benzoic acid (40 mg, 0.076 mmol) in DMF (760 μL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (22 mg, 44%). 1H NMR (500 MHz, DMSO-d$_6$) d ppm 9.12 (1H, s), 8.49-8.56 (1H, m), 7.97-8.05 (3H, m), 7.95 (1H, s), 7.90 (1H, d, J=7.93 Hz), 7.78 (1H, d, J=7.93 Hz), 7.62 (1H, s), 7.54 (1H, t, J=7.78 Hz), 7.37-7.46 (2H, m), 7.28 (2H, t, J=7.63 Hz), 7.19-7.24 (2H, m), 7.15 (1H, t, J=7.32 Hz), 4.90 (1H, t, J=5.19 Hz), 3.50-3.58 (1H, m), 3.25-3.28 (1H, m), 3.21 (3H, s), 2.88-2.96 (2H, m), 2.82 (3H, d, J=4.58 Hz), 1.22-1.32 (4H, m). LC-MS retention time: 1.57 min; m/z (MH+): 642. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=11.28 min, purity=99%; Column: Waters Xbridge Phenyl column 4.6×150 mm, 3.5 mm, R$_t$=10.86 min, purity=98%.

2-(4-fluorophenyl)-5-(3-(1-(4-fluorophenyl)cyclopropylcarbamoyl)phenyl)-6-(N-(2-hydroxyethyl)methylsulfonamido)-N-methylbenzofuran-3-carboxamide. 1-(4-fluorophenyl)cyclopropanamine hydrochloride (22 mg, 0.114 mmol) was added to a stirring solution of HATU (54 mg, 0.142 mmol), DIEA (50 μL, 0.285 mmol), and 3-(2-(4-fluorophenyl)-6-(N-(2-hydroxyethyl)methylsulfonamido)-3-(methylcarbamoyl)benzofuran-5-yl)benzoic acid (50 mg, 0.095 mmol) in DMF (950 μL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (30 mg, 47%). 1H NMR (500 MHz, DMSO-d$_6$) d ppm 9.14 (1H, s), 8.49-8.55 (1H, m), 7.99-8.04 (2H, m), 7.97-7.98 (1H, m), 7.95 (1H, s), 7.88 (1H, d, J=8.24 Hz), 7.78 (1H, d, J=7.93 Hz), 7.61 (1H, s), 7.53 (1H, t, J=7.78 Hz), 7.39-7.45 (2H, m), 7.22-7.32 (2H, m), 7.05-7.13 (2H, m), 4.90 (1H, t, J=5.04 Hz), 3.50-3.58 (1H, m), 3.24-3.28 (1H, m), 3.20 (3H, s), 2.93 (2H, br. s.), 2.81 (3H, d, J=4.58 Hz), 1.25 (4H, d, J=9.77 Hz). LC-MS retention time: 1.60 min; m/z (MH+): 660. LC data was recorded on a Shimadzu LC-10AS liquid chromatograph equipped with a Waters XBridge 5 u C18 4.6×50 mm column using a SPD-10AV UV-V is detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=11.49 min, purity=99%; Column: Waters Xbridge Phenyl column 4.6×150 mm, 3.5 mm, R$_t$=11.04 min, purity=99%.

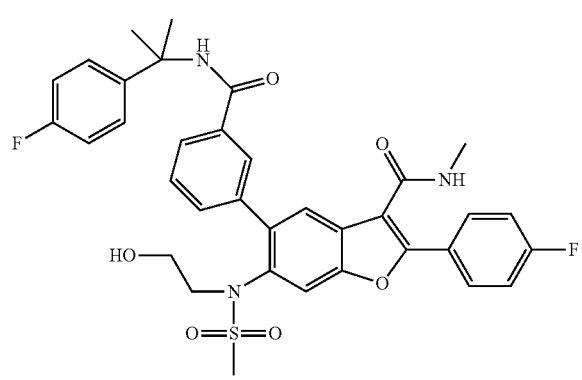

2-(4-fluorophenyl)-5-(3-(2-(4-fluorophenyl)propan-2-ylcarbamoyl)phenyl)-6-(N-(2-hydroxyethyl)methylsulfonamido)-N-methylbenzofuran-3-carboxamide. 2-(4-fluorophenyl)propan-2-amine (18 mg, 0.114 mmol) was added to a stirring solution of HATU (54 mg, 0.142 mmol), DIEA (50 µL, 0.285 mmol), and 2-(4-fluorophenyl)propan-2-amine (18 mg, 0.114 mmol) in DMF (950 µL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (18 mg, 28%). 1H NMR (500 MHz, DMSO-d$_6$) d ppm 8.50-8.56 (1H, m), 8.31 (1H, s), 7.98-8.05 (3H, m), 7.96 (1H, s), 7.83 (1H, d, J=7.63 Hz), 7.73 (1 H, d, J=7.63 Hz), 7.62 (1H, s), 7.53 (1H, t, J=7.78 Hz), 7.38-7.47 (4H, m), 7.09 (2 H, t, J=8.85 Hz), 4.90 (1H, t, J=5.19 Hz), 3.50-3.58 (1H, m), 3.26-3.29 (1H, m), 3.23 (3H, s), 2.87-2.93 (2H, m), 2.82 (3H, d, J=4.58 Hz), 1.67 (6H, s). LC-MS retention time: 1.66 min; m/z (MH+): 662. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=12.11 min, purity=99%; Column: Waters Xbridge Phenyl column 4.6×150 mm, 3.5 mm, R$_t$=11.48 min, purity=100%.

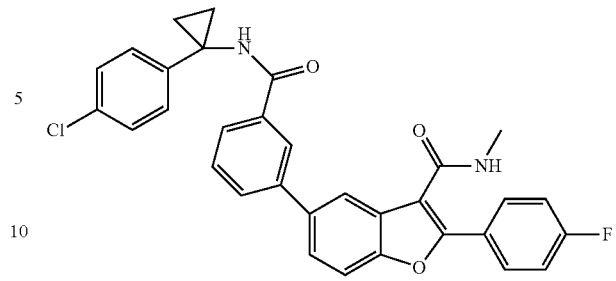

5-(3-(1-(4-chlorophenyl)cyclopropylcarbamoyl)phenyl)-2-(4-fluorophenyl)-N-methylbenzofuran-3-carboxamide.
1-(4-chlorophenyl)cyclopropanamine hydrochloride (25 mg, 0.123 mmol) was added to a stirring solution of HATU (59 mg, 0.154 mmol), DIEA (54 µL, 0.308 mmol), and 3-(2-(4-fluorophenyl)-3-(methylcarbamoyl)benzofuran-5-yl)benzoic acid (40 mg, 0.103 mmol) in DMF (1 mL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (8 mg, 14%). 1H NMR (500 MHz, DMSO-d$_6$) d ppm 9.37 (1H, s), 8.46-8.55 (1H, m), 8.22 (1H, s), 7.95-8.05 (2H, m), 7.86-7.95 (3H, m), 7.74-7.83 (2H, m), 7.59 (1H, t, J=7.63 Hz), 7.38-7.44 (2H, m), 7.30-7.36 (2H, m), 7.20-7.28 (2H, m), 2.86 (3H, d, J=4.58 Hz), 1.26-1.36 (4H, m). LC-MS retention time: 1.92 min; m/z (MH+): 539. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=14.56 min, purity=99%; Column: Waters Xbridge Phenyl column 4.6×150 mm, 3.5 mm, R$_t$=13.20 min, purity=97%.

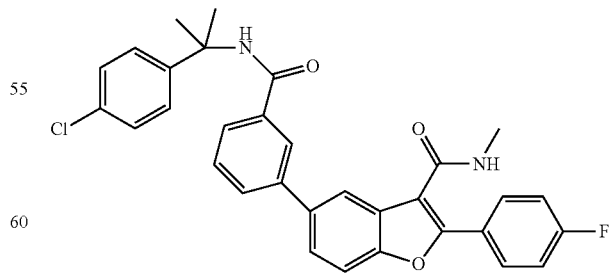

5-(3-(2-(4-chlorophenyl)propan-2-ylcarbamoyl)phenyl)-2-(4-fluorophenyl)-N-methylbenzofuran-3-carboxamide.
2-(4-chlorophenyl)propan-2-amine (21 mg, 0.123 mmol) was added to a stirring solution of HATU (59 mg, 0.154 mmol), DIEA (54 μL, 0.308 mmol), and 3-(2-(4-fluorophenyl)-3-(methylcarbamoyl)benzofuran-5-yl)benzoic acid (40 mg, 0.103 mmol) in DMF (1 mL) at rt. It was allowed to stir for 1 hour. The mixture was diluted with EtOAc and washed with sat NaHCO3, and sat NaCl. The organic phase was dried over Na2SO4, filtered and concentrated and was purified by preparative reverse phase HPLC on a C18 column using a suitably buffered H$_2$O/CH$_3$CN gradient, and concentrated to give the titled compound (32 mg, 57%). 1H NMR (500 MHz, DMSO-d$_6$) d ppm 8.64 (1H, s), 8.47-8.55 (1H, m), 8.14 (1H, s), 7.99-8.04 (2H, m), 7.92 (1H, s), 7.74-7.89 (4H, m), 7.57 (1H, t, J=7.78 Hz), 7.37-7.45 (4H, m), 7.34 (2H, d, J=8.85 Hz), 2.87 (3H, d, J=4.58 Hz), 1.69 (6H, s). LC-MS retention time: 1.95 min; m/z (MH+): 541. LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=15.18 min, purity=99%; Column: Waters Xbridge Phenyl column 4.6×150 mm, 3.5 mm, R$_t$=13.66 min, purity=99%.

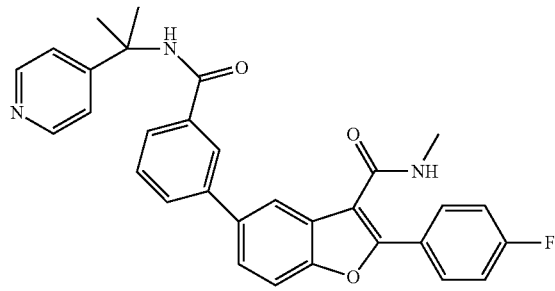

2-(4-fluorophenyl)-N-methyl-5-(3-(2-(pyridin-4-yl)propan-2-ylcarbamoyl)phenyl)benzofuran-3-carboxamide. 2-(pyridin-4-yl)propan-2-amine dihydrochloride (26 mg, 0.123 mmol) was added to a stirring solution of HATU (59 mg, 0.154 mmol), DIEA (54 μL, 0.308 mmol), and 3-(2-(4-fluorophenyl)-3-(methylcarbamoyl)benzofuran-5-yl)benzoic acid (40 mg, 0.103 mmol) in DMF (1 mL) at rt. It was allowed to stir for 1 hour. The reaction was purified by preparative reverse phase HPLC on a C18 column using a suitably buffered H$_2$O/CH$_3$CN gradient, and concentrated to give the titled compound (15 mg, 27%). 1H NMR (500 MHz, DMSO-d$_6$) d ppm 8.73 (1H, s), 8.50-8.55 (1H, m), 8.48 (2H, dd, J=4.58, 1.53 Hz), 8.16 (1H, s), 7.97-8.04 (2H, m), 7.91-7.94 (1H, m), 7.88 (1H, d, J=7.63 Hz), 7.85 (1H, d, J=7.93 Hz), 7.75-7.82 (2H, m), 7.58 (1H, t, J=7.63 Hz), 7.36-7.43 (4H, m), 2.86 (3H, d, J=4.58 Hz), 1.68 (6H, s). LC-MS retention time: 1.59 min; m/z (MH+): 508. LC data was recorded on a Shimadzu LC-10AS liquid chromatograph equipped with a Waters XBridge 5 u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, R$_t$=8.60 min, purity=95%; Column: Waters Xbridge Phenyl column 4.6×150 mm, 3.5 mm, R$_t$=9.26 min, purity=96%.

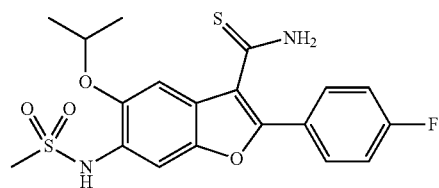

2-(4-fluorophenyl)-5-isopropoxy-6-(methylsulfonamido)benzofuran-3-carbothioamide. The reaction was run in two batches and combined for workup. In the first batch, Lawesson's reagent (27 mg, 0.067 mmol) was added to a solution of 2-(4-fluorophenyl)-5-isopropoxy-6-(methylsulfonamido)benzofuran-3-carboxamide (35 mg, 0.086 mmol) in THF (1.2 mL). The reaction was stirred at r.t. for 2 h, at which point additional Lawesson's reagent (8 mg, 0.020 mmol) was added. In the second batch, Lawesson's reagent (129 mg, 0.32 mmol) was added to a solution of 2-(4-fluorophenyl)-5-isopropoxy-6-(methylsulfonamido)benzofuran-3-carboxamide (125 mg, 0.31 mmol) in THF (3 mL) was stirred at r.t. for 1.5 h. The two batches were then combined and partitioned between EtOAc (50 mL) and water (10 mL). The organic phase was washed with sat'd NaHCO$_3$ and brine, dried over Na$_2$SO$_4$, filtered, and concentrated to give a yellow oil. The residue was purified by silica gel chromatography (Biotage 25+S silica gel cartridge, gradient elution: 20% to 80% EtOAc/hexanes over 20 column volumes, fraction collection at λ=320 nm) to give 48 mg (29% yield) of the title compound. $^1$H NMR (300 MHz, CDCl$_3$) δ ppm 7.76-7.87 (m, 2H) 7.71 (d, J=5.86 Hz, 2H) 7.53 (br. s., 1H) 7.13-7.23 (m, 2H) 6.97 (s, 1H) 6.90 (br. s., 1H) 4.74 (dt, J=12.08, 6.04 Hz, 1H) 2.93 (s, 3H) 1.40 (d, J=6.22 Hz, 6H). LC/MS was performed by using Shimadzu-VP instrument with UV detection at 220 nm and Waters Micromass. LC/MS method: solvent A=5% CH$_3$CN/95% H$_2$O/0.1% NH$_4$OAc, solvent B=95% CH$_3$CN/5% H$_2$O/0.1% NH$_4$OAc, start % B=0, final % B=100, gradient time=2 min, stop time=3 min, flow rate=5 ml/min, column: XBridge C18 5 μm 4.6×50 mm; HPLC R$_t$=1.39 min, (ES+) m/z (MH$^+$)=423.

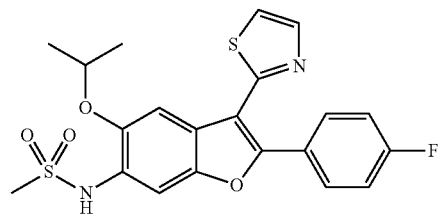

N-(2-(4-fluorophenyl)-5-isopropoxy-3-(thiazol-2-yl)benzofuran-6-yl)methanesulfonamide. Chloroacetaldehyde (50% solution in water, 100 μL, 0.79 mmol) was added to a stirred suspension of the intermediate 2-(4-fluorophenyl)-5- isopropoxy-6-(methylsulfonamido)benzofuran-3-carbothioamide (48 mg, 0.11 mmol) in ethanol (1.5 mL), and the reaction was brought to reflux (100° C. oil bath temp). After 4 h, additional chloroacetaldehyde solution (200 µL, 1.6 mmol) was added and heating was continued overnight. The reaction was cooled to r.t., diluted with EtOAc (75 mL), washed with water (10 mL), sat'd NaHCO$_3$ (2×5 mL), and brine, dried over Na$_2$SO$_4$, filtered, and concentrated to give a brown oil. The residue was purified on silica gel (Biotage 12+M column, gradient elution 10% to 40% EtOAc/hexanes over 20 column volumes, fraction collection at λ=320 nm) to give a colorless oil, 38 mg (75% yield). $^1$H NMR (300 MHz, CDCl$_3$) δ ppm 7.96 (d, J=3.29 Hz, 1H) 7.73-7.86 (m, 3H) 7.56 (s, 1H) 7.37 (d, J=3.29 Hz, 1H) 7.07-7.19 (m, 2H) 6.98 (s, 1H) 4.73 (spt, J=6.04 Hz, 1H) 2.96 (s, 3H) 1.40 (d, J=5.86 Hz, 7H). An analytically pure sample was obtained by precipitation from Et$_2$O/hexanes to give a yellow ppt., which was triturated with Et$_2$O and air dried. LC/MS was performed by using Shimadzu-VP instrument with UV detection at 220 nm and Waters Micromass. LC/MS method: solvent A=5% CH$_3$CN/95% H$_2$O/0.1% NH$_4$OAc, solvent B=95% CH$_3$CN/5% H$_2$O/0.1% NH$_4$OAc, start % B=0, final % B=100, gradient time=2 min, stop time=3 min, flow rate=5 ml/min, column: XBridge C18 5 µm 4.6×50 mm; HPLC R$_t$=1.69 min, (ES+) m/z (MH$^+$)=447. Analytical HPLC were performed using a Shimadzu-VP instrument with UV detection at 220 nm and 254 nm. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 4.6×150 mm, 3.5 µm, R$_t$=14.74 min, purity=97%; column: Waters Xbridge Phenyl 4.6×150 mm, 3.5 µm, R$_t$=12.86 min, purity=98%.

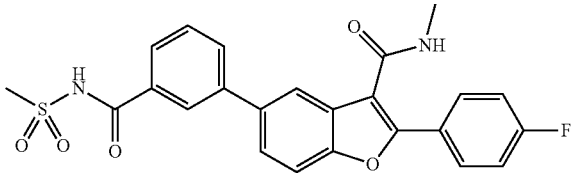

2-(4-fluorophenyl)-N-methyl-5-(3-(methylsulfonylcarbamoyl)phenyl)benzofuran-3-carboxamide. In a 1 dram vial with stir bar were combined 3-(2-(4-fluorophenyl)-3-(methylcarbamoyl)benzofuran-5-yl)benzoic acid (35 mg, 0.090 mmol), DMAP (33 mg, 0.27 mmol), EDC hydrochloride (26 mg, 0.14 mmol), and methanesulfonamide (25 mg, 0.26 mmol). DMF (0.5 mL) was added, the vial was capped, and the reaction was stirred at r.t. overnight. The reaction was filtered, purified by prep HPLC, and concentrated to give 30 mg (72% yield) of the title compound as a white powder. $^1$H NMR (500 MHz, DMSO-d$_6$) δ ppm 12.36 (br. s., 1H) 8.53 (d, J=4.58 Hz, 1H) 8.27 (s, 1H) 7.97-8.05 (m, 2H) 7.84-7.96 (m, 3H) 7.77-7.82 (m, 1H) 7.71-7.76 (m, 1H) 7.56 (t, J=7.78 Hz, 1H) 7.40 (t, J=8.85 Hz, 2H) 3.17 (s, 3H) 2.86 (d, J=4.58 Hz, 3H). LC/MS was performed by using Shimadzu-VP instrument with UV detection at 220 nm and Waters Micromass. LC/MS method: solvent A=10% CH$_3$CN/90% H$_2$O/0.1% TFA, solvent B=90% CH$_3$CN/10% H$_2$O/0.1% TFA, start % B=0, final % B=100, gradient time=2 min, stop time=3 min, flow rate=4 ml/min, column: Sunfire C18 5 µm 4.6×50 mm; HPLC R$_t$=1.56 min, (ES+) m/z (MH$^+$)=467. Analytical HPLC were performed using a Shimadzu-VP instrument with UV detection at 220 nm and 254 nm. Analytical HPLC method: solvent A=5% CH$_3$OH/95% H$_2$O/10 mM NH$_4$HCO$_3$, solvent B=95% CH$_3$OH/5% H$_2$O/10 mM NH$_4$HCO$_3$, start % B=10, final % B=100, gradient time=15 min, stop time=18 min, flow rate=1 ml/min. Column: Phenomenex Gemini C18, 4.6 mm, 3 µm, R$_t$=11.93 min, purity=100%; column: Waters Xbridge Phenyl 4.6×150 mm, 3.5 µm, R$_t$=13.97 min, purity=99%.

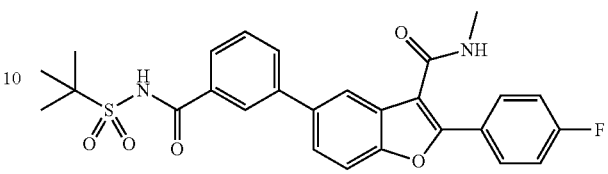

5-(3-(tert-butylsulfonylcarbamoyl)phenyl)-2-(4-fluorophenyl)-N-methylbenzofuran-3-carboxamide. In a 1 dram vial with stir bar were combined 3-(2-(4-fluorophenyl)-3-(methylcarbamoyl)benzofuran-5-yl)benzoic acid (35 mg, 0.090 mmol), DMAP (33 mg, 0.27 mmol), EDC hydrochloride (26 mg, 0.14 mmol), and tert-butylsulfonamide (37 mg, 0.27 mmol). 1,2-Dichloroethane (1 mL) and DMF (0.3 mL) were added, the vial was capped, and the reaction was stirred at r.t. overnight. The reaction was concentrated, filtered, purified by prep HPLC, and concentrated on a speedvac to give 14 mg (31% yield) of the title compound as a white powder. $^1$H NMR (500 MHz, CDCl$_3$) δ ppm 8.12 (s, 1H) 7.97 (s, 1H) 7.91 (dd, J=8.55, 5.19 Hz, 2H) 7.84 (d, J=7.63 Hz, 1H) 7.79 (d, J=7.32 Hz, 1H) 7.46-7.59 (m, 3H) 7.19 (t, J=8.55 Hz, 2H) 6.04 (br. s., 1H) 2.99 (d, J=4.58 Hz, 3H) 1.54 (s, 9H). LC/MS was performed by using Shimadzu-VP instrument with UV detection at 220 nm and Waters Micromass. LC/MS method: solvent A=10% CH$_3$CN/90% H$_2$O/0.1% TFA, solvent B=90% CH$_3$CN/10% H$_2$O/0.1% TFA, start % B=0, final % B=100, gradient time=2 min, stop time=3 min, flow rate=4 ml/min, column: Sunfire C18 5 µm 4.6×50 mm; HPLC R$_t$=1.71 min, (ES+) m/z (MH$^+$)=509. Analytical HPLC were performed using a Shimadzu-VP instrument with UV detection at 220 nm and 254 nm. Analytical HPLC method: solvent A=5% CH$_3$OH/95% H$_2$O/10 mM NH$_4$HCO$_3$, solvent B=95% CH$_3$OH/5% H$_2$O/10 mM NH$_4$HCO$_3$, start % B=10, final % B=100, gradient time=15 min, stop time=18 min, flow rate=1 ml/min. Column: Phenomenex Gemini C18, 4.6 mm, 3 µm, R$_t$=16.49 min, purity=100%; column: Waters Xbridge Phenyl 4.6×150 mm, 3.5 µm, R$_t$=15.35 min, purity=100%.

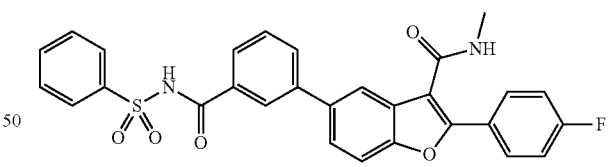

2-(4-fluorophenyl)-N-methyl-5-(3-(phenylsulfonylcarbamoyl)phenyl)benzofuran-3-carboxamide. In a 1 dram vial with stir bar were combined 3-(2-(4-fluorophenyl)-3-(methylcarbamoyl)benzofuran-5-yl)benzoic acid (35 mg, 0.090 mmol), DMAP (33 mg, 0.27 mmol), EDC hydrochloride (26 mg, 0.14 mmol), and benzenesulfonamide (43 mg, 0.27 mmol). 1,2-Dichloroethane (1 mL) and DMF (0.3 mL) were added, the vial was capped, and the suspension was stirred at r.t. overnight, over which time the solids dissolved. The reaction was concentrated, filtered, purified by prep HPLC, and concentrated to give 32 mg (67% yield) of the title compound as a white powder. $^1$H NMR (500 MHz, DMSO-d$_6$) δ ppm 12.78 (br. s., 1H) 8.52 (q, J=4.48 Hz, 1H) 8.24 (s, 1H) 7.97-8.06 (m, 4H) 7.90-7.97 (m, 2H) 7.85 (d, J=7.94 Hz, 1H) 7.74-7.81 (m, 2H) 7.66-7.73 (m, 1H) 7.63 (t, J=7.63 Hz, 2H)

7.58 (t, J=7.63 Hz, 1H) 7.40 (t, J=8.85 Hz, 2H) 2.87 (d, J=4.58 Hz, 3H). LC/MS was performed by using Shimadzu-VP instrument with UV detection at 220 nm and Waters Micromass. LC/MS method: solvent A=10% $CH_3CN$/90% $H_2O$/0.1% TFA, solvent B=90% $CH_3CN$/10% $H_2O$/0.1% TFA, start % B=0, final % B=100, gradient time=2 min, stop time=3 min, flow rate=4 ml/min, column: Sunfire C18 5 µm 4.6×50 mm; HPLC $R_t$=1.77 min, (ES+) m/z (MH+)=529. Analytical HPLC were performed using a Shimadzu-VP instrument with UV detection at 220 nm and 254 nm. Analytical HPLC method: solvent A=5% $CH_3OH$/95% $H_2O$/10 mM $NH_4HCO_3$, solvent B=95% $CH_3OH$/5% $H_2O$/10 mM $NH_4HCO_3$, start % B=10, final % B=100, gradient time=15 min, stop time=18 min, flow rate=1 ml/min. Column: Phenomenex Gemini C18, 4.6 mm, 3 µm, $R_t$=15.70 min, purity=100%; column: Waters Xbridge Phenyl 4.6×150 mm, 3.5 µm, $R_t$=14.90 min, purity=99%.

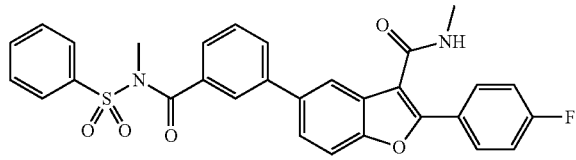

2-(4-fluorophenyl)-N-methyl-5-(3-(methyhphenylsulfonyl)carbamoyl)phenyl)benzofuran-3-carboxamide. In a 1 dram vial with stir bar were combined 3-(2-(4-fluorophenyl)-3-(methylcarbamoyl)benzofuran-5-yl)benzoic acid (35 mg, 0.090 mmol), DMAP (33 mg, 0.27 mmol), EDC hydrochloride (26 mg, 0.14 mmol), and N-methylbenzenesulfonamide (50 µL, 0.26 mmol). 1,2-Dichloroethane (0.5 mL) and DMF (0.5 mL) were added, the vial was capped, and the reaction was stirred at r.t. overnight. The reaction was filtered, purified by prep HPLC, and concentrated on a speedvac to give 27 mg (55% yield) of the title compound as a white powder. $^1H$ NMR (500 MHz, $CDCl_3$) δ ppm 7.91-8.02 (m, 5H) 7.75-7.82 (m, 2H) 7.65 (t, J=7.48 Hz, 1H) 7.47-7.60 (m, 6H) 7.15-7.24 (m, 2H) 5.91 (d, J=4.27 Hz, 1H) 3.36 (s, 3H) 3.04 (d, J=4.88 Hz, 3H). LC/MS was performed by using Shimadzu-VP instrument with UV detection at 220 nm and Waters Micromass. LC/MS method: solvent A=10% $CH_3CN$/90% $H_2O$/0.1% TFA, Solvent B=90% $CH_3CN$/10% $H_2O$/0.1% TFA, start % B=0, final % B=100, gradient time=2 min, stop time=3 min, flow rate=4 ml/min, column: Sunfire C18 5 µm 4.6×50 mm; HPLC $R_t$=1.89 min, (ES+) m/z (MH+)=543. Analytical HPLC were performed using a Shimadzu-VP instrument with UV detection at 220 nm and 254 nm. Analytical HPLC method: solvent A=5% $CH_3OH$/95% $H_2O$/10 mM $NH_4HCO_3$, solvent B=95% $CH_3OH$/5% $H_2O$/10 mM $NH_4HCO_3$, start % B=10, final % B=100, gradient time=15 min, stop time=18 min, flow rate=1 ml/min. Column: Phenomenex Gemini C18, 4.6 mm, 3 µm, $R_t$=17.42 min, purity=92%; column: Waters Xbridge Phenyl 4.6×150 mm, 3.5 µm, $R_t$=17.86 min, purity >90%.

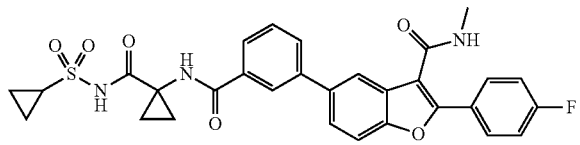

5-(3-(1-(cyclopropylsulfonylcarbamoyl)cyclopropylcarbamoyl)phenyl)-2-(4-fluorophenyl)-N-methylbenzofuran-3-carboxamide. In a 7 mL scintillation vial were combined 3-(2-(4-fluorophenyl)-3-(methylcarbamoyl)benzofuran-5-yl)benzoic acid (30 mg, 0.077 mmol), 1-amino-N-(cyclopropylsulfonyl)cyclopropanecarboxamide hydrochloride (20 mg, 0.083 mmol), and HATU (40 mg, 0.10 mmol). DMF (0.4 mL) and DIPEA (0.1 mL, 0.57 mmol) were added, the vial was capped, and the solution was stirred at r.t. for 45 min. The reaction was diluted with MeOH, filtered, purified by prep HPLC, and the collected fractions were concentrated on a speedvac to afford the title compound (23 mg, 52% yield) as a white powder. $^1H$ NMR (500 MHz, DMSO-$d_6$) δ ppm 8.99 (br. s., 1H) 8.53 (q, J=4.78 Hz, 1H) 8.25 (br. s., 1H) 8.00 (dd, J=8.85, 5.49 Hz, 2H) 7.93 (s, 1H) 7.89 (t, J=7.78 Hz, 2H) 7.72-7.83 (m, 2H) 7.58 (t, J=7.48 Hz, 1H) 7.40 (t, J=8.85 Hz, 2H) 7.07 (br. s., 1H) 2.89-2.98 (m, 1H) 2.87 (d, J=4.58 Hz, 3H) 1.35-1.56 (m, 2H) 0.77-1.28 (m, 6H). LC/MS was performed by using Shimadzu-VP instrument with UV detection at 220 nm and Waters Micromass. LC/MS method: solvent A=10% $CH_3CN$/90% $H_2O$/0.1% TFA, solvent B=90% $CH_3CN$/10% $H_2O$/0.1% TFA, start % B=0, final % B=100, gradient time=2 min, stop time=3 min, flow rate=4 ml/min, column: Sunfire C18 5 µm 4.6×50 mm; HPLC $R_t$=1.59 min, (ES+) m/z (MH+)=576. Analytical HPLC were performed using a Shimadzu-VP instrument with UV detection at 220 nm and 254 nm. Analytical HPLC method: solvent A=5% $CH_3OH$/95% $H_2O$/10 mM $NH_4HCO_3$, solvent B=95% $CH_3OH$/5% $H_2O$/10 mM $NH_4HCO_3$, start % B=10, final % B=100, gradient time=15 min, stop time=18 min, flow rate=1 ml/min. Column: Phenomenex Gemini C18, 4.6 mm, 3 µm, $R_t$=15.39 min, purity=100%; column: Waters Xbridge Phenyl 4.6×150 mm, 3.5 µm, $R_t$=14.50 min, purity=100%.

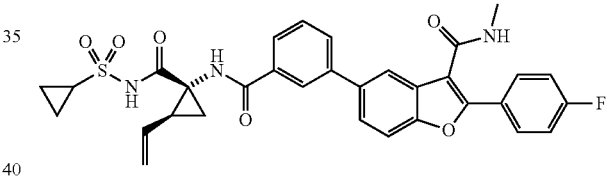

5-(3-((1R,2S)-1-(cyclopropylsulfonylcarbamoyl)-2-vinylcyclopropylcarbamoyl)phenyl)-2-(4-fluorophenyl)-N-methylbenzofuran-3-carboxamide. In a 7 mL scintillation vial were combined 3-(2-(4-fluorophenyl)-3-(methylcarbamoyl)benzofuran-5-yl)benzoic acid (30 mg, 0.077 mmol), (1R,2S)-1-amino-N-(cyclopropylsulfonyl)-2-vinylcyclopropanecarboxamide 4-methylbenzenesulfonate (30 mg, 0.075 mmol), and HATU (40 mg, 0.10 mmol). DMF (0.4 mL) and DIPEA (0.1 mL, 0.57 mmol) were added, the vial was capped, and the solution was stirred at r.t. for 45 min. The reaction was diluted with MeOH, filtered, purified by prep HPLC, and the collected fractions were concentrated on a speedvac to afford the title compound (25 mg, 54% yield) as a white powder. $^1H$ NMR (500 MHz, $CDCl_3$) δ ppm 8.01 (s, 1H) 7.97 (s, 1H) 7.88 (dd, J=8.85, 5.19 Hz, 2H) 7.80 (d, J=7.63 Hz, 1H) 7.74 (d, J=7.63 Hz, 1H) 7.59 (br. s., 1H) 7.52 (s, 2H) 7.48 (t, J=7.63 Hz, 1H) 7.18 (t, J=8.55 Hz, 2H) 6.00 (d, J=3.97 Hz, 1H) 5.61-5.73 (m, 1H) 5.39 (d, J=17.09 Hz, 1H) 5.20 (d, J=10.99 Hz, 1H) 3.02 (d, J=4.88 Hz, 3H) 2.91-2.99 (m, 1H) 2.34 (q, J=8.44 Hz, 1H) 2.05-2.09 (m, 1H) 1.49 (dd, J=9.31, 5.95 Hz, 1H) 1.41 (dd, J=5.80, 4.58 Hz, 1H) 1.30-1.35 (m, 1 H) 1.22-1.30 (m, 1H) 1.04-1.12 (m, 1H) 0.96-1.04 (m, 1H). LC/MS was performed by using Shimadzu-VP instrument with UV detection at 220 nm and Waters Micromass. LC/MS method: solvent A=10% $CH_3CN$/90% $H_2O$/0.1% TFA, solvent B=90% $CH_3CN$/10% $H_2O$/0.1% TFA, start % B=0, final % B=100, gradient time=2 min, stop time=3 min, flow rate=4 ml/min, column: Sunfire C18 5 μm 4.6×50 mm; HPLC R$_t$=1.73 min, (ES+) m/z (MH$^+$)=602. Analytical HPLC were performed using a Shimadzu-VP instrument with UV detection at 220 nm and 254 nm. Analytical HPLC method: solvent A=5% CH$_3$OH/95% H$_2$O/10 mM NH$_4$HCO$_3$, solvent B=95% CH$_3$OH/5% H$_2$O/10 mM NH$_4$HCO$_3$, start % B=10, final % B=100, gradient time=15 min, stop time=18 min, flow rate=1 ml/min. Column: Phenomenex Gemini C18, 4.6 mm, 3 μm, R$_t$=16.26 min, purity=100%; column: Waters Xbridge Phenyl 4.6×150 mm, 3.5 μm, R$_t$=15.28 min, purity=100%.

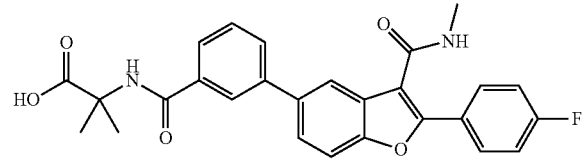

2-(3-(2-(4-fluorophenyl)-3-(methylcarbamoyl)benzofuran-5-yl)benzamido)-2-methylpropanoic acid. HATU (450 mg, 1.18 mmol) was added to a suspension of 3-(2-(4-fluorophenyl)-3-(methylcarbamoyl)benzofuran-5-yl)benzoic acid (400 mg, 1.03 mmol), methyl 2-amino-2-methylpropanoate hydrochloride (180 mg, 1.17 mmol), and DIPEA (0.6 mL, 3.4 mmol) in DCE (10 mL). After 5 min, the solids had not dissolved. Add DMF (0.5 mL) and continue stirring the suspension at r.t. overnight. The reaction was then concentrated to give a thick suspension (DMF remained after concentration). Water and Et$_2$O were added and the flask swirled until a fine grey suspension was formed. The ppt. was collected by filtration, rinsed with 1 N HCl, water, and ether, and air dried to afford 550 mg (110% yield) of the title compound as a grey solid. LC/MS was performed on a Shimadzu-VP instrument with UV detection at 220 nm and Waters Micromass. LC/MS method: solvent A=5% CH$_3$CN/95% H$_2$O/10 mM NH$_4$OAc, solvent B=95% CH$_3$CN/5% H$_2$O/10 mM NH$_4$OAc, start % B=0, sinal % B=100, gradient time=2 min, stop time=3 min, flow rate=5 ml/min, column: XBridge C18 5 μm 4.6×50 mm; HPLC R$_t$=1.49 min, (ES+) m/z (MH$^+$)=489. To a suspension of the crude ester from above (~0.1 mmol) in MeOH (7 mL)/H$_2$O (2.1 mL) in a 20 mL scintillation vial with stir bar was added 10 N NaOH soln. (0.4 mL, 4.00 mmol). The vial was capped, stirred at r.t. overnight, then quenched by pouring into 8 mL of 1 N HCl. A white ppt. formed. The suspension was extracted with EtOAc, and the insoluble grey solid was collected by filtration and air dried (61 mg). The organic phase was washed with brine, dried over Na$_2$SO$_4$, filtered, and concentrated to give a white powder. This was triturated with Et$_2$O and collected by filtration to give 360 mg of the white powder. Both crops of ppt. were identical by LC/MS and were combined to give 421 mg (86% over two steps) of the title compound as an off-white powder. $^1$H NMR (300 MHz, CD$_3$OD) δ ppm 8.59 (s, 1H) 8.50 (d, J=3.29 Hz, 1H) 8.10-8.16 (m, 1H) 7.91-8.01 (m, 3H) 7.83 (dd, J=12.99, 7.87 Hz, 2H) 7.64-7.74 (m, 2H) 7.56 (t, J=7.68 Hz, 1H) 7.27 (t, J=8.78 Hz, 2H) 2.95-3.02 (m, 3H) 1.62 (s, 6H). LC/MS was performed on a Shimadzu-VP instrument with UV detection at 220 nm and Waters Micromass. LC/MS method: solvent A=5% CH$_3$CN/95% H$_2$O/10 mM NH$_4$OAc, solvent B=95% CH$_3$CN/5% H$_2$O/10 mM NH$_4$OAc, start % B=0, final % B=100, gradient time=2 min, stop time=3 min, flow rate=5 ml/min, column: XBridge C18 5 μm 4.6×50 mm; HPLC R$_t$=1.06 min, (ES+) m/z (MH$^+$)=475. Analytical HPLC were performed using a Shimadzu-VP instrument with UV detection at 220 nm and 254 nm. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 3.5 μm 4.6×150 mm, R$_t$=10.91 min, purity=98%; column: Waters Xbridge Phenyl 3.5 μm 4.6×150 mm, R$_t$=10.21 min, purity=98%.

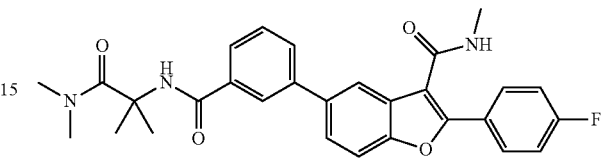

5-(3-(1-(dimethylamino)-2-methyl-1-oxopropan-2-ylcarbamoyl)phenyl)-2-(4-fluorophenyl)-N-methylbenzofuran-3-carboxamide. A solution of dimethylamine in THF (2 molar, 0.10 mL, 0.20 mmol) was added to 2-(3-(2-(4-fluorophenyl)-3-(methylcarbamoyl)benzofuran-5-yl)benzamido)-2-methylpropanoic acid (17 mg, 0.036 mmol) and HATU (15 mg, 0.039 mmol) in a 1 dram vial. DMF (0.3 mL) was added, the vial was capped, and the homogeneous solution was stirred at r.t. for 1 h, at which point DIPEA (50 μL, 0.29 mmol) was added. Stirring was continued for 3 h, at which point the reaction was filtered and purified directly by prep HPLC. Concentration of the collected fractions afforded the title compound as a white solid (13 mg, 71% yield). $^1$H NMR (500 MHz, CD$_3$OD) δ ppm 8.09-8.17 (m, 1H) 7.90-7.98 (m, 3H) 7.86 (d, J=7.94 Hz, 1H) 7.79-7.84 (m, 1H) 7.63-7.72 (m, 2H) 7.57 (t, J=7.63 Hz, 1H) 7.20-7.32 (m, 2H) 3.14 (br. s., 3H) 2.98 (s, 6H) 1.61 (s, 6H). LC/MS was performed on a Shimadzu-VP instrument with UV detection at 220 nm and Waters Micromass. LC/MS method: solvent A=5% CH$_3$CN/95% H$_2$O/10 mM NH$_4$OAc, solvent B=95% CH$_3$CN/5% H$_2$O/10 mM NH$_4$OAc, start % B=0, final % B=100, gradient time=2 min, stop time=3 min, flow rate=5 ml/min, column: XBridge C18 5 μm 4.6×50 mm; HPLC R$_t$=1.29 min, (ES+) m/z (MH$^+$)=502. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 3.5 μm 4.6×150 mm, R$_t$=14.80 min, purity=100%; column: Waters Xbridge Phenyl 3.5 μm 4.6×150 mm, R$_t$=10.37 min, purity=100%.

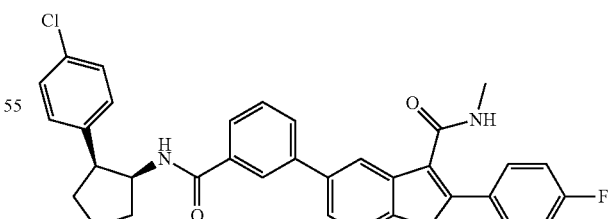

5-(3-((cis)-2-(4-chlorophenyl)cyclopentylcarbamoyl)phenyl)-2-(4-fluorophenyl)-N-methylbenzofuran-3-carboxamide. In a 1 dram vial were combined 3-(2-(4-fluorophenyl)-3-(methylcarbamoyl)benzofuran-5-yl)benzoic acid (20 mg, 0.051 mmol), cis-2-(4-chlorophenyl)cyclopentanamine (14 mg, 0.072 mmol), and HATU (31 mg, 0.082 mmol). DMF (0.4 mL) and DIPEA (50 μL, 0.29 mmol) were added, and the vial was capped and stirred at r.t. for 2 h, then diluted with MeOH, filtered, and purify directly by prep HPLC. Concentration afforded the title compound (15 mg, 52% yield) as a fluffy white solid. $^1$H NMR (500 MHz, DMSO-$d_6$) δ ppm 8.47-8.59 (m, 1H) 8.06 (d, J=8.85 Hz, 1H) 7.97-8.03 (m, 2H) 7.86 (d, J=1.83 Hz, 1H) 7.75-7.82 (m, 2H) 7.68 (s, 1H) 7.65 (dd, J=8.55, 1.83 Hz, 1H) 7.45-7.53 (m, 2H) 7.40 (t, J=8.85 Hz, 2H) 7.27 (s, 4H) 4.60-4.71 (m, J=7.67, 7.67, 7.55, 7.32 Hz, 1H) 3.33-3.41 (m, 1H) 2.87 (d, J=4.58 Hz, 3H) 1.99-2.15 (m, 3H) 1.89-1.98 (m, 1H) 1.72-1.82 (m, 1H) 1.57-1.71 (m, 1H). LC/MS was performed on a Shimadzu-VP instrument with UV detection at 220 nm and Waters Micromass. LC/MS method: solvent A=10% CH$_3$CN/90% H$_2$O/0.1% TFA, solvent B=90% CH$_3$CN/10% H$_2$O/0.1% TFA, start % B=0, final % B=100, gradient time=2 min, stop time=3 min, flow rate=4 ml/min, column: Sunfire C18 5 μm 4.6×50 mm; HPLC $R_t$=2.02 min, (ES+) m/z (MH$^+$)=567. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 3.5 μm 4.6×150 mm, $R_t$=15.42 min, purity=98%; column: Waters Xbridge Phenyl 3.5 μm 4.6×150 mm, $R_t$=13.74 min, purity=97%.

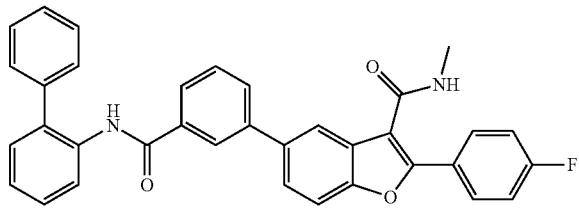

5-(3-(biphenyl-2-ylcarbamoyl)phenyl)-2-(4-fluorophenyl)-N-methylbenzofuran-3-carboxamide. In a 1 dram vial were combined 3-(2-(4-fluorophenyl)-3-(methylcarbamoyl)benzofuran-5-yl)benzoic acid (30 mg, 0.077 mmol), biphenyl-2-amine (17 mg, 0.10 mmol), and HATU (40 mg, 0.105 mmol). DMF (0.4 mL) and DIPEA (50 μL, 0.29 mmol) were added, and the vial was capped and stirred at r.t. for overnight, then diluted with MeOH, filtered, and purified directly by prep HPLC. Concentration afforded the title compound (17 mg, 41% yield) as a fluffy white solid. $^1$H NMR (500 MHz, DMSO-$d_6$) δ ppm 9.96 (s, 1H) 8.53 (q, J=4.58 Hz, 1H) 7.96-8.06 (m, 3H) 7.85-7.91 (m, 2H) 7.80 (d, J=8.55 Hz, 1H) 7.77 (d, J=7.32 Hz, 1H) 7.70 (dd, J=8.55, 1.83 Hz, 1H) 7.57-7.61 (m, 1H) 7.56 (d, J=6.10 Hz, 1H) 7.48 (d, J=7.32 Hz, 2H) 7.36-7.46 (m, 7H) 7.31 (t, J=7.48 Hz, 1H) 2.87 (d, J=4.88 Hz, 3H). LC/MS was performed by using Shimadzu-VP instrument with UV detection at 220 nm and Waters Micromass. LC/MS method: solvent A=10% CH$_3$CN/90% H$_2$O/0.1% TFA, solvent B=90% CH$_3$CN/10% H$_2$O/0.1% TFA, start % B=0, final % B=100, gradient time=2 min, stop time=3 min, flow rate=4 ml/min, column: Sunfire C18 5 μm 4.6×50 mm; HPLC $R_t$=2.02 min, (ES+) m/z (MH$^+$)=541. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 3.5 μm 4.6×150 mm, $R_t$=15.37 min, purity=100%; column: Waters Xbridge Phenyl 3.5 μm 4.6×150 mm, $R_t$=13.75 min, purity=100%.

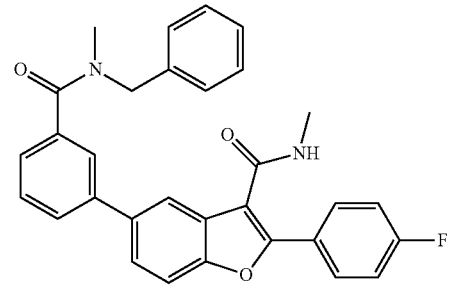

5-(3-(benzyl(methyl)carbamoyl)phenyl)-2-(4-fluorophenyl)-N-methylbenzofuran-3-carboxamide. DIPEA (50 μL, 0.29 mmol) and N-methylbenzylamine (20 μL, 0.16 mmol) were added to a stirred suspension of 3-(2-(4-fluorophenyl)-3-(methylcarbamoyl)benzofuran-5-yl)benzoic acid (20 mg, 0.051 mmol) and HATU (25 mg, 0.066 mmol) in DMF (0.5 mL) and the reaction was stirred at r.t. overnight. The reaction was then diluted with MeOH, filtered, purified by prep HPLC, and concentrated to give the title compound as a tan powder (12 mg, 47% yield). $^1$H NMR (500 MHz, DMSO-$d_6$) δ ppm 8.50 (br. s., 1H) 8.01 (dd, J=8.39, 5.65 Hz, 2H) 7.66-7.93 (m, 5H) 7.58 (br. s., 1H) 7.42-7.50 (m, 1H) 7.35-7.42 (m, 4H) 7.31 (d, J=5.80 Hz, 1H) 7.23 (d, J=4.58 Hz, 1H) 4.72 (br. s., 1H) 4.54 (br. s., 1H) 2.83-3.00 (m, 6H). LC/MS was performed by using Shimadzu-VP instrument with UV detection at 220 nm and Waters Micromass. LC/MS method: solvent A=10% CH$_3$CN/90% H$_2$O/0.1% TFA, solvent B=90% CH$_3$CN/10% H$_2$O/0.1% TFA, start % B=0, final % B=100, gradient time=2 min, stop time=3 min, flow rate=4 ml/min, column: Sunfire C18 5 μm 4.6×50 mm; HPLC $R_t$=1.85 min, (ES+) m/z (MH$^+$)=493. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. Column: Waters Sunfire C-18, 3.5 μm 4.6×150 mm, $R_t$=16.26 min, purity=99%; column: Waters Xbridge Phenyl 3.5 μm 4.6×150 mm, $R_t$=12.81 min, purity=98%.

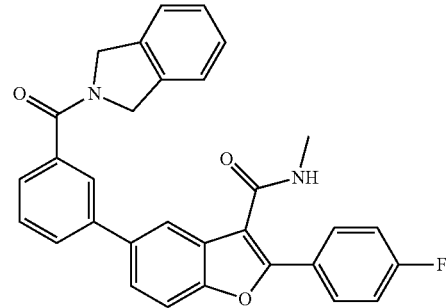

2-(4-fluorophenyl)-5-(3-(isoindoline-2-carbonyl)phenyl)-N-methylbenzofuran-3-carboxamide. Isoindoline (20 μL, 0.18 mmol) was added to a stirred suspension of 3-(2-(4-fluorophenyl)-3-(methylcarbamoyl)benzofuran-5-yl)benzoic acid (20 mg, 0.051 mmol), HATU (25 mg, 0.066 mmol), and DIPEA (50 μL, 0.29 mmol) in DMF (0.5 mL). The reaction was stirred at r.t. overnight. The reaction was then diluted with MeOH and an off-white ppt. formed. The ppt. was collected by filtration, triturated with MeOH, and air dried to afford the title compound (17 mg, 68% yield). $^1$H NMR (500 MHz, DMSO-$d_6$) δ ppm 8.50 (q, J=4.58 Hz, 1H)

7.99-8.05 (m, 2H) 7.90-7.95 (m, 2H) 7.85 (dt, J=6.10, 2.44 Hz, 1H) 7.77-7.81 (m, 1H) 7.73-7.77 (m, 1H) 7.58-7.64 (m, 2H) 7.36-7.45 (m, 3H) 7.30-7.34 (m, 1H) 7.29 (s, 2H) 4.91 (s, 2H) 4.84 (s, 2H) 2.86 (d, J=4.88 Hz, 3H). LC/MS was performed on a Shimadzu-VP instrument with UV detection at 220 nm and Waters Micromass. LC/MS method: solvent A=10% CH₃CN/90% H₂O/0.1% TFA, solvent B=90% CH₃CN/10% H₂O/0.1% TFA, start % B=0, final % B=100, gradient time=3 min, stop time=4 min, flow rate=4 ml/min, column: Sunfire C18 5 µm 4.6×50 mm; HPLC $R_t$=2.48 min, (ES+) m/z (MH⁺)=491. Analytical HPLC method: solvent A=5% CH₃CN/95% H₂O/0.1% TFA, solvent B=95% CH₃CN/5% H₂O/0.1% TFA, start % B=10, final % B=100, gradient time=15 min, stop time=18 min, flow rate=1 ml/min. Column: Waters Sunfire C-18, 3.5 µm 4.6×150 mm, $R_t$=13.81 min, purity=100%; column: Waters Xbridge Phenyl 3.5 µm 4.6×150 mm, $R_t$=13.81 min, purity=100%.

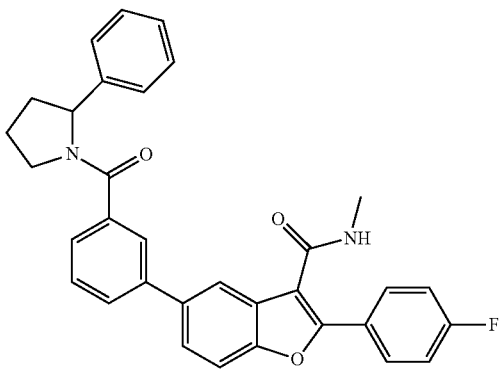

2-(4-fluorophenyl)-N-methyl-5-(3-(2-phenylpyrrolidine-1-carbonyl)phenyl)benzofuran-3-carboxamide. 2-Phenylpyrrolidine (20 mg, 0.14 mmol) was added to a stirred suspension of 3-(2-(4-fluorophenyl)-3-(methylcarbamoyl)benzofuran-5-yl)benzoic acid (20 mg, 0.051 mmol), HATU (25 mg, 0.066 mmol), and DIPEA (50 µL, 0.29 mmol) in DMF (0.5 mL). The reaction was stirred at r.t. overnight. The reaction was then diluted with MeOH, filtered, and purified by prep HPLC. Concentration afforded the title compound (21 mg, 78% yield) as a light pink solid. ¹H NMR (~3:2 ratio of amide rotamers, 500 MHz, DMSO-d₆) δ ppm 8.44-8.56 (m, 1H) 7.96-8.07 (m, 2H) 7.74-7.89 (m, 3H) 7.56-7.67 (m, 2H) 7.30-7.45 (m, 5.4H) 7.16-7.29 (m, 2.6H) 7.09 (d, J=7.02 Hz, 1H) 5.19 (t, J=6.71 Hz, 0.6H) 4.98 (d, J=6.41 Hz, 0.4H) 3.75-3.92 (m, 1.4H) 3.53-3.64 (m, 0.6H) 2.87 (m, 3H) 2.40 (dd, J=12.36, 6.56 Hz, 0.6H) 2.30-2.38 (m, 0.4H) 1.73-1.92 (m, 3H). LC/MS was performed by using Shimadzu-VP instrument with UV detection at 220 nm and Waters Micromass. LC/MS method: solvent A=10% CH₃CN/90% H₂O/0.1% TFA, solvent B=90% CH₃CN/10% H₂O/0.1% TFA, start % B=0, final % B=100, gradient time=3 min, stop time=4 min, flow rate=4 ml/min, column: Sunfire C18 5 µm 4.6×50 mm; HPLC $R_t$=1.86 min, (ES+) m/z (MH⁺)=519. Analytical HPLC method: solvent A=5% CH₃CN/95% H₂O/0.1% TFA, solvent B=95% CH₃CN/5% H₂O/0.1% TFA, start % B=10, final % B=100, gradient time=15 min, stop time=18 min, flow rate=1 ml/min. Column: Waters Sunfire C-18, 3.5 µm 4.6×150 mm, $R_t$=14.38 min, purity=99%; column: Waters Xbridge Phenyl column 3.5 µm 4.6×150 mm, $R_t$=13.01 min, purity=99%.

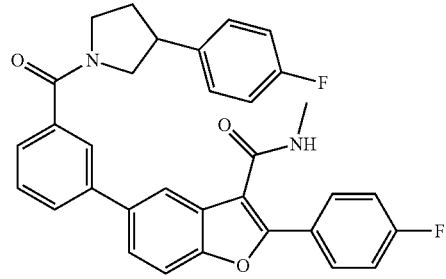

2-(4-fluorophenyl)-5-(3-(3-(4-fluorophenyl)pyrrolidine-1-carbonyl)phenyl)-N-methylbenzofuran-3-carboxamide. 3-(4-Fluorophenyl)pyrrolidine hydrochloride (25 mg, 0.12 mmol) was added to a stirred suspension of 3-(2-(4-fluorophenyl)-3-(methylcarbamoyl)benzofuran-5-yl)benzoic acid (20 mg, 0.051 mmol), HATU (25 mg, 0.066 mmol), and DIPEA (50 µL, 0.29 mmol) in DMF (0.5 mL). The reaction was stirred at r.t. overnight, then diluted with MeOH, filtered, and purified by prep HPLC. Concentration afforded the title compound (22 mg, 79% yield) as a pink solid. ¹H NMR (~1:1 ratio of amide rotamers, 500 MHz, DMSO-d₆) δ ppm 8.44-8.54 (m, 1H) 7.98-8.06 (m, 2H) 7.66-7.91 (m, 5H) 7.52-7.61 (m, 2H) 7.36-7.44 (m, 3H) 7.33 (dd, J=8.55, 5.49 Hz, 1H) 7.18 (t, J=8.85 Hz, 1H) 7.12 (t, J=8.85 Hz, 1H) 4.01 (dd, J=11.14, 7.17 Hz, 0.5H) 3.72-3.82 (m, 1.5H) 3.56-3.69 (m, 1.5H) 3.36-3.55 (m, 1.5H) 2.87 (d, J=4.58 Hz, 1.5H) 2.84 (d, J=4.58 Hz, 1.5H) 2.27-2.34 (m, 0.5H) 2.24 (dd, J=6.56, 3.51 Hz, 0.5H) 2.04-2.12 (m, 0.5H) 2.00 (dd, J=19.84, 10.38 Hz, 0.5H). LC/MS was performed on a Shimadzu-VP instrument with UV detection at 220 nm and Waters Micromass. LC/MS method: solvent A=10% CH₃CN/90% H₂O/0.1% TFA, solvent B=90% CH₃CN/10% H₂O/0.1% TFA, start % B=0, final % B=100, gradient time=3 min, stop time=4 min, flow rate=4 ml/min, column: Sunfire C18 5 µm 4.6×50 mm; HPLC $R_t$=1.89 min, (ES+) m/z (MH⁺)=537. Analytical HPLC method: solvent A=5% CH₃CN/95% H₂O/0.1% TFA, solvent B=95% CH₃CN/5% H₂O/0.1% TFA, start % B=10, final % B=100, gradient time=15 min, stop time=18 min, flow rate=1 ml/min. Column: Waters Sunfire C-18, 3.5 µm 4.6×150 mm, $R_t$=14.43 min, purity=99%; column: Waters Xbridge Phenyl 3.5 µm 4.6×150 mm, $R_t$=13.18 min, purity=99%.

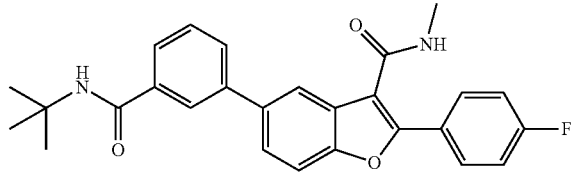

5-(3-(tert-butylcarbamoyl)phenyl)-2-(4-fluorophenyl)-N-methylbenzofuran-3-carboxamide. DIEA (50 µL, 0.29 mmol) was added to a suspension of 3-(2-(4-fluorophenyl)-3-(methylcarbamoyl)benzofuran-5-yl)benzoic acid (50 mg, 0.13 mmol) and HATU (60 mg, 0.16 mmol) in DMF (0.5 mL). The solids dissolved over 5 min, at which point tert-butylamine (20 µL, 0.19 mmol) was added. The solution was stirred at r.t. for 1 h, then diluted with CH₃CN (1 mL), filtered, purified by prep HPLC, concentrated, and dried in a vacuum oven over the weekend at 40° C. to give the title compound (39 mg, 69% yield) as a white powder. ¹H NMR (500 MHz, DMSO-d₆) δ ppm 8.53 (q, J=4.37 Hz, 1H) 8.08 (s, 1H) 8.01

(dd, J=8.24, 5.80 Hz, 2H) 7.92 (d, J=7.93 Hz, 2H) 7.84 (d, J=7.63 Hz, 1H) 7.77-7.82 (m, 2H) 7.73-7.77 (m, 1H) 7.55 (t, J=7.63 Hz, 1H) 7.40 (t, J=8.85 Hz, 2H) 2.87 (d, J=4.58 Hz, 3H) 1.42 (s, 9H). $^{13}$C NMR (125 MHz, DMSO-d$_6$) δ ppm 166.20 (s) 163.22 (s) 162.66 (d, J=246 Hz) 152.56 (s) 152.52 (s) 140.06 (s) 136.53 (s) 135.76 (s) 129.38 (d, J=12 Hz) 129.36 (s) 128.70 (s) 127.86 (s) 126.27 (s) 125.86 (s) 125.70 (d, J=2.5 Hz) 124.83 (s) 118.90 (s) 115.93 (d, J=20 Hz) 113.88 (s) 111.60 (s) 50.85 (s) 28.60 (s) 26.19 (s). LC/MS method: solvent A=5% CH$_3$CN/95% H$_2$O/10 mM NH$_4$OAc, solvent B=95% CH$_3$CN/5% H$_2$O/10 mM NH$_4$OAc, start % B=0, final % B=100, gradient time=2 min, stop time=3 min, flow rate=5 ml/min, column: XBridge C18 5 μm 4.6×50 mm; HPLC R$_t$=1.57, (ES−) m/z (M$^−$)=443. Analytical HPLC method: solvent A=5% CH$_3$CN/95% H$_2$O/0.1% TFA, solvent B=95% CH$_3$CN/5% H$_2$O/0.1% TFA, start % B=10, final % B=100, gradient time=15 min, stop time=18 min, flow rate=1 ml/min. column: Waters Sunfire C-18, 3.5 μm 4.6×150 mm, R$_t$=11.71 min, purity=100%; column: Waters Xbridge Phenyl column 3.5 μm 4.6×150 mm, R$_t$=9.53 min, purity=100%.

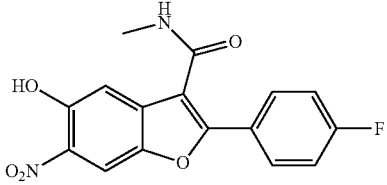

2-(4-Fluorophenyl)-5-hydroxy-N-methyl-6-nitrobenzofuran-3-carboxamide. To a mixture of 2-(4-fluorophenyl)-5-isopropoxy-N-methyl-6-nitrobenzofuran-3-carboxamide (210.5 mg, 0.565 mmol) in CH$_2$Cl$_2$ (14 mL) at 0° C. under N$_2$ was added trichloroborane (1.70 mL, 1.7 mmol) (1M solution in CH$_2$Cl$_2$). The mixture was then stirred at r.t. for 17 hr. The mixture was evaporated. The reddish orange residue was added 7 ml H$_2$O, and then 3.5 ml 1N HCl, and left standing until the solid turned yellow. The yellow solid product was then filtered and washed with 3×3 ml H$_2$O and dried (182 mg, 93%). $^1$H NMR (500 MHz, DMSO-d$_6$) δ 10.18 (broad s, 1H), 8.53 (m, 1H), 8.31 (s, 1H), 7.98 (apparent dd, J=8.85, 5.49, 2H), 7.43 (apparent t, J=8.85, 2H), 7.28 (s, 1H,), 2.84 (appeared as d, J=4.58, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=331.21, HPLC R$_t$=1.442 min.

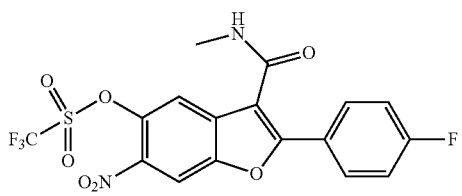

2-(4-Fluorophenyl)-3-(methylcarbamoyl)-6-nitrobenzofuran-5-yl trifluoromethanesulfonate. To a mixture of 2-(4-fluorophenyl)-5-hydroxy-N-methyl-6-nitrobenzofuran-3-carboxamide (100 mg, 0.303 mmol) in CH$_2$Cl$_2$ (4 mL) at r.t. under N$_2$ was added triethylamine (0.084 mL, 0.606 mmol). The mixture was then cooled to 0° C., and then added 1,1,1-trifluoro-N-phenyl-N-(trifluoromethylsulfonyl)methanesulfonamide (162 mg, 0.454 mmol). The orange suspension was then stirred at r.t. for 23 hr. The mixture was evaporated. The grayish-green residue was added 3 ml H$_2$O, the solid product filtered and washed with 3×3 ml H$_2$O and dried (130.8 mg, 89%). $^1$H NMR (500 MHz, DMSO-d$_6$) δ 8.84 (s, 1H), 8.62 (broad s, 1H), 8.02 (td, J=5.65, 2.44, 2H), 7.96 (s, 1H,), 7.48 (td, J=8.77, 2.59, 2H), 2.85 (appeared as d, J=3.97, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=463.25, HPLC R$_t$=1.700 min.

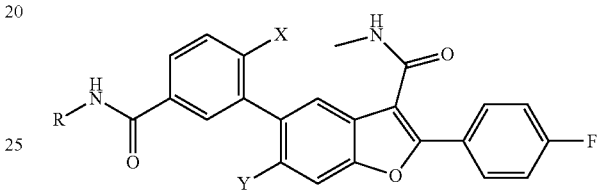

General procedure. A mixture of 2-(4-fluorophenyl)-3-(methylcarbamoyl)benzofuran-5-yl trifluoromethanesulfonate (or the 6-nitro analog) (0.3 mmol, 1 equiv.), 3-boronobenzoic acid (1.5 equiv.), cesium carbonate (1.7 equiv.) and Pd(PPh$_3$)$_4$ (0.1 equiv.) in a mixture of H$_2$O (0.6 mL)/1,4-dioxane (3.00 mL) under N$_2$ was stirred at 90° C. for about 1.5 to 5 hr. The mixture was cooled to r.t. and diluted with 3 ml 1,4-dioxane. The mixture was filtered through a Whatman PTFE 4.5 uM disk, and concentrated. The mixture was added 4 ml 1N HCl, diluted with 5 ml H$_2$O. The precipitates were filtered and washed with 3×4 ml H2O, and dried. The crude material was purified as indicated or used for the amide coupling step without further purification. To a mixture of 3-(benzofuran-5-yl)benzoic acid derivative obtained from above (0.074 mmol, 1 equiv.), amine (1.5 equiv.) and 2-(1H-benzo[d][1,2,3]triazol-1-yl)-1,1,3,3-tetramethylisouronium tetrafluoroborate (2 equiv.) in DMF (1 mL) at r.t. under N$_2$ was added N,N-diisopropylethylamine (3 equiv.). The mixture was stirred at r.t. for about 23 hr. The mixture was diluted with MeOH and purified as indicated, e.g. by Shimadzu-VP preparative reverse phase HPLC.

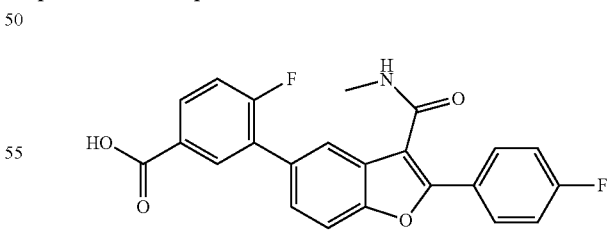

4-Fluoro-3-(2-(4-fluorophenyl)-3-(methylcarbamoyl)benzofuran-5-yl)benzoic acid. $^1$H NMR (500 MHz, DMSO-d$_6$) δ 13.17 (s, 1H), 8.51 (q, J=4.27, 1H), 8.13 (dd, J=7.78, 1.98, 1H), 8.01 (apparent dd, J=8.70, 5.34, 3H), 7.81 (d, J=8.54, 1H), 7.80 (s, 1H), 7.61 (d, J=8.54, 1H), 7.49 (dd, J=10.07, 8.85, 1H), 7.41 (apparent t, J=8.85, 2H), 2.85 (appeared as d, J=4.58, 3H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=408.29, HPLC R$_t$=1.693 min.

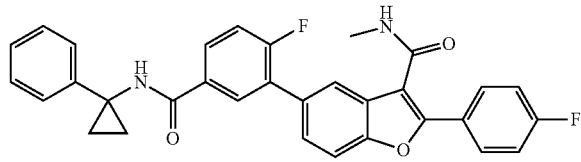

5-(2-Fluoro-5-(1-phenylcyclopropylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.79-9.35 min. (UV detection at 220 nm). ¹H NMR (500 MHz, DMSO-d₆) δ 9.33 (s, 1H), 8.51 (q, J=4.58, 1H), 8.15 (dd, J=7.48, 2.29, 1H), 8.00 (dd, J=9.00, 5.34, 2H), 7.97 (m, 1H), 7.83 (s, 1H), 7.82 (d, J=8.60, 1H), 7.64 (d, J=8.55, 1H), 7.46 (dd, J=10.22, 8.70, 1H), 7.41 (t, J=9.00, 2H), 7.29 (t, J=7.63, 1H), 7.28 (d, J=7.32, 1H,), 7.23 (apparent d, J=7.10, 2H), 7.17 (t, J=7.17, 1H), 2.85 (appeared as d, J=4.58, 3H), 1.30 (appeared as d, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=523.44, HPLC R$_t$=1.803 min.

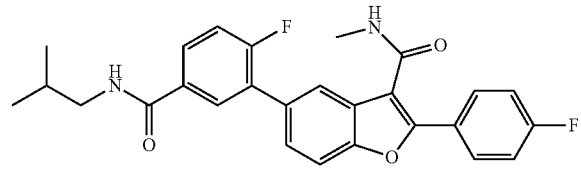

5-(2-Fluoro-5-(isobutylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.47-9.09 min. (UV detection at 220 nm). ¹H NMR (500 MHz, CD₃OD, appeared as a mixture of two isomers) δ 8.06-8.04 (m, 1H), 8.00-7.97 (m, 2H), 7.90-7.87 (m, 2H), 7.70 (d, J=8.50, major) and 7.69 (d, J=8.50, minor) (1H), 7.63-7.62 (m, 1H), 7.36-7.27 (overlapping m, 3H), 3.23 (d, J=7.02, major) and 3.23-3.22 (d, minor) (2H), 2.98 (s, major) and 2.97 (s, minor) (3H), 1.97 (m, 1H), 1.00 (d, J=6.71, major) and 0.99 (d, J=6.71, minor) (6H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=463.38, HPLC R$_t$=1.772 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=8.85 min; Column: Xbridge Phenyl 3.5 um, 4.6×150 mm, R$_t$=6.44 min.


5-(2-Chloro-5-(1-phenylcyclopropylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 9.28-9.85 min. (UV detection at 220 nm). ¹H NMR (500 MHz, CD₃OD, appeared as a mixture of two isomers) δ 9.36 (broad s, 1H), 7.98-7.94 (overlapping m, 3H), 7.85 (dd, J=8.39, 2.29, major) and 7.86-7.83 (dd, minor) (1H), 7.75 (d, J=1.83, major) and 7.75-7.74 (d, minor) (1H), 7.66 (d, J=8.55, major) and 7.66-7.64 (d, minor) (1H), 7.633 (d, J=8.00, major) and 7.626 (d, J=8.50, minor) (1H), 7.48 (dd, J=8.55, 1.83, major) and 7.49-7.47 (dd, minor) (1H), 7.29-7.25 (overlapping m, 6H), 7.17 (m, 1H), 2.95 (s, major) and 2.94 (s, minor) (3H), 1.36-1.34 (appeared as d, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺= 539.37, 541.38, HPLC R$_t$=1.868 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=10.84 min; Column: Xbridge Phenyl 3.5 um, 4.6×150 mm, R$_t$=8.37 min.

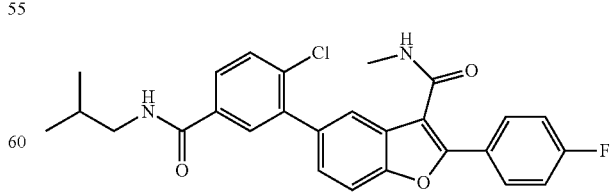

5-(2-Chloro-5-(isobutylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1%

TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 9.01-9.47 min. (UV detection at 220 nm). $^1$H NMR (500 MHz, CD$_3$OD, appeared as a mixture of two isomers) δ 7.98 (major) and 7.97 (minor) (dd, 2H), 7.91 (d, J=2.14, major) and 7.91-7.90 (d, minor) (1H), 7.82 (dd, J=8.24, 2.14, major) and 7.82-7.80 (dd, minor) (1H), 7.75 (m, 1H), 7.65 (dd, J=16, 8.39, major) and 7.64 (dd, J=16.5, 8.55, minor) (2H), 7.49 (dd, J=8.24, 1.83, major) and 7.49-7.47 (dd, minor) (1H), 7.27 (t, J=8.85, major) and 7.29-7.25 (apparent m, minor) (2H), 3.22 (d, J=7.02, major) and 3.21 (d, J=7.02, major) (2H), 2.96 (s, major) and 2.95 (s, minor) (3H), 1.95 (m, 1H), 0.98 (d, J=6.71, major) and 0.97 (d, J=6.71, minor) (6H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$= 479.33, 481.36, HPLC R$_t$=1.830 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=9.66 min; Column: Xbridge Phenyl 3.5 um, 4.6×150 mm, R$_t$=7.19 min.

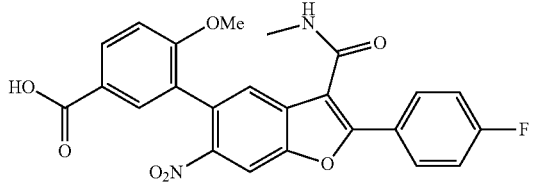

3-(2-(4-Fluorophenyl)-3-(methylcarbamoyl)-6-nitrobenzofuran-5-yl)-4-methoxybenzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=465.31, HPLC R$_t$=1.568 min.

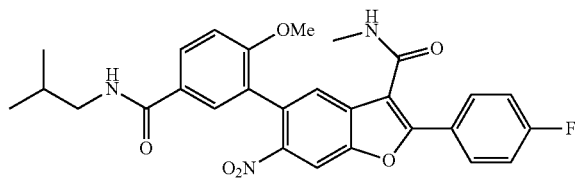

2-(4-Fluorophenyl)-5-(5-(isobutylcarbamoyl)-2-methoxyphenyl)-N-methyl-6-nitrobenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.79-8.36 min. (UV detection at 220 nm). $^1$H NMR (500 MHz, DMSO-d$_6$) δ 8.62 (q, J=4.48, 1H), 8.48 (s, 1H), 8.46 (t, J=5.80, 1H), 8.05 (dd, J=9.00, 5.34, 2H), 7.96 (dd, 1H), 7.95 (apparent s, 1H), 7.68 (s, 1H), 7.46 (t, J=8.85, 2H), 7.14 (d, J=8.55, 1H), 3.69 (s, 3H), 3.11 (broad d, 2H), 2.83 (appeared as d, J=4.58, 3H), 1.87 (m, 1H), 0.91 (d, J=6.71, 6H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$= 520.40, HPLC R$_t$=1.688 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.93 min; Column: Xbridge Phenyl 3.5 um, 4.6×150 mm, R$_t$=6.30 min.

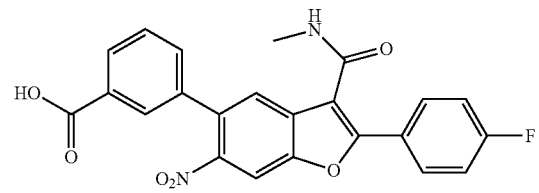

3-(2-(4-Fluorophenyl)-3-(methylcarbamoyl)-6-nitrobenzofuran-5-yl)benzoic acid. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.98-7.51 min. (UV detection at 220 nm). $^1$H NMR (500 MHz, DMSO-d$_6$) δ 13.17 (s, 1H), 8.60 (m, 1H), 8.54 (s, 1H), 8.08-8.05 (overlapping m, 2H), 8.02 (d, J=7.63, 1H), 7.95 (s, 1H), 7.74 (s, 1H), 7.67-7.61 (overlapping m, 2H), 7.46 (apprent t, J=8.85, 2H), 2.84 (appeared as d, J=4.58, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=435.27, HPLC R$_t$=1.588 min.

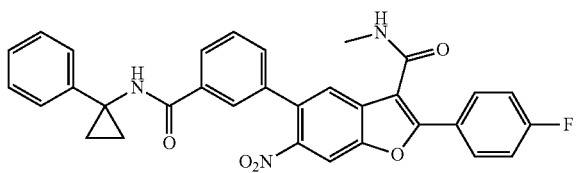

2-(4-Fluorophenyl)-N-methyl-6-nitro-5-(3-(1-phenylcyclopropylcarbamoyl)phenyl)benzofuran-3-carboxamide. 2-(4-Fluorophenyl)-N-methyl-6-nitro-5-(3-(1-phenylcyclopropylcarbamoyl)phenyl)benzofuran-3-carboxamide was prepared as described in the general procedure. The reaction mixture was concentrated, and then added excess water. The off white precipitates of the product were filtered, washed with 3 times of water and dried. ¹H NMR (500 MHz, DMSO-d₆) δ 9.31 (s, 1H), 8.60 (m, 1H), 8.55 (s, 1H), 8.05 (m, 2H), 7.99-7.97 (overlapping m, 2H), 7.75 (s, 1H), 7.59-7.53 (overlapping m, 2H), 7.46 (t, J=8.70, 2H), 7.29 (t, J=7.02, 2H), 7.24 (s, 1H), 7.23 (d, J=7.02, 1H), 7.17 (t, J=6.71, 1H), 2.83 (s, 3H), 1.29 (appeared as d, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=550.45, HPLC R$_t$=1.738 min.

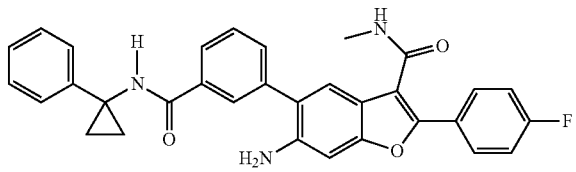

6-Amino-2-(4-fluorophenyl)-N-methyl-5-(3-(1-phenyl-cyclopropylcarbamoyl)phenyl)benzofuran-3-carboxamide. 2-(4-Fluorophenyl)-N-methyl-6-nitro-5-(3-(1-phenylcyclopropylcarbamoyl)phenyl)benzofuran-3-carboxamide (83.3 mg, 0.152 mmol) undr N₂ at r.t. was dissolved in DMF (2 ml) and then added ethyl acetate (10 mL). The mixture remained as a clear light brown solution. The mixture was added palladium (97 mg, 0.045 mmol, 5%/C), flushed with H₂ using a balloon, and the mixture stirred under H₂ for about 8 hr. The mixture was diluted with EtOAc, and filtered through a Whatman PTFE 45 uM disk. The filtrate was evaporated. The residue was titurated with 3×1 ml Et₂O (the Et₂O solution was removed by using a pipette), and the light orange solid product dried (64.4 mg, 82%). ¹H NMR (500 MHz, DMSO-d₆) δ 9.26 (s, 1H), 8.32 (q, J=4.17, 1H), 7.94-7.89 (overlapping m, 3H), 7.97 (s, 1H), 7.62 (d, J=6.8, 1H), 7.58 (q, J=1H), 7.34 (t, J=8.70, 2H), 7.29 (t, 1H), 7.28 (d, J=7.50, 1H), 7.23 (s, 2H), 7.227 (d, J=8.00, 1H), 7.17 (t, J=7.17, 1H,), 6.99 (s, 1H), 5.09 (s, 2H), 2.79 (appeared as d, J=3.97, 3H), 1.29 (appeared as d, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=520.39, HPLC R$_t$=1.497 min.

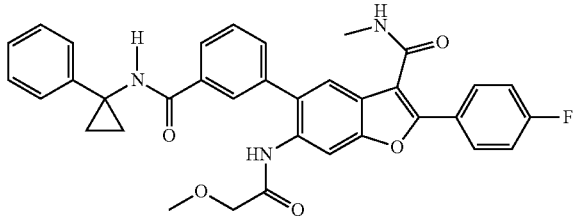

2-(4-Fluorophenyl)-6-(2-methoxyacetamido)-N-methyl-5-(3-(1-phenylcyclopropylcarbamoyl)phenyl)benzofuran-3-carboxamide. To a mixture of 2-methoxyacetic acid (10.40 mg, 0.115 mmol) in THF (3 mL) at r.t. under N₂ was added 1,1'-carbonyldiimidazole (CDI) (28.1 mg, 0.173 mmol). The mixture was stirred at 55° C. for 1 hr. The mixture was then transferred to a flask containing 6-amino-2-(4-fluorophenyl)-N-methyl-5-(3-(1-phenylcyclopropylcarbamoyl)phenyl) benzofuran-3-carboxamide (30 mg, 0.058 mmol) at r.t. under N₂. 1,8-Diazabicyclo[5.4.0]undec-7-ene (DBU) (0.035 mL, 0.231 mmol) was then added and the mixture was stirred at 55° C. for 2 hr 35 min. The mixture was then left standing at r.t. overnight. The mixture was re-stirred at 55° C. for 3 hr. The mixture was cooled to r.t., diluted with MeOH and purified by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.28-7.84 min. (UV detection at 220 nm). ¹H NMR (500 MHz, DMSO-d₆) δ 9.29 (s, 1H), 9.04 (s, 1H), 8.49 (q, J=4.58, 1H), 8.31 (s, 1H), 8.03-8.00 (overlapping m, 3H), 7.98 (m, 1H), 7.59 (s, 1H), 7.63 (s, 1H), 7.625 (d, J=2.44, 1H), 7.40 (t, J=9.00, 2H), 7.28 (apparent t, J=7.63, 2H,), 7.23 (apparent d, 2H,), 7.17 (t, J=7.17, 1H,), 3.90 (s, 2H), 3.18 (s, 3H), 2.83 (appeared as d, J=4.58, 3H), 1.28 (s, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=592.49, HPLC R$_t$=1.652 min.

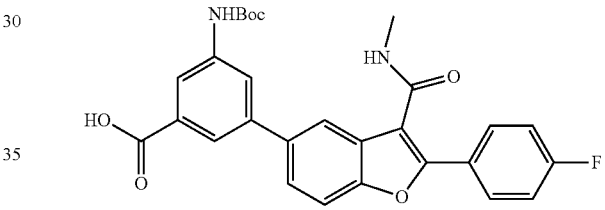

3-(tert-Butoxycarbonylamino)-5-(2-(4-fluorophenyl)-3-(methylcarbamoyl)benzofuran-5-yl)benzoic acid. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M-Me₂CCH₂+H)⁺=449.35, HPLC R$_t$=1.808 min.

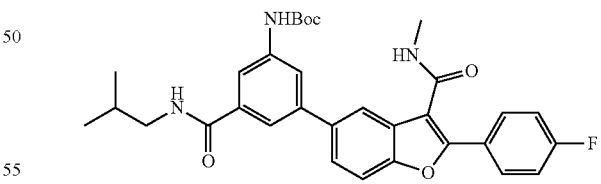

Tert-Butyl 3-(2-(4-fluorophenyl)-3-(methylcarbamoyl) benzofuran-5-yl)-5-(isobutylcarbamoyl)phenylcarbamate. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=70, Final % B=100, Gradient time=10 min, Stop time=12 min, Flow Rate=25 mL/min, Column: Waters-Sunfire 19×100 mm S5, Fraction Collection: 7.13-7.93 min. (UV detection at 220 nm). ¹H NMR (500 MHz, DMSO-d₆)) δ 9.57 (s, 1H), 8.55 (dt, J=10.38, 5.19, 1H), 8.50 (broad s, 1H), 8.01-7.98 (m, 3H), 7.89 (s, 1H), 7.86-7.85 (m, 1H), 7.81 (apparent d, 1H), 7.75 (s, 1H), 7.70 (dd, J=8.55, 1.83, 1H), 7.41 (apparent t, J=8.85, 2H), 3.11 (t, J=6.41, 2H), 2.87 (appeared as d, J=4.58, 3H), 1.88 (ddd, J=13.50, 6.64, 6.41, 1H), 1.55 (s) and 1.51 (s) (9H), 0.92 (d, J=6.50, major) and 0.91 (d, J=6.50, minor) (6H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=560.40, HPLC $R_t$=1.898 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=70, Final % B=100, Gradient time=15 min, Stop time=18 min, Flow Rate=1 ml/min, Column: Sunfire C18, 3.5 um, 4.6×150 mm, $R_t$=5.77 min; Column: Xbridge Phenyl 3.5 um, 4.6×150 mm, $R_t$=3.70 min.

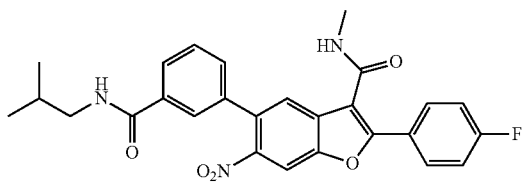

2-(4-Fluorophenyl)-5-(3-(isobutylcarbamoyl)phenyl)-N-methyl-6-nitrobenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.89-8.57 min. (UV detection at 220 nm). $^1$H NMR (500 MHz, DMSO-$d_6$) δ 8.59 (m, 2H), 8.54 (s, 1H), 8.05 (m, 2H), 7.93 (d, J=7.63, 1H), 7.90 (s, 1H), 7.75 (s, 1H), 7.57 (apparent t, J=7.63, 1H), 7.54 (apparent t, 1H), 7.46 (apparent t, J=8.85, 2H), 3.11 (t, J=6.41, 2H), 2.84 (appeared as d, J=4.58, 3H), 1.87 (m, 1H), 0.91 (d, J=6.71, 6H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=490.41, HPLC $R_t$=1.693 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=70, Final % B=100, Gradient time=15 min, Stop time=18 min, Flow Rate=1 ml/min, Column: Sunfire C18, 3.5 um, 4.6×150 mm, $R_t$=8.09 min; Column: Xbridge Phenyl 3.5 um, 4.6×150 mm, $R_t$=6.38 min.

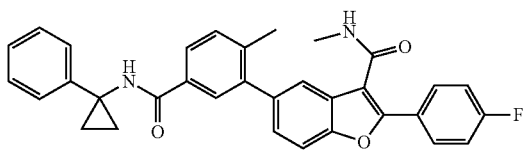

2-(4-Fluorophenyl)-N-methyl-5-(2-methyl-5-(1-phenyl-cyclopropylcarbamoyl)phenyl)benzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.92-9.62 min. (UV detection at 220 nm). $^1$H NMR (500 MHz, $CD_3OD$) δ 7.97 (dd, J=8.85, 5.49, 2H), 7.79 (m, 2H), 7.65-7.64 (d overlapping s, 1H), 7.64 (s, 1H), 7.42 (m, 1H), 7.37 (dd, J=8.24, 1.83, 1H), 7.29-7.26 (overlapping m, 6H), 7.16 (m, 1H), 2.95 (s, 3H), 2.34 (s, 3H), 1.36-1.33 (appeared as d, 4H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=519.40, HPLC $R_t$=1.832 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=9.93 min; Column: Xbridge Phenyl 3.5 um, 4.6×150 mm, $R_t$=7.64 min.

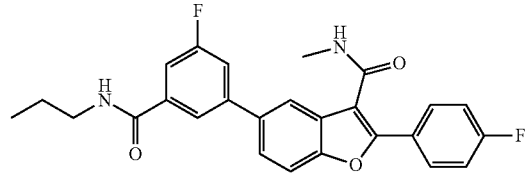

5-(3-Fluoro-5-(propylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.32-8.96 min. (UV detection at 220 nm). $^1$H NMR (500 MHz, $CD_3OD$) δ 8.00-7.97 (overlapping m, 4H), 7.74-7.69 (overlapping m, 2H), 7.65-7.62 (m, 1H), 7.58-7.55 (m, 1H), 7.29 (t, J=8.70, 2H), 3.39 (t, J=7.00, 2H), 3.00 (s, 3H), 1.69 (m, 2H), 1.02 (t, J=7.48, 3H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=449.40, HPLC $R_t$=1.752 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=8.08 min; Column: Xbridge Phenyl 3.5 um, 4.6×150 mm, $R_t$=5.87 min.

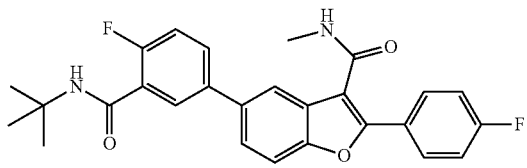

5-(3-(tert-Butylcarbamoyl)-4-fluorophenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.48-9.02 min. (UV detection at 220 nm). $^1$H NMR (500 MHz, CD$_3$OD) δ 7.97-7.94 (overlapping m, 2H), 7.90 (dd, J=6.87, 2.59, 1H), 7.88 (s, 1H), 7.78 (ddd, J=8.47, 4.65, 2.44, 1H), 7.64 (m, 2H), 7.30-7.25 (overlapping m, 3H), 2.99 (s, 3H), 1.50 (2, 9H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=463.36, HPLC R$_t$=1.788 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=9.97 min; Column: Xbridge Phenyl 3.5 um, 4.6×150 mm, R$_t$=6.81 min.

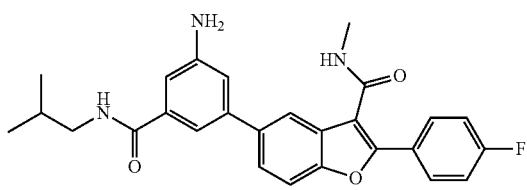

5-(3-Amino-5-(isobutylcarbamoyl)phenyl)-2-(4-fluorophenyl)-N-methylbenzofuran-3-carboxamide. Obtained as a hydrochloride salt from the deprotection of tert-Butyl 3-(2-(4-fluorophenyl)-3-(methylcarbamoyl)benzofuran-5-yl)-5-(isobutylcarbamoyl)phenylcarbamate using 4 M HCl in 1,4-dioxane (r.t.). $^1$H NMR (500 MHz, CD$_3$OD) δ 8.26 (s, 1H), 8.02 (s, 1H), 7.97 (dd, J=7.63, 5.49, 2H), 7.87 (s, 2H), 7.75 (s, 2H), 7.30 (t, J=8.39, 2H), 3.28 (d, J=7.02, 2H), 2.99 (s, 3H), 2.00 (m, 1H), 1.02 (d, J=6.71, 6H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=460.42, HPLC R$_t$=1.510 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=8.96 min; Column: Xbridge Phenyl 3.5 um, 4.6×150 mm, R$_t$=9.23 min.

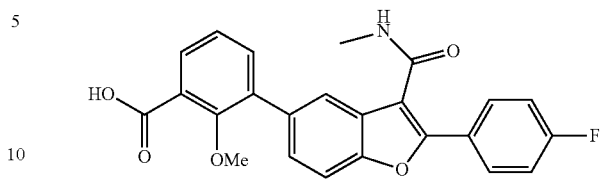

3-(2-(4-Fluorophenyl)-3-(methylcarbamoyl)benzofuran-5-yl)-2-methoxybenzoic acid. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.02-7.76 min. (UV detection at 220 nm). $^1$H NMR (500 MHz, CD$_3$OD) δ 8.00-7.97 (overlapping m, 2H), 7.84 (d, J=1.53, 1H), 7.81 (dd, J=7.63, 1.83, 1H), 7.67 (d, J=8.50, 1H), 7.63-7.60 (overlapping m, 2H), 7.32-7.26 (overlapping m, 3H), 3.50 (s, 3H), 2.97 (s, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=420.27, HPLC R$_t$=1.623 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.08 min; Column: Xbridge Phenyl 3.5 um, 4.6×150 mm, R$_t$=4.83 min.

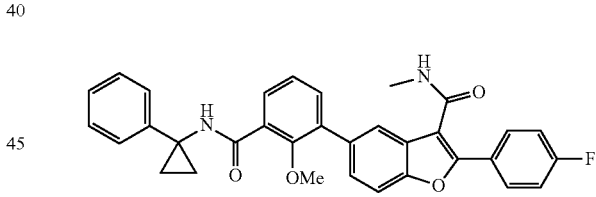

2-(4-Fluorophenyl)-5-(2-methoxy-3-(1-phenylcyclopropylcarbamoyl)phenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.65-9.45 min. (UV detection at 220 nm). $^1$H NMR (500 MHz, CD$_3$OD) δ 7.99-7.96 (overlapping m, 2H), 7.87 (d, J=1.83, 1H), 7.69-7.63 (overlapping m, 3H), 7.57 (dd, J=7.48, 1.68, 1H), 7.40 (d, J=7.63, 1H), 7.39 (s, 1H), 7.34-7.27 (overlapping m, 5H), 7.20 (t, J=7.17, 1H), 3.41 (s, 3H), 2.97 (s, 3H), 1.40-1.37 (appeared as d, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column:

Xterra MS 7 um, C18, 3.0×50 mm; (ES+) m/z (M+H)+= 535.45, HPLC R$_t$=1.833 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=9.93 min; Column: Xbridge Phenyl 3.5 um, 4.6×150 mm, R$_t$=7.75 min.

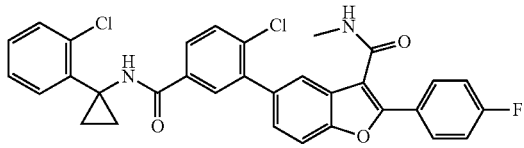

5-(2-Chloro-5-(1-(2-chlorophenyl)cyclopropylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=80, Final % B=100, Gradient time=10 min, Stop time=12 min, Flow Rate=25 mL/min, Column: Waters-Sunfire 19×100 mm S5, Fraction Collection: 5.53-6.33 min. (UV detection at 220 nm). $^1$H NMR (500 MHz, CD$_3$OD) δ 7.99-7.96 (overlapping m, 2H), 7.84 (d, J=2.14, 1H), 7.79 (dd, J=7.17, 1.98, 1H), 7.74 (dd, J=8.39, 2.29, 1H), 7.72 (d, J=1.53, 1H), 7.65 (d, J=8.55, 1H), 7.58 (d, J=8.54, 1H), 7.45 (dd, J=8.55, 1.83, 1H), 7.37 (dd, J=7.25, 1.75, 1H), 7.30-7.23 (overlapping m, 4H), 2.95 (s, 3H), 1.34-1.24 (appeared as d, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)+=573.38, HPLC R$_t$=1.945 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=12.00 min; Column: Xbridge Phenyl 3.5 um, 4.6×150 mm, R$_t$=8.98 min.

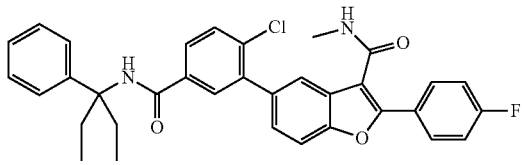

5-(2-Chloro-5-(3-phenylpentan-3-ylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=80, Final % B=100, Gradient time=10 min, Stop time=12 min, Flow Rate=25 mL/min, Column: Waters-Sunfire 19×100 mm S5, Fraction Collection: 6.08-6.89 min. (UV detection at 220 nm). $^1$H NMR (500 MHz, CD$_3$OD) δ 8.00-7.97 (overlapping m, 2H), 7.87 (d, J=2.14, 1H), 7.80 (dd, J=8.24, 2.14, 1H), 7.76 (d, J=1.53, 1H), 7.68 (d, J=8.54, 1H), 7.64 (d, J=8.00, 1H), 7.50 (dd, J=8.55, 1.53, 1H), 7.42 (d, J=7.32, 2H), 7.34-7.27 (overlapping m, 4H), 7.20 (d, J=7.32, 1H), 2.96 (s, 3H), 2.35 (m, 2H), 2.08 (m, 2H), 0.80 (t, J=7.32, 6H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)+=569.47, HPLC R$_t$=1.972 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=13.37 min; Column: Xbridge Phenyl 3.5 um, 4.6×150 mm, R$_t$=10.24 min.

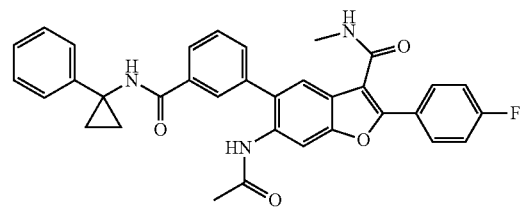

6-Acetamido-2-(4-fluorophenyl)-N-methyl-5-(3-(1-phenylcyclopropylcarbamoyl)phenyl)benzofuran-3-carboxamide. Prepared from 6-Amino-2-(4-fluorophenyl)-N-methyl-5-(3-(1-phenylcyclopropylcarbamoyl)phenyl)benzofuran-3-carboxamide in a similar manner as described. $^1$H NMR (500 MHz, DMSO-d$_6$) δ 9.34 (s, 1H), 9.28 (s, 1H), 8.48 (m, 1H), 8.03-8.00 (overlapping m, 3H), 7.93 (m, 1H), 7.89 (s, 1H), 7.58-7.56 (overlapping m, 3H), 7.40 (t, J=8.85, 2H), 7.30-7.27 (overlapping m, 2H), 7.23-7.21 (overlapping m, 2H), 7.17 (t, J=7.32, 1H), 2.83 (appeared as d, J=4.58, 3H), 1.92 (s, 3H), 1.29 (appeared as s, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)+ = 562.42, HPLC R$_t$=1.547 min.

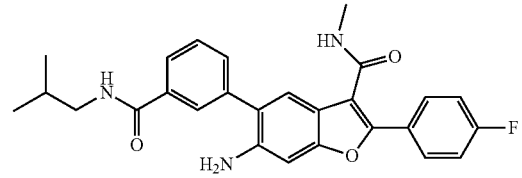

6-Amino-2-(4-fluorophenyl)-5-(3-(isobutylcarbamoyl)phenyl)-N-methylbenzofuran-3-carboxamide. Obtained from the reduction of 2-(4-fluorophenyl)-5-(3-(isobutylcarbamoyl)phenyl)-N-methyl-6-nitrobenzofuran-3-carboxamide using H$_2$ with 5% Pd/C as catalyst (1:6 DMF/EtOAc, r.t.) in a similar manner as described. $^1$H NMR (500 MHz, DMSO-d$_6$) δ 8.54 (t, J=5.95, 1H), 8.33 (q, J=4.58, 1H), 7.94-7.91 (overlapping m, 3H), 7.85 (d, J=7.32, 1H), 7.61-7.55

(overlapping m, 2H), 7.34 (t, J=8.70, 2H), 7.23 (s, 1H), 6.99 (s, 1H), 5.05 (s, 2H), 3.11 (d, J=7.02, 2H), 2.80-2.79 (appeared as d, 3H), 1.87 (m, 1H), 0.91 (d, J=6.71, 6H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=460.38, HPLC R$_t$=1.407 min.

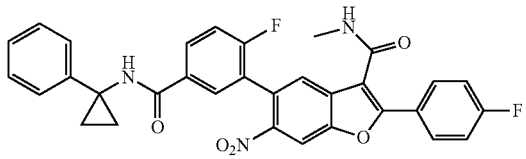

5-(2-Fluoro-5-(1-phenylcyclopropylcarbamoyl)phenyl)-2-(4-fluorophenyl)-N-methyl-6-nitrobenzofuran-3-carboxamide. $^1$H NMR (500 MHz, DMSO-d$_6$) δ 9.33 (s, 1H), 8.64 (s, 2H), 8.12 (dd, J=7.32, 2.14, 1H), 8.08-8.05 (overlapping m, 3H), 7.83 (s, 1H), 7.47 (t, J=8.85, 2H), 7.42 (t, J=9.30, 1H), 7.31-7.28 (overlapping m, 2H), 7.25-7.23 (overlapping m, 2H), 7.17 (t, J=7.17, 1H), 2.84 (appeared as d, J=4.58, 3H), 1.31-1.28 (appeared as d, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=568.39, HPLC R$_t$=1.768 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=9.28 min; Column: Xbridge Phenyl 3.5 um, 4.6×150 mm, R$_t$=7.82 min.

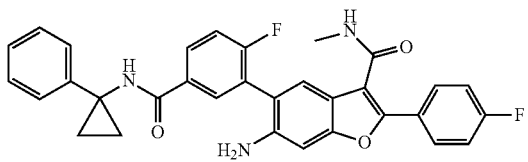

6-Amino-5-(2-fluoro-5-(1-phenylcyclopropylcarbamoyl)phenyl)-2-(4-fluorophenyl)-N-methylbenzofuran-3-carboxamide. Obtained from the reduction of 5-(2-Fluoro-5-(1-phenylcyclopropylcarbamoyl)phenyl)-2-(4-fluorophenyl)-N-methyl-6-nitrobenzofuran-3-carboxamide using H$_2$ with 5% Pd/C as catalyst (1:5 DMF/EtOAc, r.t.) in a similar manner as described. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=538.41, HPLC R$_t$=1.510 min.

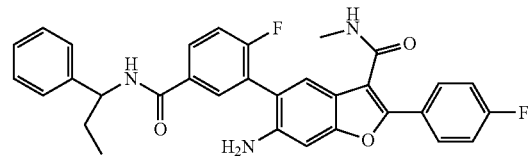

6-Amino-5-(2-fluoro-5-(1-phenylpropylcarbamoyl)phenyl)-2-(4-fluorophenyl)-N-methylbenzofuran-3-carboxamide. Obtained as a side product from the over-reduction of 5-(2-Fluoro-5-(1-phenylcyclopropylcarbamoyl)phenyl)-2-(4-fluorophenyl)-N-methyl-6-nitrobenzofuran-3-carboxamide under the conditions using H$_2$ with 5% Pd/C as catalyst (1:5 DMF/EtOAc, r.t.). The product was obtained as a TFA salt after purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.52-7.08 min. (UV detection at 220 nm). $^1$H NMR (500 MHz, CD$_3$OD) δ 7.98 (m, 1H), 7.93-7.91 (overlapping m, 3H), 7.51 (s, 1H), 7.40-7.38 (overlapping m, 2H), 7.34 (d, J=7.60, 1H), 7.33 (t, J=7.78, 2H), 7.27-7.23 (overlapping m, 4H), 4.99 (t, J=7.48, 1H), 2.92 (s, 3H), 1.94 (m, 2H), 0.99 (t, J=7.32, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=540.45, HPLC R$_t$=1.587 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.56 min; Column: Xbridge Phenyl 3.5 um, 4.6×150 mm, R$_t$=5.42 min.

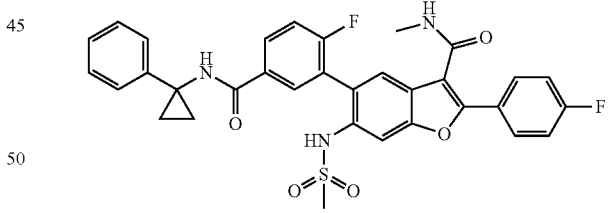

5-(2-Fluoro-5-(1-phenylcyclopropylcarbamoyl)phenyl)-2-(4-fluorophenyl)-N-methyl-6-(methylsulfonamido)benzofuran-3-carboxamide. Prepared from the coupling between 6-Amino-5-(2-fluoro-5-(1-phenylcyclopropylcarbamoyl)phenyl)-2-(4-fluorophenyl)-N-methylbenzofuran-3-carboxamide and methanesulfonyl chloride (N,N-diisopropylethylamine, ClCH$_2$CH$_2$Cl, r.t.), followed by hydrolysis of the intermediate N-(methylsulfonyl)methanesulfonamide (Cs$_2$CO$_3$, 1:5 H$_2$O/1,4-dioxane, 90° C.). Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.70-7.25 min. (UV detection at 220 nm). ¹H NMR (500 MHz, CD₃OD) δ 8.00-7.95 (overlapping m, 4H), 7.83 (s, 1H), 7.66 (s, 1H), 7.35 (t, J=9.00, 1H), 7.30-7.27 (overlapping m, 6H), 7.18 (m, 1H), 2.94 (s, 3H), 2.88 (s, 3H), 1.37-1.35 (appeared as d, 4H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=616.48, HPLC $R_t$=1.563 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=6.57 min; Column: Xbridge Phenyl 3.5 um, 4.6×150 mm, $R_t$=5.80 min.

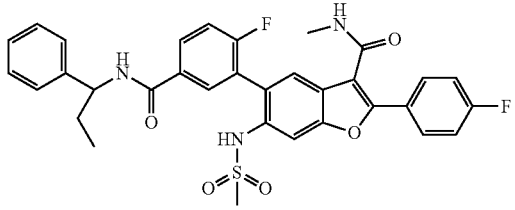

5-(2-Fluoro-5-(1-phenylpropylcarbamoyl)phenyl)-2-(4-fluorophenyl)-N-methyl-6-(methylsulfonamido)benzofuran-3-carboxamide. Prepared in a similar manner as 5-(2-fluoro-5-(1-phenylcyclopropylcarbamoyl)phenyl)-2-(4-fluorophenyl)-N-methyl-6-(methylsulfonamido) benzofuran-3-carboxamide. Purification by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.35-7.81 min. (UV detection at 220 nm). ¹H NMR (500 MHz, CD₃OD) δ 8.00-7.93 (overlapping m, 4H), 7.83 (s, 1H), 7.66 (s, 1H), 7.41 (d overlapping with s, J=8.00, 1H), 7.40 (s, 1H), 7.35-7.32 (overlapping m, 3H), 7.29 (t, J=8.10, 2H), 7.25 (t, J=7.93, 1H), 4.99 (t, J=7.48, 1H), 2.94 (s, 3H), 2.89 (s, 3H), 1.94 (m, 2H), 1.00 (t, J=7.17, 3H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=618.48, HPLC $R_t$=1.637 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=7.76 min; Column: Xbridge Phenyl 3.5 um, 4.6×150 mm, $R_t$=6.37 min.

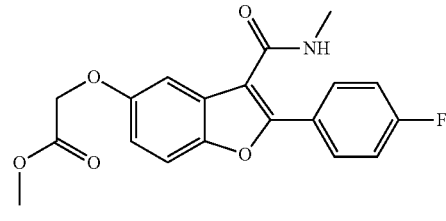

Methyl 2-(2-(4-fluorophenyl)-3-(methylcarbamoyl)benzofuran-5-yloxy)acetate. To a 50 mL round-bottomed flask was added 2-(4-fluorophenyl)-5-hydroxy-N-methylbenzofuran-3-carboxamide (285 mg, 1 mmol), potassium carbonate (207 mg, 1.500 mmol), and methyl bromoacetate (0.101 ml, 1.1 mmol) in DMF (3 mL) to give a yellow suspension. The mixture was stirred at room temperature under nitrogen overnight. The crude product was diluted with 100 mL of dichloromethane, washed with water, then brine and dried over magnesium sulfate. The residue was purified using a Biotage Horizon employing a gradient of 0 to 30% methanol in dichloromethane and a 40+M silica gel column. The product was then triturated with cold ethyl acetate to give a 73% yield (259 mgs) of product, a white amorphous solid after drying under vacuum.

The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX300 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). ¹H NMR (300 MHz, CD₃OD) δ ppm 2.93 (s, 3H), 3.79 (s, 3H), 4.75 (s, 2H), 7.01 (dd, J=8.97, 2.38 Hz, 1H), 7.15 (d, J=2.38 Hz, 1H), 7.22 (t, J=8.78 Hz, 2H), 7.46 (d, J=8.97 Hz, 1H), 7.88 (m, 2H). LCMS m/z 358.27 (M+H), Rt 1.553 min., 97.4% purity.

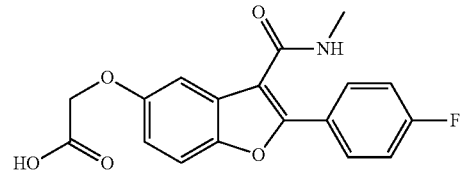

2-(2-(4-fluorophenyl)-3-(methylcarbamoyl)benzofuran-5-yloxy)acetic acid. To a 50 mL round-bottomed flask was added methyl 2-(2-(4-fluorophenyl)-3-(methylcarbamoyl) benzofuran-5-yloxy)acetate (132.3 mg, 0.370 mmol) and 2 equivalents of potassium trimethylsilanolate (95 mg, 0.740 mmol) along with a 1:1 solution of tetrahydrofuran/dichloromethane (10 ml) to give a yellow heterogeneous mixture. The mixture was stirred at room temperature overnight. The crude product was then cooled to 0° C., diluted further with dichloromethane, and acidified with 1 N HCl. The product was extracted, washed with water then brine, and dried over magnesium sulfate. After solvent evaporation, the product was triturated with hexane to give a 91% yield (115 mgs), a white amorphous solid after drying under vacuum. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX300 spectrometer. $^1$H NMR (300 MHz, DMSO-$d_6$) δ ppm 2.82 (d, J=4.39 Hz, 3H), 4.72 (s, 2H), 7.00 (dd, J=8.78, 2.56 Hz, 1H), 7.08 (d, J=2.56 Hz, 1H), 7.35 (t, J=8.97 Hz, 2H), 7.57 (d, J=8.78 Hz, 1H), 7.92 (dd, J=8.78, 5.49 Hz, 2H), 8.34 (m, 1H). LCMS m/z 344.27 (M+H), Rt 1.450 min., 96.0% purity.

overnight at 85° C. The reaction mixture was then cooled, diluted with 300 mL of cold 0.5M HCl and stirred for 30 minutes. The resulting solid was washed with 0.5 N HCl then with water and allowed to dry under vacuum giving a quantitative yield of 3-Chloro-5-(2-(4-fluorophenyl)-3-(methylcarbamoyl)benzofuran-5-yl)benzoic acid which was used without further purification. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. LCMS m/z 424.09 (M+H), Rf 2.658 min., 88% purity.

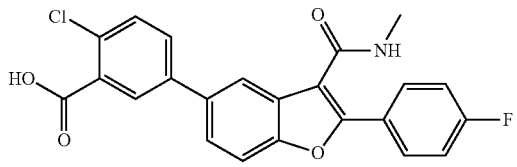

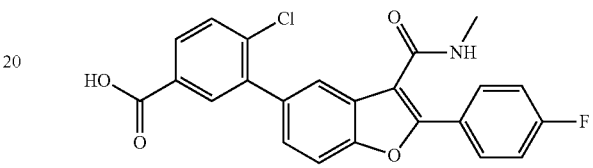

2-Chloro-5-(2-(4-fluorophenyl)-3-(methylcarbamoyl)benzofuran-5-yl)benzoic acid. To a 250 mL sealed tube was added 2-(4-fluorophenyl)-3-(methylcarbamoyl)benzofuran-5-yltrifluoromethanesulfonate (3.55 g, 8.5 mmol), dioxane (50 mL), water (10 mL), Tetrakis(triphenylphosphine)palladium(0) (0.196 g, 0.170 mmol), 5-borono-2-chlorobenzoic acid (2.55 g, 12.75 mmol), and cesium carbonate (4.15 g, 12.75 mmol). The tube was sealed and heated in an oil bath overnight at 85° C. The reaction mixture was then cooled, diluted with 300 mL of cold 0.5M HCl and stirred for 30 minutes. The resulting solid was washed with 0.5 N HCl then with water and allowed to dry under vacuum giving a quantitative yield of 2-Chloro-5-(2-(4-fluorophenyl)-3-(methylcarbamoyl)benzofuran-5-yl)benzoic acid which was used without further purification. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. LCMS m/z 424.77 (M+H), Rt 2.150 min., 90% purity.

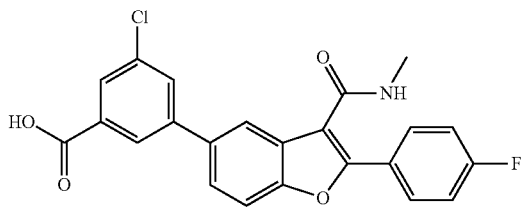

3-Chloro-5-(2-(4-fluorophenyl)-3-(methylcarbamoyl)benzofuran-5-yl)benzoic acid. To a 250 mL sealed tube was added 2-(4-fluorophenyl)-3-(methylcarbamoyl)benzofuran-5-yl trifluoromethanesulfonate (3.55 g, 8.5 mmol), dioxane (50 mL), water (10 mL), Tetrakis(triphenylphosphine)palladium(0) (0.196 g, 0.170 mmol), 5-borono-3-chlorobenzoic acid (2.55 g, 12.75 mmol), and cesium carbonate (4.15 g, 12.75 mmol). The tube was sealed and heated in an oil bath 4-Chloro-3-(2-(4-fluorophenyl)-3-(methylcarbamoyl)benzofuran-5-yl)benzoic acid. To a 250 mL sealed tube was added 2-(4-fluorophenyl)-3-(methylcarbamoyl)benzofuran-5-yltrifluoromethanesulfonate (3.55 g, 8.5 mmol), dioxane (50 mL), water (10 mL), Tetrakis(triphenylphosphine)palladium(0) (0.196 g, 0.170 mmol), 3-borono-4-chlorobenzoic acid (2.55 g, 12.75 mmol), and cesium carbonate (4.15 g, 12.75 mmol). The tube was sealed and heated in an oil bath overnight at 85° C. The reaction mixture was then cooled, diluted with 300 mL of cold 0.5M HCl and stirred for 30 minutes. The resulting solid was washed with 0.5 N HCl then with water and allowed to dry under vacuum giving a quantitative yield of 4-Chloro-5-(2-(4-fluorophenyl)-3-(methylcarbamoyl)benzofuran-5-yl)benzoic acid which was used without further purification. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), inl 0 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, DMF-$_{d7}$) δ ppm 2.95 (d, J=4.58 Hz, 3H), 7.39-7.47 (m, 2H), 7.57 (dd, J=8.55, 1.83 Hz, 1H), 7.81 (dd, J=15.72, 8.39 Hz, 2H), 7.87 (d, J=1.83 Hz, 1H), 8.04-8.14 (m, 4H), 8.40 (d, J=4.58 Hz, 1H). LCMS m/z 424.90 (M+H), Rt 2.287 min. HPLC Rt 9.749 min. (Sunfire C18) and 10.518 min. (XBridge Phenyl C18), 94% purity.

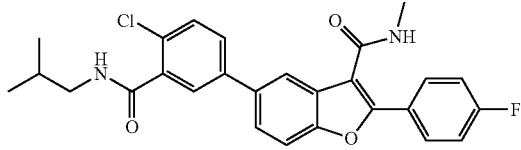

5-(4-chloro-3-(isobutylcarbamoyl)phenyl)-2-(4-fluorophenyl)-N-methylbenzofuran-3-carboxamide. To a 250 mL RBF was added 2-chloro-5-(2-(4-fluorophenyl)-3-(methylcarbamoyl)benzofuran-5-yl)benzoic acid (3.62 g, 8.55 mmol), 2-methylpropan-1-amine (1.274 mL, 12.83 mmol), N-ethyl-N,N-diisopropylamine (2.98 mL, 17.10 mmol), and 3 eq. of HATU, (2-(3H-[1,2,3]triazolo[4,5-b]pyridin-3-yl)-1,1,3,3-tetramethylisouronium hexafluorophosphate(V) (9.75 g, 25.7 mmol)) along with 114 mL of DMF. The mixture was stirred overnight at room temperature. The crude reaction mixture was transferred to a separatory funnel, diluted with 300 mL of dichloromethane and washed with 100 mL of 1 N HCl, water, and brine. After drying over magnesium sulfate the crude residue was pushed through a plug of silica gel and evaporated to a tan solid. The solid was triturated with diethyl ether then cold acetonitrile to give a 48% yield of 5-(4-chloro-3-(isobutylcarbamoyl)phenyl)-2-(4-fluorophenyl)-N-methylbenzofuran-3-carboxamide, as a light yellow powder. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 µm 4.6×150 mm column employing water/methanol/0.1% ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, ACETONE-$d_6$) δ ppm 1.02 (d, J=6.71 Hz, 6H), 1.92-2.01 (m, 1H), 2.99 (d, J=4.88 Hz, 3H), 3.28 (t, J=6.41 Hz, 2H), 7.33 (t, J=8.70 Hz, 2H), 7.56 (d, J=8.24 Hz, 1H), 7.61 (br. s., 1H), 7.66 (br. s., 1H), 7.68-7.74 (m, 2H), 7.74-7.82 (m, 2H), 8.01-8.06 (m, 1H), 8.13 (dd, J=8.70, 5.34 Hz, 2H). LCMS m/z 479.06 (M+H), Rt 2.367 min. HPLC Rt 10.263 min. (Sunfire C18) and 11.753 min. (XBridge Phenyl C18), 93% purity.

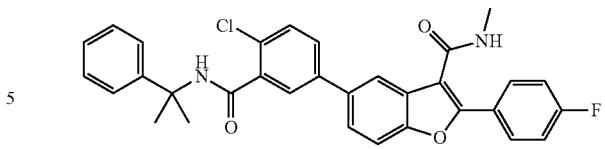

5-(4-chloro-3-(2-phenylpropan-2-ylcarbamoyl)phenyl)-2-(4-fluorophenyl)-N-methylbenzofuran-3-carboxamide. To a 2 dram vial was added 2-chloro-5-(2-(4-fluorophenyl)-3-(methylcarbamoyl)benzofuran-5-yl)benzoic acid (42.4 mg, 0.1 mmol) in DMF (2 mL) along with cumylamine (0.029 mL, 0.200 mmol), N,N-Diisopropylethylamine (0.035 mL, 0.200 mmol) and HATU (114 mg, 0.300 mmol) to give a yellow solution. The vial was shaken at room temperature overnight. The crude reaction mixture was then evacuated to near dryness, taken up in 2 mL of methanol and purified using a Shimadzu preparative HPLC employing methanol/water/ 0.1% TFA where solvent A was 10% MeOH/90% H2O/0.1% trifluoroacetic acid and solvent B was 10% H2O/90% MeOH/ 0.1% trifluoroacetic acid with a Phenomenex-Luna 10 µm C18 30×100 mm column at a gradient of 30-100% B and a flow rate of 40 mL/min. over 10 minutes with a 10 minute hold. The tubes containing purified product were evaporated overnight in a Savant/Thermo Speedvac to give a 45% yield of 5-(4-chloro-3-(2-phenylpropan-2-ylcarbamoyl)phenyl)-2-(4-fluorophenyl)-N-methylbenzofuran-3-carboxamide as a white powder. The NMR spectrum was recorded at room temperature using a Bruker DRX300 spectrometer. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute. $^1$H NMR (300 MHz, CHLOROFORM-d) δ ppm 1.87 (s, 6H), 3.02 (d, J=4.76 Hz, 3H), 6.03 (d, J=4.76 Hz, 1H), 6.62 (s, 1H), 7.13-7.23 (m, 2H), 7.24-7.31 (m, 1H), 7.33-7.42 (m, 2H), 7.45 (d, J=8.42 Hz, 1H), 7.48-7.63 (m, 5H), 7.83-8.00 (m, 4H).

LCMS m/z 542.90 (M+H), Rt 2.608 min. HPLC Rt 11.069 min. (Sunfire C18) and 12.111 min. (XBridge Phenyl C18), 97.8% purity.

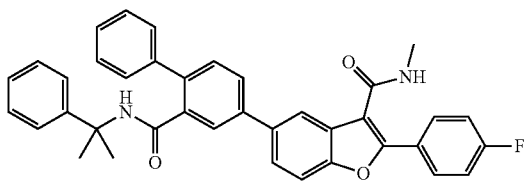
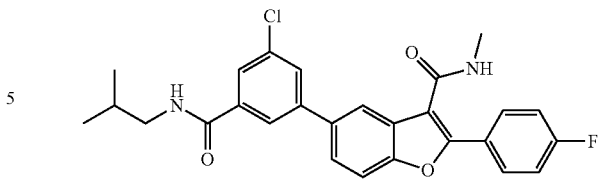

2-(4-fluorophenyl)-N-methyl-5-(2-(2-phenylpropan-2-yl-carbamoyl)biphenyl-4-yl) benzofuran-3-carboxamide. To a 2 mL microwave vial was added dioxane (2 mL), water (0.200 mL), (S-Phos) dicyclohexyl (2',6'-dimethoxybiphenyl-2-yl) phosphine, (1.912 mg, 4.66 µmol), 5-(4-chloro-3-(2-phenyl-propan-2-ylcarbamoyl)phenyl)-2-(4-fluorophenyl)-N-methylbenzofuran-3-carboxamide (0.0126 g, 0.023 mmol), potassium phosphate tribasic (0.020 g, 0.093 mmol), palladium(II) acetate (1.046 mg, 4.66 µmol), and phenylboronic acid (8.52 mg, 0.070 mmol). The vial was capped, degassed, flushed with $N_2$ and heated in the microwave for 10 minutes at 150° C. The crude product was taken up in a 1:1 solution of DMF/acetonitrile and purified by a Shimadzu preparative HPLC employing acetonitrile/0.1% TFA/water where solvent A was 10% acetonitrile/90% H2O/0.1% trifluoroacetic acid and solvent B was 10% H2O/90% acetonitrile/0.1% trifluoroacetic acid with a Waters-Atlantis OBD 19×100 mm 5 µm column at a gradient of 50-100% B and a flow rate of 25 mL/min. over 10 minutes with a 10 minute hold. The purified product was evaporated to dryness overnight in a Savant Thermo Speedvac to give a 73% yield of 2-(4-fluorophenyl)-N-methyl-5-(2-(2-phenylpropan-2-ylcarbamoyl) biphenyl-4-yl)benzofuran-3-carboxamide. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, CD$_3$OD) δ ppm 1.54 (s, 6H), 3.01 (s, 3H), 7.15-7.20 (m, 1H), 7.21-7.33 (m, 6H), 7.43-7.50 (m, 3H), 7.51-7.55 (m, 3H), 7.69-7.72 (m, 1H), 7.72-7.76 (m, 1H), 7.80 (d, J=1.53 Hz, 1H), 7.84 (dd, J=7.93, 1.83 Hz, 1H), 7.96-8.02 (m, 3H), 8.10 (br. s., 1H). LCMS m/z 583.03 (M+H), Rt 2.811 min. HPLC Rt 11.683 min. (Sunfire C18) and 12.609 min. (XBridge Phenyl C18), 99% purity.

5-(3-chloro-5-(isobutylcarbamoyl)phenyl)-2-(4-fluorophenyl)-N-methylbenzofuran-3-carboxamide. To a 250 mL round-bottomed flask was added 3-chloro-5-(2-(4-fluorophenyl)-3-(methylcarbamoyl)benzofuran-5-yl)benzoic acid (3.62 g, 8.55 mmol), 2-methylpropan-1-amine (1.274 mL, 12.83 mmol), N-ethyl-N,N-diisopropylamine (2.98 mL, 17.10 mmol), and 3 eq. of HATU (2-(3H-[1,2,3]triazolo[4,5-b]pyridin-3-yl)-1,1,3,3-tetramethylisouronium hexafluorophosphate(V) (9.75 g, 25.7 mmol)) along with 114 mL of DMF. The mixture was stirred overnight at room temperature. The crude reaction mixture was transferred to a separatory funnel, diluted with 300 mL of dichloromethane and washed with 100 mL of 1 N HCl, water, and brine. After drying over magnesium sulfate the crude residue was pushed through a plug of silica gel and evaporated to a tan solid. The solid was triturated with diethyl ether then cold acetonitrile to give a 52% yield of 5-(4-chloro-3-(isobutylcarbamoyl)phenyl)-2-(4-fluorophenyl)-N-methylbenzofuran-3-carboxamide, as a light yellow powder. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, DMSO-d$_6$) δ ppm 0.94 (d, J=6.41 Hz, 6H), 1.72-1.97 (m, 1H), 2.87 (d, J=4.58 Hz, 3H), 3.10 (t, J=6.26 Hz, 2H), 7.40 (t, J=8.85 Hz, 2H), 7.59 (d, J=8.55 Hz, 1H), 7.69-7.75 (m, 2H), 7.76-7.82 (m, 2H), 7.90 (br. s., 1H), 7.97-8.07 (m, 2H), 8.55 (br. s., 2H). LCMS m/z 479.04 (M+H), Rt 2.658 min. HPLC Rt 10.810 min. (Sunfire C18) and 12.154 min. (XBridge Phenyl C18), 92% purity.

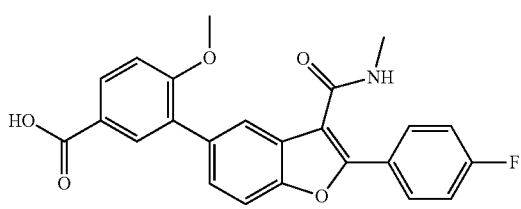

3-(2-(4-fluorophenyl)-3-(methylcarbamoyl)benzofuran-5-yl)-4-methoxybenzoic acid. To a 150 mL sealed tube was added 2-(4-fluorophenyl)-3-(methylcarbamoyl)benzofuran-5-yl trifluoromethanesulfonate (1.252 g, 3 mmol), 3-borono-4-methoxybenzoic acid (0.882 g, 4.50 mmol), cesium carbonate (1.466 g, 4.50 mmol), tetrakis(triphenyl phosphine) palladium(0) (0.069 g, 0.060 mmol), dioxane (18 mL) and water (3.60 mL). The vial was sealed and heated in an oil bath over night at 85° C. The reaction mixture was then filtered through celite and concentrated in vacuo. Cold 0.5N HCl was then added and the heterogeneous mixture was stirred for 30 minutes. The resulting product, a white solid was filtered, washed with water and dried overnight to give a quantitative yield of 3-(2-(4-fluorophenyl)-3-(methylcarbamoyl)benzofuran-5-yl)-4-methoxy benzoic acid which was carried on without further purification. LCMS m/z 420.88 (M+H), Rt 2.002 min., 88% purity.

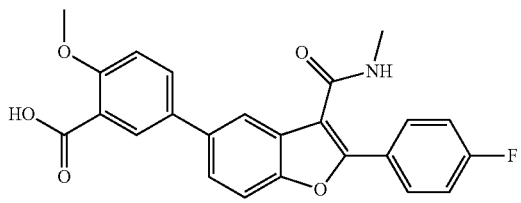

5-(2-(4-fluorophenyl)-3-(methylcarbamoyl)benzofuran-5-yl)-2-methoxybenzoic acid. To a 150 mL sealed tube was added 2-(4-fluorophenyl)-3-(methylcarbamoyl)benzofuran-5-yl trifluoromethanesulfonate (1.252 g, 3 mmol), 5-borono-2-methoxybenzoic acid (0.882 g, 4.50 mmol), cesium carbonate (1.466 g, 4.50 mmol), tetrakis(triphenyl phosphine) palladium(0) (0.069 g, 0.060 mmol), dioxane (18 mL) and water (3.60 mL). The vial was sealed and heated in an oil bath over night at 85° C. The reaction mixture was then filtered through celite and concentrated in vacuo. Cold 0.5N HCl was then added and the heterogeneous mixture was stirred for 30 minutes. The resulting product, a white solid was filtered, washed with water and dried overnight to give a quantitative yield of 5-(2-(4-fluorophenyl)-3-(methylcarbamoyl)benzofuran-5-yl)-2-methoxy benzoic acid which was carried on without further purification. LCMS m/z 420.92 (M+H), Rt 2.003 min., 87% purity.

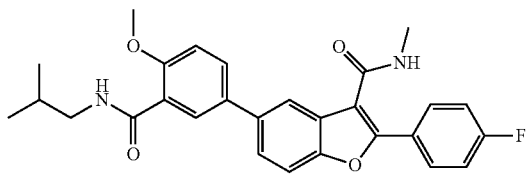

2-(4-fluorophenyl)-5-(3-(isobutylcarbamoyl)-4-methoxyphenyl)-N-methylbenzo-furan-3-carboxamide. To a vial containing (5-(2-(4-fluorophenyl)-3-(methylcarbamoyl)benzofuran-5-yl)-2-methoxybenzoic acid (378.5 mg, 0.902 mmol)) was added DMF (5 mL), N,-ethyl-N,N-diisopropylamine (0.786 mL, 4.51 mmol), 2-methylpropan-1-amine (0.448 mL, 4.51 mmol), and HATU, (2-(3H-[1,2,3]triazolo[4,5-b]pyridin-3-yl)-1,1,3,3-tetramethylisouronium hexafluorophosphate(V) (1029 mg, 2.71 mmol)). The vial was capped and the solution shaken overnight at room temperature. The crude product was diluted with ethyl acetate, washed with 0.5M HCl, and extracted. The organic layer was washed with brine, dried over magnesium sulfate, filtered and concentrated. The crude reaction mixture was taken up in acetonitrile, filtered and purified using a Shimadzu preparative HPLC employing acetonitrile/water/TFA where solvent A was 10% acetonitrile/90% H2O/0.1% trifluoroacetic acid and solvent B was 10% H2O/90% acetonitrile/0.1% trifluoroacetic acid with a Phenomenex-Luna 10 μm C18 30×100 mm at a gradient of 40-100% B and a flow rate of 25 mL/min. over 10 minutes with a 10 minute hold. The purified product was concentrated in vacuo to give a 38% yield of 2-(4-fluorophenyl)-5-(3-(isobutylcarbamoyl)-4-methoxyphenyl)-N-methylbenzo-furan-3-carboxamide as a white solid. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, Acetone-$d_6$) δ ppm 1.00 (d, J=6.41 Hz, 6H), 1.92-1.96 (m, 1H), 3.01 (d, J=4.27 Hz, 3H), 3.30 (t, J=6.26 Hz, 2H), 4.09 (s, 3H), 7.23-7.39 (m, 3H), 7.61 (br. s., 1H), 7.69 (s, 2H), 7.84 (dd, J=8.39, 1.98 Hz, 1H), 7.99 (s, 1H), 8.13 (dd, J=7.93, 5.49 Hz, 3H), 8.39 (d, J=2.14 Hz, 1H). LCMS m/z 475.15 (M+H), Rt 2.452 min. HPLC Rt 10.648 min. (Sunfire C18) and 12.301 min. (XBridge Phenyl C18), 100% purity.

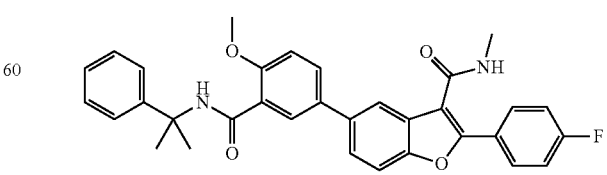

2-(4-fluorophenyl)-5-(4-methoxy-3-(2-phenylpropan-2-ylcarbamoyl)phenyl)-N-methylbenzofuran-3-carboxamide.

To a vial containing (5-(2-(4-fluorophenyl)-3-(methylcarbamoyl)benzofuran-5-yl)-2-methoxybenzoic acid (61 mg, 0.145 mmol)) was added DMF (2 mL), N,-ethyl-N,N-diisopropylamine (0.050 mL, 0.29 mmol), cumylamine (39.3 mg, 0.291 mmol), and finally TBTU, o-Benzotriazol-1-yl-N,N,N',N'-tetramethyluronium tetrafluoroborate (140 mg, 0.436 mmol)). The vial was capped and the solution shaken overnight at room temperature. The crude product was diluted with ethyl acetate, washed with 1M HCl, and extracted. The organic layer was washed with brine, dried over magnesium sulfate, filtered and concentrated. The crude reaction mixture was taken up in acetonitrile, filtered and purified using a Shimadzu preparative HPLC employing acetonitrile/water/TFA where solvent A was 10% acetonitrile/90% H2O/0.1% trifluoroacetic acid and solvent B was 10% H2O/90% acetonitrile/0.1% trifluoroacetic acid with a Phenomenex-Luna 10 μm C18 30×100 mm at a gradient of 40-100% B and a flow rate of 25 mL/min. over 10 minutes with a 10 minute hold. The purified product was concentrated in vacuo to give a 42% yield of 2-(4-fluorophenyl)-5-(4-methoxy-3-(2-phenylpropan-2-ylcarbamoyl)phenyl)-N-methylbenzofuran-3-carboxamide as a white solid. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, CD3OD) δ ppm 1.69-1.88 (m, 6H), 2.99 (s, 3H), 4.09 (s, 3H), 7.20-7.32 (m, 4H), 7.36 (t, J=7.63 Hz, 2H), 7.52 (d, J=8.24 Hz, 2H), 7.57-7.64 (m, 2H), 7.79-7.89 (m, 2H), 7.96 (t, J=6.10 Hz, 2H), 8.12 (br. s., 1H). LCMS m/z 537.13 (M+H), Rt 2.705 min. HPLC Rt 11.563 min. (Sunfire C18) and 12.876 min. (XBridge Phenyl C18), 93% purity.

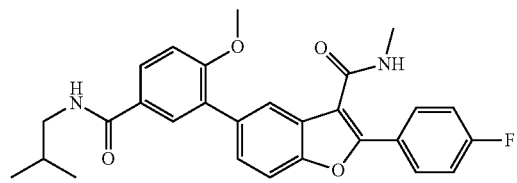

2-(4-fluorophenyl)-5-(5-(isobutylcarbamoyl)-2-methoxyphenyl)-N-methyl benzofuran-3-carboxamide. To a 100 mL round-bottomed flask was added 3-(2-(4-fluorophenyl)-3-(methylcarbamoyl)benzofuran-5-yl)-4-methoxybenzoic acid (1258 mg, 3 mmol), DMF (40 mL), 2-methylpropan-1-amine (447 μL, 4.50 mmol), N-ethyl-N,N-diisopropylamine (1.1 mL, 6.00 mmol), and finally HATU (2-(3H-[1,2,3]triazolo[4,5-b]pyridin-3-yl)-1,1,3,3-tetramethylisouronium hexafluorophosphate(V) (3422 mg, 9.00 mmol)). The mixture was stirred over night at room temperature. The crude product was diluted with ethyl acetate, washed with 1M HCl, and extracted. The organic layer was washed with brine, dried over magnesium sulfate, filtered and concentrated. The crude residue was loaded onto 40M Biotage column and purified using a Biotage Horizon with 2200 mL of 0-6% methanol in DCM). The product was concentrated in vacuo then triturated with cold acetonitrile to give a 60% yield of 2-(4-fluorophenyl)-5-(5-(isobutylcarbamoyl)-2-methoxyphenyl)-N-methyl benzofuran-3-carboxamide as a light yellow solid. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, CD$_3$OD) δ ppm 0.89-1.07 (m, 6H), 1.96 (dt, J=13.43, 6.71 Hz, 1H), 2.97 (s, 3H), 3.22 (d, J=6.10 Hz, 2H), 3.80-3.98 (m, 3H), 7.19 (d, J=9.46 Hz, 1H), 7.24-7.33 (m, 2H), 7.52-7.57 (m, 1H), 7.57-7.65 (m, 1H), 7.80 (s, 1H), 7.84-7.92 (m, 2H), 7.96-8.02 (m, 2H), 8.46 (br. s., 1H). LCMS m/z 475.02 (M+H), Rt 2.290 min. HPLC Rt 14.374 min. (Sunfire C18) and 15.689 min. (XBridge Phenyl C18), 95% purity.

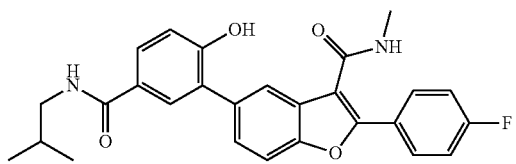

2-(4-fluorophenyl)-5-(2-hydroxy-5-(isobutylcarbamoyl)phenyl)-N-methylbenzofuran-3-carboxamide. To a 250 mL sealed tube was added toluene (150 mL) 2-(4-fluorophenyl)-5-(5-(isobutylcarbamoyl)-2-methoxyphenyl)-N-methylbenzofuran-3-carboxamide (1.187 g, 2.50 mmol) and finally, under a steady stream of N$_2$ Boron tribromide-methyl sulfide complex (8.76 g, 28.0 mmol) was quickly added. The tube was sealed and heated to 100° C. in an oil bath for 30 hours.

The crude reaction mixture was cooled to room temperature, filtered, washed with wet hexane, then diethyl ether and dried overnight under vacuum to give a 96% yield of a tan solid. The NMR spectrum was recorded at room temperature using a Bruker DRX500 spectrometer. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/ 0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/ 0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute. $^1$H NMR (500 MHz, DMF-$d_7$) δ ppm 0.92 (d, J=6.71 Hz, 6H), 1.86-1.97 (m, 1H), 2.94-2.98 (m, 3H), 3.17-3.23 (m, 2H), 7.19 (d, J=8.55 Hz, 1H), 7.42 (t, J=9.00 Hz, 2H), 7.66-7.75 (m, 2H), 7.88 (dd, J=8.39, 2.29 Hz, 1H), 8.06-8.14 (m, 3H), 8.37-8.46 (m, 2H). LCMS m/z 461.95 (M+H), Rt 2.033 min. HPLC Rt 8.929 min. (Sunfire C18) and 11.454 min. (XBridge Phenyl C18), 96% purity.

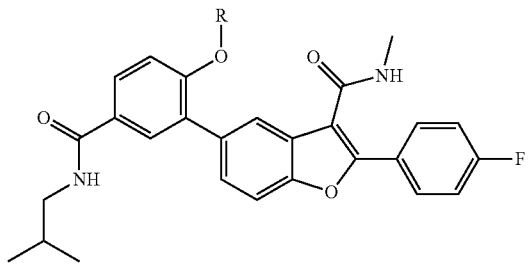

General procedure. To a 2 dram vial was added 2-(4-fluorophenyl)-5-(2-hydroxy-5-(isobutylcarbamoyl)phenyl)-N-methylbenzofuran-3-carboxamide (46.0 mg, 0.1 mmol), DMF (2 mL), and 1.5 equivalents (0.15 mmol) of either triethyl amine or potassium carbonate and 1.5 equivalents (0.15 mmol) of alkyl bromide. The vials were sealed and shaken at 22-70° C. in a dry bath. Upon reaction completion the crude products were concentrated, diluted with 2 mL of acetonitrile and purified using a Shimadzu preparative HPLC employing acetonitrile/water/0.1% TFA where solvent A was 10% acetonitrile/90% H2O/0.1% trifluoroacetic acid and solvent B was 10% H2O/90% acetonitrile/0.1% trifluoroacetic acid with a Waters Sunfire 5 μm C18 4.6×100 mm column at a gradient of 30-100% B and a flow rate of 40 mL/min. over 8 minutes with a 10 minute hold. The desired products were evaporated to dryness in a Savant Speedvac overnight obtaining 25-60% yield of the desired ethers as white powders.

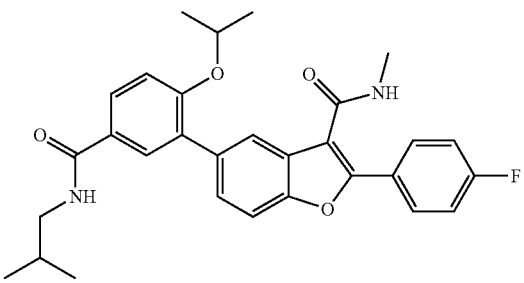

2-(4-fluorophenyl)-5-(5-(isobutylcarbamoyl)-2-isopropoxyphenyl)-N-methyl benzofuran-3-carboxamide. $^1$H NMR (500 MHz, CD$_3$OD) δ ppm 1.00 (d, J=6.71 Hz, 6H), 1.32 (d, J=6.10 Hz, 6H), 1.87-2.05 (m, 1H), 2.98 (s, 3H), 3.22 (d, J=7.02 Hz, 2H), 4.64-4.79 (m, 1H), 7.18 (d, J=8.55 Hz, 1H), 7.24-7.36 (m, 2H), 7.57-7.67 (m, 2H), 7.85 (dd, J=8.55, 2.44 Hz, 1H), 7.87 (s, 1H), 7.90 (d, J=2.44 Hz, 1H), 7.95-8.01 (m, 2H). LCMS m/z 503.12 (M+H), Rt 2.368 min. HPLC Rt 10.789 min. (Sunfire C18) and 12.428 min. (XBridge Phenyl C18), 98.7% purity.

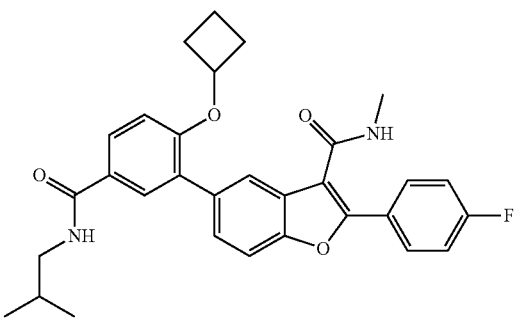

5-(2-(cyclobutyloxy)-5-(isobutylcarbamoyl)phenyl)-2-(4-fluorophenyl)-N-methyl benzofuran-3-carboxamide. $^1$H NMR (500 MHz, CD$_3$OD) δ ppm 0.99 (d, J=6.41 Hz, 6H), 1.71-1.81 (m, 1H), 1.83-1.91 (m, 1H), 1.92-2.00 (m, 1H), 2.08-2.20 (m, 2H), 2.45-2.56 (m, 2H), 2.99 (s, 3H), 3.22 (d, J=6.71 Hz, 2H), 4.80-4.84 (m, 1H), 7.01 (d, J=8.55 Hz, 1H), 7.28 (t, J=8.55 Hz, 2H), 7.58-7.66 (m, 2H), 7.83 (d, J=8.24 Hz, 1H), 7.86-7.92 (m, 2H), 7.96-8.03 (m, 2H). LCMS m/z 515.21 (M+H), Rt 2.613 min. HPLC Rt 11.161 min. (Sunfire C18) and 12.693 min. (XBridge Phenyl C18), 97% purity.

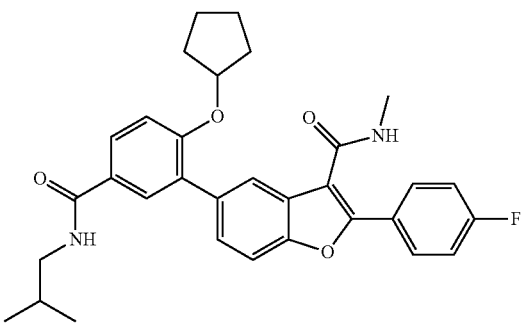

5-(2-(cyclopentyloxy)-5-(isobutylcarbamoyl)phenyl)-2-(4-fluorophenyl)-N-methyl benzofuran-3-carboxamide. $^1$H NMR (400 MHz, CD$_3$OD) δ ppm 1.04 (d, J=6.78 Hz, 6H), 1.63-1.82 (m, 4H), 1.83-2.08 (m, 5H), 3.02 (s, 3H), 3.27 (d, J=7.03 Hz, 2H), 5.02 (ddd, J=5.21, 2.89, 2.70 Hz, 1H), 7.21 (d, J=8.78 Hz, 1H), 7.28-7.36 (m, 2H), 7.58-7.69 (m, 2H), 7.88 (dd, J=8.53, 2.51 Hz, 1H), 7.91 (d, J=1.25 Hz, 1H), 7.95 (d, J=2.26 Hz, 1H), 7.99-8.06 (m, 2H). LCMS m/z 529.16 (M+H), Rt 2.685 min. HPLC Rt 12.879 min. (XBridge Phenyl C18), 100% purity.

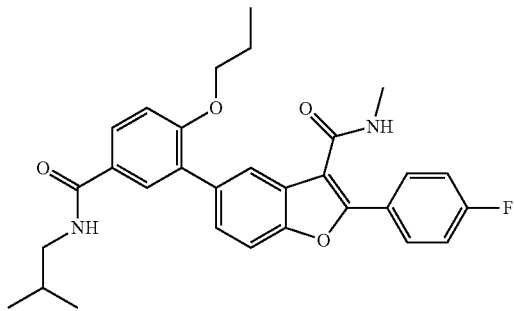

2-(4-fluorophenyl)-5-(5-(isobutylcarbamoyl)-2-propoxyphenyl)-N-methyl benzofuran-3-carboxamide. ¹H NMR (400 MHz, CD₃OD) δ ppm 1.04 (m, 9H), 1.75-1.90 (m, 2H), 1.93-2.10 (m, 1H), 3.02 (s, 3H), 3.27 (d, J=7.03 Hz, 2H), 4.11 (t, J=6.15 Hz, 2H), 7.21 (d, J=8.53 Hz, 1H), 7.32 (t, J=8.78 Hz, 2H), 7.59-7.72 (m, 2H), 7.88-7.98 (m, 3H), 7.98-8.08 (m, 2H). LCMS m/z 503.14 (M+H), Rt 2.548 min. HPLC Rt 12.554 min. (XBridge Phenyl C18), 100% purity.

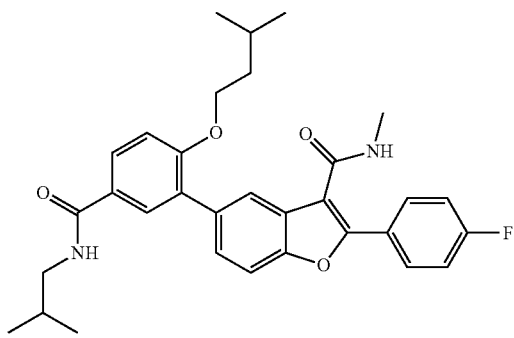

2-(4-fluorophenyl)-5-(5-(isobutylcarbamoyl)-2-(isopentyloxy)phenyl)-N-methylbenzofuran-3-carboxamide. ¹H NMR (400 MHz, CD₃OD) δ ppm 0.93-1.01 (m, 6H), 1.04 (d, J=6.78 Hz, 6H), 1.69 (q, J=6.53 Hz, 2H), 1.83 (ddd, J=13.61, 6.71, 6.53 Hz, 1H), 2.01 (dt, J=13.74, 6.81 Hz, 1H), 3.03 (s, 3H), 3.27 (d, J=7.03 Hz, 2H), 4.18 (t, J=6.27 Hz, 2H), 7.22 (d, J=8.78 Hz, 1H), 7.28-7.39 (m, 2H), 7.56-7.72 (m, 2H), 7.86-7.98 (m, 3H), 7.99-8.09 (m, 2H). LCMS m/z 531.16 (M+H), Rt 2.791 min. HPLC Rt 13.122 min. (XBridge Phenyl C18), 100% purity.

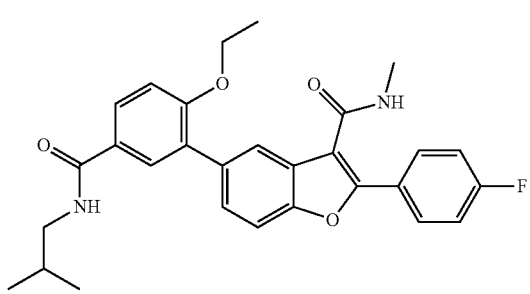

2-(4-fluorophenyl)-5-(5-(isobutylcarbamoyl)-2-ethoxyphenyl)-N-methyl benzofuran-3-carboxamide. ¹H NMR (400 MHz, CD₃OD) δ ppm 1.04 (d, J=6.53 Hz, 6H), 1.42 (t, J=6.78 Hz, 3H), 1.90-2.11 (m, 1H), 3.02 (s, 3H), 3.27 (d, J=7.03 Hz, 2H), 4.22 (q, J=6.78 Hz, 2H), 7.18-7.24 (m, 1H), 7.29-7.38 (m, 2H), 7.64-7.67 (m, 2H), 7.87-7.93 (m, 2H), 7.93-7.96 (m, 1H), 8.00-8.08 (m, 2H). LCMS m/z 489.15 (M+H), Rt 2.432 min. HPLC Rt 10.571 min. (Sunfire C18) and 12.193 min. (XBridge Phenyl C18), 93% purity.

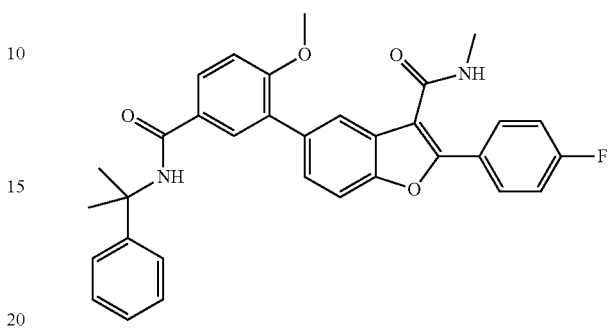

2-(4-fluorophenyl)-5-(2-methoxy-5-(2-phenylpropan-2-ylcarbamoyl)phenyl)-N-methylbenzofuran-3-carboxamide. To a 50 mL RBF was added 3-(2-(4-fluorophenyl)-3-(methylcarbamoyl)benzofuran-5-yl)-4-methoxybenzoic acid (433.9 mg, 1.035 mmol), DMF (15 mL), 2-phenylpropan-2-amine (210 mg, 1.552 mmol), N-ethyl-N-isopropylpropan-2-amine (0.360 mL, 2.069 mmol), and finally HATU, 2-(3H-[1,2,3]triazolo[4,5-b]pyridin-3-yl)-1,1,3,3-tetramethylisouronium hexafluorophosphate(V) (1180 mg, 3.10 mmol)). The mixture was stirred over night at room temperature. The resulting mixture was diluted with dichloromethane, washed with 0.5M HCl, then brine and dried over MgSO₄. The solution was concentrated to give a tan oil. The crude product was taken up in 10 mL of acetonitrile and purified using a Shimadzu preparative HPLC employing acetonitrile/water/0.1% TFA where solvent A was 10% acetonitrile/90% H2O/0.1% trifluoroacetic acid and solvent B was 10% H2O/90% acetonitrile/0.1% trifluoroacetic acid with a Phenomenex-Luna 10 μm C18 30×100 mm column at a gradient of 40-100% B and a flow rate of 40 mL/min. over 8 minutes with a 12 minute hold to give a 80% yield of product as a white powder. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/ 10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/ 0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute. All NMR spectra were recorded at room temperature using a Bruker DRX400 spectrometer. LCMS m/z 537.18 (M+H), Rt 2.492 min. HPLC Rt 10.694 min. (Sunfire C18), 99.6% purity and 12.230 min. (XBridge Phenyl C18), 99.6% purity. $^1$H NMR (400 MHz, CD$_3$OD) δ ppm 1.82 (s, 6H), 3.01 (s, 3H), 3.94 (s, 3H), 7.18-7.27 (m, 2H), 7.28-7.40 (m, 4 H), 7.50 (d, J=7.53 Hz, 2H), 7.57-7.67 (m, 2H), 7.85 (d, J=1.00 Hz, 1H), 7.89-7.95 (m, 2H), 7.98-8.09 (m, 2H).

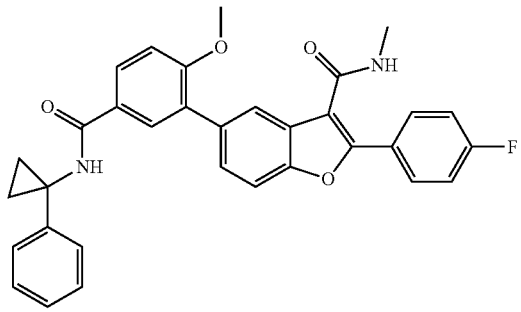

2-(4-fluorophenyl)-5-(2-methoxy-5-(1-phenylcyclopropylcarbamoyl)phenyl)-N-methylbenzofuran-3-carboxamide. To a 50 mL RBF was added 3-(2-(4-fluorophenyl)-3-(methylcarbamoyl)benzofuran-5-yl)-4-methoxybenzoic acid (433.9 mg, 1.035 mmol), DMF (15 mL), 1-phenylcyclopropan-amine, HCl (214 mg, 1.259 mmol), N-ethyl-N-isopropylpropan-2-amine (0.438 mL, 2.52 mmol), and finally HATU, 2-(3H-[1,2,3]triazolo[4,5-b]pyridin-3-yl)-1,1,3,3-tetramethylisouronium hexafluorophosphate(V) (1180 mg, 3.10 mmol)). The mixture was stirred over night at room temperature. The reaction mixture was diluted with dichloromethane, washed with 0.5M HCl, then brine and dried over MgSO$_4$. The solution was concentrated to give a tan oil. The crude product was taken up in 10 mL of acetonitrile and purified using a Shimadzu preparative HPLC employing acetonitrile/water/0.1% TFA where solvent A was 10% acetonitrile/90% H2O/0.1% trifluoroacetic acid and solvent B was 10% H2O/90% acetonitrile/0.1% trifluoroacetic acid with a Phenomenex-Luna 10 nm C18 30×100 mm column at a gradient of 40-100% B and a flow rate of 40 mL/min. over 8 minutes with a 12 minute hold to give a 77% yield of product as a white powder. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 220 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. All NMR spectra were recorded at room temperature using a Bruker DRX400 spectrometer. LCMS m/z 535.16 (M+H), Rt 2.373 min. HPLC Rt 10.314 min. (Sunfire C18), 95.78% purity and 12.230 min. (XBridge Phenyl C18), 99.6% purity. $^1$H NMR (400 MHz, CD$_3$OD) δ ppm 1.40 (dd, J=7.03, 2.01 Hz, 4H), 3.01 (s, 3H), 3.94 (s, 3H), 7.18-7.26 (m, 2 H), 7.28-7.38 (m, 6H), 7.56-7.62 (m, 1H), 7.62-7.67 (m, 1H), 7.85 (d, J=1.51 Hz, 1H), 7.94-8.05 (m, 4H).

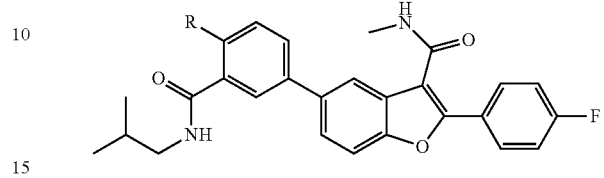

General procedure. To a Biotage microwave vial (2-5 mL) was added 5-(4-chloro-3-(isobutylcarbamoyl)phenyl)-2-(4-fluorophenyl)-N-methylbenzofuran-3-carboxamide (0.075 mmol, 1 eq.) in dry 1,4-Dioxane (1 mL) along with the desired boronic acid (0.150 mmol, 2 eq.), potassium phosphate, tribasic (0.300 mmol, 52.3 mg) in water (0.2 mL), dicyclohexyl(2',6'-dimethoxybiphenyl-3-yl)phosphine (S-Phos) (6.16 mg, 0.015 mmol), and finally palladium (II) acetate (3.37 mg, 0.015 mmol) in 1,4-dioxane (0.5 mL). The vial was flushed with nitrogen then capped and placed into a Biotage microwave for 10 minutes at 150° C. The solvent was removed in a Thermo/Savant SpeedVac and the crude products were dissolved in DMF (1.8 mL) and purified by preparative HPLC employing a Dionex PrepHPLC system equipped with an ELS (Evaporative Light Scattering) detector. A Phenomenex Gemini 5 μm C18 21.2×250 mm column was used with acetonitrile/HPLC grade water/20 mM ammonium acetate where solvent A was HPLC grade water with 20 mM ammonium acetate and solvent B was 100% acetonitrile at a gradient of 30-95% B in 23.5 minutes with a 2.5 minute hold at 20 mL/minute. HPLC purity was determined using a Waters ZQ with ESCi mass spectrometer with a Supelco Ascentis 2.7 μm C18 4.6×50 mm column employing acetonitrile/HPLC grade water/0.1% trifluoroacetic acid where solvent A was 5% acetonitrile, 95% HPLC grade water with 0.1% trifluoroacetic acid and solvent B was 95% acetonitrile, 5% HPLC grade water with 0.1% trifluoroacetic acid at a gradient of 10-95% B in 8 minutes with a 1 minute hold at 2 mL/minute. The NMR spectra were recorded at room temperature using a Varian 400 MHz flow spectrometer. Chemical shifts were reported in ppm relative to the DMSO-d6/CDCl$_3$ solvent used.

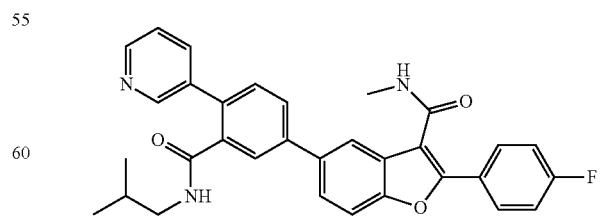

2-(4-fluorophenyl)-5-(3-(isobutylcarbamoyl)-4-(pyridin-3-yl)phenyl)-N-methylbenzofuran-3-carboxamide. LCMS m/z 522.19 (M+H), Rt 3.21 min., 100% purity.

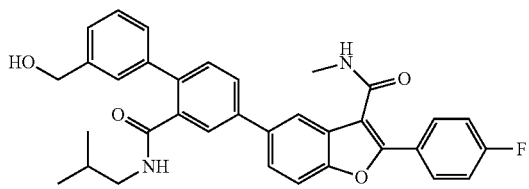

2-(4-fluorophenyl)-5-(3'-(hydroxymethyl)-2-(isobutylcarbamoyl)biphenyl-4-yl)-N-methyl benzofuran-3-carboxamide. $^1$H NMR δ ppm 0.76 (d, J=6.74 Hz, 6H), 1.68 (m, 1H), 2.29 (s, 3H), 2.81-3.00 (m, 4H), 7.07-7.18 (m, 1H), 7.22 (t, J=7.47 Hz, 1H), 7.26-7.37 (m, 2H), 7.39 (s, 1H), 7.48 (d, J=7.91 Hz, 1H), 7.72 (br. s., 2H), 7.80 (d, J=8.20 Hz, 1H), 7.92 (s, 1H), 8.01 (dd, J=7.47, 5.42 Hz, 2H), 8.22 (s, 2H), 8.46 (br. s., 1H). LCMS m/z 551.23 (M+H), Rt 4.23 min., 100% purity.

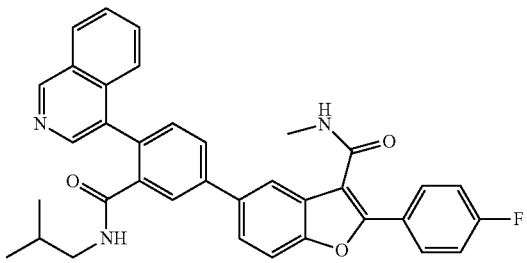

2-(4-fluorophenyl)-5-(3-(isobutylcarbamoyl)-4-(isoquinolin-4-yl)phenyl)-N-methylbenzofuran-3-carboxamide. $^1$H NMR δ ppm 0.64 (d, J=6.44 Hz, 6H), 1.38-1.48 (m, 1H), 2.37 (s, 3H), 2.93-3.02 (m, 2H), 7.14-7.24 (m, 2H), 7.25-7.33 (m, 2H), 7.40 (t, J=8.79 Hz, 1H), 7.57 (d, J=7.32 Hz, 1H), 7.75 (br. s., 2H), 7.81-7.90 (m, 1H), 7.95-8.03 (m, 2H), 8.08 (br. s., 2H), 8.18-8.25 (m, 1H), 8.31-8.37 (m, 1H), 8.48 (s, 1H), 8.55 (br. s., 1H). LCMS m/z 572.22 (M+H), Rt 3.49 min., 100% purity.

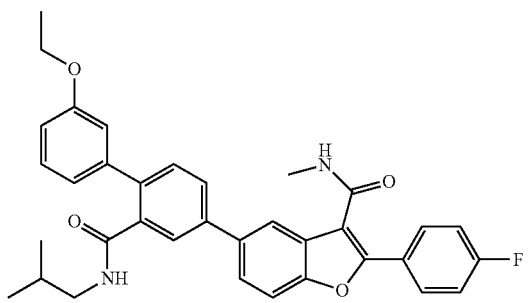

5-(3'-ethoxy-2-(isobutylcarbamoyl)biphenyl-4-yl)-2-(4-fluorophenyl)-N-methylbenzofuran-3-carboxamide. LCMS m/z 565.24 (M+H), Rt 5.28 min., 93.4% purity.

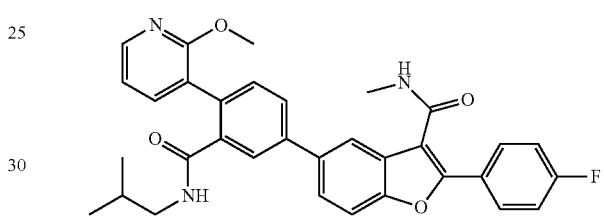

2-(4-fluorophenyl)-5-(3-(isobutylcarbamoyl)-4-(2-methoxypyridin-3-yl)phenyl)-N-methylbenzo-furan-3-carboxamide. $^1$H NMR δ ppm 0.88 (d, J=6.74 Hz, 6H), 1.68-1.83 (m, 1H), 2.37 (s, 3H), 2.96 (d, J=4.69 Hz, 2H), 3.86 (s, 3H), 7.04-7.13 (m, 1H), 7.21 (d, J=7.32 Hz, 1H), 7.28 (d, J=7.03 Hz, 1H), 7.39 (t, J=8.05 Hz, 1H), 7.48 (d, J=8.49 Hz, 1H), 7.67 (d, J=7.03 Hz, 1H), 7.82 (s, 2H), 7.88 (br. s., 2H), 8.04 (s, 1H), 8.06-8.12 (m, 1H), 8.18 (d, J=4.98 Hz, 1H), 8.54 (br. s., 1H). LCMS m/z 552.21 (M+H), Rt 4.56 min., 90.5% purity.

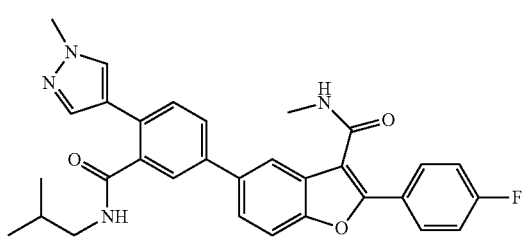

2-(4-fluorophenyl)-5-(3-(isobutylcarbamoyl)-4-(1-methyl-1H-pyrazol-4-yl)phenyl)-N-methyl benzofuran-3-carboxamide. $^1$H NMR δ ppm 0.93 (d, J=6.74 Hz, 6H), 1.82-1.99 (m, 1H), 2.37 (s, 3H), 2.89-3.00 (m, 2H), 3.94 (s, 3H), 7.15-7.25 (m, 1H), 7.25-7.33 (m, 1H), 7.39 (t, J=8.20 Hz, 1H), 7.62-7.82 (m, 5 H), 7.93 (d, J=12.89 Hz, 1H), 8.02-8.12 (m, 1H), 8.36-8.45 (m, 1H), 8.53 (d, 1H).

LCMS m/z 525.21 (M+H), Rt 4.00 min., 100% purity.

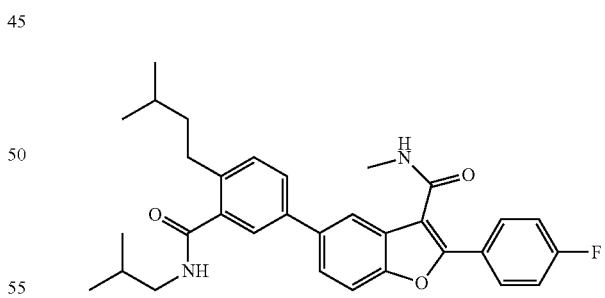

2-(4-fluorophenyl)-5-(2-(isobutylcarbamoyl)-4'-isopentylbiphenyl-4-yl)-N-methylbenzofuran-3-carboxamide. $^1$H NMR δ ppm 0.99 (dd, J=12.74, 6.59 Hz, 9 H), 1.23-1.37 (m, 3H), 1.59-1.70 (m, 1H), 1.88-2.00 (m, 1H), 2.37 (s, 3H), 2.76-2.87 (m, 2H), 2.91-2.99 (m, 2H), 3.10-3.20 (m, 2H), 7.14-7.25 (m, 1H), 7.29 (t, J=7.32 Hz, 1H), 7.38 (t, J=8.05 Hz, 2H), 7.64 (s, 1H), 7.72 (dd, J=16.26, 8.05 Hz, 2H), 7.93 (s, 1H), 8.01-8.11 (m, 2H), 8.44 (br. s., 1H), 8.52 (br. s., 1H). LCMS m/z 515.26 (M+H), Rt 5.63 min., 100% purity.

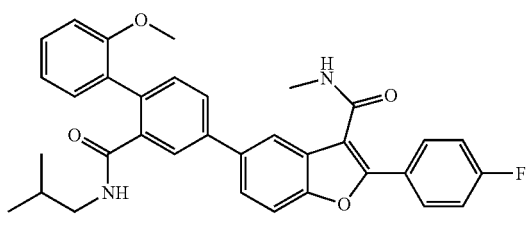

2-(4-fluorophenyl)-5-(2-(isobutylcarbamoyl)-2'-methoxybiphenyl-4-yl)-N-methylbenzofuran-3-carboxamide. $^1$H NMR δ ppm 0.85 (d, J=6.74 Hz, 6H), 1.63-1.77 (m, 1H), 2.37 (s, 3H), 2.96 (d, J=4.39 Hz, 2H), 3.77 (s, 3H), 6.99-7.09 (m, 1H), 7.21 (d, J=7.62 Hz, 1H), 7.29 (t, J=7.62 Hz, 2H), 7.34-7.46 (m, 3 H), 7.76-7.88 (m, 3H), 7.92-7.98 (m, 1H), 8.02 (s, 1H), 8.09 (dd, J=7.76, 6.00 Hz, 2H), 8.54 (br. s., 1H). LCMS m/z 551.22 (M+H), Rt 5.07 min., 93.7% purity.

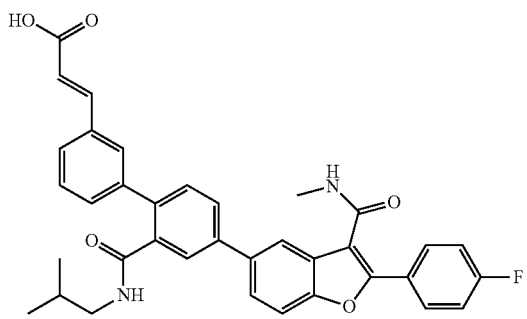

(E)-3-(4'-(2-(4-fluorophenyl)-3-(methylcarbamoyl)benzofuran-5-yl)-2'-(isobutylcarbamoyl)biphenyl-3-yl)acrylic acid. $^1$H NMR δ ppm 0.81 (d, J=6.44 Hz, 6H), 1.65-1.77 (m, 1H), 2.37 (s, 3H), 2.96 (d, J=4.39 Hz, 2H), 6.55 (d, J=15.82 Hz, 1H), 7.14-7.25 (m, 2H), 7.25-7.33 (m, 1H), 7.40 (t, J=8.49 Hz, 2H), 7.47-7.56 (m, 1H), 7.61 (d, J=8.20 Hz, 1H), 7.67 (br. s., 1H), 7.73 (br. s., 1H), 7.80 (br. s., 2H), 7.90 (d, J=7.91 Hz, 1H), 8.01 (s, 1H), 8.04-8.13 (m, 1H), 8.36 (br. s., 1H), 8.53 (br. s., 1H). LCMS m/z 591.23 (M+H), Rt 4.37 min., 100% purity.

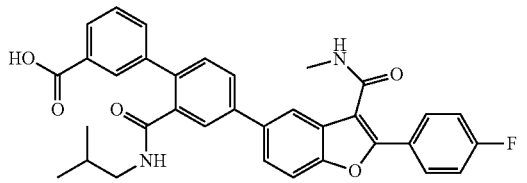

4'-(2-(4-fluorophenyl)-3-(methylcarbamoyl)benzofuran-5-yl)-2'-(isobutylcarbamoyl)biphenyl-3-carboxylic acid. $^1$H NMR δ ppm 0.80 (d, J=6.74 Hz, 6H), 1.67-1.79 (m, 1H), 2.37 (s, 3H), 2.96 (d, J=4.69 Hz, 2H), 7.16-7.25 (m, 2H), 7.26-7.32 (m, 1H), 7.33-7.44 (m, 2H), 7.50-7.62 (m, 2H), 7.66-7.73 (m, 1H), 7.76-7.84 (m, 2H), 7.90 (d, J=7.91 Hz, 1H), 7.95-8.02 (m, 1H), 8.04-8.14 (m, 1H), 8.32-8.37 (m, 1H), 8.55 (br. s., 1H). LCMS m/z 565.22 (M+H), Rt 4.22 min., 100% purity.

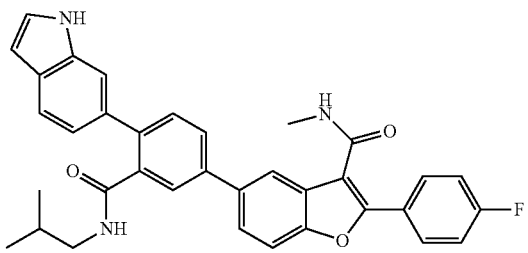

5-(4-(1H-indol-6-yl)-3-(isobutylcarbamoyl)phenyl)-2-(4-fluorophenyl)-N-methylbenzofuran-3-carboxamide. LCMS m/z 560.23 (M+H), Rt 4.90 min., 97.2% purity.

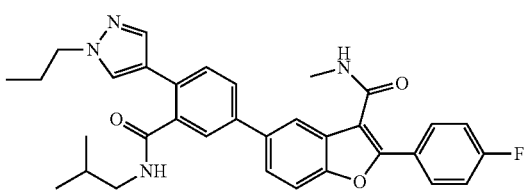

2-(4-fluorophenyl)-5-(3-(isobutylcarbamoyl)-4-(1-propyl-1H-pyrazol-4-yl)phenyl)-N-methylbenzofuran-3-carboxamide. LCMS m/z 553.25 (M+H), Rt 4.49 min., 96% purity.

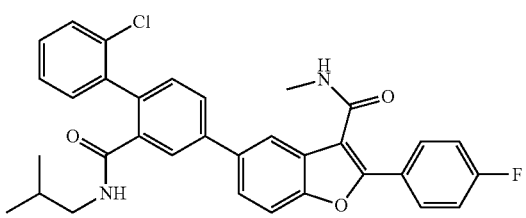

5-(2'-chloro-2-(isobutylcarbamoyl)biphenyl-4-yl)-2-(4-fluorophenyl)-N-methylbenzofuran-3-carboxamide. $^1$H NMR δ ppm 0.85 (d, J=6.44 Hz, 6H), 1.65-1.80 (m, 1H), 2.37 (s, 3H), 2.93-2.97 (m, 2H), 7.06 (br. s., 1H), 7.15-7.24 (m, 2H), 7.25-7.35 (m, 2H), 7.35-7.47 (m, 4H), 7.49-7.55 (m, 1H), 7.79-7.86 (m, 1H), 7.87-7.93 (m, 1H), 7.98-8.13 (m, 2H), 8.21-8.27 (m, 1H), 8.53 (br. s., 1H). LCMS m/z 556.19 (M+H), Rt 5.28 min., 100% purity.

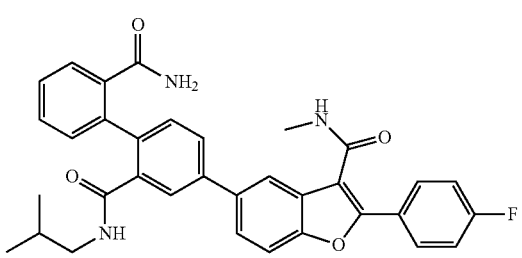

4-(2-(4-fluorophenyl)-3-(methylcarbamoyl)benzofuran-5-yl)-N-2-isobutylbiphenyl-2,2'-dicarboxamide. $^1$H NMR δ ppm 0.69 (d, J=6.44 Hz, 6H), 1.42-1.54 (m, 1H), 2.37 (s, 3H), 2.92-2.97 (m, 2H), 7.13-7.23 (m, 2H), 7.23-7.33 (m, 2H), 7.39 (t, J=8.64 Hz, 1H), 7.43-7.51 (m, 2H), 7.61 (d, J=4.69 Hz, 1H), 7.75-7.82 (m, 2H), 7.86 (s, 1H), 7.96-8.03 (m, 1H), 8.08 (d, J=5.27 Hz, 1H), 8.13-8.18 (m, 1H), 8.51 (br. s., 1H), 8.65 (br. s., 1H). LCMS m/z 564.24 (M+H), Rt 4.07 min., 98.9% purity.

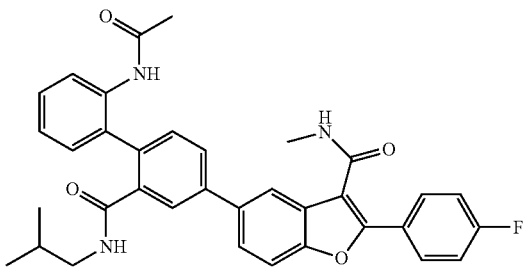

5-(2'-acetamido-2-(isobutylcarbamoyl)biphenyl-4-yl)-2-(4-fluorophenyl)-N-methylbenzofuran-3-carboxamide. $^1$H NMR δ ppm 0.50-0.73 (m, 6H), 1.33-1.50 (m, 1H), 1.90 (s, 3H), 2.37 (s, 3H), 2.92-2.97 (m, 2H), 7.20 (t, J=7.91 Hz, 3H), 7.25-7.44 (m, 6H), 7.75-7.82 (m, 2H), 7.91 (s, 1H), 7.96-8.03 (m, 1H), 8.04-8.11 (m, 1H), 8.24 (br. s., 1H), 8.52 (br. s., 1H, 9.89-9.96 (m, 1H). LCMS m/z 578.24 (M+H), Rt 4.26 min., 93.5% purity.

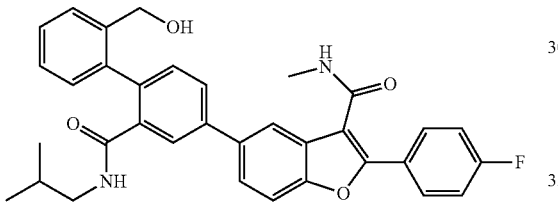

2-(4-fluorophenyl)-5-(2'-(hydroxymethyl)-2-(isobutylcarbamoyl)biphenyl-4-yl)-N-methylbenzofuran-3-carboxamide. $^1$H NMR δ ppm 0.71 (d, J=5.27 Hz, 6H), 1.45-1.57 (m, 1H), 2.37 (s, 3H), 2.90 (br. s., 2H), 2.96 (d, J=4.69 Hz, 2H), 7.13-7.25 (m, 2H), 7.25-7.35 (m, 2H), 7.35-7.44 (m, 3H), 7.56 (d, J=7.32 Hz, 1H), 7.81 (s, 2H), 7.83-7.89 (m, 2H), 8.01 (s, 1H), 8.09 (dd, J=8.64, 5.42 Hz, 2H), 8.52 (br. s., 1H). LCMS m/z 551.22 (M+H), Rt 4.58 min., 96% purity.

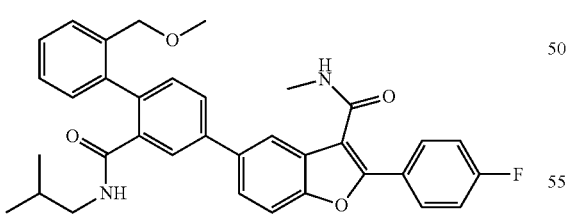

2-(4-fluorophenyl)-5-(2-(isobutylcarbamoyl)-2'-(methoxymethyl)biphenyl-4-yl)-N-methylbenzofuran-3-carboxamide. $^1$H NMR δ ppm 0.64-0.79 (m, 6H), 1.47-1.59 (m, 1H), 2.37 (s, 3H), 2.86-2.93 (m, 2H), 2.93-2.99 (m, 2H), 3.25 (s, 3H), 7.15-7.25 (m, 2H), 7.26-7.32 (m, 1H), 7.33-7.44 (m, 4H), 7.49-7.55 (m, 1H), 7.81 (s, 2H), 7.87 (br. s., 2H), 8.02 (br. s., 1H), 8.05-8.12 (m, 1H), 8.53 (br. s., 1 H).

LCMS m/z 565.22 (M+H), Rt 5.30 min., 100% purity.

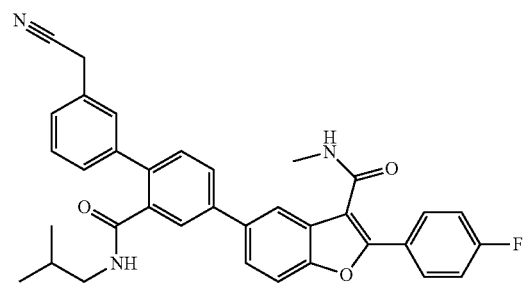

5-(3'-(cyanomethyl)-2-(isobutylcarbamoyl)biphenyl-4-yl)-2-(4-fluorophenyl)-N-methylbenzofuran-3-carboxamide. $^1$H NMR δ ppm 0.83 (d, J=6.44 Hz, 6H), 1.67-1.81 (m, 1H), 2.37 (s, 3H), 2.96 (d, J=4.39 Hz, 2H), 4.08 (s, 2H), 7.14-7.25 (m, 2H), 7.26-7.32 (m, 1H), 7.35-7.44 (m, 2H), 7.48 (d, J=5.27 Hz, 2H), 7.56 (d, J=7.91 Hz, 1H), 7.80 (br. s., 2H), 7.90 (d, J=7.62 Hz, 1H), 8.00 (s, 1H), 8.04-8.13 (m, 2H), 8.35 (br. s., 1H), 8.54 (d, J=3.81 Hz, 1H). LCMS m/z 560.23 (M+H), Rt 4.67 min., 91.5% purity.

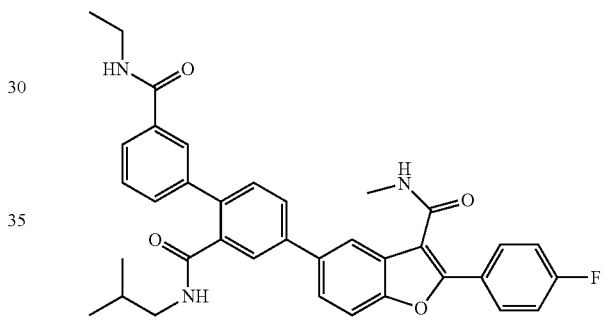

N3'-ethyl-4-(2-(4-fluorophenyl)-3-(methylcarbamoyl)benzofuran-5-yl)-N2-isobutylbiphenyl-2,3'-dicarboxamide. LCMS m/z 592.26 (M+H), Rt 4.28 min., 94.1% purity.

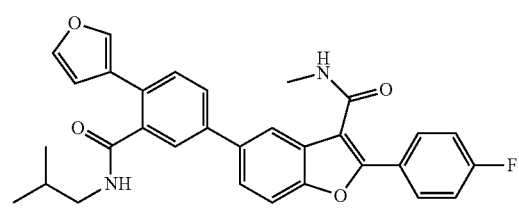

2-(4-fluorophenyl)-5-(4-(furan-3-yl)-3-(isobutylcarbamoyl)phenyl)-N-methylbenzofuran-3-carboxamide. $^1$H NMR δ ppm 0.86-1.03 (m, 6H), 1.80-1.94 (m, 1H), 2.37 (s, 3H), 2.92-3.00 (m, 2H), 6.79 (s, 1H), 7.15-7.24 (m, 2H), 7.28 (d, J=7.03 Hz, 2H), 7.35-7.42 (m, 1H), 7.69 (t, J=7.91 Hz, 2H), 7.73-7.85 (m, 3H), 7.94 (d, J=19.33 Hz, 1H), 8.04-8.12 (m, 1H), 8.41-8.48 (m, 1H), 8.53 (d, 1H).

LCMS m/z 511.17 (M+H), Rt 4.69 min., 86.5% purity.

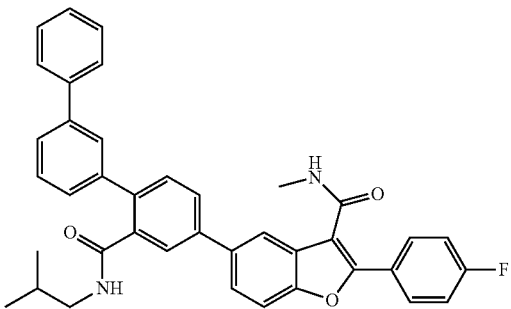

3'-phenyl-4-(2-(4-fluorophenyl)-3-(methylcarbamoyl) benzofuran-5-yl)-N2-isobutylbiphenyl-2,3'-dicarboxamide. $^1$H NMR δ ppm 0.75 (d, J=6.74 Hz, 6H), 1.59-1.72 (m, 1H), 2.37 (s, 3H), 2.94-2.98 (m, 2H), 7.15-7.24 (m, 3H), 7.25-7.33 (m, 2H), 7.34-7.47 (m, 4H), 7.49-7.58 (m, 2H), 7.63-7.74 (m, 2H), 7.75-7.83 (m, 3H), 7.89 (br. s., 1H), 8.00 (s, 1H), 8.07 (br. s., 1H), 8.54 (br. s., 1H). LCMS m/z 597.27 (M+H), Rt 5.74 min., 80% purity.

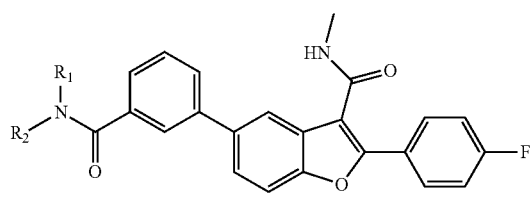

The general procedures (for amide formations) below pertain to the experimental procedures. Some of the compounds were made with different scales of the acids. The acid (0.075 mmol, 1 eq.) was dissolved in dried DMF and followed by adding HATU (0.090 mmol, 1.2 eq.) and DIPEA (0.225 mmol, 3.0 eq.). The solution was stirred for 2 minutes and added into amine (0.090 mmol, 1.2 eq.) at room temperature. The mixture was stirred 14 h and purified by prep-HPLC.

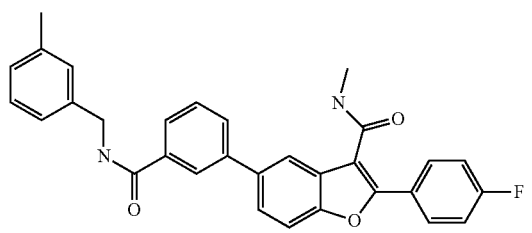

2-(4-fluorophenyl)-N-methyl-5-(3-(3-methylbenzylcarbamoyl)phenyl)benzofuran-3-carboxamide. $^1$H NMR (600 MHz, DMSO-d$_6$-CDCl$_3$) δ ppm 9.15 (1H, t, J=5.86 Hz), 8.48 (1H, d, J=4.69 Hz), 8.27 (2H, d, J=4.69 Hz), 8.00-8.08 (1H, m), 7.92-7.97 (2H, m), 7.89 (1H, d, J=7.62 Hz), 7.77 (2H, s), 7.61 (1H, t, J=7.62 Hz), 7.37 (2H, t, J=8.50 Hz), 7.24 (1H, t, J=7.32 Hz), 7.14-7.22 (2H, m), 7.08 (1H, d, J=7.03 Hz), 4.54 (2H, d, J=5.86 Hz), 2.92 (3H, d, J=4.10 Hz), 2.34 (3H, s).

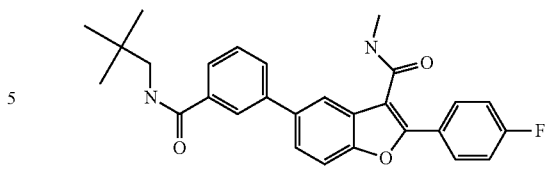

2-(4-fluorophenyl)-N-methyl-5-(3-(neopentylcarbamoyl) phenyl)benzofuran-3-carboxamide. $^1$H NMR (600 MHz, DMSO-d$_6$-CDCl$_3$) δ ppm 8.44-8.51 (m, 2H), 8.27 (s, 1H), 8.20 (s, 1H), 8.02-8.07 (m, 1H), 7.96 (s, 1H), 7.88 (t, J=7.32 Hz, 2 H), 7.77 (s, 2H), 7.59 (t, J=7.62 Hz, 1H), 7.37 (t, J=8.50 Hz, 2H), 3.20 (d, J=6.44 Hz, 2H), 2.92 (d, J=4.69 Hz, 3H), 0.98 (s, 9H).

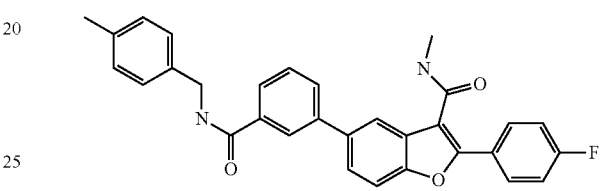

2-(4-fluorophenyl)-N-methyl-5-(3-(4-methylbenzylcarbamoyl)phenyl)benzofuran-3-carboxamide. $^1$H NMR (600 MHz, DMSO-d$_6$-CDCl$_3$) δ ppm 9.14 (t, J=5.86 Hz, 1H), 8.48 (d, J=4.69 Hz, 1H), 8.27 (s, 1H), 8.25 (s, 1H), 8.01-8.06 (m, 1H), 7.95 (s, 1H), 7.93 (d, J=7.62 Hz, 1H), 7.89 (d, J=7.62 Hz, 1H), 7.77 (s, 2H), 7.61 (t, J=7.62 Hz, 1H), 7.37 (t, J=8.50 Hz, 2H), 7.27 (d, J=7.62 Hz, 2H), 7.16 (d, J=7.62 Hz, 2H), 4.52 (d, J=5.86 Hz, 2 H), 2.92 (d, J=4.10 Hz, 3H), 2.30-2.35 (m, 3H).

HPLC purity was determined using a Waters LCT Mass Spectrometer with four way MUX source analytical LC at 220 nm with employing acetonitrile and water or Waters ZQ with ESCi mass spectrometer. A=5:95 CH$_3$CN:Water; B=95:5 CH$_3$CN:Water; Modifier=10 mM NH$_4$OAc. Retention time was recorded in minutes.

| Analytical Method A: Column Waters Xterra 2.1 × 50 mm 5 um C18 | | |
|---|---|---|
| Time | B % | Flow |
| 0.00 | 0 | 1.0 |
| 4.00 | 100 | 1.0 |
| 5.00 | 100 | 1.0 |

| Analytical Method B: Column: Waters Xbridge 2.1 × 50 mm 5 um C18 | | |
|---|---|---|
| Time | B % | Flow |
| 0.00 | 0 | 1.0 |
| 4.00 | 100 | 1.0 |
| 5.00 | 100 | 1.0 |
| 5.05 | 100 | 1.0 |
| 6.00 | 0 | 1.0 |

| Analytical Method C: Column: Waters Xbridge 4.6 × 50 mm 5 um C18 | | |
|---|---|---|
| Time | B % | Flow |
| 0.00 | 0 | 2.0 |
| 8.00 | 100 | 2.0 |
| 9.00 | 100 | 2.0 |

| Analytical Method D Column: Waters Xbridge 4.6 × 50 mm 5 um C18 | | |
|---|---|---|
| Time | B % | Flow |
| 0.00 | 0 | 1.0 |
| 8.00 | 100 | 1.0 |
| 9.00 | 100 | 1.0 |
| 9.10 | 100 | 1.0 |
| 1.00 | 0 | 10 |

| Analytical Method E Waters ZQ with ESCi mass spectrometer Column: Supelcu Ascentis 4.6 × 50 mm 2.7 um C18 | | |
|---|---|---|
| Time | B % | Flow |
| 0.00 | 10 | 3.00 |
| 5.30 | 95 | 3.00 |
| 6.00 | 95 | 3.00 |
| 6.20 | 10 | 3.00 |
| 7.00 | 10 | 3.00 |

| Analytical Method F Waters ZQ with ESCi mass spectrometer Column: Phenomenex Gemini 4.6 × 150 mm 3 um C18 | | |
|---|---|---|
| Time | B % | Flow |
| 0.00 | 10 | 1.0 |
| 10.00 | 95 | 1.0 |
| 13.00 | 95 | 1.0 |
| 13.50 | 10 | 1.0 |
| 15.00 | 10 | 1.0 |

| Structure | HPLC Rt | % Purity | Obs. MS Ion | HPLC Method |
|---|---|---|---|---|
| 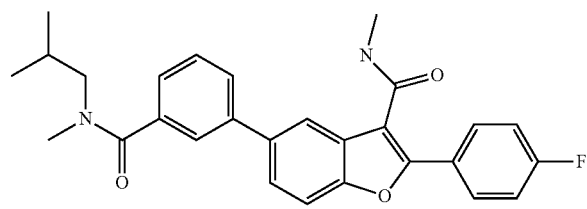 | 2.81 | 100 | 458.93 | Method A |
| 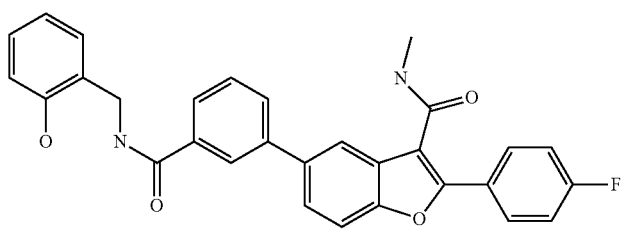 | 2.75 | 100 | 494.89 | Method A |
| 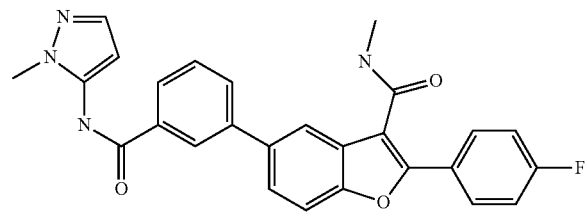 | 2.38 | 100 | 468.9 | Method A |
| 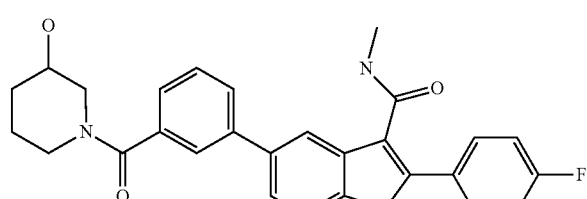 | 2.22 | 100 | 472.91 | Method A |

-continued

| Structure | HPLC Rt | % Purity | Obs. MS Ion | HPLC Method |
|---|---|---|---|---|
| 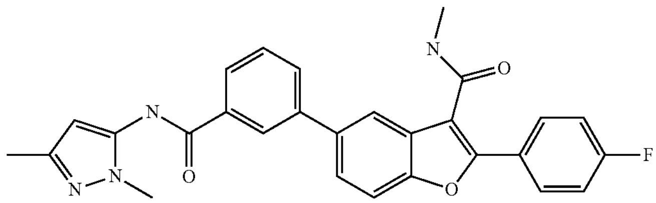 | 2.46 | 100 | 482.9 | Method A |
| 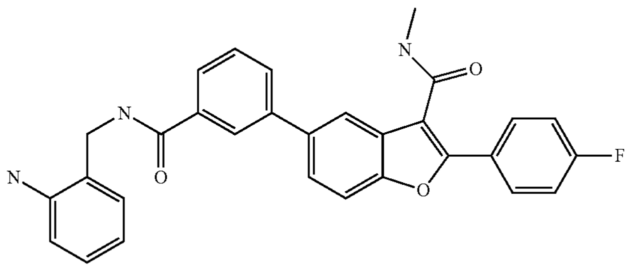 | 2.68 | 95.0177 | 493.92 | Method A |
| 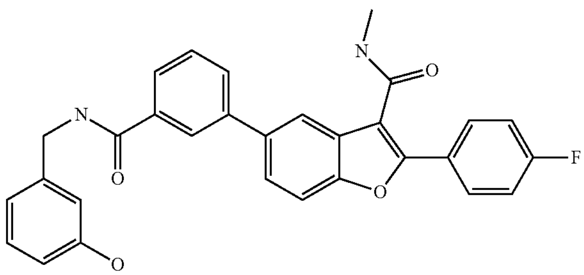 | 2.5 | 98.5972 | 494.9 | Method A |
| 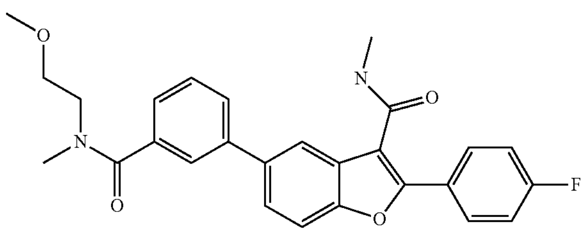 | 2.42 | 100 | 460.91 | Method A |
| 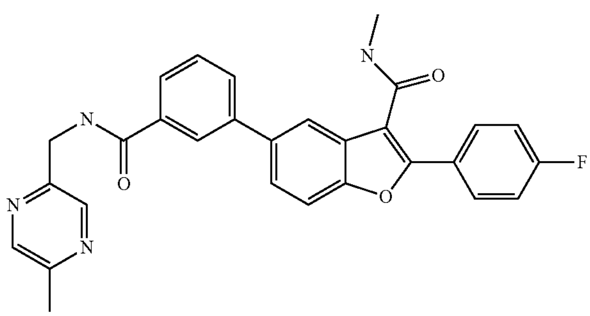 | 2.34 | 100 | 494.9 | Method A |
| 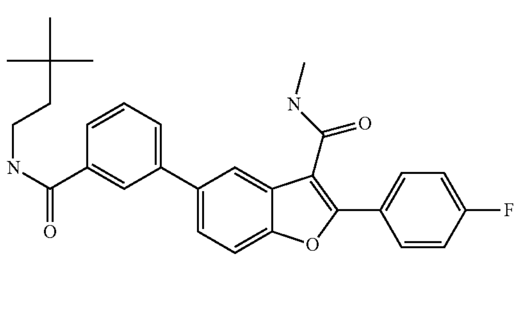 | 3.05 | 100 | 472.96 | Method A |

-continued
| Structure | HPLC Rt | % Purity | Obs. MS Ion | HPLC Method |
|---|---|---|---|---|
| 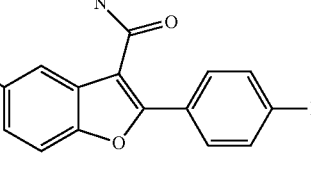 | 2.48 | 100 | 426.91 | Method A |
| 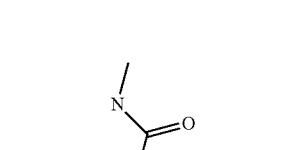 | 2.86 | 100 | 513.92 | Method A |
| 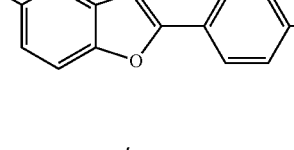 | 2.89 | 100 | 513.91 | Method A |
| 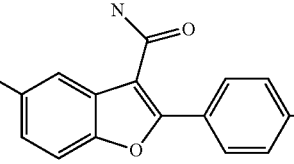 | 2.69 | 100 | 456.95 | Method A |
| 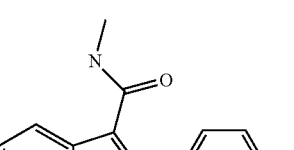 | 2.8 | 100 | 495.94 | Method A |
| 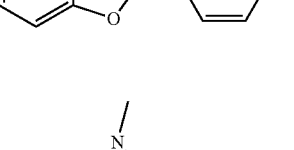 | 2.84 | 100 | 513.93 | Method A |

-continued

| Structure | HPLC Rt | % Purity | Obs. MS Ion | HPLC Method |
|---|---|---|---|---|
| 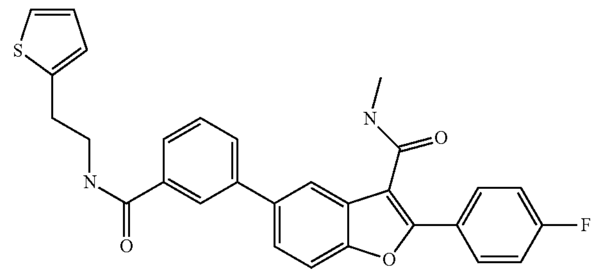 | 2.85 | 100 | 498.9 | Method A |
| 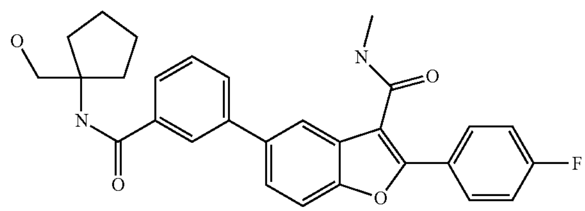 | 2.56 | 100 | 486.94 | Method A |
| Chiral | 2.1 | 100 | 458.91 | Method A |
| 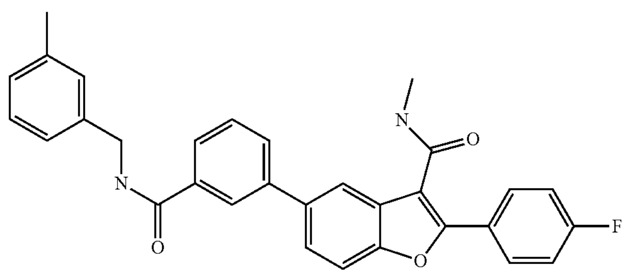 | 2.93 | 100 | 509.94 | Method A |
| 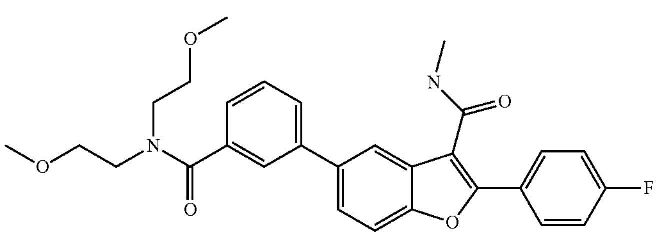 | 2.53 | 100 | 504.9 | Method A |
| 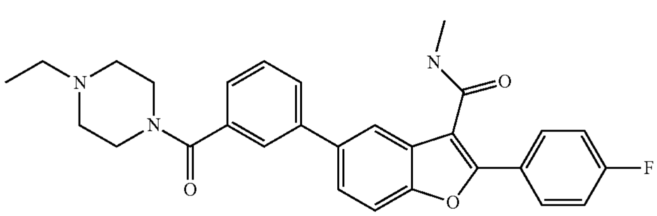 | 2.23 | 100 | 485.92 | Method A |

-continued

| Structure | HPLC Rt | % Purity | Obs. MS Ion | HPLC Method |
|---|---|---|---|---|
| 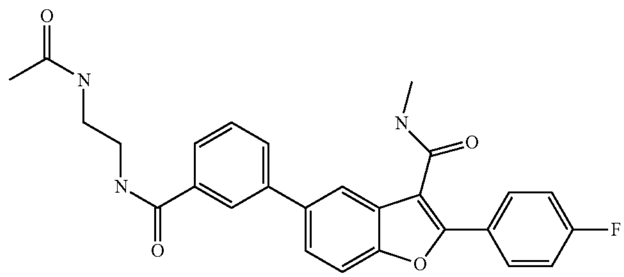 | 2.11 | 100 | 473.91 | Method A |
| 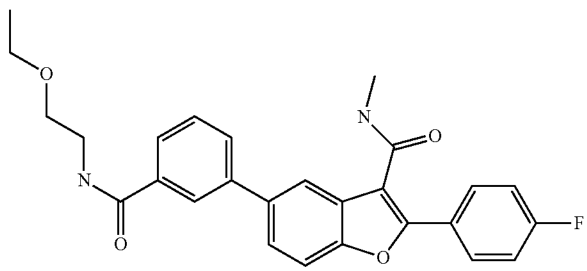 | 2.51 | 100 | 460.92 | Method A |
| 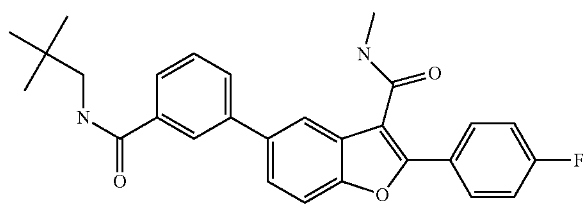 | 2.89 | 100 | 458.94 | Method A |
| 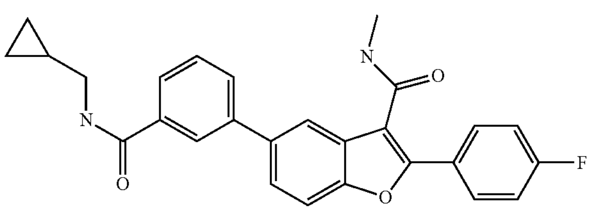 | 2.62 | 100 | 459.94 | Method A |
| 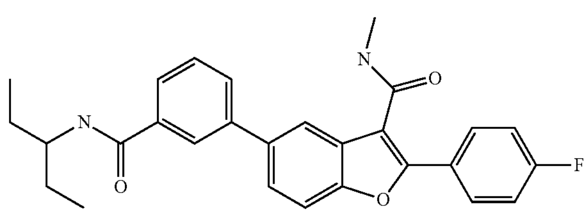 | 2.85 | 100 | 475.95 | Method A |
| 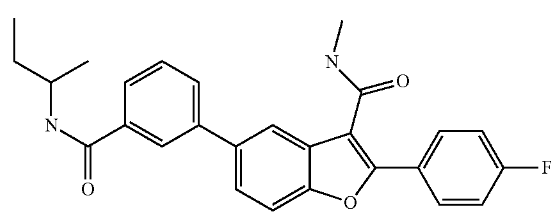 | 2.72 | 100 | 444.94 | Method A |

-continued

| Structure | HPLC Rt | % Purity | Obs. MS Ion | HPLC Method |
|---|---|---|---|---|
| 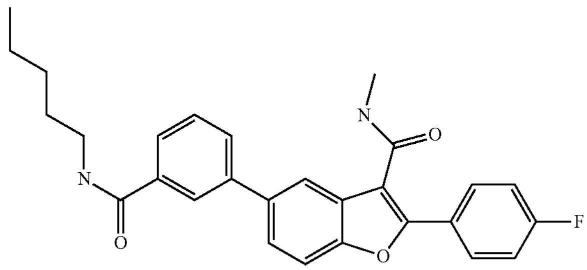 | 2.91 | 100 | 475.95 | Method A |
| 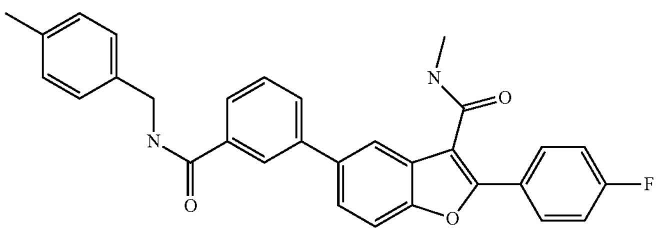 | 2.97 | 100 | 509.93 | Method A |
| 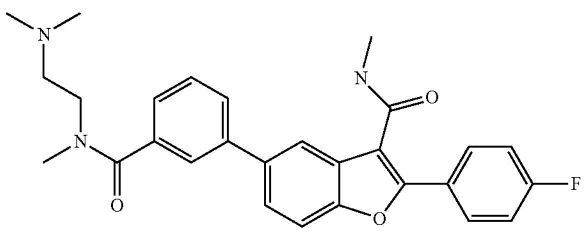 | 2 | 100 | 473.92 | Method A |
| 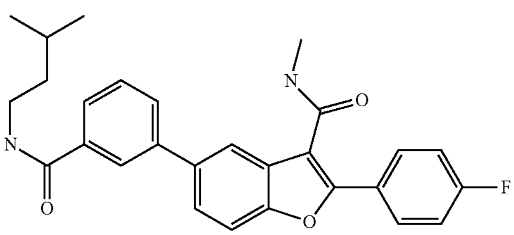 | 2.89 | 100 | 475.95 | Method A |
| 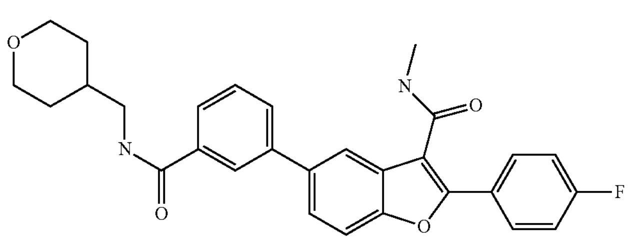 | 2.43 | 100 | 486.93 | Method A |
| 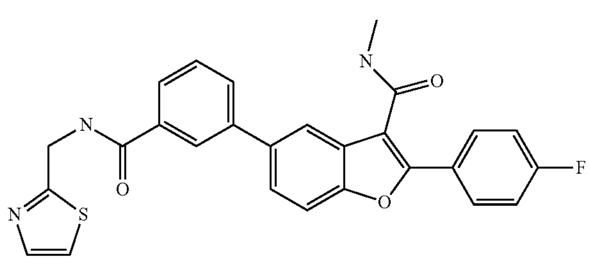 | 2.44 | 100 | 485.85 | Method A |

-continued

| Structure | HPLC Rt | % Purity | Obs. MS Ion | HPLC Method |
|---|---|---|---|---|
| 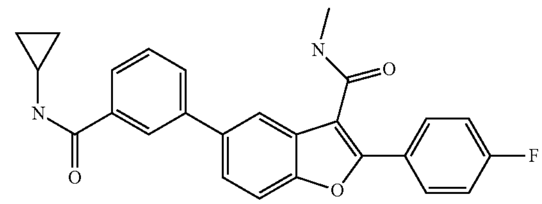 | 2.39 | 100 | 856.65 | Method B |
| 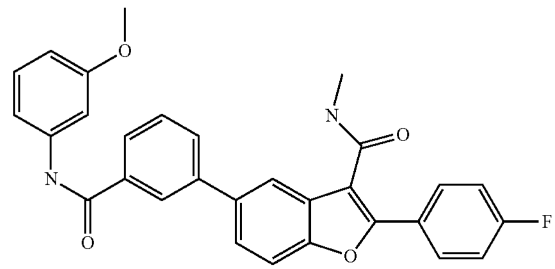 | 2.81 | 96.6226 | 494.8 | Method B |
| 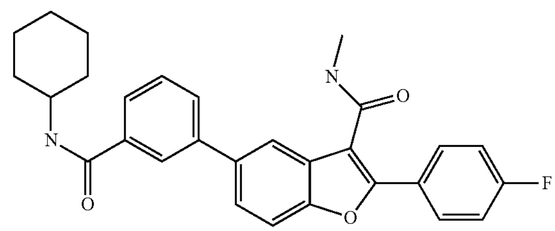 | 2.75 | 100 | 940.66 | Method B |
| 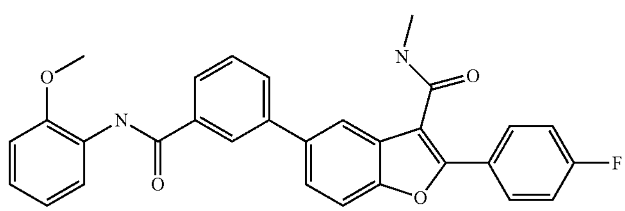 | 2.89 | 99.0179 | 988.56 | Method B |
| 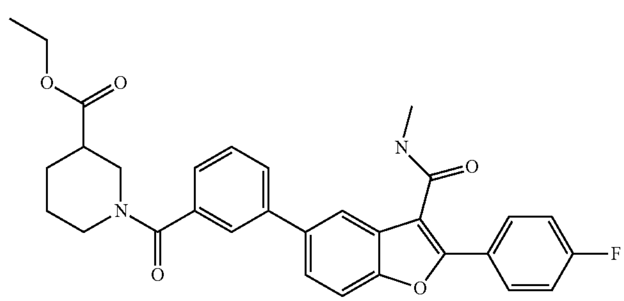 | 2.7 | 100 | 1056.6 | Method B |
| 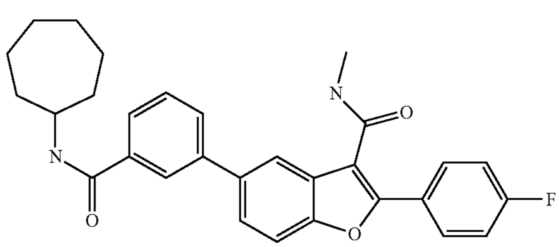 | 2.94 | 89.8624 | 968.67 | Method B |

-continued

| Structure | HPLC Rt | % Purity | Obs. MS Ion | HPLC Method |
|---|---|---|---|---|
| 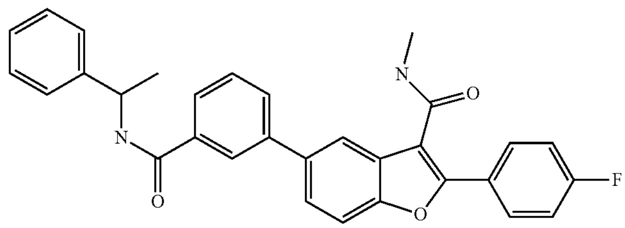 | 2.75 | 100 | 984.61 | Method B |
| 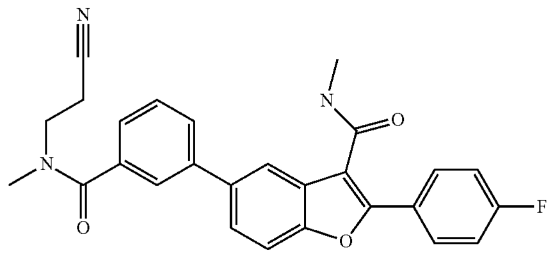 | 2.29 | 100 | 455.82 | Method B |
| 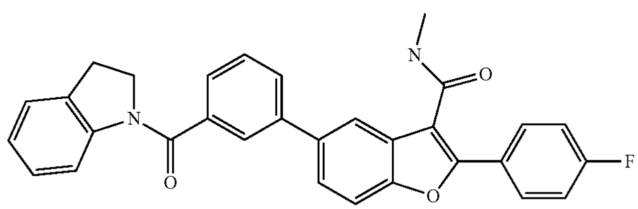 | 2.92 | 98.0936 | 980.59 | Method B |
| 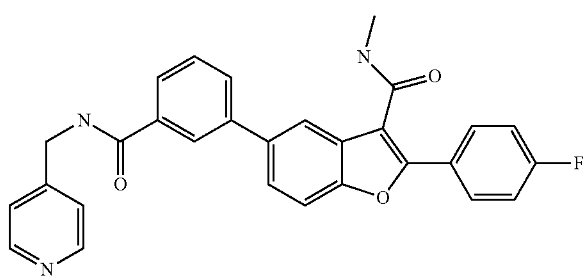 | 2.32 | 98.0376 | 479.8 | Method B |
| 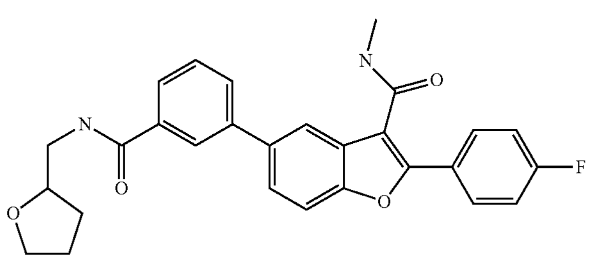 | 2.35 | 100 | 472.83 | Method B |
| 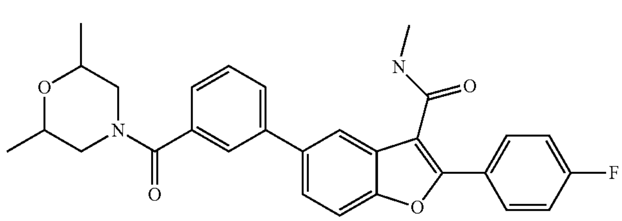 | 2.56 | 100 | 972.64 | Method B |

-continued

| Structure | HPLC Rt | % Purity | Obs. MS Ion | HPLC Method |
|---|---|---|---|---|
| 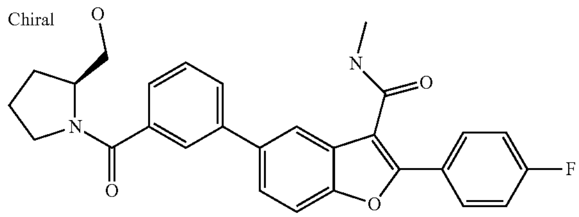 | 2.26 | 100 | 472.83 | Method B |
| 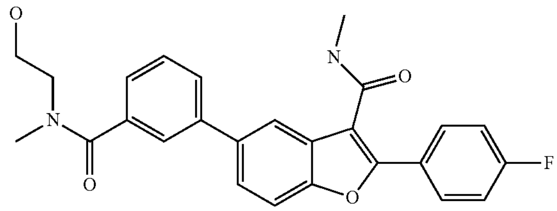 | 2.06 | 98.6458 | 892.65 | Method B |
| 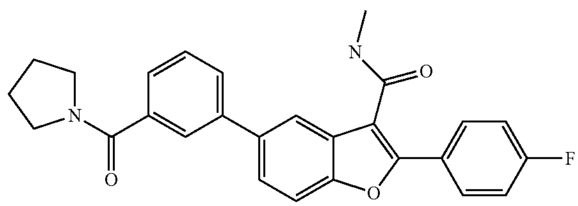 | 2.43 | 100 | 884.66 | Method B |
| 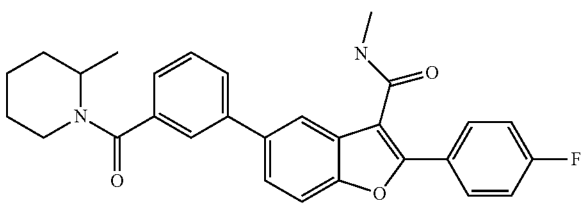 | 2.81 | 100 | 940.69 | Method B |
| 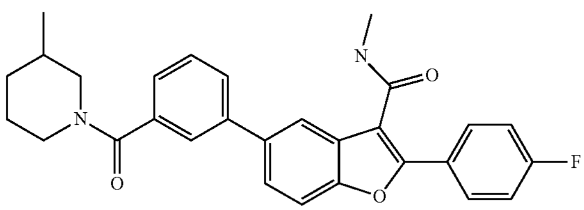 | 2.82 | 100 | 940.7 | Method B |
| 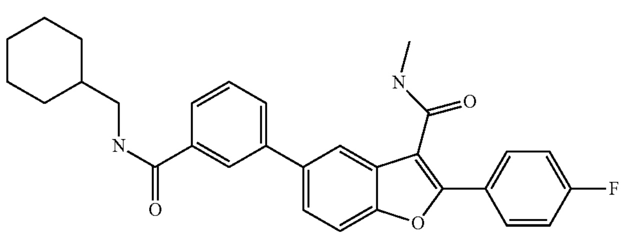 | 2.93 | 100 | 968.72 | Method B |
| 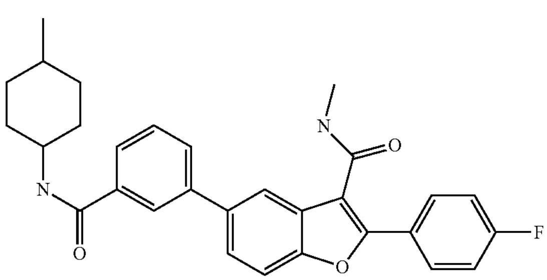 | 2.95 | 100 | 968.7 | Method B |

-continued

| Structure | HPLC Rt | % Purity | Obs. MS Ion | HPLC Method |
|---|---|---|---|---|
| 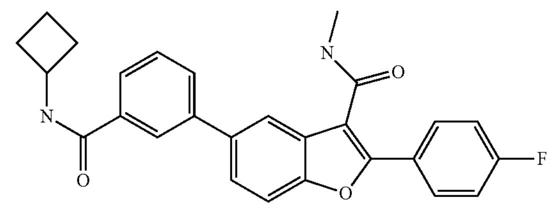 | 2.6 | 100 | 884.67 | Method B |
| 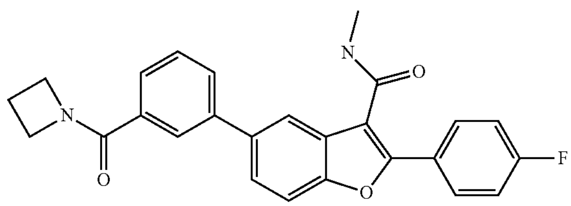 | 2.35 | 100 | 856.66 | Method B |
| 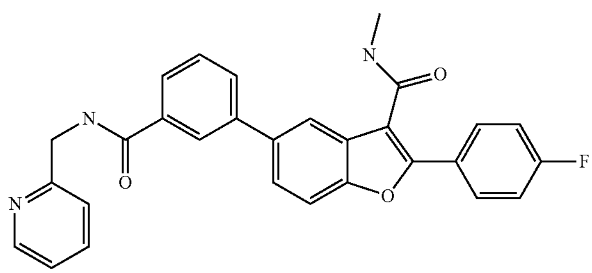 | 2.34 | 96.8795 | 958.6 | Method B |
| 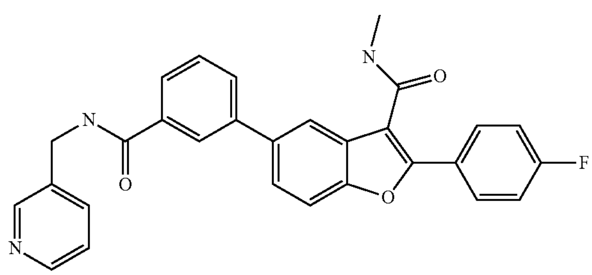 | 2.26 | 100 | 479.81 | Method B |
| 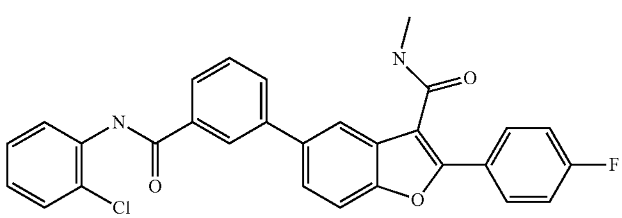 | 2.82 | 100 | 806.66 | Method B |
| 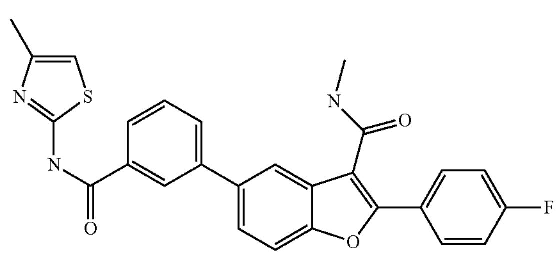 | 2.75 | 100 | 970.55 | Method B |

-continued

| Structure | HPLC Rt | % Purity | Obs. MS Ion | HPLC Method |
|---|---|---|---|---|
| 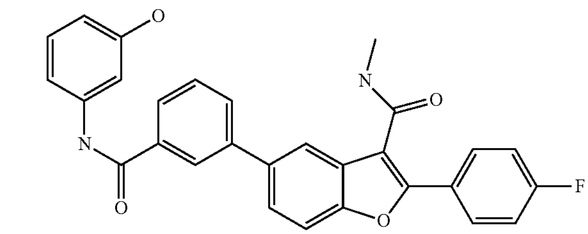 | 2.48 | 100 | 480.8 | Method B |
| 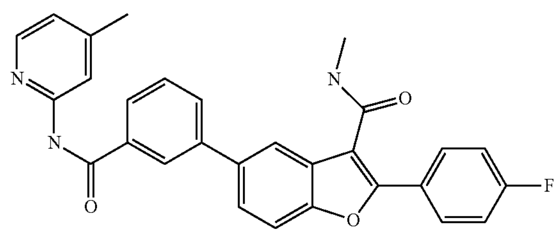 | 2.77 | 100 | 479.81 | Method B |
| 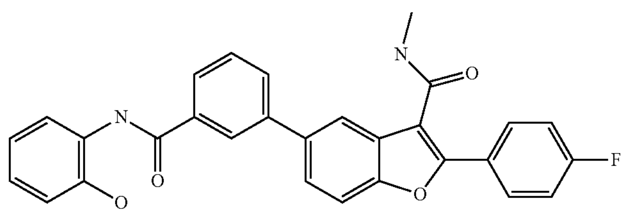 | 2.7 | 98.233 | 480.8 | Method B |
| 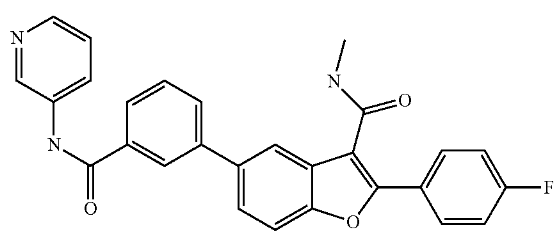 | 2.57 | 100 | 465.64 | Method B |
| 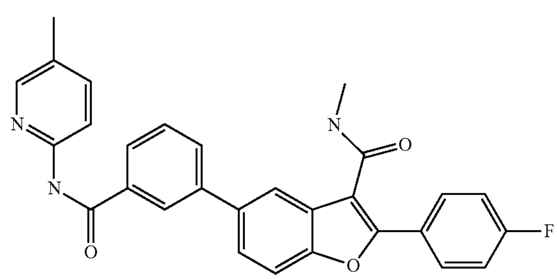 | 2.85 | 97.8741 | 958.25 | Method B |
| 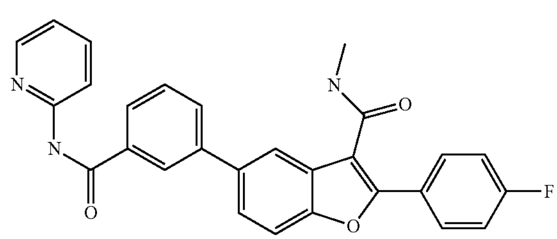 | 2.64 | 100 | 930.26 | Method B |

-continued
| Structure | HPLC Rt | % Purity | Obs. MS Ion | HPLC Method |
|---|---|---|---|---|
| 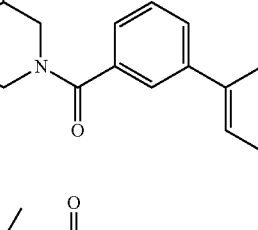 | 2.24 | 100 | 972.33 | Method B |
| 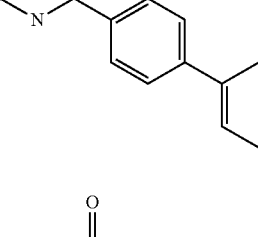 | 5.21 | 100 | 444.95 | Method C |
| 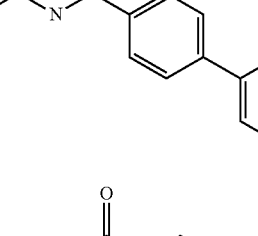 | 4.95 | 100 | 444.96 | Method C |
| Chiral 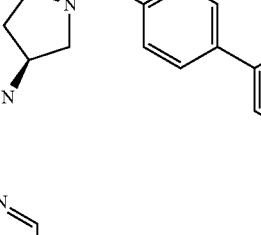 | 3.74 | 100 | 499.93 | Method C |
| 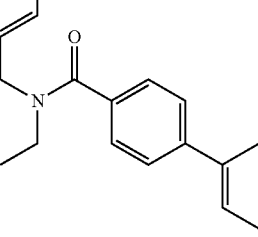 | 4.54 | 100 | 507.94 | Method C |
| 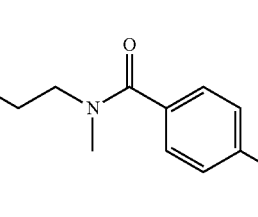 | 4.37 | 100 | 507.93 | Method C |

-continued
| Structure | HPLC Rt | % Purity | Obs. MS Ion | HPLC Method |
|---|---|---|---|---|
| 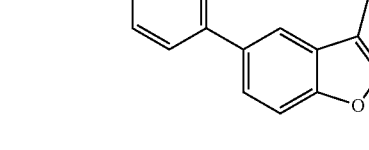 | 4.32 | 100 | 460.91 | Method C |
| 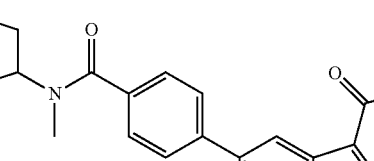 | 3.68 | 100 | 485.94 | Method C |
| 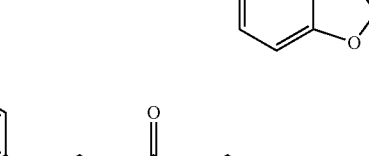 | 5.31 | 100 | 510.91 | Method C |
| 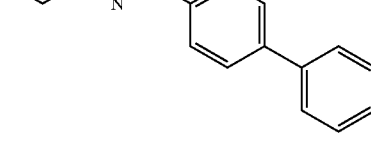 | 3.78 | 100 | 432.93 | Method C |
| 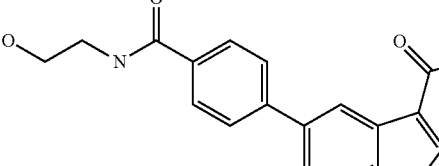 | 4.68 | 93.1925 | 466.91 | Method D |
| 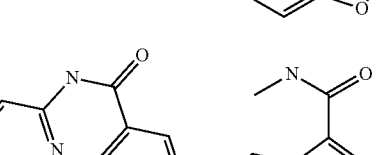 | 5.72 | 96.6697 | 464.93 | Method D |
| 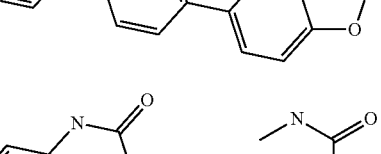 | 5.57 | 96.8314 | 489.9 | Method D |

-continued

| Structure | HPLC Rt | % Purity | Obs. MS Ion | HPLC Method |
|---|---|---|---|---|
| 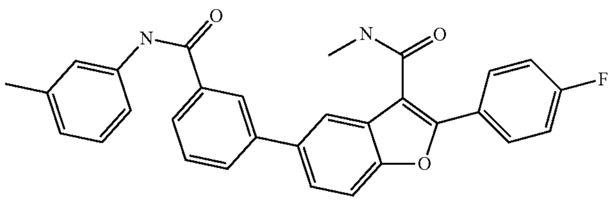 | 5.72 | 94.0943 | 478.93 | Method D |
| 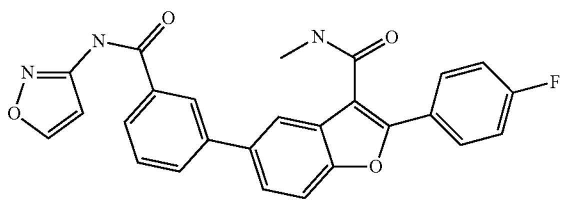 | 4.93 | 94.4826 | 455.9 | Method D |
| 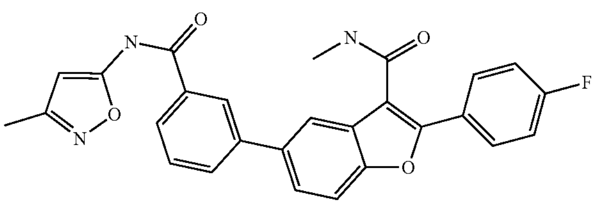 | 5.26 | 88.6355 | 469.92 | Method D |
| 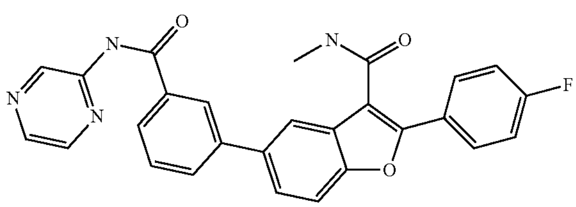 | 4.7 | 100 | 466.92 | Method D |
| 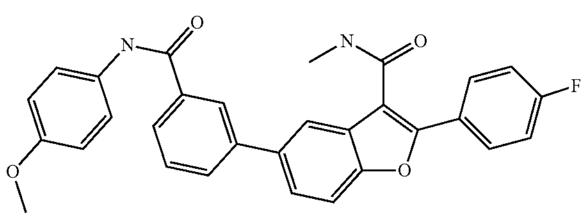 | 5.59 | 97.7461 | 494.92 | Method D |
| 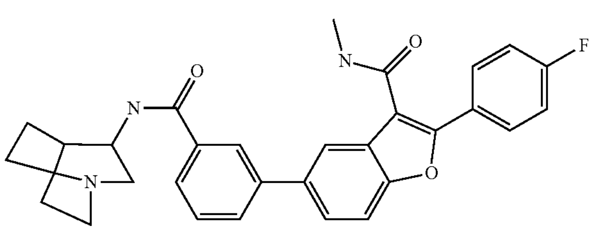 | 4.06 | 100 | 497.98 | Method D |
| 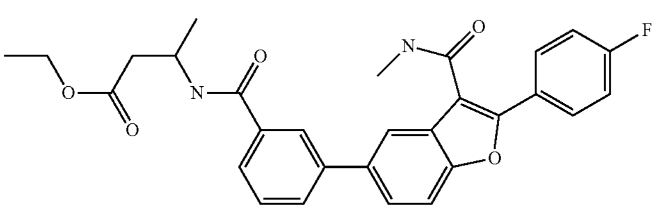 | 5.05 | 97.6492 | 502.96 | Method D |

-continued
| Structure | HPLC Rt | % Purity | Obs. MS Ion | HPLC Method |
|---|---|---|---|---|
| 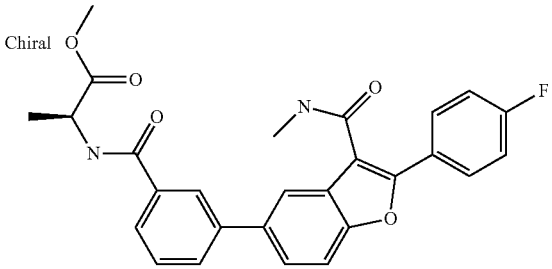 | 4.7 | 100 | 474.95 | Method D |
| 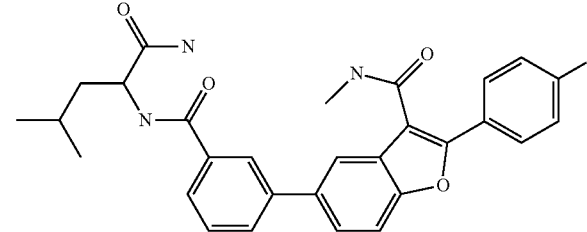 | 4.7 | 100 | 501.98 | Method D |
| 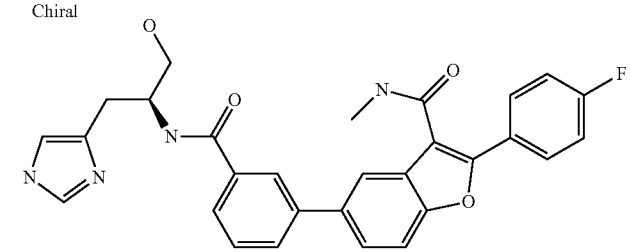 | 3.74 | 100 | 512.96 | Method D |
| 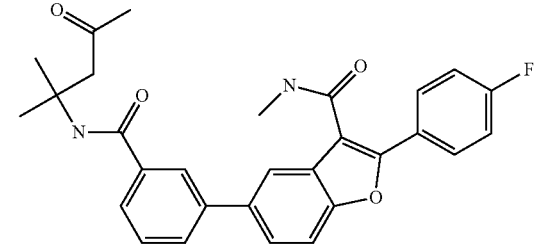 | 5.2 | 97.5131 | 486.97 | Method D |
| 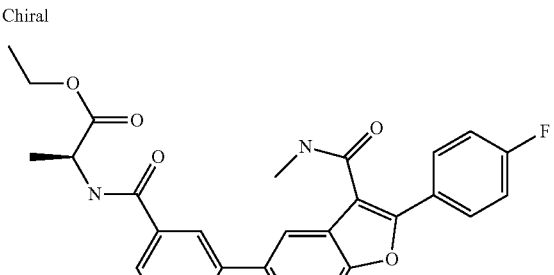 | 5.05 | 100 | 488.95 | Method D |

-continued

| Structure | HPLC Rt | % Purity | Obs. MS Ion | HPLC Method |
|---|---|---|---|---|
| Chiral | 4.74 | 100 | 508.95 | Method D |
| 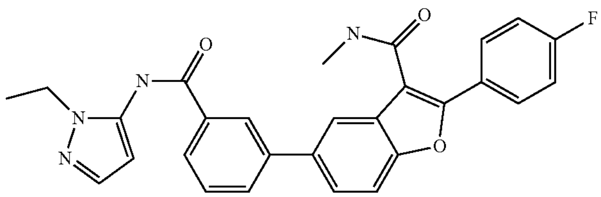 | 4.79 | 100 | 482.96 | Method D |
| 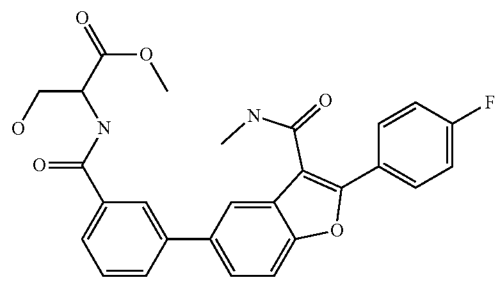 | 4.18 | 100 | 490.94 | Method D |
| Chiral | 4.8 | 100 | 474.98 | Method D |
| Chiral | 4.43 | 100 | 499.97 | Method D |
| 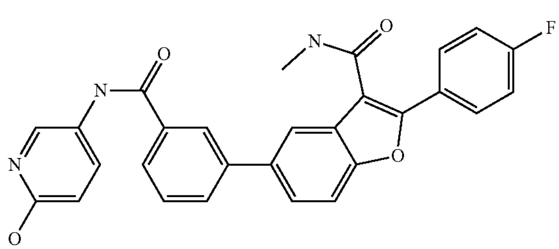 | 4.04 | 95.8428 | 481.93 | Method D |

-continued

| Structure | HPLC Rt | % Purity | Obs. MS Ion | HPLC Method |
|---|---|---|---|---|
| Chiral | 4.5 | 93.8873 | 487.97 | Method D |
| Chiral | 4.26 | 100 | 490.94 | Method D |
| 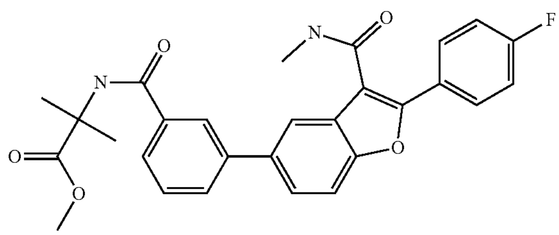 | 4.88 | 100 | 488.93 | Method D |
| Chiral | 5.11 | 100 | 488.97 | Method D |
| 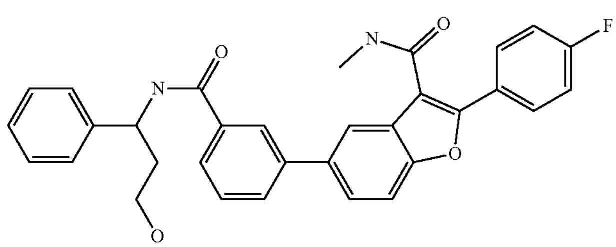 | 4.81 | 100 | 522.93 | Method D |
| Chiral | 5.06 | 100 | 520.93 | Method D |

-continued
| Structure | HPLC Rt | % Purity | Obs. MS Ion | HPLC Method |
|---|---|---|---|---|
| 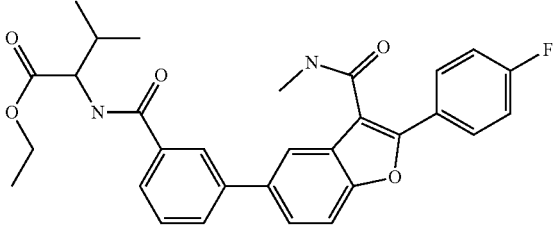 | 5.74 | 100 | 516.94 | Method D |
| Chiral 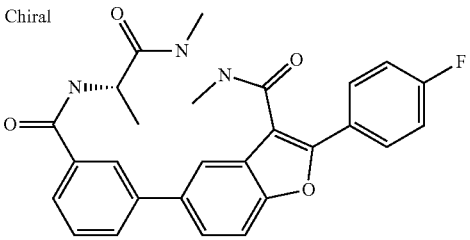 | 4.26 | 100 | 473.94 | Method D |
| Chiral 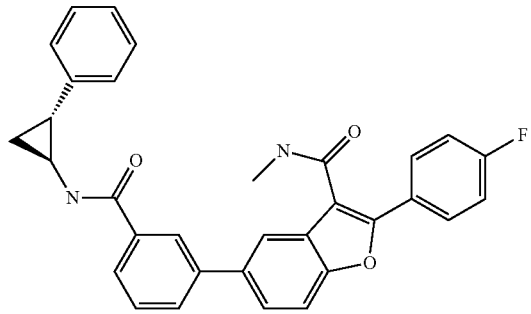 | 5.85 | 100 | 504.94 | Method D |
| Chiral 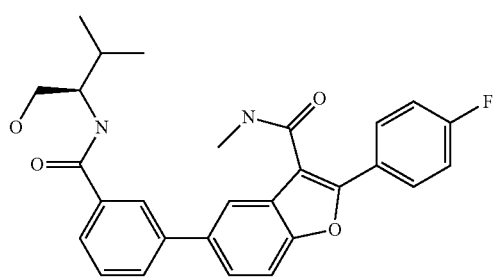 | 4.69 | 100 | 474.96 | Method D |
| 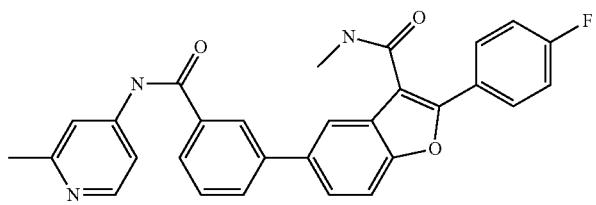 | 4.74 | 100 | 479.92 | Method D |
| 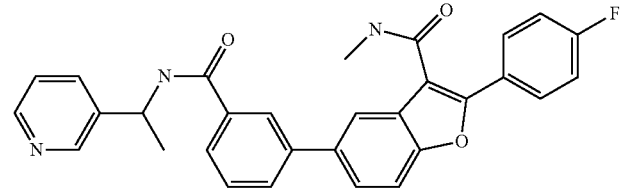 | 4.71 | 100 | 493.93 | Method D |

US 8,309,558 B2
435	436
-continued
| Structure | HPLC Rt | % Purity | Obs. MS Ion | HPLC Method |
|---|---|---|---|---|
| 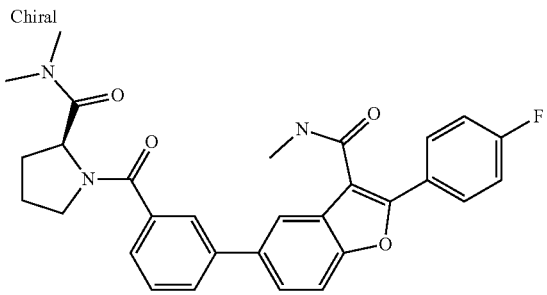 | 4.19 | 100 | 513.95 | Method D |
| 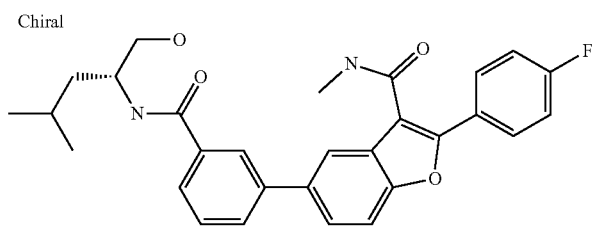 | 5.04 | 100 | 488.97 | Method D |
| 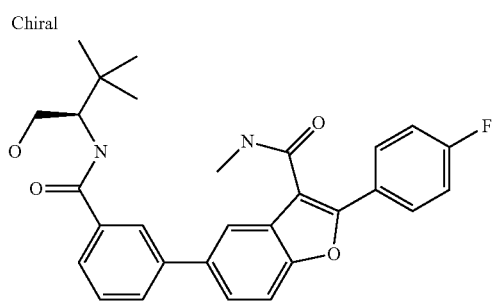 | 4.97 | 100 | 488.96 | Method D |
| 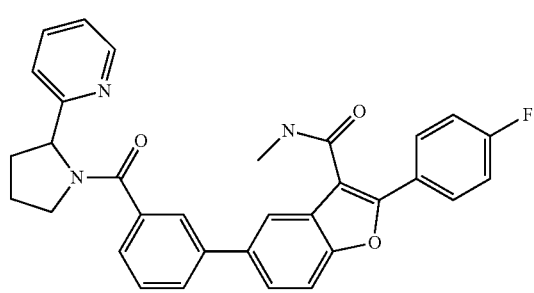 | 4.7 | 98.2446 | 519.93 | Method D |
| 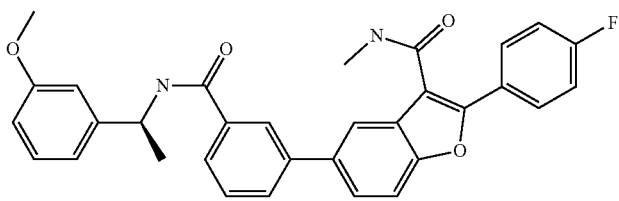 | 5.64 | 100 | 522.94 | Method D |

-continued

| Structure | HPLC Rt | % Purity | Obs. MS Ion | HPLC Method |
|---|---|---|---|---|
| 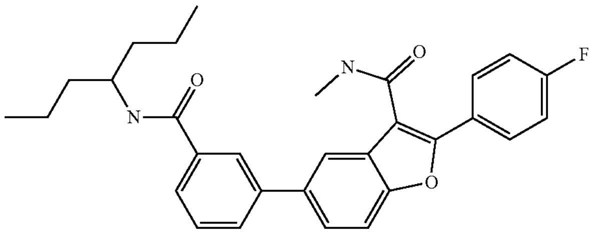 | 5.97 | 100 | 487 | Method D |
| 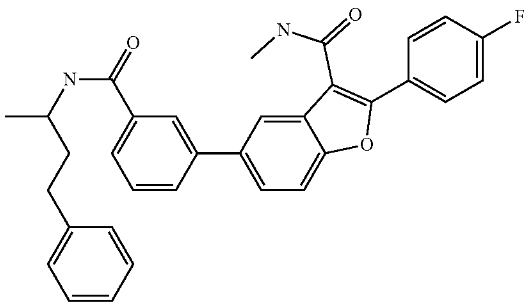 | 6.1 | 100 | 520.96 | Method D |
| 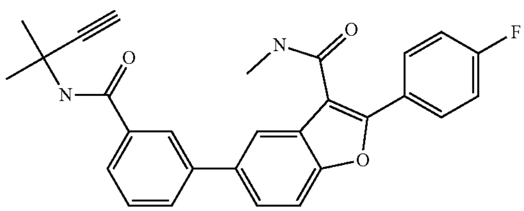 | 3.168 | 100 | 455.14 | Method E |
| 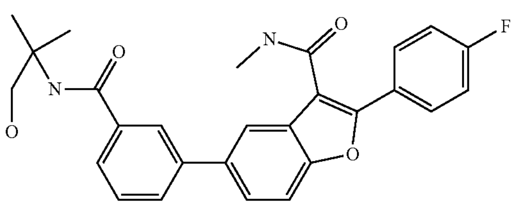 | 2.754 | 100 | 461.15 | Method E |
| 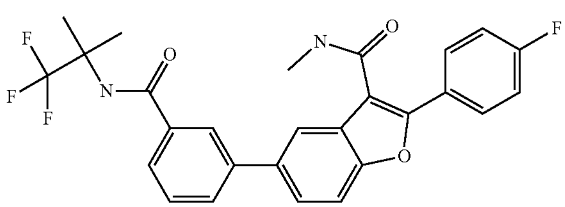 | 3.53 | 95.5615 | 499.12 | Method E |
| 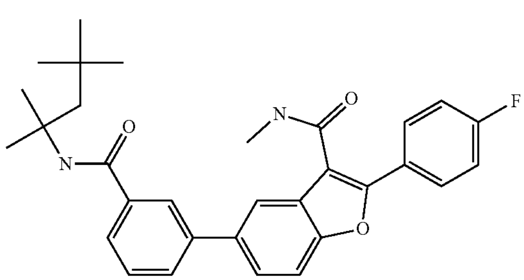 | 4.061 | 100 | 501.23 | Method E |

-continued

| Structure | HPLC Rt | % Purity | Obs. MS Ion | HPLC Method |
|---|---|---|---|---|
| 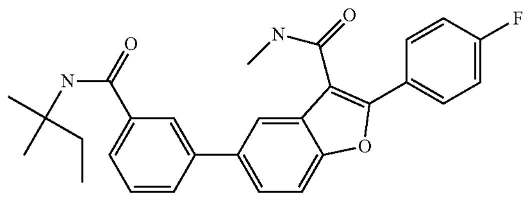 | 3.539 | 98.8021 | 459.19 | Method E |
| 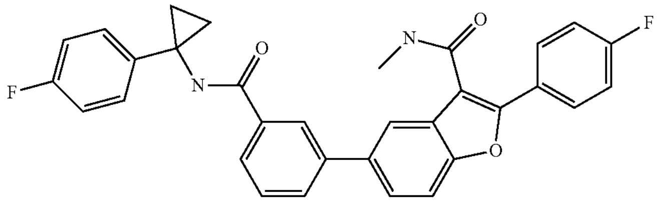 | 3.496 | 100 | 523.18 | Method E |
| 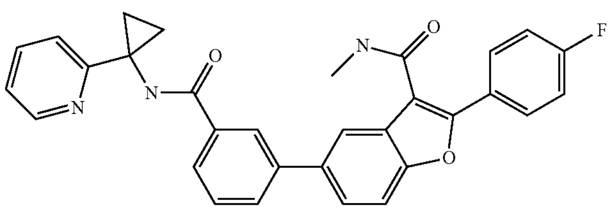 | 3.008 | 100 | 506.17 | Method E |
| 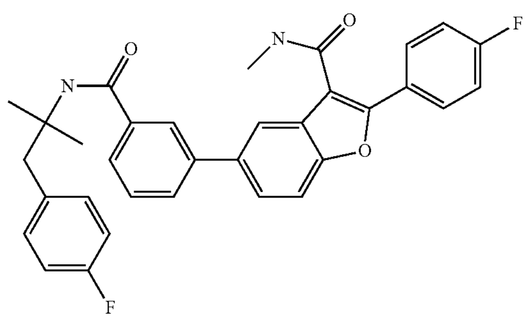 | 3.896 | 98.8111 | 539.22 | Method E |
| 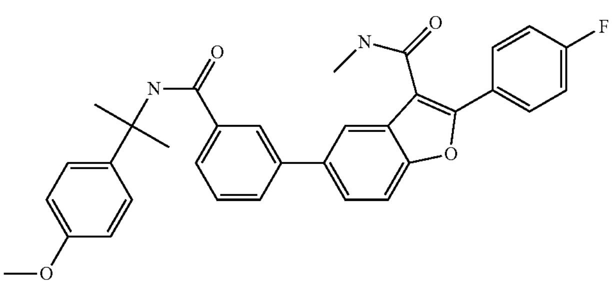 | 3.608 | 100 | 537.21 | Method E |
| 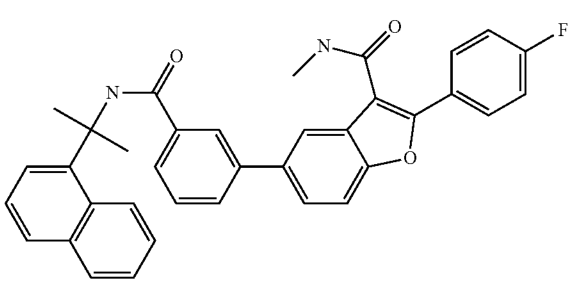 | 3.868 | 98.488 | 557.22 | Method E |

-continued

| Structure | HPLC Rt | % Purity | Obs. MS Ion | HPLC Method |
|---|---|---|---|---|
| 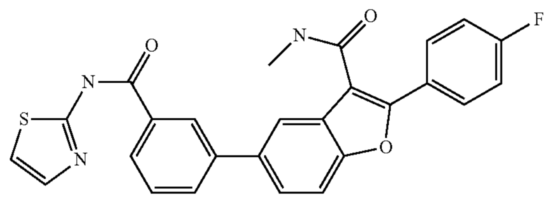 | 3.179 | 100 | 472.1 | Method E |
| 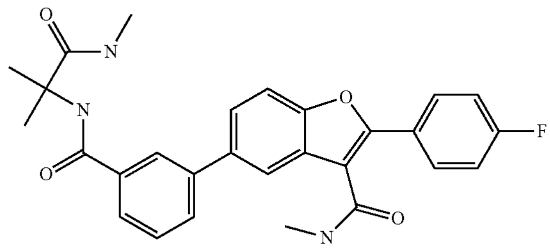 | 2.536 | 100 | 488.16 | Method E |
| 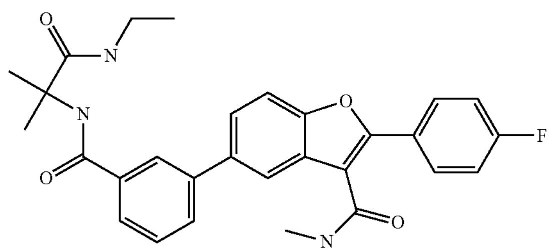 | 2.718 | 100 | 502.19 | Method E |
| 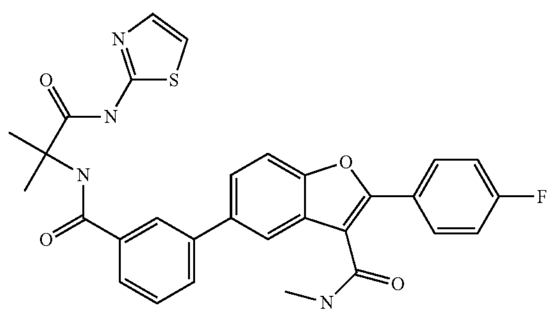 | 3.025 | 100 | 557.15 | Method E |
| 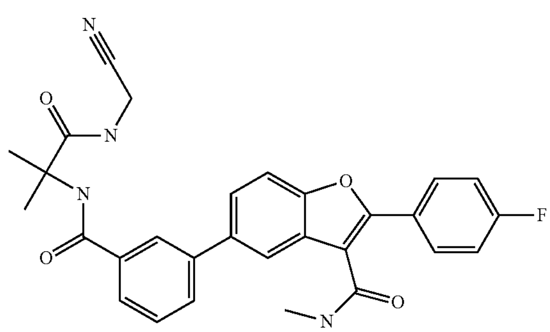 | 2.664 | 100 | 513.16 | Method E |

-continued

| Structure | HPLC Rt | % Purity | Obs. MS Ion | HPLC Method |
|---|---|---|---|---|
| 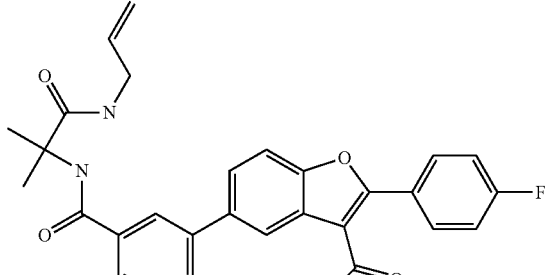 | 2.835 | 100 | 514.17 | Method E |
| 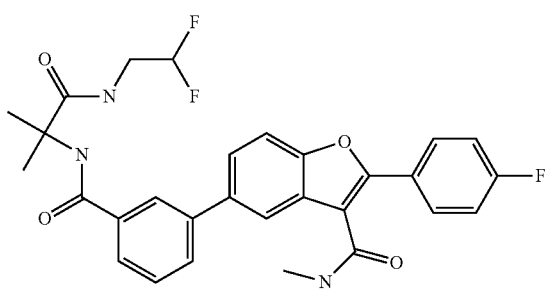 | 2.87 | 100 | 538.16 | Method E |
| 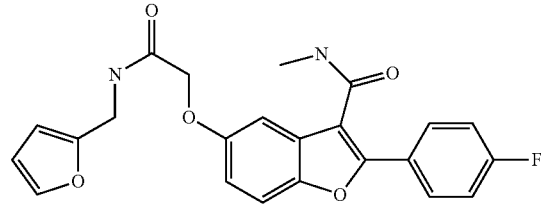 | 8.435 | 100 | 423.19 | Method F |
| 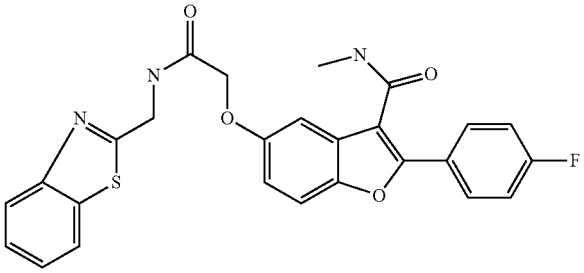 | 8.778 | 100 | 490.13 | Method F |

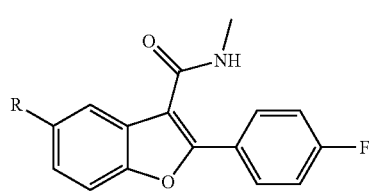

The general procedures below pertain to the experimental procedures. Some of the compounds were made with different scales. 2-(4-fluorophenyl)-3-(methylcarbamoyl)benzofuran-5-yl trifluoromethanesulfonate (0.100 mmol, 1 eq.) was dissolved in dried 1,4-Dioxane (1 mL) and added into Biotage microwave vial (0.5-2 mL) containing boronic acid (0.340 mmol, 3.4 eq.). Then Cs$_2$CO$_3$ (0.300 mmol, 3 eq.) was added as a solid and following by adding water (0.25 mL). The vial was flushed with nitrogen and Pd(PPh$_3$)$_4$ was added. After the vial was re-flushed with nitrogen and caped, it was heated in a Biotage microwave reactor at 150° C. for 15 minutes. The mixture was filtered with a 0.45 um filter and dried with a SppedVac. The sample was dissovled in DMF (1.6 mL) and purified by prep-HPLC.

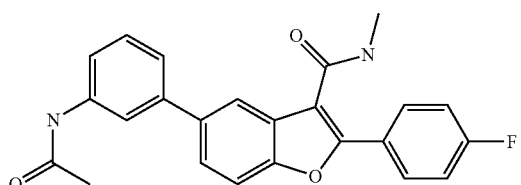

5-(3-acetamidophenyl)-2-(4-fluorophenyl)-N-methylbenzofuran-3-carboxamide. $^1$H NMR (600 MHz, DMSO-d$_6$-

CDCl₃) δ ppm 10.03 (br. s., 1H), 8.49 (d, J=4.69 Hz, 1H), 8.28 (s, 1H), 8.03 (dd, J=8.79, 5.27 Hz, 2H), 7.93 (br. s., 1H), 7.84 (s, 1H), 7.75 (d, J=8.20 Hz, 1H), 7.64 (d, J=6.44 Hz, 2H), 7.29-7.45 (m, 3H), 2.92 (s, 3H), 2.12 (s, 3H).

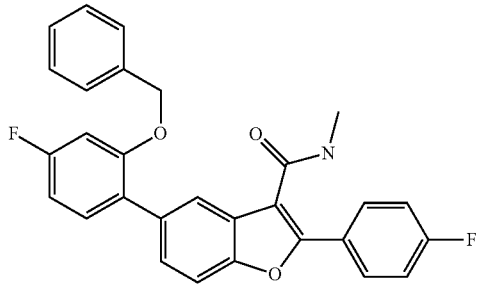

5-(2-(benzyloxy)-4-fluorophenyl)-2-(4-fluorophenyl)-N-methylbenzofuran-3-carboxamide. ¹H NMR (600 MHz, DMSO-d₆-CDCl₃) δ ppm 8.41 (d, J=4.69 Hz, 1H), 8.28 (s, 1H), 8.03 (dd, J=8.79, 5.27 Hz, 2H), 7.82 (s, 1H), 7.67 (d, J=8.20 Hz, 1H), 7.55 (d, J=7.03 Hz, 1H), 7.34-7.47 (m, 7H), 7.13 (d, J=9.37 Hz, 1H), 6.83-6.94 (m, 1H), 5.19 (s, 2H), 2.88 (d, J=4.10 Hz, 3H).

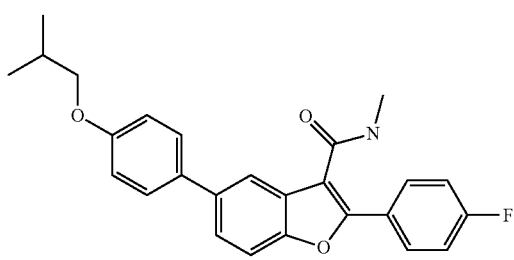

2-(4-fluorophenyl)-5-(4-isobutoxyphenyl)-N-methylbenzofuran-3-carboxamide. ¹H NMR (600 MHz, DMSO-d₆-CDCl₃) δ ppm 8.46 (d, J=4.69 Hz, 1H), 8.28 (s, 1H), 8.04 (dd, J=8.50, 5.57 Hz, 1H), 7.81 (s, 1H), 7.67-7.73 (m, 1H), 7.60-7.67 (m, 2H), 7.36 (t, J=8.79 Hz, 1H), 7.05 (d, J=8.79 Hz, 2H), 3.83 (d, J=6.44 Hz, 2H), 2.91 (d, J=4.69 Hz, 3H), 2.09 (ddd, J=13.33, 6.59, 6.44 Hz, 1H), 1.05 (d, J=7.03 Hz, 6H).

HPLC purity was determined using a Waters LCT Mass Spectrometer with four way MUX source analytical LC at 220 nm with employing acetonitrile and water or Waters ZQ with ESCi mass spectrometer. A=5:95 CH₃CN:Water; B=95:5 CH₃CN:Water; Modifier=10 mM NH₄OAc. Retention time was recorded in minutes.

| Analytical Method A: Column Waters Xterra 2.1 × 50 mm 5 um C18 | | |
|---|---|---|
| Time | B % | Flow |
| 0.00 | 0 | 1.0 |
| 4.00 | 100 | 1.0 |
| 5.00 | 100 | 1.0 |

| Analytical Method B: Column: Waters Xbridge 2.1 × 50 mm 5 um C18 | | |
|---|---|---|
| Time | B % | Flow |
| 0.00 | 0 | 1.0 |
| 4.00 | 100 | 1.0 |
| 5.00 | 100 | 1.0 |
| 5.05 | 100 | 1.0 |
| 6.00 | 0 | 1.0 |

| Analytical Method F Waters ZQ with ESCi mass spectrometer Column: Phenomenex Gemini 4.6x150 mm 3 um C18 | | |
|---|---|---|
| Time | B % | Flow |
| 0.00 | 10 | 1.0 |
| 10.00 | 95 | 1.0 |
| 13.00 | 95 | 1.0 |
| 13.50 | 10 | 1.0 |
| 15.00 | 10 | 1.0 |

| Structure | HPLC Rt | % Purity | Obs. MS Ion | HPLC Method |
|---|---|---|---|---|
| 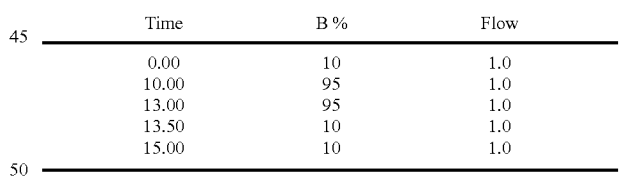 | 7.23 | 100 | 390.16 | Method F |

-continued

| Structure | HPLC Rt | % Purity | Obs. MS Ion | HPLC Method |
|---|---|---|---|---|
| 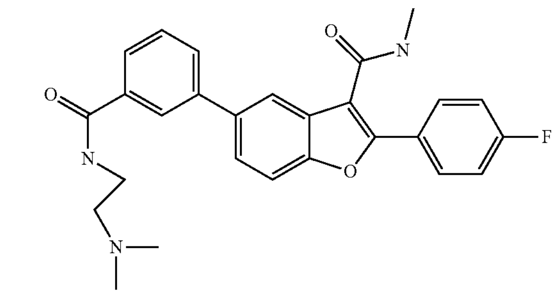 | 3.842 | 100 | 460.23 | Method F |
| 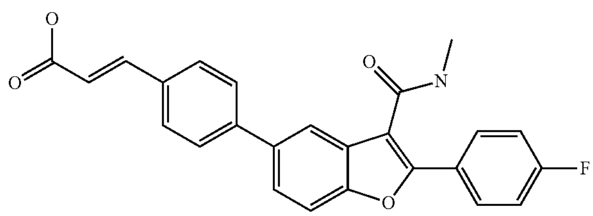 | 7.666 | 100 | 416.18 | Method F |
| 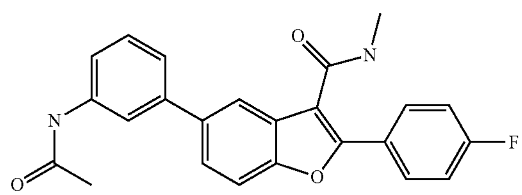 | 7.018 | 100 | 403.2 | Method F |
| 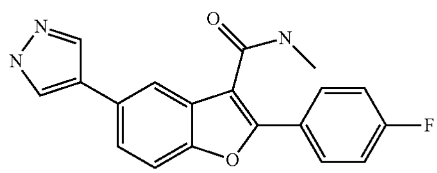 | 5.322 | 100 | 336.23 | Method F |
| 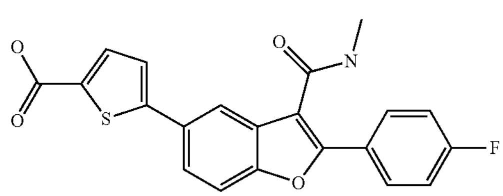 | 7.091 | 100 | 396.13 | Method F |
| 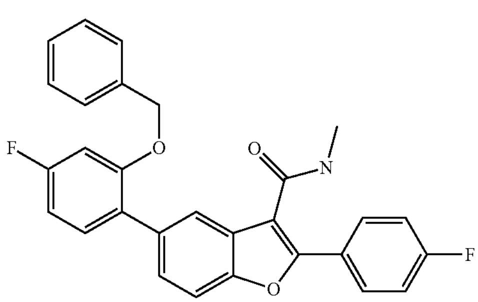 | 12.982 | 100 | 470.3 | Method F |

-continued

| Structure | HPLC Rt | % Purity | Obs. MS Ion | HPLC Method |
|---|---|---|---|---|
| 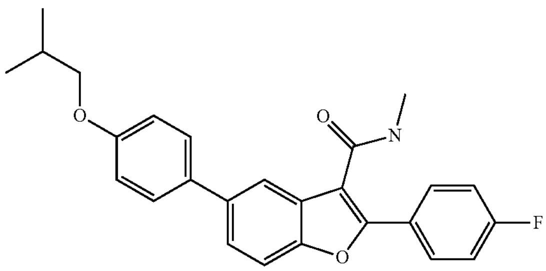 | 13.755 | 100 | 418.33 | Method F |
| 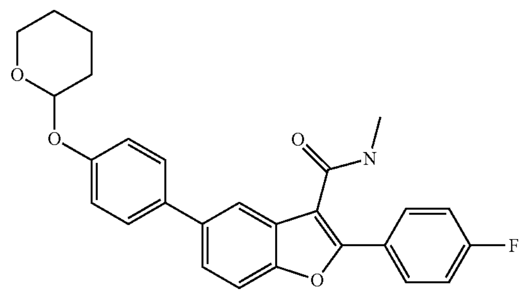 | 12.669 | 100 | 446.26 | Method F |
| 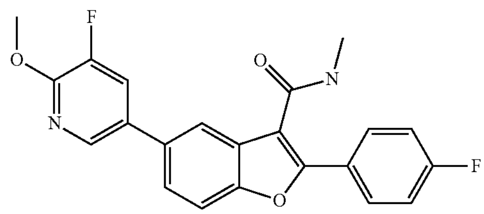 | 10.775 | 100 | 395.28 | Method F |
| 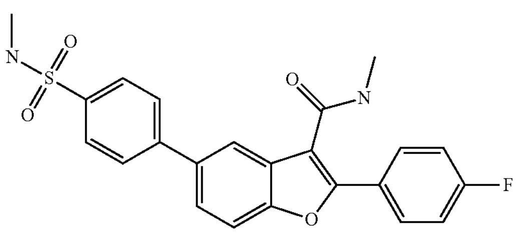 | 8.933 | 100 | 439.24 | Method F |
| 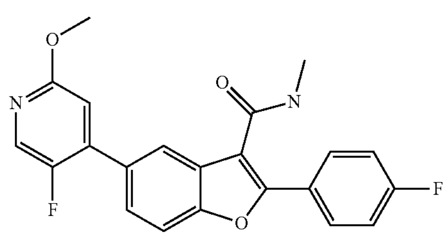 | 10.716 | 100 | 395.31 | Method F |
| 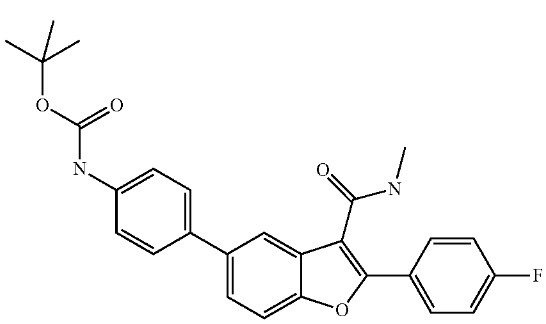 | 11.858 | 100 | 461.33 | Method F |

-continued
| Structure | HPLC Rt | % Purity | Obs. MS Ion | HPLC Method |
|---|---|---|---|---|
| 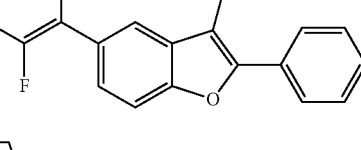 | 10.916 | 100 | 399.21 | Method F |
| 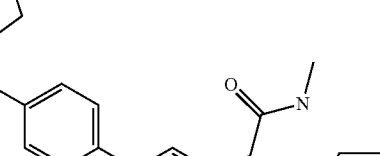 | 2.49 | 100 | 443.06 | Method B |
| 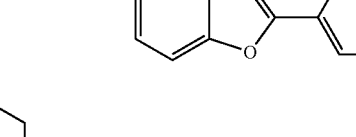 | 2.56 | 100 | 410 | Method B |
| 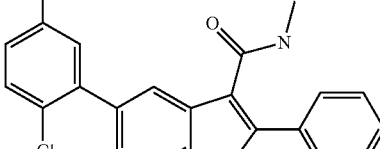 | 2.36 | 100 | 376.05 | Method B |
| 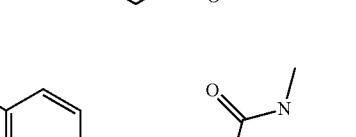 | 2.75 | 90.0925 | 457.45 | Method B |
| 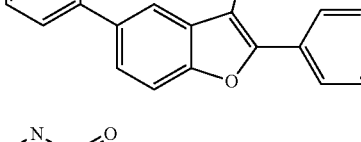 | 2.36 | 95.5596 | 447.39 | Method B |

-continued

| Structure | HPLC Rt | % Purity | Obs. MS Ion | HPLC Method |
|---|---|---|---|---|
| 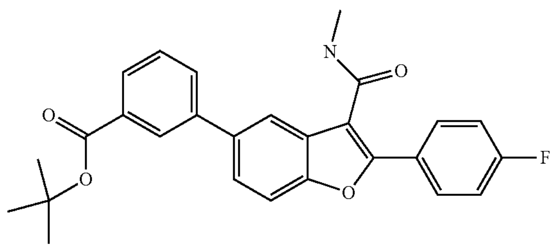 | 3.34 | 100 | 446.41 | Method B |
| 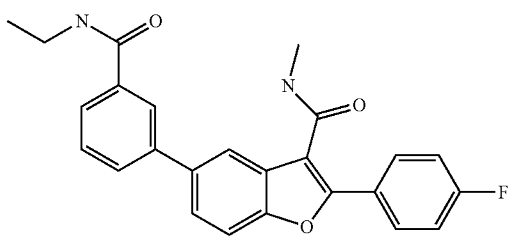 | 2.43 | 100 | 417.4 | Method B |
| 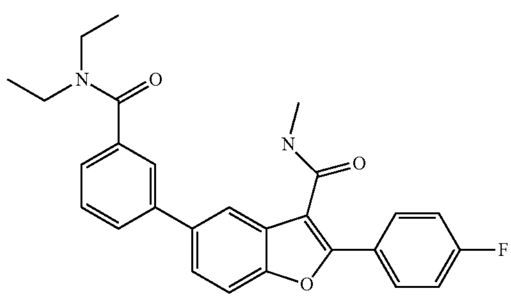 | 2.67 | 97.2446 | 445.4 | Method B |
| 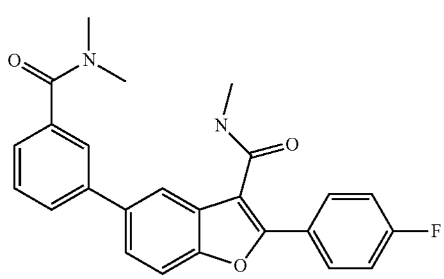 | 2.37 | 100 | 417.33 | Method B |
| 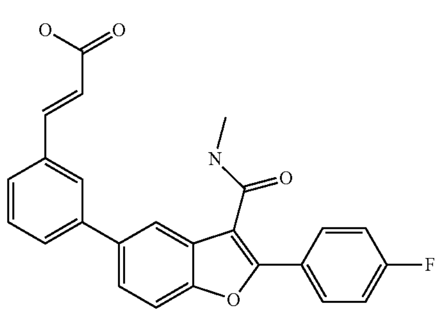 | 2.02 | 100 | 416.3 | Method B |

-continued

| Structure | HPLC Rt | % Purity | Obs. MS Ion | HPLC Method |
|---|---|---|---|---|
| 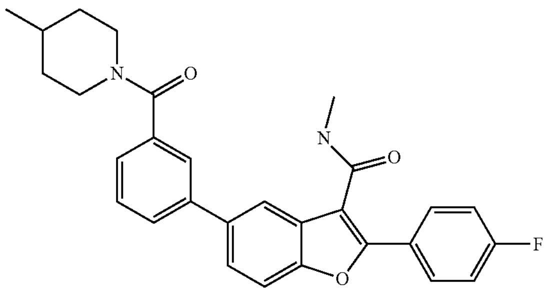 | 2.92 | 100 | 471.37 | Method B |
| 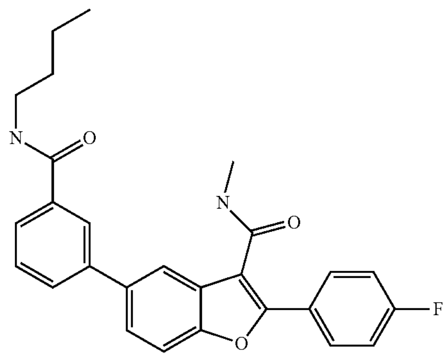 | 2.76 | 100 | 445.37 | Method B |
| 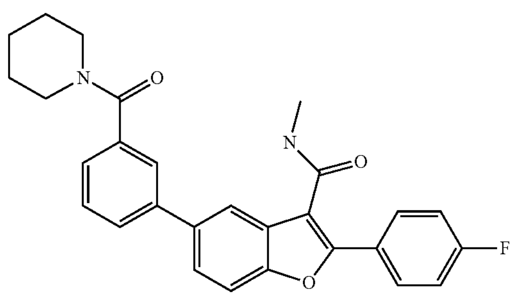 | 2.71 | 100 | 457.35 | Method B |
| 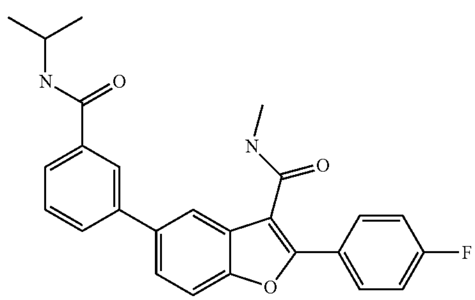 | 2.52 | 100 | 431.35 | Method B |
| 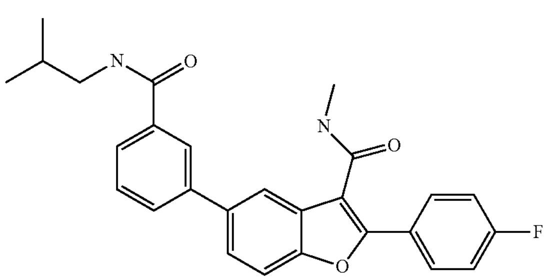 | 2.725 | 94.4043 | 445.36 | Method B |

-continued

| Structure | HPLC Rt | % Purity | Obs. MS Ion | HPLC Method |
|---|---|---|---|---|
| 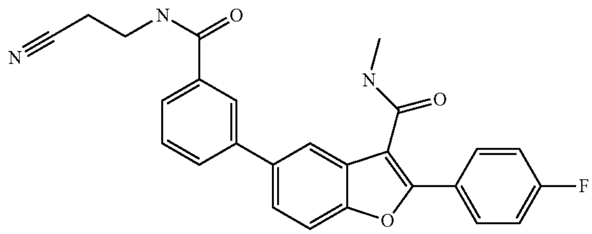 | 2.38 | 95.3608 | 442.32 | Method B |
| 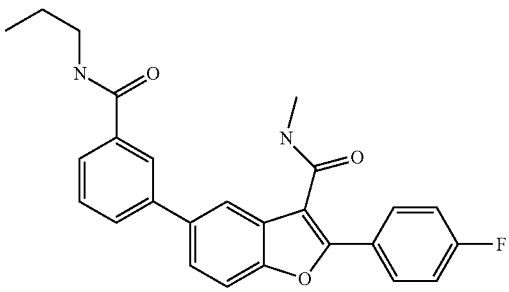 | 2.56 | 100 | 431.34 | Method B |
| 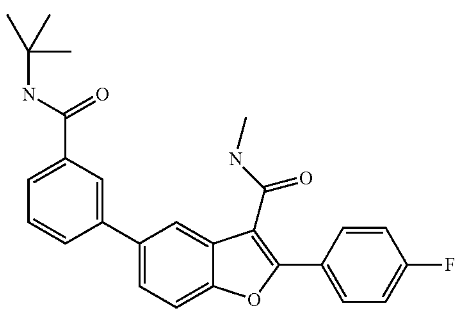 | 2.76 | 97.5284 | 445.38 | Method B |

The general procedures below pertain to the experimental procedures. 2-(4-fluorophenyl)-5-hydroxy-N-methylbenzofuran-3-carboxamide (0.120 mmol, 1 eq.) in THF (2.3 mL) was added into Biotage microwave vial (5 mL) containing ROH (2.28 eq.) and PPh$_3$ (1.4 eq.). Then DEAD (1.4 eq.) was added as neat. The vial was flushed with nitrogen, caped and heated at 140° C. for 20 minutes in a Biotage microwave reactor. The mixture was dried with SpeedVac, dissolved in DMF (1.6 mL) and purified by prep-HPLC.

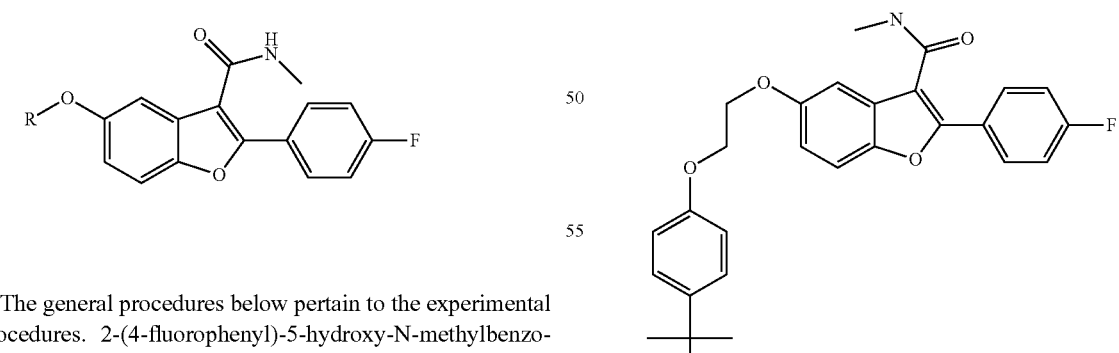

5-(2-(4-tert-butylphenoxy)ethoxy)-2-(4-fluorophenyl)-N-methylbenzofuran-3-carboxamide. $^1$H NMR (600 MHz, DMSO-d$_6$-CDCl$_3$) δ ppm 8.36 (d, J=4.69 Hz, 1H), 8.27 (s, 1H), 7.99 (dd, J=8.50, 5.57 Hz, 1H), 7.56 (d, J=8.79 Hz, 1H), 7.28-7.39 (m, 3H), 7.21 (d, J=2.34 Hz, 1H), 7.05 (dd, J=9.37, 2.34 Hz, 1H), 6.94 (d, J=8.79 Hz, 3H), 4.28-4.45 (m, 4H), 2.89 (d, J=4.69 Hz, 3H), 1.30 (s, 9H).

HPLC purity was determined using a Waters LCT Mass Spectrometer with four way MUX source analytical LC at 220 nm with employing acetonitrile and water. A=5:95 $CH_3CN$:Water; B=95:5 $CH_3CN$:Water; Modifier=10 mM $NH_4OAc$. Retention. Time was recorded in minutes.

| Analytical Method B: Column: Waters Xbridge 2.1x50 mm 5 um C18 | | |
|---|---|---|
| Time | B % | Flow |
| 0.00 | 0 | 1.0 |
| 4.00 | 100 | 1.0 |
| 5.00 | 100 | 1.0 |
| 5.05 | 100 | 1.0 |
| 6.00 | 0 | 1.0 | benzofuran-5-yl]-2-(isobutylcarbamoyl)phenyl trifluoromethanesulfonate (0.076 mmol, 45 mg), dicyclohexyl(2',6'-dimethoxybiphenyl-2-yl)phosphine (S-Phos) (6.24 mg, 0.02 mmol), boronic acid (0.175 mmol) and potassium phosphate (0.190 mmol, 40.2 mg) were added into Biotage microwave vial (5 mL), and followed by adding dioxane (3 mL) and water (0.3 mL). The vial was flushed with nitrogen and $Pd(OAc)_2$ (0.076 mmol, 1.7 mg) was added. The vial was heated in a Biotage Initiator at 110° C. for 10 minutes and dried with a SpeedVac-250 at 40° C. overnight. The samples were dissolved in DMF-MeOH, filtered via a plate with filters, and purified by prep-HPLC Prep-HPLC: Dionex APS-30000, UV 220 nm, Column: Waters Xbridge 19×200 mm, 5 um, C18. Solvents: A=Water, 20 mM $NH_4OH$, B=Acetonitrile)

| Structure | HPLC Rt | % Purity | Obs. MS Ion | HPLC Method |
|---|---|---|---|---|
| 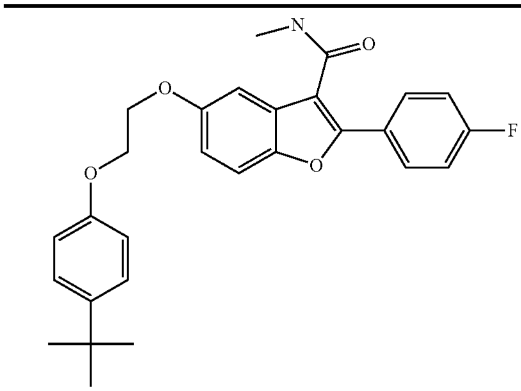 | 3.63 | 100 | 461.8073 | Method B |
| 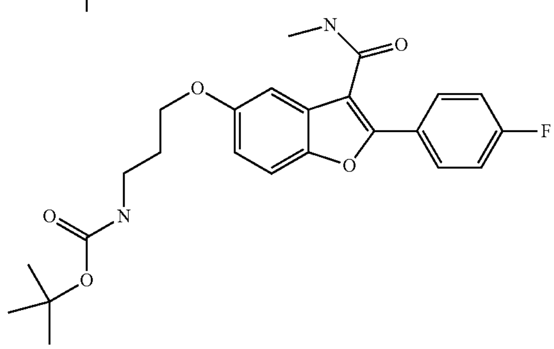 | 2.81 | 100 | 442.825 | Method B |

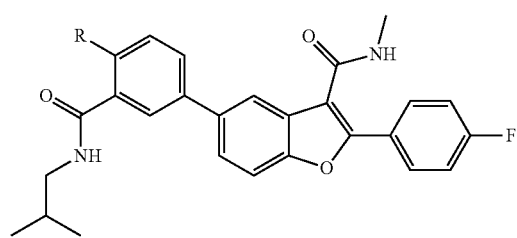

The general procedures below pertain to the experimental procedures. 4-[2-(4-fluorophenyl)-3-(methylcarbamoyl)

| Analytical Method A: Waters LCT mass spectrometer with 4 way MUX source. LC Conditions Column: Ascentis 4.6x50 mm 5 um C18 Mobile Phase A = 5:95 MeCN:Water; B = 95:5 MeCN:Water; Modifier = 10 mM $NH_4OAc$. Retention Time Rt was recorded in minutes. | | |
|---|---|---|
| Time | B % | Flow |
| 0.00' | 0 | 2.0 |
| 8.00' | 100 | 2.0 |
| 9.00' | 100 | 2.0 |

| Structure | HPLC Rt | % Purity | Obs. MS Ion | HPLC Method |
|---|---|---|---|---|
| 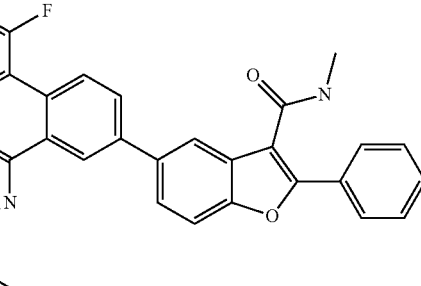 | 5.77 | 96 | 569.286 | Method A |
| 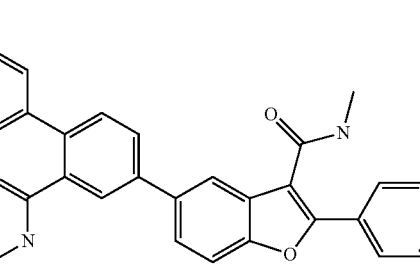 | 4.86 | 95 | 536.2426 | Method A |
| 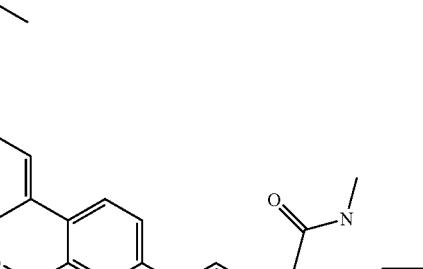 | 5.20 | 97 | 536.26428 | Method A |
| 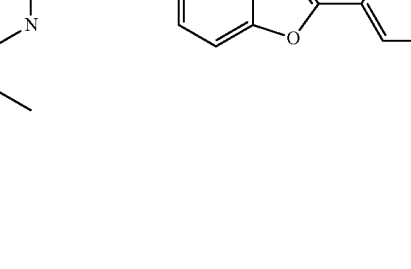 | 5.93 | 100 | 557.2553 | Method A |

The following examples/intermediates were prepared by the Suzuki coupling of the corresponding benzofuran-5-yl trifluoromethanesulfonate with 3-boronic acid (or ester) of the corresponding benzoic acid, and the acid intermediate obtained was coupled to cyclopropylamine as described before.

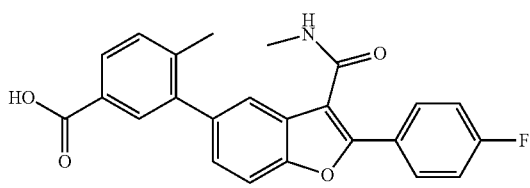

3-(2-(4-Fluorophenyl)-3-(methylcarbamoyl)benzofuran-5-yl)-4-methylbenzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$= 404.04, HPLC R$_t$=1.728 min.

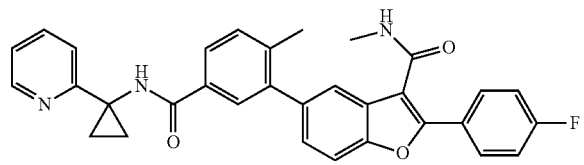

2-(4-Fluorophenyl)-N-methyl-5-(2-methyl-5-(1-(pyridin-2-yl)cyclopropylcarbamoyl)phenyl)benzofuran-3-carboxamide. The product was obtained as a TFA salt after purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=0, Final % B=100, Gradient time=10 min, Stop time=12 min, Flow Rate=25 mL/min, Column: Waters-Sunfire 19×100 mm S5, Fraction Collection: 8.80-9.26 min. (UV detection at 220 nm). The desired fractions collected were evaporated and the white solid obtained was purified again by the same method except with Start % B=50, Final % B=100, Fraction Collection: 5.34-6.15 min. $^1$H NMR (500 MHz, CD$_3$OD) δ 8.61 (d, J=5.80, 1H), 8.44 (t, J=7.32, 1H), 7.97 (dd, J=8.85, 5.19, 2H), 7.87 (s, 1H), 7.85 (d, J=6.71, 1H), 7.83-7.81 (m, 2H), 7.67 (d, J=8.24, 1H), 7.64 (d, J=0.92, 1H), 7.47 (d, J=8.55, 1H), 7.38 (dd, J=8.39, 1.68, 1H), 7.29 (t, J=8.85, 2H), 2.95 (s, 3H), 2.36 (s, 3H), 1.82 (m, 2H), 1.75 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=520.41, HPLC R$_t$=1.513 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min; Column: Sunfire C18, 3.5 um, 4.6×150 mm, R$_t$=8.90 min; Column: Xbridge Phenyl 3.5 um, 4.6×150 mm, R$_t$=9.43 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl, R$_t$=13.20 min.

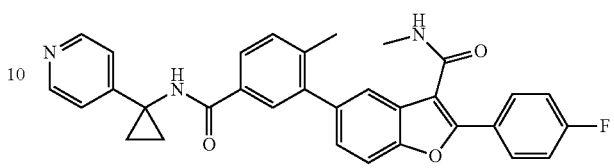

2-(4-Fluorophenyl)-N-methyl-5-(2-methyl-5-(1-(pyridin-4-yl)cyclopropylcarbamoyl)phenyl)benzofuran-3-carboxamide. The product was obtained as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 5.07-5.88 min. (UV detection at 220 nm). $^1$H NMR (500 MHz, CD$_3$OD) δ 8.68 (d, J=7.32, 1H), 7.97 (dd, J=8.85, 5.19, 2H), 7.87 (d, J=2.14, 1H), 7.86 (m overlapped with d, 1H), 7.81 (d, J=7.02, 1H), 7.67 (d, J=8.55, 1H), 7.65 (d, J=1.22, 1H), 7.48 (d, J=8.55, 1H), 7.39 (dd, J=8.39, 1.68, 1H), 7.28 (t, J=8.85, 2H), 2.95 (s, 3H), 2.37 (s, 3H), 1.83 (appeared as d, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 520.15, HPLC R$_t$=1.435 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=8.03 min; Column: Xbridge Phenyl 3.5 um, 4.6×150 mm (Start % B=10, Final % B=100), R$_t$=14.09 min.

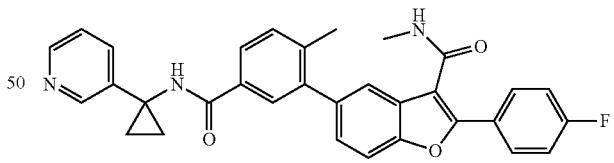

2-(4-Fluorophenyl)-N-methyl-5-(2-methyl-5-(1-(pyridin-3-yl)cyclopropylcarbamoyl)phenyl)benzofuran-3-carboxamide. The product was obtained as a TFA salt after purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 5.05-5.76 min. (UV detection at 220 nm). The desired fractions collected were evaporated and the residue obtained was purified again by the same method except with Start % B=10, Final % B=100, Fraction Collection: 8.74-9.27 min. $^1$H NMR (500

MHz, CD$_3$OD) δ 8.76 (d, J=2.44, 1H), 8.71 (dd, J=5.80, 0.92, 1H), 8.50 (ddd, J=8.32, 2.21, 1.37, 1H), 8.04 (dd, J=8.39, 5.65, 1H), 7.96 (dd, J=9.00, 5.34, 2H), 7.83 (d, J=1.53, 1H), 7.82 (m overlapped with d, 1H), 7.66 (d, J=8.24, 1H), 7.64 (d, J=1.83, 1H), 7.45 (d, J=8.55, 1H), 7.28 (t, J=8.70, 2H), 2.95 (s, 3H), 2.35 (s, 3H), 1.60 (appeared as td, J=4.20, 2.59, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=520.08, HPLC R$_t$=1.482 min.

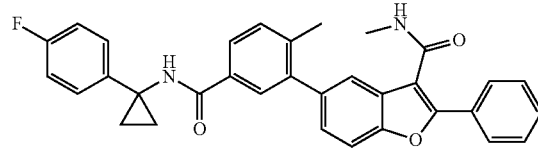

2-(4-Fluorophenyl)-5-(5-(1-(4-fluorophenyl)cyclopropylcarbamoyl)-2-methylphenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 9.08-9.63 min. (UV detection at 220 nm). $^1$H NMR (500 MHz, CD$_3$OD) δ 7.97 (dd, J=8.85, 5.19, 2H), 7.78-7.77 (overlapping m, 2H), 7.65 (d, J=8.55, 1H), 7.63 (d, J=1.22, 1H), 7.41 (d, J=8.55, 1H), 7.37-7.33 (overlapping m, 3H), 7.28 (t, J=8.85, 2H), 7.01 (t, J=8.85, 2H), 2.95 (s, 3H), 2.33 (s, 3H), 1.32 (m, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=537.08, HPLC R$_t$=1.840 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=10.20 min; Column: Xbridge Phenyl 3.5 um, 4.6×150 mm (Start % B=10, Final % B=100), R$_t$=8.16 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=14.20 min.

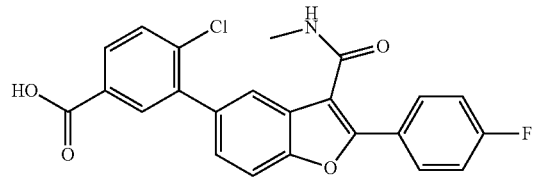

4-Chloro-3-(2-(4-fluorophenyl)-3-(methylcarbamoyl)benzofuran-5-yl)benzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$ = 424.26, 426.25, HPLC R$_t$=1.763 min.

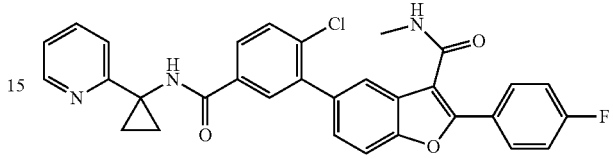

5-(2-Chloro-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.02-6.54 min. (UV detection at 220 nm). $^1$H NMR (500 MHz, CD$_3$OD) δ 8.62 (dd, J=5.80, 0.61, 1H), 8.44 (td, J=7.93, 1.53 1H), 8.04 (d, J=2.44, 1H), 7.96 (dd, J=8.85, 5.19, 2H), 7.93 (dd, J=8.39, 2.29 1H), 7.84-7.81 (overlapping m, 2H), 7.76 (d, J=1.83, 1H), 7.69 (d, J=2.44, 1H), 7.67 (d, J=2.75, 1H), 7.50 (dd, J=8.55, 1.53, 1H), 7.28 (t, J=8.70, 2H), 2.95 (s, 3H), 1.83 (m, 2H), 1.76 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=540.33, 542.33, HPLC R$_t$=1.568 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.19 min; Column: Xbridge Phenyl 3.5 um, 4.6×150 mm, R$_t$=9.89 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=10, Final % B=100, Gradient time=15 min, Stop time=18 min, Flow Rate=1 ml/min, Column: Xbridge Phenyl, R$_t$=16.19 min.

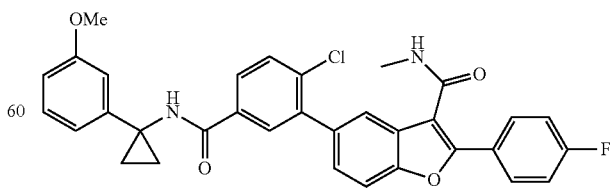

5-(2-Chloro-5-(1-(3-methoxyphenyl)cyclopropylcarbamoyl)phenyl)-2-(4-fluorophenyl)-N-methylbenzofuran-3-carboxamide. Purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=70, Final % B=100, Gradient time=10 min, Stop time=12 min, Flow Rate=25 mL/min, Column: Waters-Sunfire 19×100 mm S5, Fraction Collection: 6.61-7.41 min. (UV detection at 220 nm). $^1$H NMR (500 MHz, CD$_3$OD) δ 7.97 (dd, J=8.70, 5.34, 2H), 7.94 (d, J=2.14, 1H), 7.85 (dd, J=8.39, 1.98, 1H), 7.76 (s, 1H), 7.65 (dd, J=12.51, 8.55, 2H), 7.49 (dd, J=8.55, 1.53, 1H), 7.28 (t, J=8.70, 2H), 7.20 (t, J=7.93, 1H), 6.87 (s, 1H), 6.85 (m overlapped with s, 1H), 6.75 (dd, J=8.70, 1.68, 1H), 3.77 (s, 3H), 2.95 (s, 3H), 1.34 (appeared as d, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=569.39, HPLC R$_t$=1.858 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=10.33 min; Column: Xbridge Phenyl 3.5 um, 4.6×150 mm, R$_t$=7.96 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3, R$_t$=14.80 min.

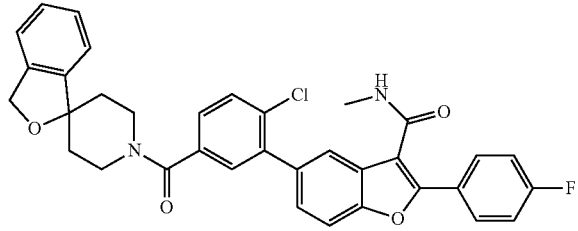

5-(2-Chloro-5-(3H-spiro[isobenzofuran-1,4'-piperidine]-1'-ylcarbonyl)phenyl)-2-(4-fluorophenyl)-N-methylbenzofuran-3-carboxamide. Purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=70, Final % B=100, Gradient time=10 min, Stop time=12 min, Flow Rate=25 mL/min, Column: Waters-Sunfire 19×100 mm S5, Fraction Collection: 7.88-8.49 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=595.39, HPLC R$_t$=1.952 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=11.75 min; Column: Xbridge Phenyl 3.5 um, 4.6×150 mm, R$_t$=8.68 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3, R$_t$=15.85 min.

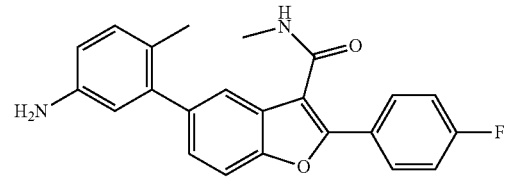

5-(5-Amino-2-methylphenyl)-2-(4-fluorophenyl)-N-methylbenzofuran-3-carboxamide. The Suzuki coupling with 4-methyl-3-(4,4,5,5-tetramethyl-1,3,2-dioxaborolan-2-yl) aniline was performed by using: dicyclohexyl(2',6'-dimethoxybiphenyl-2-yl)phosphine (S-Phos), Pd(OAc)$_2$, K$_2$CO$_3$, (1:2 H$_2$O/1,4-dioxane, 90° C.). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=375.22, HPLC R$_t$=1.362 min.

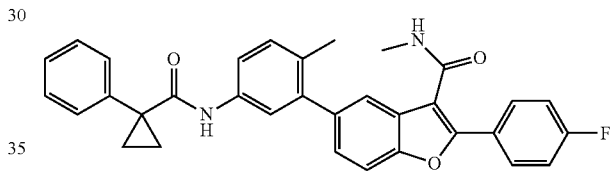

2-(4-Fluorophenyl)-N-methyl-5-(2-methyl-5-(1-phenylcyclopropanecarboxamido)phenyl)benzofuran-3-carboxamide. Purification by Shimadzu-VP preparative reverse phase HPLC first using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 10.05-10.51 min. (UV detection at 220 nm). $^1$H NMR (500 MHz, CD$_3$OD) δ 7.97 (dd, J=8.85, 5.49, 2H), 7.60 (d, J=8.55, 1H), 7.55 (d, J=1.53, 1H), 7.52 (dd overlapped with s, 1H), 7.51 (s, 1H), 7.44 (t, J=7.48, 2H), 7.36 (m, 1H), 7.30 (dd overlapped with m, J=1.53, 1H), 7.29-7.27 (overlapping m, 3H), 7.25 (d, J=2.14, 1H), 7.21 (appeared as d, 1H), 2.95 (s, 3H), 2.21 (s, 3H), 1.60 (m, 2H), 1.19 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+Na)$^+$=541.36, HPLC R$_t$=1.952 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=12.49 min; Column: Xbridge Phenyl 3.5 um, 4.6×150 mm, R$_t$=9.11 min. Analytical HPLC method: Solvent A=5%

MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3, R$_t$=15.98 min.

4-Chloro-5-(2-(4-fluorophenyl)-3-(methylcarbamoyl) benzofuran-5-yl)-2-methoxybenzoic acid. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=453.93, HPLC R$_t$=1.757 min.

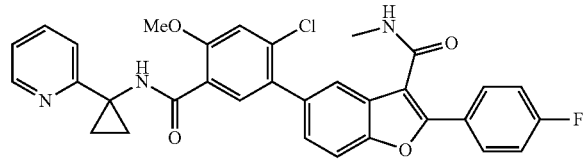

5-(2-Chloro-4-methoxy-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.00-6.58 min. (UV detection at 220 nm-). ¹H NMR (500 MHz, CD₃OD) δ 8.61 (d, J=5.80, 1H), 8.42 (td, J=8.01, 1.68, 1H), 7.99 (s, 1H), 7.96 (m, J=8.85, 5.19, 2H), 7.87 (d, J=8.24, 1H), 7.79 (ddd, J=7.40, 6.03, 0.92, 1H), 7.69 (d, J=1.83, 1H), 7.64 (d, J=8.55, 1H), 7.44 (dd, J=8.55, 1.83, 1H), 7.40 (s, 1H), 7.27 (t, J=8.85, 2H), 4.10 (s, 3H), 2.95 (s, 3H), 1.84 (m, 2H), 1.75 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=569.90, 570.79, 571.82, HPLC R$_t$=1.592 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.56 min; Column: Xbridge Phenyl 3.5 um, 4.6×150 mm, R$_t$=9.97 min. Analytical HPLC method: Solvent A=5% MeOH-95% H₂O-10 mM NH₄HCO₃, Solvent B=95% MeOH-5% H₂O-10 mM NH₄HCO₃, Start % B=10, Final % B=100, Gradient time=15 min, Stop time=18 min, Flow Rate=1 ml/min, Column: Xbridge Phenyl 3.5 um, 4.6×150 mm, R$_t$=16.35 min.

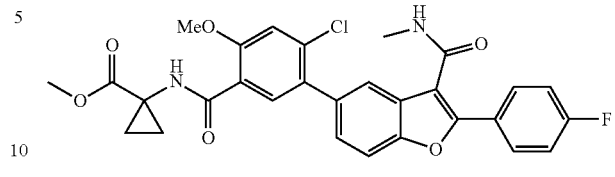

Methyl 1-(4-chloro-5-(2-(4-fluorophenyl)-3-(methylcarbamoyl)benzofuran-5-yl)-2-methoxybenzamido)cyclopropanecarboxylate. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=551.02, HPLC R$_t$=1.753 min.

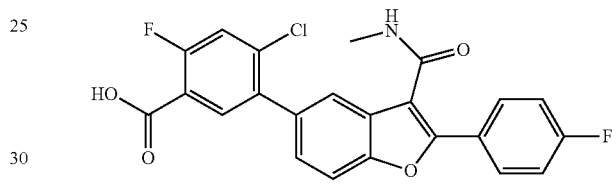

4-Chloro-2-fluoro-5-(2-(4-fluorophenyl)-3-(methylcarbamoyl)benzofuran-5-yl)benzoic acid. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=441.91, HPLC R$_t$=1.803 min.

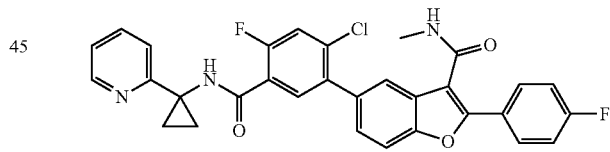

5-(2-Chloro-4-fluoro-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 5.63-6.40 min. (UV detection at 220 nm). ¹H NMR (500 MHz, CD₃OD) δ 8.60 (d, J=5.49, 1H), 8.34 (td, J=7.93, 1.83, 1H), 7.97 (m, J=8.85, 5.19, 2H), 7.90 (d, J=7.63, 1H), 7.83 (d, J=8.24, 1H), 7.73 (overlapping, 2H), 7.68 (d, J=8.54, 1H), 7.56 (d, J=10.38, 1H), 7.47 (dd, J=8.55, 1.83, 1H), 7.29 (t, J=8.70, 2H), 2.95 (s, 3H), 1.82 (m, 2H), 1.70 (m, 2H). LC/MS were performed by using Shimadzu-VP instrument with UV detection at 220 nm and Waters Micromass. HPLC method:

Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=558.04, HPLC Rt=1.558 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=3.10 min; Column: Xbridge Phenyl 3.5 um, 4.6×150 mm, $R_t$=3.60 min. Analytical HPLC method: Solvent A=5% MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3.5 um, 4.6×150 mm, $R_t$=13.24 min.

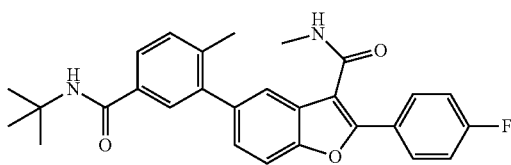

5-(5-(tert-Butylcarbamoyl)-2-methylphenyl)-2-(4-fluorophenyl)-N-methylbenzofuran-3-carboxamide. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.62-9.21 min. (UV detection at 220 nm). ¹H NMR (500 MHz, CD₃OD) δ 7.98 (m, J=8.85, 5.49, 2H), 7.67 (d overlapping with s, 1H), 7.67 (s, 1H), 7.65 (d, J=8.55, 1H), 7.63 (d, J=1.22, 1H), 7.38 (d overlapping with dd, 1H), 7.37 (dd, J=1.53, 1H), 7.28 (t, J=8.70, 2H), 2.96 (s, 3H), 2.32 (s, 3H), 1.47 (s, 9H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=459.31, HPLC $R_t$=1.763 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=17.08 min; Xbridge Phenyl 3.5 um, 4.6×150 mm, $R_t$=14.81 min.

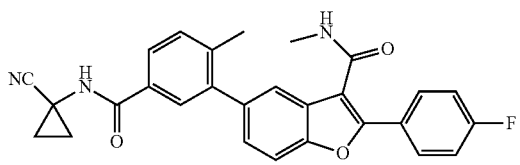

5-(5-(1-Cyanocyclopropylcarbamoyl)-2-methylphenyl)-2-(4-fluorophenyl)-N-methylbenzofuran-3-carboxamide. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.13-7.85 min. (UV detection at 220 nm). ¹H NMR (500 MHz, CD₃OD) δ 7.98 (m, J=8.70, 5.34, 2H), 7.77 (d overlapping with s, 1H), 7.76 (s, 1H), 7.66 (d, J=8.24, 1H), 7.63 (d, J=1.53, 1H), 7.44 (d, J=8.24, 1H), 7.37 (dd, J=8.39, 1.68, 1H), 7.28 (t, J=8.85, 2H), 2.95 (s, 3H), 2.34 (s, 3H), 1.59 (m, 2H), 1.36 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=468.28, HPLC $R_t$=1.633 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=14.21 min; Xbridge Phenyl 3.5 um, 4.6×150 mm, $R_t$=12.79 min.

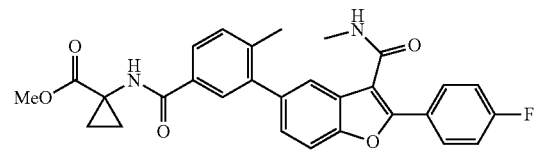

Methyl 1-(3-(2-(4-fluorophenyl)-3-(methylcarbamoyl)benzofuran-5-yl)-4-methylbenzamido)cyclopropanecarboxylate. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.26-7.97 min. (UV detection at 220 nm). ¹H NMR (500 MHz, CD₃OD) δ 7.98 (m, J=8.85, 5.19, 2H), 7.77 (dd, J=4.27, 2.14, 2H), 7.66 (d, J=8.55, 1H), 7.63 (d, J=1.22, 1H), 7.42 (d, J=8.55, 1H), 7.37 (dd, J=8.39, 1.68, 1H), 7.28 (t, J=8.85, 2H), 3.71 (s, 3H), 2.96 (s, 3H), 2.34 (s, 3H), 1.59 (m, 2H), 1.26 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=501.23, HPLC $R_t$=1.657 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=6.81 min; Xbridge Phenyl 3.5 um, 4.6×150 mm, $R_t$=5.58 min. Analytical HPLC method: Solvent A=5% MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3, R$_f$=12.48 min.

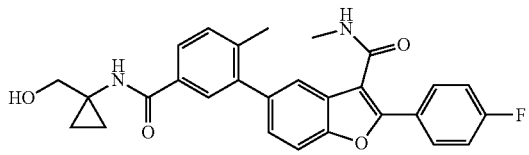

2-(4-Fluorophenyl)-5-(5-(1-(hydroxymethyl)cyclopropylcarbamoyl)-2-methylphenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.78-9.06 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=473.33, HPLC R$_f$=1.827 min.

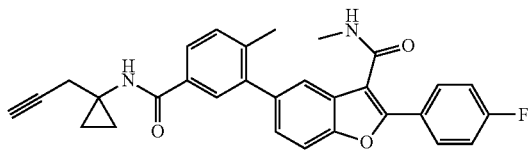

2-(4-Fluorophenyl)-N-methyl-5-(2-methyl-5-(1-(prop-2-ynylcarbamoyl)cyclopropylcarbamoyl)phenyl)benzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.43-7.91 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=524.21, HPLC R$_f$=1.642 min.

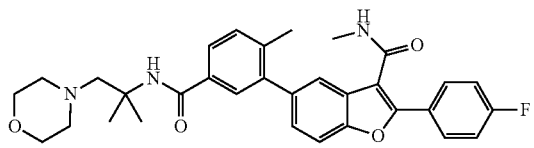

2-(4-Fluorophenyl)-N-methyl-5-(2-methyl-5-(2-methyl-1-morpholinopropan-2-ylcarbamoyl)phenyl)benzofuran-3-carboxamide. The product was obtained as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=20, Final % B=100, Gradient time=10 min, Stop time=12 min, Flow Rate=25 mL/min, Column: Waters-Sunfire 19×100 mm S5, Fraction Collection: 7.64-8.27 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=544.38, HPLC R$_f$=1.503 min.

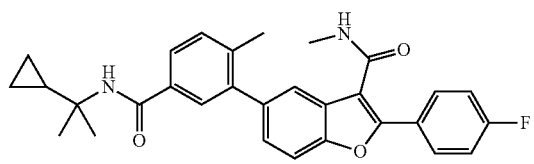

5-(5-(2-Cyclopropylpropan-2-ylcarbamoyl)-2-methylphenyl)-2-(4-fluorophenyl)-N-methylbenzofuran-3-carboxamide. The product was obtained as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 9.21-9.86 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=485.34, HPLC R$_f$=1.842 min.

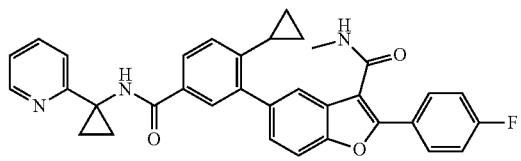

5-(2-Cyclopropyl-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.26-6.59 min. (UV detection at 220 nm). $^1$H NMR (500 MHz, CD$_3$OD) δ 8.54 (d, J=5.19, 1H), 8.17 (m, 1H), 7.98 (m, J=8.85, 5.19, 2H), 7.87-7.86 (overlapped m, 2H), 7.77 (d, J=1.53, 1H), 7.69 (d overlapped with d, 1H), 7.68 (d, J=8.24, 1H), 7.58 (m, 1H), 7.50 (dd, J=8.55, 1.83, 1H), 7.29 (t, J=8.85, 2H), 7.11 (d, J=8.55, 1H), 2.96 (s, 3H), 1.98 (m, 1H), 1.77 (m, 2H), 1.61 (m, 2H), 0.96 (m, 2H), 0.82 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=546.04, HPLC R$_t$=1.603 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.71 min; Column: Xbridge Phenyl 3.5 um, 4.6×150 mm, R$_t$=10.26 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=13.95 min.

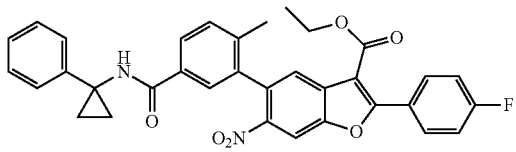

Ethyl 2-(4-fluorophenyl)-5-(2-methyl-5-(1-phenylcyclopropylcarbamoyl)phenyl)-6-nitrobenzofuran-3-carboxylate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=579.41, HPLC R$_t$=2.032 min.

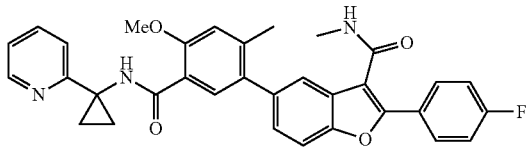

2-(4-Fluorophenyl)-5-(4-methoxy-2-methyl-5-(1-(pyridin-2-yl)cyclopropylcarbamoyl)phenyl)-N-methylbenzofuran-3-carboxamide. A mixture of 5-(2-chloro-4-methoxy-5-(1-(pyridin-2-yl)cyclopropylcarbamoyl)phenyl)-2-(4-fluorophenyl)-N-methylbenzofuran-3-carboxamide (62.7 mg, 0.11 mmol, crude), dicyclohexyl(2',4',6'-triisopropylbiphenyl-2-yl)phosphine (52.4 mg, 0.11 mmol), MeBF$_3$K (20.12 mg, 0.165 mmol), diacetoxypalladium (12.35 mg, 0.055 mmol) and potassium carbonate (76 mg, 0.550 mmol) in a mixture of H$_2$O (0.2 mL)/THF (2 mL) was stirred at 90° C. under N$_2$ for 6 hours 30 min. The mixture was left standing at r.t. overnight, and then diluted with MeOH and filtered through a Whatman 0.45 um PVDF with GMF disk. The filtrate was purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=70, Final % B=90, Gradient time=10 min, Stop time=12 min, Flow Rate=25 mL/min, Column: Waters-Sunfire 19×100 mm S5, Fraction Collection: 2.26-2.77 min. (UV detection at 220 nm) to obtain the product as a TFA salt. $^1$H NMR (500 MHz, CD$_3$OD) δ 8.60 (d, J=5.80, 1H), 8.41 (m, 1H), 7.96 (m, J=9.00, 5.34, 2H), 7.87 (s, 1H), 7.85 (d, J=9.00, 1H), 7.79 (t, J=6.56, 1H), 7.64 (d, J=8.24, 1H), 7.58 (d, J=1.53, 1H), 7.33 (dd, J=8.55, 1.83, 1H), 7.17 (s, 1H), 7.28 (t, J=8.85, 2H), 4.09 (s, 3H), 2.95 (s, 3H), 2.38 (s, 3H), 1.84 (m, 2H), 1.75 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=550.00, HPLC R$_t$=1.588 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.12 min; Column: Xbridge Phenyl 3.5 um, 4.6×150 mm, R$_t$=9.82 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=13.46 min.

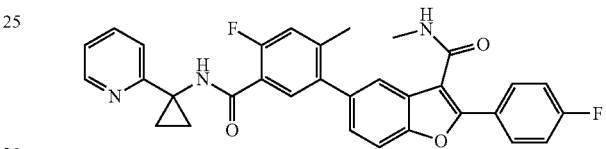

5-(4-Fluoro-2-methyl-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC twice using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 5.58-5.94 min. (UV detection at 220 nm). $^1$H NMR (500 MHz, CD$_3$OD) δ 8.57 (d, J=5.49, 1H), 8.26 (td, J=7.93, 1.53, 1H), 7.97 (m, J=9.16, 5.19, 2H), 7.79 (d, J=8.24, 1H), 7.73 (d, J=7.63, 1H), 7.67 (d, J=8.55, 1H), 7.65 (m overlapping with d, 1H), 7.62 (d, J=1.83, 1H), 7.35 (dd, J=8.39, 1.68, 1H), 7.29 (t, J=8.85, 2H), 7.25 (d, J=11.90, 1H), 2.95 (s, 3H), 2.35 (s, 3H), 1.80 (m, 2H), 1.66 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=538.04, HPLC R$_t$=1.497 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.46 min; Column: Xbridge Phenyl 3.5 um, 4.6×150 mm, R$_t$=9.66 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=12.95 min.

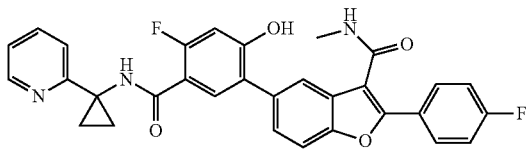

5-(4-Fluoro-2-hydroxy-5-(1-(pyridin-2-yl)cyclopropylcarbamoyl)phenyl)-2-(4-fluorophenyl)-N-methylbenzofuran-3-carboxamide. 5-(4-Fluoro-2-hydroxy-5-(1-(pyridin-2-yl)cyclopropylcarbamoyl)phenyl)-2-(4-fluorophenyl)-N-methylbenzofuran-3-carboxamide was obtained as a side product during the synthesis of 5-(4-fluoro-2-methyl-5-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC twice using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 4.16-4.55 min. (UV detection at 220 nm). $^1$H NMR (500 MHz, CD$_3$OD) δ 8.55 (broad d, J=3.66, 1H), 8.19 (t, J=7.78, 1H), 7.97 (m, J=8.85, 5.19, 2H), 7.86 (d, J=8.54, 1H), 7.82 (s, 1H), 7.74 (d, J=8.24, 1H), 7.61 (t overlapping with dd, 1H), 7.58 (dd, 2H), 7.28 (t, J=8.70, 2H), 6.79 (d, J=12.51, 1H), 2.97 (s, 3H), 1.78 (appeared as s, 2H), 1.63 (appeared as s, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$ = 540.07, HPLC R$_t$=1.342 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=8.06 min; Column: Xbridge Phenyl 3.5 um, 4.6×150 mm, R$_t$=8.56 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=10, Final % B=100, Gradient time=15 min, Stop time=18 min, Flow Rate=1 ml/min, Column: Xbridge Phenyl 3.5 um, 4.6×150 mm, R$_t$=13.91 min.

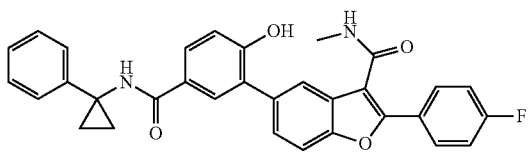

2-(4-Fluorophenyl)-5-(2-hydroxy-5-(1-phenylcyclopropylcarbamoyl)phenyl)-N-methylbenzofuran-3-carboxamide. 2-(4-Fluorophenyl)-5-(2-hydroxy-5-(1-phenylcyclopropylcarbamoyl)phenyl)-N-methylbenzofuran-3-carboxamide was obtained as a side product from a similar reaction. Purification by Shimadzu-VP preparative reverse phase HPLC twice using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.79-8.24 min. (UV detection at 220 nm). $^1$H NMR (500 MHz, CD$_3$OD) δ 7.98 (m, J=9.00, 5.34, 2H), 7.91 (d, J=2.14, 1H), 7.88 (d, J=1.53, 1H), 7.76 (dd, J=8.55, 2.14, 1H), 7.65-7.61 (overlapping m, 2H), 7.29-7.27 (overlapping m, 6H), 7.16 (m, 1H), 7.00 (d, J=8.55, 1H), 2.97 (s, 3H), 1.35 (m, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=521.28, HPLC R$_t$=1.695 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.84 min; Column: Xbridge Phenyl 3.5 um, 4.6×150 mm, R$_t$=5.71 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl, R$_t$=12.68 min.

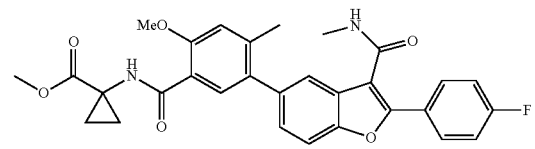

Methyl 1-(5-(2-(4-fluorophenyl)-3-(methylcarbamoyl)benzofuran-5-yl)-2-methoxy-4-methylbenzamido)cyclopropanecarboxylate. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.07-8.45 min. (UV detection at 220 nm). $^1$H NMR (500 MHz, CD$_3$OD) δ 7.98 (m, 2H), 7.85 (s, 1H), 7.63 (d, J=8.55, 1H), 7.58 (d, J=1.22, 1H), 7.33 (dd, J=8.55, 1.83, 1H), 7.27 (t, J=8.85, 2H), 7.11 (s, 1H), 4.03 (s, 3H), 3.71 (s, 3H), 2.96 (s, 3H), 2.35 (s, 3H), 1.61 (m, 2H), 1.28 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=531.23, HPLC R$_t$=1.715 min.

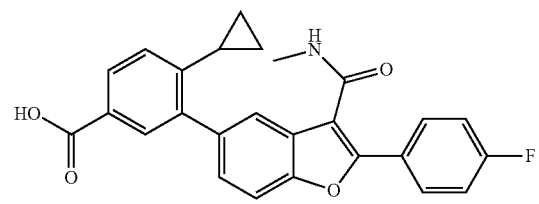

4-Cyclopropyl-3-(2-(4-fluorophenyl)-3-(methylcarbamoyl)benzofuran-5-yl)benzoic acid. 4-Cyclopropyl-3-(2-(4- fluorophenyl)-3-(methylcarbamoyl)benzofuran-5-yl)benzoic acid was prepared in a similar manner as described by using potassium cyclopropyltrifluoroborate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=430.07, HPLC R$_t$=1.802 min.

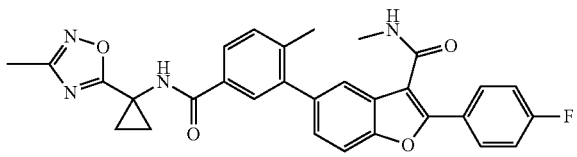

2-(4-Fluorophenyl)-N-methyl-5-(2-methyl-5-(1-(3-methyl-1,2,4-oxadiazol-5-yl)cyclopropylcarbamoyl)phenyl)benzofuran-3-carboxamide. A mixture of methyl 1-(3-(2-(4-fluorophenyl)-3-(methylcarbamoyl)benzofuran-5-yl)-4-methylbenzamido)cyclopropanecarboxylate (25.3 mg, 0.051 mmol), N'-hydroxyacetimidamide (11.23 mg, 0.152 mmol) and K$_2$CO$_3$ (41.9 mg, 0.303 mmol) in toluene (1 mL) under N$_2$ in a re-usable sealed tube was stirred at 150° C. for two hours. The mixture was evaporated, diluted with MeOH and purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.54-8.08 min. (UV detection at 220 nm), to give the product as a white solid (19.9 mg, 75%). $^1$H NMR (500 MHz, CD$_3$OD) δ 7.98 (m, J=9.00, 5.34, 2H), 7.82 (d, J=2.14, 1H), 7.81 (overlapping m, 1H), 7.66 (d, J=8.55, 1H), 7.65 (d, J=1.50, 1H), 7.44 (d, J=8.55, 1H), 7.38 (dd, J=8.24, 1.83, 1H), 7.28 (m, J=8.85, 2H), 2.95 (s, 3H), 2.36 (s, 3H), 2.31 (s, 3H), 1.75 (m, 2H), 1.58 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=525.12, HPLC R$_t$=1.700 min.

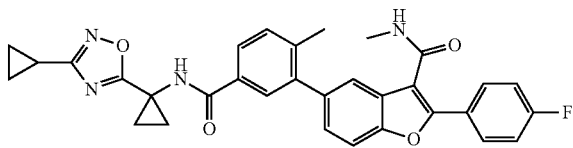

5-(5-(1-(3-Cyclopropyl-1,2,4-oxadiazol-5-yl)cyclopropylcarbamoyl)-2-methylphenyl)-2-(4-fluorophenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.32-8.92 min. (UV detection at 220 nm). $^1$H NMR (500 MHz, CD$_3$OD) δ 7.98 (m, J=8.85, 5.49, 2H), 7.81 (d, J=1.83, 1H), 7.80 (broad s overlapping with d, 1H), 7.66 (d overlapping with d, 1H), 7.64 (d, J=1.53, 1H), 7.44 (d, J=8.55, 1H), 7.38 (dd, J=8.39, 1.68, 1H), 7.28 (m, J=8.85, 2H), 2.95 (s, 3H), 2.35 (s, 3H), 2.02 (m, 1H), 1.72 (m, 2H), 1.54 (m, 2H), 1.04 (m, 2H), 0.95 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=551.09, HPLC R$_t$=1.763 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=8.73 min; Column: Xbridge Phenyl 3.5 um, 4.6×150 mm, R$_t$=6.96 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=13.22 min.

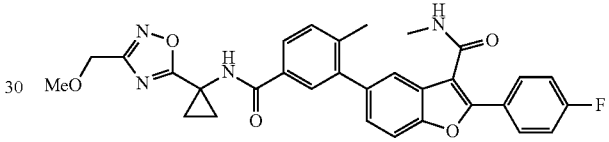

2-(4-Fluorophenyl)-5-(5-(1-(3-(methoxymethyl)-1,2,4-oxadiazol-5-yl)cyclopropylcarbamoyl)-2-methylphenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.92-8.52 min. (UV detection at 220 nm). $^1$H NMR (500 MHz, CD$_3$OD) δ 7.98 (m, J=9.00, 5.34, 2H), 7.82 (d, J=2.14, 1H), 7.81 (t overlapped with d, 1H), 7.66 (d overlapped with d, 1H), 7.65 (d, J=1.83, 1H), 7.45 (d, J=8.55, 1H), 7.38 (dd, J=8.55, 1.83, 1H), 7.28 (t, J=8.70, 2H), 4.51 (s, 2H), 3.42 (s, 3H), 2.95 (s, 3H), 2.36 (s, 3H), 1.79 (m, 2H), 1.60 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=555.23, HPLC Rt=1.700 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.11 min; Column: Xbridge Phenyl 3.5 um, 4.6×150 mm, R$_t$=5.57 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=12.51 min.

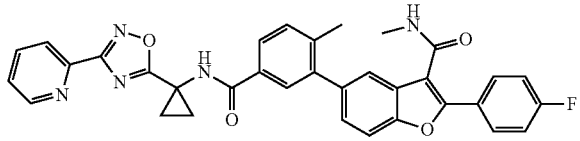

2-(4-fluorophenyl)-N-methyl-5-(2-methyl-5-(1-(3-(pyridin-2-yl)-1,2,4-oxadiazol-5-yl)cyclopropylcarbamoyl)phenyl)benzofuran-3-carboxamide. The product was obtained as a TFA salt after Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.83-8.56 min. (UV detection at 220 nm). $^1$H NMR (500 MHz, CD$_3$OD) δ 8.71 (d, J=4.88, 1H), 8.19 (d, J=7.93, 1H), 8.08 (td, J=7.78, 1.53, 1H), 7.97 (m, J=9.00, 5.34, 2H), 7.85 (s, 1H), 7.84 (m overlapping with s, 1H), 7.66-7.63 (overlapping m, 3H), 7.45 (d, J=8.55, 1H), 7.38 (dd, J=8.55, 1.83, 1H), 7.28 (m, J=8.85, 2H), 2.95 (s, 3H), 2.36 (s, 3H), 1.91 (m, 2H), 1.67 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=588.07, HPLC R$_t$=1.728 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.96 min; Column: Xbridge Phenyl 3.5 um, 4.6×150 mm, R$_t$=5.83 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=13.15 min.

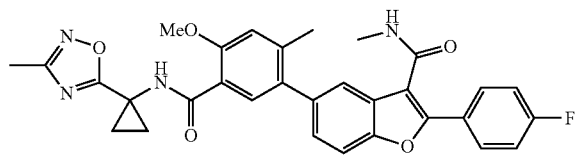

2-(4-Fluorophenyl)-5-(4-methoxy-2-methyl-5-(1-(3-methyl-1,2,4-oxadiazol-5-yl)cyclopropylcarbamoyl)phenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.80-8.36 min. (UV detection at 220 nm). $^1$H NMR (500 MHz, CD$_3$OD) δ 7.98 (m, J=9.00, 5.34, 2H), 7.86 (s, 1H), 7.63 (d, J=8.55, 1H), 7.59 (d, J=1.83, 1H), 7.33 (dd, J=8.24, 1.83, 1H), 7.27 (t, J=8.85, 2H), 7.13 (s, 1H), 4.06 (s, 3H), 2.96 (s, 3H), 2.36 (s, 3H), 2.31 (s, 3H), 1.77 (m, 2H), 1.60 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 555.10, HPLC Rt=1.723 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Xbridge Phenyl 3.5 um, 4.6×150 mm, R$_t$=5.98 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=12.98 min.

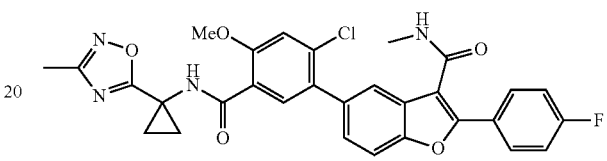

5-(2-Chloro-4-methoxy-5-(1-(3-methyl-1,2,4-oxadiazol-5-yl)cyclopropylcarbamoyl)phenyl)-2-(4-fluorophenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.06-8.56 min. (UV detection at 220 nm). $^1$H NMR (500 MHz, CD$_3$OD) δ 7.99-7.96 (m overlapping with s, 2H), 7.97 (s, 1H), 7.71 (d, J=1.53, 1H), 7.64 (d, J=8.55, 1H), 7.45 (dd, J=8.55, 1.83, 1H), 7.37 (s, 1H), 7.27 (t, J=8.85, 2H), 4.06 (s, 3H), 2.96 (s, 3H), 2.32 (s, 3H), 1.78 (m, 2H), 1.61 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 575.08, HPLC R$_t$=1.752 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=8.23 min; Column: Xbridge Phenyl 3.5 um, 4.6×150 mm, R$_t$=6.39 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=13.49 min.

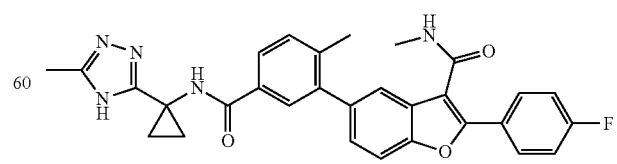

2-(4-Fluorophenyl)-N-methyl-5-(2-methyl-5-(1-(5-methyl-4H-1,2,4-triazol-3-yl)cyclopropylcarbamoyl)phenyl)benzofuran-3-carboxamide. A mixture of 5-(5-(1-cyanocyclopropylcarbamoyl)-2-methylphenyl)-2-(4-fluorophenyl)-N-methylbenzofuran-3-carboxamide (33.8 mg, 0.072 mmol), acetohydrazide (16.07 mg, 0.217 mmol) and K$_2$CO$_3$ (9.99 mg, 0.072 mmol) in n-BuOH (1 mL) under N$_2$ in a re-usable sealed tube was stirred at 150° C. for four hours. The mixture was diluted with MeOH and purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 5.93-6.53 min. (UV detection at 220 nm) to obtain the product as a TFA solvate. $^1$H NMR (500 MHz, CD$_3$OD) δ 7.97 (m, J=8.85, 5.49, 2H), 7.85 (s, 1H), 7.85 (m overlapped with s, J=1.83, 1H), 7.66 (d, J=8.55, 1H), 7.64 (d, J=1.22, 1H), 7.45 (d, J=7.63, 1H), 7.38 (dd, J=8.39, 1.68, 1H), 7.29 (t, J=8.70, 2H), 2.95 (s, 3H), 2.56 (s, 3H), 2.36 (s, 3H), 1.68 (m, 2H), 1.57 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$= 524.23, HPLC R$_t$=1.545 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=11.80 min; Column: Xbridge Phenyl 3.5 um, 4.6×150 mm, R$_t$=12.13 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3, R$_t$=11.87 min.

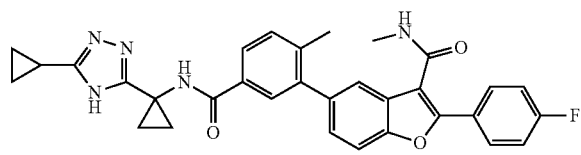

5-(5-(1-(5-Cyclopropyl-4H-1,2,4-triazol-3-yl)cyclopropylcarbamoyl)-2-methylphenyl)-2-(4-fluorophenyl)-N-methylbenzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.05-8.58 min. (UV detection at 220 nm) to obtain the product as a TFA solvate. $^1$H NMR (500 MHz, CD$_3$OD) δ 7.97 (m, J=8.85, 5.19, 2H), 7.85 (s, 1H), 7.84 (dd overlapping with s, J=1.83, 1H), 7.67 (d, J=8.24, 1H), 7.64 (d, J=1.53, 1H), 7.45 (d, J=7.63, 1H), 7.38 (dd, J=8.39, 1.68, 1H), 7.29 (t, J=8.85, 2H), 2.95 (s, 3H), 2.36 (s, 3H), 2.15 (m, 1H), 1.66 (m, 2H), 1.55 (m, 2H), 1.23 (m, 2H), 1.11 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=500.00, HPLC R$_t$=1.598 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=9.45 min; Column: Xbridge Phenyl 3.5 um, 4.6×150 mm, R$_t$=9.81 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=10, Final % B=100, Gradient time=15 min, Stop time=18 min, Flow Rate=1 ml/min, Column: Xbridge Phenyl, R$_t$=15.29 min.

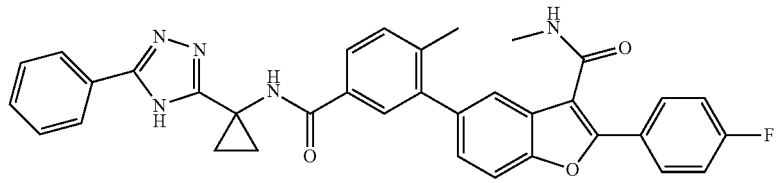

2-(4-Fluorophenyl)-N-methyl-5-(2-methyl-5-(1-(5-phenyl-4H-1,2,4-triazol-3-yl)cyclopropylcarbamoyl)phenyl)benzofuran-3-carboxamide. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.48-7.03 min. (UV detection at 220 nm) to obtain the product as a TFA solvate. $^1$H NMR (500 MHz, CD$_3$OD) δ 7.99-7.95 (overlapping m, 4H), 7.88-7.85 (overlapping m, 2H), 7.67-7.65 (overlapping m, 2H), 7.49-7.45 (overlapping m, 3H), 7.44 (d, J=7.93, 1H), 7.39 (dd, J=8.55, 1.53, 1H), 7.28 (t, J=8.70, 2H), 2.95 (s, 3H), 2.35 (s, 3H), 1.72 (m, 2H), 1.48 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$=585.89, HPLC R$_t$=1.765 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.85 min; Column: Xbridge Phenyl 3.5 um, 4.6×150 mm, R$_t$=5.81 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl, R$_t$=13.04 min.

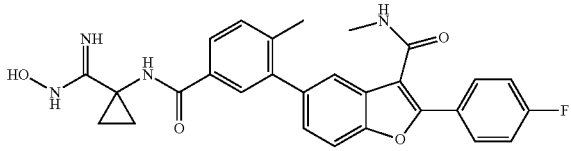

2-(4-Fluorophenyl)-5-(5-(1-(N-hydroxycarbamimidoyl) cyclopropylcarbamoyl)-2-methylphenyl)-N-methylbenzofuran-3-carboxamide. To a mixture of 5-(5-(1-cyanocyclopropylcarbamoyl)-2-methylphenyl)-2-(4-fluorophenyl)-N-methylbenzofuran-3-carboxamide (43.5 mg, 0.093 mmol) in ethanol (1.5 mL) at r.t. under N$_2$ was added hydroxylamine hydrochloride (12.93 mg, 0.186 mmol), followed by Et$_3$N (0.039 mL, 0.279 mmol). The mixture was stirred at reflux (115° C.) for about 4 hours. The mixture was cooled to r.t. and evaporated. The residue was used for the next step without further purification. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 501.13, HPLC R$_t$=1.385 min.

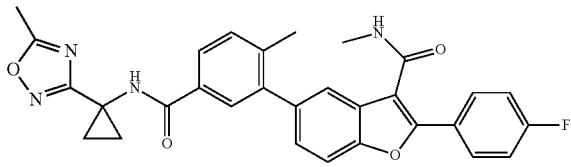

2-(4-Fluorophenyl)-N-methyl-5-(2-methyl-5-(1-(5-methyl-1,2,4-oxadiazol-3-yl)cyclopropylcarbamoyl)phenyl) benzofuran-3-carboxamide. To a mxtutre of 2-(4-fluorophenyl)-5-(5-(1-(N-hydroxycarbamimidoyl) cyclopropylcarbamoyl)-2-methylphenyl)-N-methylbenzofuran-3-carboxamide (46.5 mg, 0.093 mmol, crude) in pyridine (0.5 mL, 6.18 mmol) at r.t. under N$_2$ was added acetyl chloride (0.020 mL, 0.279 mmol). The mixture was stirred at 115° C. for 2 hours. The mixture was cooled to r.t., diluted with MeOH and purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.64-7.95 min. (UV detection at 220 nm). The residue obtained after evaporation of the combined fractions was further purified by preparative TLC, 10% MeOH/CH$_2$Cl$_2$, two 20 cm×20 cm×0.5 mm plates. R$_f$ about 0.67 (10% MeOH/CH$_2$Cl$_2$). $^1$H NMR (500 MHz, CD$_3$OD) δ 7.98 (m, J=9.00, 5.34, 2H), 7.81 (s, 1H), 7.80 ((m overlapped with s, J=2.14, 1H), 7.66 (d, J=8.55, 1H), 7.65 (d, J=1.22, 1H), 7.43 (d, J=8.55, 1H), 7.36 (dd, J=8.55, 1.83, 1H), 7.28 (m, J=8.70, 2H), 2.96 (s, 3H), 2.54 (s, 3H), 2.35 (s, 3H), 1.59 (m, 2H), 1.43 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 525.07, HPLC R$_t$=1.682 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.67 min; Column: Xbridge Phenyl 3.5 um, 4.6×150 mm, R$_t$=5.22 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=12.36 min.

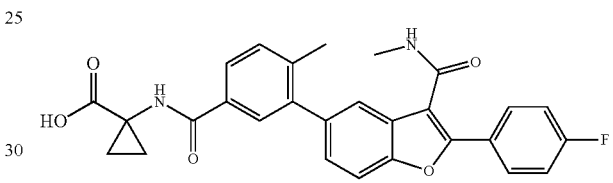

1-(3-(2-(4-Fluorophenyl)-3-(methylcarbamoyl)benzofuran-5-yl)-4-methylbenzamido)cyclopropanecarboxylic acid. $^1$H NMR (500 MHz, CD$_3$OD) δ 7.98 (m, J=9.00, 5.34, 2H), 7.78 (s, 1H), 7.77 (m overlapping with s, 1H), 7.66 (d, J=8.55, 1H), 7.64 (d, J=1.22, 1H), 7.42 (d, J=8.55, 1H), 7.38 (dd, J=8.55, 1.83, 1H), 7.28 (t, J=8.70, 2H), 2.96 (s, 3H), 2.34 (s, 3H), 1.60 (m, 2H), 1.25 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)$^+$= 487.27, HPLC R$_t$=1.625 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=5.38 min; Xbridge Phenyl 3.5 um, 4.6×150 mm, R$_t$=4.43 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3, R$_t$=10.67 min.

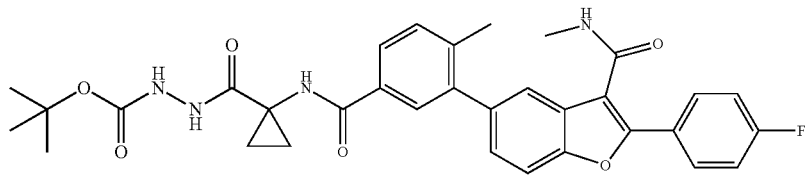

tert-Butyl 2-(1-(3-(2-(4-fluorophenyl)-3-(methylcarbamoyl)benzofuran-5-yl)-4-methylbenzamido)cyclopropanecarbonyl)hydrazinecarboxylate. To a mixture of 1-(3-(2-(4-fluorophenyl)-3-(methylcarbamoyl)benzofuran-5-yl)-4-methylbenzamido)cyclopropanecarboxylic acid (41.6 mg, 0.086 mmol), tert-butyl hydrazinecarboxylate (16.95 mg, 0.128 mmol) and 2-(1H-benzo[d][1,2,3]triazol-1-yl)-1,1,3,3-tetramethylisouronium tetrafluoroborate (54.9 mg, 0.171 mmol) in DMF (1 mL) at r.t under $N_2$ was added N,N-diisopropylethylamine (0.060 mL, 0.342 mmol). The mixture was stirred at r.t. for 19 hours. The mixture was added 5 ml $H_2O$. The white precipitates were filtered, washed with 3×2 ml $H_2O$ and dried (33.1 mg), and was used without further purification. HPLC method: Solvent A=10% MeOH-90% $H_2O$-0.1% TFA, Solvent B=90% MeOH-10% $H_2O$-0.1% TFA, Start B=0, Final % B=100, Gradient time=2 min, Stop time=3 min, Flow Rate=5 ml/min, Column: Phenomenex-Luna, 3.0×50 mm, S10; HPLC $R_t$=1.750 min.

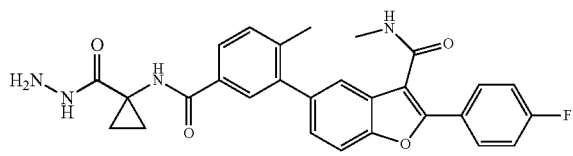

2-(4-Fluorophenyl)-5-(5-(1-(hydrazinecarbonyl)cyclopropylcarbamoyl)-2-methylphenyl)-N-methylbenzofuran-3-carboxamide. To tert-butyl 2-(1-(3-(2-(4-fluorophenyl)-3-(methylcarbamoyl)benzofuran-5-yl)-4-methylbenzamido)cyclopropanecarbonyl)hydrazinecarboxylate (33.1 mg, 0.055 mmol) in a round-bottom flask at r.t. under $N_2$ was added HCl (1 ml, 4.00 mmol, 4 M in 1,4-dioxane). The mixture was stirred at r.t. for four hours. The mixture was evaporated, and the crude hydrochloride salt used without further purification. LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z $(M+H)^+$= 501.06, HPLC $R_t$=1.483 min.

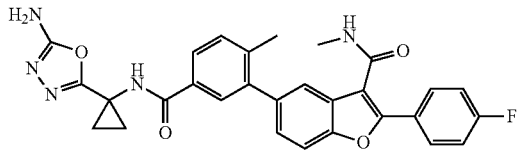

5-(5-(1-(5-Amino-1,3,4-oxadiazol-2-yl)cyclopropylcarbamoyl)-2-methylphenyl)-2-(4-fluorophenyl)-N-methylbenzofuran-3-carboxamide. To a mixture of 2-(4-fluorophenyl)-5-(5-(1-(hydrazinecarbonyl)cyclopropylcarbamoyl)-2-methylphenyl)-N-methylbenzofuran-3-carboxamide, hydrochloride (29.5 mg, 0.055 mmol, crude) in 1,4-dioxane (1 ml) at r.t. was added a solution of cyanic bromide (58.3 mg, 0.550 mmol) in acetonitrile (0.5 mL), and then sat. aq. $NaHCO_3$ (0.1 ml). The mixture was stirred at r.t. for about 5 hours. The mixture was added 0.3 ml 1N HCl, diluted with MeOH and purified by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=50, Final % B=100, Gradient time=10 min, Stop time=12 min, Flow Rate=25 mL/min, Column: Waters-Sunfire 19×100 mm S5, Fraction Collection: 6.53-7.18 min. (UV detection at 220 nm) to obtain the product as a TFA salt. $^1$H NMR (500 MHz, $CD_3OD$) δ 7.97 (dd, J=8.55, 5.19, 2H), 7.80 (s, 1H), 7.80 ((m overlapped with s, 1H), 7.66 (d, J=8.55, 1H), 7.63 (s, 1H), 7.44 (d, J=8.55, 1H), 7.37 (dd, J=8.24, 1.22, 1H), 7.29 (t, J=8.70, 2H), 2.95 (s, 3H), 2.35 (s, 3H), 1.64 (m, 2H), 1.49 (m, 2H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z $(M+H)^+$=526.05, HPLC $R_t$=1.577 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=3.23 min; Column: Xbridge Phenyl 3.5 um, 4.6×150 mm, $R_t$=3.39 min. Analytical HPLC method: Solvent A=5% MeOH-95% $H_2O$-10 mM $NH_4HCO_3$, Solvent B=95% MeOH-5% $H_2O$-10 mM $NH_4HCO_3$, Start % B=50, Final % B=100, Gradient time=15 min, Stop time=18 min, Flow Rate=1 ml/min, Column: Xbridge Phenyl 3.5 um, 4.6×150 mm, $R_t$=11.04 min.

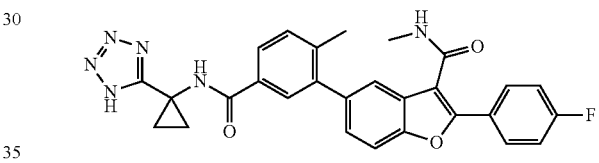

5-(5-(1-(1H-Tetrazol-5-yl)cyclopropylcarbamoyl)-2-methylphenyl)-2-(4-fluorophenyl)-N-methylbenzofuran-3-carboxamide. To a mixture of 5-(5-(1-cyanocyclopropylcarbamoyl)-2-methylphenyl)-2-(4-fluorophenyl)-N-methylbenzofuran-3-carboxamide (25.1 mg, 0.054 mmol) in DMF (1 mL) at r.t. under $N_2$ was added ammonium chloride (8.62 mg, 0.161 mmol), and then sodium azide (6.98 mg, 0.107 mmol). The mixture was stirred at 120° C. for about 4 hours. The mixture was cooled to r.t., and added with another 18 mg of $NH_4Cl$ and then 14 mg of $NaN_3$. The mixture was stirred at 120° C. for 14.5 hours. The mixture was cooled to r.t., and added with another 26 mg of $NH_4Cl$, followed by 21 mg of $NaN_3$. The mixture was re-stirred at 120° C. for 24 hours. The mixture was cooled to r.t., and diluted with MeOH and purified by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=50, Final % B=100, Gradient time=10 min, Stop time=12 min, Flow Rate=25 mL/min, Column: Waters-Sunfire 19×100 mm S5, Fraction Collection: 6.82-7.27 min. (UV detection at 220 nm). $^1$H NMR (500 MHz, $CD_3OD$) δ 7.97 (m, J=9.00, 5.34, 2H), 7.85 (d, J=1.22, 1H), 7.84 (dd overlapping with d, J=1.83, 1H), 7.67 (d, J=8.24, 1H), 7.65 (d, J=1.22, 1H), 7.45 (d, J=7.63, 1H), 7.39 (dd, J=8.55, 1.83, 1H), 7.29 (t, J=8.85, 2H), 2.95 (s, 3H), 2.36 (s, 3H), 1.70 (m, 2H), 1.58 (m, 2H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column:

Xterra MS 7 um, C18, 3.0×50 mm; (ES+) m/z (M+H)⁺= 511.28, HPLC R$_t$=1.595 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=5.10 min; Xbridge Phenyl 3.5 um, 4.6×150 mm, R$_t$=4.23 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3, R$_t$=10.58 min.

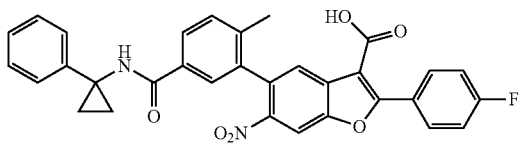

2-(4-fluorophenyl)-5-(2-methyl-5-(1-phenylcyclopropylcarbamoyl)phenyl)-6-nitrobenzofuran-3-carboxylic acid. Prepared by the hydrolysis of ethyl 2-(4-fluorophenyl)-5-(2-methyl-5-(1-phenylcyclopropylcarbamoyl)phenyl)-6-nitrobenzofuran-3-carboxylate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺= 551.34, HPLC R$_t$=1.895 min.

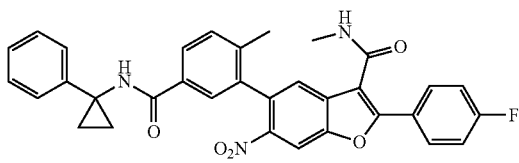

2-(4-Fluorophenyl)-N-methyl-5-(2-methyl-5-(1-phenylcyclopropylcarbamoyl)phenyl)-6-nitrobenzofuran-3-carboxamide. Prepared by the coupling of 2-(4-fluorophenyl)-5-(2-methyl-5-(1-phenylcyclopropylcarbamoyl)phenyl)-6-nitrobenzofuran-3-carboxylic acid with methylamine hydrochloride under the conditions as described. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=564.36, HPLC R$_t$=1.768 min.

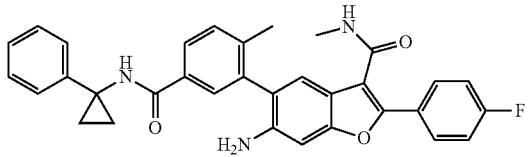

6-Amino-2-(4-fluorophenyl)-N-methyl-5-(2-methyl-5-(1-phenylcyclopropylcarbamoyl)phenyl)benzofuran-3-carboxamide. Obtained as a TFA salt from the reduction of 2-(4-fluorophenyl)-N-methyl-5-(2-methyl-5-(1-phenylcyclopropylcarbamoyl)phenyl)-6-nitrobenzofuran-3-carboxamide using H$_2$ with 5% Pd/C as catalyst (2:5 DMF/EtOAc, r.t.) after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.17-6.79 min. (UV detection at 220 nm). ¹H NMR (500 MHz, CD$_3$OD) δ 7.94 (m, J=8.85, 5.19, 2H), 7.87 (dd, J=8.09, 1.98, 1H), 7.74 (d, J=1.83, 1H), 7.50 (d, J=7.93, 1H), 7.44 (s, 1H), 7.38 (s, 1H), 7.17 (m, 1H), 7.29 (s, 1H), 7.29-7.25 (overlapping m, 5H), 2.92 (s, 3H), 2.24 (s, 3H), 1.35 (m, 4H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z (M+H)⁺=534.26, HPLC R$_t$=1.563 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=11.58 min; Xbridge Phenyl 3.5 um, 4.6×150 mm, R$_t$=4.96 min (Start % B=50). Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=10, Final % B=100, Gradient time=15 min, Stop time=18 min, Flow Rate=1 ml/min, Column: Xbridge Phenyl, Rt=15.09 min.

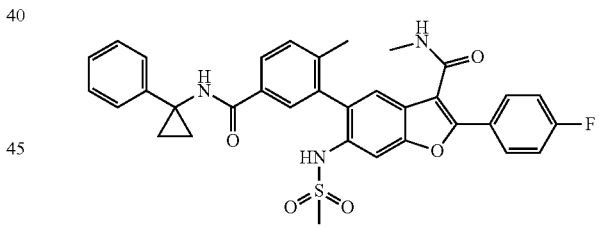

2-(4-Fluorophenyl)-N-methyl-5-(2-methyl-5-(1-phenylcyclopropylcarbamoyl)phenyl)-6-(methylsulfonamido)benzofuran-3-carboxamide. To a mixture of 6-amino-2-(4-fluorophenyl)-N-methyl-5-(2-methyl-5-(1-phenylcyclopropylcarbamoyl)phenyl)benzofuran-3-carboxamide (53.3 mg, 0.100 mmol) (crude) in ClCH$_2$CH$_2$Cl (1 ml) at r.t. under N$_2$ was added pyridine (0.024 mL, 0.300 mmol). The mixture was then added a solution of methanesulfonyl chloride (22.88 mg, 0.200 mmol) in ClCH$_2$CH$_2$Cl (0.3 ml), and stirred for about 22 hours. The mixture was diluted with MeOH and purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.75-7.37 min. (UV detection at 220 nm). ¹H NMR (500 MHz, CD$_3$OD) δ 7.98

(m, J=8.85, 5.19, 2H), 7.85 (dd, J=8.09, 1.98, 1H), 7.79 (s, 1H), 7.75 (d, J=1.53, 1H), 7.51 (s, 1H), 7.47 (d, J=7.93, 1H), 7.17 (m, 1H), 7.30-7.26 (overlapping m, 5H), 7.29 (s, 1H), 2.93 (s, 3H), 2.88 (s, 3H), 2.23 (s, 3H), 1.35 (appeared as d, 4H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=612.34, HPLC $R_t$=1.583 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=7.48 min; Xbridge Phenyl 3.5 um, 4.6×150 mm, $R_t$=6.24 min. Analytical HPLC method: Solvent A=5% MeOH-95% $H_2O$-10 mM $NH_4HCO_3$, Solvent B=95% MeOH-5% $H_2O$-10 mM $NH_4HCO_3$, Start % B=50, Final % B=100, Gradient time=15 min, Stop time=18 min, Flow Rate=1 ml/min, Column: Xbridge Phenyl, $R_t$=11.46 min.

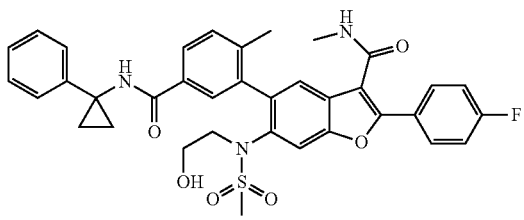

2-(4-Fluorophenyl)-6-(N-(2-hydroxyethyl)methylsulfonamido)-N-methyl-5-(2-methyl-5-(1-phenylcyclopropylcarbamoyl)phenyl)benzofuran-3-carboxamide. 2-(4-fluorophenyl)-6-(N-(2-hydroxyethyl)methylsulfonamido)-N-methyl-5-(2-methyl-5-(1-phenylcyclopropylcarbamoyl) phenyl)benzofuran-3-carboxamide was prepared from the alkylation of 2-(4-Fluorophenyl)-N-methyl-5-(2-methyl-5-(1-phenylcyclopropylcarbamoyl)phenyl)-6-(methylsulfonamido)benzofuran-3-carboxamide using (2-bromoethoxy)(tert-butyl)dimethylsilane ($K_2CO_3$, DMF 55° C.) followed by deprotection using HCl in 1,4-dioxane at r.t. Purification was preformed by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=50, Final % B=100, Gradient time=10 min, Stop time=12 min, Flow Rate=25 mL/min, Column: Waters-Sunfire 19×100 mm S5, Fraction Collection: 6.32-6.81 min. (UV detection at 220 nm). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=656.06, HPLC $R_t$=1.563 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=6.05 min; Xbridge Phenyl 3.5 um, 4.6×150 mm, $R_t$=5.38 min. Analytical HPLC method: Solvent A=5% MeOH-95% $H_2O$-10 mM $NH_4HCO_3$, Solvent B=95% MeOH-5% $H_2O$-10 mM $NH_4HCO_3$, Start % B=50, Final % B=100, Gradient time=15 min, Stop time=18 min, Flow Rate=1 ml/min, Column: Xbridge Phenyl 3.5 um, 4.6×150 mm, $R_t$=11.42 min.

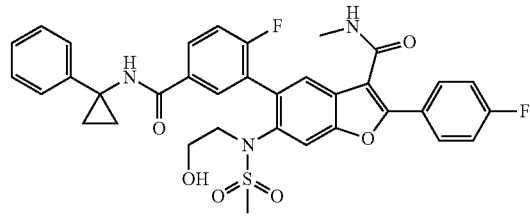

5-(2-Fluoro-5-(1-phenylcyclopropylcarbamoyl)phenyl)-2-(4-fluorophenyl)-6-(N-(2-hydroxyethyl)methylsulfonamido)-N-methylbenzofuran-3-carboxamide. Purification was preformed by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=30, Final % B=100, Gradient time=10 min, Stop time=12 min, Flow Rate=25 mL/min, Column: Waters-Sunfire 19×100 mm S5, Fraction Collection: 8.06-8.30 min. (UV detection at 220 nm). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=4 ml/min, Column: Xterra MS 7 um, C18, 3.0×50 mm; (ES+) m/z $(M+H)^+$=660.50, HPLC $R_t$=1.530 min. Analytical HPLC were performed by using Shimadzu-VP instrument with UV detection at 220 nm and 254 nm. Analytical HPLC method: Solvent A=5% MeCN-95% $H_2O$-0.1% TFA, Solvent B=95% MeCN-5% $H_2O$-0.1% TFA, Start % B=50, Final % B=100, Gradient time=15 min, Stop time=18 min, Flow Rate=1 ml/min, Column: Sunfire C18, 3.5 um, 4.6×150 mm, $R_t$=5.68 min; Xbridge Phenyl 3.5 um, 4.6×150 mm, $R_t$=5.18 min.

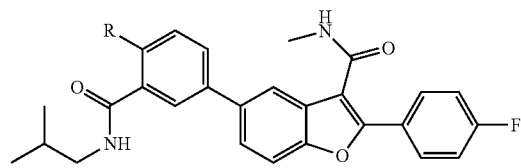

General procedure. To a Biotage microwave vial (2-5 mL) was added either 5-(4-chloro-3-(isobutylcarbamoyl)phenyl)-2-(4-fluorophenyl)-N-methylbenzofuran-3-carboxamide (0.075 mmol, 1 eq.) or 4-(2-(4-fluorophenyl)-3-(methylcarbamoyl)benzofuran-5-yl)-2-(isobutylcarbamoyl)phenyl trifluoromethane sulfonate (0.075 mmol, 1 eq.) in dry 1,4-Dioxane (1 mL) along with the desired boronic acid (0.150 mmol, 2 eq.), potassium phosphate, tribasic (0.300 mmol, 52.3 mg) in water (0.2 mL), dicyclohexyl(2',6'-dimethoxybiphenyl-3-yl)phosphine (S-Phos) (6.16 mg, 0.015 mmol), and finally palladium (II) acetate (3.37 mg, 0.015 mmol) in 1,4-dioxane (0.5 mL). The vial was flushed with nitrogen then capped and placed into the Biotage microwave for 10 minutes at 150° C. The solvent was removed in a Thermo/Savant SpeedVac and the crude products were dissolved in DMF (1.8 mL) and purified by preparative HPLC using a Shimadzu prepHPLC employing acetonitrile/water/0.1% TFA where solvent A was 10% acetonitrile/90% $H_2O$/0.1% trifluoroacetic acid and solvent B was 10% $H_2O$/90% acetonitrile/0.1% trifluoroacetic acid with a Waters Sunfire 5 μm C18 30×100 mm column at a gradient of 30-100% B and a flow rate of 40 mL/min. over 8 minutes with a 10 minute hold. The tubes with desired product were evaporated overnight in a Thermo/Savant Speedvac. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 20-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3 μm 4.6×150 mm column employing water/methanol/10 mM ammonium bicarbonate with a gradient of 20-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. Rt represents the LC retention time in minutes. All NMR spectra were recorded at room temperature using deuterated NMR solvents.

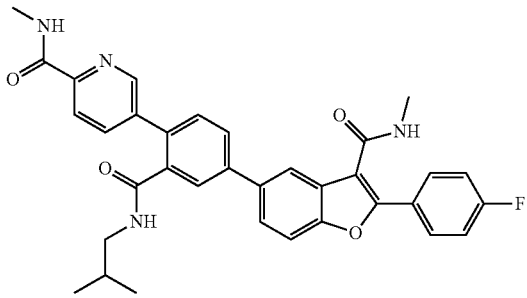

5-(4-(2-(4-Fluorophenyl)-3-(methylcarbamoyl)benzofuran-5-yl)-2-(isobutylcarbamoyl)phenyl)-N-methylpicolinamide. $^1$H NMR (400 MHz, THF-d8) δ ppm 0.75 (d, J=7 Hz, 6H), 1.63-1.71 (m, 1H), 2.93 (d, J=5 Hz, 6H), 3.00 (t, J=6 Hz, 2H), 7.23 (t, J=9 Hz, 2H), 7.37 (t, J=6 Hz, 1H), 7.44-7.51 (m, 1H), 7.53 (d, J=8 Hz, 1H), 7.60-7.66 (m, 1H), 7.67-7.73 (m, 1H), 7.80-7.88 (m, 2H), 7.98 (dd, J=8, 2 Hz, 1H), 8.05 (s, 1H), 8.08-8.18 (m, 3H), 8.30 (d, J=5 Hz, 1H), 8.66 (d, J=2 Hz, 1H). LCMS Rt 2.125 min., m/z 579.32 (M+H), HPLC Rt 8.594 min. (Sunfire C18), 98.7% purity and 11.276 min. (Gemini C18), 100% purity.

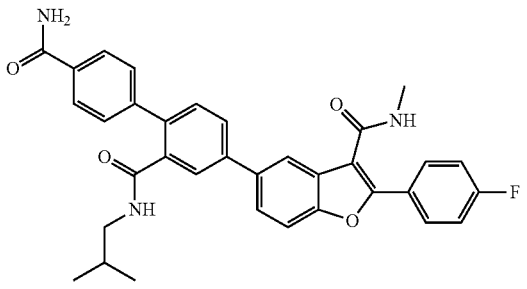

4-(2-(4-Fluorophenyl)-3-(methylcarbamoyl)benzofuran-5-yl)-N2-isobutylbiphenyl-2,4'-dicarboxamide. $^1$H NMR (400 MHz, DMF-d7) δ ppm 0.81 (d, J=6.78 Hz, 6H), 1.71-1.82 (m, 1H), 3.00 (d, J=4.77 Hz, 3H), 3.06 (t, J=6.40 Hz, 2H), 7.42-7.48 (m, 2H), 7.57 (d, J=8.28 Hz, 1H), 7.62 (m, 2H), 7.78 (d, J=8.28 Hz, 1H), 7.84 (m, 2H), 7.94 (d, J=8.03 Hz, 1H), 8.00 (d, J=8.28 Hz, 2H), 8.06-8.08 (m, 1H), 8.10-8.14 (m, 2H), 8.20 (t, J=5.77 Hz, 1H), 8.40 (d, J=4.52 Hz, 1H). LCMS Rt 2.020 min, m/z 564.25 (M+H). HPLC Rt 8.224 min. (Sunfire C18), 98.2% purity and 11.098 min. (Gemini C18), 98.3% purity.

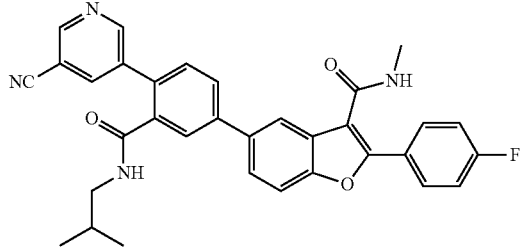

5-(4-(5-Cyanopyridin-3-yl)-3-(isobutylcarbamoyl)phenyl)-2-(4-fluorophenyl)-N-methyl benzofuran-3-carboxamide. $^1$H NMR (400 MHz, THF-d8) δ ppm 0.82 (d, J=6.78 Hz, 6H), 1.74-1.80 (m, 1H), 2.93 (d, J=4.52 Hz, 3H), 3.01-3.11 (m, 2H), 7.18-7.30 (m, 2H), 7.42-7.51 (m, 1H), 7.55 (d, J=7.78 Hz, 1H), 7.56-7.61 (m, 1 H), 7.62-7.67 (m, 1H), 7.68-7.75 (m, 1H), 7.83-7.92 (m, 2H), 8.04-8.15 (m, 3 H), 8.20 (t, J=2.13 Hz, 1H), 8.85 (dd, J=13.93, 2.13 Hz, 2H). LCMS Rt 2.278 min, m/z 547.23 (M+H). HPLC Rt 9.246 min. (Sunfire C18), 96.0% purity and 11.343 min. (Gemini C18), 98.6% purity.

An alternative approach to the coupling. To a small sized microwave vial was added 5-(4-chloro-3-(isobutylcarbamoyl)phenyl)-2-(4-fluorophenyl)-N-methylbenzofuran-3-carboxamide (47.9 mg, 0.1 mmol), BuOH (2 mL), boronic acid/ester (0.150 mmol), dicyclohexyl(2',4',6'-triisopropylbiphenyl-2-yl)phosphine (19.07 mg, 0.040 mmol), potassium phosphate, tribasic (85 mg, 0.400 mmol) and finally Tris(dibenzylideneacetone)dipalladium(0) (18.31 mg, 0.020 mmol). The vial was capped and subjected to microwave heating (130° C.) for 12 minutes. Butanol was removed under a stream of nitrogen and the crude products were dissolved in DMF (1.8 mL) and purified by preparative HPLC employing a Dionex PrepHPLC system equipped with an ELS (Evaporative Light Scattering) detector. A Waters Xbridge 19×200 mm 5 um C18 column was used with acetonitrile/HPLC grade water/10 mM ammonium acetate where solvent A was HPLC grade water with 10 mM ammonium acetate and solvent B was 100% acetonitrile at a gradient of 30-95% B in 30 minutes with a flow rate of 25 mL/minute. LCMS was run using a Waters ZQ with ESCi mass spectrometer with a Supelco Ascentis Express 3 μm C18 4.5×50 mm column employing acetonitrile/HPLC grade water/10 mM ammonium acetate where solvent A was 5% acetonitrile, 95% HPLC grade water with 10 mM ammonium acetate and solvent B was 95% acetonitrile, 5% HPLC grade water with 10 mM ammonium acetate at a gradient of 0-100% B in 8 minutes with a 1 minute hold at 2 mL/minute.

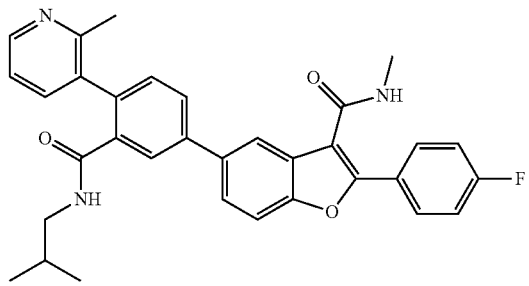

495

2-(4-Fluorophenyl)-5-(3-(isobutylcarbamoyl)-4-(2-methylpyridin-3-yl)phenyl)-N-methyl benzofuran-3-carboxamide. LCMS m/z 535.90 (M+H), Rt 4.89 min., 100% purity.

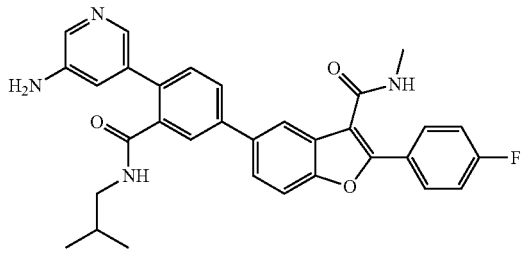

5-(4-(5-Aminopyridin-3-yl)-3-(isobutylcarbamoyl)phenyl)-2-(4-fluorophenyl)-N-methyl benzofuran-3-carboxamide. LCMS m/z 536.96 (M+H), Rt 4.37 min., 100% purity.

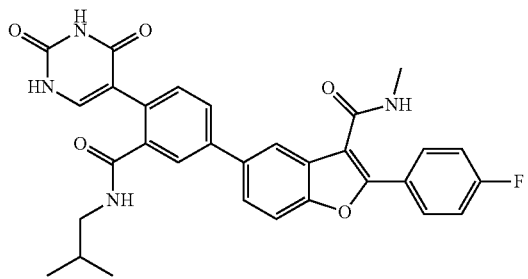

5-(4-(2,4-Dioxo-1,2,3,4-tetrahydropyrimidin-5-yl)-3-(isobutylcarbamoyl)phenyl)-2-(4-fluoro phenyl)-N-methyl-benzofuran-3-carboxamide. LCMS m/z 554.94 (M+H), Rt 3.88 min., 100% purity.

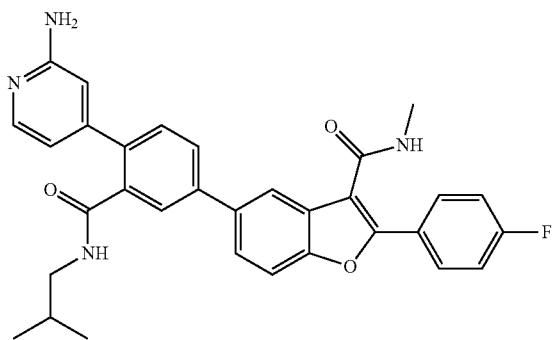

5-(4-(2-Aminopyridin-4-yl)-3-(isobutylcarbamoyl)phenyl)-2-(4-fluorophenyl)-N-methyl benzofuran-3-carboxamide. LCMS m/z 536.97 (M+H), Rt 4.55 min., 100% purity.

496

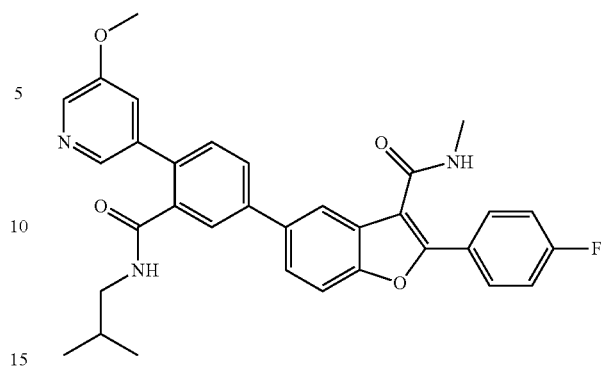

2-(4-Fluorophenyl)-5-(3-(isobutylcarbamoyl)-4-(5-methoxypyridin-3-yl)phenyl)-N-methyl benzofuran-3-carboxamide. LCMS m/z 551.96 (M+H), Rt 4.97 min., 89% purity.

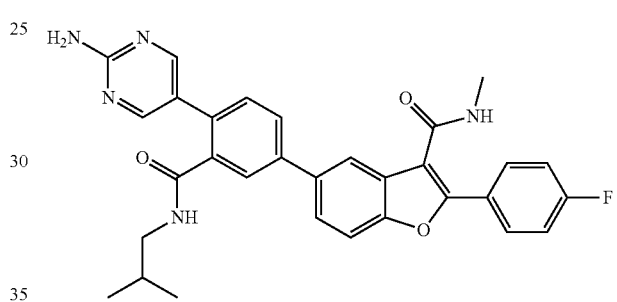

5-(4-(2-Aminopyrimidin-5-yl)-3-(isobutylcarbamoyl)phenyl)-2-(4-fluorophenyl)-N-methyl benzofuran-3-carboxamide. LCMS m/z 537.97 (M+H), Rt 4.23 min., 96% purity.

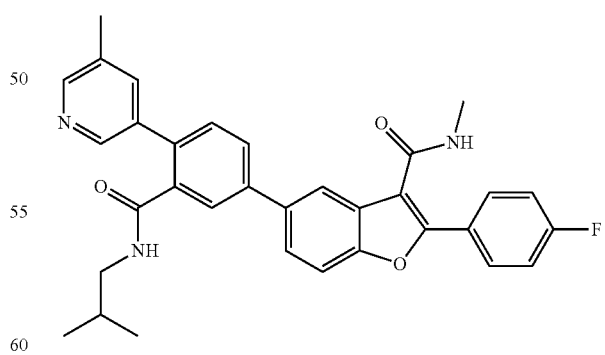

2-(4-Fluorophenyl)-5-(3-(isobutylcarbamoyl)-4-(5-methylpyridin-3-yl)phenyl)-N-methyl benzofuran-3-carboxamide. LCMS m/z 535.95 (M+H), Rt 4.99 min., 100% purity.

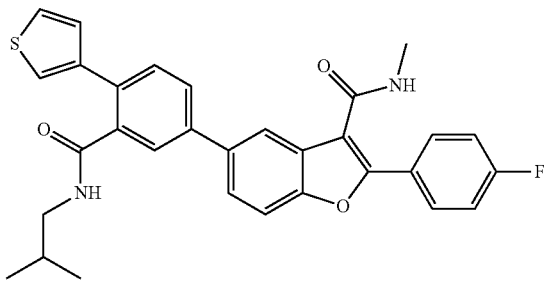

2-(4-Fluorophenyl)-5-(3-(isobutylcarbamoyl)-4-(thiophen-3-yl)phenyl)-N-methylbenzofuran-3-carboxamide. LCMS m/z 526.96 (M+H), Rt 5.83 min., 74% purity.

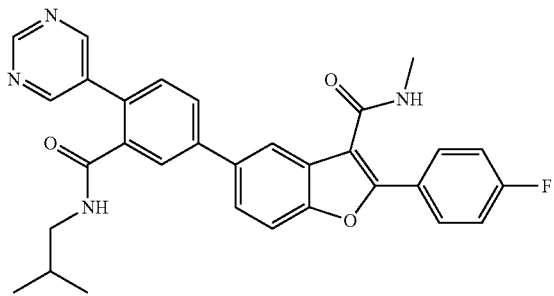

2-(4-Fluorophenyl)-5-(3-(isobutylcarbamoyl)-4-(pyrimidin-5-yl)phenyl)-N-methylbenzofuran-3-carboxamide. Purification by using a Shimadzu preparative HPLC employing CH$_3$CN/water/TFA where solvent A was 10% acetonitrile/90% H$_2$O/0.1% trifluoroacetic acid and solvent B was 10% H2O/90% acetonitrile/0.1% trifluoroacetic acid with a Waters Sunfire 5 u C18 30×100 mm column at a gradient of 30-100% B and a flow rate of 40 mL/min. over 10 minutes with a 10 minute hold. Post purification LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, DMSO-d$_6$) δ ppm 0.76 (d, J=6.78 Hz, 6H), 1.61-1.74 (m, 1H), 2.87 (d, J=4.52 Hz, 3H), 2.96 (t, J=6.27 Hz, 2H), 7.39 (t, J=8.91 Hz, 2H), 7.64 (d, J=8.03 Hz, 1H), 7.77-7.87 (m, 3H), 7.91-8.07 (m, 4H), 8.47-8.60 (m, 2H), 8.81 (s, 2H), 9.16 (s, 1H). LCMS m/z 523.22 (M+H), Rt 2.052 min. HPLC Rt 8.908 min. (Sunfire C18), 96.0% purity and 11.353 min. (Gemini C18), 98.6% purity.

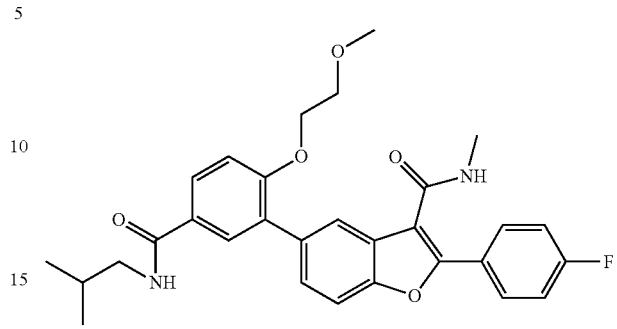

2-(4-Fluorophenyl)-5-(5-(isobutylcarbamoyl)-2-(2-methoxyethoxy)phenyl)-N-methylbenzofuran-3-carboxamide. To a small microwave vial was added 2-(4-fluorophenyl)-5-(2-hydroxy-5-(isobutylcarbamoyl)phenyl)-N-methylbenzofuran-3-carboxamide (33 mg, 0.072 mmol), tetrahydrofuran (2 mL), triphenylphosphine (37.6 mg, 0.143 mmol), 2-methoxyethanol (0.011 mL, 0.139 mmol), and di-tert-butyl azodicarboxylate (33.0 mg, 0.143 mmol). The vial was crimped and heated to 100° C. for 10 minutes. After returning to room temperature tetrahydrofuran was removed under a stream of nitrogen. The crude product was taken up in 2 mL of acetonitrile and purified using a Shimadzu preparative HPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 µm C18 30×100 mm column at a gradient of 40-100% B and a flow rate of 40 mL/min. over 8 minutes with a 10 minute hold. The desired material was concentrated to dryness. The resulting white solid (41% yield) was placed under high vacuum prior to final analysis. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. The NMR spectrum was recorded at room temperature using a Bruker DRX400 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). ¹H NMR (400 MHz, CD₃OD) δ ppm 1.04 (d, J=6.53 Hz, 6H), 1.35-1.40 (m, 3H), 1.96-2.08 (m, 1H), 2.97-3.10 (m, 3H), 3.24-3.32 (m, 2H), 3.73-3.82 (m, 2H), 4.25-4.34 (m, 2H), 7.24 (d, J=8.53 Hz, 1H), 7.29-7.38 (m, 2H), 7.63-7.72 (m, 2H), 7.91 (dd, J=8.53, 2.26 Hz, 1H), 7.94-7.99 (m, 2H), 8.00-8.09 (m, 2H), 8.48 (br. s., 1H). LCMS m/z 519.25 (M+H), Rt 2.292 min. HPLC (Sunfire C18) Rt 10.054 min, 96% purity and (XBridge Phenyl C18) Rt 11.846 min., 97% purity.

Additional examples of ether linked compounds are shown below. The compounds were synthesized in the same manner as above. The solvent (tetrahydrofuran) was removed under a stream of nitrogen and the crude products were dissolved in DMF (1.8 mL) and purified by preparative HPLC employing a Dionex PrepHPLC system equipped with an ELS (Evaporative Light Scattering) detector. A Supelco Ascentis 5 μm C18 21.2×250 mm column was used with acetonitrile/HPLC grade water/10 mM ammonium acetate where solvent A was 99.9% HPLC grade water with 10 mM ammonium acetate and solvent B was 100% acetonitrile at a gradient of 30-95% B in 20 minutes with a 2 5 minute hold at 20 mL/minute. LCMS was run using a Waters ZQ with ESCi mass spectrometer with a Supelco Ascentis Express 3 μm C18 4.5×50 mm column employing acetonitrile/HPLC grade water/10 mM ammonium acetate where solvent A was 5% acetonitrile, 95% HPLC grade water with 10 mM ammonium acetate and solvent B was 95% acetonitrile, 5% HPLC grade water with 10 mM ammonium acetate at a gradient of 0-100% B in 8 minutes with a 1 minute hold at 2 mL/minute. The NMR spectra were recorded at room temperature using a Varian 600 MHz flow spectrometer. Chemical shifts were reported in ppm relative to the 75% DMSO-d6/25% CDCl₃ (v/v) solvent used.

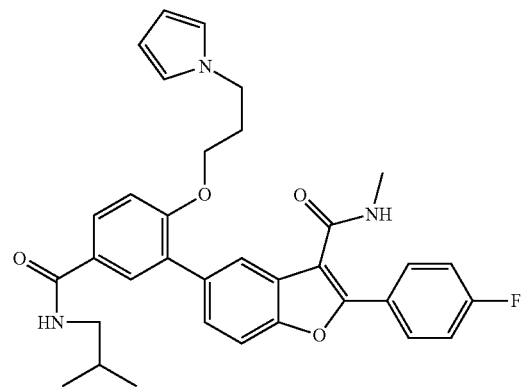

5-(2-(3-(1H-pyrrol-1-yl)propoxy)-5-(isobutylcarbamoyl)phenyl)-2-(4-fluorophenyl)-N-methyl benzofuran-3-carboxamide. ¹H NMR (600 MHz, DMSO-d6/CDCl₃) δ ppm 0.89 (d, J=6.44 Hz, 6H), 1.80-1.91 (m, 1H), 2.07 (m, 2H), 2.79 (d, J=4.10 Hz, 3H), 3.09 (t, J=6.44 Hz, 2H), 3.90-4.01 (m, 4H), 5.94 (s, 2 H), 6.61 (s, 2H), 7.08 (d, J=8.79 Hz, 1H), 7.32 (t, J=8.50 Hz, 2H), 7.58 (d, J=8.20 Hz, 1H), 7.70 (d, J=8.79 Hz, 1H), 7.79-7.87 (m, 2H), 7.92 (s, 1H), 7.97 (dd, J=8.50, 5.57 Hz, 2H), 8.32-8.42 (m, 2H). LCMS m/z 568.47 (M+H), Rt 5.98 min., 100% purity.

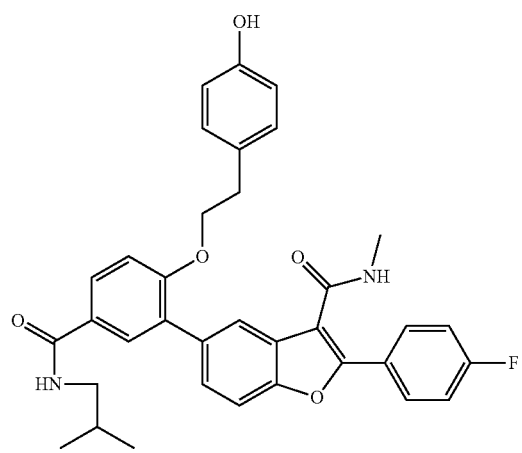

2-(4-Fluorophenyl)-5-(2-(4-hydroxyphenethoxy)-5-(isobutylcarbamoyl)phenyl)-N-methyl benzofuran-3-carboxamide. ¹H NMR (600 MHz, DMSO-d6/CDCl₃) δ ppm 0.88 (d, J=7.03 Hz, 6H), 1.85 (ddd, J=13.33, 6.59, 6.44 Hz, 1H), 2.77-2.94 (m, 5H), 3.08 (t, J=6.15 Hz, 2H), 4.20 (t, J=6.44 Hz, 2H), 6.59-6.68 (m, 2H), 6.98 (d, J=8.20 Hz, 2H), 7.13 (d, J=8.79 Hz, 1H), 7.32 (t, J=8.79 Hz, 1H), 7.41 (d, J=8.79 Hz, 1H), 7.59 (d, J=8.20 Hz, 1H), 7.75 (s, 1H), 7.81-7.91 (m, 2H), 8.00 (dd, J=8.20, 5.27 Hz, 1H), 8.33 (t, J=5.57 Hz, 1H), 8.39 (d, J=4.10 Hz, 1H). LCMS m/z 581.48 (M+H), Rt 5.30 min., 90% purity.

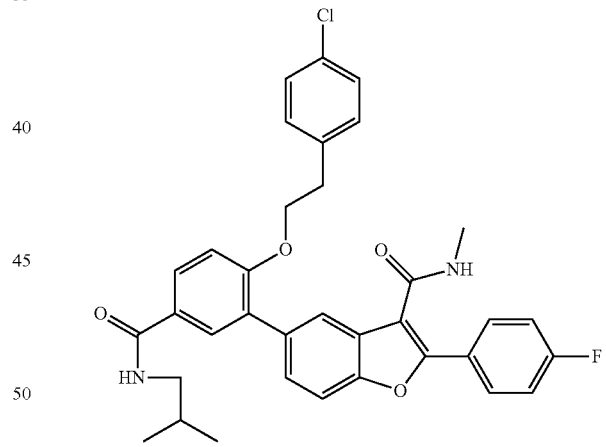

2-(4-Fluorophenyl)-5-(2-(4-chlorophenethoxy)-5-(isobutylcarbamoyl)phenyl)-N-methyl benzofuran-3-carboxamide. ¹H NMR (600 MHz, DMSO-d6/CDCl₃) δ ppm 0.88 (d, J=7.03 Hz, 6H), 1.80-1.90 (m, 1H), 2.84 (d, J=4.69 Hz, 3H), 2.96 (t, J=6.15 Hz, 2H), 3.08 (t, J=6.15 Hz, 2H), 4.26 (t, J=6.44 Hz, 2H), 7.14 (d, J=8.79 Hz, 1H), 7.19 (d, J=8.20 Hz, 2H), 7.23-7.27 (m, 2H), 7.29-7.39 (m, 3H), 7.58 (d, J=8.79 Hz, 1H), 7.73 (s, 1H), 7.83-7.89 (m, 2H), 8.00 (dd, J=8.50, 5.57 Hz, 2H), 8.33 (t, J=5.27 Hz, 1H), 8.38 (d, J=4.10 Hz, 1H). LCMS m/z 599.47 (M+H), Rt 6.52 min., 92% purity.

501

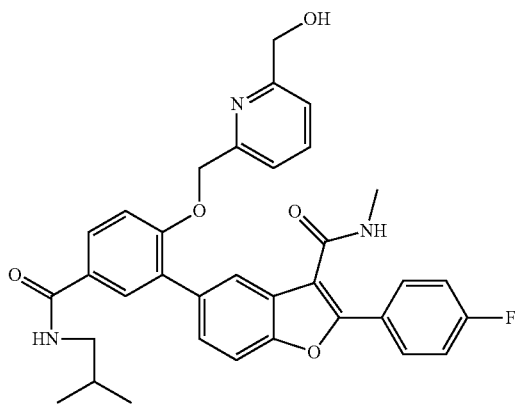

2-(4-Fluorophenyl)-5-(2-(6-(hydroxymethyl)pyridin-2-yl)methoxy)-5-(isobutylcarbamoyl)phenyl)-N-methylbenzofuran-3-carboxamide. $^1$H NMR (600 MHz, DMSO-d6/CDCl$_3$) δ ppm 0.89 (d, J=6.44 Hz, 6H), 1.79-1.91 (m, 1H), 2.82 (d, J=4.10 Hz, 3H), 3.09 (t, J=6.44 Hz, 2H), 4.56 (s, 2H), 5.23 (s, 2H), 7.24 (t, J=9.37 Hz, 2H), 7.32 (t, J=8.79 Hz, 2H), 7.37 (d, J=8.20 Hz, 1H), 7.60-7.65 (m, 1H), 7.66-7.70 (m, 1H), 7.75 (t, J=7.62 Hz, 1H), 7.84-7.90 (m, 2H), 7.93 (s, 1H), 7.96-8.03 (m, 2H), 8.36 (t, J=5.57 Hz, 1H), 8.40 (d, 1H). LCMS m/z 582.48 (M+H), Rt 4.57 min., 93% purity.

502

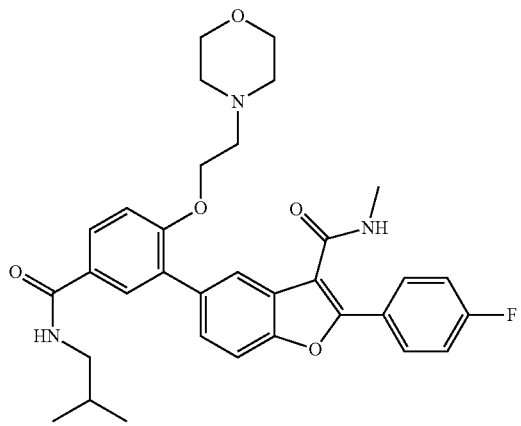

2-(4-Fluorophenyl)-5-(5-(isobutylcarbamoyl)-2-(2-morpholinoethoxy)phenyl)-N-methyl benzofuran-3-carboxamide. $^1$H NMR (600 MHz, DMSO-d6/CDCl$_3$) δ ppm 0.89 (d, J=6.44 Hz, 6H), 1.79-1.91 (m, 1H), 2.38 (br. s., 4H), 2.64 (t, J=5.57 Hz, 2H), 2.84 (d, J=4.10 Hz, 3H), 3.08 (t, J=6.15 Hz, 2H), 3.52 (t, J=4.39 Hz, 4H), 4.17 (t, J=5.57 Hz, 2H), 7.16 (d, J=8.79 Hz, 1H), 7.32 (t, J=8.79 Hz, 2H), 7.56-7.61 (m, 1H), 7.61-7.66 (m, 1H), 7.75 (s, 1H), 7.83-7.91 (m, 2H), 7.98 (dd, J=8.20, 5.86 Hz, 2H), 8.35 (t, J=5.27 Hz, 1H), 8.38 (d, 1H). LCMS m/z 574.35 (M+H), Rt 3.95 min., 100% purity.

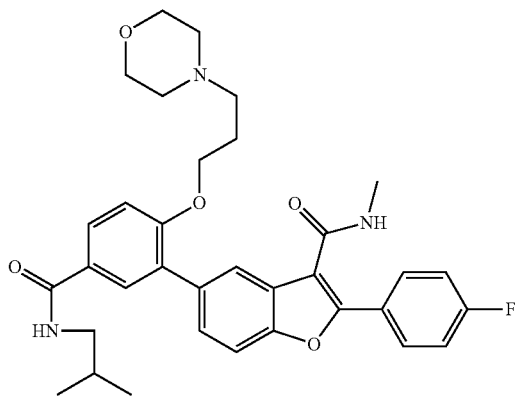

2-(4-Fluorophenyl)-5-(5-(isobutylcarbamoyl)-2-(3-morpholinopropoxy)phenyl)-N-methyl benzofuran-3-carboxamide. $^1$H NMR (600 MHz, DMSO-d6/CDCl$_3$) δ ppm 0.89 (d, J=7.03 Hz, 6H), 1.77-1.91 (m, 3H), 2.23-2.43 (m, 6H), 2.84 (d, J=4.10 Hz, 3H), 3.08 (t, J=6.44 Hz, 2H), 3.53 (br. s., 4H), 4.09 (t, J=5.86 Hz, 2H), 7.14 (d, J=8.20 Hz, 1H), 7.32 (t, J=8.79 Hz, 2H), 7.53 (d, J=9.37 Hz, 1H), 7.65 (d, J=8.79 Hz, 1H), 7.78 (s, 1H), 7.84-7.92 (m, 2H), 7.98 (dd, J=7.91, 5.57 Hz, 2H), 8.31-8.43 (m, 2H). LCMS m/z 588.40 (M+H), Rt 4.05 min., 98.7% purity.

2-(4-Fluorophenyl)-5-(5-(isobutylcarbamoyl)-2-(pyridin-2-ylmethoxy)phenyl)-N-methyl benzofuran-3-carboxamide. $^1$H NMR (600 MHz, DMSO-d6/CDCl$_3$) δ ppm 0.89 (d, J=7.03 Hz, 6H), 1.82-1.91 (m, 1H), 2.79-2.86 (m, 3H), 3.09 (t, J=6.44 Hz, 2H), 5.27 (s, 2H), 7.22-7.30 (m, 2H), 7.33 (t, J=8.50 Hz, 2H), 7.40 (d, J=7.62 Hz, 1H), 7.62 (d, J=8.79 Hz, 1H), 7.66-7.71 (m, 1H), 7.76 (t, J=7.62 Hz, 1H), 7.84-7.91 (m, 2H), 7.94 (s, 1H), 7.99 (dd, J=8.50, 5.57 Hz, 2H), 8.35-8.44 (m, 2H), 8.53 (d, J=4.69 Hz, 1H). LCMS m/z 552.29 (M+H), Rt 4.29 min., 100% purity.

503

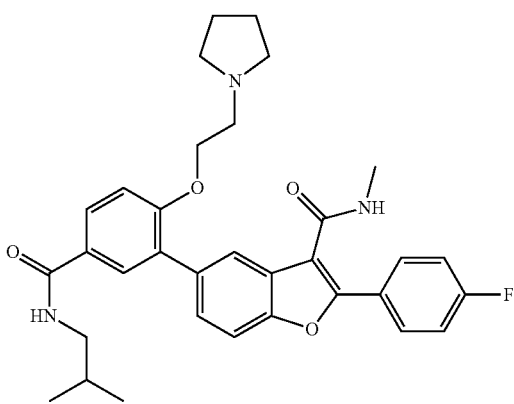

2-(4-Fluorophenyl)-5-(5-(isobutylcarbamoyl)-2-(2-(pyrrolidin-1-yl)ethoxy)phenyl)-N-methyl benzofuran-3-carboxamide. $^1$H NMR (600 MHz, DMSO-d6/CDCl$_3$) δ ppm 0.89 (d, J=6.44 Hz, 6H), 1.64 (br. s., 4H), 1.80-1.91 (m, 1H), 2.47 (br. s., 4H), 2.75-2.82 (m, 2H), 2.84 (d, J=4.10 Hz, 3H), 3.08 (t, J=6.44 Hz, 2H), 4.16 (t, J=5.27 Hz, 2H), 7.16 (d, 1H), 7.32 (t, J=8.79 Hz, 2H), 7.56-7.61 (m, 1H), 7.61-7.66 (m, 1H), 7.78 (s, 1H), 7.86 (d, J=8.20 Hz, 1H), 7.89 (s, 1H), 7.98 (dd, J=8.20, 5.27 Hz, 2H), 8.31-8.43 (m, 2H). LCMS m/z 558.37 (M+H), Rt 3.52 min., 100% purity.

504

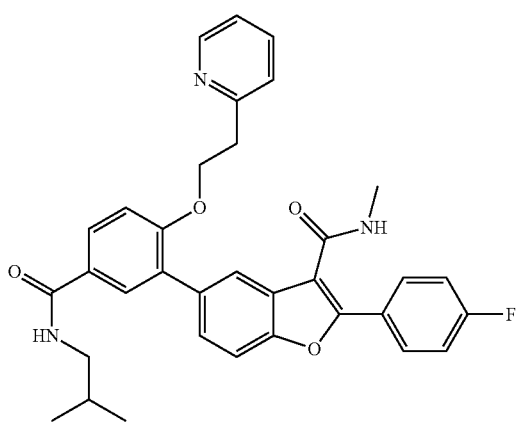

2-(4-Fluorophenyl)-5-(5-(isobutylcarbamoyl)-2-(2-(pyridin-2-yl)ethoxy)phenyl)-N-methyl benzofuran-3-carboxamide. $^1$H NMR (600 MHz, DMSO-d6/CDCl$_3$) δ ppm 0.88 (d, J=6.44 Hz, 6H), 1.79-1.91 (m, 1H), 2.84 (d, J=4.69 Hz, 3H), 3.08 (t, J=6.15 Hz, 2H), 3.21 (t, J=6.15 Hz, 2H), 4.47 (t, J=6.15 Hz, 2H), 7.20 (dd, J=19.92, 8.20 Hz, 2H), 7.29-7.41 (m, 4H), 7.50 (d, J=8.79 Hz, 1H), 7.67 (s, 1H), 7.79-7.91 (m, 3H), 8.00 (dd, J=8.50, 5.57 Hz, 2H), 8.34 (t, J=5.57 Hz, 1H), 8.45 (d, J=4.10 Hz, 1H), 8.51 (d, J=4.69 Hz, 1H). LCMS m/z 566.34 (M+H), Rt 4.32 min., 100% purity.

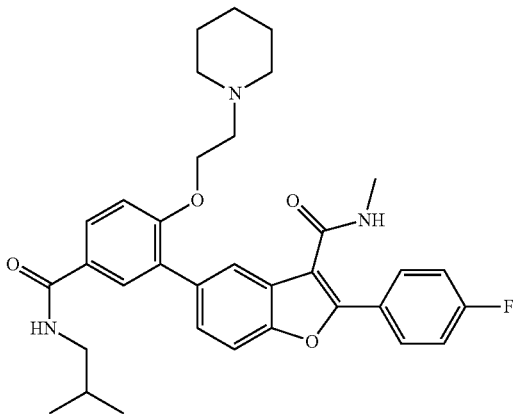

2-(4-Fluorophenyl)-5-(5-(isobutylcarbamoyl)-2-(2-(piperidin-1-yl)ethoxy)phenyl)-N-methylbenzofuran-3-carboxamide. $^1$H NMR (600 MHz, DMSO-d6/CDCl$_3$) δ ppm 0.89 (d, J=6.44 Hz, 6H), 1.32-1.38 (m, 2H), 1.38-1.43 (m, 2H), 1.44-1.52 (m, 2H), 1.79-1.93 (m, 1H), 2.32-2.45 (m, 4H), 2.57-2.68 (m, 2H), 2.84 (d, J=4.10 Hz, 3H), 3.08 (t, J=6.15 Hz, 2H), 4.10-4.20 (m, 2H), 7.16 (d, J=8.79 Hz, 1H), 7.32 (t, J=8.79 Hz, 2H), 7.61 (q, J=8.79 Hz, 2H), 7.76 (s, 1H), 7.86 (d, J=8.20 Hz, 1H), 7.89 (s, 1H), 7.98 (dd, J=8.20, 5.86 Hz, 2H), 8.31-8.44 (m, 2H). LCMS m/z 572.37 (M+H), Rt 3.89 min., 95.4% purity.

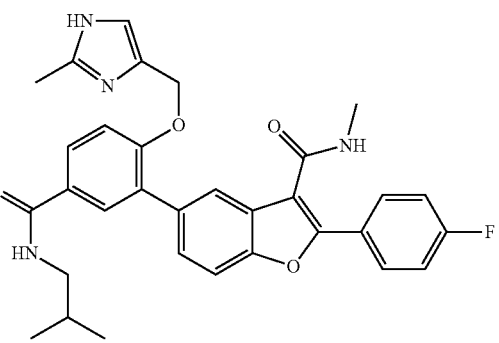

2-(4-Fluorophenyl)-5-(5-(isobutylcarbamoyl)-2-((2-methyl-1H-imidazol-4-yl)methoxy)phenyl)-N-methylbenzofuran-3-carboxamide. $^1$H NMR (600 MHz, DMSO-d6/CDCl$_3$) δ ppm 0.89 (d, J=6.44 Hz, 6H), 1.85 (dd, J=12.01, 6.74 Hz, 1H), 2.14-2.38 (m, 3H), 2.81-2.88 (m, 3H), 3.04-3.12 (m, 2H), 5.00 (s, 1H), 6.91-7.03 (m, 1H), 7.32 (t, J=9.08 Hz, 2H), 7.50-7.68 (m, 2H), 7.70 (d, J=6.44 Hz, 1H), 7.79 (d, J=4.10 Hz, 2H), 7.86 (d, J=11.72 Hz, 1H), 7.94 (s, 1H), 7.96-8.04 (m, 1H), 8.34 (t, J=5.57 Hz, 1H), 8.40 (d, J=4.69 Hz, 1H). LCMS m/z 555.34 (M+H), Rt 3.57 min., 93.3% purity.

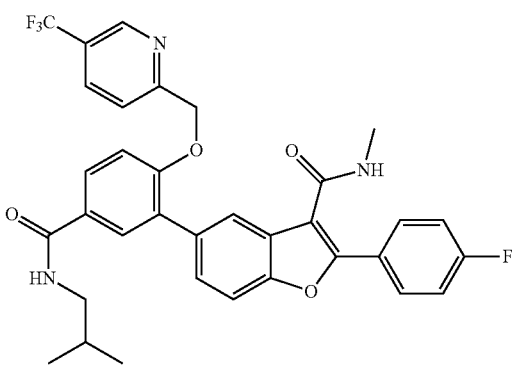

2-(4-Fluorophenyl)-5-(5-(isobutylcarbamoyl)-2-((5-(trifluoromethyl)pyridin-2-yl)methoxy)phenyl)-N-methylbenzofuran-3-carboxamide. $^1$H NMR (600 MHz, DMSO-d6/CDCl$_3$) δ ppm 0.90 (d, J=7.03 Hz, 6H), 1.82-1.92 (m, 1H), 2.79 (d, J=4.69 Hz, 3H), 3.09 (t, J=6.15 Hz, 2H), 5.39 (s, 2H), 7.27 (d, J=8.79 Hz, 1H), 7.34 (t, J=8.50 Hz, 2H), 7.62 (t, J=8.50 Hz, 2H), 7.71 (d, J=8.20 Hz, 1H), 7.89 (d, J=8.20 Hz, 1H), 7.92 (s, 1H), 7.95-8.02 (m, 3H), 8.16 (d, J=8.20 Hz, 1H), 8.39 (t, J=5.57 Hz, 1H), 8.44 (d, J=4.69 Hz, 1H), 8.90 (s, 1H). LCMS m/z 620.32 (M+H), Rt 5.09 min., 97.9% purity.

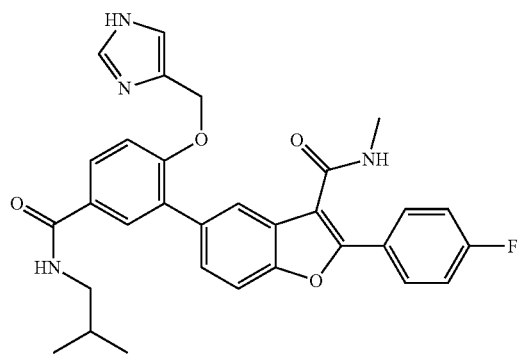

5-(2-((1H-imidazol-4-yl)methoxy)-5-(isobutylcarbamoyl)phenyl)-2-(4-fluorophenyl)-N-methylbenzofuran-3-carboxamide. LCMS m/z 541.29 (M+H), Rt 3.51 min., 100% purity.

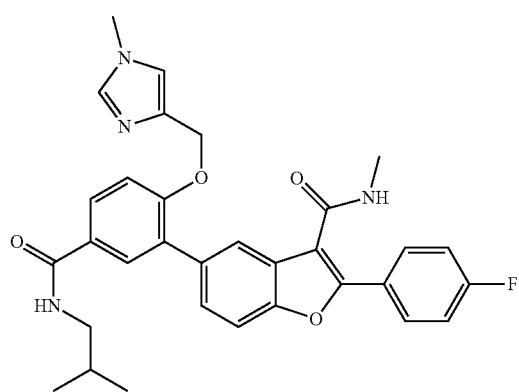

2-(4-Fluorophenyl)-5-(5-(isobutylcarbamoyl)-2-((1-methyl-1H-imidazol-4-yl)methoxy)phenyl)-N-methylbenzofuran-3-carboxamide. $^1$H NMR (600 MHz, DMSO-d6/CDCl$_3$) δ ppm 0.88 (d, J=6.44 Hz, 6H), 1.83 (dt, J=13.48, 6.74 Hz, 1H), 2.84 (d, J=4.69 Hz, 3H), 3.06 (t, J=6.44 Hz, 2H), 3.63 (s, 3H), 3.88 (s, 2H), 7.00 (s, 1H), 7.32 (t, J=8.79 Hz, 2H), 7.55 (d, J=8.20 Hz, 1H), 7.63-7.70 (m, 3H), 7.74 (d, J=14.65 Hz, 2H), 7.94 (s, 1H), 7.99 (dd, J=8.20, 5.27 Hz, 2H), 8.23 (s, 1H), 8.39 (d, J=4.10 Hz, 1H). LCMS m/z 555.35 (M+H), Rt 4.11 min., 100% purity.

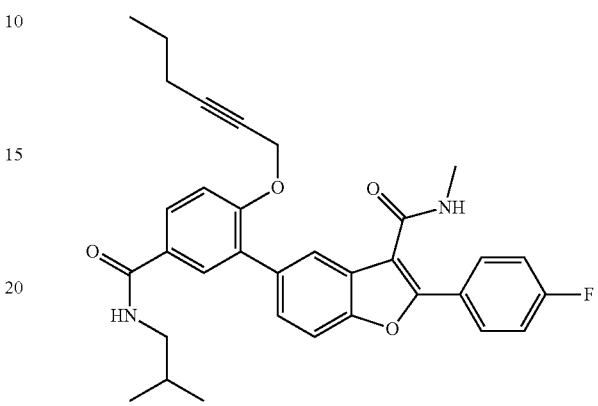

2-(4-Fluorophenyl)-5-(2-(hex-2-ynyloxy)-5-(isobutylcarbamoyl)phenyl)-N-methylbenzofuran-3-carboxamide. $^1$H NMR (600 MHz, DMSO-d6/CDCl$_3$) δ ppm 0.83-0.97 (m, 9H), 1.36-1.48 (m, 2H), 1.82-1.90 (m, 1H), 2.16 (t, J=6.74 Hz, 2H), 2.84 (d, J=4.69 Hz, 3H), 3.09 (t, J=6.44 Hz, 2H), 4.82 (br. s., 2H), 7.23 (d, J=8.20 Hz, 1H), 7.29-7.33 (m, 2H), 7.51 (d, J=8.79 Hz, 1H), 7.65 (d, J=8.20 Hz, 1H), 7.72 (s, 1H), 7.84-7.91 (m, 2H), 7.99 (dd, J=8.20, 5.27 Hz, 2H), 8.36 (t, J=5.57 Hz, 1H), 8.40 (d, J=4.10 Hz, 1H). LCMS m/z 541.35 (M+H), Rt 5.20 min., 95.3% purity.

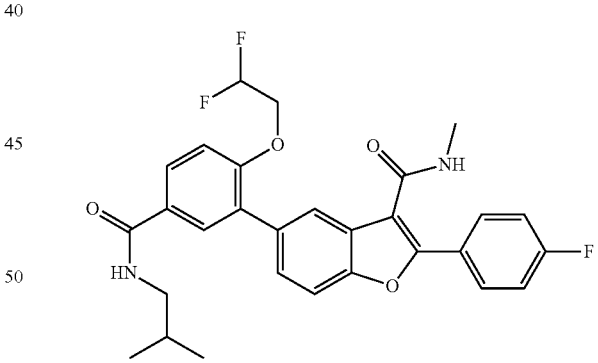

5-(2-(2,2-Difluoroethoxy)-5-(isobutylcarbamoyl)phenyl)-2-(4-fluorophenyl)-N-methyl benzofuran-3-carboxamide. $^1$H NMR (600 MHz, DMSO-d6/CDCl$_3$) δ ppm 0.89 (d, J=6.44 Hz, 6H), 1.86 (dt, J=13.48, 6.74 Hz, 1H), 2.84 (d, J=4.10 Hz, 3H), 3.09 (t, J=6.44 Hz, 2H), 4.39 (td, J=14.35, 2.93 Hz, 2H), 6.15-6.40 (m, 1H), 7.23 (d, J=8.79 Hz, 1H), 7.32 (t, J=8.79 Hz, 2H), 7.56 (d, J=8.79 Hz, 1H), 7.66 (d, J=8.20 Hz, 1H), 7.79 (s, 1H), 7.89 (d, J=8.79 Hz, 1H), 7.93 (s, 1H), 7.99 (dd, J=8.20, 5.27 Hz, 2H), 8.35-8.44 (m, 2H). LCMS m/z 525.27 (M+H), Rt 4.44 min., 97.4% purity.

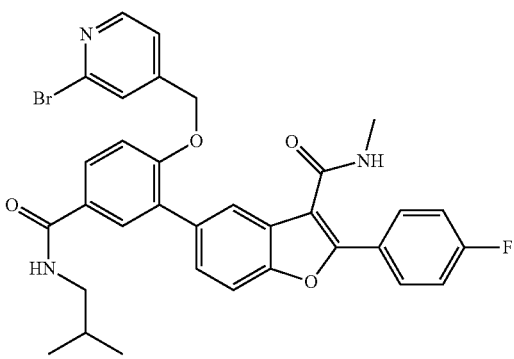

5-(2-((2-Bromopyridin-4-yl)methoxy)-5-(isobutylcarbamoyl)phenyl)-2-(4-fluorophenyl)-N-methylbenzofuran-3-carboxamide. $^1$H NMR (600 MHz, DMSO-d6/CDCl$_3$) δ ppm 0.89 (d, J=6.44 Hz, 6H), 1.81-1.91 (m, 1H), 2.82 (d, J=4.69 Hz, 3H), 3.09 (t, J=6.15 Hz, 2H), 5.27 (s, 2H), 7.21 (d, J=8.79 Hz, 1H), 7.33 (t, J=8.50 Hz, 2H), 7.37 (d, J=4.69 Hz, 1H), 7.54 (s, 1H), 7.61 (d, J=8.79 Hz, 1H), 7.70 (d, J=8.79 Hz, 1H), 7.83 (s, 1H), 7.89 (d, J=8.79 Hz, 1H), 7.94 (s, 1H), 7.99 (dd, J=8.20, 5.27 Hz, 2H), 8.32 (d, J=5.27 Hz, 1H), 8.38 (d, J=4.69 Hz, 2H). LCMS m/z 630.26 (M+H), Rt 4.71 min., 98.4% purity.

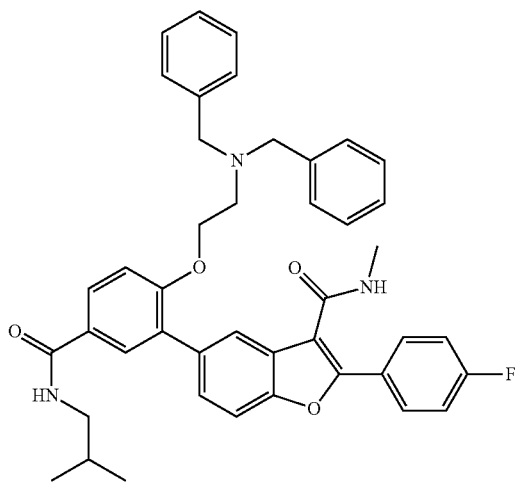

5-(2-(2-(Dibenzylamino)ethoxy)-5-(isobutylcarbamoyl)phenyl)-2-(4-fluorophenyl)-N-methylbenzofuran-3-carboxamide. Post purification LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. The NMR spectrum was recorded at room temperature using a Bruker DRX400 spectrometer. $^1$H NMR (400 MHz, CD$_3$OD) δ ppm 0.96 (d, J=6.53 Hz, 6 H), 1.83-2.07 (m, 1H), 2.81 (t, J=5.40 Hz, 2H), 2.90 (s, 3H), 3.19 (d, J=7.03 Hz, 2H), 3.53 (s, 4H), 4.10 (t, J=5.40 Hz, 2H), 6.99 (d, J=8.53 Hz, 1H), 7.14 (dd, J=5.52, 3.01 Hz, 2H), 7.17-7.23 (m, 8H), 7.23-7.29 (m, 2H), 7.41-7.47 (m, 1H), 7.48-7.55 (m, 1H), 7.75-7.82 (m, 2H), 7.84 (d, J=2.26 Hz, 1H), 7.92 (dd, J=8.66, 5.40 Hz, 2H). LCMS m/z 684.40 (M+H), R$_t$=1.897 min. HPLC Rt 14.159 min. (XBridge Phenyl C18), 100% purity.

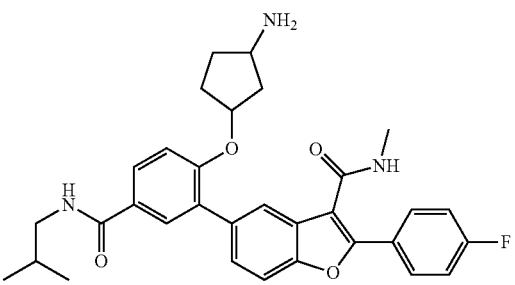

5-(2-(3-Aminocyclopentyloxy)-5-(isobutylcarbamoyl)phenyl)-2-(4-fluorophenyl)-N-methyl benzofuran-3-carboxamide. Post purification LC/MS data was obtained on a Shimadzu analytical LC/Micromass Platform LC (ESI+/−) at 220 nm using the following set of conditions: Luna 10 μm C18, 3.0×50 mm column, with a gradient of 0-100% B (B=95% HPLC grade acetonitrile/10 mM ammonium acetate/5% HPLC grade water), (A=95% HPLC grade water/10 mM ammonium acetate/5% HPLC grade acetonitrile), in 4 minutes with a 1 minute hold at a rate of 5 mL/minute. HPLC purity was determined using a Shimadzu analytical LC at 254 nm and 256 nm with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. The NMR spectrum was recorded at room temperature using a Bruker DRX400 spectrometer. $^1$HNMR (400 MHz, THF-d8) δ ppm 0.93 (d, J=6.78 Hz, 6H), 1.77-1.97 (m, 3H), 2.04-2.19 (m, 2H), 2.19-2.32 (m, 2H), 2.90 (d, J=4.52 Hz, 3H), 3.17 (t, J=6.40 Hz, 2H), 3.69-3.82 (m, 2H), 7.04 (d, J=8.53 Hz, 1H), 7.21 (t, J=8.78 Hz, 2H), 7.41-7.50 (m, 1H), 7.50-7.56 (m, 1H), 7.60-7.72 (m, 2H), 7.81 (dd, J=8.66, 2.13 Hz, 1H), 7.85 (d, J=1.25 Hz, 1H), 7.90 (d, J=2.01 Hz, 1H), 7.99-8.10 (m, 2H), 8.42 (br. s., 2H). LCMS Rt 1.937 min., m/z 542.34 (M−H) and m/z 544.29 (M+H). HPLC Rt 6.870 min. (Sunfire C18), 99.1% purity and 11.133 min. (Gemini C18), 98.9% purity.

An alternative synthesis to these ether linked analogs was carried out using phenol template in DMF with alkyl bromides and DBU. To a 2 dram vial was added 2-(4-fluorophenyl)-5-(2-hydroxy-5-(isobutylcarbamoyl)phenyl)-N-methylbenzofuran-3-carboxamide (46.0 mg, 0.1 mmol), DMF (2 mL), 4.0 equivalents of DBU, 1,8-Diazabicyclo[5.4.0]undec-7-ene (0.4 mmol) and 3.0 equivalents (0 3 mmol) of alkyl bromide. The vials were sealed and shaken at 75° C. in a dry bath. Upon reaction completion the crude products were concentrated, diluted with 2 mL of acetonitrile and purified using a Shimadzu preparative HPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 μm C18 4.6×100 mm column at a gradient of 30-100% B and a flow rate of 40 mL/min. over 8 minutes with a 10 minute hold. The desired products were evaporated to dryness in a Savant Speedvac overnight obtaining 25-60% yield of the desired ethers as powders. The NMR spectrum was recorded at room temperature using a Bruker DRX400 spectrometer. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

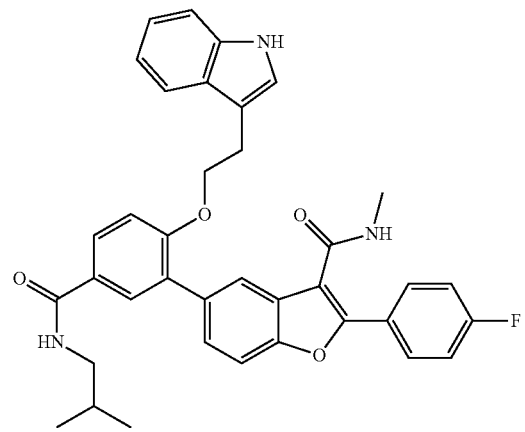

5-(2-(2-(1H-indol-3-yl)ethoxy)-5-(isobutylcarbamoyl)phenyl)-2-(4-fluorophenyl)-N-methyl benzofuran-3-carboxamide. $^1$H NMR (500 MHz, CD$_3$OD) δ ppm 0.92-1.04 (m, 6H), 1.87-2.03 (m, 1H), 2.95 (s, 3H), 3.15-3.24 (m, 4H), 4.37 (t, J=6.71 Hz, 2H), 6.94 (t, J=7.48 Hz, 1H), 6.98 (s, 1H), 7.07 (t, J=7.63 Hz, 1H), 7.18 (d, J=8.55 Hz, 1H), 7.24-7.36 (m, 3H), 7.44-7.50 (m, 2H), 7.51-7.56 (m, 1H), 7.84 (td, J=4.27, 2.44 Hz, 2H), 7.88 (d, J=2.14 Hz, 1H), 7.94-8.03 (m, 2H). LCMS m/z 604.31 (M+H), Rt 2.621 min. HPLC Rt 11.054 min. (Sunfire C18), 98.1% purity and 12.561 min. (XBridge Phenyl C18), 97.8% purity.

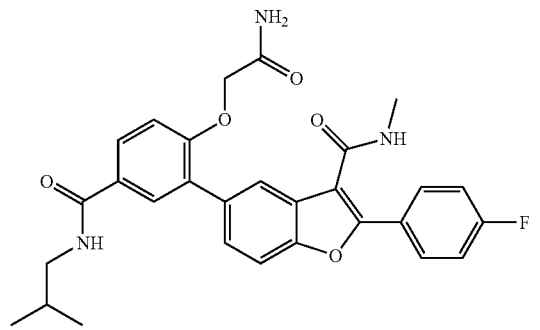

5-(2-(2-Amino-2-oxoethoxy)-5-(isobutylcarbamoyl)phenyl)-2-(4-fluorophenyl)-N-methyl benzofuran-3-carboxamide. $^1$H NMR (400 MHz, THF-d8) δ ppm 0.86-1.02 (m, 6H), 1.81-1.99 (m, 1H), 2.91 (d, J=4.77 Hz, 3H), 3.06-3.29 (m, 2H), 4.46 (s, 2H), 6.43 (br. s., 1H), 6.69 (br. s., 1H), 7.08 (d, J=8.78 Hz, 1H), 7.16-7.27 (m, 2H), 7.53 (br. s., 1H), 7.56-7.62 (m, 2H), 7.86 (dd, J=8.53, 2.26 Hz, 1H), 7.93 (d, J=2.26 Hz, 1H), 7.97 (s, 1H), 8.09-8.19 (m, 2H). LCMS m/z 518.36 (M+H), Rt 1.880 min. HPLC (Sunfire C18) Rt 8.209 min, 100% purity and (XBridge Phenyl C18) Rt 11.254 min., 99.8% purity.

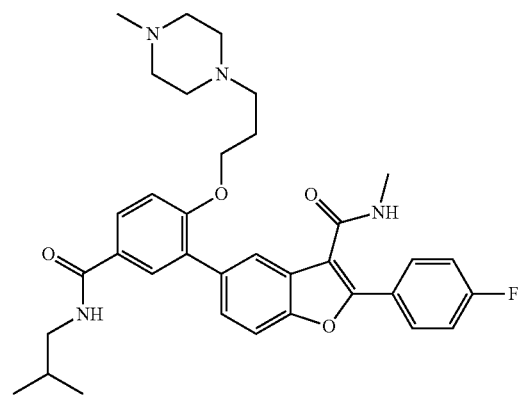

5-(2-(2-(1H-indol-3-yl)ethoxy)-5-(isobutylcarbamoyl)phenyl)-2-(4-fluorophenyl)-N-methyl benzofuran-3-carboxamide. $^1$H NMR (500 MHz, CD$_3$OD) δ ppm 0.87-1.03 (m, 6H), 1.83-2.00 (m, 1H), 2.17 (dd, J=9.77, 5.49 Hz, 2H), 2.81-2.90 (s, 3H), 2.90-3.00 (s, 3H), 3.12-3.25 (m, 4H), 3.42 (br. s., 8H), 4.21 (t, J=5.65 Hz, 2H), 7.17 (d, J=8.85 Hz, 1H), 7.22-7.33 (m, 2H), 7.53 (dd, J=8.55, 1.83 Hz, 1H), 7.65 (d, J=8.24 Hz, 1H), 7.86 (td, J=8.47, 2.29 Hz, 3H), 7.89-7.96 (m, 2H). LCMS m/z 601.36 (M+H), Rt 1.375 min. HPLC Rt 6.010 min. (Sunfire C18), 99.3% purity and 11.793 min. (XBridge Phenyl C18), 98.4% purity.

511

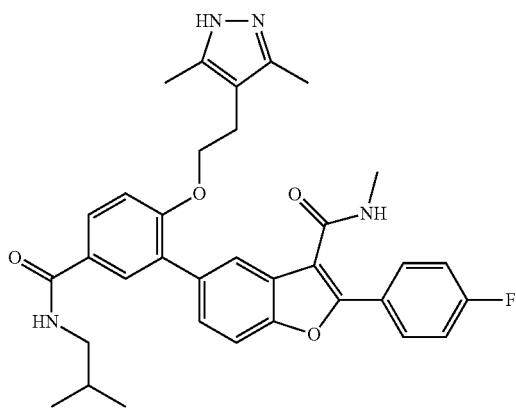

5-(2-(2-(3,5-Dimethyl-1H-pyrazol-4-yl)ethoxy)-5-(isobutylcarbamoyl)phenyl)-2-(4-fluorophenyl)-N-methylbenzofuran-3-carboxamide. $^1$H NMR (500 MHz, CD$_3$OD) δ ppm 0.89-1.01 (m, 6H), 1.86-1.98 (m, 1H), 2.02 (s, 6H), 2.90 (t, J=5.95 Hz, 2H), 2.95 (s, 3H), 3.14-3.22 (m, 2H), 4.24 (t, J=5.95 Hz, 2H), 7.18 (d, J=8.55 Hz, 1H), 7.24-7.33 (m, 2H), 7.37 (dd, J=8.39, 1.68 Hz, 1H), 7.59 (d, J=8.55 Hz, 1H), 7.68 (d, J=1.83 Hz, 1H), 7.80 (d, J=2.44 Hz, 1H), 7.85 (dd, J=8.70, 2.29 Hz, 1H), 7.93-8.02 (m, 2H). LCMS m/z 583.32 (M+H), Rt 1.698 min. HPLC Rt 7.270 min. (Sunfire C18), 92.6% purity and 11.994 min. (XBridge Phenyl C18), 92.0% purity.

512

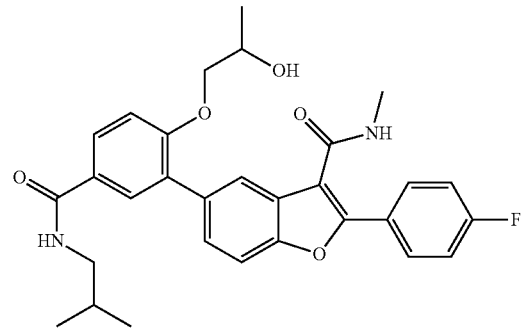

2-(4-Fluorophenyl)-5-(2-(2-hydroxypropoxy)-5-(isobutylcarbamoyl)phenyl)-N-methyl benzofuran-3-carboxamide. $^1$H NMR (400 MHz, CD$_3$OD) δ ppm 1.04 (d, J=6.53 Hz, 6H), 1.27 (d, J=6.27 Hz, 3H), 1.93-2.08 (m, 1H), 3.03 (s, 3H), 3.27 (d, J=7.03 Hz, 2H), 3.97-4.15 (m, 3H), 7.23 (d, J=8.53 Hz, 1H), 7.32 (t, J=8.91 Hz, 2H), 7.67 (d, J=1.00 Hz, 2H), 7.86-7.93 (m, 1H), 7.96 (d, J=2.26 Hz, 2H), 8.03 (dd, J=9.04, 5.27 Hz, 2H). LCMS m/z 519.28 (M+H), Rt 2.100 min. HPLC Rt 9.279 min. (Sunfire C18), 98.4% purity and 11.674 min. (XBridge Phenyl C18), 98.8% purity.

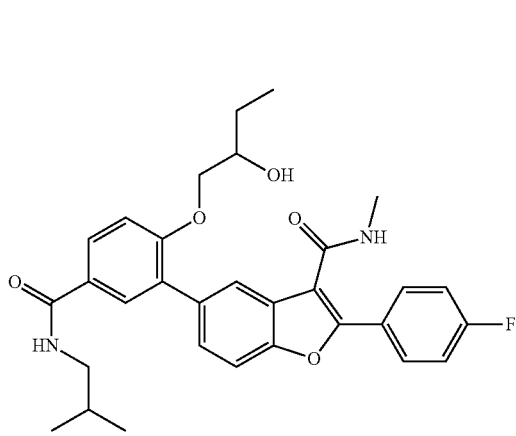

2-(4-Fluorophenyl)-5-(2-(2-hydroxybutoxy)-5-(isobutylcarbamoyl)phenyl)-N-methylbenzofuran-3-carboxamide. $^1$H NMR (400 MHz, CD$_3$OD) δ ppm 0.93-1.15 (m, 9H), 1.45-1.61 (m, 1H), 1.61-1.77 (m, 1H), 2.01 (dt, J=13.55, 6.78 Hz, 1H), 3.03 (s, 3H), 3.27 (d, J=7.03 Hz, 2H), 3.81-3.90 (m, 1H), 4.10 (d, J=5.02 Hz, 2H), 7.24 (d, J=8.78 Hz, 1H), 7.28-7.38 (m, 2H), 7.62-7.72 (m, 2H), 7.91 (dd, J=8.53, 2.26 Hz, 1H), 7.96 (d, J=2.01 Hz, 2H), 8.00-8.08 (m, 2H). LCMS m/z 533.30 (M+H), Rt 2.238 min. HPLC Rt 11.383 min. (Sunfire C18), 95.4% purity and 11.896 min. (XBridge Phenyl C18), 98.5% purity.

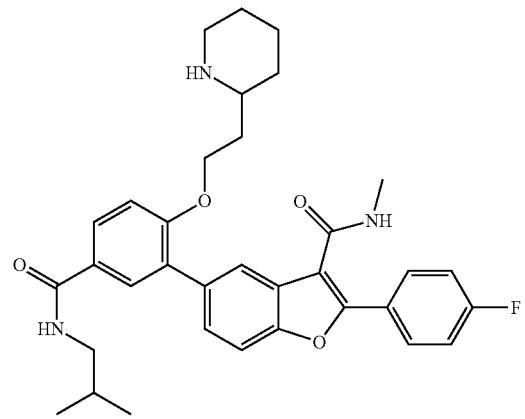

2-(4-Fluorophenyl)-5-(5-(isobutylcarbamoyl)-2-(2-(piperidin-2-yl)ethoxy)phenyl)-N-methyl benzofuran-3-carboxamide. $^1$H NMR (500 MHz, CD$_3$OD) δ ppm 0.92-1.04 (m, 6H), 1.32-1.48 (m, 2H), 1.59 (d, J=14.34 Hz, 1H), 1.78 (br. s., 2H), 1.88-2.06 (m, 3H), 2.11-2.25 (m, 1H), 2.85 (m, 1H), 2.96 (s, 3H), 3.11-3.27 (m, 4H), 4.17-4.37 (m, 2H), 7.23 (d, J=8.85 Hz, 1H), 7.26-7.36 (m, 2H), 7.55 (dd, J=8.55, 1.83 Hz, 1H), 7.70 (d, J=8.55 Hz, 1H), 7.83-8.01 (m, 5 H). LCMS m/z 572.33 (M+H), Rt 1.663 min. HPLC Rt 7.638 min. (Sunfire C18), 98.8% purity and 12.003 min. (XBridge Phenyl C18), 97.3% purity.

513

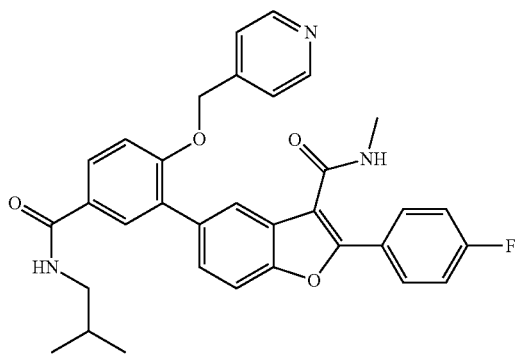

514

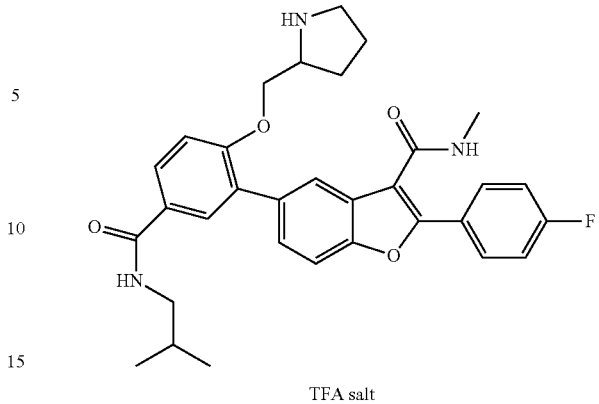

TFA salt 2-(4-Fluorophenyl)-5-(5-(isobutylcarbamoyl)-2-(pyridin-4-ylmethoxy)phenyl)-N-methyl benzofuran-3-carboxamide. $^1$H NMR (500 MHz, CD$_3$OD) δ ppm 0.98 (d, J=6.71 Hz, 6H), 1.83-2.07 (m, 1H), 2.92 (s, 3H), 3.22 (d, J=7.02 Hz, 2H), 5.54 (s, 2H), 7.19-7.39 (m, 3H), 7.62 (dd, J=8.55, 1.53 Hz, 1H), 7.65-7.72 (m, 1H), 7.88-7.99 (m, 5H), 8.01 (d, J=6.41 Hz, 2H), 8.79 (d, J=6.71 Hz, 2H). LCMS m/z 552.28 (M+H), Rt 1.600 min. HPLC Rt 6.831 min. (Sunfire C18), 99.5% purity and 11.871 min. (XBridge Phenyl C18), 99.3% purity.

2-(4-Fluorophenyl)-5-(5-(isobutylcarbamoyl)-2-(pyrrolidin-2-ylmethoxy)phenyl)-N-methyl benzofuran-3-carboxamide, TFA. To a 10 mL RBF was added dichloroethane (1 mL), tert-butyl 2-((2-(2-(4-fluorophenyl)-3-(methylcarbamoyl)benzofuran-5-yl)-4-(isobutylcarbamoyl)phenoxy)methyl)pyrrolidine-1-carboxylate (10.2 mg, 15.8 μmol) and TFA, trifluoroacetic acid, (800 mL). The solution was stirred for 30 minutes at room temperature, then evaporated on the rotovap. The product was diluted with dichloroethane and evaporated once more to give a white solid (99% yield). $^1$H NMR (400 MHz, CD$_3$OD) δ ppm 1.04 (d, J=6.53 Hz, 6H), 1.93-2.12 (m, 4H), 2.24-2.37 (m, 1H), 3.00 (s, 3H), 3.13-3.22 (m, 1H), 3.25-3.30 (m, 2H), 3.30-3.36 (m, 1H), 4.10 (dd, J=7.15, 2.89 Hz, 1H), 4.29 (dd, J=10.67, 7.15 Hz, 1H), 4.51 (dd, J=10.54, 3.26 Hz, 1H), 7.28 (d, J=8.53 Hz, 1H), 7.35 (t, J=8.78 Hz, 2H), 7.60 (dd, J=8.53, 1.51 Hz, 1H), 7.73 (d, J=8.53 Hz, 1H), 7.92-8.08 (m, 5H). LCMS m/z 544.22 (M+H), Rt 1.577 min. HPLC Rt 6.775 min. (Sunfire C18), 99.7% purity and 11.724 min. (XBridge Phenyl C18), 100% purity.

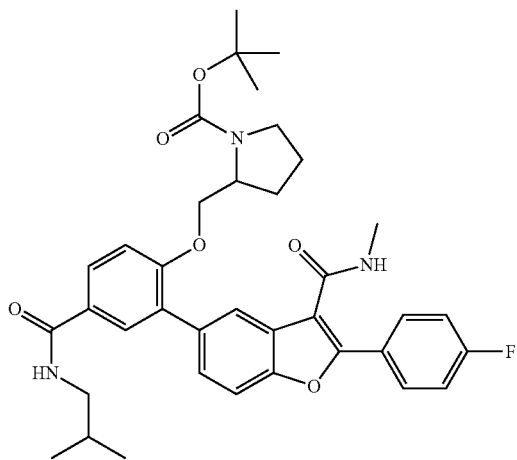

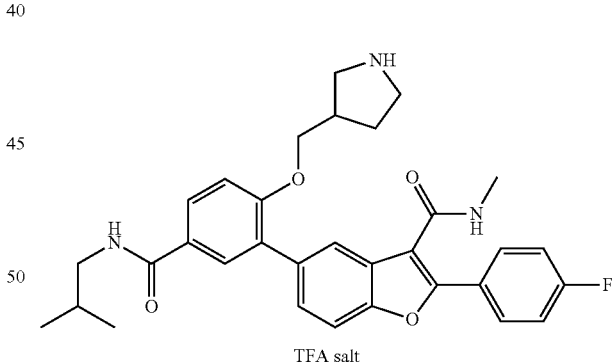

TFA salt tert-Butyl 2-(2-(2-(4-fluorophenyl)-3-(methylcarbamoyl)benzofuran-5-yl)-4-(isobutyl carbamoyl)phenoxy)methyl)pyrrolidine-1-carboxylate. $^1$H NMR (400 MHz, CD$_3$OD) δ ppm 1.04 (d, J=6.53 Hz, 6H), 1.48 (s, 9H), 1.65-1.84 (m, 2H), 1.91-2.12 (m, 3H), 3.02 (s, 3H), 3.06-3.21 (m, 1H), 3.27 (d, J=7.28 Hz, 2H), 3.29-3.34 (m, 1H), 4.09 (br. s., 1H), 4.18-4.30 (m, 2H), 7.26 (d, J=7.53 Hz, 1H), 7.29-7.37 (m, 2H), 7.58 (br. s., 1H), 7.68 (d, J=8.53 Hz, 1H), 7.82-7.96 (m, 3H), 7.99-8.08 (m, 2H). LCMS m/z 666.32 (M+Na), Rt 2.716 min. HPLC Rt 11.711 min. (Sunfire C18), 98.4% purity and 12.663 min. (XBridge Phenyl C18), 98.8% purity.

2-(4-Fluorophenyl)-5-(5-(isobutylcarbamoyl)-2-(pyrrolidin-3-ylmethoxy)phenyl)-N-methyl benzofuran-3-carboxamide, TFA. $^1$H NMR (400 MHz, THF-d8) δ ppm 0.93 (d, J=6.78 Hz, 6H), 1.77-1.98 (m, 2H), 2.10 (dd, J=13.05, 6.78 Hz, 1H), 2.76-2.86 (m, 1H), 2.88-2.98 (m, 3H), 3.18 (t, J=6.40 Hz, 5H), 3.55 (br. s., 1H), 4.02-4.26 (m, 2H), 7.08 (d, J=8.53 Hz, 1H), 7.23 (t, J=8.78 Hz, 2H), 7.48 (dd, J=8.53, 1.76 Hz, 1H), 7.59 (d, J=8.53 Hz, 1H), 7.70 (t, J=5.77 Hz, 1H), 7.80-7.89 (m, 2H), 7.94 (dd, J=9.79, 1.76 Hz, 2H), 7.99 (dd, J=8.91, 5.40 Hz, 2H). HPLC Rt 6.130 min. (Sunfire C18), 98.9% purity and 10.184 min. (XBridge Phenyl C18), 98.6% purity. LCMS m/z 544.18 (M+H), Rt 1.557 min.

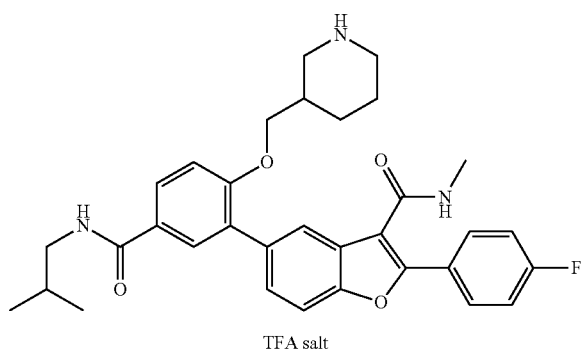

TFA salt

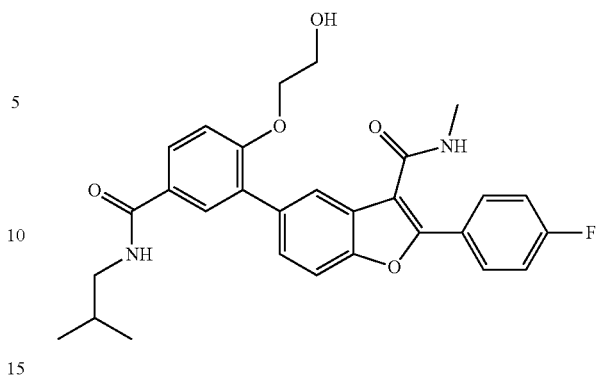

2-(4-Fluorophenyl)-5-(5-(isobutylcarbamoyl)-2-(piperidin-3-ylmethoxy)phenyl)-N-methyl benzofuran-3-carboxamide, TFA. ¹H NMR (400 MHz, THF-d8) δ ppm 0.93 (d, J=6.78 Hz, 6H), 1.40-1.57 (m, 1H), 1.75-2.00 (m, 4H), 2.33 (br. s., 1H), 2.80-3.00 (m, 5H), 3.18 (t, J=6.40 Hz, 2H), 3.32 (d, J=12.05 Hz, 1H), 3.45 (d, J=10.79 Hz, 1H), 3.90-4.12 (m, 2H), 7.03 (d, J=8.53 Hz, 1H), 7.22 (t, J=8.78 Hz, 2H), 7.47 (dd, J=8.53, 1.51 Hz, 1H), 7.58 (d, J=8.53 Hz, 1H), 7.71 (t, J=5.65 Hz, 1H), 7.75-7.86 (m, 2H), 7.92 (s, 2H), 8.01 (dd, J=8.78, 5.52 Hz, 2H). LCMS m/z 558.20 (M+H), Rt 1.595 min. HPLC Rt 6.443 min. (Sunfire C18), 99.2% purity and 10.418 min. (XBridge Phenyl C18), 99.2% purity.

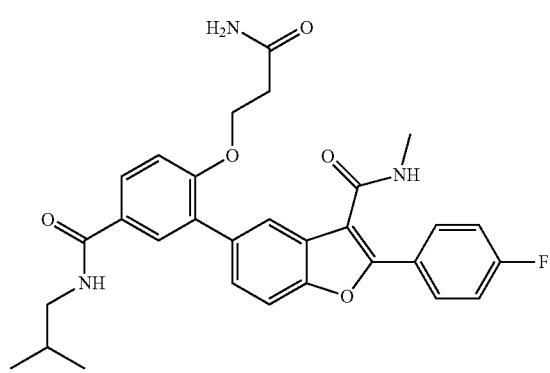

5-(2-(3-Amino-3-oxopropoxy)-5-(isobutylcarbamoyl)phenyl)-2-(4-fluorophenyl)-N-methyl benzofuran-3-carboxamide. ¹H NMR (400 MHz, THF-d8) δ ppm 0.88-0.97 (m, 6H), 1.77 (dt, J=6.71, 3.29 Hz, 1H), 1.89 (dt, J=13.36, 6.74 Hz, 1H), 2.65 (br. s., 1H), 2.96 (s, 3H), 3.10-3.21 (m, 3H), 3.60-3.65 (m, 1H), 6.90 (d, J=8.28 Hz, 1H), 7.16-7.25 (m, 2H), 7.48-7.56 (m, 1H), 7.66-7.73 (m, 2H), 7.73-7.80 (m, 2H), 7.84 (t, J=5.40 Hz, 1H), 7.89 (br. s., 1H), 7.92-8.03 (m, 3H). LCMS Rt 1.835 min., m/z 532.26 (M+H). HPLC Rt 7.465 min. (Sunfire C18), 100% purity and 10.929 min. (XBridge Phenyl C18), 92.9% purity.

2-(4-Fluorophenyl)-5-(2-(2-hydroxyethoxy)-5-(isobutylcarbamoyl)phenyl)-N-methylbenzofuran-3-carboxamide. To a small screw cap vial was added 2-(4-fluorophenyl)-5-(2-hydroxy-5-(isobutylcarbamoyl)phenyl)-N-methylbenzofuran-3-carboxamide (92 mg, 0.2 mmol) in DMF (4 mL), (2-Bromoethoxy)-tert-butyldimethylsilane (0.129 mL, 0.600 mmol), and DBU (0.121 mL, 0.800 mmol). The vial was capped and shaken at 80° C. overnight. The DMF was removed under a stream of nitrogen to give a tan oil which was taken up in 6 mL of acetonitrile and purified using a Shimadzu preparative HPLC employing acetonitrile/water/10 mM ammonium acetate where solvent A was 5% acetonitrile/95% H₂O/10 mM ammonium acetate and solvent B was 5% H₂O/95% acetonitrile/10 mM ammonium acetate with a Phenomenex-Luna 10 μm C18 30×100 mm column at a gradient of 40-100% B and a flow rate of 30 mL/min. over 8 minutes with a 10 minute hold. The solvent was removed on the rotovap to give 44 mgs of the TBS protected alcohol as a clear colorless oil. LCMS m/z 619.47 (M+H), Rt 3.123 min., 96% purity. To the TBS protected alcohol was then added 2.5 mL of tetrahydrofuran along with 2 eq. of 1 M HCl solution (0.14 mmol, 140 μL). The mixture was stirred for 1 hour at room temperature. The reaction mixture was transferred to a separatory funnel, diluted with ethyl acetate, washed with sodium bicarbonate, brine and dried over magnesium sulfate. The organic solvent was evaporated and the product placed under vacuum. The crude product was diluted with 2 mL of acetonitrile, and purified using a Shimadzu preparative HPLC employing acetonitrile/water/ammonium acetate where solvent A was 5% acetonitrile/95% H₂O/10 mM ammonium acetate and solvent B was 5% H2O/95% acetonitrile/10 mM ammonium acetate with a Xbridge C18 5 μm OBD 19×100 mm column at a gradient of 30-100% B and a flow rate of 20 mL/min. over 7 minutes with a 13 minute hold. 18.3 mgs of a white solid (17% yield, 2 steps) was obtained after solvent evaporation. ¹H NMR (400 MHz, THF-d8) δ ppm 0.93 (d, J=6.78 Hz, 6H), 1.80-1.98 (m, 1H), 2.91 (d, J=4.77 Hz, 3H), 3.13-3.23 (m, 2H), 3.79 (t, J=4.89 Hz, 2H), 4.10 (t, J=4.89 Hz, 2H), 7.08 (d, J=8.53 Hz, 1H), 7.21 (t, J=8.78 Hz, 2H), 7.52 (br. s., 1H), 7.52-7.54 (m, 2H), 7.59 (br. s., 1H), 7.84 (dd, J=8.53, 2.26 Hz, 1H), 7.92 (d, J=2.26 Hz, 1H), 8.02 (s, 1H), 8.09-8.20 (m, 2H). LCMS m/z 505.36 (M+H), Rt 2.013 min. HPLC Rt 8.901 min. (Sunfire C18), 92.5% purity and 11.479 min. (XBridge Phenyl C18), 92.0% purity. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/ 0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute.

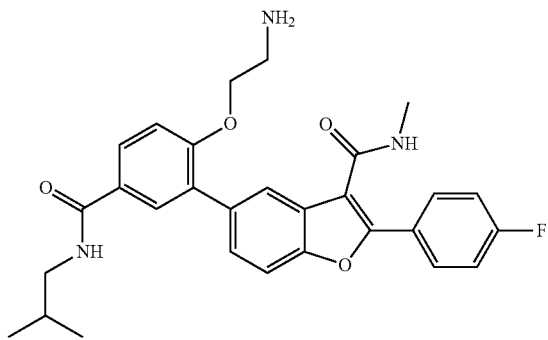

5-(2-(2-Aminoethoxy)-5-(isobutylcarbamoyl)phenyl)-2-(4-fluorophenyl)-N-methylbenzofuran-3-carboxamide. To a 2 dram vial was added 2-(4-fluorophenyl)-5-(2-hydroxy-5-(isobutylcarbamoyl)phenyl)-N-methyl benzofuran-3-carboxamide (92.0 mg, 0.20 mmol) in 3 mL of DMF along with 2-(2-bromoethyl)isoindoline-1,3-dione (152 mg, 0.600 mmol) and DBU (0.120 mL, 0.800 mmol). The vial was capped and shaken at 75° C. over night. The crude reaction mixture was then evacuated to near dryness, taken up in 6 mL of acetonitrile and purified using a Shimadzu preparative HPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 μm C18 30×100 mm column at a gradient of 40-100% B and a flow rate of 40 mL/min. over 10 minutes with a 10 minute hold to give 5-(2-(2-(1,3-dioxoisoindolin-2-yl)ethoxy)-5-(isobutyl carbamoyl)phenyl)-2-(4-fluorophenyl)-N-methylbenzofuran-3-carboxamide as a white solid (30 mgs, 23% yield). $^1$H NMR (400 MHz, DMF-d$_7$) δ ppm 0.93 (d, J=6.78 Hz, 6H), 1.86-1.99 (m, 1H), 2.97 (d, J=4.77 Hz, 3H), 3.14-3.26 (m, 2H), 4.06 (t, J=5.90 Hz, 2H), 4.47 (t, J=5.90 Hz, 2H), 7.33 (d, J=9.29 Hz, 1H), 7.36-7.49 (m, 4H), 7.74-7.86 (m, 5H), 7.97-8.02 (m, 2H), 8.11-8.17 (m, 2H), 8.20 (d, J=4.27 Hz, 1H), 8.42 (s, 1H). LCMS m/z 634.25 (M+H), Rt 2.408 min. HPLC Rt 9.339 min. (Sunfire C18), 100% purity and 11.696 min. (Gemini C18), 98.9% purity. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/ 0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 30-100% B (B=95% HPLC grade acetonitrile/ 0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3 μm 4.6× 150 mm column employing water/methanol/10 mM ammonium bicarbonate with a gradient of 30-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. To a 100 mL RBF fitted with a reflux condenser was added 5-(2-(2-(1,3-dioxoisoindolin-2-yl)ethoxy)-5-(isobutylcarbamoyl) phenyl)-2-(4-fluorophenyl)-N-methylbenzofuran-3-carboxamide (26.4 mg, 0.042 mmol) in methanol and anhydrous hydrazine (1.308 μL, 0.042 mmol) solution (Aldrich, 215155-50G). The flask was placed in a pre-equilibrated oil bath and refluxed for 2 hours. The crude product was concentrated on the rotovap to remove methanol, diluted with dichloromethane, washed with a 0.5M sodium hydroxide solution and extracted. The solvent was removed and the crude product was purified using the Shimadzu preparative HPLC employing acetonitrile/water/0.1% TFA mentioned above with a gradient of 20-100% B to give (13 mgs, 58%) of a white solid. $^1$H NMR (400 MHz, CD$_3$OD) δ ppm 0.94 (d, J=6.78 Hz, 6H), 1.91 (dt, J=13.55, 6.78 Hz, 1H), 2.91 (s, 3H), 3.18 (d, J=7.28 Hz, 2H), 3.33 (t, J=5.02 Hz, 2H), 4.30 (t, J=5.14 Hz, 2H), 7.21 (d, J=8.78 Hz, 1H), 7.26 (t, J=8.78 Hz, 2H), 7.50-7.59 (m, 1H), 7.60-7.68 (m, 1H), 7.81-8.00 (m, 5H). LCMS m/z 504.31 (M+H), Rt 1.538 min. HPLC Rt 6.435 min. (Sunfire C18), 97.1% purity and 11.376 min. (XBridge Phenyl C18), 100% purity.

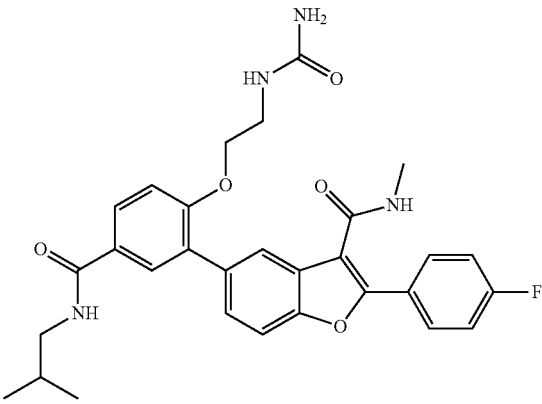

2-(4-Fluorophenyl)-5-(5-(isobutylcarbamoyl)-2-(2-ureidoethoxy)phenyl)-N-methylbenzofuran-3-carboxamide. To a 2 dram vial was added 5-(2-(2-aminoethoxy)-5-(isobutylcarbamoyl)phenyl)-2-(4-fluorophenyl)-N-methylbenzofuran-3-carboxamide (22.7 mg, 0.045 mmol) in ethanol (2 mL) along with water (0.667 mL) and potassium cyanate (5.34 μL, 0.135 mmol). The vial was sealed and the mixture heated to 80° C. with shaking for 24 hours. 3 additional equivalents of potassium cyanate was added to the reaction mixture and the vial re-capped and heated for 3 days. The crude reaction mixture was evaporated, diluted with acetonitrile, filtered and purified using a Shimadzu preparative HPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 µm C18 30×100 mm column at a gradient of 30-100% B and a flow rate of 40 mL/min. over 8 minutes with a 6 minute hold. The solvent was evaporated to give 10 mgs (40%) of a white solid. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 20-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3 µm 4.6×150 mm column employing water/methanol/10 mM ammonium bicarbonate with a gradient of 20-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 0.94 (d, J=6.53 Hz, 6H), 1.82-1.98 (m, 1H), 2.88 (d, J=4.77 Hz, 3H), 3.14-3.23 (m, 2H), 3.47 (q, J=4.94 Hz, 2H), 4.03 (t, J=4.52 Hz, 2H), 5.55 (br. s., 1H), 6.18 (br. s., 1H), 7.03 (d, J=8.53 Hz, 1H), 7.21-7.32 (m, 2H), 7.46-7.51 (m, 1H), 7.51-7.56 (m, 1H), 7.56-7.62 (m, 1H), 7.80 (dd, J=8.53, 2.26 Hz, 1H), 7.84 (d, J=4.52 Hz, 1H), 7.91-8.02 (m, 3H), 8.22 (d, J=1.25 Hz, 1H). LCMS Rt 1.988 min., m/z 547.24 (M+H). HPLC Rt 8.126 min. (Sunfire C18), 99.7% purity and 11.214 min. (Gemini C18), 99.5% purity.

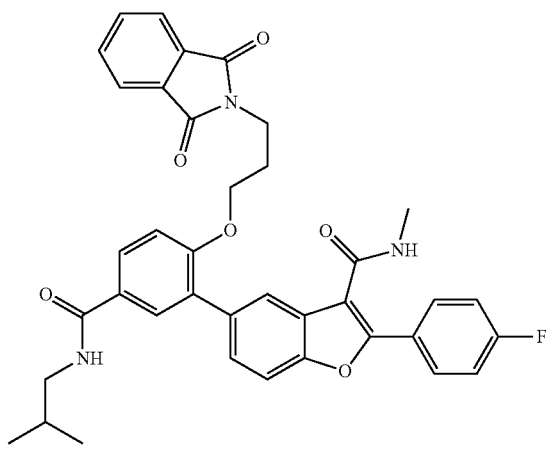

5-(2-(3-(1,3-Dioxoisoindolin-2-yl)propoxy)-5-(isobutylcarbamoyl)phenyl)-2-(4-fluorophenyl)-N-methylbenzofuran-3-carboxamide. $^1$H NMR (400 MHz, THF-d8) δ ppm 0.93 (d, J=6.78 Hz, 6H), 1.81-1.97 (m, 1H), 2.09 (m, 2H), 2.90 (d, J=4.77 Hz, 3H), 3.12-3.26 (m, 2H), 3.79 (t, J=6.65 Hz, 2H), 4.11 (t, J=5.90 Hz, 2 H), 7.03 (d, J=8.78 Hz, 1H), 7.16-7.28 (m, 2H), 7.45 (d, J=4.27 Hz, 1H), 7.48-7.51 (m, 1H), 7.51-7.56 (m, 1H), 7.59 (dd, J=8.78, 1.76 Hz, 1H), 7.65-7.74 (m, 4 H), 7.79-7.90 (m, 3H), 8.08-8.24 (m, 2H). LCMS m/z 648.19 (M+H), Rt 2.458 min. HPLC Rt 10.158 min. (Sunfire C18), 99.4% purity and 12.111 min. (Gemini C18), 99.7% purity.

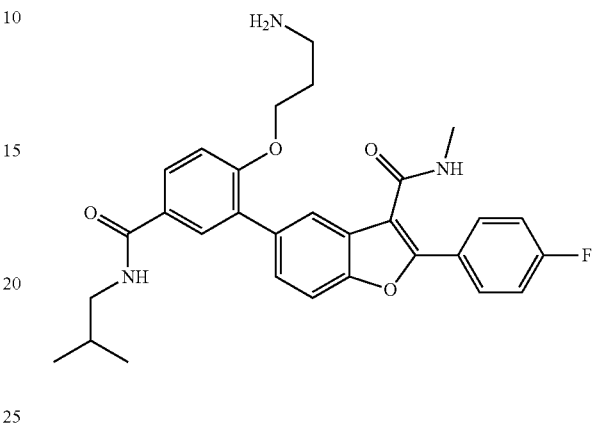

5-(2-(2-Aminoethoxy)-5-(isobutylcarbamoyl)phenyl)-2-(4-fluorophenyl)-N-methylbenzofuran-3-carboxamide. $^1$H NMR (400 MHz, THF-d8) δ ppm 0.93 (d, J=6.53 Hz, 6H), 1.82-1.93 (m, 1H), 2.15 (m, 2H), 2.91 (d, J=4.52 Hz, 3H), 3.08-3.24 (m, 4H), 4.17 (t, J=5.65 Hz, 2H), 7.06 (d, J=8.53 Hz, 1H), 7.18-7.28 (m, 2 H), 7.47 (dd, J=8.53, 1.76 Hz, 1H), 7.53-7.66 (m, 2H), 7.82 (dd, J=8.53, 2.26 Hz, 2H), 7.90 (d, J=2.26 Hz, 1H), 7.95 (d, J=1.51 Hz, 1H), 7.97-8.05 (m, 2H), 8.28 (br. s., 2H). LCMS Rt 1.537 min., m/z 518.16 (M+H). HPLC Rt 10.734 min. (Sunfire C18), 99.2% purity and 10.881 min. (Gemini C18), 99.3% purity. The LC/MS data was obtained on a Shimadzu analytical LC/Micromass Platform LC (ESI+) at 220 nm using the following set of conditions: Waters Sunfire 5 µm C18 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

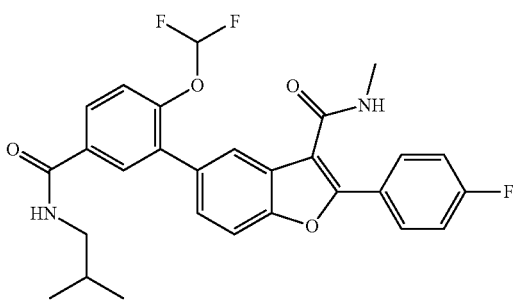

5-(2-(Difluoromethoxy)-5-(isobutylcarbamoyl)phenyl)-2-(4-fluorophenyl)-N-methylbenzofuran-3-carboxamide. To a small microwave vial was added 2-(4-fluorophenyl)-5-(2-hydroxy-5-(isobutylcarbamoyl)phenyl)-N-methylbenzofuran-3-carboxamide (23.02 mg, 0.05 mmol), acetonitrile (400 µL), water (400 µL), and 2-chloro-2,2-difluoro-1-phenylethanone (47.6 mg, 0.250 mmol). The vial was sealed and the reaction mixture subjected to microwave heating (Biotage Initiator) at 110° C. for 8 minutes. The crude reaction mixture was further diluted with acetonitrile, filtered, and purified using a Shimadzu preparative HPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 µm C18 30×100 mm column at a gradient of 30-100% B and a flow rate of 40 mL/min. over 10 minutes with a 10 minute hold. The solvent was evaporated to give product (35%) as a white solid. $^1$H NMR (500 MHz, THF-d8) δ ppm 0.86-1.01 (m, 6H), 1.89 (dt, J=13.50, 6.83 Hz, 1H), 2.90 (d, J=4.58 Hz, 3H), 3.12-3.28 (m, 2H), 6.61-7.04 (m, 1H), 7.18-7.27 (m, 2H), 7.31 (d, J=8.54 Hz, 1H), 7.49 (dd, J=8.55, 1.83 Hz, 1H), 7.53 (d, J=4.27 Hz, 1H), 7.59 (d, J=8.55 Hz, 1H), 7.78 (t, J=5.49 Hz, 1H), 7.82 (d, J=1.22 Hz, 1H), 7.91 (dd, J=8.55, 2.44 Hz, 1H), 7.98 (d, J=2.14 Hz, 1H), 8.09-8.17 (m, 2H). LCMS m/z 511.21 (M+H), Rt 2.393 min. HPLC Rt 12.213 min. (Sunfire C18), 99.3% purity and 15.427 min. (XBridge C18), 99.8% purity. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 30-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters Phenyl XBridge C18 3.5 µm 4.6×150 mm column employing water/methanol/10 mM ammonium bicarbonate with a gradient of 30-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

3-Bromo-N-isobutyl-5-isopropoxybenzamide. To a large screw top vial was added 3-bromo-5-hydroxybenzoic acid (1 g, 4.61 mmol), pyridine (10 mL), N1-((ethylimino)methylene)-N3,N3-dimethylpropane-1,3-diamine, HCl (0.972 g, 5.07 mmol) (EDAC) along with 2-methylpropan-1-amine (0.504 mL, 5.07 mmol). The vial was capped and the mixture shaken over night. The reaction mixture was acidified with 10 mL of an ice cold 1 M HCl solution. The mixture was diluted with dichloromethane, extracted, washed with brine and dried over magnesium sulfate. The reaction mixture was filtered then added to the top of a 240 g Thomson silica gel cartridge. The product was eluted with 0-12% (3000 mL) methanol in dichloromethane to give 3-bromo-5-hydroxy-N-isobutylbenzamide (95%) as a yellow solid. LCMS Rt 1.632 min., m/z 273.99 (M+H), 93% purity. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 30-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. To a sealed tube was added 3-bromo-5-hydroxy-N-isobutylbenzamide (380.4 mg, 1.398 mmol), DMF (15 mL), 2-iodopropane (0.210 mL, 2.097 mmol), and potassium carbonate (290 mg, 2.097 mmol). The tube was sealed and heated to 90° C. overnight. The reaction mixture was cooled, transferred to a separatory funnel, diluted with ethyl acetate and extracted. The organic solution was washed with 1M HCl, brine, dried over magnesium sulfate, filtered and evaporated to dryness. The resulting orange oil was taken up in dichloromethane and purified using the Biotage Horizon with a 110 g Thomson silica gel column employing 0-5% methanol and 2000 mL of solvent to give a near quantitative yield of 3-bromo-N-isobutyl-5-isopropoxybenzamide as a light yellow solid. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 µm 4.6×150 mm column employing water/acetonitrile/0.1% TFA with a gradient of 30-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. $^1$H NMR (400 MHz, CDCl$_3$) δ ppm 0.87-1.04 (m, 6H), 1.23-1.37 (m, 6H), 1.79-2.00 (m, 1H), 3.25 (t, J=6.40 Hz, 2H), 4.57 (dt, J=12.05, 6.02 Hz, 1H), 6.29 (br. s., 1H), 7.08-7.19 (m, 1H), 7.21-7.26 (m, 1H), 7.38 (s, 1H). LCMS Rt 2.413 min., m/z 315.01 (M+H), 95% purity.

3-Bromo-N-isobutyl-4-(trifluoromethoxy)benzamide. To a large screw top vial was added previously synthesized 3-bromo-4-(trifluoromethoxy)benzoic acid (100 mg, 0.351 mmol), pyridine (5 mL), 2-methylpropan-1-amine (0.038 mL, 0.386 mmol), N1-((ethylimino)methylene)-N3,N3-dimethylpropane-1,3-diamine, HCl (EDAC) (74.0 mg, 0.386 mmol) and HATU, 2-(7-aza-1H-benzotriazole-1-yl)-1,1,3,3-tetramethyluronium hexafluorophosphate (400 mg, 1.053 mmol). The vial was capped and shaken overnight at room temperature. The crude reaction mixture was diluted with methanol and purified using a Shimadzu preparative HPLC employing methanol/water/0.1% TFA where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 30-100% B and a flow rate of 40 mL/min. over 9 minutes with a 11 minute hold to give 75 mgs (62%) of a yellow solid. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, CD$_3$OD) δ ppm 0.98-1.11 (m, 6H), 1.91-2.09 (m, 1H), 3.22-3.30 (m, 2H), 7.57 (dd, J=8.53, 1.51 Hz, 1H), 7.96 (dd, J=8.53, 2.26 Hz, 1H), 8.25 (d, J=2.01 Hz, 1H), 8.68 (br. s., 1H). HPLC Rt 17.141 min. (Sunfire C18), 99.5% purity and 15.912 min. (Gemini C18), 100% purity. LCMS Rt 2.367 min., m/z 341.99 (M+H).

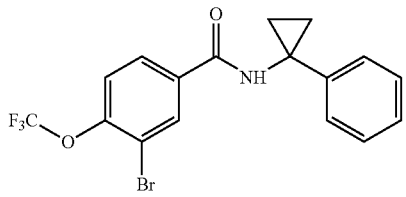

3-Bromo-N-(1-phenylcyclopropyl)-4-(trifluoromethoxy)benzamide. $^1$H NMR (400 MHz, CD$_3$OD) δ ppm 1.40 (d, J=4.52 Hz, 4H), 7.16-7.30 (m, 1H), 7.32-7.41 (m, 4H), 7.58 (dd, J=8.66, 1.38 Hz, 1H), 7.99 (dd, J=8.66, 2.13 Hz, 1H), 8.28 (d, J=2.01 Hz, 1H), 9.42 (br. s., 1H). LCMS Rt 2.56 min., m/z 401.97 (M+H). HPLC Rt 15.171 min. (Sunfire C18), 98.8% purity and 16.066 min. (Gemini C18), 100% purity.

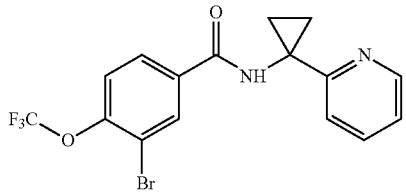

3-Bromo-N-(1-(pyridin-2-yl)cyclopropyl)-4-(trifluoromethoxy)benzamide. $^1$H NMR (400 MHz, CD$_3$OD) δ ppm 1.70-1.80 (m, 2H), 1.80-1.91 (m, 2H), 7.57 (dd, J=8.78, 1.25 Hz, 1H), 7.76-7.88 (m, 1H), 8.03 (dd, J=8.53, 2.26 Hz, 1H), 8.33 (d, J=2.01 Hz, 1H), 8.43 (t, J=8.03 Hz, 1H), 8.63 (d, J=5.52 Hz, 1H). LCMS Rt 1.420 min, m/z 402.95 (M+H).

HPLC Rt 5.611 min. (Sunfire C18), 93.8% purity and 11.206 min. (Gemini C18), 98.4% purity.

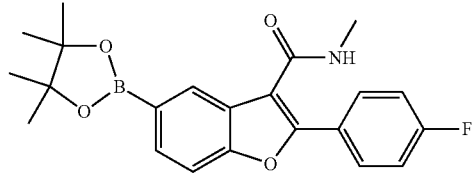

2-(4-Fluorophenyl)-N-methyl-5-(4,4,5,5-tetramethyl-1,3,2-dioxaborolan-2-yl)benzofuran-3-carboxamide. To a sealed tube was added 2-(4-fluorophenyl)-3-(methylcarbamoyl)benzofuran-5-yl trifluoro methanesulfonate (2.000 g, 4.79 mmol), dioxane (20 mL), triethylamine (1.993 mL, 14.38 mmol), 4,4,4',4',5,5,5',5'-octamethyl-2,2'-bi(1,3,2-dioxaborolane) (4.87 g, 19.17 mmol), and finally PdCl$_2$(dppf) (0.235 g, 0.144 mmol). The vial was flushed with N$_2$, sealed and heated overnight in an oil bath at 80° C. The reaction mixture was cooled, diluted with dichloromethane, and washed with a 0.1M HCl solution then brine. The brown mixture was pulled through a plug of 1:1 magnesium sulfate/celite to give a dark brown solid after solvent evaporation. The crude product was taken up in 50 mL of dichloromethane and added to the top of a pre-equilibrated 240 g Thomson silica gel cartridge. The product was eluted with 0-2% methanol in dichloromethane to give a 80% yield of 2-(4-fluorophenyl)-N-methyl-5-(4,4,5,5-tetramethyl-1,3,2-dioxaborolan-2-yl)benzofuran-3-carboxamide as a tan solid. $^1$H NMR (400 MHz, THF-d8) δ ppm 1.34 (s, 12H), 2.92-2.95 (m, 3H), 7.20 (t, J=8.91 Hz, 2H), 7.50 (d, J=8.28 Hz, 2H), 7.74 (dd, J=8.28, 1.00 Hz, 1H), 8.08-8.13 (m, 2H), 8.14 (s, 1 H). LCMS m/z 396.18 (M+H), Rt 2.455 min., 90% purity.

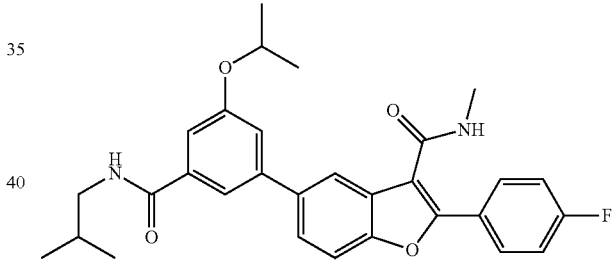

2-(4-Fluorophenyl)-5-(3-(isobutylcarbamoyl)-5-isopropoxyphenyl)-N-methylbenzofuran-3-carboxamide. To a medium sized microwave vial was added 1 (465 mg, 1.0 mmol), dioxane (15 mL), water (1.500 mL), 3-bromo-N-isobutyl-5-isopropoxybenzamide (377 mg, 1.200 mmol), dicyclohexyl(2',6'-dimethoxybiphenyl-2-yl)phosphine (82 mg, 0.200 mmol), potassium phosphate, tribasic (849 mg, 4.00 mmol) and finally palladium(II) acetate (44.9 mg, 0.200 mmol). The vial was capped and subjected to microwave heating (150° C.) in a Biotage Initiator for 13 minutes. The reaction mixture was diluted with 150 mL of dichloromethane, washed with a 1M HCl solution, then water and finally brine. The solution was filtered through pad of 1:1 celite/magnesium sulfate then evaporated to give a brown oil. The crude product was taken up in dichloromethane and added to the top of a pre-equilibrated 100 g Biotage silica gel cartridge. The product was eluted with a 0-3% methanol in dichloromethane solvent mixture to give product as a light tan solid (51%). $^1$H NMR (400 MHz, THF-d8) δ ppm 0.95 (d, J=6.53 Hz, 6H), 1.35 (d, J=6.02 Hz, 6H), 1.83-1.98 (m, 1H), 2.90-2.98 (m, 3H), 3.14-3.29 (m, 2H), 4.66-4.82 (m, 1H), 7.18-7.25 (m, 2H), 7.26-7.29 (m, 1H), 7.38-7.42 (m, 1H), 7.48 (m, 1H), 7.58-7.65 (m, 2H), 7.65-7.72 (m, 2H), 7.96 (d, J=1.00 Hz, 1H), 8.08-8.16 (m, 2H). LCMS Rt 2.588 min., m/z 503.25 (M+H), 98% purity.

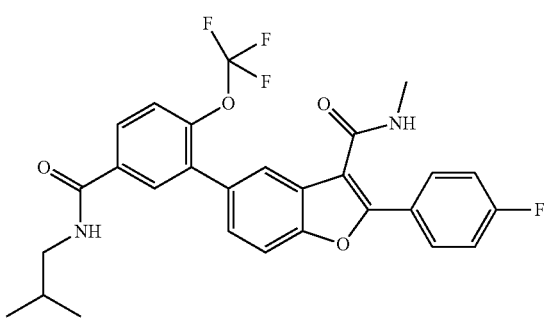

2-(4-Fluorophenyl)-5-(5-(isobutylcarbamoyl)-2-(trifluoromethoxy)phenyl)-N-methylbenzofuran-3-carboxamide. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 mm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Phenyl Xbridge C18 3.5 mm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 0.94 (dd, J=6.78, 2.26 Hz, 6H), 1.82-1.97 (m, 1H), 2.90 (d, J=4.77 Hz, 3H), 3.12-3.24 (m, 2H), 7.17-7.29 (m, 2H), 7.47 (dd, J=8.53, 1.76 Hz, 2H), 7.61 (d, J=8.53 Hz, 1H), 7.71-7.81 (m, 2H), 7.83 (d, J=1.26 Hz, 1H), 7.92-7.98 (m, 1H), 7.99-8.05 (m, 1H), 8.07-8.15 (m, 2H). LCMS Rt 2.565 min., m/z 529.13 (M+H). HPLC Rt 11.166 min. (Sunfire C18), 99.5% purity and 11.813 min. (Phenyl Xbridge C18), 86.7% purity.

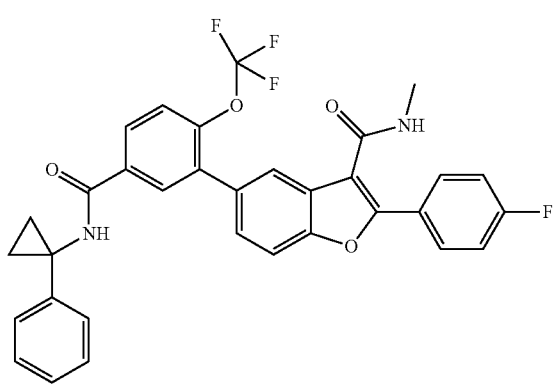

2-(4-Fluorophenyl)-N-methyl-5-(5-(1-phenylcyclopropylcarbamoyl)-2-(trifluoromethoxy)phenyl)benzofuran-3-carboxamide. $^1$H NMR (400 MHz, THF-d8) δ ppm 1.20-1.39 (m, 4H), 2.89 (d, J=4.52 Hz, 3H), 7.06-7.15 (m, 1H), 7.17-7.27 (m, 4H), 7.29-7.35 (m, 2H), 7.44 (br. s., 1H), 7.47 (m, 2H), 7.61 (d, J=8.53 Hz, 1H), 7.83 (d, J=1.26 Hz, 1H), 7.98 (dd, J=8.66, 2.38 Hz, 1H), 8.05 (d, J=2.01 Hz, 1H), 8.08-8.15 (m, 2H), 8.50 (br. s., 1H). LCMS Rt 2.796 min., m/z 589.23 (M+H). HPLC Rt 11.419 min. (Sunfire C18), 98.9% purity and 12.424 min. (Phenyl Xbridge C18), 100% purity.

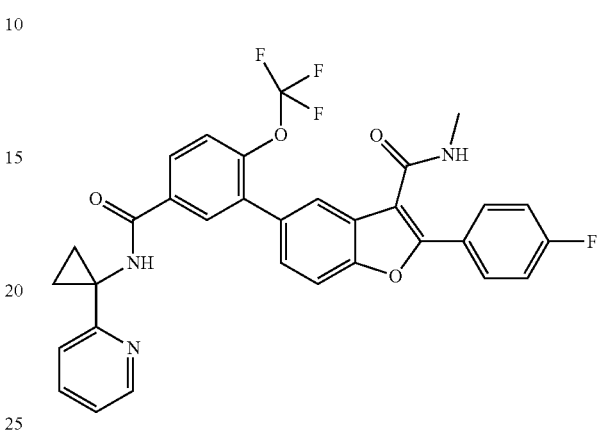

2-(4-Fluorophenyl)-N-methyl-5-(5-(1-(pyridin-2-yl)cyclopropylcarbamoyl)-2-(trifluoro methoxy)phenyl)benzofuran-3-carboxamide. $^1$H NMR (400 MHz, THF-d8) δ ppm 1.21-1.33 (m, 2H), 1.62-1.70 (m, 2H), 2.89 (d, J=4.77 Hz, 3H), 7.01 (m, 1H), 7.18-7.28 (m, 2H), 7.40 (d, J=8.03 Hz, 1H), 7.43 (br. s., 1H), 7.46-7.58 (m, 3H), 7.62 (d, J=8.53 Hz, 1H), 7.86 (d, J=1.26 Hz, 1H), 8.04 (dd, J=8.66, 2.38 Hz, 1H), 8.07-8.17 (m, 3H), 8.36-8.42 (m, 1H), 8.57 (br. s., 1H). LCMS Rt 1.768 min., m/z 590.13 (M+H). HPLC Rt 7.645 min. (Sunfire C18), 99.0% purity and 12.041 min. (Phenyl Xbridge C18), 99.9% purity.

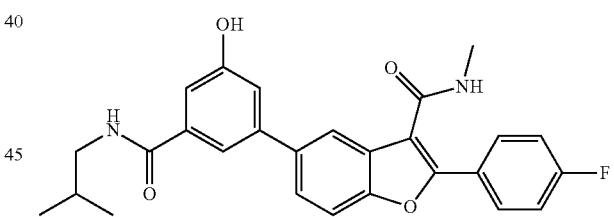

2-(4-Fluorophenyl)-5-(3-hydroxy-5-(isobutylcarbamoyl) phenyl)-N-methylbenzofuran-3-carboxamide. To a 250 mL RBF was added 2-(4-fluorophenyl)-5-(3-(isobutylcarbamoyl)-5-isopropoxyphenyl)-N-methylbenzofuran-3-carboxamide (1.3409 g, 2.67 mmol) in dichloromethane (20 mL). The flask was sealed with a septa, placed under N$_2$ and stirred for 5 minutes. To this mixture was then added (cold) 1M trichloroborane (8.00 mL, 8.00 mmol) in dichloromethane. The solution was stirred at room temperature for 6 hours. The reaction mixture was cooled to 0° C. and methanol was added to quench the reaction. The flask was allowed to warm to room temperature and the volatiles were removed to give a quantitative yield of a tan solid. $^1$H NMR (400 MHz, CD$_3$OD) δ ppm 1.06 (d, J=6.78 Hz, 6H), 1.97-2.12 (m, 1H), 3.01-3.12 (m, 3H), 3.29 (t, J=6.53 Hz, 2H), 7.27-7.40 (m, 4 H), 7.64 (s, 1H), 7.72 (s, 2H), 7.98 (s, 1H), 8.03 (dd, J=8.66, 5.40 Hz, 2H), 8.56 (br. s., 1H). LCMS Rt 2.157 min., m/z 461.03 (M+H), 97.6% purity.

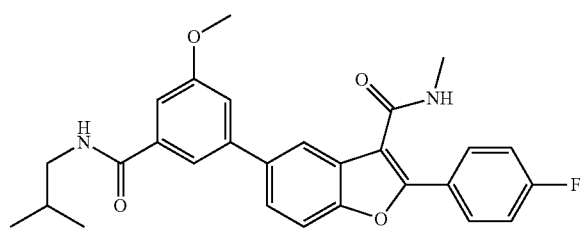

2-(4-Fluorophenyl)-5-(3-(isobutylcarbamoyl)-5-methoxyphenyl)-N-methylbenzofuran-3-carboxamide. The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters Phenyl XBridge C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 0.87-1.03 (m, 6H), 1.83-1.99 (m, 1H), 2.93 (d, J=4.77 Hz, 3H), 3.16-3.25 (m, 2H), 3.88 (s, 3H), 7.18-7.26 (m, 2H), 7.29-7.32 (m, 1H), 7.42 (dd, J=2.38, 1.38 Hz, 1H), 7.50 (br. s., 1H), 7.57-7.66 (m, 2H), 7.71 (br. s., 2H), 7.97 (d, J=1.25 Hz, 1H), 8.08-8.16 (m, 2H). LCMS m/z 475.22 (M+H), Rt 2.373 min. HPLC Rt 10.268 min. (Sunfire C18), 96.7% purity and 12.104 min. (XBridge Phenyl C18), 99.2% purity.

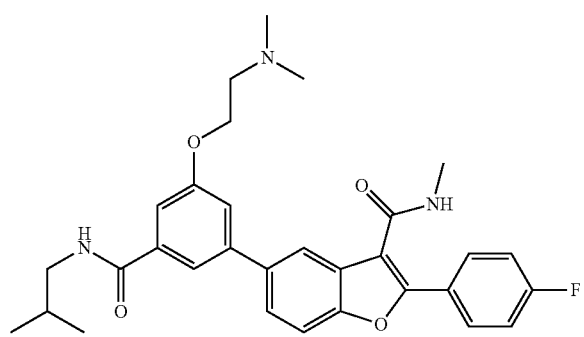

5-(3-(2-(Dimethylamino)ethoxy)-5-(isobutylcarbamoyl)phenyl)-2-(4-fluorophenyl)-N-methyl benzofuran-3-carboxamide. $^1$H NMR (400 MHz, THF-d8) δ ppm 0.95 (d, J=6.78 Hz, 6H), 1.87-1.98 (m, 1H), 2.89 (s, 6H), 2.93 (d, J=4.52 Hz, 3H), 3.21 (t, J=6.40 Hz, 2H), 3.47-3.54 (m, 2H), 4.54-4.64 (m, 2H), 7.22 (t, J=8.66 Hz, 2H), 7.42 (s, 1H), 7.51 (br. s., 1H), 7.58 (d, J=5.27 Hz, 1H), 7.61 (s, 1H), 7.62-7.69 (m, 1H), 7.80 (s, 1H), 7.83 (br. s., 1H), 7.98 (s, 1H), 8.12 (dd, J=8.91, 5.40 Hz, 2H). LCMS Rt 1.543 min., m/z 532.28 (M+H). HPLC Rt 6.816 min. (Sunfire C18), 96.0% purity and 12.073 min. (Phenyl Xbridge C18), 98.2% purity.

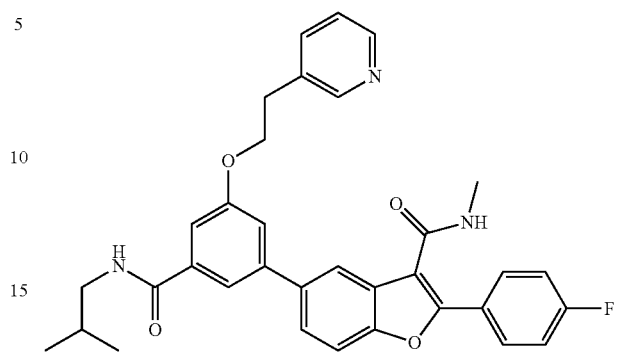

2-(4-Fluorophenyl)-5-(3-(isobutylcarbamoyl)-5-(2-(pyridin-3-ylethoxy)phenyl)-N-methyl benzofuran-3-carboxamide. $^1$H NMR (400 MHz, THF-d8) δ ppm 0.94 (d, J=6.53 Hz, 6H), 1.83-1.98 (m, 1H), 2.92 (d, J=4.27 Hz, 3H), 3.13-3.30 (m, 4H), 4.32-4.47 (m, 2H), 7.22 (t, J=8.66 Hz, 2H), 7.32 (s, 1H), 7.41-7.53 (m, 3H), 7.55-7.67 (m, 2H), 7.72 (br. s., 2H), 7.91-8.01 (m, 2H), 8.11 (dd, J=8.03, 5.52 Hz, 2H), 8.55 (br. s., 1H), 8.72 (br. s., 1H). LCMS Rt 1.632 min., m/z 566.26 (M+H). HPLC Rt 7.216 min. (Sunfire C18), 98.1% purity and 12.073 min. (Phenyl Xbridge C18), 99.0% purity.

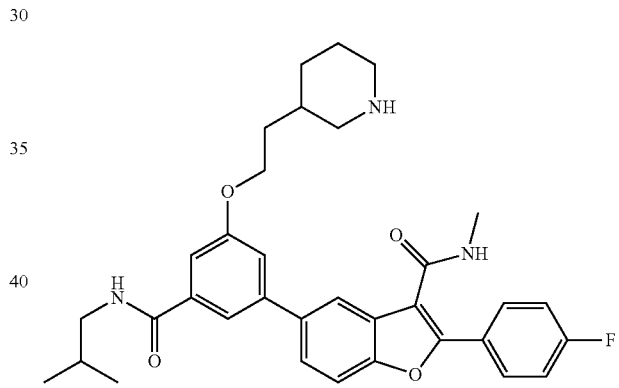

2-(4-Fluorophenyl)-5-(3-(isobutylcarbamoyl)-5-(2-(piperidin-3-yl)ethoxy)phenyl)-N-methyl benzofuran-3-carboxamide. The LC/MS data was obtained on a Waters Acquity SDS analytical LC/Micromass Platform LC (ESI+) at 220 nm using the following set of conditions: Waters Acquity HPLC BEH 1.7 μm C18, 2.1×50 mm column, with a gradient of 2-98% B (B=100% HPLC grade acetonitrile/0.05% TFA), (A=100% HPLC grade water/0.05% TFA), in 2.2 minutes at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 20-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. $^1$H NMR (400 MHz, CD$_3$OD) δ ppm 0.99 (d, J=6.78 Hz, 6H), 1.36 (dd, J=12.30, 3.01 Hz, 1H), 1.69-1.89 (m, 3H), 1.91-2.16 (m, 4H), 2.77 (t, J=12.17 Hz, 1H), 2.87-2.95 (m, 1H), 3.23 (d, J=7.03 Hz, 2H), 3.29-3.40 (m, 4H), 3.43-3.52 (m, 1H), 4.19 (t, J=6.02 Hz, 2H), 7.24 (t, J=8.78 Hz, 2H), 7.36 (dd, J=10.54, 1.51 Hz, 2H), 7.58-7.68 (m, 2H), 7.70

(s, 1H), 7.87-7.98 (m, 3H). LCMS m/z 572.16 (M+H). HPLC Rt 6.518 min. (Sunfire C18), 98% purity.

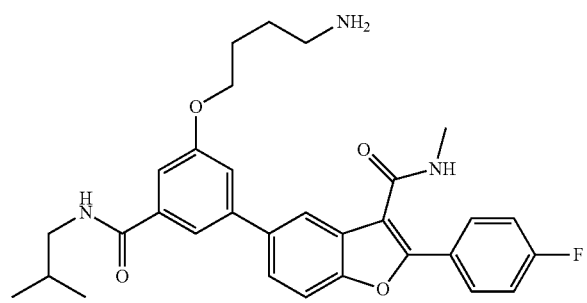

5-(3-(4-Aminobutoxy)-5-(isobutylcarbamoyl)phenyl)-2-(4-fluorophenyl)-N-methylbenzofuran-3-carboxamide. $^1$H NMR (400 MHz, CD$_3$OD) δ ppm 0.99 (d, J=6.78 Hz, 6H), 1.86-2.04 (m, 5H), 2.95-3.00 (m, 3H), 3.06 (t, J=7.15 Hz, 2H), 3.21-3.27 (m, 2H), 4.19 (t, J=5.40 Hz, 2H), 7.23-7.31 (m, 2H), 7.38 (dd, J=3.76, 1.25 Hz, 2H), 7.64-7.70 (m, 2H), 7.71 (s, 1H), 7.91-7.99 (m, 3H), 8.60 (br. s., 1 H). LCMS m/z 532.00 (M+H). HPLC Rt 6.386 min. (Sunfire C18), 100% purity.

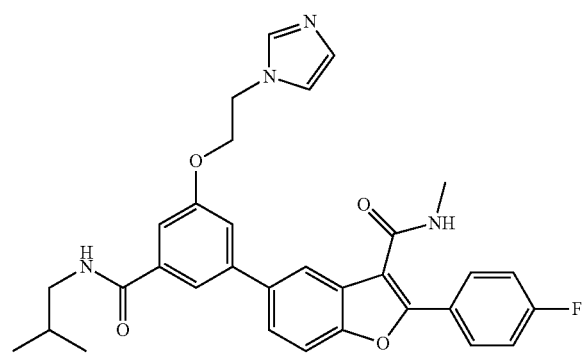

5-(3-(2-(1H-imidazol-1-yl)ethoxy)-5-(isobutylcarbamoyl)phenyl)-2-(4-fluorophenyl)-N-methyl benzofuran-3-carboxamide. $^1$H NMR (400 MHz, CD$_3$OD) δ ppm 1.06 (d, J=6.78 Hz, 6H), 2.03 (d, J=6.78 Hz, 1H), 3.05 (s, 3H), 3.31 (d, J=7.03 Hz, 2H), 4.62 (t, J=4.77 Hz, 2H), 4.79 (br. s., 2H), 7.35 (t, J=8.78 Hz, 2H), 7.49 (d, J=2.76 Hz, 2H), 7.68 (s, 1H), 7.73-7.77 (m, 2H), 7.83 (s, 1H), 7.88 (s, 1H), 7.98-8.07 (m, 3H), 9.17 (s, 1H). LCMS m/z 555.00 (M+H). HPLC Rt 6.295 min. (Sunfire C18), 95.2% purity.

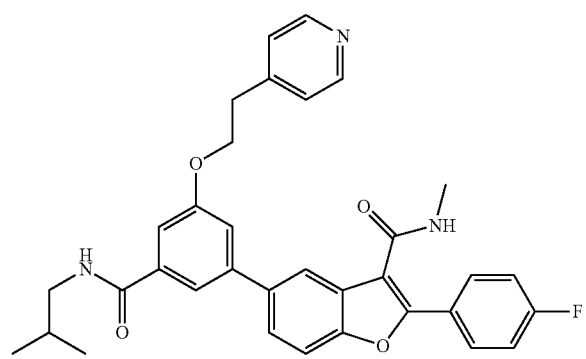

2-(4-Fluorophenyl)-5-(3-(isobutylcarbamoyl)-5-(2-(pyridin-4-yl)ethoxy)phenyl)-N-methyl benzofuran-3-carboxamide. $^1$H NMR (400 MHz, CD$_3$OD) δ ppm 1.05 (d, J=6.53 Hz, 6H), 1.95-2.09 (m, 1H), 3.04 (s, 3H), 3.24-3.33 (m, 2H), 3.54 (t, J=5.90 Hz, 2H), 4.60 (t, J=5.77 Hz, 2H), 7.27-7.38 (m, 2H), 7.41-7.49 (m, 2H), 7.71-7.75 (m, 2H), 7.78 (t, J=1.51 Hz, 1H), 7.96-8.05 (m, 3H), 8.12 (d, J=6.53 Hz, 2H), 8.80 (d, J=6.78 Hz, 2H). LCMS m/z 566.00 (M+H). HPLC Rt 6.4921 min. (Sunfire C18), 98.6% purity.

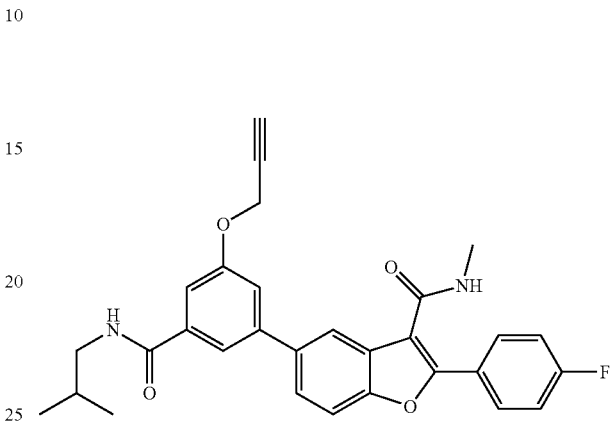

2-(4-Fluorophenyl)-5-(3-(isobutylcarbamoyl)-5-(prop-2-ynyloxy)phenyl)-N-methylbenzofuran-3-carboxamide. $^1$H NMR (400 MHz, CD$_3$OD) δ ppm 1.07 (d, J=6.78 Hz, 6H), 1.94-2.18 (m, 1H), 3.00-3.13 (m, 4H), 3.30 (d, J=7.03 Hz, 2H), 4.94-4.98 (m, 2H), 7.27-7.42 (m, 2H), 7.47-7.59 (m, 2H), 7.68-7.79 (m, 2H), 7.82 (t, J=1.51 Hz, 1H), 7.98-8.11 (m, 3H). LCMS m/z 499.00 (M+H). HPLC Rt 9.984 min. (Sunfire C18), 99.4% purity.

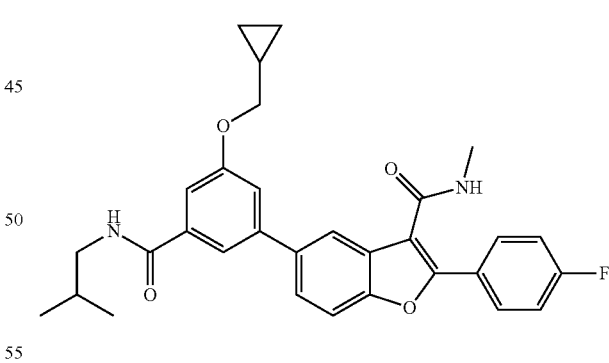

5-(3-(Cyclopropylmethoxy)-5-(isobutylcarbamoyl)phenyl)-2-(4-fluorophenyl)-N-methyl benzofuran-3-carboxamide. $^1$H NMR (400 MHz, CD$_3$OD) δ ppm 0.48 (d, J=14.81 Hz, 2H), 0.72 (d, J=7.78 Hz, 2H), 1.06 (d, J=6.53 Hz, 6H), 1.51-1.59 (m, 1H), 1.98-2.10 (m, 1H), 3.05 (s, 3H), 3.30 (d, J=7.03 Hz, 2H), 4.04 (d, J=6.78 Hz, 2H), 7.33 (t, J=8.66 Hz, 2H), 7.43 (s, 2H), 7.49 (br. s., 1H), 7.75 (d, J=9.04 Hz, 3H), 7.97-8.09 (m, 3H). LCMS m/z 515.17 (M+H). HPLC Rt 10.878 min. (Sunfire C18), 91.4% purity.

531

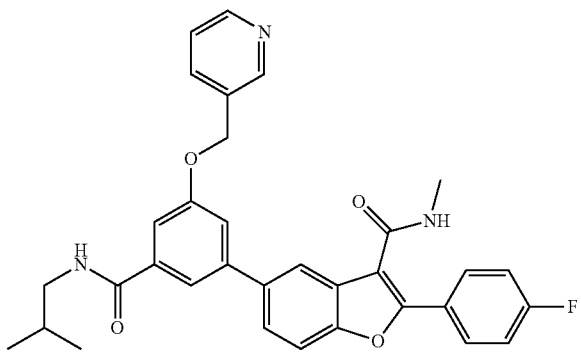

2-(4-Fluorophenyl)-5-(3-(isobutylcarbamoyl)-5-(pyridin-3-ylmethoxy)phenyl)-N-methyl benzofuran-3-carboxamide. $^1$H NMR (400 MHz, CD$_3$OD) δ ppm 1.06 (d, J=6.78 Hz, 6H), 2.03 (dt, J=13.55, 6.78 Hz, 1H), 3.04 (s, 3H), 3.30 (d, J=7.03 Hz, 2H), 5.52 (s, 2H), 7.33 (t, J=8.78 Hz, 2H), 7.59 (dd, J=6.40, 1.38 Hz, 2H), 7.69-7.80 (m, 2H), 7.84 (s, 1H), 7.96-8.09 (m, 4H), 8.64 (d, J=8.28 Hz, 1H), 8.83 (d, J=4.52 Hz, 1H), 9.02 (s, 1H). LCMS m/z 552.05 (M+H). HPLC Rt 6.401 min. (Sunfire C18), 100% purity.

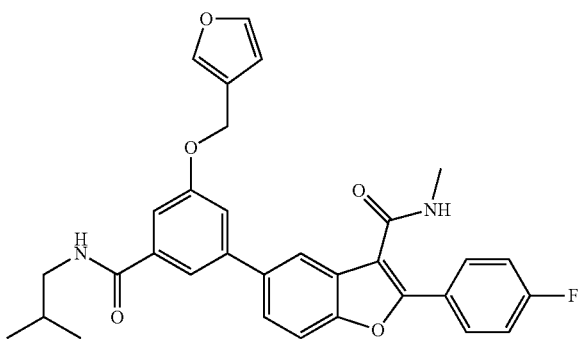

2-(4-Fluorophenyl)-5-(3-(furan-3-ylmethoxy)-5-(isobutylcarbamoyl)phenyl)-N-methyl benzofuran-3-carboxamide. $^1$H NMR (400 MHz, CD$_3$OD) δ ppm 1.06 (d, J=6.53 Hz, 6H), 1.96-2.14 (m, 1H), 3.06 (s, 3H), 3.30 (d, J=7.03 Hz, 2H), 5.19 (s, 2H), 6.64 (s, 1H), 7.33 (t, J=8.78 Hz, 2H), 7.51 (s, 2H), 7.59 (br. s., 1H), 7.70-7.82 (m, 4H), 8.01 (d, J=11.54 Hz, 3H). LCMS m/z 541.00 (M+H). HPLC Rt 10.426 min. (Sunfire C18), 90.0% purity.

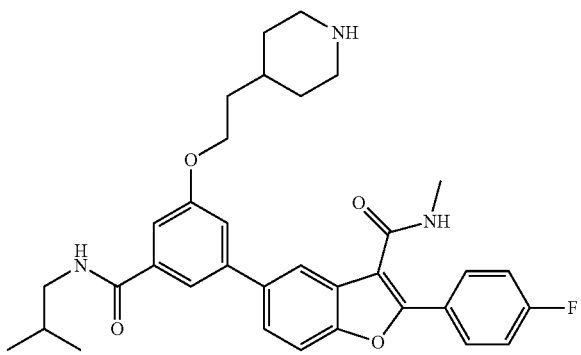

2-(4-Fluorophenyl)-5-(3-(isobutylcarbamoyl)-5-(2-(piperidin-4-yl)ethoxy)phenyl)-N-methyl benzofuran-3-car-

532 boxamide. $^1$H NMR (400 MHz, CD$_3$OD) δ ppm 1.06 (d, J=6.53 Hz, 6H), 1.96-2.14 (m, 1H), 3.06 (s, 3H), 3.30 (d, J=7.03 Hz, 2H), 5.19 (s, 2H), 6.64 (s, 1H), 7.33 (t, J=8.78 Hz, 2H), 7.51 (s, 2H), 7.59 (br. s., 1H), 7.70-7.82 (m, 4H), 8.01 (d, J=11.54 Hz, 3H). LCMS m/z 572.17 (M+H). HPLC Rt 6.571 min. (Sunfire C18), 95.8% purity.

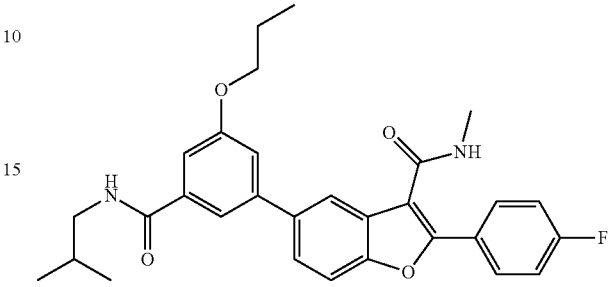

2-(4-Fluorophenyl)-5-(3-(isobutylcarbamoyl)-5-propoxyphenyl)-N-methylbenzofuran-3-carboxamide. $^1$H NMR (400 MHz, THF-d8) δ ppm 0.87-0.98 (m, 6H), 1.07 (t, J=7.40 Hz, 3H), 1.79-1.96 (m, 3H), 2.93 (d, J=4.52 Hz, 3H), 3.21 (t, J=6.40 Hz, 2H), 4.05 (t, J=6.53 Hz, 2H), 7.22 (t, J=8.66 Hz, 2H), 7.30 (br. s., 1H), 7.39-7.56 (m, 2H), 7.56-7.79 (m, 4H), 7.97 (s, 1H), 8.12 (dd, J=8.53, 5.52 Hz, 2H). LCMS m/z 503.15 (M+H). HPLC Rt 11.141 min. (Sunfire C18), 98.9% purity.

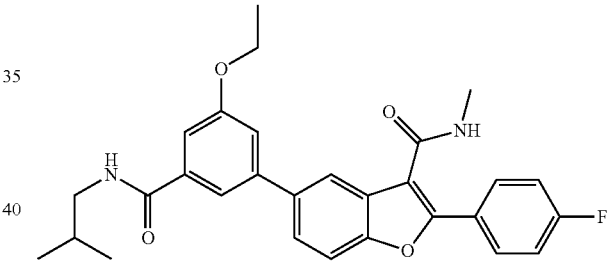

2-(4-Fluorophenyl)-5-(3-(isobutylcarbamoyl)-5-ethoxyphenyl)-N-methylbenzofuran-3-carboxamide. $^1$H NMR (400 MHz, CD$_3$OD) δ ppm 1.06 (d, J=6.78 Hz, 6H), 1.47-1.62 (m, 3H), 1.92-2.15 (m, 1H), 3.05 (s, 3H), 3.30 (d, J=7.03 Hz, 2H), 4.26 (q, J=6.94 Hz, 2H), 7.33 (t, J=8.78 Hz, 2H), 7.43 (s, 2H), 7.70-7.83 (m, 3H), 7.97-8.09 (m, 3H). LCMS m/z 489.00 (M+H). HPLC Rt 10.464 min. (Sunfire C18), 93.7% purity.

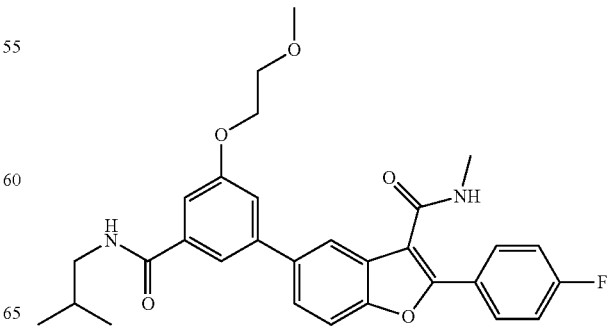

2-(4-Fluorophenyl)-5-(3-(isobutylcarbamoyl)-5-(2-methoxyethoxy)phenyl)-N-methylbenzofuran-3-carboxamide. ¹H NMR (400 MHz, THF-d8) δ ppm 0.86-1.05 (m, 6H), 1.82-2.02 (m, 1H), 2.86-3.04 (m, 3H), 3.21 (t, J=6.40 Hz, 2H), 3.34-3.45 (m, 3H), 3.72 (t, J=4.77 Hz, 2H), 4.21 (t, J=4.77 Hz, 2H), 7.22 (t, J=8.78 Hz, 2H), 7.33 (s, 1H), 7.42 (s, 1H), 7.49 (br. s., 1H), 7.55-7.83 (m, 4H), 7.97 (s, 1H), 8.12 (dd, J=8.78, 5.52 Hz, 2H). LCMS m/z 519.10 (M+H). HPLC Rt 9.676 min. (Sunfire C18), 100% purity.

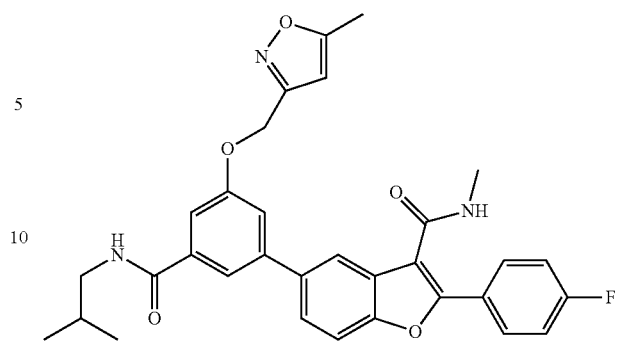

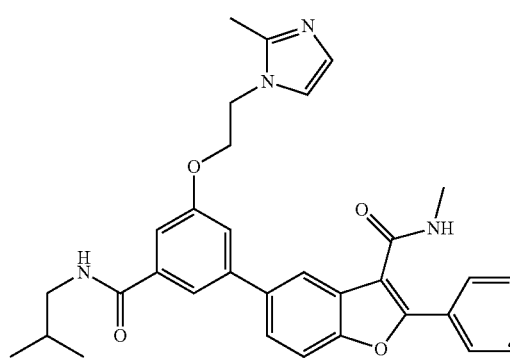

2-(4-Fluorophenyl)-5-(3-(isobutylcarbamoyl)-5-((5-methylisoxazol-3-yl)methoxy)phenyl)-N-methylbenzofuran-3-carboxamide. ¹H NMR (400 MHz, THF-d8) δ ppm 0.92-0.99 (m, 6H), 1.83-1.99 (m, 1H), 2.40 (s, 3H), 2.90-2.98 (m, 3H), 3.17-3.27 (m, 2H), 5.18-5.25 (m, 1H), 6.17-6.25 (m, 1H), 7.17-7.27 (m, 2H), 7.41-7.46 (m, 1H), 7.47-7.54 (m, 2H), 7.57-7.68 (m, 3H), 7.68-7.74 (m, 1H), 7.76 (d, J=1.51 Hz, 1H), 7.98 (d, J=1.26 Hz, 1H), 8.07-8.19 (m, 2H). LCMS m/z 556.00 (M+H). HPLC Rt 10.106 min. (Sunfire C18), 90.0% purity.

2-(4-Fluorophenyl)-5-(3-(isobutylcarbamoyl)-5-(2-(2-methyl-1H-imidazol-1-yl)ethoxy)phenyl)-N-methylbenzofuran-3-carboxamide. ¹H NMR (400 MHz, CD₃OD) δ ppm 0.99 (d, J=6.53 Hz, 6H), 1.90-2.03 (m, 1H), 2.78 (s, 3H), 2.94-3.02 (m, 3H), 3.23 (d, J=7.03 Hz, 2H), 4.53 (t, J=4.89 Hz, 2H), 4.65 (t, J=4.89 Hz, 2H), 7.22-7.32 (m, 2H), 7.38 (d, J=1.51 Hz, 2H), 7.46 (d, J=2.01 Hz, 1H), 7.63-7.69 (m, 3H), 7.75 (t, J=1.51 Hz, 1H), 7.91-8.00 (m, 3H). LCMS m/z 569.12 (M+H). HPLC Rt 6.340 min. (Sunfire C18), 100% purity.

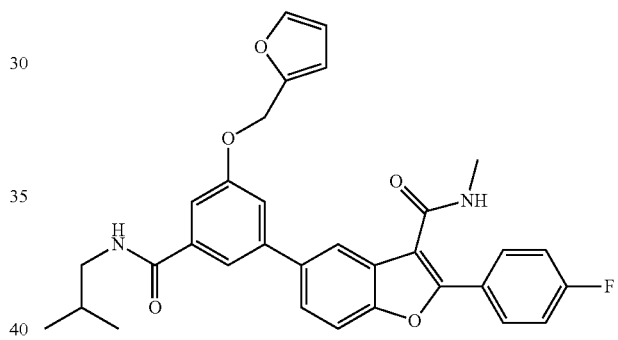

2-(4-Fluorophenyl)-5-(3-(isobutylcarbamoyl)-5-((5-methylisoxazol-3-yl)methoxy)phenyl)-N-methylbenzofuran-3-carboxamide. ¹H NMR (500 MHz, THF-d8) δ ppm 0.98 (d, J=6.71 Hz, 6H), 1.88-2.01 (m, 1H), 2.92-3.00 (m, 3H), 3.20-3.27 (m, 2H), 5.17 (s, 2H), 6.42 (dd, J=3.05, 1.83 Hz, 1H), 6.53 (d, J=3.36 Hz, 1H), 7.21-7.30 (m, 3H), 7.43 (d, J=1.53 Hz, 1H), 7.55 (d, J=12.51 Hz, 1H), 7.59-7.66 (m, 3H), 7.67-7.71 (m, 1H), 7.78 (s, 1H), 8.02 (s, 1H), 8.13-8.18 (m, 2H). LCMS m/z 541.17 (M+H). HPLC Rt 10.401 min. (Sunfire C18), 90.0% purity.

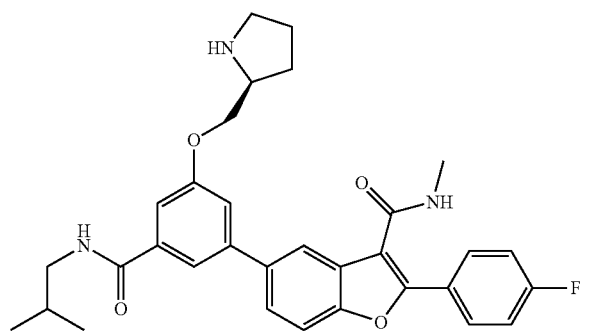

(S)-2-(4-Fluorophenyl)-5-(3-(isobutylcarbamoyl)-5-(pyrrolidin-2-ylmethoxy)phenyl)-N-methyl benzofuran-3-carboxamide. ¹H NMR (400 MHz, CD₃OD) δ ppm 1.06 (d, J=6.78 Hz, 6H), 1.98-2.12 (m, 2H), 2.16-2.32 (m, 2H), 2.34-2.48 (m, 1H), 3.04 (s, 3H), 3.31 (d, J=7.03 Hz, 2H), 3.44-3.55 (m, 2H), 4.12-4.22 (m, 1H), 4.34 (dd, J=10.54, 8.28 Hz, 1H), 4.51-4.62 (m, 1H), 7.27-7.42 (m, 2H), 7.49-7.59 (m, 2H), 7.71-7.82 (m, 2H), 7.85 (s, 1H), 7.97-8.10 (m, 3H). LCMS m/z 544.12 (M+H). HPLC Rt 6.326 min. (Sunfire C18), 95.8% purity.

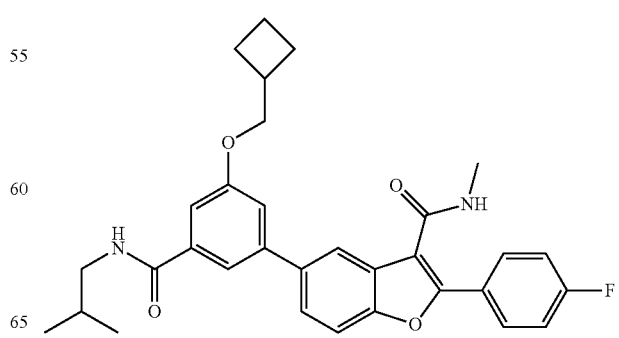

5-(3-(Cyclobutylmethoxy)-5-(isobutylcarbamoyl)phenyl)-2-(4-fluorophenyl)-N-methyl benzofuran-3-carboxamide. ¹H NMR (500 MHz, THF-d8) δ ppm 0.95 (d, J=6.71 Hz, 6H), 1.86-2.02 (m, 6H), 2.10-2.21 (m, 2H), 2.87-2.97 (m, 3H), 3.20 (d, J=6.71 Hz, 2H), 4.07 (d, J=6.71 Hz, 2H), 7.23 (t, J=8.85 Hz, 2H), 7.32 (s, 1H), 7.43 (s, 1H), 7.57-7.63 (m, 2H), 7.63-7.68 (m, 1H), 7.73 (s, 1H), 7.79-7.86 (m, 1H), 7.99 (s, 1H), 8.09-8.16 (m, 2H). LCMS m/z 529.00 (M+H). HPLC Rt 11.771 min. (Sunfire C18), 94.2% purity.

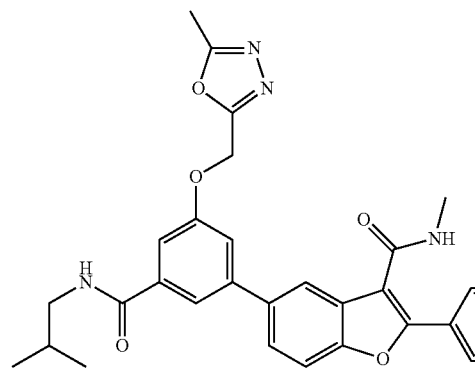

2-(4-Fluorophenyl)-5-(3-(isobutylcarbamoyl)-5-((5-methyl-1,3,4-oxadiazol-2-yl)methoxy)phenyl)-N-methylbenzofuran-3-carboxamide. ¹H NMR (400 MHz, THF-d8) δ ppm 0.90-1.02 (m, 6H), 1.84-2.00 (m, 1H), 2.50 (s, 3H), 2.94 (d, J=4.77 Hz, 3H), 3.17-3.27 (m, 2H), 5.39 (s, 2H), 7.18-7.29 (m, 2H), 7.46-7.56 (m, 3H), 7.58-7.68 (m, 2H), 7.71 (br. s., 1H), 7.79 (s, 1H), 8.00 (d, J=1.51 Hz, 1H), 8.08-8.21 (m, 2H). LCMS m/z 557.11 (M+H). HPLC Rt 8.964 min. (Sunfire C18), 92.0% purity.

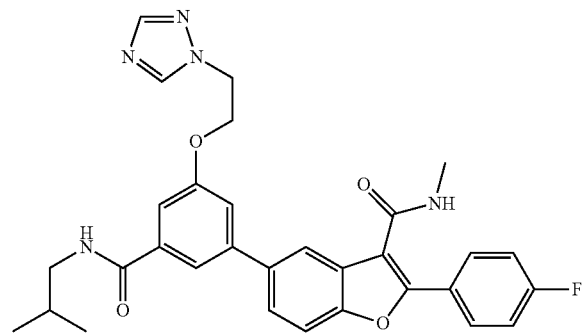

5-(3-(2-(1H-1,2,4-triazol-1-yl)ethoxy)-5-(isobutylcarbamoyl)phenyl)-2-(4-fluorophenyl)-N-methylbenzofuran-3-carboxamide. ¹H NMR (400 MHz, THF-d8) δ ppm 0.87-1.01 (m, 6H), 1.83-1.98 (m, 1H), 2.93 (d, J=4.52 Hz, 3H), 3.13-3.26 (m, 2H), 4.49 (t, J=5.14 Hz, 2H), 4.61 (t, J=5.02 Hz, 2H), 7.19-7.27 (m, 2H), 7.28-7.33 (m, 1H), 7.39-7.42 (m, 1H), 7.43-7.52 (m, 1H), 7.57-7.66 (m, 2H), 7.71-7.77 (m, 1H), 7.81 (s, 1H), 7.96 (d, J=1.00 Hz, 1H), 8.06-8.17 (m, 3H), 8.30 (s, 1H). LCMS m/z 556.11 (M+H). HPLC Rt 7.969 min. (Sunfire C18), 92.0% purity.

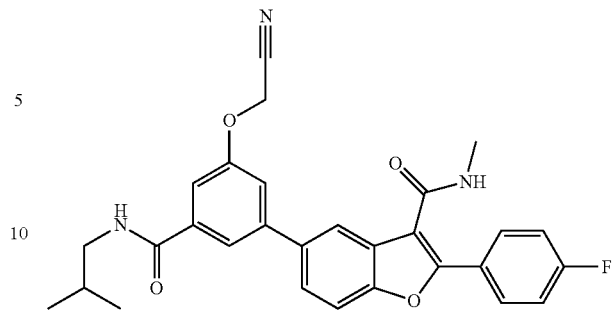

5-(3-(Cyanomethoxy)-5-(isobutylcarbamoyl)phenyl)-2-(4-fluorophenyl)-N-methylbenzofuran-3-carboxamide. ¹H NMR (500 MHz, THF-d8) δ ppm 0.96 (d, J=6.71 Hz, 6H), 1.85-1.98 (m, 1H), 2.85-2.98 (m, 3H), 3.16-3.27 (m, 2H), 5.11 (s, 2H), 7.18-7.29 (m, 2H), 7.42-7.49 (m, 1H), 7.54 (s, 1H), 7.60-7.71 (m, 2H), 7.79-7.88 (m, 2H), 8.00 (s, 1H), 8.08-8.19 (m, 2H). LCMS m/z 500.00 (M+H). HPLC Rt 9.584 min. (Sunfire C18), 95.9% purity.

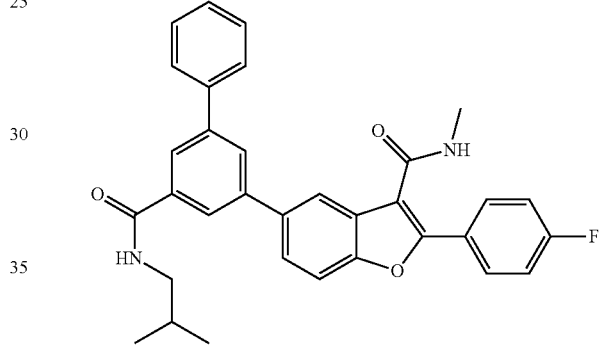

2-(4-Fluorophenyl)-5-(5-(isobutylcarbamoyl)biphenyl-3-yl)-N-methylbenzofuran-3-carboxamide. To a Biotage microwave vial was added 1,4-dioxane (2.0 mL), water (200 µL), dicyclohexyl(2',6'-dimethoxybiphenyl-2-yl)phosphine (16.42 mg, 0.040 mmol), 5-(3-chloro-5-(isobutylcarbamoyl)phenyl)-2-(4-fluorophenyl)-N-methylbenzofuran-3-carboxamide (96 mg, 0.2 mmol), potassium phosphate tribasic (170 mg, 0.800 mmol), palladium(II) acetate (8.98 mg, 0.040 mmol), and phenylboronic acid (73.2 mg, 0.600 mmol). The vial was capped, degassed, flushed with $N_2$ and heated in the microwave for 15 minutes at 150° C. The solvent was removed in a Thermo/Savant SpeedVac and the crude product was dissolved in DMF (1.8 mL) and purified by preparative HPLC using a Shimadzu prepHPLC employing acetonitrile/water/0.1% TFA where solvent A was 10% acetonitrile/90% water/0.1% trifluoroacetic acid and solvent B was 10% water/90% acetonitrile/0.1% trifluoroacetic acid with a Waters Sunfire 5 µm C18 30×100 mm column at a gradient of 30-100% B and a flow rate of 40 mL/min. over 8 minutes with a 10 minute hold. The tubes with desired product were evaporated overnight in a SAVANT/THERMO Speedvac. The LC/MS data was obtained on a Shimadzu analytical LC/Micromass Platform LC (ESI+) at 220 nm using the following set of conditions: Waters Sunfire 5 µm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 20-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3 μm 4.6×150 mm column employing water/methanol/10 mM ammonium bicarbonate with a gradient of 20-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, CD$_3$OD) δ ppm 0.99 (d, J=6.78 Hz, 6H), 1.92-2.05 (m, 1H), 2.91-3.03 (m, 3H), 3.21-3.27 (m, 2H), 7.25 (t, J=8.78 Hz, 2H), 7.36-7.42 (m, 1H), 7.49 (t, J=7.53 Hz, 2H), 7.65-7.70 (m, 1H), 7.75 (d, J=8.28 Hz, 3H), 7.91-7.98 (m, 2H), 8.00 (d, J=1.51 Hz, 1H), 8.03-8.10 (m, 3H). LCMS m/z 521.33 (M+H), Rt 2.715 min. HPLC (Sunfire C18) Rt 11.531 min, 95% purity and (XBridge Phenyl C18) Rt 12.868 min., 92% purity.

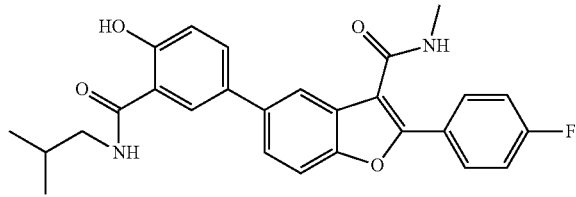

2-(4-Fluorophenyl)-5-(4-hydroxy-3-(isobutylcarbamoyl)phenyl)-N-methylbenzofuran-3-carboxamide. To a 350 mL sealed tube was added 2-(4-fluorophenyl)-5-(3-(isobutylcarbamoyl)-4-methoxyphenyl)-N-methylbenzofuran-3-carboxamide (1.14 g, 2.4 mmol), dichloroethane (250 mL) and boron tribromide-methyl sulfide complex (6.0 g, 19.2 mmol). The vessel was sealed and the mixture heated with stirring at 90° C. overnight. The reaction mixture was cooled to 0° C. and 100 mL of cold methanol was added and the mixture stirred for 30 minutes then evaporated to near dryness. The addition of methanol followed by evaporation was repeated to give a tan solid (78%). The LC/MS data was obtained on a Shimadzu analytical LC/Micromass Platform LC (ESI+) at 220 nm using the following set of conditions: Waters Sunfire 5 μm C18, 4.6×50 mm column, with a gradient of 0-100% B (B=90% HPLC grade acetonitrile/0.1% TFA/10% HPLC grade water), (A=90% HPLC grade water/0.1% TFA/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 40-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Gemini C18 3 μm 4.6×150 mm column employing water/methanol/10 mM ammonium bicarbonate with a gradient of 50-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, THF-d8) δ ppm 0.97 (d, J=6.71 Hz, 6H), 1.83-2.07 (m, 1H), 2.92 (d, J=4.88 Hz, 3H), 3.24 (t, J=6.41 Hz, 2H), 6.96 (d, J=8.55 Hz, 1H), 7.23 (t, J=8.70 Hz, 2H), 7.50-7.55 (m, 1H), 7.55-7.59 (m, 2H), 7.67 (dd, J=8.55, 2.14 Hz, 1H), 7.89 (s, 1H), 7.99 (d, J=2.14 Hz, 1H), 8.09 (dd, J=8.70, 5.34 Hz, 2H), 8.35 (br. s., 1H). LCMS m/z 461.18 (M+H), Rt 2.613 min. HPLC (Sunfire C18) Rt 10.033 min., 100% purity and (Gemini C18) Rt 9.748 min., 100% purity.

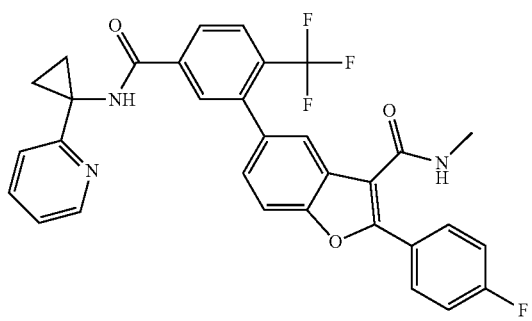

2-(4-Fluorophenyl)-N-methyl-5-(5-(1-(pyridin-2-yl)cyclopropylcarbamoyl)-2-(trifluoromethyl)phenyl)benzofuran-3-carboxamide. To a Biotage microwave vial was added 2-(4-fluorophenyl)-N-methyl-5-(4,4,5,5-tetramethyl-1,3,2-dioxaborolan-2-yl)benzofuran-3-carboxamide (39.5 mg, 0.1 mmol), dioxane (2 mL), water (0.200 mL), 3-chloro-N-(1-(pyridin-2-yl)cyclopropyl)-4-(trifluoromethyl)benzamide (37.5 mg, 0.110 mmol) (prepared from the coupling of 3-chloro-4-(trifluoromethyl)benzoic acid with 1-(pyridin-2-yl)cyclopropanamine dihydrochloride using HATU and N,N-Diisopropylethylamine in DMF at r.t.), dicyclohexyl(2',6'-dimethoxybiphenyl-2-yl)phosphine (S-Phos, 8.21 mg, 0.020 mmol), tribasic potassium phosphate, (85 mg, 0.400 mmol) and finally palladium(II) acetate (4.49 mg, 0.020 mmol). The vial was capped and subjected to microwave heating (100° C.) for 10 minutes. After cooling the reaction mixture, the solvent was removed and the crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 5 minute hold. The solvent was removed yielding 11.2 mgs (20% yield) of the desired pyridylcarboxamide as a yellow solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.22-1.33 (m, 2H), 1.63-1.69 (m, 2H), 2.87 (d, J=4.77 Hz, 3H), 7.03 (dd, J=7.40, 4.89 Hz, 1H), 7.23 (t, J=8.66 Hz, 2H), 7.33 (d, J=8.28 Hz, 1H), 7.40 (d, J=7.53 Hz, 2H), 7.52-7.63 (m, 2H), 7.73 (d, J=1.25 Hz, 1H), 7.90 (d, J=8.03 Hz, 1H), 7.97 (s, 1H), 8.05-8.16 (m, 3H), 8.40 (d, J=4.77 Hz, 1H), 8.69 (s, 1H). LCMS Rt=2.193 min., m/z 574.3 (M+H). HPLC Rt=7.435 min. (Sunfire C18), 97.5% purity and 11.823 min. (Gemini C18), 100% purity.

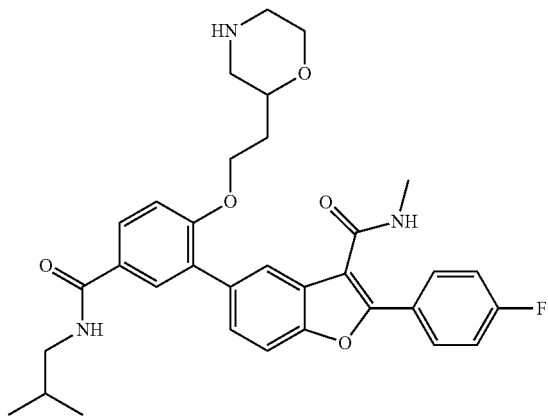

2-(4-Fluorophenyl)-5-(5-(isobutylcarbamoyl)-2-(2-(morpholin-2-yl)ethoxy)phenyl)-N-methyl benzofuran-3-carboxamide, TFA. To a 2 dram vial was added 2-(4-fluorophenyl)-5-(2-hydroxy-5-(isobutylcarbamoyl)phenyl)-N-methylbenzofuran-3-carboxamide (46.0 mg, 0.1 mmol), DMF (2 mL), 4.0 equivalents (60 μL, 0.400 mmol) of DBU, 1,8-Diazabicyclo[5.4.0]undec-7-ene (0.4 mmol) and 4.0 equivalents of tert-butyl 2-(2-bromoethyl)morpholine-4-carboxylate (236 mg, 0.400 mmol). The vial was capped and the reaction mixture heated for eighteen hours at 85° C. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 nm C18 19×150 mm column at a gradient of 20-100% B and a flow rate of 25 mL/min. over 20 minutes with a 10 minute hold. The solvent mixture was removed on the rotovap and the resulting white solid (19.2 mgs) was taken up in 2 mL of dichloroethane containing 200 uL of trifluoroacetic acid. The acid mixture was stirred for 60 minutes. The volatiles were then removed, the process repeated again giving 20 mgs (29% yield, 2 steps) of 2-(4-fluorophenyl)-5-(5-(isobutylcarbamoyl)-2-(2-(morpholin-2-yl)ethoxy)phenyl)-N-methylbenzofuran-3-carboxamide, TFA as a white solid. The NMR spectrum was recorded at room temperature using a Bruker DRX400 spectrometer. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 0.93 (d, J=6.53 Hz, 6H), 1.87 (m, 3H), 2.90 (d, J=4.77 Hz, 3H), 3.08-3.12 (m, 2H), 3.16-3.20 (m, 2H), 3.31 (d, J=9.54 Hz, 2H), 3.95-4.11 (m, 3H), 4.23-4.31 (m, 1H), 4.35 (br. s., 1H), 7.08 (d, J=8.78 Hz, 1H), 7.25 (t, J=8.66 Hz, 2 H), 7.45 (dd, J=8.53, 1.76 Hz, 1H), 7.54 (t, J=5.65 Hz, 1H), 7.62 (d, J=8.53 Hz, 1H), 7.84 (dd, J=8.53, 2.26 Hz, 1H), 7.88 (d, J=2.01 Hz, 1H), 7.91 (d, J=4.02 Hz, 1H), 7.98-8.07 (m, 3H). LCMS m/z 574.5 (M+H), R$_f$=2.390 min. HPLC (Sunfire C18) Rt=6.870 min., 99.3% purity and (XBridge Phenyl C18) Rt=10.973 min., 99.2% purity.

tert-Butyl 2-(2-bromoethyl)morpholine-4-carboxylate. To a 25 mL round-bottomed flask was added 2-(morpholin-2-yl)ethanol (100 mg, 0.762 mmol), DCM (1 mL), and triethylamine (0.106 mL, 0.762 mmol). Di-tert-butyl dicarbonate (0.177 mL, 0.762 mmol) in DCM (1 mL) was then added dropwise via syringe. The mixture was stirred at room temperature under nitrogen for 3 hours. Volatiles were removed and NMR was taken of the colorless oil (176 mgs, 100% yield, 96% purity). $^1$H NMR (500 MHz, DMSO-d$_6$) δ ppm 1.39 (s, 9H), 1.47-1.61 (m, 2H), 2.83 (br. s., 1H), 3.28-3.42 (m, 3H), 3.46 (q, J=6.10 Hz, 2H), 3.68 (d, J=11.29 Hz, 1H), 3.76 (d, J=10.38 Hz, 2H), 4.45 (t, J=5.04 Hz, 1H).

To a 25 mL round-bottomed flask at 0° C. was added tert-butyl 2-(2-hydroxyethyl)morpholine-4-carboxylate (0.176 g, 0.762 mmol), DCM (4 mL), 1H-imidazole (0.104 g, 1.524 mmol), perbromomethane (0.379 g, 1.143 mmol), and triphenylphosphine (0.190 g, 0.723 mmol). The mixture was stirred overnight slowly reaching room temperature. The yellow solution was further diluted with 50 mL of DCM, washed with water, brine, dried over sodium sulfate, and filtered. The crude product was then pushed through a plug of silica gel and the solvent was removed to give 213 mgs of a light yellow oil. $^1$H NMR (400 MHz, DMSO-d6) δ ppm 1.40 (s, 9H), 1.94 (q, J=6.86 Hz, 1H), 2.56-2.66 (m, 1H), 2.76-2.91 (m, 1 H), 3.35-3.47 (m, 4H), 3.50-3.61 (m, 1H), 3.68 (br. s., 1H), 3.74-3.86 (m, 2H).

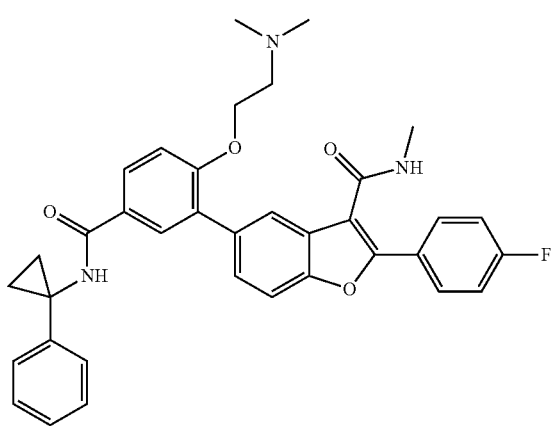

5-(2-(2-(Dimethylamino)ethoxy)-5-(1-phenylcyclopropylcarbamoyl)phenyl)-2-(4-fluorophenyl)-N-methylbenzofuran-3-carboxamide, TFA. To a small microwave vial was added 2-(4-fluorophenyl)-5-(2-hydroxy-5-(1-phenylcyclopropylcarbamoyl)phenyl)-N-methylbenzofuran-3-carboxamide (11.3 mgs, 0.022 mmol) (obtained from the de-methylation of the methoxy precursor using Boron tribromide-methyl sulfide complex (1,2-dichloroethane, 90° C.)), dioxane (2 mL), triphenylphosphine (105 mg, 0.400 mmol), 2-(dimethylamino)ethanol (0.025 mL, 0.250 mmol), and di-tert-butyl azodicarboxylate (69.1 mg, 0.300 mmol). The vial was crimped and the reaction mixture subjected to microwave heating (140° C.) for 20 minutes in a Biotage Initiator. The solvent was removed under a stream of nitrogen, the crude product taken up in 2 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Sunfire 5 μm C18 19×150 mm column at a gradient of 20-100% B and a flow rate of 20 mL/min. over 20 minutes with a 5 minute hold. The solvent was removed to give 14.5 mgs (90% yield) of 5-(2-(2-(dimethylamino)ethoxy)-5-(1-phenylcyclopropyl carbamoyl)phenyl)-2-(4-fluorophenyl)-N-methyl-benzofuran-3-carboxamide, TFA salt as a white solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% TFA/10% HPLC grade water), (A=90% HPLC grade water/0.1% TFA/10% HPLC grade methanol), in 4 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic ac with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. The NMR spectrum was recorded at room temperature using a Bruker DRX400 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). $^1$H NMR (400 MHz, THF-d8) δ ppm 1.22-1.27 (m, 2H), 1.28-1.33 (m, 2H), 2.70 (s, 6H), 2.90 (d, J=4.52 Hz, 3H), 3.41-3.46 (m, 2H), 4.47-4.53 (m, 2H), 7.06-7.12 (m, 1H), 7.14-7.27 (m, 5H), 7.28-7.35 (m, 2H), 7.47 (dd, J=8.53, 1.76 Hz, 1H), 7.54-7.61 (m, 2H), 7.89 (dd, J=8.53, 2.26 Hz, 1H), 7.94 (dd, J=4.02, 2.01 Hz, 2H), 8.03-8.10 (m, 2H), 8.28 (s, 1H). LCMS m/z 592.4 (M+H), $R_t$=2.065 min. HPLC $R_t$=7.025 min. (Sunfire C18), 95.2% purity and 11.979 min. (Gemini C18), 95.7% purity.

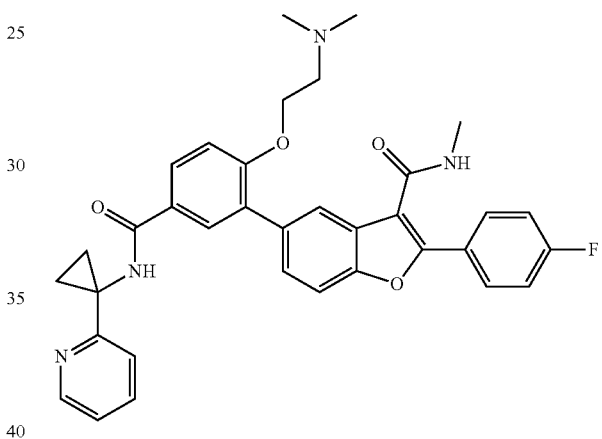

5-(2-(2-(Dimethylamino)ethoxy)-5-(1-(pyridin-2-yl)cyclopropylcarbamoyl)phenyl)-2-(4-fluoro phenyl)-N-methyl-benzofuran-3-carboxamide, TFA. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. ¹H NMR (400 MHz, THF-d8) δ ppm 1.32-1.37 (m, 2H), 1.59-1.65 (m, 2H), 2.77 (s, 6H), 2.90 (d, J=4.77 Hz, 3H), 3.47-3.54 (m, 2H), 4.48-4.55 (m, 2H), 7.17 (d, J=8.53 Hz, 1H), 7.20-7.27 (m, 2H), 7.31 (dd, J=6.90, 5.65 Hz, 1H), 7.49-7.59 (m, 2H), 7.61-7.70 (m, 2 H), 7.86 (td, J=7.78, 1.51 Hz, 1H), 7.94 (dd, J=8.53, 2.26 Hz, 1H), 7.97 (d, J=1.00 Hz, 1H), 7.99-8.09 (m, 3H), 8.54 (d, J=4.27 Hz, 1H), 9.07 (s, 1H). LCMS Rt=2.412 min., m/z 593.4 (M+H). HPLC R$_t$=5.185 min. (Sunfire C18), 96.4% purity and 11.558 min. (Gemini C18), 98.2% purity.

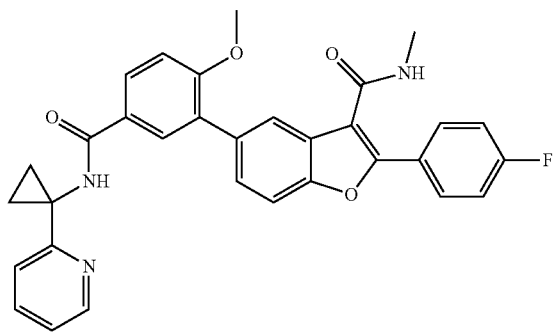

2-(4-Fluorophenyl)-5-(2-methoxy-5-(1-(pyridin-2-yl)cyclopropylcarbamoyl)phenyl)-N-methyl benzofuran-3-carboxamide. The LC/MS data was obtained on a Shimadzu analytical LC/Micromass Platform LC (ESI+) at 220 nm using the following set of conditions: Phenomenex-Luna 10 nM C18, 3.0×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 5 mL/minute. HPLC purity was determined using a Shimadzu analytical LC at 254 nm and 256 nm with a Waters Sunfire C18 3.5 nm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Phenomenex Gemini C18 3.0 nm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. ¹H NMR (400 MHz, DMSO-d6) δ ppm 1.31-1.40 (m, 2H), 1.56-1.65 (m, 2H), 2.82 (d, J=4.52 Hz, 3H), 3.85 (s, 3H), 7.24 (d, J=8.53 Hz, 1H), 7.30 (dd, J=6.78, 5.52 Hz, 1H), 7.39 (t, J=8.91 Hz, 2H), 7.46 (d, J=8.03 Hz, 1H), 7.52 (dd, J=8.53, 1.76 Hz, 1H), 7.68-7.75 (m, 2H), 7.86 (s, 1H), 7.93-8.02 (m, 4H), 8.45 (d, J=4.52 Hz, 1H), 8.49 (d, J=4.27 Hz, 1H), 9.23 (s, 1H). LCMS Rt=2.557 min., m/z 536.10 (M+H). HPLC Rt=6.683 min. (Sunfire C18), 96.3% purity and 11.493 min. (Gemini C18), 99.5% purity.

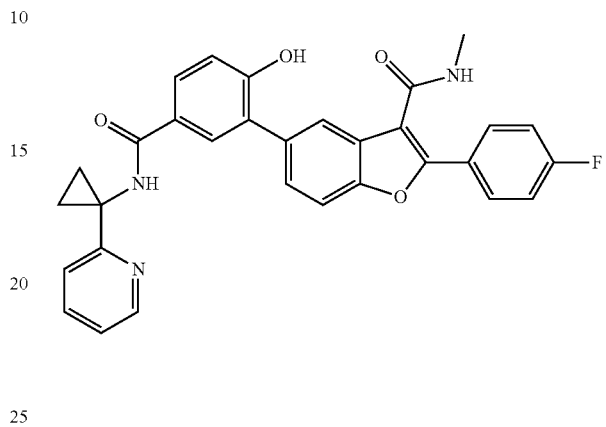

2-(4-Fluorophenyl)-5-(2-hydroxy-5-(1-(pyridin-2-yl)cyclopropylcarbamoyl)phenyl)-N-methylbenzofuran-3-carboxamide. To a 100 mL round-bottomed flask equipped with a reflux condenser was added 2-(4-fluorophenyl)-5-(2-methoxy-5-(1-(pyridin-2-yl)cyclopropylcarbamoyl)phenyl)-N-methylbenzofuran-3-carboxamide (400 mg, 0.747 mmol), DCE (42 mL) and boron tribromide-methyl sulfide complex (1868 mg, 5.97 mmol). The solution was placed under nitrogen and stirred overnight at 90° C. The reaction mixture was cooled to room temperature, quenched with methanol and evaporated to near dryness. The mixture was taken up in 10 mL of methanol and purified using a Shimadzu preparative HPLC employing methanol/water/0.1% trifluoroacetic acid where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 40-100% B and a flow rate of 40 mL/min. over 10 minutes with a 5 minute hold. The solvent was evaporated giving 234 mgs (60% yield) of 2-(4-fluorophenyl)-5-(2-hydroxy-5-(1-(pyridin-2-yl)cyclopropylcarbamoyl)phenyl)-N-methylbenzofuran-3-carboxamide as a white solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 4 mL/minute. ¹H NMR (400 MHz, THF-d8) δ ppm 1.25-1.31 (m, 2H), 1.59-1.66 (m, 2H), 2.90 (d, J=4.52 Hz, 3H), 6.91 (d, J=8.53 Hz, 1H), 7.08 (dd, J=6.90, 5.40 Hz, 1H), 7.17-7.24 (m, 2H), 7.45-7.65 (m, 5H), 7.79 (dd, J=8.41, 2.13 Hz, 1H), 7.88 (d, J=1.25 Hz, 1H), 7.93 (d, J=2.01 Hz, 1H), 8.08-8.17 (m, 2H), 8.39-8.45 (m, 1H), 8.49 (br. s., 1H). LCMS R$_t$=1.495 min., m/z 522.33 (M+H), 94% purity.

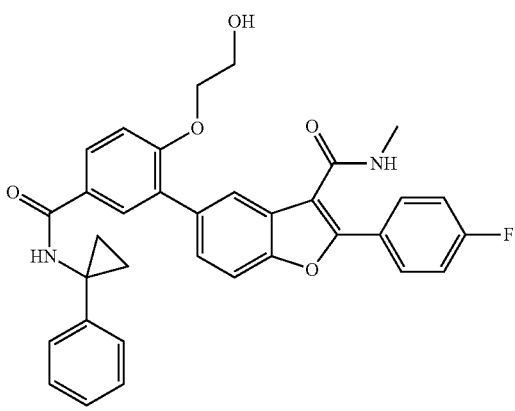

2-(4-Fluorophenyl)-5-(2-(2-hydroxyethoxy)-5-(1-phenyl-cyclopropylcarbamoyl)phenyl)-N-methyl benzofuran-3-carboxamide. To a small screw cap vial was added 2-(4-fluorophenyl)-5-(2-hydroxy-5-(1-phenylcyclopropyl carbamoyl)phenyl)-N-methylbenzofuran-3-carboxamide (19.5 mg, 0.037 mmol) in DMF (1.3 mL), (2-bromoethoxy)(tert-butyl)dimethylsilane (0.024 mL, 0.112 mmol), and DBU (1,8-diazabicyclo[5.4.0]undec-7-ene, 0.023 mL, 0.150 mmol). The vial was capped and shaken at 80° C. for 18 hours. The DMF was removed under a stream of nitrogen to give 5-(2-(2-(tert-butyldimethylsilyloxy)ethoxy)-5-(1-phenylcyclopropyl carbamoyl)phenyl)-2-(4-fluorophenyl)-N-methylbenzofuran-3-carboxamide as a tan oil. To the mixture was then added 1.3 mL of tetrahydrofuran along with 2 eq. of 1 M HCl (0.075 mL, 0.075 mmol). The solution was stirred for 1 hour at room temperature. The reaction mixture was transferred to a separatory funnel, diluted with ethyl acetate, washed sequentially with sodium bicarbonate, brine and dried over magnesium sulfate. The product mixture was filtered and the solvent was evaporated. The crude product was taken up in 1.8 mL of acetonitrile and 200 μL of DMF and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Sunfire C18 19×150 mm column at a gradient of 20-100% B and a flow rate of 20 mL/min. over 20 minutes with a 5 minute hold. 15.2 mgs of 2-(4-fluorophenyl)-5-(2-(2-hydroxyethoxy)-5-(1-phenylcyclopropyl carbamoyl)phenyl)-N-methyl benzofuran-3-carboxamide (70% yield, 2 steps) was obtained after solvent evaporation. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.20-1.27 (m, 2H), 1.28-1.36 (m, 2H), 2.87-2.96 (m, 3H), 3.75-3.83 (m, 3H), 4.10 (t, J=4.89 Hz, 2H), 7.04-7.13 (m, 2H), 7.16-7.25 (m, 4H), 7.29-7.35 (m, 2H), 7.43 (d, J=4.27 Hz, 1H), 7.51-7.59 (m, 2H), 7.87 (dd, J=8.53, 2.26 Hz, 1H), 7.94 (d, J=2.26 Hz, 1H), 8.02 (s, 1H), 8.11-8.18 (m, 2H), 8.25 (s, 1H). LCMS R$_t$=2.671 min., m/z 565.3 (M+H). HPLC Rt=9.454 min. (Sunfire C18), 95.0% purity and 11.611 min. (Gemini C18), 99.7% purity.

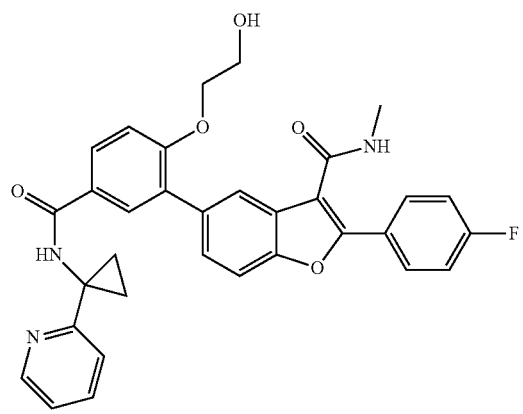

2-(4-Fluorophenyl)-5-(2-(2-hydroxyethoxy)-5-(1-(pyridin-2-yl)cyclopropylcarbamoyl)phenyl)-N-methylbenzofuran-3-carboxamide. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 mm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.23-1.29 (m, 2H), 1.62-1.68 (m, 2H), 2.91 (d, J=4.77 Hz, 3H), 3.80 (t, J=4.77 Hz, 2 H), 4.13 (t, J=4.89 Hz, 2H), 6.99 (m, 1H), 7.14 (d, J=8.53 Hz, 1H), 7.17-7.25 (m, 2H), 7.37-7.47 (m, 2H), 7.49-7.61 (m, 3H), 7.93 (dd, J=8.53, 2.26 Hz, 1H), 8.00 (d, J=2.26 Hz, 1H), 8.03-8.06 (m, 1H), 8.11-8.18 (m, 2H), 8.33 (s, 1H), 8.35-8.41 (m, 1H). LCMS m/z 566.4 (M+H), R$_t$=2.038 min. HPLC (Sunfire C18) Rt=5.916 min., 100% purity and (XBridge Phenyl C18) Rt=10.474 min., 100% purity.

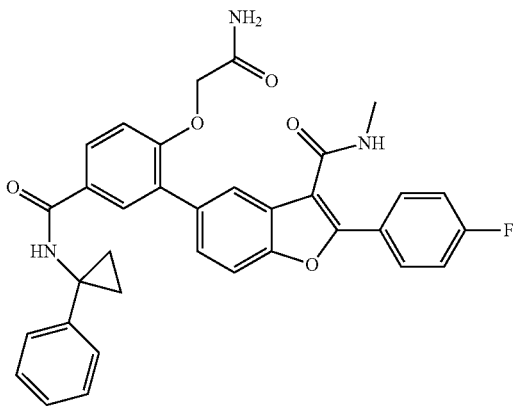

5-(2-(2-Amino-2-oxoethoxy)-5-(1-phenylcyclopropylcarbamoyl)phenyl)-2-(4-fluorophenyl)-N-methylbenzofuran-3-carboxamide. To a small screw cap vial was added 2-(4-fluorophenyl)-5-(2-hydroxy-5-(1-phenylcyclopropyl carbamoyl)phenyl)-N-methylbenzofuran-3-carboxamide (15.6 mg, 0.030 mmol) in DMF (2 mL), 2-bromoacetamide (41.4 mg, 0.300 mmol), and DBU (1,8-diazabicyclo[5.4.0]undec-7-ene, 0.060 mL, 0.400 mmol). The vial was capped and shaken at 75° C. overnight. The crude reaction mixture was cooled, evaporated, taken up in 2 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Xterra C18 19×100 mm column at a gradient of 25-100% B and a flow rate of 25 mL/min. over 12 minutes with a 8 minute hold. The solvent was evaporated overnight giving 9.9 mgs (54.9% yield) of carboxamide as a white solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.21-1.26 (m, 2H), 1.26-1.33 (m, 2H), 2.87-2.92 (m, 3H), 4.47 (s, 2H), 7.05-7.13 (m, 2H), 7.15-7.25 (m, 4 H), 7.27-7.34 (m, 2H), 7.45-7.51 (m, 1H), 7.52-7.61 (m, 2H), 7.84-7.92 (m, 2 H), 7.93-8.00 (m, 2H), 8.09-8.20 (m, 3H), 8.29 (s, 1H). LCMS R$_t$=2.522 min., m/z 578.3 (M+H). HPLC Rt=8.693 min. (Sunfire C18), 91.0% purity and 11.423 min. (Gemini C18), 92% purity.

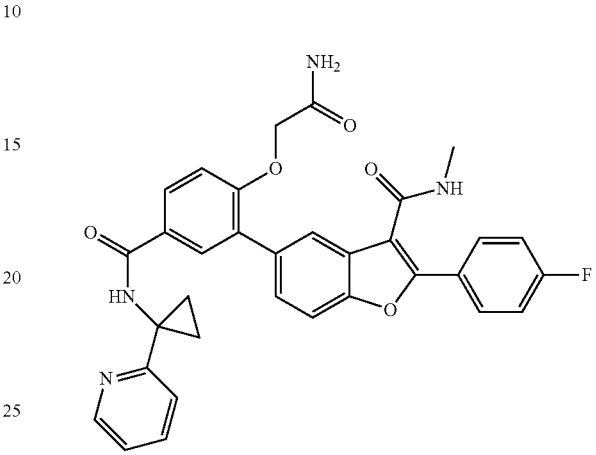

5-(2-(2-Amino-2-oxoethoxy)-5-(1-(pyridin-2-yl)cyclopropylcarbamoyl)phenyl)-2-(4-fluoro phenyl)-N-methylbenzofuran-3-carboxamide. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.25-1.37 (m, 2H), 1.57-1.67 (m, 2H), 2.88-2.96 (m, 3H), 4.49 (s, 2H), 6.51 (br. s., 1H), 6.79 (br. s., 1H), 7.10 (d, J=8.78 Hz, 1H), 7.17-7.27 (m, 3H), 7.52-7.66 (m, 4H), 7.72-7.82 (m, 1H), 7.94 (dd, J=8.53, 2.26 Hz, 1H), 7.99 (s, 1H), 8.03 (d, J=2.26 Hz, 1H), 8.08-8.18 (m, 2H), 8.50 (d, J=4.27 Hz, 1H), 8.91 (br. s., 1H). LCMS Rt=2.578 min., m/z 580.3 (M+2H). HPLC R$_t$=9.368 min. (Sunfire C18), 96.0% purity and 10.756 min. (Gemini C18), 97.9% purity.

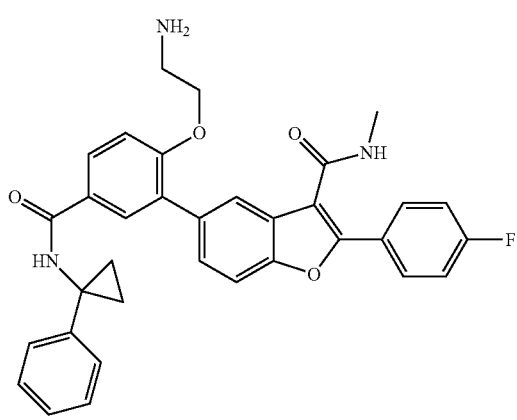

5-(2-(2-Aminoethoxy)-5-(1-phenylcyclopropylcarbamoyl)phenyl)-2-(4-fluorophenyl)-N-methyl benzofuran-3-carboxamide, TFA. To a 2 dram vial was added 2-(4-fluorophenyl)-5-(2-hydroxy-5-(1-phenylcyclopropylcarbamoyl)phenyl)-N-methylbenzofuran-3-carboxamide (40.2 mg, 0.078 mmol) in 3 mL of DMF along with 3 eq. of 2-(2-bromoethyl)isoindoline-1,3-dione (58.8 mg, 0.232 mmol) and 4 eq. of DBU (1,8-diaza bicyclo[5.4.0]undec-7-ene, 0.046 mL, 0.308 mmol). The vial was capped and shaken at 75° C. over night. The crude reaction mixture was evaporated, taken up in 2 mL of acetonitrile and purified using a Shimadzu preparative HPLC employing acetonitrile/water/0.1% trifluoroacetic acid where solvent A was 10% acetonitrile/90% water/0.1% trifluoroacetic acid and solvent B was 10% water/90% acetonitrile/0.1% trifluoroacetic acid with a Xterra C18 19×100 mm column at a gradient of 25-100% B and a flow rate of 25 mL/min. over 12 minutes with a 8 minute hold. The solvent was evaporated yielding 10.7 mgs of the phthalimide intermediate as a white solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 4 mL/minute. LCMS m/z 694.4 (M+H), Rt=3.128 min., 93.7% purity. To a small screw cap vial was added the phthalimide intermediate, 5-(2-(2-(1,3-dioxoisoindolin-2-yl)ethoxy)-5-(1-phenylcyclo-propylcarbamoyl)phenyl)-2-(4-fluorophenyl)-N-methylbenzofuran-3-carboxamide (10.7 mg, 0.015 mmol) in 2 mL of methanol and anhydrous hydrazine (0.780 μL, 0.025 mmol). The vial was placed in a pre-equilibrated oil bath set to 75° C. and the solution refluxed for 90 minutes. The product was cooled to room temperature and the solvent was evaporated. The resulting oil was diluted with 10 mL of DCM, washed with 1 mL of 0.5M NaOH and extracted. The solvent was evaporated and the crude product was taken up in 1.8 mL of acetonitrile and 200 μL of DMF and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Sunfire C18 19×150 mm column at a gradient of 20-100% B and a flow rate of 20 mL/min. over 20 minutes with a 5 minute hold. The solvent was evaporated giving 7.0 mgs (14% yield, 2 steps) of 5-(2-(2-aminoethoxy)-5-(1-phenyl cyclopropylcarbamoyl)phenyl)-2-(4-fluorophenyl)-N-methylbenzofuran-3-carboxamide, TFA as a white solid. The LC/MS data was obtained on a Shimadzu analytical LC/Micromass Platform LC (ESI+) at 220 nm using the following set of conditions: Sunfire 5 μm C18, 4.6×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.21-1.27 (m, 2H), 1.28-1.35 (m, 2H), 2.89 (d, J=4.77 Hz, 3H), 3.39 (t, J=4.77 Hz, 2H), 4.38 (t, J=5.02 Hz, 2H), 7.05-7.13 (m, 1H), 7.16-7.28 (m, 5 H), 7.29-7.35 (m, 2H), 7.49-7.60 (m, 2H), 7.62 (br. s., 1H), 7.87 (dd, J=8.53, 2.26 Hz, 1H), 7.96-8.05 (m, 3H), 8.07 (d, J=1.00 Hz, 1H), 8.30 (s, 1H). LCMS Rt=2.023 min., m/z 564.3 (M+H). HPLC $R_t$=6.931 min. (Sunfire C18), 100% purity and 11.423 min. (Gemini C18), 98.9% purity.

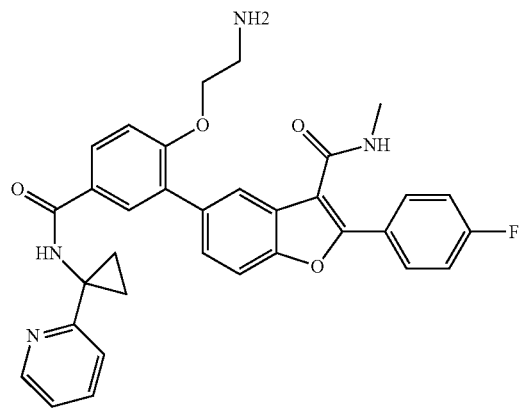

5-(2-(2-Aminoethoxy)-5-(1-(pyridin-2-yl)cyclopropylcarbamoyl)phenyl)-2-(4-fluorophenyl)-N-methylbenzofuran-3-carboxamide, 2 TFA. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.23-1.33 (m, 2H), 1.60-1.67 (m, 2H), 2.89 (d, J=4.77 Hz, 3H), 3.41 (t, J=5.14 Hz, 2H), 4.40 (t, J=5.14 Hz, 2H), 6.58 (br. s., 2H), 7.01-7.11 (m, 1H), 7.16-7.29 (m, 3H), 7.46 (d, J=8.03 Hz, 1H), 7.52-7.70 (m, 4H), 7.93 (dd, J=8.53, 2.26 Hz, 1H), 7.98-8.05 (m, 3H), 8.07 (s, 1H), 8.41 (d, J=4.77 Hz, 1H), 8.56 (s, 1H). LCMS m/z 565.4 (M+H), Rt=1.628 min. HPLC (Sunfire C18) Rt=5.048 min., 99.9% purity and (XBridge Phenyl C18) Rt=10.531 min., 100% purity.

5-Bromo-2,4-dimethoxy-N-(1-(pyridin-2-yl)cyclopropyl) benzamide. To a 250 mL round-bottomed flask was added chloroform (60 mL) along with 2,4-dimethoxybenzoic acid (2.0 g, 10.98 mmol). The solution was cooled to 0° C. and bromine (0.566 mL, 10.98 mmol) was added dropwise over 5 minutes. The solution was allowed to warm to room temperature and stirred overnight. The resulting solid was filtered, washed with cold chloroform and dried under vacuum to give 2.49 g (8.6 mmol, 78% yield) of 5-bromo-2,4-dimethoxybenzoic acid as a yellow solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1.0 mL/minute. $^1$H NMR (400 MHz, DMSO-d6) δ ppm 3.88 (s, 3H), 3.95 (s, 3H), 6.78 (s, 1H), 7.86 (s, 1H). LCMS R$_t$=1.453 min., m/z 262.99 (M+H), 93% purity.

To a 2 dram vial was added 5-bromo-2,4-dimethoxybenzoic acid (1.044 g, 4 mmol), DMF (48.2 mL), N,N-Diisopropylethylamine (2.79 mL, 16.00 mmol), 1-(pyridin-2-yl)cyclopropanamine, 2HCl (0.911 g, 4.40 mmol), and finally HATU (2-(3H-[1,2,3]triazolo[4,5-b]pyridin-3-yl)-1,1,3,3-tetramethyl isouronium hexafluorophosphate(V), 6.08 g, 16.00 mmol). The vial was capped and shaken for 16 hours at room temperature. The crude reaction mixture was diluted with 10 mL of DCM, washed with 5 mL of 1M HCl, extracted, washed with 20 mL of brine, and dried over magnesium sulfate. The solution was pushed through a plug of silica gel and evaporated to dryness. Trituration with 20 mL of diethyl ether gave 1.6 grams of 5-bromo-2,4-dimethoxy-N-(1-(pyridin-2-yl)cyclopropyl)benzamide as a tan solid (76% yield). $^1$H NMR (400 MHz, THF-d8) δ ppm 1.22-1.32 (m, 2H), 1.59-1.67 (m, 2H), 3.94 (s, 3H), 4.02 (s, 3H), 6.72 (s, 1H), 7.09 (m, 1H), 7.47 (d, J=8.03 Hz, 1H), 7.62 (td, J=7.72, 1.88 Hz, 1H), 8.20 (s, 1H), 8.39-8.52 (m, 2H). LCMS Rt=2.162 min., m/z 379.2 (M+2H), 96% purity.

5-Bromo-2-methoxy-4-methylbenzoic acid. The LC/MS data was obtained on a Shimadzu analytical LC/Micromass Platform LC (ESI+) at 220 nm using the following set of conditions: Waters Sunfire 5 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 4 mL/minute. Yellow solid, 63.5% yield. LCMS R$_t$=1.545 min., m/z 246.99 (M+H), 90% purity. $^1$H NMR (400 MHz, DMSO-d$_6$) δ ppm 2.21-2.44 (m, 3H), 3.82 (s, 3H), 7.17 (s, 1H), 7.78 (s, 1H), 12.72 (br. s., 1H).

5-Bromo-2-methoxy-4-methyl-N-(1-(pyridin-2-yl)cyclopropyl)benzamide. The LC/MS data was obtained on a Shimadzu analytical LC/Micromass Platform LC (ESI+) at 220 nm using the following set of conditions: Phenomenex Luna 3 μm C18, 2.0×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. Tan solid, 68% yield, 100% purity. $^1$H NMR (400 MHz, DMSO-d$_6$) δ ppm 1.34-1.42 (m, 2H), 1.58-1.66 (m, 2H), 2.39 (s, 3H), 3.96 (s, 3H), 7.05 (s, 1H), 7.40 (dd, J=6.90, 5.90 Hz, 1H), 7.76 (d, J=8.03 Hz, 1H), 7.97 (td, J=7.78, 1.76 Hz, 1H), 8.10 (s, 1H), 8.60 (d, J=5.27 Hz, 1H), 8.88 (s, 1H). LCMS Rt=3.525 min., m/z 362.88 (M+H), 98% purity.

Methyl 4-hydroxy-2-methoxybenzoate. To a 250 mL Erlenmeyer flask was added methyl 4-amino-2-methoxybenzoate (7.5 g, 41.4 mmol) and a 25% solution of sulfuric acid (40 mL, 188 mmol). The solution was cooled to 0° C. and a saturated solution of sodium nitrite (4.29 g, 62.2 mmol) was added drop wise. The orange mixture was stirred for 15 minutes. The resulting diazonium solution was then very slowly poured into a 1 L flask containing 500 mL of 3% sulfuric acid. The solution was stirred for 5 minutes then transferred to a separatory funnel. The reaction mixture was diluted with 150 mL of DCM, extracted, dried over magnesium sulfate and concentrated. to a red solid. The resulting solid was triturated with hexane to give 5.71 grams of the desired phenol as a red powder (73% yield). The LC/MS data was obtained on a Shimadzu analytical LC/Micromass Platform LC (ESI+) at 220 nm using the following set of conditions: Waters Sunfire 5 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 4 mL/minute. $^1$H NMR (400 MHz, DMSO-d6) δ ppm 3.67-3.72 (m, 3H), 3.74 (s, 3H), 6.39 (dd, J=8.66, 2.13 Hz, 1H), 6.45 (d, J=2.13 Hz, 1H), 7.59 (d, J=8.66 Hz, 1H). LCMS Rt=1.070 min., m/z 183.09 (M+H), 96% purity.

Methyl 4-(2-amino-2-oxoethoxy)-5-bromo-2-methoxybenzoate. To a sealed tube was added 2-bromoacetamide (2.272 g, 16.47 mmol), DMF (50 mL), cesium carbonate (7.15 g, 21.96 mmol) and methyl 4-hydroxy-2-methoxybenzoate (1.00 g, 5.49 mmol). The tube was sealed and heated for 16 hours at 85° C. The reaction mixture was diluted with DCM, washed sequentially with 10 mL of 1M HCl, water, and brine. The solution was dried over sodium sulfate, filtered and the solvent removed to give 1.2 grams of methyl 4-(2-amino-2-oxoethoxy)-2-methoxybenzoate (78% yield) as a yellow powder. The LC/MS data was obtained on a Shimadzu analytical LC/Micromass Platform LC (ESI+) at 220 nm using the following set of conditions: Waters Sunfire 5 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 4 mL/minute. $^1$H NMR (400 MHz, THF-d8) δ ppm 3.71-3.76 (m, 3H), 3.80-3.84 (m, 3H), 4.45 (s, 2H), 6.56 (dd, J=8.66, 2.38 Hz, 1H), 6.65 (d, J=2.26 Hz, 1H), 6.77 (br. s., 1H), 6.92 (br. s., 1H), 7.75 (d, J=8.78 Hz, 1H). LCMS Rt=1.385 min., m/z 240.2 (M+H), 92% purity.

To a 250 mL round-bottomed flask was added methyl 4-(2-amino-2-oxoethoxy)-2-methoxybenzoate (1.2 g, 5.14 mmol) and chloroform (40 mL). The mixture was placed under a nitrogen atmosphere and cooled to 0° C. Bromine (0.263 mL, 5.14 mmol) was added drop wise (in 3 mL of chloroform) and the solution was allowed to warm to room temperature overnight. The orange solid was cooled with an ice bath, filtered, washed sequentially with cold chloroform, then diethyl ether. The product was dried under vacuum giving 1.7 grams (91% yield) of methyl 4-(2-amino-2-oxoethoxy)-5-bromo-2-methoxybenzoate as an orange solid. The LC/MS data was obtained on a Shimadzu analytical LC/Micromass Platform LC (ESI+) at 220 nm using the following set of conditions: Waters Sunfire 5 µm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 4 mL/minute. $^1$H NMR (400 MHz, THF-d8) δ ppm 3.76 (s, 3H), 3.88 (s, 3H), 4.63 (s, 2H), 6.76 (s, 1H), 7.10 (br. s., 2H), 7.96 (s, 1H). LCMS Rt=1.793 min., m/z 319.1 (M+H), 90% purity.

5-(2,4-Dimethoxy-5-(1-(pyridin-2-yl)cyclopropylcarbamoyl)phenyl)-2-(4-fluorophenyl)-N-methyl benzofuran-3-carboxamide. To a microwave vial was added 5-bromo-2,4-dimethoxy-N-(1-(pyridin-2-yl)cyclopropyl)benzamide (41.5 mg, 0.110 mmol), 2-(4-fluorophenyl)-N-methyl-5-(4,4,5,5-tetramethyl-1,3,2-dioxaborolan-2-yl)benzofuran-3-carboxamide (39.5 mg, 0.1 mmol), dioxane (2.00 mL), water (0.200 mL), dicyclohexyl(2',6'-dimethoxybiphenyl-2-yl)phosphine (S-Phos, 8.21 mg, 0.020 mmol), tribasic potassium phosphate (85 mg, 0.400 mmol) and palladium(II) acetate (4.49 mg, 0.020 mmol). The solvent was removed and the crude reaction mixture was taken up in 2 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 3.5 µm C18 4.6×150 mm column at a gradient of 20-100% B and a flow rate of 25 mL/min. over 20 minutes with a 10 minute hold. The solvent was evaporated giving 18.1 mgs (30.4% yield) of the desired pyridylcarboxamide as a yellow solid. The LC/MS data was obtained on a Shimadzu analytical LC/Micromass Platform LC (ESI+) at 220 nm using the following set of conditions: Phenomenex Luna 10 µm C18, 3.0×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 5 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.26-1.37 (m, 2 H), 1.60-1.67 (m, 2H), 2.89 (d, J=4.77 Hz, 3H), 3.87 (s, 3H), 4.07 (s, 3H), 6.78 (s, 1H), 7.10-7.23 (m, 3H), 7.39-7.44 (m, 1H), 7.46-7.52 (m, 2H), 7.57 (d, J=7.78 Hz, 1H), 7.68 (td, J=7.72, 1.63 Hz, 1H), 7.74 (d, J=1.25 Hz, 1H), 8.09 (s, 1 H), 8.11-8.19 (m, 2H), 8.47 (d, J=4.52 Hz, 1H), 8.59 (s, 1H). LCMS m/z 566.2 (M+H), R$_t$=2.608 min. HPLC (Sunfire C18) Rt=6.816 min, 93.9% purity and (Gemini C18) Rt=11.676 min., 95.8% purity.

2-(4-Fluorophenyl)-5-(4-methoxy-2-methyl-5-(1-(pyridin-2-yl)cyclopropylcarbamoyl)phenyl)-N-methylbenzofuran-3-carboxamide. Alternative synthesis. To a sealed tube was added 5-bromo-2-methoxy-4-methyl-N-(1-(pyridin-2-yl)cyclopropyl)benzamide (1.9024 g, 5.27 mmol), dioxane (70 mL), 2-(4-fluorophenyl)-N-methyl-5-(4,4,5,5-tetramethyl-1,3,2-dioxaborolan-2-yl)benzofuran-3-carboxamide (2.529 g, 6.40 mmol), cesium carbonate (2.57 g, 7.90 mmol), water (14.00 mL) and finally tetrakis(triphenylphosphine)palladium(0) (0.304 g, 0.263 mmol). The vessel was sealed and heated for 16 hours at 85° C. in an oil bath. The mixture was cooled to room temperature, diluted with 20 ml of DCM and pushed through a plug of celite. The resulting dark solution was concentrated to a grey oil. To this residue was added 20 ml of 0.5N HCl, followed by 20 ml of water. The flask was cooled in an ice bath for 30 minutes and the resulting solids were collected by filtration and washed with 10 ml of water and dried under vacuum. The crude product was taken up in 1:1 ethyl acetate/hexane and pushed through a plug of silica gel. Solvent was removed giving 1.65 grams of the product as a light tan solid.

Methyl 4-(2-amino-2-oxoethoxy)-5-(2-(4-fluorophenyl)-3-(methylcarbamoyl)benzofuran-5-yl)-2-methoxybenzoate. To a sealed tube was added methyl 4-(2-amino-2-oxoethoxy)-5-bromo-2-methoxybenzoate (318 mg, 1.0 mmol), dioxane (30 mL), water (6.00 mL), 2-(4-fluorophenyl)-N-methyl-5-(4,4,5,5-tetramethyl-1,3,2-dioxaborolan-2-yl)benzofuran-3-carboxamide (593 mg, 1.500 mmol), cesium carbonate (489 mg, 1.500 mmol), and tetrakis(triphenylphosphine)palladium(0) (23.11 mg, 0.020 mmol). The vessel was sealed and the mixture heated overnight at 85° C. The reaction mixture was cooled, diluted with 200 mL of DCM, washed sequentially with 50 mL of 1M HCl then brine. The product was extracted and the resulting yellow solution was evaporated to dryness. The aqueous layers were combined, cooled for 5 minutes in an ice bath and the solids that formed were filtered and dried under vacuum. The solids were then combined and triturated sequentially with diethyl ether then ice cold acetonitrile (10 mL each) giving 171.6 mgs (30% yield) of methyl 4-(2-amino-2-oxoethoxy)-5-(2-(4-fluorophenyl)-3-(methylcarbamoyl)benzofuran-5-yl)-2-methoxybenzoate as a white solid. The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters Phenyl XBridge C18 3.5 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, CD$_3$OD) δ ppm 3.04 (s, 3H), 3.92 (s, 3H), 4.03 (s, 3H), 4.71 (s, 2H), 6.85 (s, 1H), 7.33 (t, J=8.78 Hz, 2H), 7.57-7.64 (m, 1H), 7.66-7.73 (m, 1H), 7.87 (s, 1H), 7.96 (s, 1H), 8.00-8.08 (m, 2H). LCMS m/z 507.3 (M+H), Rt=2.635 min. HPLC Rt=8.193 min. (Sunfire C18), 100% purity and Rt=10.678 min. (Phenyl XBridge C18), 100% purity.

4-(2-Amino-2-oxoethoxy)-5-(2-(4-fluorophenyl)-3-(methylcarbamoyl)benzofuran-5-yl)-2-methoxybenzoic acid. To a 50 mL round-bottomed flask was added methyl 4-(2-amino-2-oxoethoxy)-5-(2-(4-fluorophenyl)-3-(methyl carbamoyl) benzofuran-5-yl)-2-methoxybenzoate (171.6 mg, 0.295 mmol) in a 1:1 mixture of methanol (7 mL) and THF (7 mL). To this solution was then added 4 eq. of 1M aqueous sodium hydroxide (1.2 mL, 1.2 mmol). The reaction mixture was stirred overnight at room temperature. Solvent was removed and the crude product was diluted with 50 mL of 1:1 DCM/ ethyl acetate, washed sequentially with 10 mL of 1M HCl then brine. The product solution was dried over sodium sulfate, filtered and evaporated to dryness. The aqueous layers were combined, cooled in an ice bath and the product that formed on the sides of the flask were filtered and dried under vacuum. The solids were combined, taken up in 10 mL of DMF and purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 40-100% B and a flow rate of 40 mL/min. over 12 minutes with a 10 minute hold. Solvent was removed giving 87 mgs (60% yield) of 4-(2-amino-2-oxoethoxy)-5-(2-(4-fluorophenyl)-3-(methylcarbamoyl)benzofuran-5-yl)-2-methoxybenzoic acid as a white powder. The LC/MS data was obtained on a Shimadzu analytical LC/Micromass Platform LC (ESI+) at 220 nm using the following set of conditions: Waters Sunfire 5 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 4 mL/minute. HPLC purity was determined using a Shimadzu analytical LC at 254 nm and 256 nm with a Waters Sunfire C18 3.5 μm 4.6×150 mm column employing water/ acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute. $^1$H NMR (400 MHz, DMF-d7) δ ppm 2.97 (d, J=4.52 Hz, 3H), 4.02 (s, 3H), 4.79 (s, 2H), 6.97 (s, 1H), 7.31 (br. s., 1H), 7.38-7.46 (m, 2H), 7.51 (br. s., 1H), 7.67-7.77 (m, 2H), 7.92 (s, 1H), 7.95 (s, 1H), 8.09-8.16 (m, 2H), 8.35 (d, 1H). LCMS m/z 493.00 (M+H), Rt=1.618 min. HPLC (Sunfire C18) Rt=7.108 min, 100% purity and (XBridge Phenyl C18) Rt=6.383 min., 99.3% purity.

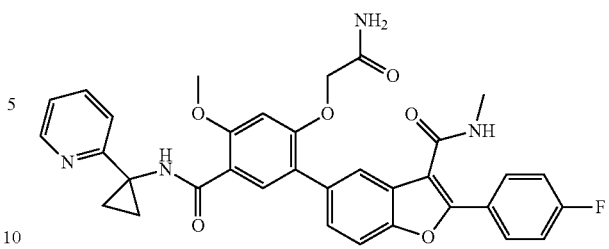

5-(2-(2-Amino-2-oxoethoxy)-4-methoxy-5-(1-(pyridin-2-yl)cyclopropylcarbamoyl)phenyl)-2-(4-fluorophenyl)-N-methylbenzofuran-3-carboxamide. To a 25 mL flask was added 4-(2-amino-2-oxoethoxy)-5-(2-(4-fluorophenyl)-3-(methyl carbamoyl)benzofuran-5-yl)-2-methoxybenzoic acid (48.8 mg, 0.099 mmol), DMF (2 mL), N-ethyl-N-diisopropylpropan-2-amine (0.069 mL, 0.396 mmol), 1-(pyridin-2-yl)cyclopropanamine (19.94 mg, 0.149 mmol) and finally HATU (2-(3H-[1,2,3]triazolo[4,5-b]pyridin-3-yl)-1,1,3,3-tetramethyl isouronium hexafluorophosphate(V), 151 mg, 0.396 mmol). The flask was sealed with a septa, placed under N$_2$ and stirred at room temperature overnight. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 22 minutes with a 8 minute hold. The solvent was removed giving 53.0 mgs (87% yield) of 5-(2-(2-amino-2-oxoethoxy)-4-methoxy-5-(1-(pyridin-2-yl)cyclopropylcarbamoyl)phenyl)-2-(4-fluorophenyl)-N-methylbenzofuran-3-carboxamide as a yellow powder. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/ 0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/ acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/ 10 mM ammonium bicarbonate/5% HPLC grade methanol), in 10 minutes with a 10 minute hold at a rate of 1 mL/minute. $^1$H NMR (400 MHz, DMF-d7) δ ppm 1.46-1.53 (m, 2H), 1.69-1.76 (m, 2H), 2.96 (d, J=4.77 Hz, 3H), 4.16 (s, 3H), 4.82 (s, 2H), 7.04 (s, 1H), 7.34 (br. s., 1H), 7.36-7.48 (m, 3H), 7.52 (br. s., 1H), 7.66-7.78 (m, 3H), 7.92-8.01 (m, 2H), 8.03 (d, J=2.76 Hz, 1H), 8.08-8.14 (m, 2H), 8.36 (d, J=4.77 Hz, 1H), 8.57-8.62 (m, 1H), 8.94 (s, 1H). LCMS m/z 609.5 (M+H), Rt=2.030 min. HPLC (Sunfire C18) Rt=5.800 min, 99.4% purity and (XBridge Phenyl C18) Rt=9.546 min., 99.7% purity.

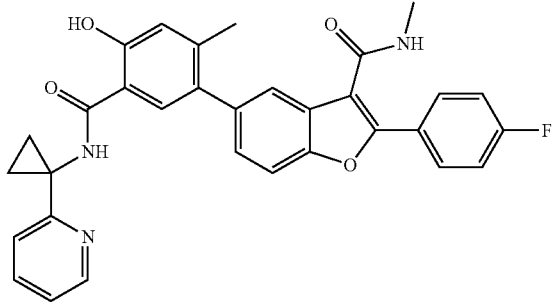

2-(4-Fluorophenyl)-5-(4-hydroxy-2-methyl-5-(1-(pyridin-2-yl)cyclopropylcarbamoyl)phenyl)-N-methylbenzofuran-3-carboxamide. To a 250 mL round-bottomed flask was added 2-(4-fluorophenyl)-5-(4-methoxy-2-methyl-5-(1-(pyridin-2-yl)cyclopropylcarbamoyl)phenyl)-N-methylbenzofuran-3-carboxamide (1.0008 g, 1.821 mmol), and DCM (18 mL). The solution was placed under an atmosphere of nitrogen and cooled to 0° C. To the tan mixture was added dropwise 1M trichloroborane (9.10 mL, 9.10 mmol). The mixture was allowed to slowly warm to room temperature overnight. The reaction mixture was cooled to 0° C. and 100 mL of cold methanol was added and the mixture stirred for 30 minutes then evaporated to near dryness. The addition of methanol followed by evaporation was repeated to give a tan solid (82% yield). The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=95% HPLC grade acetonitrile/10 mM Ammonium acetate/5% HPLC grade water), (A=95% HPLC grade water/10 mM Ammonium acetate/5% HPLC grade acetonitrile), in 4 minutes with a 1 minute hold at a rate of 0.8 mL/minute. $^1$H NMR (400 MHz, THF-d8) δ ppm 1.26-1.37 (m, 2H), 1.57-1.66 (m, 2H), 2.28 (s, 3H), 3.02 (d, J=4.02 Hz, 3H), 6.77 (s, 1H), 7.18 (t, J=8.78 Hz, 3 H), 7.32 (d, J=8.28 Hz, 1H), 7.51 (d, J=8.53 Hz, 1H), 7.69-7.79 (m, 1H), 7.83-7.97 (m, 3H), 8.08 (s, 1H), 8.22-8.39 (m, 4H), 8.66 (br. s., 1H). LCMS m/z 536.5 (M+H), 534.4 (M−H), Rt=3.446 min., 90% purity.

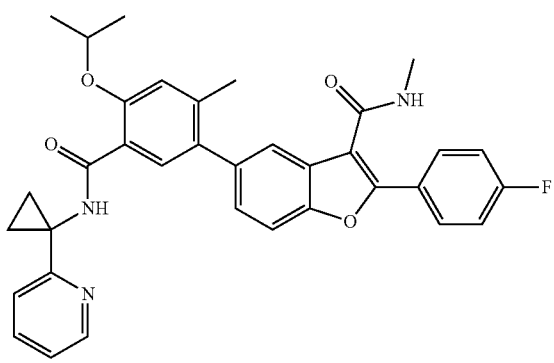

2-(4-Fluorophenyl)-5-(4-isopropoxy-2-methyl-5-(1-(pyridin-2-yl)cyclopropylcarbamoyl)phenyl)-N-methylbenzofuran-3-carboxamide, TFA. To a microwave vial was added 2-(4-fluorophenyl)-5-(4-hydroxy-2-methyl-5-(1-(pyridin-2-yl)cyclopropylcarbamoyl)phenyl)-N-methylbenzofuran-3-carboxamide (16.6 mg, 0.031 mmol), dioxane (2 mL), triphenylphosphine (32.5 mg, 0.124 mmol), (E)-di-tert-butyl diazene-1,2-dicarboxylate (21.41 mg, 0.093 mmol) and propan-2-ol (5.92 μL, 0.077 mmol). The vial was sealed and subjected to microwave heating (140° C.) for 20 minutes. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 5 minute hold. The solvent was removed giving 6 mgs (25% yield) of 2-(4-fluorophenyl)-5-(4-isopropoxy-2-methyl-5-(1-(pyridin-2-yl)cyclopropylcarbamoyl)phenyl)-N-methylbenzofuran-3-carboxamide as a colorless powder. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.24-1.31 (m, 2H), 1.46 (d, J=6.02 Hz, 6H), 1.64-1.69 (m, 2H), 2.29 (s, 3H), 2.89 (d, J=4.52 Hz, 3H), 4.83-4.95 (m, 1H), 6.98-7.04 (m, 1H), 7.07 (s, 1H), 7.16-7.24 (m, 2H), 7.26 (dd, J=8.28, 1.76 Hz, 1H), 7.47 (d, J=8.03 Hz, 2H), 7.52-7.59 (m, 2H), 7.62 (d, J=1.26 Hz, 1H), 7.95 (s, 1H), 8.11-8.19 (m, 2H), 8.36-8.43 (m, 1H), 8.61 (s, 1H). LCMS m/z 578.4 (M+H), Rt=2.746 min. HPLC (Sunfire C18) Rt=7.695 min, 98.38% purity and (XBridge Phenyl C18) Rt=12.003 min., 95.9% purity.

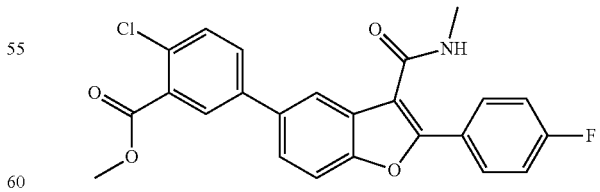

Methyl 2-chloro-5-(2-(4-fluorophenyl)-3-(methylcarbamoyl)benzofuran-5-yl)benzoate. To a 150 mL sealed tube was added 2-(4-fluorophenyl)-3-(methylcarbamoyl)benzofuran-5-yl trifluoromethanesulfonate (0.5 g, 1.198 mmol), dioxane (7.18 mL), water (1.437 mL), tetrakis(triphenylphosphine) palladium(0) (0.028 g, 0.024 mmol), 4-chloro-3-(methoxycarbonyl)phenyl boronic acid (0.385 g, 1.797 mmol), and cesium carbonate (0.586 g, 1.797 mmol). The tube was sealed and heated in an oil bath overnight at 85° C. The reaction mixture was cooled; the crude product was diluted with 100 mL of ethyl acetate, washed sequentially with 50 mL of water then brine. The product solution was dried over magnesium sulfate and filtered. Solvent was evaporated to give a crude yellow solid. The solid was triturated with diethyl ether (30 mL x2) and hexane (30 mL×1) then dried under vacuum to give 394 mgs of a ivory colored solid (53% yield). The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, THF-d8) δ ppm 2.92 (d, J=4.77 Hz, 3H), 3.91 (s, 3H), 7.18-7.27 (m, 2H), 7.52-7.55 (m, 1H), 7.57 (d, J=8.53 Hz, 1H), 7.63 (d, J=1.25 Hz, 2H), 7.82 (dd, J=8.41, 2.38 Hz, 1H), 7.96-8.00 (m, 1H), 8.09-8.17 (m, 3H). LCMS m/z 438.3 (M+H), Rt=3.518 min., 90% purity.

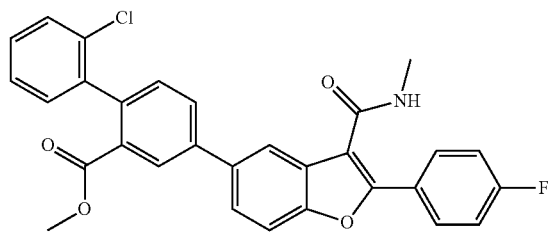

Methyl 2'-chloro-4-(2-(4-fluorophenyl)-3-(methylcarbamoyl)benzofuran-5-yl)biphenyl-2-carboxylate. To a microwave vial was added dioxane (6 mL), water (0.600 mL), dicyclohexyl(2',6'-dimethoxy biphenyl-2-yl)phosphine (S-Phos, 16.42 mg, 0.040 mmol), methyl 2-chloro-5-(2-(4-fluorophenyl)-3-(methyl carbamoyl)benzofuran-5-yl)benzoate (87.6 mg, 0 2 mmol), tribasic potassium phosphate (0.170 g, 0.800 mmol), palladium(II) acetate (8.98 mg, 0.040 mmol), and 2-chlorophenylboronic acid (0.094 g, 0.600 mmol). The vial was capped, degassed, flushed with $N_2$ and heated in the microwave for 10 minutes at 130° C. The solvent was removed and the crude reaction mixture was taken up in 4 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 10 minute hold. The solvent was removed to give 43.8 mgs (80% yield) of methyl 2'-chloro-4-(2-(4-fluorophenyl)-3-(methylcarbamoyl)benzofuran-5-yl)biphenyl-2-carboxylate as a yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, THF-d8) δ ppm 2.92-2.97 (m, 3H), 3.60-3.62 (m, 3H), 7.19-7.26 (m, 2H), 7.27-7.34 (m, 3H), 7.37 (d, J=8.03 Hz, 1H), 7.41-7.45 (m, 1H), 7.46-7.52 (m, 1H), 7.62-7.67 (m, 1H), 7.68-7.73 (m, 1H), 7.92 (dd, J=7.91, 2.13 Hz, 1H), 8.05 (d, J=1.25 Hz, 1H), 8.12-8.19 (m, 2H), 8.29 (d, J=2.01 Hz, 1H). LCMS m/z 514.2 (M+H), Rt=3.908 min., 93% purity.

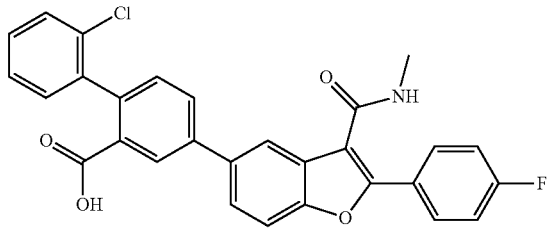

2'-Chloro-4-(2-(4-fluorophenyl)-3-(methylcarbamoyl)benzofuran-5-yl)biphenyl-2-carboxylic acid. To a 25 mL round-bottomed flask was added methyl 2'-chloro-4-(2-(4-fluorophenyl)-3-(methylcarbamoyl)benzofuran-5-yl)biphenyl-2-carboxylate (43.8 mg, 0.079 mmol), methanol (1 mL), THF (1 mL) and 8 equivalents of a 1M solution of sodium hydroxide (0.63 mL, 0.63 mmol). The mixture was stirred at room temperature for 48 hours. The crude product was diluted with 20 mL of ethyl acetate, made acidic with 0.5M HCl, extracted, washed with brine, dried over sodium sulfate, filtered and evaporated to dryness giving 47.2 mgs (96% yield) of 2'-chloro-4-(2-(4-fluorophenyl)-3-(methylcarbamoyl)benzofuran-5-yl)-5-methylbiphenyl-2-carboxylic acid as yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. LCMS m/z 500.2 (M+H), Rt=3.426 min., 90% purity.

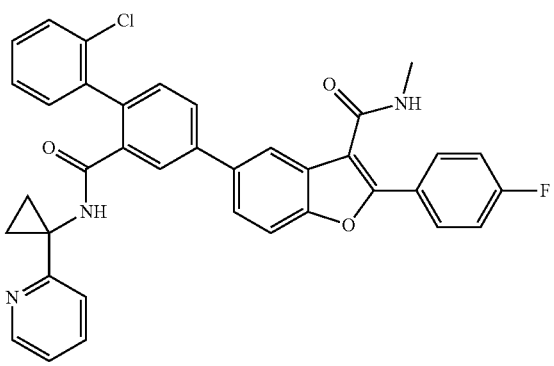

5-(2'-Chloro-2-(1-(pyridin-2-yl)cyclopropylcarbamoyl)biphenyl-4-yl)-2-(4-fluoro phenyl)-N-methylbenzofuran-3-carboxamide. To a 25 mL flask was added 2'-chloro-4-(2-(4-fluorophenyl)-3-(methylcarbamoyl)benzofuran-5-yl) biphenyl-2-carboxylic acid (39.6 mg, 0.079 mmol), DMF (2 mL), N-ethyl-N,N-isopropylpropan-2-amine (0.055 mL, 0.317 mmol), 1-(pyridin-2-yl)cyclopropanamine (15.94 mg, 0.119 mmol), and finally HATU (2-(3H-[1,2,3]triazolo[4,5-b]pyridin-3-yl)-1,1,3,3-tetramethylisouronium hexafluorophosphate (V), (120 mg, 0.317 mmol). The flask was sealed and the mixture stirred over night at room temperature. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 10 minute hold. Solvent was removed giving 40.7 mgs (70% yield) of 5-(2'-chloro-2-(1-(pyridin-2-yl)cyclopropylcarbamoyl)biphenyl-4-yl)-2-(4-fluorophenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. ¹H NMR (400 MHz, THF-d8) δ ppm 0.90-1.10 (m, 2H), 1.42-1.53 (m, 2H), 2.94 (d, J=4.52 Hz, 3H), 7.11 (dd, J=6.90, 5.40 Hz, 1H), 7.18-7.27 (m, 2 H), 7.30-7.43 (m, 5H), 7.44-7.49 (m, 1H), 7.52-7.58 (m, 1H), 7.59-7.67 (m, 2H), 7.73 (dd, J=8.53, 1.76 Hz, 1H), 7.81 (dd, J=7.78, 2.01 Hz, 1H), 7.95-8.01 (m, 2 H), 8.06 (d, J=1.51 Hz, 1H), 8.09-8.17 (m, 2H), 8.41 (d, J=4.02 Hz, 1H). LCMS m/z 617.3 (M+H), Rt=2.765 min. HPLC (Sunfire C18) Rt=7.823 min, 100% purity and (XBridge Phenyl C18) Rt=11.871 min., 99.8% purity.

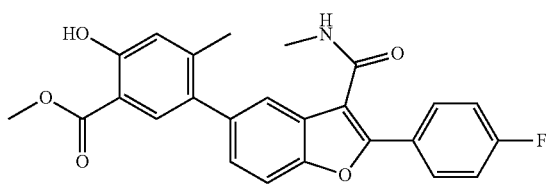

Methyl 5-(2-(4-fluorophenyl)-3-(methylcarbamoyl)benzofuran-5-yl)-2-hydroxy-4-methylbenzoate. To a 100 mL round-bottomed flask was added methyl 5-(2-(4-fluorophenyl)-3-(methylcarbamoyl)benzofuran-5-yl)-2-methoxy-4-methylbenzoate (350.5 mg, 0.783 mmol) in DCM (8 mL). To this solution was then added, under nitrogen, a 1M solution of boron trichloride (3.92 mL, 3.92 mmol) and the mixture was stirred overnight at room temperature. The reaction mixture was cooled in an ice bath and 10 mL of methanol was slowly added. The solvent was removed under vacuum. The flask was again cooled, 25 mL of ice cold methanol was added and the resulting solid was filtered to give 264.5 mgs (78% yield) of methyl 5-(2-(4-fluorophenyl)-3-(methylcarbamoyl)benzofuran-5-yl)-2-hydroxy-4-methylbenzoate as an ivory colored solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. ¹H NMR (400 MHz, DMF-d7) δ ppm 2.30 (s, 3H), 2.95 (d, J=4.77 Hz, 3H), 3.98 (s, 3H), 7.02 (s, 1H), 7.38-7.48 (m, 3H), 7.68-7.73 (m, 2H), 7.76 (d, J=8.53 Hz, 1H), 8.08-8.15 (m, 2H), 8.33 (br. s., 1H). LCMS Rt=3.636, m/z 434.3 (M+H), 100% purity.

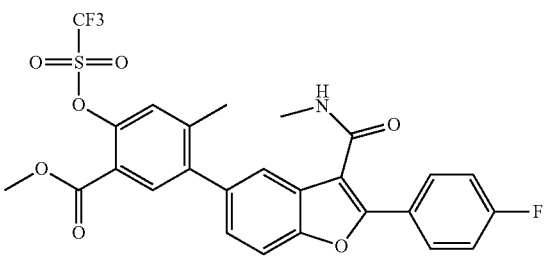

Methyl 5-(2-(4-fluorophenyl)-3-(methylcarbamoyl)benzofuran-5-yl)-4-methyl-2-(trifluoromethylsulfonyloxy)benzoate. To a 25 mL round-bottomed flask was added methyl 5-(2-(4-fluorophenyl)-3-(methylcarbamoyl)benzofuran-5-yl)-2-hydroxy-4-methylbenzoate (260 mg, 0.600 mmol), DCM (6 mL), triethylamine (0.166 mL, 1.200 mmol) and 1,1,1-trifluoro-N-phenyl-N-(trifluoromethylsulfonyl)methanesulfonamide (321 mg, 0.900 mmol). The solution was stirred overnight at room temperature. To the reaction mixture was then added DMF (6 mL) along with triethylamine (0.166 mL, 1.200 mmol) and 1,1,1-trifluoro-N-phenyl-N-(trifluoromethylsulfonyl)methanesulfonamide (321 mg, 0.900 mmol). The mixture was heated to 65° C. for forty eight hours. The crude product mixture was returned to room temperature, diluted with 100 mL of DCM, washed sequentially with 50 mL of cold 0.1M HCl, water and brine. The solvent was evaporated and the resulting crude product was triturated with 10 mL of diethyl ether (×2) to give 180.7 mgs (44.7% yield) of an ivory colored solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. ¹H NMR (500 MHz, DMSO-d6) δ ppm 2.37 (s, 3H), 2.82 (d, J=4.58 Hz, 3H), 3.88 (s, 3H), 7.36-7.47 (m, 3H), 7.56-7.65 (m, 2H), 7.78 (d, J=8.54 Hz, 1H), 7.91 (s, 1H), 7.95-8.05 (m, 2H), 8.47 (d, 1H). LCMS m/z 566.3 (M+H), Rt=3.913 min., 90% purity.

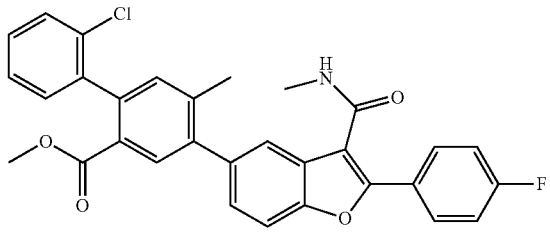

Methyl 2'-chloro-4-(2-(4-fluorophenyl)-3-(methylcarbamoyl)benzofuran-5-yl)-5-methylbiphenyl-2-carboxylate. To a small sealed tube was added methyl 5-(2-(4-fluorophenyl)-3-(methylcarbamoyl)benzofuran-5-yl)-4-methyl-2-(trifluoromethylsulfonyloxy)benzoate (67.3 mg, 0.1 mmol), dioxane (3 mL), water (0.600 mL), 2-chlorophenylboronic acid (18.76 mg, 0.120 mmol), cesium carbonate (32.6 mg, 0.100 mmol) and tetrakis(triphenylphosphine)palladium(0) (2.311 mg, 2.000 mmol). The tube was sealed and heated overnight at 80° C. The reaction was cooled to room temperature, filtered through a plug of celite and concentrated to near dryness under a stream of nitrogen. The crude reaction mixture was taken up in 6 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 3.5 μm C18 19×150 mm column at a gradient of 30-100% B and a flow rate of 25 mL/min. over 20 minutes with a 10 minute hold. The solvent was removed giving 48 mgs (89% yield) of methyl 2'-chloro-4-(2-(4-fluorophenyl)-3-(methylcarbamoyl)benzofuran-5-yl)-5-methylbiphenyl-2-carboxylate as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (500 MHz, THF-d8) δ ppm 2.35 (s, 3H), 2.91 (d, J=4.58 Hz, 3 H), 3.57 (s, 3H), 7.21-7.26 (m, 3H), 7.27-7.30 (m, 1H), 7.30-7.34 (m, 2H), 7.38 (dd, J=8.39, 1.68 Hz, 1H), 7.41-7.44 (m, 1H), 7.50 (d, J=4.27 Hz, 1H), 7.63 (d, J=8.24 Hz, 1H), 7.75 (d, J=1.53 Hz, 1H), 7.92 (s, 1H), 8.13-8.19 (m, 2H). LCMS m/z 528.4 (M+H), Rt=4.036 min., 98.3% purity.

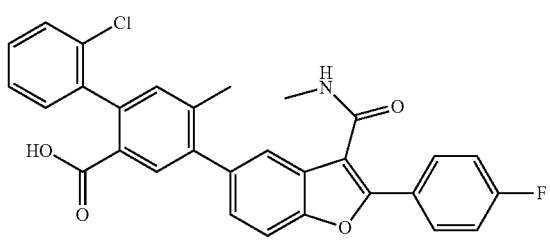

2'-Chloro-4-(2-(4-fluorophenyl)-3-(methylcarbamoyl) benzofuran-5-yl)-5-methyl biphenyl-2-carboxylic acid. To a 25 mL round-bottomed flask was added methyl 2'-chloro-4-(2-(4-fluorophenyl)-3-(methylcarbamoyl)benzofuran-5-yl)-5-methylbiphenyl-2-carboxylate (48 mg, 0.091 mmol), THF (2.2 mL), methanol (2.2 mL), and aqueous 1M sodium hydroxide (0.728 mL, 0.728 mmol). The flask was sealed and stirred at room temperature for 48 hours. Volatiles were removed and the crude product was diluted with 30 mL of ethyl acetate, washed sequentially with 10 mL of 1M HCl, brine, dried over sodium sulfate, filtered and evaporated to dryness. The resulting product was triturated with 10 mL of diethyl ether giving 47.2 mgs (96% yield) of 2'-chloro-4-(2-(4-fluorophenyl)-3-(methylcarbamoyl)benzofuran-5-yl)-5-methylbiphenyl-2-carboxylic acid as a yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, DMF-d7) δ ppm 2.42 (s, 3H), 2.97 (d, J=4.52 Hz, 3H), 7.30 (s, 1H), 7.39-7.48 (m, 5H), 7.50-7.57 (m, 2H), 7.78-7.85 (m, 2H), 7.99 (s, 1H), 8.10-8.17 (m, 2H), 8.35-8.43 (m, 1H). LCMS m/z 514.3 (M+H), Rt=3.950 min., 95.4% purity.

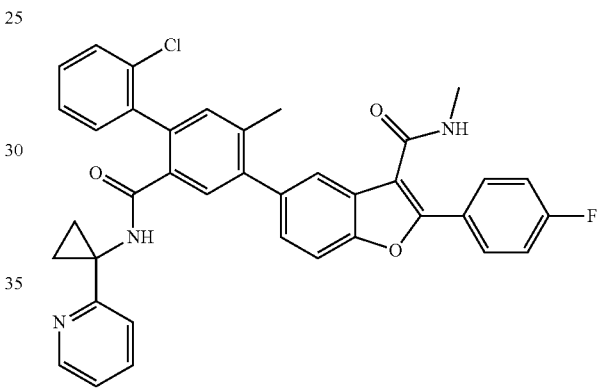

5-(2'-Chloro-5-methyl-2-(1-(pyridin-2-yl)cyclopropylcarbamoyl)biphenyl-4-yl)-2-(4-fluorophenyl)-N-methylbenzofuran-3-carboxamide, TFA. To a 25 mL flask was added 2'-chloro-4-(2-(4-fluorophenyl)-3-(methylcarbamoyl)benzofuran-5-yl)-5-methylbiphenyl-2-carboxylic acid (47.2 mg, 0.087 mmol), DMF (2 mL), N-ethyl-N,N-diisopropyl propan-2-amine (0.061 mL, 0.349 mmol), 1-(pyridin-2-yl)cyclopropanamine (17.56 mg, 0.131 mmol) and finally HATU (2-(3H-[1,2,3]triazolo[4,5-b]pyridin-3-yl)-1,1,3,3-tetramethylisouronium hexafluorophosphate(V), 133 mg, 0.349 mmol). The flask was sealed with a septa, placed under N$_2$ and stirred at room temperature for 5 hours. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 30-100% B and a flow rate of 25 mL/min. over 20 minutes with a 10 minute hold. The solvent was evaporated to give 66.1 mgs (92% yield) of 5-(2'-chloro-5-methyl-2-(1-(pyridin-2-yl)cyclopropyl carbamoyl)biphenyl-4-yl)-2-(4-fluorophenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10%

HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 0.85-0.96 (m, 1H), 0.99-1.09 (m, 1H), 1.38-1.53 (m, 2H), 2.33 (s, 3H), 2.90 (d, J=4.52 Hz, 3H), 7.07-7.14 (m, 1H), 7.20-7.28 (m, 3H), 7.30-7.36 (m, 3H), 7.37-7.42 (m, 2H), 7.44-7.49 (m, 1H), 7.56 (d, J=4.52 Hz, 1H), 7.58-7.65 (m, 3H), 7.77 (d, J=1.51 Hz, 1H), 7.89 (s, 1H), 8.10-8.18 (m, 2H), 8.37-8.42 (m, 1H). LCMS m/z 631.39 (M+H), Rt=2.925 min. HPLC (Sunfire C18) Rt=8.118 min, 99.9% purity and (XBridge Phenyl C18) Rt=11.519 min., 100% purity.

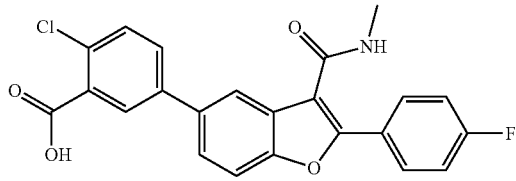

2-Chloro-5-(2-(4-fluorophenyl)-3-(methylcarbamoyl)benzofuran-5-yl)benzoic acid. Alternative Procedure: To a 150 mL sealed tube was added 2-(4-fluorophenyl)-3-(methylcarbamoyl)benzofuran-5-yl trifluoromethanesulfonate (1.0 g, 2.4 mmol), dioxane (14.4 mL), water (2.9 mL), tetrakis(triphenyl phosphine)palladium(0) (0.055 g, 0.048 mmol), 5-borono-2-chlorobenzoic acid (0.720 g, 3.59 mmol), and cesium carbonate (1.171 g, 3.59 mmol). The tube was sealed and heated in an oil bath overnight at 85° C. The reaction mixture was cooled, diluted with 150 mL of ethyl acetate, washed sequentially with 20 mL of 0.5M HCl then brine. The product solution was filtered through a plug of celite then evaporated to dryness. The resulting solid was taken up in 10 mL of 1:1 DMF and acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 3.5 μm C18 4.6×150 mm column at a gradient of 50-100% B and a flow rate of 40 mL/min. over 20 minutes with a 5 minute hold. Solvent was evaporated giving 319.5 mgs (32% yield) of 2-chloro-5-(2-(4-fluorophenyl)-3-(methylcarbamoyl)benzofuran-5-yl)benzoic acid as a white powder. The LC/MS data was obtained on a Shimadzu analytical LC/Micromass Platform LC (ESI+) at 220 nm using the following set of conditions: Phenomenex Luna 10 μm C18, 3.0×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 5 mL/minute. $^1$H NMR (400 MHz, DMSO-d6) δ ppm 2.83-2.91 (m, 3H), 7.35-7.45 (m, 2H), 7.65 (d, J=8.53 Hz, 1H), 7.69-7.75 (m, 1H), 7.76-7.82 (m, 1H), 7.85-7.93 (m, 2H), 7.98-8.05 (m, 2H), 8.08 (d, J=2.26 Hz, 1H), 8.43-8.53 (m, 1H), 13.50 (br. s., 1H). LCMS m/z 424.0 (M+H), Rt=3.105 min., 100% purity.

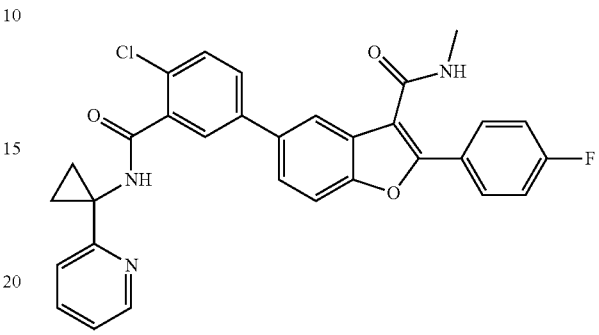

5-(4-Chloro-3-(1-(pyridin-2-yl)cyclopropylcarbamoyl)phenyl)-2-(4-fluorophenyl)-N-methyl benzofuran-3-carboxamide. To a 250 mL round-bottomed flask was added 2-chloro-5-(2-(4-fluorophenyl)-3-(methylcarbamoyl)benzofuran-5-yl)benzoic acid (0.299 g, 0.705 mmol), 1-(pyridin-2-yl)cyclopropanamine (0.142 g, 1.058 mmol), DMF (8.50 mL), N-ethyl-N,N-diisopropylpropan-2-amine (0.493 mL, 2.82 mmol), and HATU (2-(3H-[1,2,3]triazolo[4,5-b]pyridin-3-yl)-1,1,3,3-tetramethylisouronium hexafluorophosphate(V), 1.073 g, 2.82 mmol). The flask was sealed, placed under N$_2$ and stirred overnight at room temperature. The reaction mixture was diluted with 50 mL of ethyl acetate, washed with 5 mL of 1M HCl, extracted, dried over magnesium sulfate, filtered and evaporated to a red oil. The crude reaction mixture was then evacuated to near dryness, taken up in 8 mL of 1:1 methanol and DMF and purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 50-100% B and a flow rate of 40 mL/min. over 8 minutes with a 7 minute hold. Solvent was evaporated giving 261.3 mgs (66.4% yield) of 5-(4-chloro-3-(1-(pyridin-2-yl)cyclopropylcarbamoyl)phenyl)-2-(4-fluorophenyl)-N-methylbenzofuran-3-carboxamide as a light yellow solid. The LC/MS data was obtained on a Shimadzu analytical LC/Micromass Platform LC (ESI+) at 220 nm using the following set of conditions: Waters Sunfire 5 nm C18, 4.6×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 3 minutes with a 1 minute hold at a rate of 4 mL/minute. HPLC purity was determined using a Shimadzu analytical LC at 254 nm and 256 nm with a Waters Sunfire C18 3.5 nm 4.6×150 mm column employing water/acetonitrile/0.1% trifluoroacetic acid with a gradient of 20-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 nm 4.6×

150 mm column employing water/methanol/10 mM ammonium bicarbonate with a gradient of 20-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, DMSO-d6) δ ppm 1.33-1.40 (m, 2H), 1.56-1.64 (m, 2H), 2.83-2.91 (m, 3H), 7.27 (dd, J=6.78, 5.27 Hz, 1H), 7.35-7.45 (m, 2H), 7.63 (d, J=8.28 Hz, 1H), 7.69-7.96 (m, 7H), 7.97-8.06 (m, 2H), 8.50 (d, J=4.52 Hz, 2H), 9.34 (s, 1H). LCMS m/z 540.39 (M+H), Rt=1.643 min., 94.2% purity. HPLC (Sunfire C18) Rt=6.388 min, 94% purity and (Gemini C18) Rt=11.238 min., 99.6% purity.

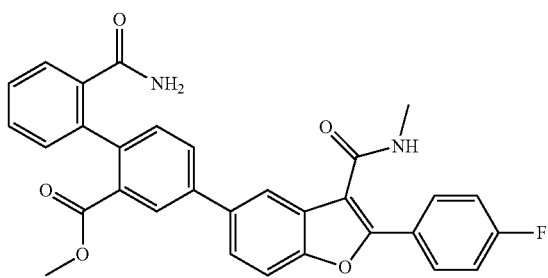

Methyl 2'-carbamoyl-4-(2-(4-fluorophenyl)-3-(methylcarbamoyl)benzofuran-5-yl)biphenyl-2-carboxylate. To a microwave vial was added dioxane (9 mL), water (0.900 mL), 2-carbamoylphenylboronic acid (148 mg, 0.900 mmol), methyl 2-chloro-5-(2-(4-fluorophenyl)-3-(methylcarbamoyl)benzofuran-5-yl)benzoate (131 mg, 0.3 mmol), tribasic potassium phosphate (255 mg, 1.200 mmol), dicyclohexyl (2',6'-dimethoxybiphenyl-2-yl)phosphine (S-Phos, 24.63 mg, 0.060 mmol), and palladium(II) acetate (13.47 mg, 0.060 mmol). The vial was capped, degassed, flushed with N$_2$ and heated in the microwave for 13 minutes at 130° C. The reaction mixture was filtered and solvent removed under a stream of nitrogen. The crude product was then taken up in 4 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 10 minute hold. The solvent was removed giving 58.3 mgs (36% yield) of methyl 2'-carbamoyl-4-(2-(4-fluorophenyl)-3-(methylcarbamoyl)benzofuran-5-yl)biphenyl-2-carboxylate as a yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, THF-d8) δ ppm 2.93 (d, J=4.52 Hz, 3H), 3.62 (s, 3H), 6.35 (br. s., 2H), 7.09-7.15 (m, 1H), 7.22 (t, J=8.91 Hz, 2H), 7.31-7.43 (m, 3H), 7.52 (d, J=4.27 Hz, 1H), 7.58-7.71 (m, 3H), 7.81 (dd, J=8.03, 2.01 Hz, 1H), 8.01 (d, J=1.25 Hz, 1H), 8.09-8.20 (m, 3H). LCMS m/z 523.3 (M+H), Rt=3.051 min., 96% purity.

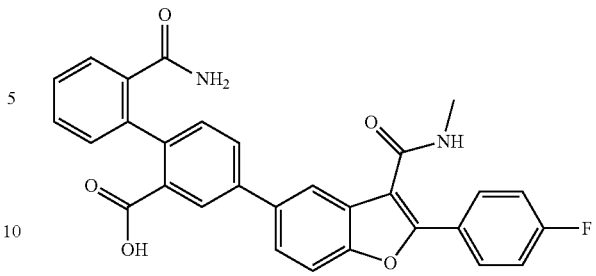

2'-Carbamoyl-4-(2-(4-fluorophenyl)-3-(methylcarbamoyl)benzofuran-5-yl)biphenyl-2-carboxylic acid. To a 25 mL round-bottomed flask was added methyl 2'-carbamoyl-4-(2-(4-fluorophenyl)-3-(methylcarbamoyl)benzofuran-5-yl)biphenyl-2-carboxylate (58.3 mg, 0.107 mmol), methanol (1 mL), THF (1 mL) and 8 equivalents of a 1M solution of sodium hydroxide (0.856 mL, 0.856 mmol). The mixture was diluted with 20 mL of ethyl acetate, made acidic with 0.5M HCl and the crude product was extracted, washed with brine, and dried over sodium sulfate. The product solution was filtered and evaporated to dryness giving 52 mgs (98% yield) of 2'-carbamoyl-4-(2-(4-fluorophenyl)-3-(methylcarbamoyl) benzofuran-5-yl)biphenyl-2-carboxylic acid as a yellow solid. The LC/MS data was obtained on a Shimadzu analytical LC/Micromass Platform LC (ESI+) at 220 nm using the following set of conditions: Phenomenex Luna 3 nm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. LCMS m/z 509.3 (M+H), Rt=2.695 min., 90% purity.

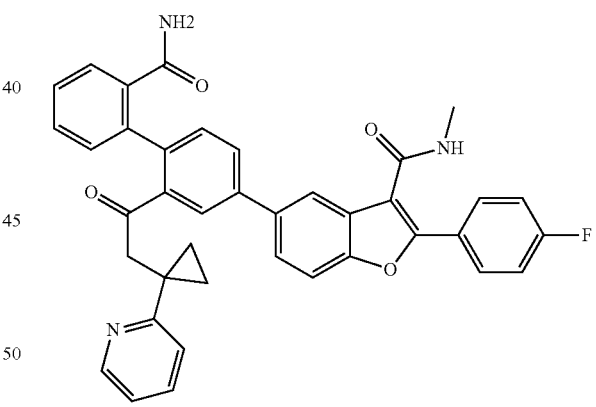

4-(2-(4-Fluorophenyl)-3-(methylcarbamoyl)benzofuran-5-yl)-N2-(1-(pyridin-2-yl)cyclopropyl)biphenyl-2,2'-dicarboxamide, TFA To a 25 mL round-bottomed flask was added 2'-carbamoyl-4-(2-(4-fluorophenyl)-3-(methylcarbamoyl) benzofuran-5-yl)biphenyl-2-carboxylic acid (52 mg, 0.104 mmol), DMF (2 mL), N-ethyl-N,N-isopropylpropan-2-amine (0.075 mL, 0.429 mmol), 1-(pyridin-2-yl)cyclopropanamine (21.57 mg, 0.161 mmol) and finally HATU (2-(3H-[1,2,3]triazolo[4,5-b]pyridin-3-yl)-1,1,3,3-tetramethylisouronium hexafluoro phosphate (V), 163 mg, 0.429 mmol). The flask was sealed and the mixture stirred at room temperature over night. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 20 minutes with a 10 minute hold. The solvent was evaporated giving 2 rotomers as shown above. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. Isomer A: $^1$H NMR (400 MHz, THF-d8) δ ppm 0.53-0.79 (m, 2H), 1.36 (d, J=4.27 Hz, 2H), 2.95 (d, J=4.52 Hz, 3H), 6.79 (br. s., 1H), 6.88-7.00 (m, 2H), 7.16-7.26 (m, 4H), 7.39 (td, J=7.72, 1.88 Hz, 1H), 7.46-7.53 (m, 3H), 7.57-7.61 (m, 1H), 7.61-7.65 (m, 2H), 7.69 (ddd, J=10.23, 8.22, 1.88 Hz, 2H), 7.91 (d, J=2.01 Hz, 1H), 8.04 (d, J=1.51 Hz, 1H), 8.13-8.19 (m, 2H), 8.25-8.31 (m, 2H), 9.01 (s, 1H). LCMS m/z 625.4 (M+H), Rt=2.310 min. HPLC (Sunfire C18) Rt=6.796 min, 100% purity and (XBridge Phenyl C18) Rt=10.793 min., 100% purity. Isomer B: $^1$H NMR (400 MHz, THF-d8) δ ppm 0.64-0.92 (m, 2H), 1.39 (d, J=4.02 Hz, 2H), 2.93 (d, J=4.77 Hz, 3H), 6.76 (br. s., 1H), 6.88 (dd, J=6.90, 5.14 Hz, 1H), 6.96 (d, J=8.03 Hz, 1H), 7.11-7.18 (m, 1H), 7.20-7.30 (m, 3H), 7.31-7.43 (m, 3H), 7.50 (br. s., 1H), 7.59 (dd, J=7.15, 1.88 Hz, 1H), 7.62-7.67 (m, 1H), 7.68-7.76 (m, 2H), 7.82 (dd, J=7.78, 2.01 Hz, 1H), 7.92 (d, J=1.76 Hz, 1H), 8.07 (d, J=1.76 Hz, 1H), 8.09-8.17 (m, 2H), 8.26 (d, J=4.27 Hz, 1H), 8.98 (s, 1H). LCMS m/z 625.4 (M+H), Rt=2.275 min. HPLC (Sunfire C18) Rt=6.688 min, 100% purity and (XBridge Phenyl C18) Rt=10.821 min., 100% purity.

Ethyl 4-fluoro-2-(4-fluorophenyl)-5-hydroxybenzofuran-3-carboxylate. To a mixture of ethyl 2-(4-fluorophenyl)-5-hydroxybenzofuran-3-carboxylate (500 mg, 1.665 mmol) in acetonitrile (10 mL) at r.t. under $N_2$ was added 1-(chloromethyl)-4-fluoro-1,4-diazoniabicyclo[2.2.2]octane tetrafluoroborate (708 mg, 1.998 mmol). The mixture was stirred at r.t. (the mixture turned bright yellow in color) for 20 hours. The mixture was evaporated. The residue was added with 10 ml $H_2O$. The aqueous decanted, and the residue further washed with 2×5 ml $H_2O$. The mixture was dissolved in MeOH (about 10 ml), and the insoluble filtered. The filtrate was purified by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=60, Final % B=100, Gradient time=10 min, Stop time=12 min, Flow Rate=25 mL/min, Column: Waters-Sunfire 19×100 mm S5, Fraction Collection: 6.44-7.24 min. (UV detection at 220 nm). The desired fractions were combined and evaporated to give a yellow solid. The yellow solid was further purified by Biotage Horizon flash chromatography (0 to 70% EtOAc/Hexane, 3×80 g silica gel column) to give a light yellow solid (108.9 mg). $^1$H NMR (500 MHz, $CD_3OD$) δ 7.95 (m, 2H), 7.26 (t overlapping with dd, 2H), 7.25 (dd, 1H), 7.03 (t, J=8.39, 1H), 4.39 (q, J=7.17, 2H), 1.36 (t, J=7.17, 3H). $^{19}$F NMR (470.45 MHz, $CD_3OD$) δ −112.36, −142.29. The position of the F atom at C4 was confirmed by $^1$H-$^1$H through bond correlation between H6 and H7, $^1$H-$^{13}$C HMBC and F-C4 coupling in $^{13}$C NMR (125.75 MHz, $CD_3OD$) (δ 144.8 ppm, d, J=247, C4). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=319.14, HPLC Rt=1.718 min. The minor fractions collected at about 7.69-8.20 min. was confirmed by $^1$H-$^1$H through bond correlation, $^1$H-$^{13}$C HMBC and F-C6 coupling in $^{13}$C NMR (125.75 MHz, $CD_3OD$) (δ 152.5 ppm, d, J=242 Hz, C6) to be the isomer of the F-atom at C6 (C4: C6 about 3:1 based on preparative HPLC % area of the UV trace); $^1$H NMR (500 MHz, $CD_3OD$) δ 8.04 (dd, J=8.55, 5.49, 2H), 7.59 (d, J=8.85, 1H), 7.38 (d, J=10.07, 1H), 7.25 (t, J=8.70, 2H), 4.40 (q, J=7.17, 2H), 1.41 (t, J=7.17, 3H). $^{19}$F NMR (470.45 MHz, $CD_3OD$) δ −112.29, −138.52. LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=319.14, HPLC R$_f$=1.798 min.

4-Fluoro-2-(4-fluorophenyl)-5-hydroxybenzofuran-3-carboxylic acid. To a mixyure of ethyl 4-fluoro-2-(4-fluorophenyl)-5-hydroxybenzofuran-3-carboxylate (108.9 mg, 0.342 mmol) in a mixture of MeOH (2 mL)/THF (2 mL) at r.t. under $N_2$ was added sodium hydroxide (1.0 mL, 1.0 mmol) (1 M aq.). The mixture was stirred at 100° C. for 1.5 hours. The mixture was cooled to r.t., added with 1.5 ml 1N HCl, and then added 10 ml $H_2O$. The white precipitates were filtered and washed with 3×2 ml $H_2O$ and dried (73 mg). $^1$H NMR (500 MHz, $CD_3OD$) δ 7.98 (m, 2H), 7.25 (t overlapping with dd, 2H), 7.24 (dd, 1H), 7.02 (t, J=8.39, 1H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=291.01, HPLC R$_f$=1.478 min.

4-Fluoro-2-(4-fluorophenyl)-5-hydroxy-N-methylbenzofuran-3-carboxamide. To a mixture of 4-fluoro-2-(4-fluorophenyl)-5-hydroxybenzofuran-3-carboxylic acid (73 mg, 0.252 mmol), methylamine, HCl (25.5 mg, 0.377 mmol), HOBT hydrate (65.5 mg, 0.428 mmol) and EDC hydrochloride (87 mg, 0.453 mmol) at r.t. under $N_2$ was added N,N-diisopropylethylamine (0.220 mL, 1.258 mmol). The mixture was stirred at r.t. for 16 hours. After concentration, the mixture was added with 5 ml 1N HCl, and then 14 ml $H_2O$. The white solid was filtered and washed with 3×5 ml $H_2O$ and dried (64 mg). $^1$H NMR (500 MHz, $CD_3OD$) δ 7.89 (dd, J=8.09, 5.34, 2H), 7.25 (t overlapping with dd, 2H), 7.23 (dd, 1H), 6.99 (t, J=8.55, 1H), 2.96 (s, 3H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=304.06, HPLC R$_t$=1.262 min.

4-Fluoro-2-(4-fluorophenyl)-3-(methylcarbamoyl)benzofuran-5-yl trifluoromethanesulfonate. To a white suspension of 4-fluoro-2-(4-fluorophenyl)-5-hydroxy-N-methylbenzofuran-3-carboxamide (64 mg, 0.211 mmol) in CH₂Cl₂ (2 mL) at r.t. under N₂ was added triethylamine (0.059 mL, 0.422 mmol). The mixture was cooled to 0° C., and then added 1,1,1-trifluoro-N-phenyl-N-(trifluoromethylsulfonyl)methanesulfonamide (113 mg, 0.317 mmol). The mixture was then stirred at r.t. (the white suspension turned into a light yellow solution after stirring for about 10 min) for 2 hours 35 min. The mixture was left standing at r.t. overnight, and then evaporated. The residue was cooled in an ice-water bath, added with 2 ml H₂O. The solids were filtered and washed with 3×2 ml H₂O, and dried (94 mg). ¹H NMR (500 MHz, CD₃OD) δ 7.95 (m, 2H), 7.59 (dd, J=9.00, 1.00, 1H), 7.50 (dd, J=9.00, 7.50, 1H), 7.30 (t, J=8.55, 2H), 2.99 (s, 3H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=436.04, HPLC R$_t$=1.678 min.

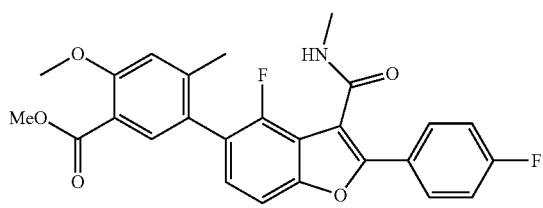

Methyl 5-(4-fluoro-2-(4-fluorophenyl)-3-(methylcarbamoyl)benzofuran-5-yl)-2-methoxy-4-methylbenzoate. A mixture of the above prepared 4-fluoro-2-(4-fluorophenyl)-3-(methylcarbamoyl)benzofuran-5-yltrifluoromethanesulfonate (assumed 0.211 mmol), methyl 2-methoxy-4-methyl-5-(4,4,5,5-tetramethyl-1,3,2-dioxaborolan-2-yl)benzoate (0.078 g, 0.253 mmol), (Ph₃P)₄Pd (0.024 g, 0.021 mmol) and cesium carbonate (0.103 g, 0.317 mmol) in a mixture of H₂O (0.2 mL)/1,4-dioxane (1 mL) was stirred at 95° C. for 2 hours 30 min. The mixture was left standing at r.t. overnight. The mixture was diluted with 3.5 ml 1,4-dioxane, filtered through a Whatman PVDF 0.45 um disk (with 3×1 ml washing). The filtrate was concentrated. The mixture was added with 3.5 ml 1N HCl, and then 6 ml H₂O (yellow solid deposited on the wall of the flask). The aqueous was decanted, and the residue washed with 3×2 ml H₂O and dried. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=466.27, HPLC R$_t$=1.708 min.

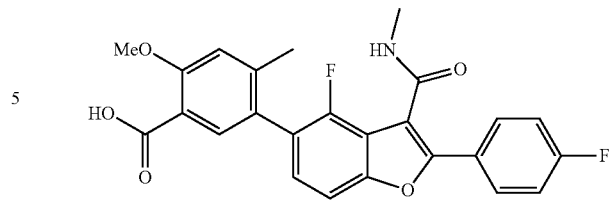

5-(4-Fluoro-2-(4-fluorophenyl)-3-(methylcarbamoyl)benzofuran-5-yl)-2-methoxy-4-methylbenzoic acid. To the above prepared methyl 5-(4-fluoro-2-(4-fluorophenyl)-3-(methylcarbamoyl)benzofuran-5-yl)-2-methoxy-4-methylbenzoate (assumed 0.211 mmol) in a mixture MeOH (2 mL)/THF (2 mL) at r.t. under N₂ was added sodium hydroxide (0.84 mL, 0.84 mmol). The mixture was stirred at r.t. for 24 hours. The mixture was added with 2 ml 1N HCl, and concentrated until off white solids formed. The mixture was added with 5 ml H₂O, the solids filtered and washed with 3×2 ml H₂O and dried (75.1 mg). ¹H NMR (500 MHz, CD₃OD) δ 7.95 (m, 2H), 7.73 (s, 1H), 7.51 (d, J=8.24, 1H), 7.30-7.25 (t overlapping with m, 3H), 7.13 (s, 1H), 3.99 (s, 3H), 2.96 (s, 3H), 2.28 (s, 3H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=452.23, HPLC R$_t$=1.582.

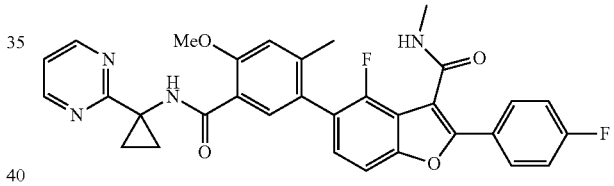

4-Fluoro-2-(4-fluorophenyl)-5-(4-methoxy-2-methyl-5-(1-(pyrimidin-2-yl)cyclopropylcarbamoyl)phenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (30 mg, 0.066 mmol), 1-(pyrimidin-2-yl)cyclopropanamine, TFA (33.1 mg, about 75% pure, assumed 0.133 mmol,) and 2-(1H-benzo[d][1,2,3]triazol-1-yl)-1,1,3,3-tetramethylisouronium tetrafluoroborate (64.0 mg, 0.199 mmol) in DMF (1 mL) at r.t. under N₂ was added N,N-diisopropylethyl amine (0.058 mL, 0.332 mmol). The mixture was stirred at r.t. for 20 hours. The mixture was diluted with MeOH and purified by Shimadzu-VP preparative reverse phase HPLC using the separation method: Solvent A=10% MeOH-90% H2O-0.1% TFA, Solvent B=90% MeOH-10% H2O-0.1% TFA, Start % B=50, Final % B=100, Gradient time=10 min, Stop time=12 min, Flow Rate=25 mL/min, Column: Waters-Sunfire 19×100 mm S5, UV detection at 220 nm, Fraction Collection: 7.25-7.73 min. The residue after evaporation of the combined fractions was further purified by preparative TLC (two of 500 um×20×20 cm plates, 5% MeOH/CH₂Cl₂) to give 4-fluoro-2-(4-fluorophenyl)-5-(4-methoxy-2-methyl-5-(1-(pyrimidin-2-yl)cyclopropylcarbamoyl)phenyl)-N-methylbenzofuran-3-carboxamide as a white solid. Analytical TLC Rf=0.32 (5% MeOH/CH₂Cl₂). ¹H NMR (500 MHz, CD₃OD) δ 8.65 (d, J=4.88, 2H), 7.95 (m, 2H), 7.89 (s, 1H), 7.50 (d, J=8.55, 1H), 7.28 (t, J=8.70, 2H), 7.28-7.25 (m overlapping with t, 1H), 7.23 (t, J=4.88, 1H), 7.17 (s, 1H), 4.09 (s, 3H), 2.95 (s, 3H), 2.30 (s, 3H), 1.79 (m, 2H), 1.51 (m, 2H). $^{19}$F NMR (470.45 MHz, CD$_3$OD) δ-112.81, -123.16. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 569.38, HPLC Rt=1.660 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.29 min; Column: Xbridge Phenyl 3.5 um, 4.6×150 mm, R$_t$=5.18 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=9.39 min.

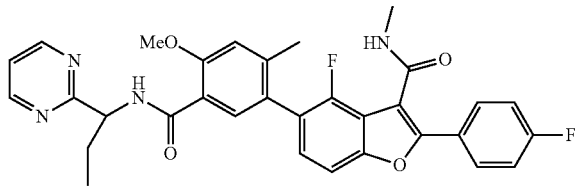

4-Fluoro-2-(4-fluorophenyl)-5-(4-methoxy-2-methyl-5-(1-(pyrimidin-2-yl)propylcarbamoyl)phenyl)-N-methylbenzofuran-3-carboxamide. 4-Fluoro-2-(4-fluorophenyl)-5-(4-methoxy-2-methyl-5-(1-(pyrimidin-2-yl)propylcarbamoyl)phenyl)-N-methylbenzofuran-3-carboxamide was formed as a minor side product during the synthesis of 4-fluoro-2-(4-fluorophenyl)-5-(4-methoxy-2-methyl-5-(1-(pyrimidin-2-yl)cyclopropylcarbamoyl)phenyl)-N-methylbenzofuran-3-carboxamide as described above, and was isolated during purification by preparative reverse phase HPLC (Fraction Collection: 7.82-8.48 min) $^1$H NMR (500 MHz, DMSO-d$_6$) δ 9.08 (d, J=7.32, 1H), 8.87 (d, J=4.88, 2H), 8.70 (q, J=4.58, 1H), 7.94 (m, 2H), 7.78 (s, 1H), 7.62 (d, J=8.24, 1H), 7.46 (t, J=4.88, 1H), 7.42 (t, J=9.00, 2H), 7.30 (dd, J=8.39, 7.17, 1H), 7.24 (s, 1H), 5.16 (m, 1H), 4.08 (s, 3H), 2.80 (d, J=4.58, 3H), 2.24 (s, 3H), 1.97 (m, 2H), 0.82 (t, J=7.32, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=571.35, HPLC R$_t$=1.743 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.33 min; Column: Xbridge Phenyl 3.5 um, 4.6×150 mm, R$_t$=5.69 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=10.23 min.

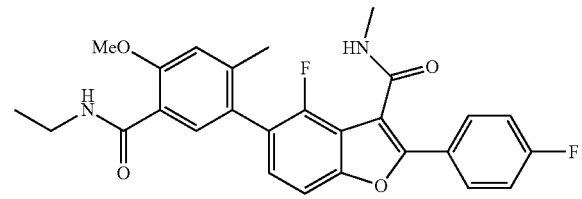

5-(5-(Ethylcarbamoyl)-4-methoxy-2-methylphenyl)-4-fluoro-2-(4-fluorophenyl)-N-methylbenzofuran-3-carboxamide. 5-(5-(Ethylcarbamoyl)-4-methoxy-2-methylphenyl)-4-fluoro-2-(4-fluorophenyl)-N-methylbenzofuran-3-carboxamide was formed as a minor side product during the synthesis of 4-fluoro-2-(4-fluorophenyl)-5-(4-methoxy-2-methyl-5-(1-(pyrimidin-2-yl)cyclopropylcarbamoyl)phenyl)-N-methylbenzofuran-3-carboxamide as described above, and was isolated during purification by preparative TLC (the band right above the major product band). $^1$H NMR (500 MHz, CD$_3$OD) δ 7.95 (m, 2H), 7.81 (s, 1H), 7.51 (d, J=8.55, 1H), 7.30-7.25 (t overlapping with dd, 3H), (7.13 (s, 1H), 4.04 (s, 3H), 3.46 (q, J=7.17, 2H), 2.95 (s, 3H), 2.28 (s, 3H), 1.25 (t, J=7.17, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 479.30, HPLC R$_t$=1.670 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.94 min; Column: Xbridge Phenyl 3.5 um, 4.6×150 mm, R$_t$=5.31 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=9.20 min.

Methyl 2,4-dimethyl-5-(4,4,5,5-tetramethyl-1,3,2-dioxaborolan-2-yl)benzoate. A mixutre of methyl 5-iodo-2,4-dimethylbenzoate (1 g, 3.45 mmol), 4,4,4',4',5,5,5',5'-octamethyl-2,2'-bi(1,3,2-dioxaborolane) (1.050 g, 4.14 mmol), potassium acetate (1.015 g, 10.34 mmol) and PdCl$_2$(dppf)(Cl$_2$CH$_2$) ([1,1'-bis(diphenylphosphino)ferrocene]dichloropalladium(II), dichloromethane) (0.284 g, 0.345 mmol) in DMF (25 mL) under N$_2$ was stirred at 100° C. for 20 hours. The mixture was cooled to r.t., added with 30 ml H$_2$O. The dark solid was filtered and washed with 3×5 ml H$_2$O and dried. The solid was purified by Biotage Horizon flash chromatography (0 to 70% EtOAc/Hexane) to give the product as a white solid (442.7 mg). $^1$H NMR (500 MHz, CD$_3$OD) δ 8.26 (s, 1H), 7.11 (s, 1H), 3.88 (s, 3H), 2.56 (s, 3H), 2.53 (s, 3H), 1.37 (s, 12H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)+= 291.14, HPLC R$_t$=1.933 min.

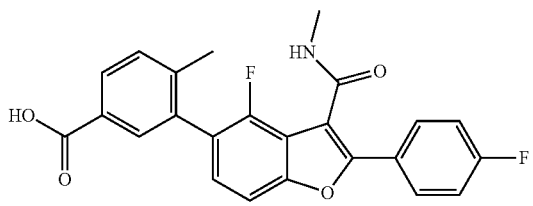

3-(4-Fluoro-2-(4-fluorophenyl)-3-(methylcarbamoyl) benzofuran-5-yl)-4-methylbenzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)+=422.19, HPLC R$_t$=1.653 min.

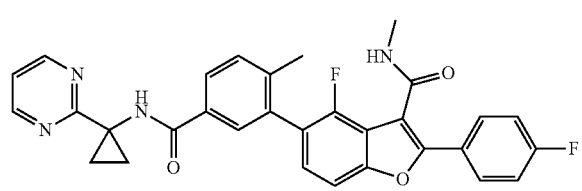

4-Fluoro-2-(4-fluorophenyl)-N-methyl-5-(2-methyl-5-(1-(pyrimidin-2-yl)cyclopropylcarbamoyl)phenyl)benzofuran-3-carboxamide. Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 6.80-7.18 min. (UV detection at 220 nm). The material obtained was further purified by preparative TLC (500 um×20×20 cm plate, 5% MeOH/CH$_2$Cl$_2$). Analytical TLC Rf=0.35 (5% MeOH/CH$_2$Cl$_2$). $^1$H NMR (500 MHz, CD$_3$OD) δ 8.64 (d, J=4.88, 2H), 7.96 (m, 2H), 7.90 (dd, J=7.93, 1.83, 1H), 7.84 (d, J=1.83, 1H), 7.54 (d, J=8.54, 1H), 7.46 (d, J=7.93, 1H), 7.34-7.27 (m overlapping with t, 3H), 7.22 (t, J=4.88, 1H), 2.96 (s, 3H), 2.29 (s, 3H), 1.77 (m, 2H), 1.46 (m, 2H). $^{19}$F NMR (470.45 MHz, CD$_3$OD) δ -112.72, -123.10. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)+=539.32, HPLC Rt=1.585 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=5.64 min; Column: Xbridge Phenyl 3.5 um, 4.6×150 mm, R$_t$=4.66 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=8.43 min.

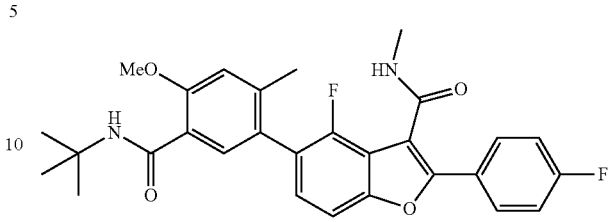

5-(5-(tert-Butylcarbamoyl)-4-methoxy-2-methylphenyl)-4-fluoro-2-(4-fluorophenyl)-N-methylbenzofuran-3-carboxamide. Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 8.68-9.29 min. (UV detection at 220 nm). $^1$H NMR (500 MHz, CD$_3$OD) δ 7.88 (dd, J=8.55, 5.19, 2H), 7.72 (s, 1H), 7.43 (d, J=8.55, 1H), 7.23-7.17 (overlapping m, 3H), 7.06 (s, 1H), 3.98 (s, 3H), 2.89 (s, 3H), 2.20 (s, 3H), 1.41 (s, 9H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)+=507.33, HPLC R$_t$=1.837 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=10.19 min; Column: Xbridge Phenyl 3.5 um, 4.6×150 mm, R$_t$=7.50 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=11.25 min.

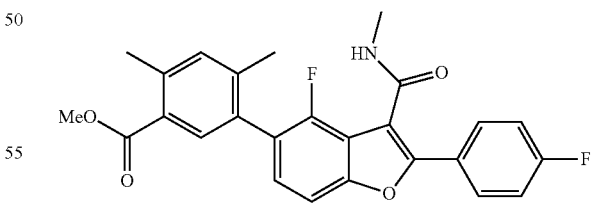

Methyl 5-(4-fluoro-2-(4-fluorophenyl)-3-(methylcarbamoyl)benzofuran-5-yl)-2,4-dimethylbenzoate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)+=450.11, HPLC R$_t$=1.852 min.

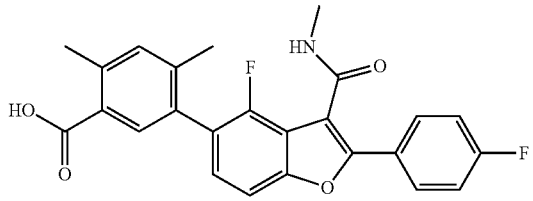

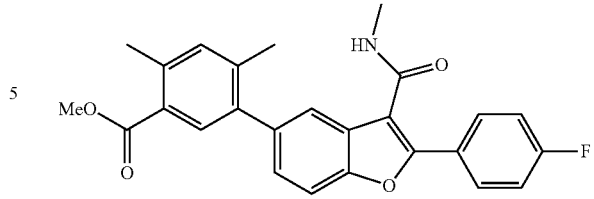

5-(4-Fluoro-2-(4-fluorophenyl)-3-(methylcarbamoyl)benzofuran-5-yl)-2,4-dimethylbenzoic acid. $^1$H NMR (500 MHz, CD$_3$OD) δ 7.95 (m, 2H), 7.80 (s, 1H), 7.51 (d, J=8.55, 1H), 7.30-7.25 (s and overlapping m, 4H), 2.96 (s, 3H), 2.63 (s, 3H), 2.23 (s, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=436.09, HPLC R$_t$=1.735 min.

Methyl 5-(2-(4-fluorophenyl)-3-(methylcarbamoyl)benzofuran-5-yl)-2,4-dimethylbenzoate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=432.10, HPLC R$_t$=1.928 min.

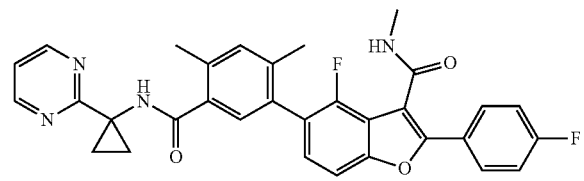

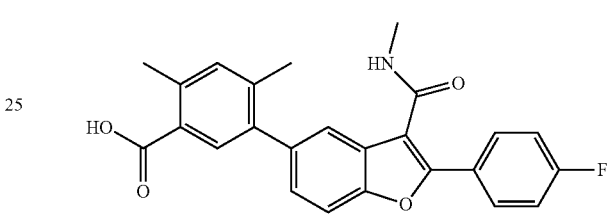

5-(2,4-Dimethyl-5-(1-(pyrimidin-2-yl)cyclopropylcarbamoyl)phenyl)-4-fluoro-2-(4-fluorophenyl)-N-methylbenzofuran-3-carboxamide. Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Sunfire Prep C18 19×100 5 µm, Fraction Collection: 6.93-7.43 min. (UV detection at 220 nm). $^1$H NMR (500 MHz, DMSO-d$_6$, peaks were generally broad) δ 8.93 (s, 1H), 8.71 (broad s, 1H), 8.68 (m, 2H), 7.93 (m, 2H), 7.65 (m, 1H), 7.44 (m, 2H), 7.33 (m, 2H), 7.27 (m, 1H), 7.25 (m, 1H), 2.81 (s, 3H), 2.45 (s, 3H), 2.17 (s, 3H), 1.57 (s, 2H), 1.33 (s, 2H). $^{19}$F NMR (470.45 MHz, DMSO-d$_6$) δ-110.88, -121.61. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=553.22, HPLC R$_t$=1.645 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.26 min; Column: Xbridge Phenyl 3.5 um, 4.6×150 mm, R$_t$=5.23 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=9.00 min.

5-(2-(4-Fluorophenyl)-3-(methylcarbamoyl)benzofuran-5-yl)-2,4-dimethylbenzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=418.10, HPLC R$_t$=1.810 min.

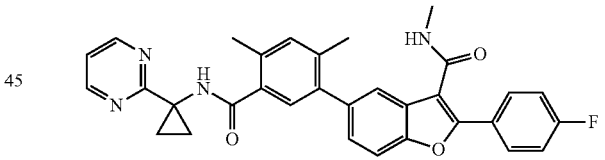

5-(2,4-Dimethyl-5-(1-(pyrimidin-2-yl)cyclopropylcarbamoyl)phenyl)-2-(4-fluorophenyl)-N-methylbenzofuran-3-carboxamide. Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Sunfire Prep C18 19×100 5 um, Fraction Collection: 7.75-8.16 min. (UV detection at 220 nm). $^1$H NMR (500 MHz, CD$_3$OD) δ 8.67 (d, J=4.88, 2H), 7.97 (m, 2H), 7.65 (s overlapped with d, 1H), 7.64 (d, J=8.50, 1H), 7.50 (s, 1H), 7.38 (dd, J=8.55, 1.83, 1H), 7.28 (t, J=8.85, 2H), 7.24 (t, J=4.88, 1H), 7.22 (s, 1H), 2.95 (s, 3H), 2.52 (s, 3H), 2.30 (s, 3H), 1.76 (m, 2H), 1.46 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=535.23, HPLC R$_t$=1.722 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.24 min; Column: Xbridge Phenyl 3.5 um, 4.6×150 mm, R$_t$=5.62 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=9.24 min.

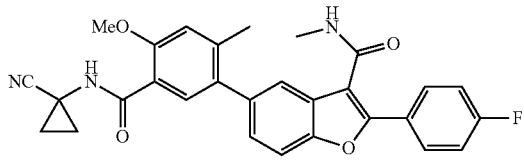

5-(5-(1-Cyanocyclopropylcarbamoyl)-4-methoxy-2-methylphenyl)-2-(4-fluorophenyl)-N-methylbenzofuran-3-carboxamide. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=498.21, HPLC R$_t$=1.647 min.

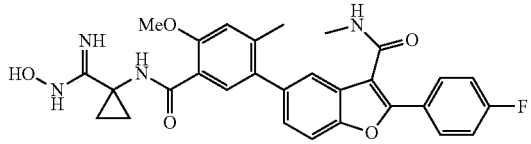

2-(4-Fluorophenyl)-5-(5-(1-(N-hydroxycarbamimidoyl)cyclopropylcarbamoyl)-4-methoxy-2-methylphenyl)-N-methylbenzofuran-3-carboxamide. Purification was performed by Shimadzu-VP preparative reverse phase HPLC using the separation method: Solvent A=10% MeOH-90% H2O-0.1% TFA, Solvent B=90% MeOH-10% H2O-0.1% TFA, Start % B=30, Final % B=100, Gradient time=10 min, Stop time=12 min, Flow Rate=25 mL/min, Column: Waters-Sunfire 19×100 mm S5, Fraction Collection: 6.82-7.62 min. (UV detection at 220 nm). ¹H NMR (500 MHz, CD$_3$OD) δ 7.96 (dd, J=8.24, 5.80, 2H), 7.88 (s, 1H), 7.63 (d, J=8.24, 1H), 7.57 (s, 1H), 7.32 (d, J=8.54, 1H), 7.28 (t, J=8.70, 2H), 7.13 (s, 1H), 4.05 (s, 3H), 2.96 (s, 3H), 2.36 (s, 3H), 1.67 (m, 2H), 1.50 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=531.22, HPLC R$_t$=1.457 min.

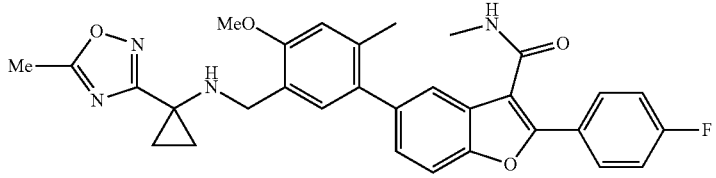

2-(4-Fluorophenyl)-5-(4-methoxy-2-methyl-5-(1-(5-methyl-1,2,4-oxadiazol-3-yl)cyclopropylcarbamoyl)phenyl)-N-methylbenzofuran-3-carboxamide. 2-(4-Fluorophenyl)-5-(4-methoxy-2-methyl-5-(1-(5-methyl-1,2,4-oxadiazol-3-yl)cyclopropylcarbamoyl)phenyl)-N-methylbenzofuran-3-carboxamide was prepared from 2-(4-fluorophenyl)-5-(5-(1-(N-hydroxycarbamimidoyl)cyclopropylcarbamoyl)-4-methoxy-2-methylphenyl)-N-methylbenzofuran-3-carboxamide under similar conditions as described but using PhMe as a solvent. The crude mixture was purified by preparative TLC (20×20 cm×500 um plates, 5% MeOH/CH$_2$Cl$_2$) to give the product, which was further purified by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Waters-Sunfire 19×100 mm S5, Fraction Collection: 7.95-8.47 min. (UV detection at 220 nm). Analytical TLC Rf=0.38 (5% MeOH/CH$_2$Cl$_2$). ¹H NMR (500 MHz, CD$_3$OD) δ 7.97 (dd, J=7.93, 5.49, 2H), 7.87 (s, 1H), 7.62 (d, J=8.24, 1H), 7.58 (s, 1H), 7.33 (d, J=8.55, 1H), 7.27 (t, J=8.39, 2H), 7.11 (s, 1H), 4.05 (s, 3H), 2.96 (s, 3H), 2.54 (s, 3H), 2.36 (s, 3H), 1.60 (m, 2H), 1.45 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=555.34, HPLC R$_t$=1.735 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.75 min; Column: Xbridge Phenyl 3.5 um, 4.6×150 mm, R$_t$=5.93 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=11.98 min.

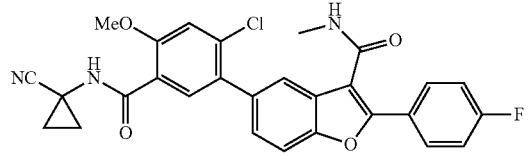

5-(2-Chloro-5-(1-cyanocyclopropylcarbamoyl)-4-methoxyphenyl)-2-(4-fluorophenyl)-N-methylbenzofuran-3-carboxamide. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=518.20, 520.18, HPLC R$_t$=1.692 min.

nomenex-Luna, 3.0×50 mm, S10; (ES+) m/z (M+H)⁺=575.10, HPLC R$_t$=1.817 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=7.92 min; Column: Xbridge Phenyl 3.5 um, 4.6×150 mm, R$_t$=6.21 min.

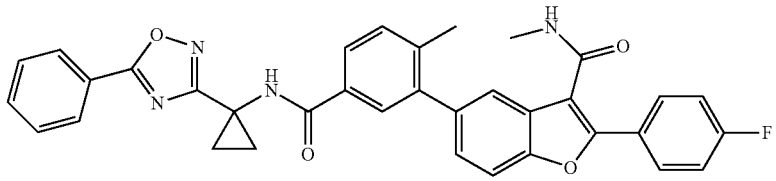

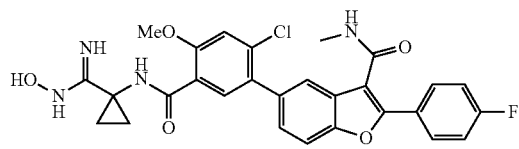

5-(2-Chloro-5-(1-(N-hydroxycarbamimidoyl)cyclopropylcarbamoyl)-4-methoxyphenyl)-2-(4-fluorophenyl)-N-methylbenzofuran-3-carboxamide. LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=551.21, HPLC R$_t$=1.478 min.

2-(4-Fluorophenyl)-N-methyl-5-(2-methyl-5-(1-(5-phenyl-1,2,4-oxadiazol-3-yl)cyclopropylcarbamoyl)phenyl)benzofuran-3-carboxamide. The mixture was first purified by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Waters-Sunfire 19×100 mm S5, Fraction Collection: 9.11-9.39 min. (UV detection at 220 nm) to isolate the desired product. The residue after evaporation of the desired fractions was further purified by preparative TLC (5% MeOH/CH₂Cl₂, 20 cm×20 cm×0.5 mm plate). Analytical TLC Rf=0.52 (5% MeOH/CH₂Cl₂). ¹H NMR (500 MHz, CD₃OD) δ 8.11 (d, J=7.02, 2H), 7.99 (m, 2H), 7.84 (s, 1H), 7.83 (m overlapping with s, 1H), 7.68-7.64 (overlapping m, 3H), 7.60-7.57 (overlapping

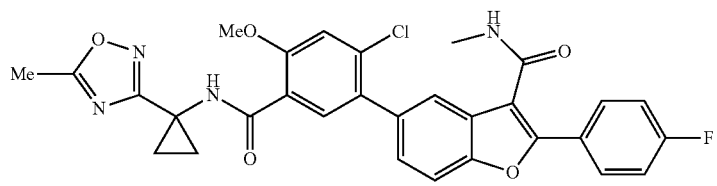

5-(2-Chloro-4-methoxy-5-(1-(5-methyl-1,2,4-oxadiazol-3-yl)cyclopropylcarbamoyl)phenyl)-2-(4-fluorophenyl)-N-methylbenzofuran-3-carboxamide. The mixture first purified by by Shimadzu-VP preparative reverse phase HPLC using the separation method: Solvent A=10% MeOH-90% H₂O-0.1% TFA, Solvent B=90% MeOH-10% H₂O-0.1% TFA, Start % B=60, Final % B=100, Gradient time=5 min, Stop time=6 min, Flow Rate=25 mL/min, Column: Waters-Sunfire 19×50 mm S5, Fraction Collection: 3.85-4.21 min. (UV detection at 220 nm). The residue obtained after evaporation of the desired fractions was further purified by preparative TLC (5% MeOH/CH₂Cl₂, 20 cm×20 cm×0.5 mm plates). ¹H NMR (500 MHz, CD₃OD) δ 7.98 (dd overlapping with s, J=5.19, 2H), 7.97 (s, 1H), 7.71 (d, J=1.22, 1H), 7.65 (d, J=8.55, 1H), 7.45 (dd, J=8.55, 1.83, 1H), 7.36 (s, 1H), 7.28 (t, J=8.85, 2H), 4.05 (s, 3H), 2.96 (s, 3H), 2.54 (s, 3H), 1.61 (m, 2H), 1.46 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Phem, 2H), 7.45 (d, J=8.55, 1H), 7.40 (d, J=8.24, 1.83, 1H), 7.28 (m, 2H), 2.96 (s, 3H), 2.36 (s, 3H), 1.72 (m, 2H), 1.50 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=4 ml/min, Column: Phenomenex-Luna, 3.0×50 mm, S10; (ES+) m/z (M+H)⁺=587.20, HPLC R$_t$=1.950 min.

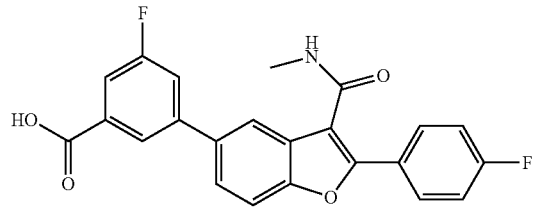

3-fluoro-5-(2-(4-fluorophenyl)-3-(methylcarbamoyl)benzofuran-5-yl)benzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=408.15, HPLC R$_t$=1.757 min.

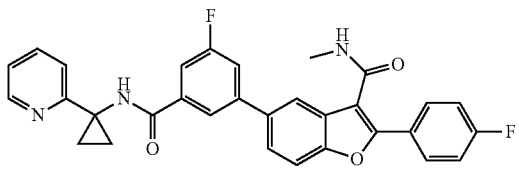

5-(3-Fluoro-5-(1-(pyridin-2-yl)cyclopropylcarbamoyl)phenyl)-2-(4-fluorophenyl)-N-methylbenzofuran-3-carboxamide. The product precipitated from the reaction mixture during the coupling of 3-fluoro-5-(2-(4-fluorophenyl)-3-(methylcarbamoyl)benzofuran-5-yl)benzoic acid (0.068 mmol scale) with 1-(pyridin-2-yl)cyclopropanamine dihydrochloride (TBTU, iPr$_2$NET, DMF, r.t.). The mixture was diluted with 4 ml H$_2$O, the off white solid filtered and washed with 3×2 ml H$_2$O. The solid was further washed with 3×1 ml MeOH and dried. $^1$H NMR (500 MHz, DMSO-d$_6$) δ 9.50 (s, 1H), 8.52 (d, J=4.58, 1H), 8.47 (d, J=3.97, 1H), 8.17 (s, 1H), 8.03-8.00 (overlapping m, 3H), 7.83 (overlapping m, 3H), 7.73 (d, 1H), 7.70 (dt overlapping with d, 1H), 7.43-7.40 (overlapping m, 3H), 7.17 (dd, J=6.87, 5.34, 1H), 2.88 (d, J=4.27, 3H), 1.59 (m, 2H), 1.32 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=524.25, HPLC R$_t$=1.512 min.

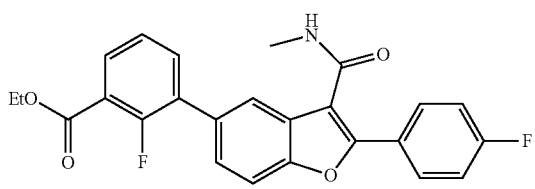

Ethyl 2-fluoro-3-(2-(4-fluorophenyl)-3-(methylcarbamoyl)benzofuran-5-yl)benzoate. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=436.01, HPLC R$_t$=1.820 min.

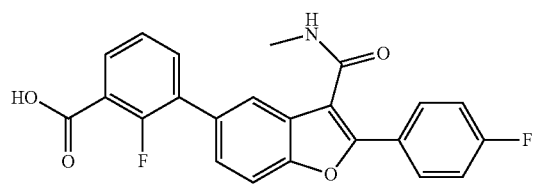

2-Fluoro-3-(2-(4-fluorophenyl)-3-(methylcarbamoyl)benzofuran-5-yl)benzoic acid. LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=408.01, HPLC R$_t$=1.623 min.

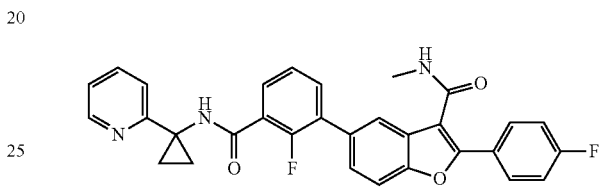

5-(2-Fluoro-3-(1-(pyridin-2-yl)cyclopropylcarbamoyl)phenyl)-2-(4-fluorophenyl)-N-methylbenzofuran-3-carboxamide. The product was obtained as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=10, Final % B=100, Gradient time=10 min, Stop time=12 min, Flow Rate=25 mL/min, Column: Waters-Sunfire 19×100 mm S5, Fraction Collection: 8.11-8.43 min. (UV detection at 220 nm). $^1$H NMR (500 MHz, CD$_3$OD) δ 8.64 (d, J=5.19, 1H), 8.42 (t, J=7.78, 1H), 7.97 (dd, J=8.24, 5.49, 2H), 7.91 (d, J=8.24, 1H), 7.88 (s, 1H), 7.80 (q, J=6.61, 2H), 7.76 (t, J=7.17, 1H), 7.71 (d, J=8.55, 1H), 7.60 (d, J=8.24, 1H), 7.43 (t, J=7.78, 1H), 7.29 (t, J=8.55, 2H), 2.97 (s, 3H), 1.84 (m, 2H), 1.74 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=524.08, HPLC Rt=1.417 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=15 min, Stop time=18 min, Flow Rate=1 ml/min, Column: Sunfire C18, 3.5 um, 4.6×150 mm, R$_t$=8.57 min; Column: Xbridge Phenyl 3.5 um, 4.6×150 mm, R$_t$=9.09 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=12.08 min.

Ethyl 3-(4-Fluorophenyl)-3-oxopropanoate. To a suspension of diethyl carbonate (7.69 g, 65.14 mmol, 1.8 eq) and NaH (hexane washed) (90.47 mmol, 2.5 eq) in dry THF (30 ml) p-fluoroacetophenone (36.19 mmol) was added dropwise at 60° C. The reaction was maintained at gentle reflux by adjusting the temperature and the addition rate (exothermic). After the addition was complete, the reaction was heated at reflux for 4 h, and then cooled to room temperature. The reaction mixture was poured carefully into ice cold acetic acid (6.0 ml) and water (20 ml). The product was extracted with ether, and the combined ether layers were washed with saturated aqueous bicarbonate, brine and dried. Ether was evaporated and the crude product was purified by silica gel (60-120) column chromatography using 2% EtOAc/hexane as eluent. Yield: 7.3 g (96%). $^1$H NMR (400 MHz, CDCl$_3$): δ 1.27 (t, 3H, J=7.12 Hz), 3.96 (s, 2H), 4.24 (q, 2H, J=7.12 Hz), 7.17 (t, 2H, J=7.59 Hz), 7.98 (m, 2H). LCMS: (ES+) m/z=211 (M+H).

Ethyl 2-(4-fluorophenyl)-5-hydroxybenzofuran-3-carboxylate. To a stirred solution of zinc chloride (8.39 g, 1.14 mmol, 1 eq) in toluene at ambient temperature, ethyl 3-(4-fluorophenyl)-3-oxopropanoate (13 g, 2.74 mmol, 1 eq) was added and stirred at 70° C. for 15 min. Benzoquinone (6.66 g, 0.72 mmol, 1 eq) was added portion wise into the reaction mixture and stirred at the same temperature for 15-20 min. Dean-stark apparatus was assembled and the reaction mixture was heated at 140° C. for 12 h and cooled to ambient temperature. Reaction completion was judged by TLC. EtOAc was added to the reaction mass and filtered through the filter paper, to remove the inorganic material. Brine was added to the reaction mixture (filtrate) and extracted, dried over sodium sulphate and concentrated to get the crude material. Further it was purified by column chromatography using 10% EtOAc/Hexane system. Yield: 8.0 g (43%). $^1$H NMR (400 MHz, CDCl$_3$): δ 1.38-1.42 (t, 3H, J=7.14 Hz), 4.37-4.42 (q, 2H, J=7.13 Hz), 5.2 (br s, 1H), 6.87-6.9 (q, 1H, J=3.81 Hz), 7.14-7.18 (q, 2H, J=5.82 Hz), 7.36-7.39 (d, 1H, J=8.80 Hz), 7.50-7.51 (d, 1H, J=2.56 Hz), 8.00-8.03 (m, 2H). LCMS: (ES+) m/z=301 (M+H).

2-(4-fluorophenyl)-5-hydroxybenzofuran-3-carboxylic acid. To a mixture of 2-(4-fluorophenyl)-5-hydroxybenzofuran-3-carboxylate (1 g, 3.5 mmol, 1 eq) in a 1:1 mixture of MeOH/THF at ambient temperature was added 5 eq. of NaOH and heated to 60° C. for 3 h. The mixture was cooled to ambient temperature and to 0° C. in an ice-water bath, it was acidified slowly with 1.5 N HCl and then concentrated. The mixture with white precipitates was diluted with water and filtered to get the solid. It is further washed with water and dried in vacuum. Yield: 0.9 g (94.6%). $^1$H NMR (400 MHz, DMSO-d$_6$): δ 6.82-6.85 (m, 1H), 7.35-7.40 (m, 3H), 7.46-7.49 (d, 1H, J=8.84 Hz), 8.02-8.05 (m, 2H), 9.4 (s, 1H), 13.05 (s, 1H). LCMS: (ES−) m/z=271.1

2-(4-fluorophenyl)-5-hydroxy-N-methylbenzofuran-3-carboxamide. To a mixture of 2-(4-fluorophenyl)-5-hydroxybenzofuran-3-carboxylic acid (1 g, 3.7 mmol, 1 eq), methylamine in THF (2 M solution) (0.689 g, 21.5 mmol, 1 eq), HOBT (0.83 g, 6.2 mmol, 1.7 eq), EDC.HCl (1.24 g, 6.6 mmol, 1.8 eq) in DMF at ambient temperature under nitrogen was added Diisopropyl ethylamine (2.32 g, 18.5 mmol, 3.0 eq). The clear mixture was stirred at ambient temperature for 12 h. The LCMS indicated the desired product. The mixture was concentrated cooled in an ice-water bath, further diluted with water. The white solid was filtered and washed with water and dried in vacuum. Yield: 0.85 g (90%). $^1$H NMR (400 MHz, DMSO-d$_6$): δ 2.81-2.82 (d, 3H, J=4.5 Hz), 6.80-6.83 (m, 1H), 6.94-6.95 (d, 1H, J=2.3 Hz), 7.34-7.38 (t, 2H, J=8.7 Hz), 7.44-7.47 (d, 1H, J=8.8 Hz), 7.90-7.93 (m, 2H), 8.39-8.40 (d, 1H, J=4.4 Hz), 9.3 (s, 1H). LCMS: (ES+) m/z=286.1 (M+H).

2-(4-fluorophenyl)-3-(methylcarbamoyl)benzofuran-5-yl trifluoromethanesulfonate. To a mixture of 2-(4-fluorophenyl)-5-hydroxy-N-methylbenzofuran-3-carboxamide (5 g, 17.5 mmol, 1 eq) in Dichloromethane (50 ml) at ambient temperature under N$_2$ was added triethylamine (2.6 g, 26 mmol, 1.5 eq). The mixture was cooled to 0° C. and then added 1,1,1-trifluoro-N-phenyl-N(trifluoromethylsulphonyl)methane sulphonamide (7.5 g, 21 mmol, 1.2 eq). The mixture was then stirred at ambient temperature for 12 h. The reaction mixture was concentrated, diluted with water and extracted with EtOAc. The organic layer is further washed twice with water, dried over sodium sulphate and concentrated to get the product. The product was further purified by column chromatography using 230-400 silica gel and 50% EtOAc/Hexane. Yield: 6.2 g (85%). $^1$H NMR (400 MHz, DMSO-d$_6$): δ 2.83-2.84 (d, 3H, J=4.6 Hz), 7.40-7.44 (t, 2H, J=8.9 Hz), 7.51-7.53 (m, 1H), 7.75-7.76 (d, 1H, J=2.52 Hz), 7.88-7.90 (d, 1H, J=8.96 Hz), 7.94-7.98 (m, 2H),) 8.51-8.52 (d, 1H, J=4.6 Hz). LCMS: (ES+) m/z=418 (M+H).

3-(2-(4-fluorophenyl)-3-(methylcarbamoyl)benzofuran-5-yl)-4-methylbenzoate. To a mixture of 2-(4-fluorophenyl)-3-(methylcarbamoyl)benzofuran-5-yl trifluoromethanesulfonate (3.5 g, 8.4 mmol, 1 eq), boronic acid (1.95 g, 10.1 mmol, 1.2 eq), in 1,4-dioxane/H$_2$O (5:1) was added cesium carbonate (8.21 g, 26 mmol, 3 eq) and the nitrogen gas was passed through the mixture for 10 min. Then tetrakistriphenylphosphine palladium (0.97 g, 0.8 mmol, 0.1 eq) was added to the reaction mixture and the nitrogen gas was again passed through the mixture for 10 min. The above reaction mixture was heated in microwave for one hour at 90° C. About 50 ml of water is added to the reaction mixture and extracted with EtOAc. The organic layer was further washed twice with water and dried over sodium sulphate and concentrated to get the product. The product obtained was further purified by column chromatography using 40% EtOAc/Hexane as eluent. Yield; 1.5 g (40%) $^1$H NMR (400 MHz, DMSO-d$_6$): δ 2.32 (s, 3H), 2.81-2.82 (d, 3H, J=4.56 Hz), 3.85 (s, 3H), 7.39-7.43 (t, 2H, J=8.9 Hz), 7.39-7.43 (m, 1H), 7.49-7.51 (d, 1H, J=8.16 Hz), 7.56 (s, 1H), 7.75-7.77 (d, 1H, J=8.6), 7.83 (s, 1H), 7.89-7.91 (d, 1H, J=7.82 Hz), 7.98-8.02 (m, 2H), 8.48-8.49 (d, 1H, J=4.6 Hz). LCMS: (ES+) m/z=418 (M+H).

3-(2-(4-fluorophenyl)-3-(methylcarbamoyl)benzofuran-5-yl)-4-methylbenzoic acid. To a mixture of methyl 3-(2-(4-fluorophenyl)-3-(methylcarbamoyl)benzofuran-5-yl)-4-methylbenzoate (1 g, 2.4 mmol, 1 eq) in a 1:1 mixture of MeOH/THF at ambient temperature was added 5 eq. of NaOH and heated to 60° C. for 5 h. The mixture was cooled to ambient temperature and then in an ice-water bath, quenched slowly with 1.5 N HCl and then concentrated. The mixture with white precipitates was diluted with water and filtered to get the solid. It is further washed with water and dried in vacuum. Yield: 0.850 g (90%). This acid was also prepared by the coupling of 2-(4-fluorophenyl)-3-(methylcarbamoyl)benzofuran-5-yl trifluoromethanesulfonate with 4-methyl-3-(4,4,5, 5-tetramethyl-1,3,2-dioxaborolan-2-yl)benzoic acid (Cs$_2$CO$_3$, (Ph$_3$)$_4$Pd, H$_2$O/1,4-dioxane (1:5), 90° C.) in a similar manner as described. $^1$H NMR (400 MHz, DMSO-d$_6$): δ 2.32 (s, 3H), 2.82-2.83 (d, 3H, J=4.6 Hz), 7.36-7.48 (m, 6H), 7.56-7.57 (d, 1H, J=1.44 Hz), 7.75-7.77 (d, 1H, J=8.48 Hz), 7.81-8.03 (m, 2H), 8.46-8.48 (d, 1H, J=4.7 Hz), 12.92 (s, 1H). LCMS: (ES+) m/z=404.0 (M+H).

1-(pyrimidin-2-yl)cyclopropanamine. 2-Cyano pyrimidine (5 g, 47.6 mmol, 1 eq) was taken in a Dry THF under Argon atmosphere, then Titanium isopropoxide (17 ml, 57.1 mmol, 1.2 eq) was added slowly at ambient temperature and the reaction mixture was stirred for 15 mins. Ethyl magnesium bromide (1M solution) in THF (107 ml, 809 mmol, 2.5 eq) was added via syringe slowly at ambient temperature, (During the addition of EtMgBr reaction mass becomes black). Then the reaction mass was stirred for an hour.

BF$_3$.EtO (16.7 ml, 119.0 mmol, 2.5 eq) was added slowly through syringe at 0° C. The mixture was allowed to attain ambient temperature and stirred for another one hour. 50 ml of Water was added to the reaction mixture and filtered through the Celite and washed the bed with water and Ethyl acetate. The reaction mass was basified with 10% NaOH solution (pH=9) then extracted with DCM and washed with brine solution. The required product was purified by silica gel (230-400) column chromatography using DCM/methanol as the eluent. Yield: 2.1 g (30%). $^1$H NMR (400 MHz, DMSO-d$_6$): δ 1.49-1.52 (m, 2H), 1.59-1.62 (m, 2H), 7.47-7.49 (t, 1H, J=4.80), 8.83-8.84 (d, 2H, J=4.80).

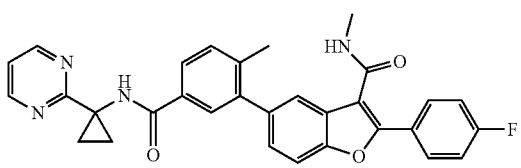

2-(4-fluorophenyl)-N-methyl-5-(2-methyl-5-(1-(pyrimidin-2-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.1 g, 0.25 mmol, 1 eq), 1-(pyrimidin-2-yl)cyclopropanamine (0.041 g, 0.3 mmol, 1.2 eq) (60% purity), HOBT (0.057 g, 0.42 mmol, 1.7 eq), EDC.HCl (0.086 g, 0.44 mmol, 1.8 eq) in DCM at ambient temperature under nitrogen was added Diisopropylethylamine (0.16 g, 1.3 mmol). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and finally purified by preparative HPLC. Yield: 0.15 g (14%). $^1$H NMR (400 MHz, DMSO-d$_6$): δ 1.33-1.36 (m, 2H), 1.59-1.61 (m, 2H), 2.31 (s, 3H), 2.82-2.83 (d, 3H, J=4.8 Hz), 7.26-7.29 (t, 1H, J=4.8 Hz), 7.39-7.45 (m, 4H), 7.59 (s, 1H), 7.76-7.78 (d, 1H, J=8.4 Hz), 7.86-7.87 (d, 2H, J=4.4 Hz), 7.98-8.02 (m, 2H), 8.47-8.50 (m, 1H), 8.67-8.68 (d, 2H, J=4.8 Hz), 9.20 (s, 1H). LCMS: (ES+) m/z=521.2 (M+H). Column-Ascentis Express C18 (5×2.1 mm-2.7 μm) Mphase A: 2% MeCN-98% H$_2$O-10 mM NH$_4$COOH Mphase B: 98% MeCN-2% H$_2$O-10 mM NH$_4$COOH Flow: 1 mL/Min.

| Time | % A | % B |
|---|---|---|
| 0.0 | 100.0 | 0 |
| 1.5 | 0.0 | 100.0 |
| 3.2 | 0.0 | 100.0 |
| 3.6 | 100.0 | 0.0 |

RT min: 1.908, wavelength: 220 nm

HPLC Method: Column-ZORBAX C18 (4.6×150 mm-5.0 μm)

A: Buffer: 20 mM Ammonium acetate

B: Methanol

FLOW: 1 ml/min

| Time | B % |
|---|---|
| 0 | 10 |
| 12 | 100 |
| 15 | 100 |

Wavelength: 254 nm, RT min: 19.7
Wavelength: 220 nm, RT min: 19.7
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: ACN:Buffer (95:5)
FLOW: 1 ml/min

| Time | B % |
|---|---|
| 1 | 10 |
| 13 | 100 |
| 16 | 100 |

Wavelength: 254 nm, RT min: 17.2
Wavelength: 220 nm, RT min: 17.2
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 15.764
Wavelength: 220 nm, RT min: 15.764

3-fluoro-5-iodo-4-methylbenzoic acid. 3-Fluoro-4-methylbenzoic acid (1 g, 6.48 mmol, 1 eq) was dissolved in trifluoromethanesulphonic acid (10 ml) and the reaction was cooled to 0° C. To the above solution N-Iodosuccinimide (1.46 g, 6.48 mmol, 1 eq) was added in portion and the reaction was stirred at room temperature for 14 h. Later the above solution was poured into 50 ml of ice water, the solid obtained was filtered. The solid was dissolved in ethylacetate, washed with sodiumthiosulphate solution and brine, the organic layer was concentrated to get the desired product as light brown solid. Yield: 1.5 g (83%). $^1$HNMR (400 MHz, CDCl$_3$): δ 2.35 (s, 3H), 7.68 (d, 1H, J=8 Hz), 8.14 (s, 1H). 13.50 (br, 1H).

Methyl 3-fluoro-5-iodo-4-methylbenzoate. 3-Fluoro-5-iodo-4-methylbenzoic acid (1.3 g, 4.6 mmol, 1 eq) was dissolved in Methanol and treated with conc. Sulphuric acid (0.49 ml, 9.2 mmol, 2 eq). The above solution was stirred at 50° C. for 15 h. Later on solvent was removed and to the resulting residue diethylether was added and the organic layer was washed with 10% sodium bicarbonate solution and water. Finally, the organic layer was concentrated and purified by flash silica gel column chromatography using 240-400 silica gel and using 10% EtOAc in hexane as the eluent. Yield: 1 g (77%). $^1$H NMR (400 MHz CDCl$_3$). δ 2.39 (s, 3H), 3.90 (s, 3H), 7.64 (d, 1H, J=8 Hz), 8.25 (s, 1H).

Methyl 3-fluoro-4-methyl-5-(3,3,4,4-tetramethylborolan-1-yl)benzoate. A mixture of methyl 3-fluoro-5-iodo-4-methylbenzoate (0.85 g, 2.89 mmol, 1 eq), Potassium acetate (1.41 g, 14.45 mmol, 5 eq), bispinacolatodiboron (1.1 g, 4.33 mmol, 1.5 eq) and 1,1-bis(diphenylphosphino)ferrocene)-dichloropalladium (II) (0.047 g, 0.057 mmol, 0.02 eq) were dissolved in DMF and the reaction was stirred at 90° C. for 18 h. Later solvent was removed, water was added and extracted with dichloromethane, organic layer was washed with 2 M HCl, 10% lithium chloride and brine. The organic layer was concentrated and hexane was added. The solid obtained was filtered and dried to get the desired product as a white solid. Yield: 0.35 g, (41%). 1HNMR (400 MHz CDCl$_3$): δ 1.35 (s, 12H), 2.49 (s, 3H), 3.90 (s, 3H), 7.69-7.71 (d, 1H, J=8 Hz), 8.18 (s, 1H).).

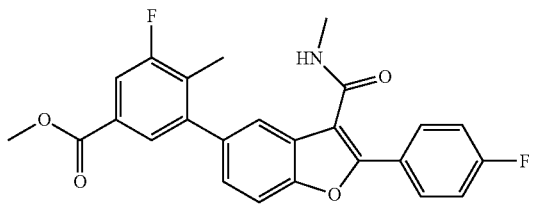

Methyl 3-fluoro-5-(2-(4-fluorophenyl)-3-(methylcarbamoyl)benzofuran-5-yl)-4-methylbenzoate. To a mixture of 2-(4-fluorophenyl)-3-(methylcarbamoyl)benzofuran-5-yl trifluoromethanesulfonate (0.5 g, 1.2 mmol, 1 eq), boronic ester (0.42 g, 1.4 mmol, 1.2 eq) in 1,4-dioxane/H$_2$O (5:1) was added cesium carbonate (1.17 g, 3.6 mmol, 3 eq) and the nitrogen gas was passed through the solution for 10 min. Then tetrakistriphenylphosphine palladium (0.14 g, 0.12 mmol, 0.1 eq) was added to the reaction mixture and the nitrogen gas was passed again through the solution for 15 min. The above reaction mixture was heated in microwave for one hour at 90° C. About 100 ml of water is added to the reaction mixture and extracted with EtOAc. The organic layer was further washed twice with water, dried and concentrated to get the product. The product obtained was further purified by column chromatography using 40% EtOAc/Hexane as the eluent. Yield: 0.5 g (40%). $^1$H NMR (400 MHz, DMSO-d$_6$): δ 2.23 (d, 3H, J=1.9 Hz), 2.82-2.83 (d, 3H, J=4.6 Hz), 3.8 (s, 3H), 7.39-7.43 (t, 2H, J=8.4 Hz), 7.39-7.43 (1H, m), 7.61 (s, 1H), 7.70-7.72 (d, 2H, J=7.2 Hz), 7.78-7.80 (d, 1H, J=8.4 Hz), 7.99-8.03 (m, 2H), 8.49-8.51 (d, 1H, J=4.7 Hz). LCMS: (ES+) m/z=436 (M+H). Phenomina Luna C18 (4.6×3.0 mm-5 μm) Mphase A: 10% CH$_3$OH-90% H$_2$O-10 mM NH$_4$OAc Mphase B: 90% CH$_3$OH-10% H$_2$O-10 mM NH$_4$OAc Flow: 5 ml/Min

| Time | % B |
|---|---|
| 0.0 | 0.0 |
| 2.0 | 100.0 |
| 3.0 | 0.0 |

RT min: 2.135, wavelength: 220 nm

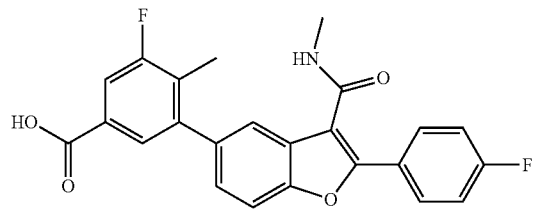

3-(2-(4-fluorophenyl)-3-(methylcarbamoyl)benzofuran-5-yl)-4-methylbenzoic acid. To a mixture of methyl 3-fluoro-5-(2-(4-fluorophenyl)-3-(methylcarbamoyl)benzofuran-5-yl)-4-methylbenzoate (0.3 g, 0.68 mmol, 1 eq) in a 1:1 mixture of MeOH/THF at ambient temperature was added 5 eq. of NaOH and heated to 60° C. for 5 h. The mixture was cooled to ambient temperature and then cooled in an ice-water bath. It was acidified slowly with 1.5 N HCl and then concentrated. The mixture with white precipitates was diluted with water and filtered to get the solid. It is further washed with water and dried in vacuum. Yield: 0.2 g (60%). $^1$H NMR (400 MHz, DMSO-d$_6$): δ 2.22 (s, 3H), 2.82-2.84 (d, 3H, J=4.6 Hz), 7.39-7.43 (m, 3H,), 7.61 (s, 1H), 7.66-7.70 (d, 1H, J=8.6 Hz), 7.66-7.70 (m, 1H), 7.78-7.80 (d, 1H, J=8.5 Hz), 8.01-8.03 (m, 2H), 8.49-8.51 (d, 1H, J=4.76 Hz), 13.2 (s, 1H). LCMS: (ES−) m/z=420.0 (M−H) Chromolith SpeedROD C18 (4.6×3.0 mm-5.0 μm) Mphase A: 10% CH$_3$OH-90% H$_2$O-0.1% TFA Mphase B: 90% CH$_3$OH-10% H$_2$O-0.1% TFA.

Flow: 5 ml/Min

| Time | % B |
|---|---|
| 0.0 | 0.0 |
| 2.0 | 100.0 |
| 3.0 | 0.0 |

RT min: 2.040, wavelength: 220 nm 1-(pyridin-2-yl)cyclopropanamine. 2-Cyano pyridine (5 g, 48.0 mmol, 1 eq) was taken in dry THF under Argon atmosphere. To this mixture was added slowly Titanium isopropoxide (17 ml, 57.6 mmol, 1.2 eq) at ambient temperature. The reaction mass was stirred for 15 mins. Ethyl Magnesium Bromide (1 M solution) in THF (107 ml, 809 mmol, 2.5 eq) was added via syringe slowly at room temperature, (During the addition of EtMgBr reaction mass becomes black). Then the reaction mass stirred for an hour and BF$_3$.Et$_2$O (16.7 ml, 120.0 mmol, 2.5 eq) was added slowly at 0° C. After the completion of addition process, reaction mass was allowed to attain ambient temperature and the stirring continued for one more hour. Finally, 50 ml of water was added and the reaction mass was filtered through the Celite. The bed was further washed with water and Ethyl acetate. The filtrate was basified with 10% NaOH solution (pH=9) then extracted with DCM and washed with brine solution, the required product was purified by silica gel (60-120) column chromatography using DCM/methanol as the eluent. Yield: 1.3 g (23%). $^1$H NMR (400 MHz, CDCl$_3$): δ 1.12-1.14 (m, 2H), 1.27-1.29 (m, 2H), 2.12 (broad s, 2H), 7.03-7.07 (t, 1H), 7.33-7.35 (d, 1H), 7.60-7.62 (t, 1H), 8.48-8.49 (d, 1H).

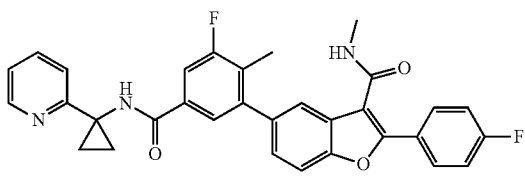

5-(3-fluoro-2-methyl-5-(1-(pyridin-2-yl)cyclopropylcarbamoyl)phenyl)-2-(4-fluorophenyl)-N-methylbenzofuran-3-carboxamide. To a mixture of 3-fluoro-5-(2-(4-fluorophenyl)-3-(methylcarbamoyl)benzofuran-5-yl)-4-methyl benzoic acid (0.2 g, 0.47 mmol, 1 eq), 1-(pyridin-2-yl)cyclopropanamine (0.075 g, 5.5 mmol, 1.2 eq) (60% purity), HOBT (0.81 g, 0.015 mmol, 1.7 eq), EDC.HCl (0.16 g, 00.83 mmol, 1.8 eq) in DCM at ambient temperature and under nitrogen was added Diisopropylethylamine (0.30 g, 2.3 mmol, 5.0 eq). The clear mixture was stirred at ambient temperature for 12 h. The mixture was concentrated, diluted with water and extracted with EtOAc. The organic layer is further washed with water, dried over sodium sulphate and concentrated. The product obtained was further purified by column chromatography (neutral alumina) using 0.5% Methanol/DCM and further purification was done using preparative HPLC. Yield: 0.1 g (50%). $^1$H NMR (400 MHz, CDCl$_3$): δ 1.39-1.42 (m, 2H), 1.67-1.70 (m, 2H), 2.21-2.22 (d, 3H, J=2.24 Hz), 2.9-3.0 (d, 3H, J=4.88 Hz), 5.98-5.99 (s, 1H), 7.06-7.09 (dd, 1H, J=5.2, 7.2 Hz), 7.18-7.36 (m, 5H), 7.53-7.62 (m, 4H), 7.76 (d, 1H, J=1.36 Hz), 7.94-7.97 (m, 2H), 8.4 (s, 1H). LCMS: (ES+) m/z=538.2 (M+H). LCMS Method: Column-Atlantis dC18 (50×4.6 mm-5 μm) A: 10 mM NH$_4$OAc; B: acetonitrile
Flow: 1 mL/Min

| Time | % B |
|---|---|
| 0.0-3.0 | 30-95 |
| 3.0-4.0 | 95 |
| 4.0-4.5 | 95-30 |
| 4.5-6.0 | 30 |

RT min: 3.665, wavelength: 220 nm
HPLC Method Info: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 10.441
Wavelength: 220 nm, RT min: 10.441
Purity: 96%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.592
Wavelength: 220 nm, RT min: 9.592
Purity: 95.9%

Methyl 3,5-dihydroxy-4-methylbenzoate. 3,5-dihydroxy-4-methylbenzoic acid (5.0 g, 29.79 mmol, 1.0 eq) and PTSA (1.13 g, 5.94 mmol, 0.2 eq) were dissolved in 50 ml of methanol, and the mixture was heated to reflux for 6 h. Methanol was evaporated. The resultant solid was washed with 10% sodium bicarbonate solution. The aqueous solution was extracted thrice with ethyl acetate. The combined organic layer was dried over sodium sulphate and evaporated under vacuum. Yield: 5.25 g (96%). $^1$H NMR (400 MHz, DMSO-d$_6$): δ 1.98 (s, 3H), 3.78 (s, 3H), 6.93 (s, 2H), 9.53 (s, 2H). LCMS: (ES+) m/z=183 (M+H) Method: Column: Phenomenex Luna C18 (4.6×30) mm, 5 micron Mphase A: 10% MeOH-90% H$_2$O-10 mM NH$_4$OAc Mphase B: 90% MeOH-10% H$_2$O-10 mM NH$_4$OAc
Flow: 5 ml/min

| Time (min.) | %A | %B |
|---|---|---|
| 0.0 | 100.0 | 0.0 |
| 2.0 | 0.0 | 100.0 |
| 3.0 | 0.0 | 0.0 |

RT min: 0.956
Wavelength: 220 nm

Methyl 3-(benzyloxy)-5-hydroxy-4-methylbenzoate. Methyl 3,5-dihydroxy-4-methylbenzoate (3.5 g, 19.22 mmol, 1.0 eq) was dissolved in 300 ml of DMF. To this solution potassium carbonate (2.52 g, 18.26 mmol, 0.95 eq) was added. To this stirred suspension, benzyl bromide (3.12 g, 18.26 mmol, 0.95 eq) (diluted with 50 ml of DMF) was added dropwise over a period of 3 h. The solution was stirred overnight at ambient temperature. Then DMF was evaporated under reduced pressure. The residue was washed with water and the product was extracted thrice with DCM. The combined DCM layers was dried over sodium sulphate and evaporated under vacuum. The required product was purified by silica gel (240-400) column chromatography using 10% ethyl acetate/hexane as the eluent. Yield: 1.6 g (30%). $^1$H NMR (400 MHz, DMSO-d$_6$): δ 2.07 (s, 3H), 3.81 (s, 3H), 5.14 (s, 2H), 7.08 (s, 1H), 7.14 (s, 1H), 7.33-7.35 (d, 1H, J=7.04 Hz), 7.39-7.42 (t, 2H, J=7.40 Hz), 7.46-7.48 (d, 2H, J=7.48 Hz), 9.78 (s, 1H).

Methyl 3-(benzyloxy)-4-methyl-5-(trifluoromethylsulfonyloxy)benzoate. Methyl 3-(benzyloxy)-5-hydroxy-4-methylbenzoate (3.0 g, 11.02 mmol, 1.0 eq) was dissolved in DCM followed by N-phenyl bis(trifluoromethylsulphonimide) (5.9 g, 16.53 mmol, 1.5 eq). To this stirred solution TEA (3.34 g, 33.06 mmol, 3.0 eq) was added dropwise. The resultant solution was stirred overnight at ambient temperature. To this reaction mass water was added and the DCM layer was separated. The aqueous layer was extracted twice with DCM. The combined DCM layer was dried over sodium sulphate and evaporated. The resultant oil was purified by silica gel (60-120) column chromatography using 5% ethyl acetate/hexane as the eluent. Yield: 4.0 g (80%). ¹H NMR (400 MHz, DMSO): δ 2.26 (s, 3H), 3.90 (s, 3H), 5.77 (s, 2H), 7.36-7.39 (d, 1H, J=8.20 Hz), 7.43-7.45 (t, 2H, J=7.60 Hz), 7.51 (s, 3H), 7.70 (s, 1H).

Methyl 3-(benzyloxy)-4-methyl-5-(4,4,5,5-tetramethyl-1,3,2-dioxaborolan-2-yl)benzoate. To the solution of methyl 3-(benzyloxy)-4-methyl-5(trifluoromethylsulfonyloxy)benzoate (1.2 g, 2.96 mmol, 1.0 eq) in 1,4-dioxane was added PdCl₂(dppf) in DCM complex (242 mg, 0.296 mmol, 0.1 eq) followed by bis(pinacolato)diboron (1.5 g, 5.93 mmol, 2.0 eq). To this stirred solution TEA (1.5 g, 14.83 mmol, and 5.0 eq) was added. The reaction mixture was slowly heated to 110° C. and maintained for two days in a sealed tube. 1,4-Dioxane was evaporated under reduced pressure. To the residue water was added and the aqueous layer was extracted thrice with DCM. The combined DCM layer was dried over sodium sulphate and evaporated under vacuum. The crude was purified by silica gel (60-120) column chromatography using 1% ethyl acetate/hexane as the eluent. Yield: 0.8 g (70%). ¹H NMR (400 MHz, CDCl₃): δ 1.39 (s, 12H), 2.53 (s, 3H), 3.91 (s, 3H), 5.17 (s, 2H), 7.33-7.35 (d, 1H, J=7.36 Hz), 7.39-7.42 (t, 2H, J=7.50 Hz), 7.48-7.50 (d, 2H, J=7.40 Hz), 7.67-7.68 (d, 1H, J=1.20 Hz), 8.00-8.01 (d, 1H, J=1.40 Hz).

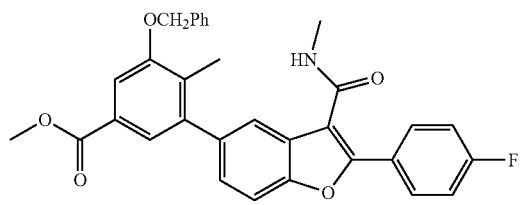

Methyl 3-(benzyloxy)-5-(2-(4-fluorophenyl)-3-(methylcarbamoyl)benzofuran-5-yl)-4-methylbenzoate. To a mixture of 2-(4-fluorophenyl)-3-(methylcarbamoyl)benzofuran-5-yl trifluoromethanesulfonate (0.5 g, 1.2 mmol, 1 eq), boronic ester (0.55 g, 1.4 mmol, 1.2 eq), in 1,4-dioxane/H₂O (5:1) was added cesium carbonate (1.37 g, 4.2 mmol, 3 eq) and the nitrogen gas was passed through the solution for 10 min. Then tetrakistriphenylphosphinepalladium (0.12 g, 0.16 mmol, 0.1 eq) was added to the reaction mixture and the nitrogen gas was passed again for 15 min. The above reaction mixture was heated in microwave for one hour at 90° C. About 100 ml of water is added to the reaction mixture and extracted with EtOAc. The organic layer was further washed twice with water and dried over sodium sulphate and concentrated to get the product. The product obtained was further purified by column chromatography using 60-120 silica gel and 40% EtOAc/Hexane system. Yield: 0.3 g (48%). ¹H NMR (400 MHz, DMSO-d₆): δ 2.20 (s, 3H), 2.82-2.83 (d, 3H, J=4.6 Hz), 3.8 (s, 3H), 5.3 (s, 2H), 7.39-7.46 (m, 6H), 7.52-7.56 (m, 4H), 7.62 (s, 1H), 7.76-7.78 (d, 1H, J=8.44 Hz), 7.99-8.03 (m, 2H), 8.49-8.50 (d, 1H, J=4.52 Hz). LCMS: (ES+) m/z=524.0 (M+H). Chromolith SpeedROD C18 (4.6X3.0 mm-5.0 μm)
Mphase A: 10% CH₃OH-90% H₂O-0.1% TFA
Mphase B: 90% CH₃OH-10% H₂O-0.1% TFA
Flow: 5 ml/Min

| Time | % B |
|---|---|
| 0.0 | 0.0 |
| 2.0 | 100.0 |
| 3.0 | 0.0 |

RT min: 2.303, wavelength: 220 nm

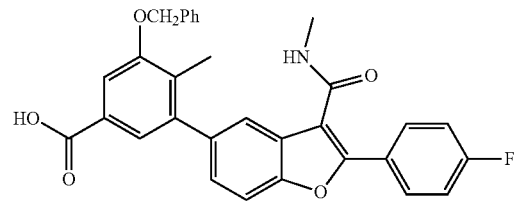

3-(benzyloxy)-5-(2-(4-fluorophenyl)-3-(methylcarbamoyl)benzofuran-5-yl)-4-methylbenzoic acid. To a mixture of methyl 3-(benzyloxy)-5-(2-(4-fluorophenyl)-3-(methylcarbamoyl)benzofuran-5-yl)-4-methylbenzoate (0.3 g, 0.57 mmol, 1 eq) in a 1:1 mixture of MeOH/THF at ambient temperature was added 5 eq. of NaOH, and the resulting mixture was heated to 60° C. for 5 h. The mixture was cooled to ambient temperature and then cooled in ice-water bath. The reaction mixture was acidified with 1.5 N HCl and then concentrated. The mixture with white precipitates was diluted with water and filtered to get the solid. It is further washed with water and dried in vacuum. Yield: 0.2 g (70%). ¹H NMR (400 MHz, DMSO-d₆): δ 2.19 (s, 3H), 2.82-2.83 (d, 3H, J=4.56 Hz), 5.27 (s, 2H), 7.34-7.46 (m, 6H), 7.50-7.55 (m, 4H), 7.60 (s, 1H), 7.75-7.77 (d, 1H, J=8.44 Hz), 7.99-8.03 (m, 2H), 8.49-8.50 (d, 1H), 13.0 (s, 1H). LCMS: (ES+) m/z=510 (M+H). Ascentis Express C18 (5.0×2.1-2.7 nm) Mphase A: 2% MeCN-98% H₂O-10 mM NH₄COOH
Mphase B: 98% MeCN-2% H₂O-10 mM NH₄COOH
Flow: 5 ml/Min

| Time | % A | %B |
|---|---|---|
| 0.0 | 100.0 | 0.0 |
| 1.5 | 0.0 | 100.0 |
| 3.2 | 0.0 | 100.0 |
| 3.6 | 100.0 | 0.0 |

RT min: 1.963, wavelength: 220 nm

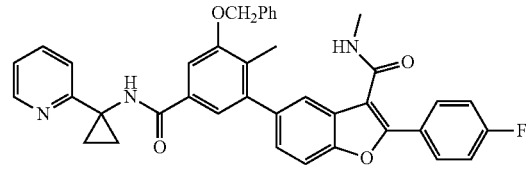

5-(3-(benzyloxy)-2-methyl-5-(1-(pyridin-2-yl)cyclopropylcarbamoyl)phenyl)-2-(4-fluorophenyl)-N-methylbenzofuran-3-carboxamide. To a mixture of 3-(benzyloxy)-5-(2-(4-fluorophenyl)-3-(methylcarbamoyl)benzofuran-5-yl)-4-methylbenzoic acid (0.2 g, 0.40 mmol, 1 eq), 1-(pyridin-2-yl)cyclopropanamine (0.064 g, 0.47 mmol, 1.2 eq) (60% purity), HOBT (0.68 g, 0.012 mmol, 1.7 eq), EDC.HCl (0.064 g, 0.72 mmol, 1.8 eq) in DCM at ambient temperature under nitrogen was added Diisopropylethylamine (0.26 g, 2.0 mmol, 5.0 eq). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and preparative HPLC. Yield: 0.17 g (70%). ¹H NMR (400 MHz, DMSO-d₆): δ 1.26-1.27 (m, 2H), 1.54-

1.56 (m, 2H), 2.18 (s, 3H), 2.81-2.82 (s, 3H), 5.26 (s, 2H) 7.13-7.15 (q, 1H, J=4.4 Hz), 7.30-7.43 (m, 6H), 7.58 (d, 4H), 7.65-7.69 (t, 2H, J=3.9 Hz), 7.74-7.79 (d, 1H, J=8.0 Hz), 7.97-8.01 (m, 2H), 8.43-8.48 (dd, 2H, J=4.89 Hz), 9.186 (s, 1H). LCMS: (ES+) m/z=626 (M+H) Ascentis Express C18 (5.0×2.1-2.7 μm) Mphase A: 2% MeCN-98% H$_2$O-10 mM NH$_4$COOH Mphase B: 98% MeCN-2% H$_2$O-10 mM NH$_4$COOH Flow: 5 ml/Min

| Time | % A | % B |
|---|---|---|
| 0.0 | 100.0 | 0.0 |
| 1.5 | 0.0 | 100.0 |
| 3.2 | 0.0 | 100.0 |
| 3.6 | 100.0 | 0.0 |

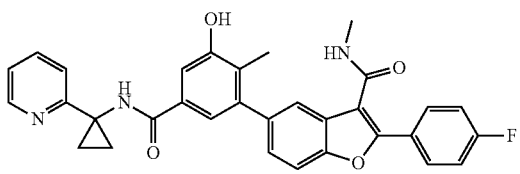

2-(4-fluorophenyl)-5-(3-hydroxy-2-methyl-5-(1-(pyridin-2-yl)cyclopropylcarbamoyl)phenyl)-N-ethylbenzofuran-3-carboxamide. To a solution of 3-(benzyloxy)-5-(2-(4-fluorophenyl)-3-(methylcarbamoyl)benzofuran-5-yl)-4-methylbenzoic acid (0.17 g, 0.27 mmol, 1 eq) in DCM was added BCl$_3$ in DCM (0.32 g, 2.7 mmol, 10 eq). The clear mixture was stirred at ambient temperature for overnight. LCMS showed the desired product. The mixture was quenched with 10% NaHCO$_3$ and extracted with EtOAc. The organic layer is further washed with water, dried over sodium sulphate and concentrated. The product obtained was further purified by column chromatography (neutral alumina) using 0.5% Methanol/DCM and it was further purified with preparative HPLC. Yield: 0.048 g (33%). $^1$H NMR (400 MHz, DMSO-d$_6$): δ 1.22-1.24 (m, 2H), 1.51-1.53 (m, 2H), 2.09 (s, 3H,), 2.82-2.83 (s, 3H, J=4.4 Hz), 7.12-7.15 (q, 1H), 7.30-7.32 (d, J=8 Hz, 1H), 7.37-7.43 (m, 5H), 7.58 (s, 1H), 7.65-7.69 (t, 1H, J=8 Hz), 7.74-7.76 (d, 1H, J=8.8 Hz), 7.97-8.01 (m, 2H), 8.43-8.48 (dd, 2H, J=16, 4.8 Hz), 9.18 (s, 1H), 9.77 (s, 1H). LCMS: (ES+) m/z=536.2 (M+H). Column-Ascentis Express C18 (5×2.1 mm-2.7 μm) Mphase A: 2% MeCN-98% H$_2$O-10 mM NH$_4$COOH Mphase B: 98% MeCN-2% H$_2$O-10 mM NH$_4$COOH Flow: 1 mL/Min

| Time | % A | % B |
|---|---|---|
| 0.0 | 100.0 | 0 |
| 1.5 | 0.0 | 100.0 |
| 3.2 | 0.0 | 100.0 |
| 3.6 | 100.0 | 0.0 |

RT min: 1.862, wavelength: 220 nm
HPLC Method Info: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 2 | 10 |
| 12 | 100 |
| 15 | 100 |

Wavelength: 254 nm, RT min: 9.255
Wavelength: 220 nm, RT min: 9.255
Purity: 95.2%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.046
Wavelength: 220 nm, RT min: 9.046
Purity: 95.8%

2-fluoro-3-iodo-4-methylbenzonitrile. A solution of 2,2,6,6-tetramethyl-4-piperidine (TMP) (550 mg, 3.93 mmol, 2.1 eq) in THF (5 ml) was cooled to −78° C. under nitrogen atmosphere. N-Butyl lithium (1.6 M in hexane, 1.52 ml, 3.96 mmol, 2.1 eq) was added slowly maintaining the temperature below −70° C. After addition, the reaction mixture was warmed to −50° C. and stirred for one hour. The clear solution became turbid indicating the salt formation. The reaction mixture was cooled to −80° C., and a solution of 2-fluoro-4-methylbenzonitrile (250 mg, 1.85 mmol, 1.0 eq) in THF (1 ml) was slowly added maintaining temperature below −70° C. The mixture was then warmed to −50° C. and stirred for 30 minutes. The mixture was re-cooled to −78° C. and a saturated solution of iodine (516 mg, 2.03 mmol, 1.1 eq) in THF (1 ml) was added slowly maintaining the temperature below −70° C. After addition, the mixture was warmed to ambient temperature. The reaction mixture was poured into a saturated solution of Na$_2$S$_2$O$_3$ (10 ml) and stirred for 30 minutes. The organic layer was separated, and the aqueous layer was extracted with ethyl acetate. The organic layers were combined, washed with brine and dried over sodium sulphate. The volatiles were evaporated under reduced pressure. The crude product was purified under silica gel (60-120) column chromatography using 0.5% ethyl acetate/hexane as eluent. Yield: 187 mg (38%). $^1$H NMR (400 MHz, CDCl$_3$): δ 2.55 (s, 3H), 7.13-7.15 (d, 1H, J=7.92 Hz), 7.48-7.50 (t, 1H, J=4.80 Hz).

2-fluoro-3-iodo-4-methylbenzoic acid. A mixture of 2-fluoro-3-iodo-4-methylbenzonitrile (450 mg, 1.71 mmol, 1.0 eq) in dioxane 2 ml and 60% sulphuric acid (2 ml) was heated at 115° C. in an oil bath for 12 h. After the mixture was cooled to room temperature, it was poured on to 10 g of ice. The tan solid was filtered, washed with water followed by ethyl acetate. The solid collected was dried to afford 2-fluoro-3-iodo-4-methylbenzoic acid as a tan crystalline solid. The filtrate was transferred to a separatory funnel. The ethyl acetate layer was separated, washed with brine, dried over sodium sulphate and concentrated to afford additional 2-fluoro-3-iodo-4-methylbenzoic acid. Yield: 450 mg (93%). $^1$H NMR (400 MHz, DMSO-d$_6$): δ 2.48 (s, 3H), 7.27-7.29 (d, 1H, J=8.00 Hz), 7.74-7.78 (t, 1H, J=7.82 Hz), 13.2 (b, 1H).

Methyl 2-fluoro-3-iodo-4-methylbenzoate. To the solution of 2-fluoro-3-iodo-4-methylbenzoic acid (450 mg, 1.6 mmol, 1.0 eq) in methanol (5 ml), catalytic amount of conc.HCl (0.1 ml) was added. The resultant solution was heated to reflux at 80° C. for overnight. Methanol was evaporated. To this residue, water was added and the aqueous layer was extracted thrice with ethyl acetate. The combined ethyl acetate extracts were dried over sodium sulphate, filtered and evaporated to afford methyl 2-fluoro-3-iodo-4-methylbenzoate. Yield: 450 mg (95%). $^1$H NMR (400 MHz, DMSO): δ 2.49 (s, 3H), 3.85 (s, 3H), 7.30-7.32 (d, 1H, J=7.84 Hz), 7.76-7.80 (t, 1H, J=7.82 Hz). LCMS: (ES+) m/z=295 (M+H).

Methyl 2-fluoro-4-methyl-3-(4,4,5,5-tetramethyl-1,3,2-dioxaborolan-2-yl)benzoate. To the solution of methyl 2-fluoro-3-iodo-4-methylbenzoate (1.1 g, 3.74 mmol, 1.0 eq) in DMSO was added [1,1'-bis(diphenylphosphino)ferrocene]-dichloropalladium (305 mg, 0.37 mmol, 0.1 eq) followed by bis(pinacolato)diboron (1.9 g, 7.48 mmol, 2.0 eq). To this solution potassium acetate (1.83 g, 18.7 mmol, 5.0 eq) was added and nitrogen gas was passed through for 10 minutes. The resultant solution was irradiated with microwave at 80° C. for 40 minutes. Reaction mixture was quenched with brine solution. The aqueous layer was extracted thrice with ethyl acetate. The combined organic layer was dried over sodium sulphate and the clear ethyl acetate layer was evaporated under vacuum. The crude was purified by silica gel (60-120) column chromatography using 1% ethyl acetate/hexane as eluent. Yield: 400 mg (36%). $^1$H NMR (400 MHz, CDCl$_3$): δ 1.38 (s, 12H), 2.46 (s, 3H), 3.89 (s, 3H), 6.98-7.00 (d, 1H, J=7.84 Hz), 7.81-7.85 (t, 1H, J=7.82 Hz). LCMS: (ES+) m/z=295 (M+H).

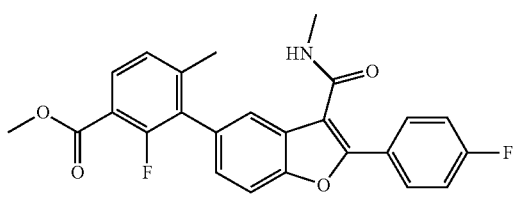

Methyl 2-fluoro-3-(2-(4-fluorophenyl)-3-(methylcarbamoyl)benzofuran-5-yl)-4-methylbenzoate. To a mixture of 2-(4-fluorophenyl)-3-(methylcarbamoyl)benzofuran-5-yl trifluoromethanesulfonate (0.4 g, 0.96 mmol, 1 eq), boronic ester (0.366 g, 1.24 mmol, 1.3 eq), in 1,4-dioxane/H$_2$O (5:1) was added cesium carbonate (0.938 g, 2.87 mmol, 3 eq) and the nitrogen gas was passed through for 10 min. Then tetrakistriphenylphosphine palladium (0.111 g, 0.095 mmol, 0.1 eq) was added to the reaction mixture and nitrogen gas was again passed through the mixture for 15 min. The above reaction mixture was heated in microwave for one hour at 90° C. About 100 ml of water is added to the reaction mixture and extracted with EtOAc. The organic layer was further washed twice with water and dried over sodium sulphate, concentrated to get the product. The product obtained was further purified by column chromatography using 60-120 silica gel and 25% EtOAc/Hexane as eluent. Yield: 0.320 g (76%). $^1$H NMR (400 MHz, DMSO-d$_6$): δ 2.19 (s, 3H), 2.81-2.82 (d, 3H, J=4.64 Hz), 3.85 (s, 3H), 7.31-7.34 (d, 2H, J=8.28 Hz), 7.39-7.44 (t, 2H, J=8.90 Hz), 7.54 (s, 1H), 7.79-7.85 (m, 2H), 7.97-8.01 (m, 2H), 8.45-8.46 (d, 1H, J=4.32 Hz) LCMS: (ES+) m/z=436 (M+H). Method: Column: Chromolith SpeedRod C18 (4.6×30) mm, 5 micron Mphase A: 10% MeOH-90% H2O-0.1% TFA Mphase B: 90% MeOH-10% H2O-0.1% TFA
Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 2.034
Wavelength: 220 nm

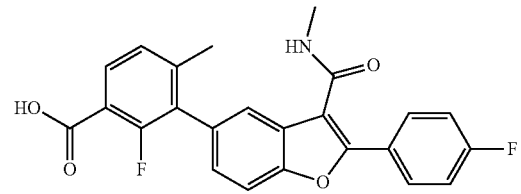

2-fluoro-3-(2-(4-fluorophenyl)-3-(methylcarbamoyl)benzofuran-5-yl)-4-methylbenzoic acid. To a mixture of methyl 3-fluoro-5-(2-(4-fluorophenyl)-3-(methylcarbamoyl)benzofuran-5-yl)-4-methylbenzoate (0.320 g, 1 eq) in a 1:1 mixture of MeOH/THF, 1 M solution of NaOH (0.088 g, 2.20 mmol, 3.0 eq) was added and heated to 90° C. for 3 h. The mixture was cooled to ambient temperature and then in an ice-water bath. It was acidified with 1.5 N HCl and then volatiles were evaporated. The mixture with white precipitate was diluted with water and filtered to get the product. It was further washed with water and dried in vacuum. Yield: 0.220 g (71%). $^1$H NMR (400 MHz, DMSO-d$_6$): δ 2.17 (s, 3H), 2.81-2.82 (d, 3H, J=4.60 Hz), 7.28-7.33 (m, 2H, J=4.33 Hz), 7.39-7.44 (m, 2H, J=8.88 Hz), 7.53 (d, 1H, J=1.24 Hz), 7.78-7.83 (m, 2H, J=5.93 Hz), 7.97-8.01 (m, 2H), 8.45-8.47 (d, 1H, J=4.60 Hz), 13.13 (s, 1H). LCMS: (ES+) m/z=422.0 (M+H). Method: Column: Chromolith SpeedRod C18 (4.6×30) mm, 5 micron Mphase A: 10% MeOH-90% H2O-0.1% TFA Mphase B: 90% MeOH-10% H2O-0.1% TFA Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 1.961
Wavelength: 220 nm

5-(2-fluoro-6-methyl-3-(1-(pyridin-2-yl)cyclopropylcarbamoyl)phenyl)-2-(4-fluorophenyl)-N-methylbenzofuran-3-carboxamide. To the solution of 2-fluoro-3-(2-(4-fluorophenyl)-3-(methylcarbamoyl)benzofuran-5-yl)-4-methylbenzoic acid (0.1 g, 0.273 mmol, 1.0 eq) in DMF (5.0 ml), 1-(pyridin-2-yl)cyclopropanamine (0.038 g, 0.285 mmol, 1.2 eq), TBTU (0.130 g, 0.403 mmol, 1.7 eq) and DIPEA (0.154 g, 1.187 mmol, 5.0 eq) were added. Mixture was stirred at ambient temperature for 12 h under nitrogen atmosphere. DMF was concentrated and to this residue water was added and extracted with ethyl acetate. The combined organic layer was dried over sodium sulphate and ethyl acetate was evaporated. The crude was purified by preparative TLC eluted with hexane/EtOAc (5:5). The product was further purified by recrystallization with DCM and hexane. Yield: 0.045 g (39%). $^1$H NMR (400 MHz, DMSO-$d_6$): δ 1.23-1.25 (m, 2H), 1.51-1.54 (m, 2H), 2.18 (s, 3H), 2.81-2.82 (d, 3H, J=4.0 Hz), 7.13-7.15 (t, 1H, J=3.78 Hz), 7.27-7.29 (d, 1H, J=8.00 Hz), 7.33-7.35 (d, 1H, J=4.26 Hz), 7.39-7.44 (m, 3H, J=5.26 Hz), 7.56-7.60 (t, 2H, J=7.56 Hz), 7.68-7.72 (m, 1H), 7.80-7.82 (d, 1H, J=8.44 Hz), 7.96-8.00 (m, 2H), 8.43-8.49 (m, 2H), 9.12 (s, 1H). LCMS: (ES+) m/z=538.0 (M+H). Method: Column: Chromolith SpeedRod C18 (4.6×30) mm, 5 micron Mphase A: 10% MeOH-90% H2O-0.1% TFA Mphase B: 90% MeOH-10% H2O-0.1% TFA Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 1.813
Wavelength: 220 nm
HPLC Method:
COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 3 | 10 |
| 14 | 100 |
| 17 | 100 |

Wavelength: 254 nm, RT min: 10.566 (Purity: 98.287%)
Wavelength: 220 nm, RT min: 10.041 (Purity: 97.3%)
COLUMN: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 10.041 (Purity: 98.3%)
Wavelength: 220 nm, RT min: 10.041 (Purity: 97.3%)

2-methyloxazole-4-carbonitrile. Ethylacetimidate hydrochloride (25 g, 340 mmol, 1 eq) and aminoacetonitrile (38.5 g, 410 mmol, 1.2 eq) were suspended in dichloromethane (300 ml) at room temperature. Triethylamine (148.4 ml, 380 mmol, 1.1 eq) was added dropwise over 1 h. After the completion of addition, the reaction mixture was cooled to 0° C., water (125 ml) was added, organic layer was separated and the aq. layer was extracted with 50 ml of dichloromethane. The combined dichloromethane mixture was concentrated to 50 ml. Diethyl ether (500 ml) was added to this solution, which was then cooled to 0° C. To the above solution ethylformate (13.93 g, 190 mmol, 0.55 eq) was added followed by the addition of Potassium tert-butoxide (20.6 g, 172 mmol, 0.51 eq). The reaction was allowed to stir at room temperature for 90 minutes and at 50° C. for 90 minutes. Chlorotrimethylsilane (56.5 g, 520 mmol, 1.5 eq) was added at reflux condition and the reaction was stirred at 50° C. for 5 h. Later water was added and the product was extracted with dichloromethane and the organic layer was washed with water and purified by column chromatography yielding product as colorless oil. Yield: 6 g (16%) overall yield. $^1$HNMR (400 MHz, DMSO-$d_6$): δ 2.5 (s, 3H), 8.07 (s, 1H).

1-(2-methyloxazol-4-yl)cyclopropanamine 2-Methyloxazole-4-carbonitrile (5 g, 46.1 mmol, 1 eq) was dissolved in dry THF at room temperature, and to which titanium(IV) isopropoxide (16 ml, 655 mmol, 1.2 eq) was added dropwise over a period of 15 minutes. The resulting mixture was stirred for 10 min and ethyl magnesium bromide (85 ml, 17 volumes) was added slowly dropwise at ambient temperature and the reaction was stirred for 1 h. Later BF$_3$.etherate (16.7 ml, 115 mmol, 2.5 eq) was added slowly at ambient temperature and the above solution was stirred at ambient temperature for 3 h. Finally water was added and the pH was brought to 10 using 10% sodium hydroxide solution. The reaction mixture was extracted with dichloromethane, concentrated and purified by combiflash chromotagraphy. Yield: 1.5 g (20%). $^1$H NMR (400 MHz, DMSO-$d_6$): δ 0.93 (m, 2H), 1.00 (m, 2H), 1.98 (br s, 2H), 2.39 (s, 3H), 7.33 (s, 1H). LCMS: (ES+) m/z=138.9 (M+H).

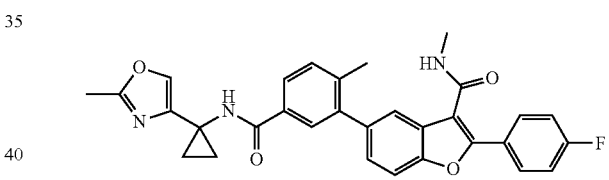

2-(4-fluorophenyl)-N-methyl-5-(2-methyl-5-(1-(1-methyl-1H-pyrazol-3-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.15 g, 0.37 mmol, 1 eq), 1-(2-methyloxazol-4-yl)cyclopropanamine (0.066 g, 0.47, 1.2 eq), HOBT (0.092 g, 0.68 mmol, 1.7 eq), EDC.HCl (0.14 g, 0.73 mmol, 1.8 eq) in DCM at ambient temperature under nitrogen was added Diisopropylethylamine (0.26 g, 2.2 mmol, 5.0 eq). The clear mixture was stirred at ambient temperature for 12 h. The mixture was concentrated, diluted with water and extracted with EtOAc. The organic layer is further washed with water, dried over sodium sulphate and concentrated. The product obtained was further purified by column chromatography (neutral alumina) using 0.5% Methanol/DCM as an eluent followed by preparative HPLC. Yield: 0.02 g (20%). $^1$H NMR (400 MHz, DMSO-$d_6$): δ 1.10-1.13 (m, 2H), 1.21-1.24 (m, 2H), 2.29 (s, 3H), 2.33 (s, 3H), 2.81-2.82 (d, 3H, J=4.6 Hz), 7.38-7.43 (m, 4H), 7.57 (s, 1H), 7.61 (s, 1H), 7.75-7.71 (d, 1H, J=8.4 Hz), 7.80-7.81 (s and m, 2H), 7.97-8.01 (m, 2H), 8.47-8.48 (d, 1H, J=4.76 Hz), 9.1 (s, 1H). LCMS: (ES+) m/z=524.2 (M+H). LCMS Method: Chromolith SpeedROD C18 (4.6×3.0 mm-5.0 μm) Mphase A: 2% MeCN-98% H$_2$O-10 mM NH$_4$COOH Mphase B: 98% MeCN-2% H$_2$O-10 mM NH$_4$COOH Flow: 1 mL/Min

601

| Time | % B |
|---|---|
| 0.0 | 0.0 |
| 2.0 | 100.0 |
| 3.0 | 100.0 |

RT min: 2.018, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 4 | 10 |
| 12 | 100 |
| 15 | 100 |

Wavelength: 254 nm, RT min: 10.757
Wavelength: 220 nm, RT min: 10.757
Purity: 96.7%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.993
Wavelength: 220 nm, RT min: 9.993
Purity: 96.7%

1-(pyrimidin-5-yl)cyclopropanamine. 5-Cyano pyrimidine (5 g, 47.6 mmol, 1 eq) was taken in a Dry THF under Argon atmosphere, then Titanium isopropoxide (17 ml, 57.1 mmol, 1.2 eq) was added slowly at ambient temperature and the resulting mass was stirred for 15 mins. To the above stirred solution was added Ethyl magnesium bromide (1 M solution in THF, 107 ml, 809.3 mmol, 2.5 eq) slowly via syringe at ambient temperature. (During the addition of EtMgBr reaction mass turned black). Then the reaction mass was stirred for an hour, $BF_3.EtO$ (16.7 ml, 119.0 mmol, 2.5 eq) was added slowly through syringe at 0° C. Then the reaction was allowed to attain ambient temperature and the stirring was continued for another one hour. Finally the reaction was quenched by adding 50 ml of water and the reaction mass was passed through Celite and the bed was washed with water and Ethyl acetate. The filtrate was basified with 10% NaOH solution (pH=9) and then extracted with DCM and washed with brine solution. The required product was purified by silica gel (60-120) column chromatography using DCM/methanol as the eluent. Yield: 0.1 g (5%) $^1$H NMR (400 MHz, DMSO-$d_6$): 1.04-1.08 (q, 2H, J=3.96 Hz), 1.18-1.25 (q, 2H, J=3.96 Hz), 8.26 (d, 2H), 9.05 (s, 1H). LCMS: (ES+) m/z=136 (M+H).

602

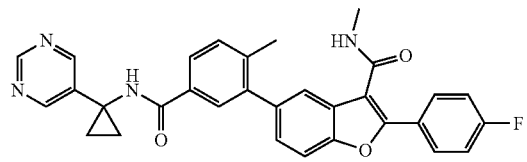

2-(4-fluorophenyl)-N-methyl-5-(2-methyl-5-(1-(pyrimidin-5-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.1 g, 0.25 mmol, 1 eq), 1-(pyrimidin-5-yl)cyclopropanamine (0.041 g, 0.3 mmol, 1.2 eq) (60% purity), HOBT (0.057 g, 0.42 mmol, 1.7 eq), EDC.HCl (0086 g, 0.44 mmol, 1.8 eq) in DCM at ambient temperature under nitrogen was added Diisopropylethylamine (0.162 g, 1.2 mmol, 5.0 eq). The clear mixture was stirred at ambient temperature for overnight. The mixture was concentrated, diluted with water and extracted with EtOAc. The organic layer is further washed with water, dried over sodium sulphate and concentrated. The product obtained was further purified by column chromatography (neutral alumina) using 0.5% Methanol/DCM and finally it was purified by preparative HPLC. Yield: 0.02 g (20%). $^1$H NMR (400 MHz, DMSO-$d_6$): δ 1.34-1.35 (m, 2H), 1.41-1.42 (m, 2H), 2.29 (s, 3H), 2.81-2.82 (d, 3H, J=4.56 Hz), 738-7.45 (m, 4H), 7.58 (d, 1H, J=0.96 Hz), 7.75 (d, 1H, J=8.4 Hz), 7.81 (s, 1H), 7.83 (m, 1H), 7.98-8.01 (m, 2H), 8.46-8.47 (d, 1H, J=4.6 Hz), 8.64 (s, 2H), 9.01 (s, 1H), 9.31 (s, 1H). LCMS: (ES+) m/z=521.2 (M+H). LCMS Method: Column-Ascentis Express C18 (5×2.1 mm-2.7 µm) Mphase A: 2% ACN-98% $H_2O$-10 mM $NH_4COOH$ Mphase B: 98% ACN-2% $H_2O$-10 mM $NH_4COOH$ Flow: 1 mL/Min

| Time | % A | % B |
|---|---|---|
| 0.0 | 100.0 | 0 |
| 1.5 | 0.0 | 100.0 |
| 3.2 | 0.0 | 100.0 |
| 3.6 | 100.0 | 0.0 |

RT min: 1.825, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 10.061
Wavelength: 220 nm, RT min: 10.061
Purity: 92.3%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.542
Wavelength: 220 nm, RT min: 9.542
Purity: 92.5%

1-(1-methyl-1H-pyrazol-3-yl)cyclopropanamine. Ethyl magnesium bromide (2.5 mol, 1 M in ether) was added at −78° C. to a solution of a 1-methyl-1H-pyrazole-3-carbonitrile (0.5 g, 1 mmol) and Ti(Oi-Pr)$_4$ (1.1 mmol) in Et$_2$O (5 mL). The yellow solution was stirred for 10 min. After the solution was warmed to ambient temperature (1 h), BF$_3$OEt$_2$ (2 mmol) was added. After the mixture was stirred for 1 h, 1 N HCl and ether were added. NaOH (10%) was added to the resulting two clear phases and the mixture was extracted with ether. The combined ether layers were dried (Na$_2$SO$_4$), filtered, and concentrated under reduced pressure. The residue was purified by flash chromatography on silica gel (Et$_2$O). $^1$H NMR (400 MHz, CDCl$_3$): δ 0.94-1.05 (m, 4H), 2.32 (s, 2H), 3.83 (s, 3H), 5.92 (d, 1H), 7.23-7.24 (d, 1H). LCMS: (ES+) m/z observed 137.7.

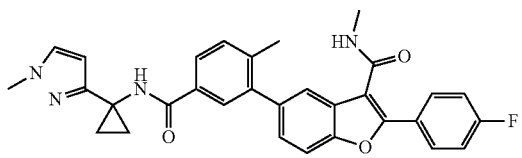

2-(4-fluorophenyl)-N-methyl-5-(2-methyl-5-(1-(1-methyl-1H-pyrazol-3-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.15 g, 0.37 mmol, 1 eq), 1-(1-methyl-1H-pyrazol-3-yl)cyclopropanamine (0.061 g, 0.44 mmol, 1.2 eq), HOBT (0.057 g, 0.42 mmol, 1.7 eq), EDC.HCl (0.086 g, 0.44 mmol, 1.8 eq) in DCM at ambient temperature under nitrogen was added diisopropylethylamine (0.16 g, 1.2 mmol, 5.0 eq). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and finally by preparative HPLC. Yield: 0.06 g (40%) $^1$H NMR (400 MHz, DMSO-d$_6$): δ 1.12-1.16 (m, 2H), 1.20-1.23 (m, 2H), 2.29 (s, 3H), 2.82-2.83 (d, 3H, J=4.64 Hz), 3.37 (s, 3H), 5.9-6.0 (d, 1H, J=2.12 Hz), 7.39-7.48 (m, 5H), 7.58 (d, 1H, J=1.68 Hz), 7.75-7.77 (d, 1H, J=9.7 Hz), 7.81-7.83 (t, 2H, J=2.87 Hz), 7.98-8.46 (m, 2H), 8.47-8.48 (d, 1H, J=4.52 Hz), 9.14 (s, 1H). LCMS: (ES+) m/z=523.2 (M+H). LCMS Method: Column-Ascentis Express C18 (5×2.1 mm-2.7 μm) Mphase A: 2% MeCN-98% H$_2$O-10 mM NH$_4$COOH Mphase B: 98% MeCN-2% H$_2$O-10 mM NH$_4$COOH Flow: 1 mL/Min

| Time | % A | % B |
|---|---|---|
| 0.0 | 100.0 | 0.0 |
| 1.0 | 70.0 | 30.0 |
| 2.5 | 0.0 | 100.0 |
| 4.0 | 0.0 | 100.0 |

RT min: 1.882, wavelength: 220 nm
HPLC Method Info: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.999
Wavelength: 220 nm, RT min: 16.999
Purity: 96%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 15.556
Wavelength: 220 nm, RT min: 15.556
Purity: 97%

Methyl 2-methoxy-4-methylbenzoate. Methyl 2-methoxy-4-methylbenzoic acid (1.5 g, 9.0 mmol, 1 eq) was dissolved in DMF, methyl iodide (0.86 ml, 13.5 mmol, 1.5 eq) was added to it followed by the addition of potassium carbonate (3.11 g, 22.5 mmol, 2.5 eq). The above mixture was stirred at room temperature for 12 h. Finally, the reaction mixture was passed through celite. The filtrate was evaporated and water was added and the product was extracted with ethyl acetate. The organic layer was washed with water and concentrated. Yield: 1.6 g (98%). $^1$HNMR (400 MHz, CDCl$_3$): δ 2.31 (s, 3H), 3.86 (s, 3H), 3.89 (s, 3H), 6.77 (s, 1H), 6.79 (d, 1H), 7.14 (d, 1H).

Methyl 5-iodo-2-methoxy-4-methylbenzoate. Methyl 2-methoxy-4-methylbenzoate (1.5 g, 8.32 mmol, 1 eq) was dissolved in methanol. To this solution was added dropwise iodine monochloride (6.75 g, 41.6 mmol, 5 eq) in methanol at room temperature. The reaction mixture was heated at 50° C. for 15 h. Finally, methanol was concentrated, diluted with water and extracted with ethyl acetate. The organic layer was washed with 0.1 N HCl (50 ml), water (100 ml) and brine solution (100 ml). The product was purified by column chromatography using 60-120 silica gel and using 5% ethyl acetate/hexane as eluent. Yield: 1.7 g (80%). $^1$HNMR (400 MHz, CDCl$_3$): δ 2.44 (s, 3H), 3.86 (s, 3H), 3.88 (s, 3H), 6.86 (s, 1H), 8.20 (s, 1H). LCMS: (ES+) m/z=307.0 (M+H).

Methyl 2-methoxy-4-methyl-5-(4,4,5,5-tetramethyl-1,3,2-dioxaborolan-2-yl)benzoate. Methyl 5-iodo-2-methoxy-4- methylbenzoate (1.5 g, 4.9 mmol, 1 eq), Bispinacolatodiboron (1.49 g, 5.8 mmol, 1.2 eq), potassium acetate (1.44 g, 14.7 mmol, 3 eq) and Pd(dppf)Cl₂ (0.4 g, 0.49 mmol, 0.1 eq) were dissolved in DMF. Nitrogen gas was passed through the mixture for 10 minutes and the mixture was stirred at 90° C. for 14 hours. Later the solution was passed through celite. The filtrate was evaporated and diluted with water and extracted with ethyl acetate and purified by column chromatography using 60-120 silica gel and using 20% ethyl acetate/hexane as eluent. Yield: 1.2 g (80%). ¹HNMR (400 MHz, CDCl₃): δ 1.33 (s, 12H), 2.56 (s, 3H), 3.86 (s, 3H), 3.91 (s, 3H), 6.75 (s, 1H), 8.21 (s, 1H). LCMS: (ES+) m/z=307.2 (M+H).

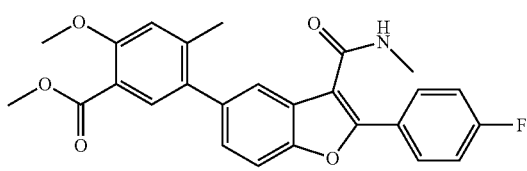

Methyl 5-(2-(4-fluorophenyl)-3-(methylcarbamoyl)benzofuran-5-yl)-2-methoxy-4-methylbenzoate. Methyl-2-methoxy-4-methyl-5-(4,4,5,5-tetramethyl-1,3,2-dioxaborolan-2-yl)benzoate (1.2 g, 3.92 mmol, 1 eq), 2-(4-fluorophenyl)-3-(methylcarbamoyl)benzofuran-5-yltrifluoromethanesulfonate (1.6 g, 3.92 mmol, 1 eq), Cesium carbonate (3.8 g, 11.7 mmol, 3 eq) and Tetrakis triphenylphosphinepalladium (0.13 g, 0.11 mmol, 0.03 eq) were dissolved in 1,4-dioxane/water and the above solution was stirred at 90° C. for 10 h. Then the reaction mixture was diluted with water and product was extracted with ethyl acetate and purified by combiflash chromatography using 40% ethyl acetate/hexane as eluent. Yield: 0.95 g (55%). ¹HNMR (400 MHz, DMSO-d₆): δ 2.3 (s, 3H), 2.82 (d, J=4.6 Hz, 3H), 3.78 (s, 3H), 3.88 (s, 3H), 7.15 (s, 1H), 7.51 (s, 1H), 7.64 (m, 2H), 7.65 (m, 2H), 7.74 (d, 1H, J=8.48 Hz), 8.00-8.01 (m, 2H), 8.48 (d, 1H). LCMS: (ES+) m/z=448 (M+H).

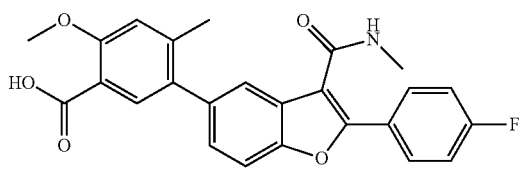

5-(2-(4-fluorophenyl)-3-(methylcarbamoyl)benzofuran-5-yl)-2-methoxy-4-methylbenzoic acid. Methyl 5-(2-(4-fluorophenyl)-3-(methylcarbamoyl)benzofuran-5-yl)-2-methoxy-4-methylbenzoate (0.9 g, 2 mmol, 1 eq) and sodium hydroxide (0.4 g, 10 mmol, 5 eq) were dissolved in methanol/water (20/5 ml) and the reaction was stirred at 50° C. for 10 h. Then the reaction mixture was concentrated and diluted with water and the pH of the solution was brought to 3 by using Conc HCl. The solid obtained was filtered and dried overnight. Yield: 0.72 g (82%). ¹H NMR (400 MHz, DMSO-d₆): δ 2.29 (s, 3H), 2.87 (d, 3H), 3.87 (s, 3H), 7.09 (s, 1H), 7.40-7.60 (m, 3H), 7.57 (m, 2H), 7.65 (d, 1H, J=8.74 Hz), 7.98-8.01 (m, 2H), 8.46 (q, 1H, J=4.40 Hz), 12.5 (br s, 1H). LCMS: (ES+) m/z=434 (M+H) Method: Mphase A: water Mphase B: 0.1% acetone in water Flow-2 mL/Min

| Time | % B |
|---|---|
| 0-20 | 100 |

RT min: 1.741
Wavelength: 220 nm
Additional LCMS were performed by using Shimadzu-VP instrument with UV detection at 220 nm and Waters Micromass. HPLC method: Solvent A=10% MeOH 90% H₂O 0.1% TFA, Solvent B=90% MeOH 10% H₂O 0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=434.10, HPLC R$_f$=1.653 min.

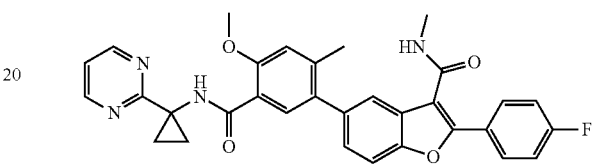

2-(4-fluorophenyl)-5-(4-methoxy-2-methyl-5-(1-(pyrimidin-2-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.2 g, 0.46 mmol, 1 eq), 1-(pyrimidin-2-yl)cyclopropanamine (0.074 g, 0.55 mmol, 1.2 eq), HOBT (0.105 g, 0.77 mmol, 1.7 eq), EDC.HCl (0.0.158 g, 0.82 mmol, 1.8 eq), in DCM at ambient temperature and under nitrogen atmosphere was added diisopropylethylamine (0.297 g, 2.2 mmol, 5.0 eq). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and preparative HPLC. Yield: 0.055 g (45%). ¹HNMR (400 MHz, DMSO-d₆): δ 1.43-1.44 (m, 2H), 1.59-1.62 (m, 2H), 2.31 (s, 3H), 2.81-2.82 (d, 3H, J=4.56 Hz), 4.01 (s, 3H), 7.17 (s, 1H), 7.26-7.29 (t, 1H, J=4.8 Hz), 7.33-7.36 (dd, 1H, J=8.4, 4 Hz), 7.38-7.43 (t, 2H, J=8.8 Hz), 7.50-7.51 (d, 1H, J=1.6 Hz), 7.72-7.76 (m, 2H), 7.97-8.01 (m, 2H), 8.48-8.49 (d, 1H, J=4.4 Hz), 8.7 (d, 2H, J=4.8 Hz), 8.87 (s, 1H). LCMS: (ES+) m/z=551.2 (M+H) Column-Ascentis Express C18 (5×2.1 mm-2.7 µm) Mphase A: 2% MeCN-98% H₂O-10 mM NH₄COOH Mphase B: 98% MeCN-2% H₂O-10 mM NH₄COOH Flow-1 mL/Min

| Time | % A | % B |
|---|---|---|
| 0.0 | 100.0 | 0.0 |
| 1.0 | 70.0 | 30.0 |
| 2.5 | 0.0 | 100.0 |
| 4.0 | 0.0 | 100.0 |

RT min: 1.946, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 25 | 100 |
| 30 | 100 |

Wavelength: 254 nm, RT min: 18.209
Wavelength: 220 nm, RT min: 18.209
Purity: 99.4%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 25 | 100 |
| 30 | 100 |

Wavelength: 254 nm, RT min: 16.549
Wavelength: 220 nm, RT min: 16.549
Purity: 99.5%

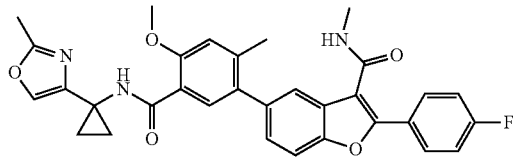

2-(4-fluorophenyl)-5-(4-methoxy-2-methyl-5-(1-(2-methyloxazol-4-yl)cyclopropylcarbamoyl)phenyl)-N-methylbenzofuran-3-carboxamide. 5-(2-(4-Fluorophenyl)-3-(methylcarbamoyl)benzofuran-5-yl)-2-methoxy-4-methylbenzoic acid (0.15 g, 0.34 mmol, 1 eq), 1-(2-methyloxazol-4-yl)cyclopropanamine (0.047 g, 0.34 mmol, 1 eq), EDCI.HCl (0.076 g, 0.4 mmol, 1.2 eq), HOBT (0.054 g, 0.4 mmol, 2 eq) and TEA (0.14 ml, 1.02 mmol, 3 eq) were dissolved in dichloromethane and the reaction was stirred at room temperature for 14 h. The reaction was diluted with water and the product was extracted with dichloromethane and purified by preparative HPLC yielding the desired product. Yield: 47 mg (25%) $^1$H NMR (400 MHz, DMSO-d$_6$): δ 1.12-1.15 (m, 2H), 1.21-1.24 (m, 2H), 2.29 (s, 3H), 2.34 (s, 3H), 2.81-2.82 (d, 3H, J=4.60 Hz), 3.95 (s, 3H), 7.12 (s, 1H), 7.31-7.32 (m, 1H), 7.34-7.40 (t, 2H, J=3.21 Hz), 7.56 (s, 1H), 7.61 (s, 1H), 7.71 (s, 1H), 7.73 (s, 1H), 7.97-8.01 (m, 2H), 8.46-8.48 (m, 1H), 8.67 (s, 1H). LCMS: (ES+) m/z=554.2 (M+H). : Column-Ascentis Express C18 (5×2.1 mm-2.7 μm) Mphase A: 2% ACN-98% H$_2$O-10 mM NH$_4$COOH Mphase B: 98% ACN-2% H$_2$O-10 mM NH$_4$COOH
Flow: 1 mL/Min

| Time | % A | % B |
| --- | --- | --- |
| 0.0 | 100.0 | 0 |
| 1.0 | 70.0 | 30.0 |
| 2.5 | 0.0 | 100.0 |
| 4.0 | 0.0 | 100.0 |

RT min: 1.964, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 12 | 100 |
| 15 | 100 |

Wavelength: 254 nm, RT min: 11.403
Wavelength: 220 nm, RT min: 11.402
Purity: 98.8%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 12 | 100 |
| 15 | 100 |

Wavelength: 254 nm, RT min: 10.588
Wavelength: 220 nm, RT min: 10.588
Purity: 98.96%

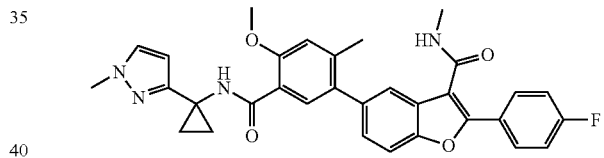

2-(4-fluorophenyl)-5-(4-methoxy-2-methyl-5-(1-(1-methyl-1H-pyrazol-3-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.15 g, 0.35 mmol, 1 eq), 1-(1-methyl-1H-pyrazol-3-yl)cyclopropanamine (0.058 g, 0.42 mmol, 1.2 eq), HOBT (0.08 g, 0.069 mmol, 1.7 eq), EDC.HCl (0.073 g, 0.014 mmol, 1.8 eq), in DCM at ambient temperature under nitrogen was added Diisopropylethylamine (0.297 g, 2.2 mmol, 5.0 eq). The clear mixture was stirred at ambient temperature for 12 h. The mixture was concentrated, diluted with water and extracted with EtOAc. The organic layer is further washed with water, dried over sodium sulphate and concentrated. The product obtained was further purified by column chromatography (neutral alumina) using 0.5% Methanol/DCM and the final purification was done by preparative HPLC. Yield: 0.06 g (45%) $^1$H NMR (400 MHz, DMSO-d$_6$): δ 1.18-1.20 (m, 4H), 2.29 (s, 3H), 2.81-2.82 (d, 3H, J=4.64 Hz), 3.73 (s, 3H), 3.96 (s, 3H), 6.06-6.07 (d, 1H, J=2.4 Hz), 7.12 (s, 1H), 7.32-7.34 (dd, 1H, J=8.4, 1.6 Hz), 7.38.-7.42 (t, 2H, J=8.8 Hz), 7.48.-7.49 (d, 2H, J=2.34 Hz), 7.59 (s, 1H), 7.71-7.73 (d, 1H, J=8.4 Hz), 7.97-7.97-8.01 (m, 2H), 8.47-8.48 (d, 1H, J=4.8 Hz), 8.69 (s, 1H). LCMS: (ES+) m/z=553.2 (M+H). : Column-Ascentis Express C18 (5×2.1 mm-2.7 μm) Mphase A: 2% MeCN-98%

H₂O-10 mM NH₄COOH Mphase B: 98% MeCN-2% H₂O-10 mM NH₄COOH Flow-1 mL/Min

| Time | % A | % B |
|------|------|------|
| 0.0 | 100.0 | 0 |
| 1.5 | 0.0 | 100.0 |
| 3.2 | 0.0 | 100.0 |

RT min: 1.937, wavelength: 220 nm

HPLC Method: SUNFIRE C18 (4.6×150) mm, 3.5 micron

Buffer: 0.05% TFA in water pH 2.5

Mobile Phase A: Buffer:MeCN (95:5)

Mobile Phase B: MeCN:Buffer (95:5)

FLOW: 1 ml/min

| Time | B % |
|------|------|
| 0 | 10 |
| 12 | 100 |
| 15 | 100 |

Wavelength: 254 nm, RT min: 11.289

Wavelength: 220 nm, RT min: 11.289

Purity: 99.3%

: XBridge phenyl (4.6×150) mm, 3.5 micron

Buffer: 0.05% TFA in water pH 2.5

Mobile Phase A: Buffer:MeCN (95:5)

Mobile Phase B: MeCN:Buffer (95:5)

FLOW: 1 ml/min

| Time | B % |
|------|------|
| 0 | 10 |
| 12 | 100 |
| 15 | 100 |

Wavelength: 254 nm, RT min: 10.548

Wavelength: 220 nm, RT min: 10.548

Purity: 99.5%

1-(1-methyl-1H-imidazol-4-yl)cyclopropanamine 1-Methyl-1H-imidazole-4-carbonitrile (0.5 g, 4.6 mmol, 1 eq) was dissolved in THF, and to which titanium isopropoxide (1.6 g, 5.6 mmol, 2.5 eq) was added dropwise over 15 minutes. The mixture was stirred for 15 minutes at room temperature, and then ethyl magnesium bromide (1.6 g, 11.5 mmol, 2.5 eq) was added at room temperature over 15 minutes. The reaction mixture was stirred for 1 h. BF₃ etherate (0.8 g, 5.6 mmol, 2.2 eq) was added and the mixture stirred at room temperature for 1 h. 1 N NaOH solution was added to the mixture to bring the pH to 9-10. Reaction mass was filtered through celite and the filtrate washed with DCM. The organic mixture was concentrated and the residue purified by flash chromatography on silica gel using 10% chloroform/methanol. Yield: 0.6 g ¹H NMR (400 MHz, CDCl₃): δ 0.97 (t, J=3.4 Hz, 2H), 1.00 (t, J=3.4 Hz, 2H), 3.63 (s, 3H), 7.28 (s, 1H), 7.31 (s, 1H). LCMS: (ES+) m/z=138.2 (M+H).

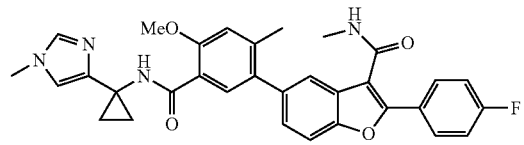

2-(4-fluorophenyl)-5-(4-methoxy-2-methyl-5-(1-(1-methyl-1H-imidazol-4-yl)cyclopropylcarbamoyl)phenyl)-N-methylbenzofuran-3-carboxamide. 5-(2-(4-Fluorophenyl)-3-(methylcarbamoyl)benzofuran-5-yl)-2-methoxy-4-methylbenzoic acid (0.2 g, 1 eq), 1-(1-methyl-1H-imidazol-4-yl)cyclopropanamine (0.07 g, 1.1 eq), EDCI.HCl (0.13 g, 1.5 eq), HOBT (0.094 g, 1.5 eq) and TEA (0.19 ml, 3 eq) were dissolved in dichloromethane and the above solution was stirred at room temperature for 18 h. Later water was added and organic layer was separated. The organic layer was washed with water and the crude product was purified by Prep. HPLC. Yield: 24.69 mg (10%) ¹HNMR (400 MHz, CDCl₃): δ 1.39 (s, 4H), 2.30 (s, 3H), 2.99-3.01 (d, J=4.6 Hz, 3H), 3.81 (s, 3H), 4.04 (s, 3H), 5.90 (s, 1H), 6.87 (s, 1H), 7.16-7.25 (m, 3H), 7.24 (s, 1H), 7.51 (d, J=8.4 Hz, 1H), 7.65 (s, 1H), 7.98-7.99 (m, 3H), 8.29 (s, 1H), 8.95 (s, 1H). LCMS: (ES+) m/z=553.2 (M+H). Method: Column-Ascentis Express C18 (5×2.1 mm-2.7 µm) Mphase A: 2% ACN-98% H₂O-10 mM NH₄COOH Mphase B: 98% ACN-2% H₂O-10 mM NH₄COOH Flow: 1 mL/Min

| Time | % A | % B |
|------|------|------|
| 0.0 | 100.0 | 0 |
| 1.5 | 0.0 | 100.0 |
| 3.2 | 0.0 | 100.0 |

RT min: 1.854

Wavelength: 220 nm

HPLC COLUMN: SUNFIRE C18 (4.6×150) mm, 3.5 micron

Buffer: 0.05% TFA in water pH 2.5

Mobile Phase A: Buffer:MeCN (95:5)

Mobile Phase B: MeCN:Buffer (95:5)

FLOW: 1 ml/min

| Time | B % |
|------|------|
| 0 | 10 |
| 25 | 100 |
| 30 | 100 |

Wavelength: 254 nm, RT min: 11.685

Wavelength: 220 nm, RT min: 11.685

Purity: 99.1%

HPLC COLUMN: XBridge phenyl (4.6×150) mm, 3.5 micron

Buffer: 0.05% TFA in water pH 2.5

Mobile Phase A: Buffer:MeCN (95:5)

Mobile Phase B: 0.05% TFA in MeCN:Buffer (95:5)

FLOW: 1 ml/min

| Time | B % |
| --- | --- |
| 0 | 10 |
| 25 | 100 |
| 30 | 100 |

Wavelength: 254 nm, RT min: 13.396
Wavelength: 220 nm, RT min: 13.396
Purity: 96.5%
Preparative HPLC Method:
Column: Symmetry C18 (19×250×10μ)
Mobile Phase: 0.1% TFA (A), MeCN (B)

| Gradient: | | | |
| --- | --- | --- | --- |
| Time | Flow | A | B |
| 0 | 15 ml/min | 95 | 5 |
| 10 | 15 ml/min | 55 | 45 |

RT: 10.5 min 1-(5-methylisoxazol-3-yl)cyclopropanamine. 5-Methylisoxazole-3-carbonitrile (1.0 g, 1 mmol) was dissolved in THF. Ti (Oi-Pr) 4 (1.2 mmol) was added dropwise over a period of 5-10 min and the reaction mixture was stirred at r.t for 15 min. It was then cooled down to 0° C. and EtMgBr (2.5 mmol) was added dropwise over a period of 10-15 min. It was stirred at 0° C. for 15 min. and then stirred at rt for 1 hr. The mixture was cooled again to 0° C. and $BF_3OEt_2$ (2 mmol) was added dropwise over a period of 5-10 min at 0° C. After the mixture was stirred for 10 min at 0° C. and 1 hr at rt, 1 N NaOH was added at 0° C. DCM was added to the reaction mixture which was then stirred for 5-10 min. This alkaline solution was filtered through celite and washed with DCM. The organic layer was concentrated and residue purified by flash chromatography on silica gel using 10% chloroform/methanol. Yield: 0.6 g $^1$H NMR (400 MHz, $CDCl_3$): δ 0.96-1.05 (m, 4H), 2.36 (s, 3H), 5.59 (s, 1H). LCMS: (ES+) m/z observed 138.7.

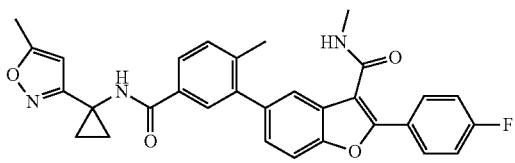

2-(4-fluorophenyl)-N-methyl-5-(2-methyl-5-(1-(5-methylisoxazol-3-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.15 g, 0.37 mmol, 1 eq), amine (0.06 g, 0.43 mmol, 1.2 eq), HOBT (0.084 g, 0.62 mmol, 1.7 eq), EDC.HCl (0.127 g, 0.087 mmol, 1.8 eq) in DCM at ambient temperature under nitrogen was added Diisopropylethylamine (0.239 g, 1.8 mmol, 5.0 eq). The clear mixture was stirred at ambient temperature for 12 h. LCMS showed the desired product. The mixture was concentrated, diluted with water and extracted with EtOAc. The organic layer is further washed with water, dried over sodium sulphate, filtered and then concentrated. The product obtained was further purified by column chromatography (neutral alumina) using 0.5% Methanol/DCM and preparative HPLC. Yield: 0.03 g (20%). $^1$H NMR (400 MHz, DMSO-$d_6$): δ 1.24-1.29 (m, 4H), 2.29 (s, 3H), 2.32 (s, 3H), 2.81-2.82 (d, 3H, J=4.6 Hz), 6.05 (s, 1H), 7.38-7.44 (m, 4H), 7.57 (d, 1H, J=1.6 Hz), 7.75-7.82 (m, 3H), 7.97-8.0 (m, 2H), 8.46-8.47 (m, 1H), 9.24 (s, 1H). LCMS: (ES+) m/z=524.2 (M+H). LCMS Method: Column-Ascentis Express C18 (5×2.1 mm-2.7 μm) Mphase A: 2% ACN-98% $H_2O$-10 mM $NH_4COOH$ Mphase B: 98% ACN-2% $H_2O$-10 mM $NH_4COOH$ Flow-1 mL/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.966, wavelength: 220 nm
HPLC Method: Column-ATLANTIS T3 (4.6×150 mm-5.0 μm)
A: Buffer: 20 mM Ammonium acetate in Water
B: MeCN
FLOW: 1 ml/min

| Time | B % |
| --- | --- |
| 20 | 0 |
| 35 | 5 |
| 35 | 30 |
| 100 | 35 |
| 100 | 40 |

Wavelength: 254 nm, RT min: 15.155
Wavelength: 220 nm, RT min: 15.155
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: ACN:Buffer (95:5)
FLOW: 1 ml/min

| Time | B % |
| --- | --- |
| 0 | 10 |
| 12 | 100 |
| 15 | 100 |

Wavelength: 254 nm, RT min: 18.678
Wavelength: 220 nm, RT min: 18.678
Purity: 99.4%
: XBridge phenyl (4.6×150) mm, 3.5 micron
Buffer: 0.05% TFA in water pH 2.5
Mobile Phase A: Buffer:ACN (95:5)
Mobile Phase B: ACN:Buffer (95:5)
FLOW: 1 ml/min

| Time | B % |
| --- | --- |
| 0 | 10 |
| 12 | 100 |
| 15 | 100 |

Wavelength: 254 nm, RT min: 17.135
Wavelength: 220 nm, RT min: 17.135
Purity: 99.5%

5-methylthiazole-2-carbaldehyde. To a solution of BuLi (5 mmol) in ether at −78° C. was added dropwise a solution of 5-methylthiazole (5 mol) in ether at −78° C. for 1.5 hours. A solution of DMF (5 mmol) in ether was added at once and the reaction was allowed to warm to room temperature and stirred overnight. Ice was added to the mixture followed by the slow addition of 4 N HCl. The mixture was extracted with ether. The aq. layer was bought to pH 7.5 with solid $NaHCO_3$ and extracted with ether. The combined ethereal extracts was dried, filtered and concentrated to get crude residue, which was purified by flash chromatography on silica gel using 10% EtOAc/Hexane. Yield: 6 g $^1$H NMR (400 MHz, $CDCl_3$): δ 2.56 (s, 3H), 7.79 (s, 1H), 9.90 (s, 1H). LCMS: (ES+) m/z=128 (M+H).

5-methylthiazole-2-carbaldehyde oxime. To a solution of 5-methylthiazole-2-carbaldehyde (4.8 mmol) in DCM was added pyridine (4.8 mmol) and $HONH_2.HCl$ (4.8 mmol). The reaction mixture was stirred at ambient temperature for 12 hours, then diluted with DCM and extracted with water. The organic extract was dried, filtered and concentrated to obtain crude oxime. Yield: 6 g; LCMS: (ES+) m/z=143 (M+H).

5-methylthiazole-2-carbonitrile. 5-Methylthiazole-2-carbaldehyde oxime (4.2 mmol) was dissolved in DCM and added with CDI (4.3 mmol) portionwise. The reaction mixture and stir at rt overnight, and then added with water. The mixture was extracted with DCM, and the organic layer was dried and concentrated to get the crude residue, which was purified by flash chromatography on silica gel using 10% EtOAc/Hexane. Yield: 3.2 g; 1H NMR (400 MHz, $CDCl_3$): δ 2.59 (s, 3H), 7.71 (s, 1H).

1-(5-methylthiazol-2-yl)cyclopropanamine 5-Methylithiazole-2-carbonitrile (1.0 g, 1 mmol) was dissolved in THF. $Ti(Oi-Pr)_4$ (1.2 mmol) was added dropwise to the mixture over a period of 5-10 min and the reaction mixture was stirred at rt for 15 min. It was then cooled down to 0° C. and EtMgBr (2.5 mmol) was added dropwise over a period of 10-15 min. The reaction mixture was stirred again at 0° C. for 15 min. and then stirred at ambient temperature for 1 h. $BF_3.OEt_2$ (2.5 mmol) was then added dropwise over a period of 5-10 min to the mixture that was cooled again to 0° C. After the mixture was stirred for 10 min at 0° C. and 1 h at ambient temperature, 1 N NaOH was added to the mixture cooled to 0° C. DCM was added to the reaction mixture and stirred for 5-10 min. This alkaline solution was filtered through celite and washed with DCM. The organic layer was concentrated and the residue purified by flash chromatography on silica gel using 10% chloroform/methanol. Yield: 0.6 g; $^1$H NMR (400 MHz, $CDCl_3$): δ 1.20 (m, 2H) 1.31 (m, 2H), 2.40 (s, 3H), 7.26 (s, 1H). LCMS: (ES+) m/z observed 154.7.

2-(4-fluorophenyl)-5-(4-methoxy-2-methyl-5-(1-(5-methylthiazol-2-yl)cyclopropylcarbamoyl)phenyl)-N-methylbenzofuran-3-carboxamide. 5-(2-(4-fluorophenyl)-3-(methylcarbamoyl)benzofuran-5-yl)-2-methoxy-4-methylbenzoic acid (0.2 g, 1 eq), 1-(5-methylthiazol-2-yl)cyclopropanamine (0.07 g, 1 eq), EDCI.HCl (0.13 g, 1.5 eq), HOBT (0.094 g, 1.5 eq) and TEA (0.19 ml, 3 eq) were dissolved in dichloromethane and the above solution was stirred at room temperature for 18 h. Then water was added to the mixture and the organic layer was separated. The organic layer was washed with water and the product was purified by Prep. HPLC. Yield: 65 mg (25%)$^1$HNMR (400 MHz, $CDCl_3$): δ 1.43-1.46 (m, 2H), 1.74-1.77 (m, 2H), 2.32 (s, 3H), 2.37 (s, 3H), 3.01-3.03 (d, J=5.2 Hz, 3H), 4.04 (s, 3H), 5.89 (m, 1H), 6.91 (s, 1H), 7.16 (t, 2H), 7.27 (m, 2H), 7.51 (d, J=4 Hz, 1H), 7.66 (s, 1H), 8.00 (m, 2H), 8.13 (s, 1H), 8.7 (s, 1H). LCMS: (ES+) m/z=570.2 (M+H).

General procedure. 5-(5-(1-cyanocyclopropylcarbamoyl)-2-methylphenyl)-2-(4-fluorophenyl)-N-methylbenzofuran-3-carboxamide (448 mg) was dissolved in butan-1-ol (22.50 mL) and distributed evenly into 15 pre-weighed hydrazides in microwave vials (2-5 mL size) and followed by adding $K_2CO_3$ (8.85 mg) as a solid. The vial was flashed with argon and capped, then heated at 165° C. for 30 minutes in a Biotage microwave reactor. The samples were dried by SpeedVac, dissolved in DMF (1.8 mL) and purified by preparative HPLC. Purification method: Cw313a (19×100 mm): Solvent A=5:95 MeCN:Water; Solvent B=95:5 MeCN:Water; Modifier=10 mM $NH_4OAc$; 0' (25 mL/min)=30% B, 0.5° (12.5 mL/min)=30% B, 2' (12.5 mL/min)=30% B, 2.5'=30% B, 22'=95% B, 36'=95% B. HPLC purity was determined using a Waters ZQ with ESCi mass spectrometer. Solvent A=5:95 MeCN:Water; Solvent B=95:5 MeCN:Water; Modifier=10 mM $NH_4OAc$. Retention time was recorded in minutes.

| Analytical Method A Waters Xbridge 4.6x50 mm 5 um C18v | | |
|---|---|---|
| Time | B % | Flow (mL/min) |
| 0.00' | 5 | 2.00 |
| 8.00' | 95 | 2.00 |
| 9.00' | 95 | 2.00 |
| 9.01' | 5 | 2.00 |
| 10.00 | 5 | 2.00 |

| Structure | HPLC Rt | % Purity | Obs. MS Ion | HPLC Method |
|---|---|---|---|---|
| 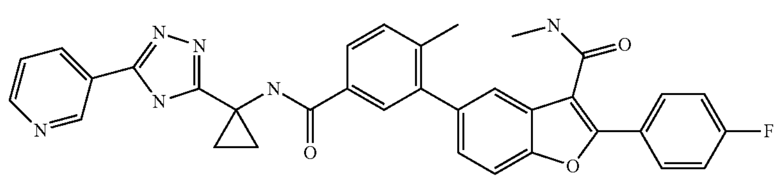 | 4.73 | 89.3 | 587.33 | A |

| | | | | |
|---|---|---|---|---|
| 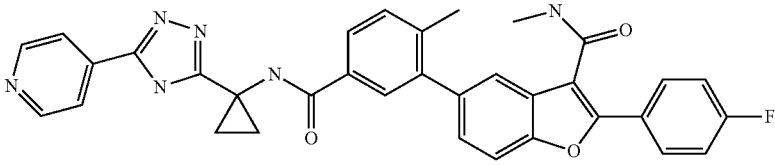 | 4.76 | 90.6 | 587.33 | A |
| 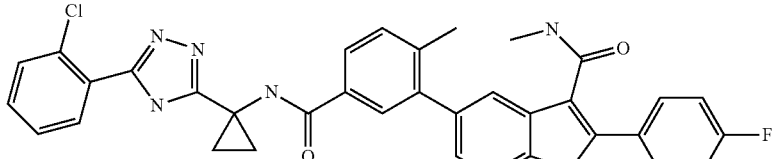 | 5.44 | 88.5 | 620.37 | A |
| 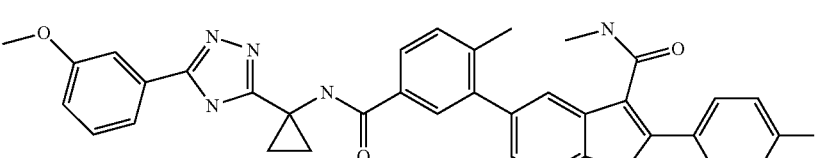 | 5.4 | 93.4 | 616.33 | A |
| 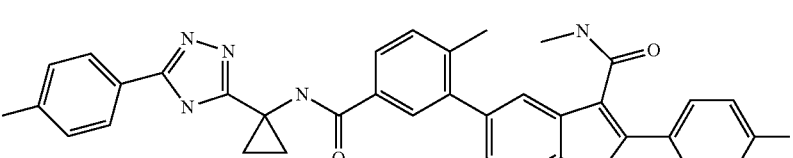 | 5.37 | 100 | 620.187 | A |
| 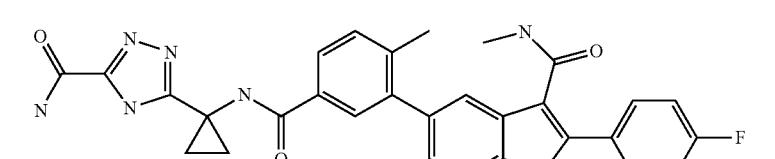 | 3.85 | 98.3 | 553.181 | A |
| 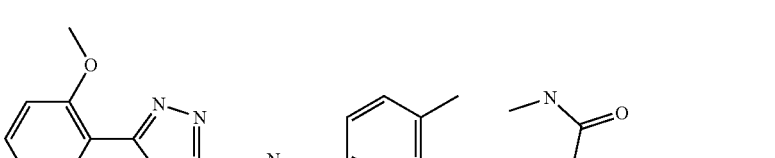 | 5 | 100 | 616.218 | A |
| 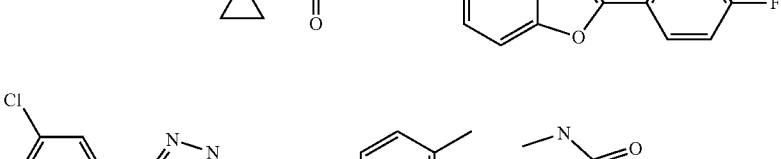 | 5.84 | 88.8 | 620.29 | A |
| 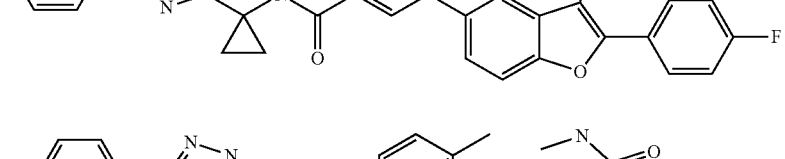 | 4.86 | 100 | 616.166 | A |

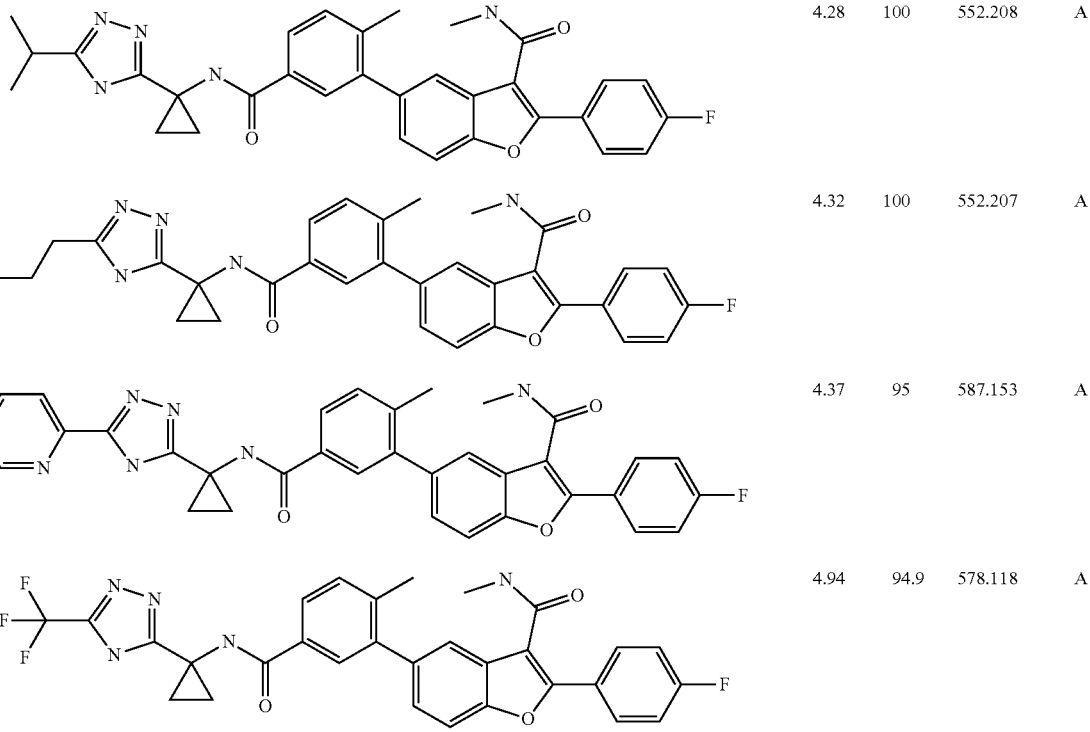
| | | | |
|---|---|---|---|
| 4.28 | 100 | 552.208 | A |
| 4.32 | 100 | 552.207 | A |
| 4.37 | 95 | 587.153 | A |
| 4.94 | 94.9 | 578.118 | A |
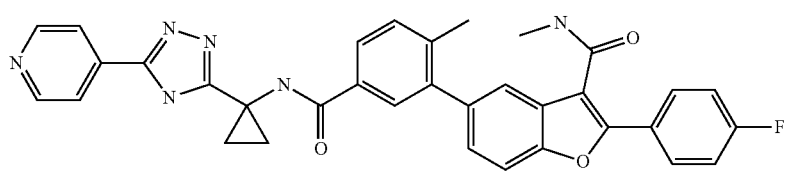
$^1$H NMR (600 MHz, <DMSO-d$_6$_CDCl$_3$>) δ ppm 1.41 (br. s., 2 H) 1.62 (br. s., 2 H) 2.28-2.47 (m, 3 H) 2.89 (d, J = 4.69 Hz, 3 H) 7.29-7.51 (m, 5 H) 7.66 (s, 1 H) 7.75 (d, J = 8.79 Hz, 1 H) 7.86-7.99 (m, 2 H) 8.05 (dd, J = 8.20, 5.86 Hz, 2 H) 8.44 (d, J = 4.10 Hz, 1 H) 8.61 (br. s., 1 H) 9.17 (s, 1 H) 9.32 (br. s., 2 H)
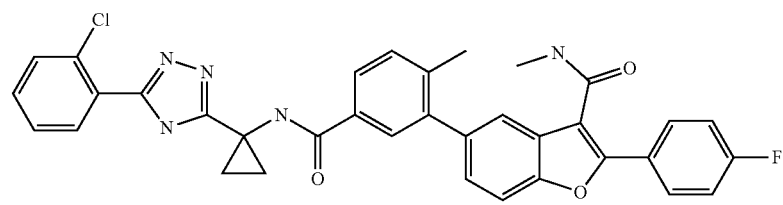
$^1$H NMR (600 MHz, <DMSO-d$_6$_CDCl$_3$>) δ ppm 1.42 (br. s., 2 H) 1.61 (br. s., 2 H) 2.22-2.44 (m, 3 H) 2.56-2.63 (m, 3 H) 7.32-7.55 (m, 4 H) 7.66 (s, 1 H) 7.76 (d, J = 8.79 Hz, 1 H) 7.89-8.03 (m, 2 H) 8.04 (dd, J = 8.50, 5.57 Hz, 2 H) 8.44 (d, J = 4.10 Hz, 1 H) 8.66 (d, J = 4.10 Hz, 2 H) 9.33 (br. s., 1 H) 14.09 (br. s., 1 H)
$^1$H NMR (600 MHz, <DMSO-d$_6$_CDCl$_3$>) δ ppm 1.42 (br. s., 2 H) 1.60 (br. s., 2 H) 2.37 (s, 3 H) 2.89 (d, J = 4.10 Hz, 3 H) 7.31-7.51 (m, 4 H) 7.51-7.59 (m, 1 H) 7.66 (s, 1 H) 7.75 (d, J = 8.20 Hz, 1 H) 7.80-7.94 (m, 2 H) 8.05 (dd, J = 8.20, 5.86 Hz, 2 H) 8.27 (s, 1 H) 8.44 (d, J = 4.10 Hz, 1 H) 9.31 (br. s., 1 H) 13.93 (br. s., 1 H)

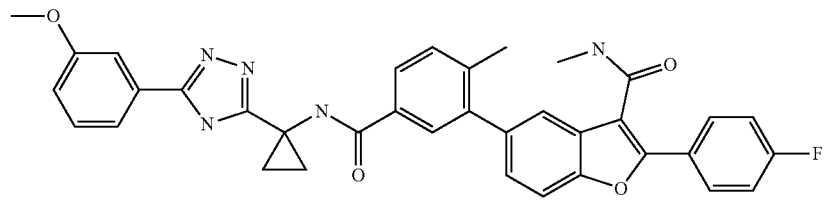

<sup>1</sup>H NMR (600 MHz, <DMSO-d<sub>6</sub>_CDCl<sub>3</sub>>) δ ppm 1.40 (br. s., 2 H) 1.60 (br. s., 2 H) 2.36 (s, 3 H) 2.89 (d, J = 4.69 Hz, 3 H) 3.86 (s, 3 H) 7.23-7.49 (m, 5 H) 7.53 (br. s., 1 H) 7.55-7.62 (m, 1 H) 7.65 (s, 1 H) 7.75 (d, J = 8.20 Hz, 1 H) 7.90 (d, J = 8.20 Hz, 1 H) 8.05 (dd, J = 8.20, 5.86 Hz, 1 H) 8.27 (s, 1 H) 8.44 (d, J = 4.69 Hz, 1 H) 9.31 (br. s., 1 H) 13.77 (br. s., 1 H)

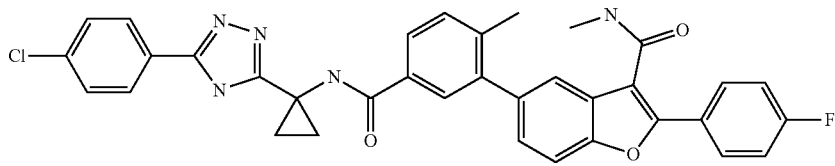

<sup>1</sup>H NMR (600 MHz, <DMSO-d<sub>6</sub>_CDCl<sub>3</sub>>) δ ppm 1.40 (br. s., 2 H) 1.60 (br. s., 2 H) 2.37 (s, 3 H) 2.89 (d, J = 4.69 Hz, 3 H) 7.32-7.54 (m, 4 H) 7.65 (s, 1 H) 7.75 (d, J = 8.79 Hz, 1 H) 7.85-7.96 (m, 1 H) 7.96-8.11 (m, 3 H) 8.27 (s, 1 H) 8.43 (br. s., 1 H) 9.31 (s, 1 H) 13.84 (br. s., 1 H)

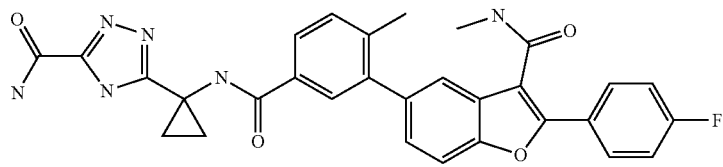

<sup>1</sup>H NMR (600 MHz, <DMSO-d<sub>6</sub>_CDCl<sub>3</sub>>) δ ppm 1.39 (br. s., 2 H) 1.57 (br. s., 2 H) 2.36 (s, 3 H) 2.89 (d, J = 4.69 Hz, 3 H) 7.36-7.60 (m, 3 H) 7.75 (d, J = 8.20 Hz, 1 H) 7.85-7.96 (m, 1 H) 8.04 (dd, J = 8.20, 5.27 Hz, 2 H) 8.27 (s, 1 H) 8.43 (d, J = 4.69 Hz, 1 H) 9.27 (br. s., 1 H) 14.10 (br. s., 1 H)

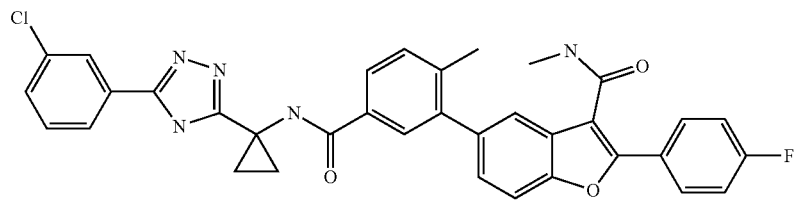

<sup>1</sup>H NMR (600 MHz, <DMSO-d<sub>6</sub>_CDCl<sub>3</sub>>) δ ppm 1.41 (br. s., 2 H) 1.61 (br. s., 2 H) 2.37 (s, 3 H) 2.89 (d, J = 4.69 Hz, 3 H) 7.28-7.58 (m, 4 H) 7.65 (s, 1 H) 7.75 (d, J = 8.79 Hz, 1 H) 7.86-8.02 (m, 1 H) 8.02-8.18 (m, 3 H) 8.27 (s, 1 H) 8.44 (d, J = 4.10 Hz, 1 H) 9.31 (br. s., 1 H) 13.90 (br. s., 1 H)

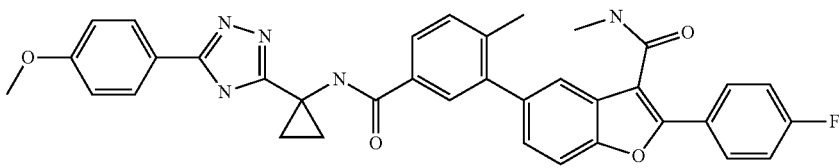

<sup>1</sup>H NMR (600 MHz, <DMSO-d<sub>6</sub>_CDCl<sub>3</sub>>) δ ppm 1.39 (br. s., 2 H) 1.59 (br. s., 2 H) 2.36 (br. s., 3 H) 2.89 (d, J = 4.10 Hz, 3 H) 3.85 (s, 3 H) 6.99 (m, 2H) 7.29-7.54 (m, 4 H) 7.65 (s, 1 H) 7.75 (d, J = 8.20 Hz, 1 H) 7.82-7.99 (m, 3 H) 7.99-8.14 (m, 2 H) 8.27 (s, 1 H) 8.43 (br. s., 1 H) 9.29 (s, 1 H) 13.63 (br. s., 1 H)

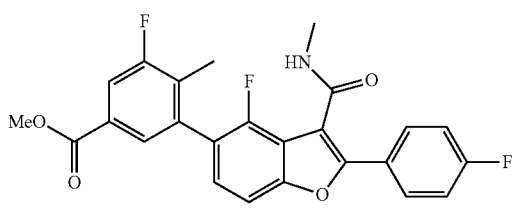

Methyl 3-fluoro-5-(4-fluoro-2-(4-fluorophenyl)-3-(methylcarbamoyl)benzofuran-5-yl)-4-methylbenzoate. LC/MS were performed by using Shimadzu-VP instrument with UV detection at 220 nm and Waters Micromass. HPLC method: Solvent A=10% MeOH-90% H<sub>2</sub>O-0.1% TFA, Solvent B=90% MeOH-10% H<sub>2</sub>O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)<sup>+</sup>=454.08, HPLC R<sub>t</sub>=1.838 min.

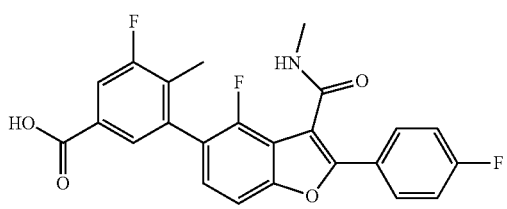

3-Fluoro-5-(4-fluoro-2-(4-fluorophenyl)-3-(methylcarbamoyl)benzofuran-5-yl)-4-methylbenzoic acid. $^1$H NMR (500 MHz, CD$_3$OD) δ 7.96 (m, 2H), 7.76 (s, 1H), 7.75-7.73 (d, 1H), 7.56 (d, J=8.24, 1H), 7.33-7.28 (t overlapping with m, 3H), 2.96 (s, 3H), 2.20 (s, 3H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$= 440.09, HPLC R$_t$=1.720.

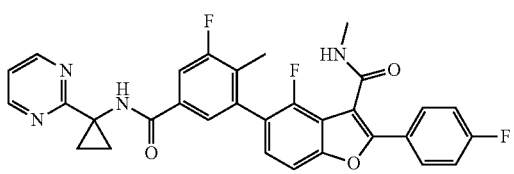

4-Fluoro-5-(3-fluoro-2-methyl-5-(1-(pyrimidin-2-yl)cyclopropylcarbamoyl)phenyl)-2-(4-fluorophenyl)-N-methylbenzofuran-3-carboxamide. Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Sunfire Prep C18 19×100 5 um, Fraction Collection: 7.27-7.77 mM. (UV detection at 220 nm). The material obtained was further purified by preparative TLC (500 um×20×20 cm plate, 5% MeOH/CH$_2$Cl$_2$). Analytical TLC Rf=0.30 (5% MeOH/CH$_2$Cl$_2$). $^1$H NMR (500 MHz, DMSO-d$_6$) δ 9.29 (s, 1H), 8.73 (m, 2H), 8.68 (d, J=4.58, 2H), 7.95 (dd, J=8.55, 5.49, 1H), 7.78 (d, J=10.38, 1H), 7.74 (s, 1H), 7.69 (d, J=8.54, 1H), 7.43 (t, J=9.00, 2H), 7.39 (d, 1H), 7.28 (t, J=4.88, 1H), 2.81 (d, J=4.58, 3H), 2.14 (s, 3H), 1.61 (m, 2H), 1.35 (m, 2H). $^{19}$F NMR (470.45 MHz, DMSO-d$_6$) δ -110.73, -115.40, -121.76 (The $^{19}$F chemical shift was referenced to CFCl$_3$ at 0.0 ppm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=557.12, HPLC R$_t$=1.662 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.31 min; Column: Xbridge Phenyl 3.5 um, 4.6×150 mm, R$_t$=5.29 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=10.25 min.

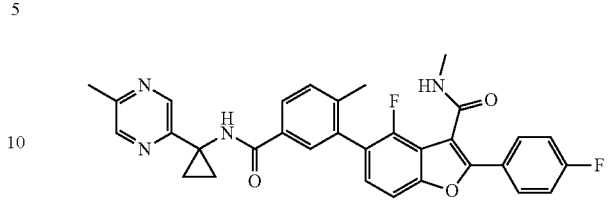

4-Fluoro-2-(4-fluorophenyl)-N-methyl-5-(2-methyl-5-(1-(5-methylpyrazin-2-yl)cyclopropylcarbamoyl)phenyl)benzofuran-3-carboxamide. This example was prepared from the coupling of 3-(4-fluoro-2-(4-fluorophenyl)-3-(methylcarbamoyl)benzofuran-5-yl)-4-methylbenzoic acid with 1-(5-methylpyrazin-2-yl)cyclopropanamine (obtained from 5-methylpyrazine-2-carbonitrile by the reaction using Ti(OiPr)$_4$/EtMgBr/BF$_3$OEt$_2$), and was isolated as a TFA salt after purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=50, Final % B=100, Gradient time=10 min, Stop time=12 min, Flow Rate=25 mL/min, Column: Sunfire Prep C18 19×100 5 μm, Fraction Collection: 7.15-7.72 min. (UV detection at 220 nm). $^1$H NMR (500 MHz, CD$_3$OD) δ 8.44 (s, 1H), 8.43 (s, 1H), 7.95 (m, 2H), 7.90 (dd, J=7.93, 1.83, 1H), 7.83 (s, 1H), 7.55 (d, J=8.55, 1H), 7.49 (d, J=7.93, 1H), 7.33 (d, J=8.24, 1H), 7.29 (t, J=8.85, 2H), 2.96 (s, 3H), 2.51 (s, 3H), 2.30 (s, 3H), 1.67 (m, 2H), 1.41 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=553.22, HPLC R$_t$=1.647 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.01 min; Column: Xbridge Phenyl 3.5 um, 4.6×150 mm, R$_t$=5.04 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=10.24 min.

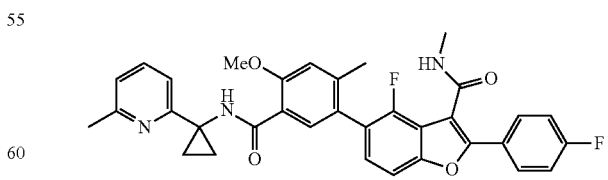

2-(4-Fluorophenyl)-5-(4-methoxy-2-methyl-5-(1-(6-methylpyridin-2-yl)cyclopropylcarbamoyl)phenyl)-N-methyl-benzofuran-3-carboxamide. Purification was performed by Shimadzu-VP preparative reverse phase HPLC using the separation method: Solvent A=10% MeOH-90% H$_2$O-0.1%

TFA, Solvent B=90% MeOH-10% H₂O-0.1% TFA, Start % B=20, Final % B=100, Gradient time=10 min, Stop time=12 min, Flow Rate=25 mL/min, Column: Sunfire Prep C18 19×100 5 μm, Fraction Collection: 8.12-8.62 min. (UV detection at 220 nm). The material obtained was further purified by preparative TLC (500 um×20×20 cm plate, 5% MeOH/CH₂Cl₂). Analytical TLC Rf=0.44 (5% MeOH/CH₂Cl₂). $^1$H NMR (500 MHz, CD₃OD) δ 7.98 (m, 2H), 7.79 (s, 1H), 7.63 (d, J=8.54, 1H), 7.59 (d, J=1.22, 1H), 7.56 (t, J=7.78, 1H), 7.34 (dd, J=8.50, 1.83, 1H), 7.32 (d, J=5.19, 1H), 7.28 (apparent t, 2H), 7.14 (s, 1H), 7.01 (d, J=7.63, 1H), 4.08 (s, 3H), 2.96 (s, 3H), 2.47 (s, 3H), 2.37 (s, 3H), 1.67 (m, 2H), 1.33 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=564.27, HPLC R$_t$=1.518 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=2.83 min; Column: Xbridge Phenyl 3.5 um, 4.6×150 mm, R$_t$=3.65 min. Analytical HPLC method: Solvent A=5% MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3.5 um, 4.6×150 mm, R$_t$=13.04 min.

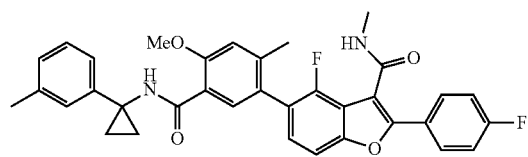

2-(4-Fluorophenyl)-5-(4-methoxy-2-methyl-5-(1-m-tolylcyclopropylcarbamoyl)phenyl)-N-methylbenzofuran-3-carboxamide. Purification was performed by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Sunfire Prep C18 19×100 5 um, Fraction Collection: 9.77-10.40 min. (UV detection at 220 nm). $^1$H NMR (500 MHz, CD₃OD) δ 7.96 (m, 2H), 7.76 (s, 1H), 7.61 (d, J=8.54, 1H), 7.58 (d, J=1.83, 1H), 7.31 (dd, J=8.24, 1.83, 1H), 7.26 (apparent t, 2H), 7.17 (t, J=7.63, 1H), 7.12 (d overlapped with s, 1H), 7.11 (s, 1H), 7.07 (d, J=7.32, 1H), 6.99 (d, J=7.32, 1H), 4.06 (s, 3H), 2.94 (s, 3H), 2.35 (s, 3H), 2.32 (s, 3H), 1.35 (broad m, 2H), 1.34 (broad m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=563.27, HPLC R$_t$=1.962 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=12.30 min; Column: Xbridge Phenyl 3.5 um, 4.6×150 mm, R$_t$=9.32 min. Analytical HPLC method: Solvent A=5% MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3.5 um, 4.6×150 mm, R$_t$=12.78 min.

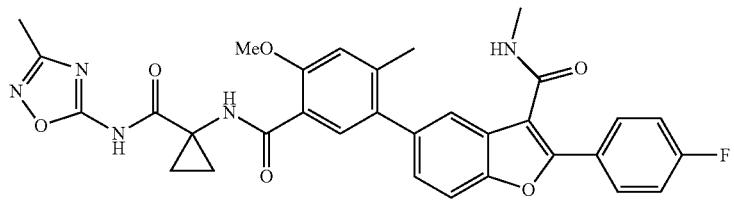

2-(4-Fluorophenyl)-5-(4-methoxy-2-methyl-5-(1-(3-methyl-1,2,4-oxadiazol-5-ylcarbamoyl)cyclopropylcarbamoyl)phenyl)-N-methylbenzofuran-3-carboxamide. Purification was performed by Shimadzu-VP preparative reverse phase HPLC using the separation method: Solvent A=10% MeOH-90% H₂O-0.1% TFA, Solvent B=90% MeOH-10% H₂O-0.1% TFA, Start % B=50, Final % B=100, Gradient time=10 min, Stop time=12 min, Flow Rate=25 mL/min, Column: Sunfire Prep C18 19×100 5 um, Fraction Collection: 7.07-7.87 min. (UV detection at 220 nm). $^1$H NMR (500 MHz, DMSO-d₆) δ 8.74 (s, 1H), 8.48 (q, J=4.78, 1H), 7.99 (m, 2H), 7.74 (s, 1H), 7.73 (d overlapped with s, 1H), 7.50 (d, J=1.53, 1H), 7.41 (t, J=9.00, 2H), 7.33 (dd, J=8.39, 1.68, 1H), 7.17 (s, 1H), 4.00 (s, 3H), 2.82 (d, J=4.78, 3H), 2.31 (s, 3H), 2.25 (s, 3H), 1.55 (m, 2H), 1.23 (m, 2H). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+Na)⁺=620.22, HPLC R$_t$=1.668 min. Analytical HPLC were performed by using Shimadzu-VP instrument with UV detection at 220 nm and 254 nm. Analytical HPLC method: Solvent A=5% MeCN-95% H₂O-0.1% TFA, Solvent B=95% MeCN-5% H₂O-0.1% TFA, Start % B=50, Final % B=100, Gradient time=15 min, Stop time=18 min, Flow Rate=1 ml/min, Column: Sunfire C18, 3.5 um, 4.6×150 mm, R$_t$=6.33 min; Column: Xbridge Phenyl 3.5 um, 4.6×150 mm, R$_t$=5.18 min. Analytical HPLC method: Solvent A=5% MeOH-95% H₂O-10 mM NH₄HCO₃, Solvent B=95% MeOH-5% H₂O-10 mM NH₄HCO₃, Start % B=50, Final % B=100, Gradient time=15 min, Stop time=18 min, Flow Rate=1 ml/min, Column: Xbridge Phenyl 3.5 um, 4.6×150 mm, R$_t$=8.65 min.

The following examples were synthesized in a similar fashion to that described for 2-(4-fluorophenyl)-5-(4-isopropoxy-2-methyl-5-(1-(pyridin-2-yl)cyclopropylcarbamoyl)phenyl)-N-methylbenzofuran-3-carboxamide using the same conditions for preparative HPLC, analytical HPLC and LCMS.

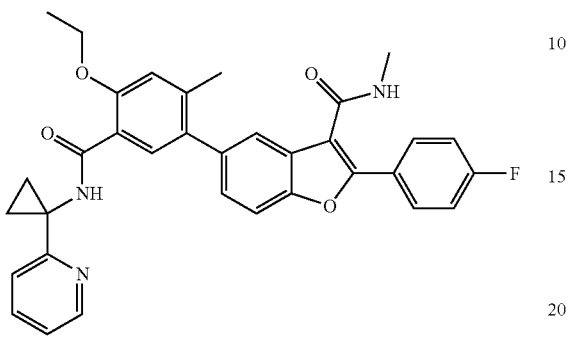

5-(4-Ethoxy-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.28-1.35 (m, 2H), 1.53 (t, J=6.86 Hz, 3H), 1.63-1.70 (m, 2H), 2.29 (s, 3 H), 2.88 (d, J=4.52 Hz, 3H), 4.29 (q, J=6.86 Hz, 2H), 7.04 (s, 1H), 7.14-7.28 (m, 4H), 7.53-7.63 (m, 4H), 7.68-7.75 (m, 1H), 7.91 (s, 1H), 8.11-8.18 (m, 2H), 8.51 (d, J=4.02 Hz, 1H), 8.72 (s, 1H). LCMS m/z 564.6 (M+H), rt=2.676 min. HPLC (Sunfire C18) rt=7.536 min, 99.6% purity and (XBridge Phenyl C18) rt=11.754 min., 96.9% purity.

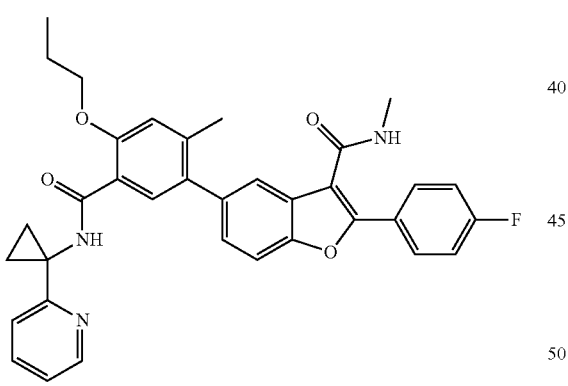

2-(4-Fluorophenyl)-N-methyl-5-(2-methyl-4-propoxy-5-(1-(pyridin-2-yl)cyclopropylcarbamoyl)phenyl)benzofuran-3-carboxamide. $^1$H NMR (400 MHz, THF-d8) δ ppm 1.10 (t, J=7.40 Hz, 3H), 1.27-1.34 (m, 2H), 1.64-1.70 (m, 2H), 1.90-2.00 (m, 2H), 2.29 (s, 3H), 2.88 (d, J=4.52 Hz, 3H), 4.20 (t, J=6.53 Hz, 2H), 7.05 (s, 1H), 7.12-7.17 (m, 1H), 7.17-7.29 (m, 3H), 7.52-7.60 (m, 3H), 7.61 (d, J=1.25 Hz, 1H), 7.65-7.72 (m, 1H), 7.93 (s, 1H), 8.10-8.19 (m, 2H), 8.49 (d, J=4.77 Hz, 1H), 8.69 (s, 1H). LCMS m/z 578.6 (M+H), rt=2.838 min. HPLC (Sunfire C18) rt=8.074 min, 99.8% purity and (XBridge Phenyl C18) rt=12.011 min., 99.4% purity.

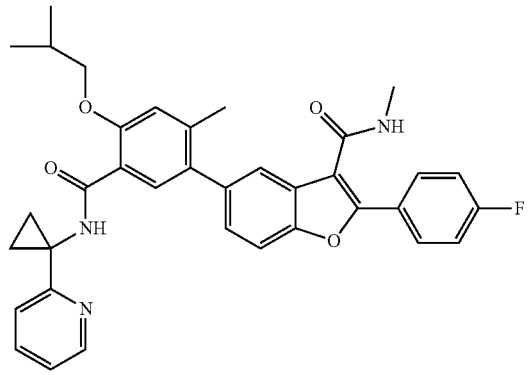

2-(4-Fluorophenyl)-5-(4-isobutoxy-2-methyl-5-(1-(pyridin-2-yl)cyclopropylcarbamoyl)phenyl)-N-methylbenzofuran-3-carboxamide. $^1$H NMR (400 MHz, THF-d8) δ ppm 1.10 (d, J=6.78 Hz, 6H), 1.24-1.33 (m, 2H), 1.64-1.71 (m, 2H), 2.17-2.27 (m, 1H), 2.29 (s, 3H), 2.88 (d, J=4.77 Hz, 3H), 4.03 (d, J=6.27 Hz, 2H), 7.03-7.12 (m, 2H), 7.18-7.31 (m, 3H), 7.50 (d, J=8.03 Hz, 1H), 7.54-7.66 (m, 4H), 7.95 (s, 1H), 8.10-8.22 (m, 2H), 8.43 (d, J=4.02 Hz, 1H), 8.63 (s, 1H). LCMS m/z 592.6 (M+H), rt=2.991 min. HPLC (Sunfire C18) rt=8.511 min, 100% purity and (XBridge Phenyl C18) rt=12.194 min., 99.4% purity.

5-(4-Butoxy-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.00 (t, J=7.40 Hz, 3H), 1.27-1.37 (m, 2H), 1.56 (m, 2H), 1.64-1.71 (m, 2 H), 1.86-1.99 (m, 2H), 2.29 (s, 3H), 2.88 (d, J=4.77 Hz, 3H), 4.24 (t, J=6.53 Hz, 2 H), 7.05 (s, 1H), 7.14-7.30 (m, 4H), 7.51-7.64 (m, 4H), 7.71 (td, J=7.78, 1.76 Hz, 1H), 7.92 (s, 1H), 8.08-8.18 (m, 2H), 8.51 (d, J=5.02 Hz, 1H), 8.71 (s, 1H). LCMS m/z 592.5 (M+H), rt=2.940 min. HPLC (Sunfire C18) rt=8.291 min, 100% purity and (XBridge Phenyl C18) rt=12.116 min., 100% purity.

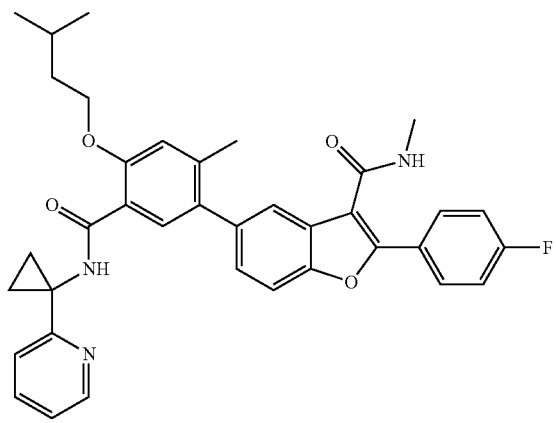

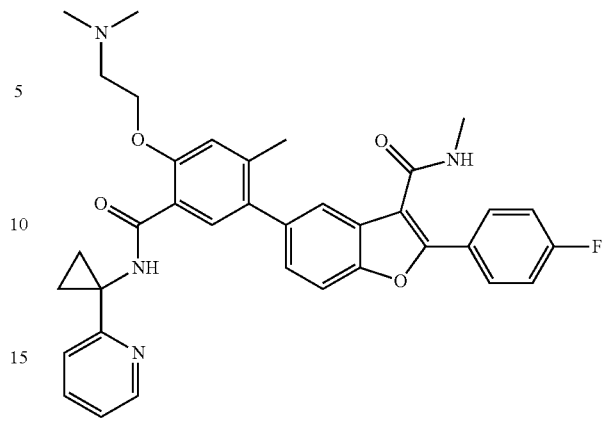

2-(4-Fluorophenyl)-5-(4-(isopentyloxy)-2-methyl-5-(1-(pyridin-2-yl)cyclopropyl carbamoyl)phenyl)-N-methylbenzofuran-3-carboxamide. $^1$H NMR (400 MHz, THF-d8) δ ppm 1.00 (d, J=6.53 Hz, 6H), 1.24-1.32 (m, 2H), 1.64-1.70 (m, 2H), 1.79-1.92 (m, 3H), 2.29 (s, 3H), 2.88 (d, J=4.77 Hz, 3H), 4.27 (t, J=6.53 Hz, 2H), 7.06-7.12 (m, 2H), 7.18-7.29 (m, 3H), 7.48-7.59 (m, 3H), 7.59-7.65 (m, 2H), 7.94 (s, 1H), 8.11-8.18 (m, 2H), 8.42-8.47 (m, 1H), 8.62 (s, 1H). LCMS m/z 606.6 (M+H), rt=3.085 min. HPLC (Sunfire C18) rt=8.664 min, 100% purity and (XBridge Phenyl C18) rt=12.283 min., 100% purity.

5-(4-(2-(Dimethylamino)ethoxy)-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.34-1.38 (m, 2H), 1.60-1.66 (m, 2H), 2.28 (s, 3H), 2.88 (d, J=4.77 Hz, 3H), 2.91 (s, 6H), 3.64 (t, J=5.02 Hz, 2H), 4.64 (t, J=5.02 Hz, 2H), 7.16 (s, 1H), 7.19-7.29 (m, 4H), 7.51-7.58 (m, 2H), 7.61-7.69 (m, 3H), 7.89 (br. s., 1H), 8.07-8.14 (m, 2H), 8.51 (d, J=5.02 Hz, 1H), 8.85 (s, 1H). LCMS m/z 607.5 (M+H), rt=1.952 min. HPLC (Sunfire C18) rt=5.690 min, 100% purity and (XBridge Phenyl C18) rt=11.743 min., 99.6% purity.

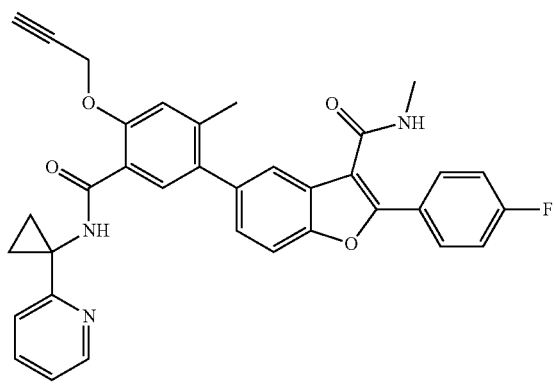

2-(4-Fluorophenyl)-N-methyl-5-(2-methyl-4-(prop-2-ynyloxy)-5-(1-(pyridin-2-yl)cyclopropyl carbamoyl)phenyl) benzofuran-3-carboxamide. $^1$H NMR (400 MHz, THF-d8) δ ppm 1.28 (q, J=4.02 Hz, 2H), 1.62-1.69 (m, 2H), 2.30 (s, 3H), 2.89 (d, J=4.52 Hz, 3H), 3.19 (t, J=2.38 Hz, 1H), 5.00 (d, J=2.51 Hz, 2H), 7.00 (ddd, J=7.15, 4.77, 1.38 Hz, 1H), 7.15 (s, 1H), 7.18-7.31 (m, 3H), 7.46-7.59 (m, 4H), 7.63 (d, J=1.00 Hz, 1H), 7.94 (s, 1H), 8.11-8.20 (m, 2H), 8.35-8.41 (m, 1H), 8.46 (s, 1H). LCMS m/z 574.5 (M+H), rt=2.625 min. HPLC (Sunfire C18) rt=7.381 min, 100% purity and (XBridge Phenyl C18) rt=11.309 min., 98.4% purity.

5-(4-(3-(Dimethylamino)propoxy)-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.31-1.37 (m, 2H), 1.62-1.69 (m, 2H), 2.29 (s, 3H), 2.35 (t, J=6.02 Hz, 2H), 2.76 (s, 6H), 2.88 (d, J=4.52 Hz, 3H), 3.35 (t, J=6.53 Hz, 2H), 4.33 (t, J=5.77 Hz, 2H), 7.08 (s, 1H), 7.18-7.30 (m, 4H), 7.52-7.65 (m, 4H), 7.67 (s, 1H), 7.80 (td, J=7.72, 1.63 Hz, 1H), 8.07-8.15 (m, 2H), 8.51 (d, J=5.02 Hz, 1H), 8.92 (s, 1H). LCMS m/z 621.6 (M+H), rt=2.048 min. HPLC (Sunfire C18) rt=5.911 min, 100% purity and (XBridge Phenyl C18) rt=11.653 min., 100% purity.

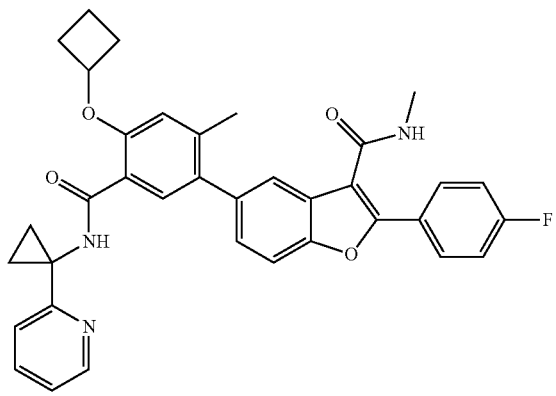

5-(4-Cyclobutoxy-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.27-1.36 (m, 2H), 1.62-1.69 (m, 2H), 1.75-1.81 (m, 1H), 1.92 (d, J=10.04 Hz, 1H), 2.23-2.36 (m, 5H), 2.51-2.64 (m, 2H), 2.88 (d, J=4.77 Hz, 3H), 4.92 (t, J=7.28 Hz, 1H), 6.87 (s, 1H), 7.13 (ddd, J=7.47, 4.96, 1.13 Hz, 1H), 7.17-7.28 (m, 3H), 7.51-7.63 (m, 4H), 7.64-7.72 (m, 1H), 7.91 (s, 1H), 8.10-8.20 (m, 2H), 8.48 (d, J=5.02 Hz, 1H), 8.64 (s, 1H). LCMS m/z 590.5 (M+H), rt=2.823 min. HPLC (Sunfire C18) rt=7.996 min, 91.3% purity and (XBridge Phenyl C18) rt=12.013 min., 91.7% purity.

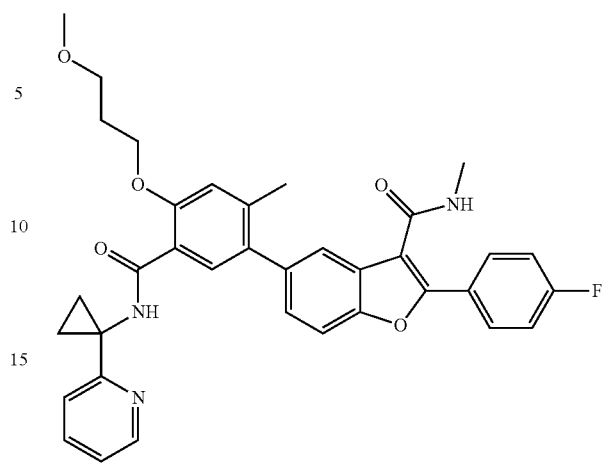

2-(4-Fluorophenyl)-5-(4-(3-methoxypropoxy)-2-methyl-5-(1-(pyridin-2-yl)cyclopropylcarbamoyl)phenyl)-N-methylbenzofuran-3-carboxamide. $^1$H NMR (400 MHz, THF-d8) δ ppm 1.24-1.32 (m, 2H), 1.64-1.69 (m, 2H), 2.10-2.20 (m, 2H), 2.29 (s, 3H), 2.89 (d, J=4.77 Hz, 3H), 3.22 (s, 3H), 3.53-3.58 (m, 2H), 4.31 (t, J=5.90 Hz, 2H), 7.00 (ddd, J=7.40, 4.77, 1.13 Hz, 1H), 7.05 (s, 1H), 7.16-7.30 (m, 3H), 7.43-7.48 (m, 1H), 7.50-7.59 (m, 3H), 7.62 (d, J=1.25 Hz, 1H), 7.96 (s, 1H), 8.11-8.21 (m, 2H), 8.38 (dd, J=4.77, 1.00 Hz, 1H), 8.69 (s, 1H). LCMS m/z 608.5 (M+H), rt=2.625 min. HPLC (Sunfire C18) rt=7.536 min, 100% purity and (XBridge Phenyl C18) rt=11.788 min., 99.2% purity.

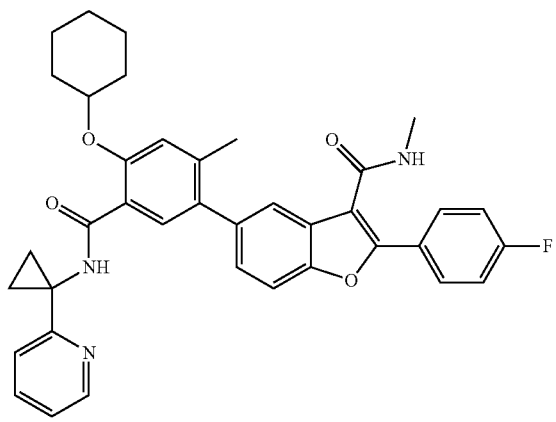

5-(4-(Cyclohexyloxy)-2-methyl-5-(1-(pyridin-2-yl)cyclopropylcarbamoyl)phenyl)-2-(4-fluoro phenyl)-N-methylbenzofuran-3-carboxamide. $^1$H NMR (400 MHz, THF-d8) δ ppm 1.26-1.34 (m, 2H), 1.33-1.55 (m, 3H), 1.56-1.64 (m, 1H), 1.65-1.70 (m, 4H), 1.76-1.87 (m, 2H), 2.06-2.18 (m, 2H), 2.28 (s, 3H), 2.88 (d, J=4.77 Hz, 3H), 4.65 (t, J=3.89 Hz, 1H), 7.05-7.13 (m, 2H), 7.17-7.31 (m, 3H), 7.50-7.59 (m, 3H), 7.59-7.68 (m, 2H), 7.96 (s, 1H), 8.10-8.20 (m, 2H), 8.46 (d, J=4.02 Hz, 1H), 8.74 (s, 1H). LCMS m/z 618.6 (M+H), rt=3.070 min. HPLC (Sunfire C18) rt=8.723 min, 100% purity and (XBridge Phenyl C18) rt=12.421 min., 99.8% purity.

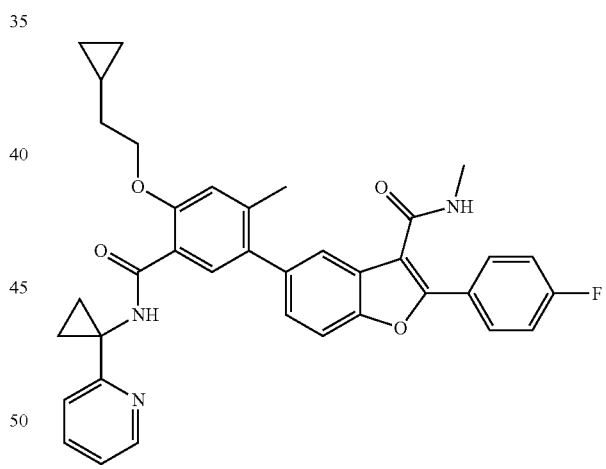

5-(4-(2-Cyclopropylethoxy)-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 0.13-0.20 (m, 2H), 0.45-0.54 (m, 2H), 0.89 (s, 1H), 1.28-1.34 (m, 2H), 1.63-1.70 (m, 2H), 1.83 (q, J=6.69 Hz, 2H), 2.29 (s, 3H), 2.88 (d, J=4.77 Hz, 3H), 4.30 (t, J=6.65 Hz, 2H), 7.08 (s, 1H), 7.13-7.30 (m, 4H), 7.53-7.64 (m, 4H), 7.70 (td, J=7.78, 1.76 Hz, 1H), 7.93 (s, 1H), 8.10-8.19 (m, 2H), 8.50 (d, J=5.02 Hz, 1H), 8.73 (s, 1H). LCMS m/z 604.5 (M+H), rt=2.948 min. HPLC (Sunfire C18) rt=8.483 min, 100% purity and (XBridge Phenyl C18) rt=12.218 min., 100% purity.

631

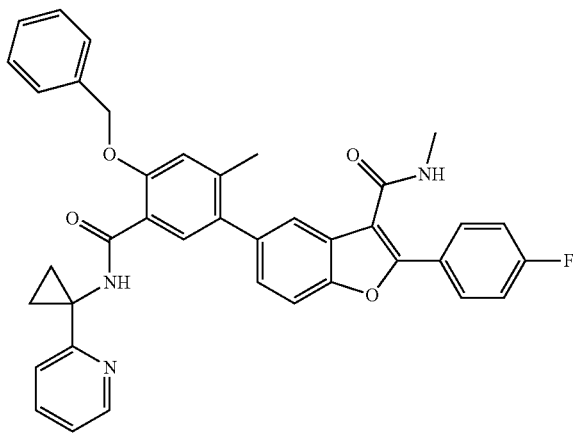

5-(4-(Benzyloxy)-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.07-1.16 (m, 2H), 1.52-1.60 (m, 2H), 2.30 (s, 3H), 2.88 (d, J=4.77 Hz, 3H), 5.32 (s, 2H), 7.08 (ddd, J=7.40, 4.89, 1.25 Hz, 1H), 7.16-7.29 (m, 4H), 7.31-7.42 (m, 3H), 7.46 (d, J=8.03 Hz, 1H), 7.51-7.60 (m, 5H), 7.63 (d, J=1.25 Hz, 1H), 7.93 (s, 1H), 8.10-8.18 (m, 2H), 8.43 (d, J=5.02 Hz, 1H), 8.59 (s, 1H). LCMS m/z 626.5 (M+H), rt=2.896 min. HPLC (Sunfire C18) rt=8.369 min, 100% purity and (XBridge Phenyl C18) rt=12.173 min., 100% purity.

632

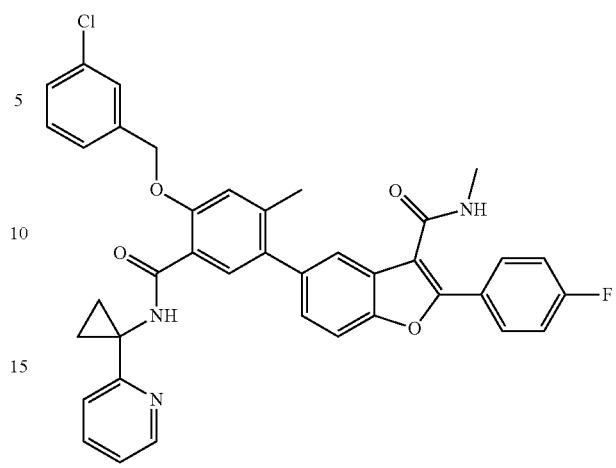

5-(4-(3-Chlorobenzyloxy)-2-methyl-5-(1-(pyridin-2-yl)cyclopropylcarbamoyl)phenyl)-2-(4-fluoro phenyl)-N-methylbenzofuran-3-carboxamide. $^1$H NMR (400 MHz, THF-d8) δ ppm 1.17-1.24 (m, 2H), 1.57-1.63 (m, 2H), 2.29 (s, 3H), 2.88 (d, J=4.52 Hz, 3H), 5.33 (s, 2H), 7.12-7.17 (m, 2H), 7.18-7.29 (m, 3H), 7.33-7.42 (m, 2H), 7.46-7.59 (m, 4H), 7.60-7.69 (m, 3H), 7.89 (s, 1H), 8.09-8.18 (m, 2H), 8.45-8.51 (m, 1H), 8.64 (s, 1H). LCMS m/z 660.5 (M), 663.5 (M+3H), rt=3.023 min. HPLC (Sunfire C18) rt=8.546 min, 97.9% purity and (XBridge Phenyl C18) rt=12.308 min., 97.4% purity.

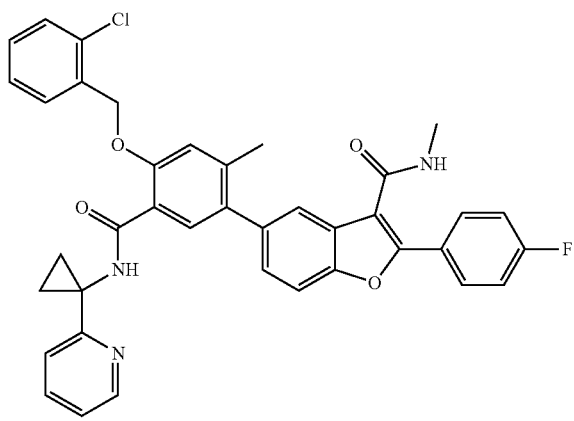

5-(4-(2-Chlorobenzyloxy)-2-methyl-5-(1-(pyridin-2-yl)cyclopropylcarbamoyl)phenyl)-2-(4-fluoro phenyl)-N-methylbenzofuran-3-carboxamide. $^1$H NMR (400 MHz, THF-d8) δ ppm 1.05-1.18 (m, 2H), 1.51-1.61 (m, 2H), 2.31 (s, 3H), 2.89 (d, J=4.77 Hz, 3H), 5.34-5.52 (m, 2H), 7.01-7.08 (m, 1H), 7.17-7.25 (m, 3H), 7.28 (dd, J=8.53, 1.76 Hz, 1H), 7.32-7.38 (m, 2H), 7.41-7.60 (m, 5H), 7.64 (d, J=1.25 Hz, 1H), 7.66-7.71 (m, 1H), 7.91 (s, 1H), 8.11-8.19 (m, 2H), 8.40 (d, J=4.02 Hz, 1H), 8.48 (s, 1H). LCMS m/z 660.5 (M), 663.4 (M+3H), rt=3.028 min. HPLC (Sunfire C18) rt=8.764 min, 100% purity and (XBridge Phenyl C18) rt=12.324 min., 99.7% purity.

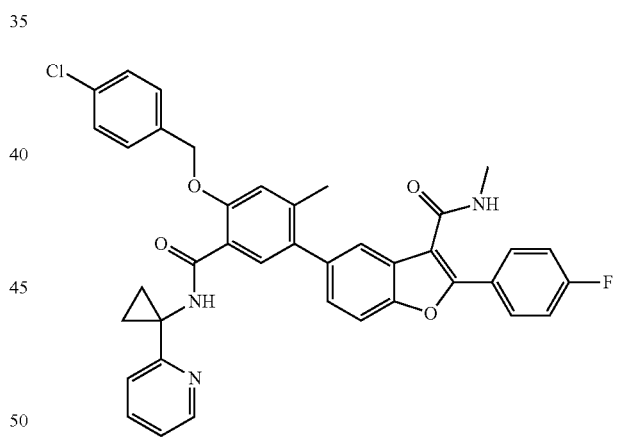

5-(4-(4-Chlorobenzyloxy)-2-methyl-5-(1-(pyridin-2-yl)cyclopropylcarbamoyl)phenyl)-2-(4-fluoro phenyl)-N-methylbenzofuran-3-carboxamide. $^1$H NMR (400 MHz, THF-d8) δ ppm 1.15-1.21 (m, 2H), 1.55-1.63 (m, 2H), 2.28 (s, 3H), 2.88 (d, J=4.77 Hz, 3H), 5.32 (s, 2H), 7.14 (s, 1H), 7.15-7.28 (m, 4H), 7.38-7.44 (m, 2H), 7.51-7.60 (m, 5H), 7.62 (d, J=1.25 Hz, 1H), 7.67 (td, J=7.78, 1.76 Hz, 1H), 7.88 (s, 1H), 8.09-8.18 (m, 2H), 8.50 (d, J=4.27 Hz, 1H), 8.65 (s, 1H). LCMS m/z 660.5 (M), 663.5 (M+3H), rt=3.046 min. HPLC (Sunfire C18) rt=8.679 min, 97.9% purity and (XBridge Phenyl C18) rt=12.268 min., 97.5% purity.

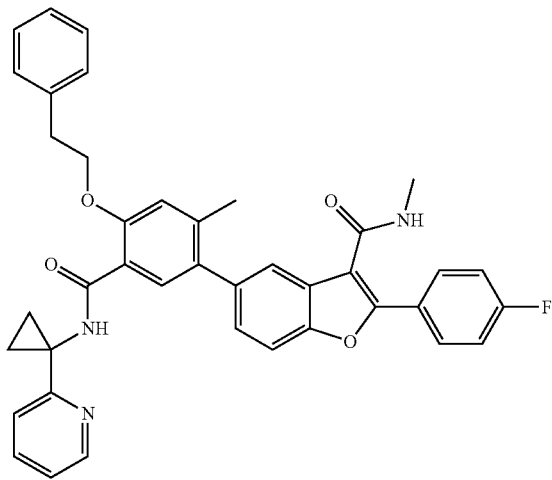

2-(4-Fluorophenyl)-N-methyl-5-(2-methyl-4-phenethoxy-5-(1-(pyridin-2-yl)cyclopropyl carbamoyl)phenyl)benzofuran-3-carboxamide. ¹H NMR (400 MHz, THF-d8) δ ppm 1.12-1.18 (m, 2H), 1.59-1.65 (m, 2H), 2.29 (s, 3H), 2.87 (d, J=4.77 Hz, 3H), 3.23 (t, J=6.53 Hz, 2H), 4.51 (t, J=6.53 Hz, 2H), 7.05-7.14 (m, 3H), 7.16-7.26 (m, 5H), 7.29 (d, J=7.03 Hz, 2H), 7.39 (d, J=8.03 Hz, 1H), 7.52-7.64 (m, 4H), 7.94 (s, 1H), 8.11-8.18 (m, 2H), 8.39 (s, 1H), 8.43-8.47 (m, 1H). LCMS m/z 640.6 (M+H), rt=2.996 min. HPLC (Sunfire C18) rt=8.448 min, 99.7% purity and (XBridge Phenyl C18) rt=12.341 min., 98.2% purity.

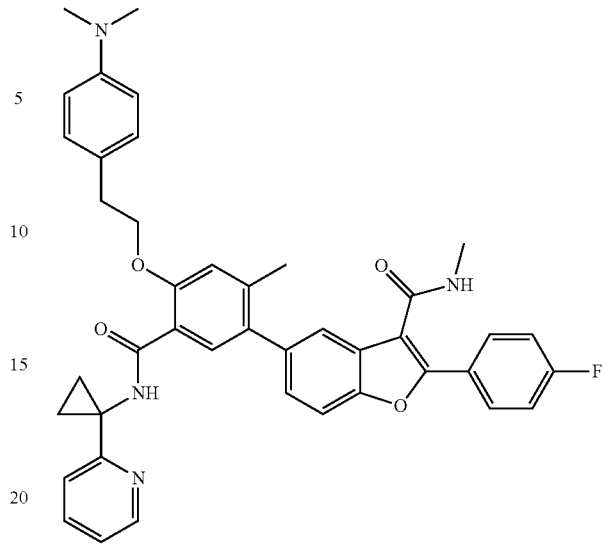

5-(4-(4-(Dimethylamino)phenethoxy)-2-methyl-5-(1-(pyridin-2-yl)cyclopropylcarbamoyl)phenyl)-2-(4-fluorophenyl)-N-methylbenzofuran-3-carboxamide. ¹H NMR (400 MHz, THF-d8) δ ppm 1.08-1.18 (m, 2H), 1.58-1.65 (m, 2H), 2.29 (s, 3H), 2.78 (s, 6H), 2.88 (d, J=4.52 Hz, 3H), 3.10 (t, J=6.27 Hz, 2 H), 4.45 (t, J=6.40 Hz, 2H), 6.55 (d, J=8.78 Hz, 2H), 7.00 (ddd, J=7.53, 4.77, 1.00 Hz, 1H), 7.07-7.14 (m, 3H), 7.17-7.34 (m, 4H), 7.49 (td, J=7.72, 1.88 Hz, 1H), 7.53-7.57 (m, 2H), 7.61 (d, J=1.26 Hz, 1H), 7.97 (s, 1H), 8.11-8.20 (m, 2H), 8.31 (s, 1H), 8.36-8.41 (m, 1H). LCMS m/z 683.6 (M+H), rt=2.303 min. HPLC (Sunfire C18) rt=6.475 min, 100% purity and (XBridge Phenyl C18) rt=12.563 min., 97.9% purity.

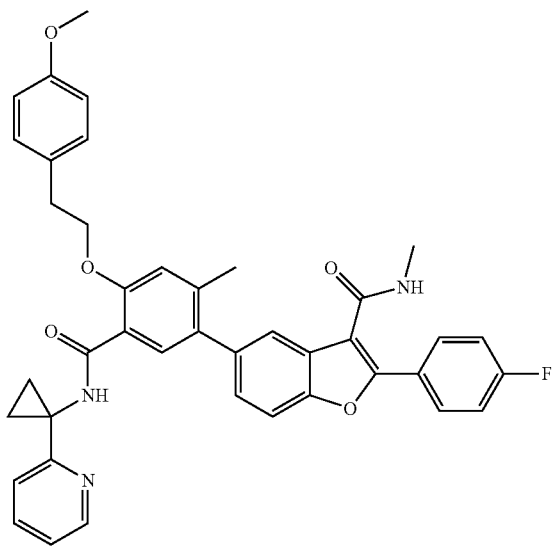

2-(4-Fluorophenyl)-5-(4-(4-methoxyphenethoxy)-2-methyl-5-(1-(pyridin-2-yl)cyclopropyl carbamoyl)phenyl)-N-methylbenzofuran-3-carboxamide. ¹H NMR (400 MHz, THF-d8) δ ppm 1.14-1.23 (m, 2H), 1.61-1.67 (m, 2H), 2.28 (s, 3H), 2.87 (d, J=4.77 Hz, 3H), 3.16 (t, J=6.53 Hz, 2H), 3.58 (s, 3H), 4.47 (t, J=6.53 Hz, 2H), 6.70-6.77 (m, 2H), 7.09 (s, 1H), 7.13 (dd, J=7.03, 5.52 Hz, 1H), 7.16-7.26 (m, 5H), 7.39 (d, J=8.03 Hz, 1H), 7.51-7.68 (m, 4H), 7.94 (s, 1H), 8.08-8.19 (m, 2H), 8.42 (s, 1H), 8.49 (d, 1H). LCMS m/z 670.6 (M+H), rt=2.965 min. HPLC (Sunfire C18) rt=8.329 min, 100% purity and (XBridge Phenyl C18) rt=12.301 min., 98.7% purity.

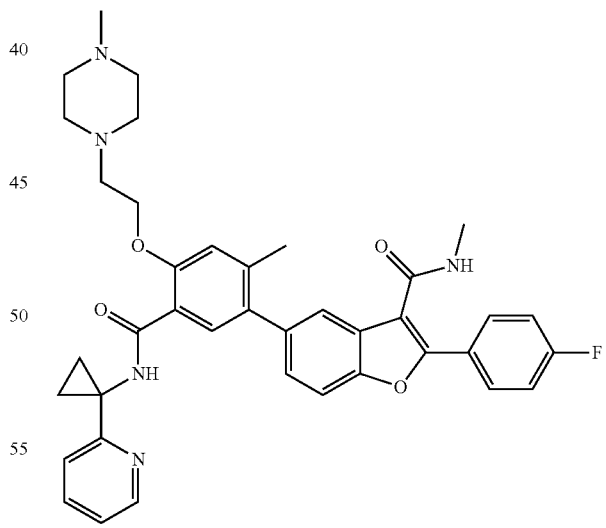

2-(4-Fluorophenyl)-N-methyl-5-(2-methyl-4-(2-(4-methylpiperazin-1-yl)ethoxy)-5-(1-(pyridin-2-yl)cyclopropylcarbamoyl)phenyl)benzofuran-3-carboxamide. ¹H NMR (400 MHz, THF-d8) δ ppm 1.39-1.48 (m, 2H), 1.62-1.69 (m, 2H), 2.28 (s, 3H), 2.69 (s, 3H), 2.88 (d, J=4.77 Hz, 3H), 3.35-3.45 (m, 4H), 3.45-3.56 (m, 6 H), 4.53 (t, J=4.77 Hz, 2H), 7.10 (s, 1H), 7.18-7.29 (m, 3H), 7.33-7.44 (m, 1H), 7.52-7.66 (m, 3H), 7.69-7.78 (m, 2H), 7.92-8.02 (m, 1H), 8.06-8.17 (m, 2H), 8.61 (d, J=5.27 Hz, 1H), 9.10 (s, 1H). LCMS m/z 662.6 (M+H), rt=1.983 min. HPLC (Sunfire C18) rt=5.590 min, 99.5% purity and (XBridge Phenyl C18) rt=11.491 min., 99.1% purity.

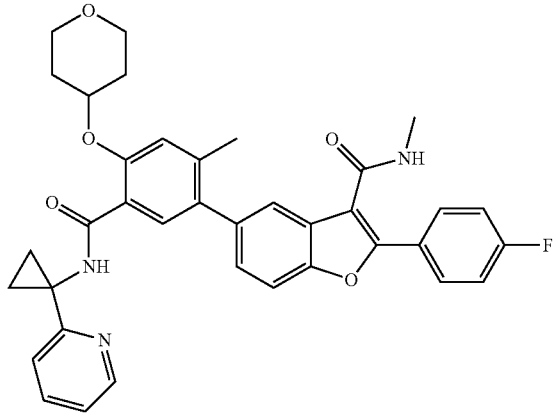

2-(4-Fluorophenyl)-N-methyl-5-(2-methyl-5-(1-(pyridin-2-yl)cyclopropylcarbamoyl)-4-(tetrahydro-2H-pyran-4-yloxy)phenyl)benzofuran-3-carboxamide. ¹H NMR (400 MHz, THF-d8) δ ppm 1.25-1.35 (m, 2H), 1.63-1.70 (m, 2H), 1.76-1.90 (m, 2H), 2.09-2.20 (m, 2H), 2.28 (s, 3H), 2.88 (d, J=4.77 Hz, 3H), 3.49-3.57 (m, 2H), 3.93 (ddd, J=11.80, 4.52, 4.27 Hz, 2H), 4.84 (ddd, J=8.47, 4.52, 4.33 Hz, 1H), 7.01 (ddd, 1H), 7.12 (s, 1H), 7.18-7.29 (m, 3H), 7.42-7.48 (m, 1H), 7.51-7.59 (m, 3H), 7.62 (d, J=1.25 Hz, 1H), 7.94 (s, 1H), 8.09-8.18 (m, 2H), 8.37-8.43 (m, 1H), 8.59 (s, 1H). LCMS m/z 620.6 (M+H), rt=2.570 min. HPLC (Sunfire C18) rt=7.425 min, 99.3% purity and (XBridge Phenyl C18) rt=11.581 min., 99.4% purity.

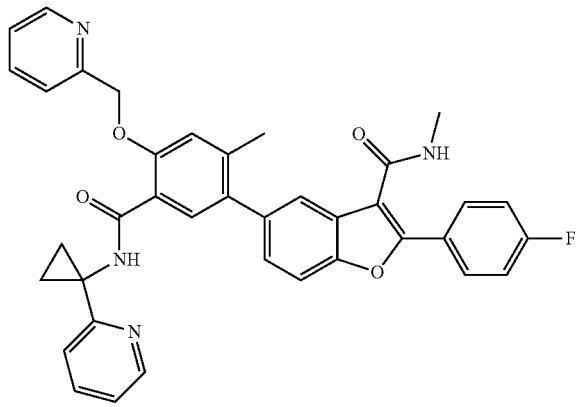

2-(4-Fluorophenyl)-N-methyl-5-(2-methyl-5-(1-(pyridin-2-yl)cyclopropylcarbamoyl)-4-(pyridin-2-ylmethoxy)phenyl)benzofuran-3-carboxamide. ¹H NMR (400 MHz, THF-d8) δ ppm 1.24-1.32 (m, 2H), 1.64-1.71 (m, 2H), 2.30 (s, 3H), 2.89 (d, J=4.77 Hz, 3H), 5.45 (s, 2H), 6.93-7.02 (m, 1H), 7.15-7.31 (m, 5H), 7.41-7.52 (m, 3H), 7.57 (d, J=8.53 Hz, 2H), 7.64 (d, J=1.25 Hz, 1H), 7.76 (td, J=7.65, 1.76 Hz, 1H), 7.99 (s, 1H), 8.12-8.21 (m, 2H), 8.33-8.41 (m, 1H), 8.55 (d, J=4.02 Hz, 1H), 9.58 (s, 1H). LCMS m/z 627.5 (M+H), rt=2.368 min. HPLC (Sunfire C18) rt=6.703 min, 99.7% purity and (XBridge Phenyl C18) rt=11.521 min., 99.7% purity.

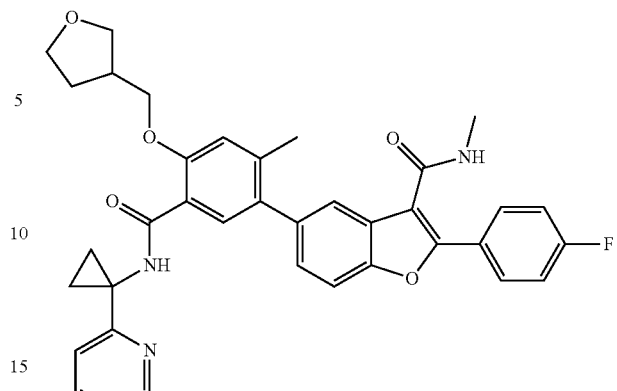

2-(4-Fluorophenyl)-N-methyl-5-(2-methyl-5-(1-(pyridin-2-yl)cyclopropylcarbamoyl)-4-((tetrahydrofuran-3-yl)methoxy)phenyl)benzofuran-3-carboxamide. ¹H NMR (400 MHz, THF-d8) δ ppm 1.23-1.33 (m, 2H), 1.63-1.69 (m, 2H), 1.76-1.85 (m, 1H), 2.07-2.17 (m, 1H), 2.29 (s, 3H), 2.78-2.86 (m, 1H), 2.88 (d, J=4.52 Hz, 3H), 3.60-3.66 (m, 1 H), 3.73-3.88 (m, 3H), 4.16-4.24 (m, 2H), 7.00 (ddd, J=7.40, 4.77, 1.13 Hz, 1H), 7.07 (s, 1H), 7.17-7.30 (m, 3H), 7.45 (d, J=7.78 Hz, 1H), 7.51-7.66 (m, 4H), 7.95 (s, 1H), 8.10-8.19 (m, 2H), 8.39 (d, J=4.02 Hz, 1H), 8.55 (s, 1H). LCMS m/z 620.6 (M+H), rt=2.850 min. HPLC (Sunfire C18) rt=7.376 min, 99.1% purity and (XBridge Phenyl C18) rt=11.673 min., 98.7% purity.

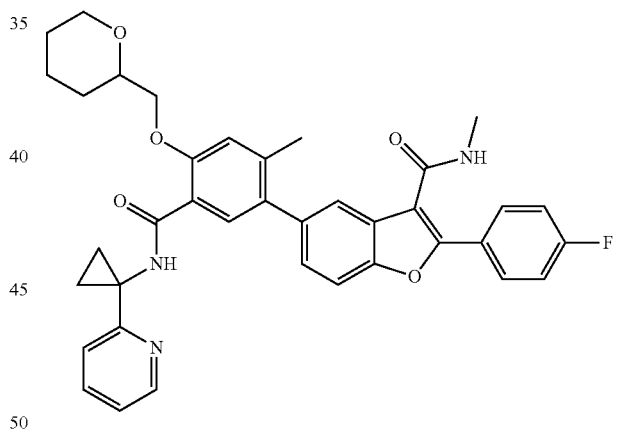

2-(4-Fluorophenyl)-N-methyl-5-(2-methyl-5-(1-(pyridin-2-yl)cyclopropylcarbamoyl)-4-((tetrahydro-2H-pyran-2-yl)methoxy)phenyl)benzofuran-3-carboxamide. ¹H NMR (400 MHz, THF) ppm 1.27 (m, 2H), 1.48 (m, 4H), 1.67 (m, 2H), 1.80 (m, 2H), 2.28 (s, 3H), 2.89 (d, J=5 Hz, 3H), 3.40 (d, J=3 Hz, 1H), 3.77 (m, 1H), 3.90 (d, J=11 Hz, 1H), 4.06 (dd, J=10, 7 Hz, 1H), 4.31 (dd, J=10, 3 Hz, 1H), 7.01 (ddd, 1H), 7.05 (s, 1H), 7.23 (m, 3H), 7.53 (m, 4H), 7.62 (d, J=1 Hz, 1H), 7.97 (s, 1H), 8.16 (m, 2H), 8.40 (m, 1 H), 9.02 (s, 1H). LCMS m/z 634.6 (M+H), rt=2.876 min. HPLC (Sunfire C18) rt=7.981 min, 100% purity and (XBridge Phenyl C18) rt=12.164 min., 100% purity.

637

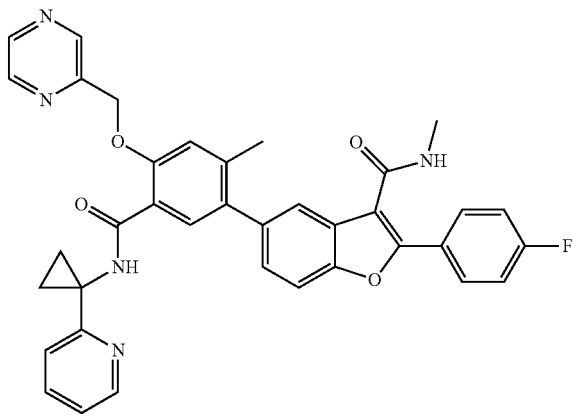

2-(4-Fluorophenyl)-N-methyl-5-(2-methyl-4-(pyrazin-2-ylmethoxy)-5-(1-(pyridin-2-yl)cyclopropylcarbamoyl)phenyl)benzofuran-3-carboxamide. $^1$H NMR (400 MHz, THF-d8) δ ppm 1.24-1.32 (m, 2H), 1.64-1.70 (m, 2H), 2.31 (s, 3H), 2.89 (d, J=4.77 Hz, 3H), 5.52 (s, 2H), 6.97 (ddd, J=6.84, 4.96, 1.51 Hz, 1H), 7.17-7.25 (m, 3H), 7.28 (dd, J=8.53, 1.76 Hz, 1H), 7.40-7.49 (m, 2H), 7.52-7.61 (m, 2H), 7.64 (d, J=1.25 Hz, 1H), 7.98 (s, 1H), 8.10-8.21 (m, 2H), 8.33-8.41 (m, 1H), 8.52-8.60 (m, 2H), 8.81 (d, J=1.26 Hz, 1H), 9.22 (s, 1H). LCMS m/z 628.6 (M+H), rt=2.462 min. HPLC (Sunfire C18) rt=7.028 min, 100% purity and (XBridge Phenyl C18) rt=11.429 min., 100% purity.

638

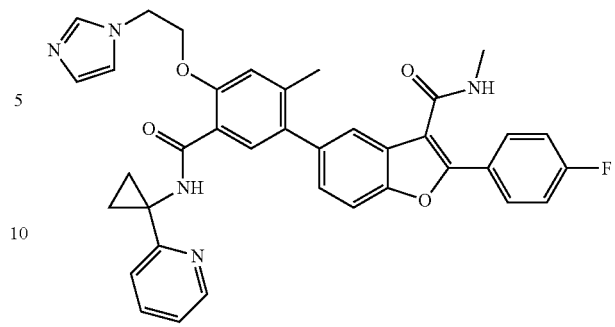

5-(4-(2-(1H-Imidazol-1-yl)ethoxy)-2-methyl-5-(1-(pyridin-2-yl)cyclopropylcarbamoyl)phenyl)-2-(4-fluorophenyl)-N-methylbenzofuran-3-carboxamide. $^1$H NMR (400 MHz, THF-d8) δ ppm 1.24-1.32 (m, 2H), 1.59-1.65 (m, 2H), 2.27 (s, 3H), 2.88 (d, J=4.52 Hz, 3H), 4.61 (t, J=4.64 Hz, 2H), 4.78 (t, J=4.52 Hz, 2H), 7.03 (s, 1H), 7.17-7.29 (m, 4H), 7.44 (s, 1H), 7.48-7.69 (m, 5 H), 7.71-7.81 (m, 2H), 8.06-8.15 (m, 2H), 8.49 (d, J=4.02 Hz, 1H), 8.59 (s, 1H), 9.02 (s, 1H). LCMS m/z 630.5 (M+H), rt=2.015 min. HPLC (Sunfire C18) rt=5.895 min, 100% purity and (XBridge Phenyl C18) rt=11.013 min., 100% purity.

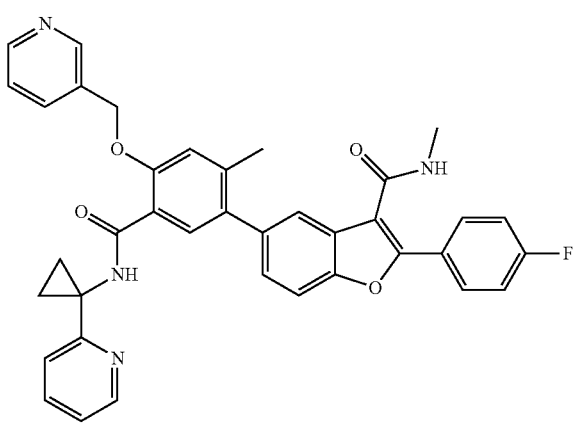

2-(4-Fluorophenyl)-N-methyl-5-(2-methyl-5-(1-(pyridin-2-yl)cyclopropylcarbamoyl)-4-(pyridin-3-ylmethoxy)phenyl)benzofuran-3-carboxamide $^1$H NMR (400 MHz, THF-d8) δ ppm 1.26-1.36 (m, 2H), 1.54-1.62 (m, 2H), 2.26 (s, 3H), 2.87 (d, J=4.77 Hz, 3H), 5.51 (s, 2H), 7.13 (s, 1H), 7.17-7.29 (m, 3H), 7.41-7.48 (m, 1H), 7.55 (d, J=8.03 Hz, 1H), 7.58-7.65 (m, 2H), 7.75-7.85 (m, 3H), 7.99 (td, J=7.78, 1.76 Hz, 1H), 8.06-8.14 (m, 2H), 8.50 (d, J=8.03 Hz, 1H), 8.62 (d, J=4.52 Hz, 1H), 8.77-8.84 (m, 1H), 8.96-9.07 (m, 2H). LCMS m/z 627.5 (M+H), rt=2.062 min. HPLC (Sunfire C18) rt=5.808 min, 100% purity and (XBridge Phenyl C18) rt=11.143 min., 99.5% purity.

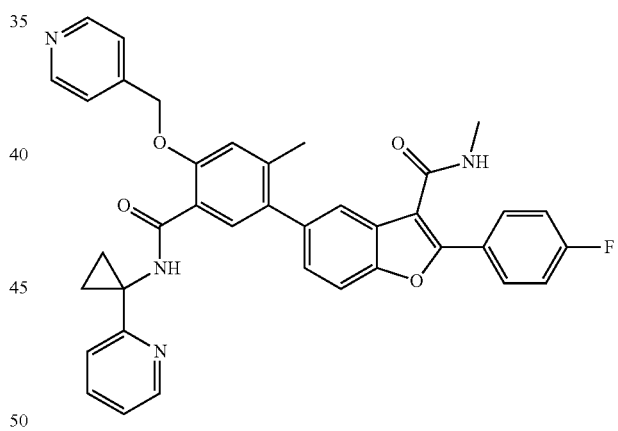

2-(4-Fluorophenyl)-N-methyl-5-(2-methyl-5-(1-(pyridin-2-yl)cyclopropylcarbamoyl)-4-(pyridin-4-ylmethoxy)phenyl)benzofuran-3-carboxamide. $^1$H NMR (400 MHz, THF-d8) δ ppm 1.34-1.43 (m, 2H), 1.58-1.65 (m, 2H), 2.23 (s, 3H), 2.88 (d, J=4.77 Hz, 3H), 5.60 (s, 2H), 7.02 (s, 1H), 7.17-7.28 (m, 3H), 7.48 (td, J=6.53, 1.00 Hz, 1H), 7.55 (d, J=8.03 Hz, 1H), 7.58-7.65 (m, 2H), 7.77 (s, 1H), 7.85 (d, J=8.03 Hz, 1H), 7.96-8.06 (m, 3H), 8.06-8.15 (m, 2H), 8.63 (d, J=4.52 Hz, 1H), 8.85 (d, J=6.53 Hz, 2H), 9.14 (s, 1H). LCMS m/z 627.5 (M+H), rt=2.030 min. HPLC (Sunfire C18) rt=5.740 min, 100% purity and (XBridge Phenyl C18) rt=11.278 min., 100% purity.

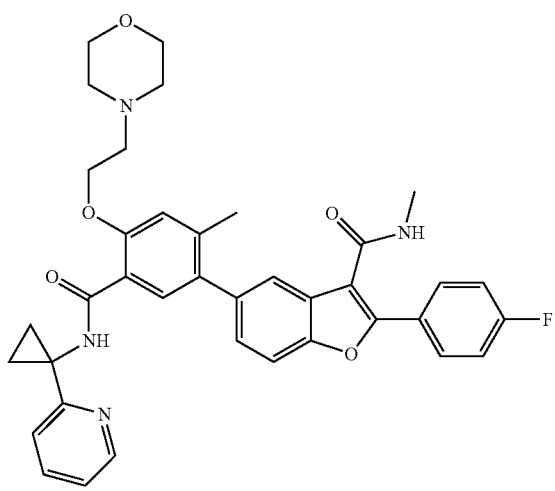

2-(4-Fluorophenyl)-N-methyl-5-(2-methyl-4-(2-morpholinoethoxy)-5-(1-(pyridin-2-yl)cyclopropylcarbamoyl)phenyl)benzofuran-3-carboxamide. ¹H NMR (400 MHz, THF-d8) δ ppm 1.43-1.55 (m, 2H), 1.65-1.72 (m, 2H), 2.27 (s, 3H), 2.88 (d, J=4.77 Hz, 3H), 3.37 (br. s., 4H), 3.68 (t, J=4.89 Hz, 2H), 3.81 (br. s., 4H), 4.66 (t, J=4.77 Hz, 2H), 7.12-7.32 (m, 4H), 7.50 (td, J=6.53, 1.00 Hz, 1H), 7.56 (d, J=8.53 Hz, 1H), 7.62 (d, J=1.25 Hz, 1H), 7.63-7.70 (m, 2H), 7.78 (d, J=8.03 Hz, 1H), 8.02-8.16 (m, 3H), 8.60-8.70 (m, 1H), 9.26 (s, 1H). LCMS m/z 649.5 (M+H), rt=2.112 min. HPLC (Sunfire C18) rt=9.464 min, 100% purity and (XBridge Phenyl C18) rt=15.487 min., 99.9% purity.

An alternative approach to the synthesis of 4' ether linked analogs is the treatment of the 4'-phenol-benzofuran with alkyl bromides and an excess of cesium carbonate in DMF. This route is shown below.

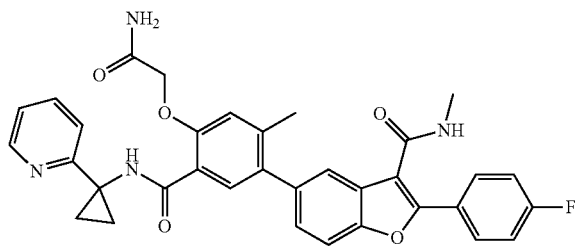

5-(4-(2-Amino-2-oxoethoxy)-2-methyl-5-(1-(pyridin-2-yl)cyclopropylcarbamoyl)phenyl)-2-(4-fluorophenyl)-N-methylbenzofuran-3-carboxamide. To a sealed tube was added DMF (2 mL), 2-(4-fluorophenyl)-5-(4-hydroxy-2-methyl-5-(1-(pyridin-2-yl)cyclopropylcarbamoyl)phenyl)-N-methylbenzofuran-3-carboxamide (40.2 mg, 0.075 mmol), 2-bromoacetamide (31.0 mg, 0.225 mmol) and cesium carbonate (98 mg, 0.300 mmol). The tube was sealed and the mixture heated overnight at 85° C. The reaction mixture was cooled to room temperature, diluted with methanol (2 mL) and the crude product was purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 30-100% B and a flow rate of 40 mL/min. over 12 minutes with a 10 minute hold. The LC/MS data was obtained on a Shimadzu analytical LC/Micromass Platform LC (ESI+) at 220 nm using the following set of conditions: The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. Obtained 34.5 mgs of TFA salt of 5-(4-(2-amino-2-oxoethoxy)-2-methyl-5-(1-(pyridin-2-yl)cyclopropylcarbamoyl)phenyl)-2-(4-fluorophenyl)-N-methylbenzofuran-3-carboxamide, as a white solid (77.0% yield). ¹H NMR (400 MHz, CD₃OD) δ ppm 1.75-1.88 (m, 4H), 2.35 (s, 3H), 2.93 (s, 3H), 4.87 (s, 2H), 7.08 (s, 1H), 7.23-7.35 (m, 3H), 7.56 (d, J=1.25 Hz, 1H), 7.63 (d, J=8.53 Hz, 1H), 7.76-7.88 (m, 3H), 7.91-8.00 (m, 2H), 8.43 (td, J=7.97, 1.63 Hz, 1H), 8.56-8.63 (m, 1H). LCMS m/z 593.5 (M+H), rt=2.232 min., 100% purity. HPLC (Sunfire C18) rt=6.306 min, 99.5% purity and (XBridge Phenyl C18) rt=9.889 min., 99.1% purity.

The following examples were synthesized in a similar fashion to that described for 5-(4-(2-amino-2-oxoethoxy)-2-methyl-5-(1-(pyridin-2-yl)cyclopropylcarbamoyl)phenyl)-2-(4-fluorophenyl)-N-methylbenzofuran-3-carboxamide, and using the same conditions for preparative HPLC, analytical HPLC and LCMS.

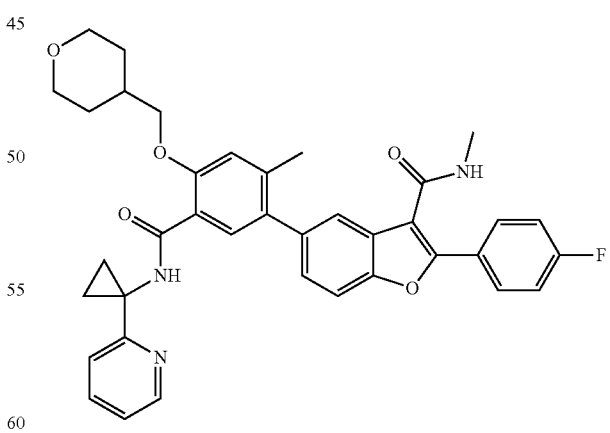

2-(4-Fluorophenyl)-N-methyl-5-(2-methyl-5-(1-(pyridin-2-yl)cyclopropylcarbamoyl)-4-((tetrahydro-2H-pyran-4-yl)methoxy)phenyl)benzofuran-3-carboxamide. ¹H NMR (400 MHz, THF-d8) δ ppm 1.27-1.35 (m, 2H), 1.41-1.55 (m, 2H), 1.63-1.69 (m, 2H), 1.75-1.80 (m, 2 H), 2.21 (d, 1H), 2.28 (s, 3H), 2.88 (d, J=4.77 Hz, 3H), 3.32-3.44 (m, 2H), 3.92 (dd, J=11.29, 3.01 Hz, 2H), 4.09 (d, J=6.27 Hz, 2H), 7.05 (s, 1H), 7.13-7.29 (m, 4 H), 7.47-7.64 (m, 4H), 7.70 (t, J=7.65 Hz, 1H), 7.89 (s, 1H), 8.08-8.19 (m, 2H), 8.50 (d, J=4.52 Hz, 1H), 8.62 (s, 1H). LCMS m/z 634.5 (M+H), rt=2.650 min. HPLC (Sunfire C18) rt=7.225 min, 100% purity and (XBridge Phenyl C18) rt=12.039 min., 99.5% purity.

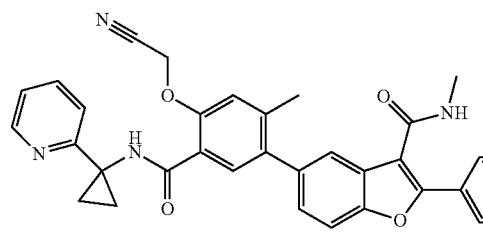

5-(4-(Cyanomethoxy)-2-methyl-5-(1-(pyridin-2-yl)cyclopropylcarbamoyl)phenyl)-2-(4-fluoro phenyl)-N-methyl-benzofuran-3-carboxamide. ¹H NMR (400 MHz, THF-d8) δ ppm 1.29-1.35 (m, 2H), 1.62-1.67 (m, 2H), 2.33 (s, 3H), 2.89 (d, J=4.77 Hz, 3H), 5.20 (s, 2H), 7.08-7.13 (m, 1H), 7.17 (s, 1H), 7.22 (t, J=8.91 Hz, 2H), 7.28 (dd, J=8.53, 1.76 Hz, 1H), 7.51-7.57 (m, 1H), 7.58 (d, J=8.28 Hz, 2H), 7.63-7.69 (m, 2H), 7.85 (s, 1H), 8.10-8.18 (m, 2H), 8.40-8.49 (m, 2H). LCMS m/z 575.5 (M+H), rt=2.475 min. HPLC (Sunfire C18) rt=7.165 min, 98.8% purity and (XBridge Phenyl C18) rt=11.124 min., 98.7% purity.

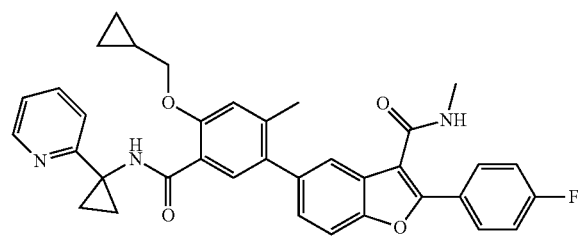

5-(4-(Cyclopropylmethoxy)-2-methyl-5-(1-(pyridin-2-yl)cyclopropylcarbamoyl)phenyl)-2-(4-fluorophenyl)-N-methylbenzofuran-3-carboxamide. ¹H NMR (400 MHz, THF-d8) δ ppm 0.39-0.49 (m, 2H), 0.62-0.71 (m, 2H), 1.27-1.37 (m, 2H), 1.38-1.49 (m, 1H), 1.64-1.70 (m, 2H), 2.28 (s, 3 H), 2.88 (d, J=4.77 Hz, 3H), 4.08 (d, J=7.03 Hz, 2H), 7.01 (s, 1H), 7.14-7.28 (m, 4H), 7.52-7.65 (m, 4H), 7.71 (dd, J=7.53, 1.51 Hz, 1H), 7.91-7.96 (m, 1H), 8.09-8.18 (m, 2H), 8.52 (d, J=4.77 Hz, 1H), 8.90 (s, 1H). LCMS m/z 590.6 (M+H), rt=2.841 min. HPLC (Sunfire C18) rt=8.029 min, 100% purity and (XBridge Phenyl C18) rt=12.101 min., 100% purity.

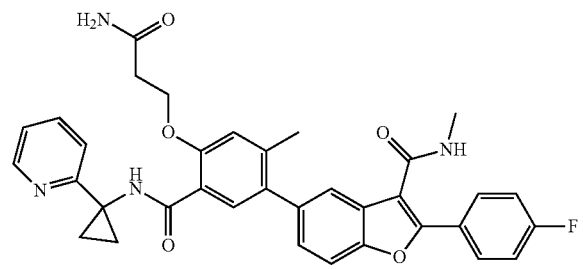

5-(4-(3-Amino-3-oxopropoxy)-2-methyl-5-(1-(pyridin-2-yl)cyclopropylcarbamoyl)phenyl)-2-(4-fluorophenyl)-N-methylbenzofuran-3-carboxamide. ¹H NMR (400 MHz, THF-d8) δ ppm 1.34-1.41 (m, 2H), 1.61-1.66 (m, 2H), 2.29 (s, 3H), 2.73 (t, J=5.65 Hz, 2H), 2.89 (d, J=4.77 Hz, 3H), 4.45 (t, J=5.77 Hz, 2H), 6.56 (br. s., 1H), 7.02 (br. s., 1H), 7.08 (s, 1H), 7.15 (m, 1H), 7.17-7.30 (m, 3H), 7.52-7.63 (m, 4H), 7.66-7.74 (m, 1H), 7.91 (s, 1H), 8.10-8.20 (m, 2H), 8.47-8.55 (m, 1H), 8.85 (s, 1H). LCMS m/z 607.6 (M+H), rt=2.308 min. HPLC (Sunfire C18) rt=6.441 min, 96.7% purity and (XBridge Phenyl C18) rt=10.639 min., 98.8% purity.

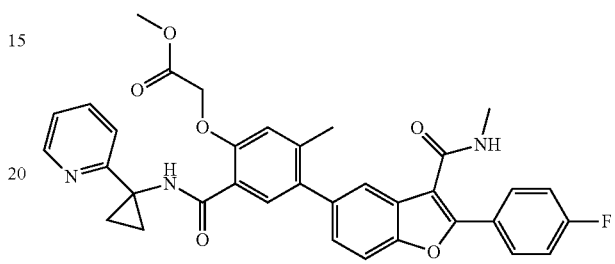

Methyl 2-(4-(2-(4-fluorophenyl)-3-(methylcarbamoyl)benzofuran-5-yl)-5-methyl-2-(1-(pyridin-2-yl)cyclopropylcarbamoyl)phenoxy)acetate. ¹H NMR (400 MHz, THF-d8) δ ppm 1.32-1.40 (m, 2H), 1.68 (m, 2H), 2.29 (s, 3H), 2.88 (d, J=4.52 Hz, 3H), 3.80 (s, 3H), 4.95 (s, 2H), 7.00-7.10 (m, 2H), 7.17-7.31 (m, 3 H), 7.47-7.67 (m, 5H), 7.99-8.05 (m, 1H), 8.10-8.20 (m, 2H), 8.45 (d, J=4.02 Hz, 1H), 9.23 (s, 1H). LCMS m/z 608.5 (M+H), rt=2.507 min., 98.6% purity. HPLC (Sunfire C18) rt=7.203 min, 99.1% purity and (XBridge Phenyl C18) rt=11.494 min., 97.1% purity.

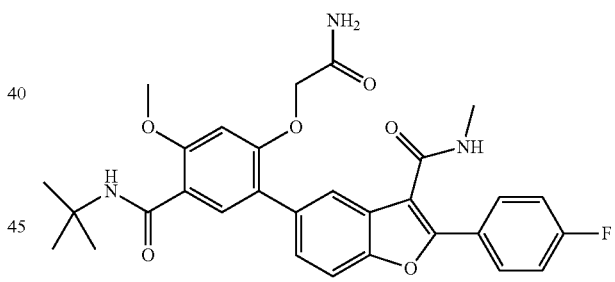

5-(2-(2-Amino-2-oxoethoxy)-5-(tert-butylcarbamoyl)-4-methoxyphenyl)-2-(4-fluorophenyl)-N-methylbenzofuran-3-carboxamide. To a 25 mL flask was added 4-(2-amino-2-oxoethoxy)-5-(2-(4-fluorophenyl)-3-(methyl carbamoyl) benzofuran-5-yl)-2-methoxybenzoic acid (49.2 mg, 0.1 mmol), DMF (2 mL), N-ethyl-N-diisopropylpropan-2-amine (0.069 mL, 0.396 mmol), 2-methylpropan-2-amine (18 mg, 26 µL, 0.246 mmol) and finally HATU (2-(3H-[1,2,3]triazolo[4,5-b]pyridin-3-yl)-1,1,3,3-tetramethyl isouronium hexafluorophosphate(V), 151 mg, 0.396 mmol). The flask was sealed with a septum, placed under N₂ and stirred at room temperature overnight. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 µm C18 19×150 mm column at a gradient of 20-100% B and a flow rate of 25 mL/min. over 22 minutes with a 8 minute hold. The solvent was removed giving 28.3 mgs (52% yield) of 5-(2-(2-amino-2-oxoethoxy)-4-methoxy-5-(1-(pyridin-2-yl)cyclopropylcarbamoyl)phenyl)-2-(4-fluorophenyl)-N-methylbenzofuran-3-carboxamide as a yellow powder. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.43 (s, 9H), 2.91 (d, J=4.77 Hz, 3H), 4.03 (s, 3H), 4.51 (s, 2H), 6.43 (br. s., 1H), 6.71-6.77 (m, 1H), 6.78 (s, 1H), 7.21 (t, J=8.78 Hz, 2H), 7.46-7.52 (m, 1H), 7.52-7.54 (m, 1H), 7.54-7.59 (m, 1H), 7.67 (s, 1H), 7.92 (s, 1H), 8.10-8.16 (m, 2H), 8.19 (s, 1 H). LCMS rt=2.976 min., m/z 548.2 (M+H), 98.3% purity. HPLC rt=9.088 min. (Sunfire C18), 99.0% purity and 11.588 min. (Gemini C18), 99.4% purity.

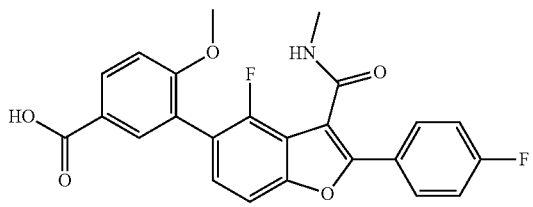

3-(4-fluoro-2-(4-fluorophenyl)-3-(methylcarbamoyl)benzofuran-5-yl)-4-methoxy benzoic acid. To a small sealed tube was added 4-fluoro-2-(4-fluorophenyl)-3-(methylcarbamoyl)benzofuran-5-yl trifluoromethanesulfonate (64.5 mg, 0.111 mmol), dioxane (6 mL), water (1.200 mL), 3-borono-4-methoxybenzoic acid (26.1 mg, 0.133 mmol), cesium carbonate (54.2 mg, 0.167 mmol) and finally Tetrakis(triphenylphosphine)palladium(0) (2.6 mg, 2.2 μmol). The tube was sealed and the reaction mixture heated at 85° C. for twenty hours. The reaction mixture was cooled to room temperature, pushed through a plug of celite and evaporated to a dark oil under a stream of nitrogen. The residue was triturated with 15 mL of ice water then air dried overnight giving 17.2 mgs (35.4% yield) of 3-(4-fluoro-2-(4-fluorophenyl)-3-(methylcarbamoyl)benzofuran-5-yl)-4-methoxy benzoic acid as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. LCMS rt=2.770 min., m/z 438.3 (M+H), 93% purity.

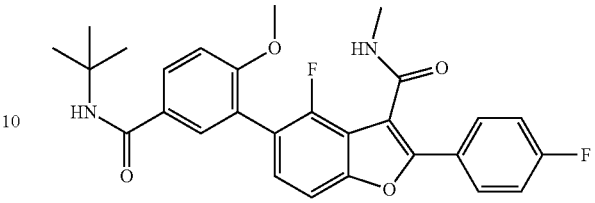

5-(5-(tert-Butylcarbamoyl)-2-methoxyphenyl)-4-fluoro-2-(4-fluorophenyl)-N-methylbenzofuran-3-carboxamide. To a 25 mL RBF was added 3-(4-fluoro-2-(4-fluorophenyl)-3-(methylcarbamoyl)benzofuran-5-yl)-4-methoxybenzoic acid (17.2 mg, 0.039 mmol), DMF (1 mL), N-ethyl-N-isopropylpropan-2-amine (0.027 mL, 0.157 mmol), 2-methylpropan-2-amine (0.012 mL, 0.118 mmol), and HATU, (2-(3H-[1,2,3]triazolo[4,5-b]pyridin-3-yl)-1,1,3,3-tetramethyl isouronium hexafluorophosphate(V) (59.8 mg, 0.157 mmol). The mixture was stirred at room temperature under nitrogen overnight. The crude reaction was diluted with 2 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire C18 19×150 mm column at a gradient of 30-100% B and a flow rate of 25 mL/min. over 20 minutes with a 7 minute hold. Solvent was removed giving 15.7 mgs (80% yield) of 5-(5-(tert-butylcarbamoyl)-2-methoxyphenyl)-4-fluoro-2-(4-fluorophenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl C18 3.5 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.42 (s, 9H), 2.87 (d, J=4.77 Hz, 3H), 3.79 (s, 3H), 6.92 (s, 1H), 7.06 (d, J=8.53 Hz, 1H), 7.17-7.30 (m, 3H), 7.39 (d, J=8.28 Hz, 1H), 7.71-7.77 (m, 2H), 7.87 (dd, J=8.78, 2.26 Hz, 1H), 8.03-8.12 (m, 2H). LCMS m/z 493.4 (M+H), rt=3.281 min. HPLC (Sunfire C18) rt=14.257 min, 98.7% purity and (XBridge Phenyl C18) rt=14.852 min., 98.8% purity.

The procedures which follow utilize the methods as described within

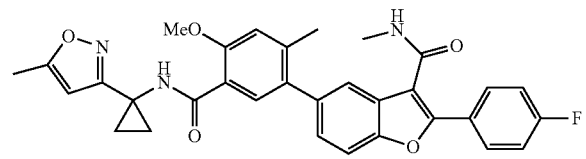

2-(4-Fluorophenyl)-5-(4-methoxy-2-methyl-5-(1-(5-methylisoxazol-3-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.2 g, 0.46 mmol, 1 eq), 1-(5-methylisoxazol-3-yl)cyclopropanamine (0.074 g, 0.5 mmol, 1.1 eq), HOBT (0.094 g, 0.69 mmol, 1.5 eq), EDC.HCl (0.0.13 g, 0.69 mmol, 1.5 eq), in DCM at ambient temperature and under a nitrogen atmosphere was added diisopropylethylamine (0.19 ml, 1.3 mmol, 3.0 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by Preparative TLC (Eluent Hexane:Ethyl acetate 1:1, 300 ml). Yield: 0.1 g (39.22%). 1H NMR (400 MHz, CD$_3$OD): δ 1.39-1.48 (m, 4H), 2.36 (s, 3H), 2.380-2.382 (d, 3H, J=0.8 Hz), 2.96 (s, 3H,), 4.05, (s, 3H), 6.05 (d, 1H, J=0.8 Hz), 7.12 (s, 1H), 7.26-7.34 (m, 3H), 7.58-7.59 (d, 1H, J=1.2 Hz), 7.62-7.64 (d, 1H, J=8.8 Hz), 7.81 (s, 1H), 7.96-7.98 (m, 2H). LCMS: (ES+) m/z=554.2 (M+H)$^+$ Column-Ascentis Express C18 (5×2.1 mm-2.7 μm)

Mphase A: 2% MeCN-98% H$_2$O-10 mM NH$_4$COOH
Mphase B: 98% MeCN-2% H$_2$O-10 mM NH$_4$COOH
Flow: 1 ML/Min

| Time | % A | % B |
|---|---|---|
| 0.0 | 100.0 | 0 |
| 1.5 | 0.0 | 100.0 |
| 3.2 | 0.0 | 100.0 |

RT min: 2.054, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 19.86
Wavelength: 220 nm, RT min: 19.86
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 17.976
Wavelength: 220 nm, RT min: 17.976

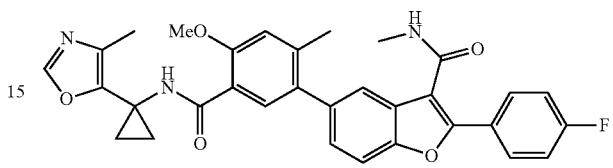

2-(4-Fluorophenyl)-5-(4-methoxy-2-methyl-5-(1-(4-methyloxazol-5-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.2 g, 0.46 mmol, 1 eq), 1-(4-methyloxazol-5-yl)cyclopropanamine (0.06 g, 0.46 mmol, 1.0 eq), HOBT (0.062 g, 0.46 mmol, 1.0 eq), EDC.HCl (0.08, 0.46 mmol, 1.0 eq), in DCM at ambient temperature and under a nitrogen atmosphere was added diisopropylethylamine (0.19 ml, 1.3 mmol, 3.0 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by Preparative TLC (Eluent Hexane:Ethyl acetate 1:1, 300 ml). Yield: 0.020 g (8.3%).

1H NMR (400 MHz, CD$_3$OD): δ 1.31-1.40 (m, 4H), 2.28 (s, 3H), 2.35 (s, 3H), 2.96 (s, 3H), 4.04 (s, 3H), 7.11 (s, 1H), 7.26-7.34 (m, 3H), 7.575-7.578 (d, 1H, J=1.2 Hz), 7.62-7.64 (d, 1H, J=8.4 Hz), 7.76 (s, 1H), 7.97-8.0 (m, 3H).
LCMS: (ES+) m/z=554.2 (M+H)$^+$
Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ML/Min

| Time | % A | % B |
|---|---|---|
| 0.0 | 100.0 | 0 |
| 1.5 | 0.0 | 100.0 |
| 3.2 | 0.0 | 100.0 |

RT min: 1.995, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 1 | 10 |
| 26 | 100 |
| 30 | 100 |

Wavelength: 254 nm, RT min: 18.553
Wavelength: 220 nm, RT min: 18.553
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.866
Wavelength: 220 nm, RT min: 16.866

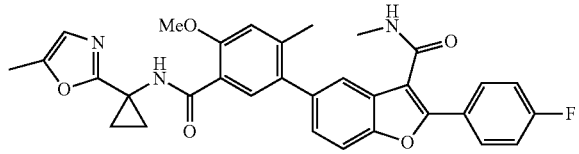

2-(4-Fluorophenyl)-5-(4-methoxy-2-methyl-5-(1-(5-methyloxazol-2-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.2 g, 0.46 mmol, 1 eq), 1-(5-methyloxazol-2-yl)cyclopropanamine (0.06 g, 0.46 mmol, 1.0 eq), HOBT (0.062 g, 0.46 mmol, 1.0 eq), EDC.HCl (0.08, 0.46 mmol, 1.0 eq), in DCM at ambient temperature and under a nitrogen atmosphere was added diisopropylethylamine (0.19 ml, 1.3 mmol, 3.0 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by Combiflash column chromatography (4 g flash column, CV 4.8 ml, 18 ml/min, max pressure 200 psi) using 0.5% Methanol/DCM. Yield: 0.030 g (11.76%). $^1$H NMR (400 MHz, CD$_3$OD): δ 1.43-1.46 (m, 2H), 1.61-1.65 (m, 2H), 2.29 (d, 3H, J=0.8 Hz), 2.37 (s, 3H), 2.96 (s, 3H), 4.06 (s, 3H), 6.69 (s, 1H,), 7.14 (s, 1H), 7.28 (apparent t, 2H), 7.34 (dd, 1H, J=1.6, 8.4 Hz), 7.59 (d, 1H, J=1.2 Hz), 7.64 (d, 1H, J=8.4 Hz), 7.88 (s, 1H), 7.96-8.00 (m, 2H). LCMS: (ES+) m/z=554.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 2.043, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 2 | 10 |
| 25 | 100 |
| 30 | 100 |

Wavelength: 254 nm, RT min: 18.681
Wavelength: 220 nm, RT min: 18.681
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 17.000
Wavelength: 220 nm, RT min: 17.000

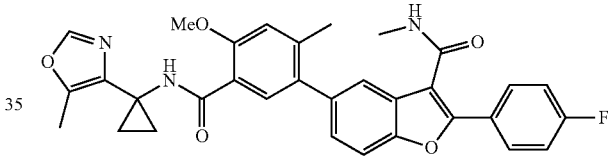

2-(4-Fluorophenyl)-5-(4-methoxy-2-methyl-5-(1-(5-methyloxazol-4-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.2 g, 0.46 mmol, 1 eq), 1-(5-methyloxazol-4-yl)cyclopropanamine (0.06 g, 0.46 mmol, 1.0 eq), HOBT (0.062 g, 0.46 mmol, 1.0 eq), EDC.HCl (0.08, 0.46 mmol, 1.0 eq), in DCM at ambient temperature and under a nitrogen atmosphere was added diisopropylethylamine (0.19 ml, 1.3 mmol, 3.0 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by by Combiflash column chromatography (4 g flash column, CV 4.8 ml, 18 ml/min, max pressure 200 psi) using 0.5% Methanol/DCM. Yield: 0.045 g (17.6%) $^1$H NMR (400 MHz, DMSO-d$_6$): δ 1.11-1.14 (m, 2H), 1.20-1.23 (m, 2H), 2.29 (s, 3H), 2.31 (s, 3H), 2.82 (d, 3H, J=4.4 Hz), 3.95 (s, 3H), 7.12 (s, 1H), 7.33 (dd, 1H, J=1.6, 8.4 Hz), 7.40 (apparent t, 2H, J=8.8 Hz), 7.49 (d, 1H, J=1.2 Hz), 7.60 (s, 1H), 7.72 (d, 1H, J=8.4 Hz), 7.97-8.01 (m, 2H), 8.04 (s, 1H), 8.46-8.48 (m, 1H), 8.67 (s, 1H).
LCMS: (ES+) m/z=554.2 (M+H)$^+$
Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ML/Min

| Time | % A | % B |
|---|---|---|
| 0.0 | 100.0 | 0 |
| 1.5 | 0.0 | 100.0 |
| 3.2 | 0.0 | 100.0 |

RT min: 1.931, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 3 | 10 |
| 25 | 100 |
| 30 | 100 |

Wavelength: 254 nm, RT min: 18.891
Wavelength: 220 nm, RT min: 18.891
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 17.019
Wavelength: 220 nm, RT min: 17.019

Methyl 2-Formamidoacetate. To an ethylformate (110 g, 148 mmol, 9.3 eq) solution containing glycine methyl ester hydrochloride (20.0 g, 159 mmol, 1 eq)) was added PTSA (20 mg) and the solution was brought to boil. Boiling TEA (17.69 g, 175 mmol, 1.1 eq) was added dropwise and the reaction mixture was refluxed overnight. The reaction mixture was then cooled to room temperature. A white TEA salt was filtered and the filtrate was concentrated to afford a light brown liquid. The crude product was purified by silica gel (230-400) column chromatography using 50% EtOAc/hexane to EtOAc as eluent. Yield: 20 g (85%). $^1$H NMR (400 MHz, CDCl$_3$): δ 3.7 (s, 3H), 4.04 (d, 2H, J=5.6 Hz), 6.88 (s, 1H), 8.20 (s, 1H).

LCMS: (ES+) m/z=118 (M+H)$^+$
ATLANTIS C18 (5.0×4.6-5.0 µm)
Mphase A: 10 mM Ammonium acetate
Mphase B: MeCN
Flow: 5 ml/Min

| Time | % A | % B |
|---|---|---|
| 0.0 | 95.0 | 5.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 2.115
Wavelength: 220 nm

Methyl isocyanoacetate. To the solution of Methyl 2-Formamidoacetate (10.0 g, 85 mmol, 1 eq) and TEA (21.58 g, 213 mmol, 2.5 eq) in methylene chloride at 0° C. was added POCl$_3$ (13.06 g, 85 mmol, 1 eq) dropwise. The solution turned red immediately. After all addition of the POCl$_3$ the reaction mixture was stirred for an additional 1 h at room temperature. To the reaction mixture was slowly added a Na$_2$CO$_3$ solution. The reaction mixture was stirred for 30 min. The organic phase was separated from aqueous phase, washed with saturated NaCl solution and dried over K$_2$CO$_3$. The resultant solution was filtered and the filtrate was evaporated under reduced pressure to give a dark brown oil. The compound was used with out further purification. Yield: 7.0 g (70%). $^1$H NMR (400 MHz, CDCl$_3$): δ 3.80 (s, 3H), 4.23 (s, 2H).

Methyl 5-methyoxazole-4-carboxylate. A stirred mixture of methyl isocyanoacetate (7.0 g, 70 mmol, 1 eq) and DBU (10.06 g, 70 mmol, 1 eq) in THF was cooled to 0° C., and a solution of acetic anhydride (7.14 g, 70 mmol, 1 eq) in THF was added dropwise over 15 min. The reaction mixture was stirred for 12 h at room temperature. The solvent was removed by Rota-vapor and water was added. The mixture was extracted with EtOAc. The crude product was purified by silica gel (230-400) column chromatography using 30% EtOAc/hexane. Yield: 6.8 g (98%). $^1$H NMR (400 MHz, CDCl$_3$): δ 2.54 (s, 3H), 3.80 (s, 3H), 7.69 (s, 1H).

LCMS: (ES+) m/z=142 (M+H)$^+$
Method: Column: Chromolith SpeedRod C18 (4.6×30) mm, 5 micron
Mphase A: 10% MeOH-90% H$_2$O-0.1% TFA
Mphase B: 90% MeOH-10% H$_2$O-0.1% TFA
Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 0.629
Wavelength: 220 nm

5-Methoxyoxazole-4-carboxamide. A mixture of NH$_4$OH (50 mL) and methyl 5-methyoxazole-4-carboxylate (7.8 g, 50 mmol, 1 eq) in a pressure tube was stirred at room temperature for 12 h. Water was then added to the reaction mixture, which was extracted with DCM to give the product. Yield: 4.1 g (47%). $^1$H NMR (400 MHz, CDCl$_3$): δ 2.66 (s, 3H), 5.68 (s, 1H), 6.81 (s, 1H), 7.68 (s, 1H). LCMS: (ES+) m/z=127 (M+H)$^+$ Method: Column: Chromolith SpeedRod C18 (4.6×30) mm, 5 micron
Mphase A: 10% MeOH-90% H$_2$O-0.1% TFA
Mphase B: 90% MeOH-10% H$_2$O-0.1% TFA Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 0.365
Wavelength: 220 nm 5-methyloxazole-4-carbonitrile. 5-Methoxyoxazole-4-carboxamide (2.1 g, 16 mmol, 1 eq) was dissolved in pyridine (30 mL) and treated with $POCl_3$ (3.8 g, 25 mmol, 1.5 eq). The resultant slurry which turned to a brown solution was stirred for 5 h at room temperature. The reaction mixture was diluted with ice and the aqueous layer was adjusted to pH 3 with 6M HCl. The mixture was extracted with ether. The organic layer was separated and washed with water, brine, dried to give the product. Yield: 0.4 g (30%). $^1$H NMR (400 MHz, $CDCl_3$): δ 2.53 (s, 3H), 7.79 (s, 1H). LCMS: (ES+) m/z=109.2 $(M+H)^+$ Column: Chromolith speed Rod C18 (4.6×30) mm, 5 μm
Mphase A: 10% MeOH-90% $H_2O$-10 mM $NH_4OAc$
Mphase B: 90% MeOH-10% $H_2O$-10 mM $NH_4OAc$
Flow: 5 ml/min

| Time (min): | 02 | 3 | |
|---|---|---|---|
| % B: | 0 | 100 | 0 |

RT: 0.780
Wavelength: 220 nm 1-(5-methyloxazole-4-yl)cyclopropanamine 5-methyloxazole-4-carbonitrile (0.9 g, 8.3 mmol, 1 eq) was dissolved in dry THF at room temperature, and titanium(IV) isopropoxide (2.84 g, 10 mmol, 1.2 eq) was added dropwise over a period of 15 minutes. The resulting mixture was stirred for 10 min and ethyl magnesium bromide (2.75 g, 2.5 eq) was added dropwise and slowly at ambient temperature, and the reaction was stirred for 1 h. $BF_3$.etherate (2.84 g, 20 mmol, 2.5 eq) was then added slowly at ambient temperature and the above mixture was stirred at ambient temperature for 3 h. Water was then added to the mixture and the pH was brought to 10 using 10% sodium hydroxide solution. The reaction mixture was extracted with dichloromethane, concentrated and purified by Combiflash chromatgraphy. Yield: 0.6 g (65%). $^1$H NMR (400 MHz, $CDCl_3$): δ 0.89 (t, J=4 Hz, 2H), 0.93 (t, J=4 Hz, 2H), 2.18 (s, 2H), 2.36 (s, 3H), 7.61 (s, 1H). LCMS: (ES+) m/z=138.7 $(M)^+$ Column: ATLANTIS C18 50×4.6 mm 5 nm
Mphase A: 10 mM Ammonium acetate
Mphase B MeCN
Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT: 2.763
Wavelength: 220 nm

Ethyl 4-methyloxazole-5-carboxylate. Ethyl 2-chloro-3-oxobutanoate (10 g, 254 mmoles, 1 eq) was dissolved in formamide (8.4 ml) and the reaction was stirred at 120° C. for 12 hours. The reaction mixture was then cooled to 0° C., added with water and extracted with ethyl acetate. The organic layer was separated and washed with brine and the product was purified by column chromatography (eluent 100% ethyl acetate), Yield: 7.9 g (85%). $^1$H NMR (400 MHz, $CDCl_3$): δ 1.34-1.37 (t, 3H, J=7.2 Hz), 2.45 (s, 3H), 4.32-4.38 (q, 2H, J=7.2 Hz), 7.85 (s, 1H). LCMS: (ES+) m/z=156.2 $(M+H)^+$ Column: XBRIDGE C18 (4.6×30) mm, 5 nm
Mphase A: 10% MeOH-90% $H_2O$-10 mM $NH_4OAc$
Mphase B: 90% MeOH-10% $H_2O$-10 mM $NH_4OAc$
Flow: 5 ml/min

| Time (min): | 0 | 2 | 3 |
|---|---|---|---|
| % B: | 0 | 100 | 0 |

RT: 0.892, Wavelength 220 nm 4-methyloxazole-5-carboxamide. A mixture of ethyl 4-methyloxazole-5-carboxylate (7.8 g, 50 mmoles) and ammonium hydroxide in a seal tube was stirred at rt for 12 hours. After completion of the reaction, solid was filtered and washed with water. The aqueous was extracted with ethyl acetate. The organic extract was dried and concentrated and combined with the filtered solid. Yield: 4.1 g (47%) $^1$H NMR (400 MHz, $CDCl_3$): δ 2.38 (s, 3H), 7.92 (s, 1H). LCMS: (ES+) m/z=126.7 $(M)^+$ ATLANTIS C18 (5.0×4.6-5.0 μm)

Mphase A: 10 mM Ammonium acetate
Mphase B: MeCN
Flow: 5 ml/Min

| Time | % A | % B |
|---|---|---|
| 0.0 | 95.0 | 5.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 1.666
Wavelength: 220 nm 4-methyloxazole-5-carbonitrile. 4-methyloxazole-5-carboxamide (2.1 g, 16 mmoles, 1 eq) was dissolved in pyridine (30 ml) and treated with $POCl_3$ (2.31 ml 25 mmoles, 1.5 eq), and the reaction was stirred at room temperature for 5 hours. The reaction was then diluted with ice, and aqueous layer was adjusted to pH3 with 6M HCl and extracted with diethyl ether. The organic layer was separated and washed with water, brine and dried to give the product. Yield: 0.4 g (30%) $^1$H NMR (400 MHz, $CDCl_3$): δ 2.52 (s, 3H), 7.79 m (s, 1H). LCMS (ES+) m/z=109.1 $(M+H)^+$ Column: Chromolith speed Rod C18 (4.6×30) mm, 5 μm
Mphase A: 10% MeOH-90% $H_2O$-10 mM $NH_4OAc$
Mphase B: 90% MeOH-10% $H_2O$-10 mM $NH_4OAc$
Flow: 5 ml/min

| Time (min): | 02 | 3 | |
|---|---|---|---|
| % B: | 0 | 100 | 0 |

RT min: 0.775
Wavelength: 220 nm 1-(4-methyloxazol-5-yl)-cyclopropanamine. 4-Methyloxazole-5-carbonitrile (0.4 g, 3.7 mmole. 1 eq) was dissolved in dry THF, and added with titanium isopropoxide (1.32 g, 4.4 mmole, 1.2 eq) dropwise over 15 minutes. A solution of ethylmagnesium bromide (1.23 g, 9.3 mmole, 2.5 eq) in THF was added at rt over 15 minutes, and the reaction was stirred at rt for 1 hour. BF3 etherate (0.63 g, 4.4 mmole, 1.2 eq) was then added and the mixture stirred at rt for 1 hour, After which, 1N NaOH solution was added to adjust the pH to 9-10. The reaction mixture was passed through celite and washed with ethyl acetate. The organic layer was washed with brine, concentrated and purified by column chromatography yielding 0.3 g (78%) of the product. $^1$H NMR (400 MHz, CDCl$_3$): δ 0.91 (t, J=4 Hz, 2H), 0.96 (t, J=4 Hz, 2H), 2.18 (s, 2H), 2.06 (s, 3H), 7.64 (s, 1H). LCMS (ES+) m/z=138.8 (M)$^+$ Column: ATLANTIS C18 50×4.6 mm 5 μm
Mphase A: 10 mM Ammonium acetate
Mphase B MeCN
Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 2.781
Wavelength: 220 nm
N-acetyl-N-(2-oxopropyl)acetamide. A mixture of Glycine (5 g, 66 mmole, 1 eq), pyridine 32.4 ml, 401 mmole, 6 eq) and acetic anhydride (50 ml, 532 mmole, 8 eq) was heated to reflux for 12 hours. The mixture was then concentrated under reduced pressure and purified by column chromatography (eluent Hexane:ethyl acetate 50%). Yield 3 g (57%) $^1$H NMR (400 MHz, CDCl$_3$): δ 2.21 (s, 3H), 2.32 (s, 6H), 4.49 (s, 2H). LCMS: (ES+) m/z=158 (M)$^+$ Method: Column: Chromolith SpeedRod C18 (4.6×30) mm, 5 micron
Mphase A: 10% MeOH-90% H$_2$O-0.1% TFA
Mphase B: 90% MeOH-10% H$_2$O-0.1% TFA Flow: 5 ml/min

| Time (min.) | % A | % B |
|---|---|---|
| 0.0 | 100.0 | 0.0 |
| 2.0 | 0.0 | 100.0 |
| 3.0 | 0.0 | 0.0 |

RT min: 0.375
Wavelength: 220 nm
1-aminopropan-2-one. N-acetyl-N-(2-oxopropyl)acetamide (50 g, 318 mmole) was dissolved in a mixture of conc.HCl (150 ml) and water (150 ml), and the reaction mixture was heated to reflux under a nitrogen atmosphere for 6 hours. The reaction mixture was then concentrated and the dark red oily residue was taken to the next step. (Crude Yield: 46 g).

Methyl 2-oxo-2-(2-oxopropylamino)acetate. Methoxy oxalyl chloride (173 ml, 1890 mmole, 3 eq) was added dropwise to a suspension of 1-aminopropan-2-one hydrochloride (946 g, 630 mmole, 1 eq) in benzene, and the resulting mixture heated to reflux for 4 hours. After evaporation of benzene, the residue was made alkaline with 3N Na$_2$CO$_3$ and extracted with chloroform. The crude product was taken to the next step. (Crude Yield: 47 g).

Methyl 5-methyloxazole-2-carboxylate. A mixture of methyl 2-oxo-2-(2-oxopropylamino)acetate (47 g, 296 mmole, 1 eq) and in POCl$_3$ (400 mL) was refluxed for 3 hours. After evaporation, the mixture was poured into ice water. The aqueous was made alkaline with K$_2$CO$_3$ and extracted with CHCl$_3$ and purified by column chromatography. Yield: 27 g (40%) $^1$H NMR (400 MHz, CDCl$_3$): δ 2.40 (s, 3H), 3.96 (s, 3H), 6.96 (s, 1H). LCMS: (ES+) m/z=142.2 (M+H)$^+$ Column: XBRIDGE C18 (4.6×30) mm, 5 μm
Mphase A: 10% MeOH-90% H$_2$O-10 mM NH$_4$OAc
Mphase B: 90% MeOH-10% H$_2$O-10 mM NH$_4$OAc
Flow: 5 ml/min

| Time (min): | 0 | 2 | 3 |
|---|---|---|---|
| % B: | 0 | 100 | 0 |

RT min: 0.922, Wavelength 220 nm
Methyl 5-methyloxazole-2-carboxamide. A mixture of methyl 5-methyloxazole-2-carboxylate (26 g, 184 mmoles) and ammonium hydroxide (400 ml) in a sealed tube was stirred at rt for 12 hours. After completion of the reaction, solid was filtered and washed with water. The aqueous layer was extracted with ethyl acetate. The organic extract was dried, concentrated and combined with the filtered solid. Yield (23 g, 82%) $^1$H NMR (400 MHz, CDCl$_3$): δ 2.40 (s, 3H), 6.14 (s, 1H), 6.85 (s, 1H), 6.96 (s, 1H). LCMS (ES+) m/z=127.0 (M+H)$^+$ Column: Chromolith speed ROD C18 (4.6×30) mm, 5 μm
Mphase A: 10% MeOH-90% H$_2$O-0.1% TFA
Mphase B: 90% MeOH-10% H$_2$O-0.1% TFA
Flow: 5 ml/min

| Time (min): | 0 | 2 | 3 |
|---|---|---|---|
| % B: | 0 | 100 | 0 |

RT min: 0.268, Wavelength 220 nm
Methyl 5-methyloxazole-2-carbonitrile. 5-methyloxazole-2-carboxamide (5 g, 39.7, 1 eq) was dissolved in pyridine (75 ml) and treated with POCl$_3$ (5.51 ml, 59.5 mmoles, 1.5 eq), and the reaction was stirred at rt for 5 hours. The reaction mixture was diluted with ice-water, and the pH of the aqueous was adjusted to 3 using 6M HCl and extracted with diethyl ether. The organic layer was washed with water, brine and dried to give the product. Yield: 4 g (80%) $^1$H NMR (400 MHz, CDCl$_3$): δ2.09 (s, 3H), 6.62 (s, 1H). LCMS (ES+) m/z=109.3 (M+H)$^+$ Column: Chromolith speed Rod C18 (4.6×30) mm, 5 μm
Mphase A: 10% MeOH-90% H$_2$O-10 mM NH$_4$OAc
Mphase B: 90% MeOH-10% H$_2$O-10 mM NH$_4$OAc
Flow: 5 ml/min

| Time (min): | 0 | 2 | 3 |
|---|---|---|---|
| % B: | 0 | 100 | 0 |

RT min: 0.777
Wavelength: 220 nm
1-(5-methyloxazol-2-yl)-cyclopropanamine. 5-methyloxazole-2-carbonitrile (2 g, 18 mmole. 1 eq) was dissolved in dry THF, and titanium isopropoxide (6.31 g, 22.2 mmole, 1.2 eq) was added dropwise over 15 minutes. A solution of ethyl magnesium bromide (6.15 g, 46.25, 2.5 eq) in THF was added at rt over 15 minutes, and the reaction mixture was stirred at rt for 1 hour. BF$_3$ etherate (6.5 g, 46.25, 1.2 eq) was then added and the mixture stirred at rt for 1 hour. 1N NaOH solution was added to the mixture to adjust the pH to 9-10.

The reaction mixture was passed through celite and washed with ethyl acetate. The organic layer was washed with brine, concentrated and purified by column chromatography to yield 0.5 g of the product. $^1$H NMR (400 MHz, CDCl$_3$): δ $^1$H NMR (400 MHz, CDCl$_3$): δ 0.76 (t, J=4 Hz, 4H), 2.17 (s, 3H), 7.31 (s, 1H). LCMS: (ES+) m/z=138.9 (M+H)$^+$ Column: ATLANTIS C18 50×4.6 mm 5 nm
Mphase A: 10 mM Ammonium acetate
Mphase B MeCN
Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 2.813
Wavelength: 220 nm 5-methylthiazole-2-carbaldehyde. To a solution of BuLi (32 mL, 51 mmol, 1 eq, 1.6 M in hexane) in ether at −78° C. was added dropwise a solution of 5-methylthiazole (5 g, 50 mol, 1 eq) in ether at −78° C. for 1.5 hours. A solution of DMF (5.8 mL, 75 mmol, 1.5 eq) in ether was added at once, and the reaction was allowed to warm to room temperature and stirred overnight. Ice was added to the mixture followed by the slow addition of 4 N HCl. The mixture was extracted with ether. The aq. layer was bought to pH 7.5 with solid NaHCO$_3$ and extracted with ether. The combined ethereal extracts were dried and concentrated to give a crude residue which was purified by flash chromatography on silica gel using 10% EtOAc/Hexane. Yield: 6.1 g $^1$H NMR (400 MHz, CDCl$_3$): δ 2.56 (s, 3H), 7.79 (s, 1H), 9.90 (s, 1H). LCMS: (ES+) m/z=128.2 (M+H)$^+$ Column: Chromolith speed Rod C18 (4.6×30) mm, 5 μm
Mphase A: 10% MeOH-90% H$_2$O-10 mM NH$_4$OAc
Mphase B: 90% MeOH-10% H$_2$O-10 mM NH$_4$OAc
Flow: 5 ml/min

| Time (min): | 0 | 2 | 3 |
|---|---|---|---|
| % B: | 0 | 100 | 0 |

RT min: 0.767, Wavelength: 220 nm 5-methylthiazole-2-carbaldehyde oxime. To a solution of 5-methylthiazole-2-carbaldehyde (6.1 g, 48 mmol) in EtOH (30 mL), was added pyridine (4 mL, 49 mmol) and HONH$_2$.HCl (3.3 g, 47 mmol). The mixture was stirred at ambient temperature for 12 hours. The reaction mixture was diluted with DCM and extracted with water. The organic solution was dried, filtered and concentrated to give the crude oxime. Yield: 6 g LCMS: (ES+) m/z=143.8 (M+H)$^+$ Column: ATLANTIS C18 50×4.6 mm 5 μm
Mphase A: 10 mM Ammonium acetate
Mphase B MeCN
Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 3.624, Wavelength: 220 nm 5-methylthiazole-2-carbonitrile. 5-Methylthiazole-2-carbaldehyde oxime (6 g, 42 mmol, 1 eq) was dissolved in DCM (100 mL) and CDI (7.8 g, 48 mmol) was added portion-wise to the reaction mixture. The mixture was then stirred at rt overnight, added with water and extracted with DCM. The organic layer was dried and concentrated to give a crude residue, which was purified by flash chromatography on silica gel using 10% EtOAc/Hexane. Yield: 3.2 g $^1$H NMR (400 MHz, CDCl$_3$): δ 2.59 (s, 3H), 7.71 (s, 1H) LCMS: (ES+) m/z=125.2 (M+H)$^+$ Column: Chromolith speed Rod C18 (4.6×30) mm, 5 μm
Mphase A: 10% MeOH-90% H$_2$O-10 mM NH$_4$OAc
Mphase B: 90% MeOH-10% H$_2$O-10 mM NH$_4$OAc
Flow: 5 ml/min

| Time (min): | 0 | 2 | 3 |
|---|---|---|---|
| % B: | 0 | 100 | 0 |

RT min: 0.780, Wavelength: 220 nm 1-(5-methylthiazol-2-yl)cyclopropanamine 5-methylithiazole-2-carbonitrile (1.0 g, 8 mmol, 1 eq) was dissolved in THF. Ti(Oi-Pr)$_4$ (2.74 g, 9.6 mmol, 1.2 eq) was added dropwise over a period of 5-10 min and the reaction mixture was stirred at rt for 15 min. The mixture was then cooled to 0° C. and EtMgBr (2.68 g, 10 mL, 20 mmol, 2.5 eq, 2M in THF) was added dropwise over a period of 10-15 min. The mixture was stirred at 0° C. for 15 min. and then at ambient temperature for 1 h. The mixture was cooled again to 0° C. and, BF$_3$.OEt$_2$ (2.5 mmol) was added dropwise over a period of 5-10 min at 0° C. After the mixture was stirred for 10 min at 0° C. and 1 h at ambient temperature, 1 N NaOH was added at 0° C. DCM was added to the reaction mixture which was stirred for 5-10 min. The mixture was filtered through celite and washed with DCM. The organic layer was concentrated to give a residue which was purified by flash chromatography on silica gel using 10% chloroform/methanol. Yield: 0.6 g $^1$H NMR (400 MHz, CDCl$_3$): δ 1.20 (t, J=4 Hz, 2H) 1.31 (t, J=4 Hz, 2H), 2.40 (s, 3H), 7.26 (s, 1H). LCMS: (ES+) m/z=154.7 (M)$^+$ Column: ATLANTIS C18 50×4.6 mm 5 μm
Mphase A: 10 mM Ammonium acetate
Mphase B MeCN
Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 2.960, Wavelength: 220 nm

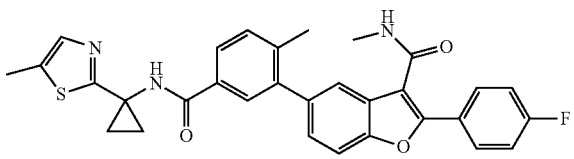

2-(4-Fluorophenyl)-N-methyl-5-(2-methyl-5-(1-(5-methylthiazol-2-yl)cyclopropylcarbamoyl)phenyl)benzofuran-3-carboxamide. 34244-fluorophenyl)-3-(methylcarbamoyl)benzofuran-5-yl)-4-methylbenzoic acid (0.2 g, 0.5 mmol, 1 eq), 1-(5-methylthiazol-2-yl)cyclopropanamine (0.093 g, 0.6 mmol, 1.2 eq), EDCI.HCl (0.103 g, 0.54 mmol, 1.1 eq), HOBT (0.067 g, 0.5 mmol, 1.5 eq) and TEA (0.21 ml, 1.5 mmol, 3 eq) were dissolved in dichloromethane and the mixture was stirred at room temperature for 18 h. The mixture was then added with water, and the organic layer was separated and washed with water, and the product was purified by preparative TLC. Yield: 25 mg (15%). $^1$H NMR (400 MHz, DMSO-d$_6$): δ 1.34-1.37 (m, 2H), 1.50-1.53 (m, 2H), 2.31 (s, 3H), 2.35 (s, 3H), 2.83-2.84 (d, J=4.8 Hz, 3H), 7.27 (d, J=1.2 Hz, 1H), 7.39-7.47 (m, 4H), 7.60 (d, J=1.6 Hz, 1H), 7.76-7.78 (d, J=8.4 Hz 1H), 7.83-7.85 (m, 2H), 8.02 (m, 2H), 8.45 (m, 1H), 9.51 (s, 1H) LCMS: (ES+) m/z=540 (M+H)$^+$ Method: Column-Ascentis Express C18 (5×2.1 mm-2.7 μm)

Mphase A: 2% MeCN-98% H$_2$O-10 mM NH$_4$COOH

Mphase B: 98% MeCN-2% H$_2$O-10 mM NH$_4$COOH

Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 2.015, Wavelength: 220 nm

HPLC COLUMN: SUNFIRE C18 (4.6×150) mm, 3.5 micron

Buffer: 0.05% TFA in water pH 2.5

Mobile Phase A: Buffer:MeCN (95:5)

Mobile Phase B: MeCN:Buffer (95:5)

FLOW: 1 ml/min

| Time | B % |
|---|---|
| 0 | 10 |
| 25 | 100 |
| 30 | 100 |

Wavelength: 254 nm, RT min: 18.846

Wavelength: 220 nm, RT min: 18.846

Purity: 99.7%

HPLC COLUMN: XBridge phenyl (4.6×150) mm, 3.5 micron

Mobile Phase A: 0.05% TFA in water:MeCN (95:5)

Mobile Phase B: 0.05% TFA in MeCN:water (95:5)

FLOW: 1 ml/min

| Time | B % |
|---|---|
| 0 | 10 |
| 25 | 100 |
| 30 | 100 |

Wavelength: 254 nm, RT min: 17.065

Wavelength: 220 nm, RT min: 17.065

Purity: 99.8%

1-(1-methyl-1H-imidazol-4-yl)cyclopropanamine 1-methyl-1H-imidazole-4-carbonitrile (0.5 g, 4.6 mmol, 1 eq) was dissolved in THF, and titanium isopropoxide (1.6 g, 5.6 mmol, 2.5 eq) was added dropwise over 15 minutes to the mixture, which was then stirred for 15 minutes at room temperature. Ethyl magnesium bromide (1.6 g, 6 mL, 12 mmol, 2.6 eq, 2M in THF) was added to the mixture at room temperature over 15 minutes, and the reaction mixture stirred for 1 h. BF$_3$ etherate (0.8 g, 5.6 mmol, 2.2 eq) was added and the reaction mixture stirred at room temperature for another 1 h. 1 N NaOH solution was added to the mixture to adjust the pH to 9-10. The reaction mixture was filtered through celite and washed with DCM. The organic layer was concentrated to give a residue which was purified by flash chromatography on silica gel using 10% chloroform/methanol. Yield: 0.6 g $^1$H NMR (400 MHz, CDCl$_3$): δ 0.97 (t, J=3.4 Hz, 2H), 1.00 (t, J=3.4 Hz, 2H), 3.63 (s, 3H), 7.28 (s, 1H), 7.31 (s, 1H). LCMS: (ES+) m/z=138.2 (M+H)$^+$ Column: ATLANTIS C18 50×4.6 mm 5 μm Mphase A: 10 mM Ammonium acetate Mphase B MeCN Flow: 1.0 ml/min

| Time (min) | % B | % A |
|---|---|---|
| 0.0 | 5.0 | 95.0 |
| 4.0 | 95.0 | 5.0 |
| 5.5 | 95.0 | 5.0 |
| 6.0 | 5.0 | 95.0 |
| 7.0 | 5.0 | 95.0 |

RT min: 1.949, Wavelength: 220 nm 2-(4-Fluorophenyl)-N-methyl-5-(2-methyl-5-(1-(1-methyl-1H-imidazol-4-yl)cyclopropylcarbamoyl)phenyl)benzofuran-3-carboxamide. 34244-fluorophenyl)-3-(methylcarbamoyl)benzofuran-5-yl)-4-methylbenzoic acid (0.15 g, 0.37 mmol, 1 eq), 1-(1-methyl-1H-imidazol-4-yl)cyclopropanamine (0.061 g, 0.44 mmol, 1.2 eq), EDCI.HCl (0.078 g, 0.40 mmol, 1.1 eq), HOBT (0.049 g, 0.37 mmol, 1.0 eq) and TEA (0.15 ml, 1.1 mmol, 3 eq) were dissolved in dichloromethane and the above mixture was stirred at room temperature for 18 h. The mixture was then added with water. The organic layer was separated, washed with water, concentrated and the crude product purified by Prep. HPLC. Yield: 24.69 mg (10%). $^1$HNMR (400 MHz, DMSO-d$_6$): δ 1.04-1.07 (m, 2H), 1.17-120 (m, 2H), 2.29 (s, 3H), 2.82 (d, J=4.4 Hz, 3H), 3.54 (s, 3H), 6.7 (s, 1H), 7.37-7.43 (m, 5H), 7.58 (s, 1H), 7.74-7.77 (d, J=8.8 Hz, 1H), 7.81-7.82 (m, 2H), 7.97-8.01 (m, 2H), 8.46-8.47 (m, 1H), 9.06 (s, 1H) LCMS: (ES+) m/z=523.2 (M+H)$^+$ Method: Column-Ascentis Express C18 (5×2.1 mm-2.7 nm)
Mphase A: 2% ACN-98% H$_2$O-10 mM NH$_4$COOH
Mphase B: 98% ACN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.854, Wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 7.220
Wavelength: 220 nm, RT min: 7.220
Purity: 99.4%
HPLC COLUMN: XBridge phenyl (4.6×150) mm, 3.5 micron
Buffer: 0.05% TFA in water pH 2.5
Mobile Phase A: Buffer:MeCN (95:5)
Mobile Phase B: 0.05% TFA in MeCN:Buffer (95:5)
FLOW: 1 ml/min

| Time | B % |
|---|---|
| 0 | 10 |
| 12 | 100 |
| 15 | 100 |

Wavelength: 254 nm, RT min: 8.541
Wavelength: 220 nm, RT min: 8.541
Purity: 99.3%

1-(pyrimidin-5-yl)cyclopropaneamine Pyrimidine-5-carbonitrile (5 g, 47.6 mmol, 1 eq) was taken in a dry THF under an argon atmosphere. Titanium isopropoxide (17 ml, 57.1 mmol, 1.2 eq) was then added slowly at ambient temperature and the resulting mixture was stirred for 15 mins. To the above stirred mixture was slowly added ethyl magnesium bromide (107 ml, 2.2 eq, 1 M in THF) via syringe at ambient temperature (during the addition of EtMgBr, the reaction mixture turned black). The reaction mass was stirred for an hour, and BF$_3$.EtO (16.7 ml, 135 mmol, 2.8 eq) was then added slowly through syringe to the mixture at 0° C. The reaction was then allowed to warm to ambient temperature and the stirring was continued for another one hour. Finally the reaction was quenched by adding 50 ml of water, and the reaction mixture was passed through Celite and the bed washed with water and ethyl acetate. The filtrate was basified with 10% NaOH solution (pH=9) and then extracted with DCM and washed with brine. The required product was purified by silica gel (60-120) column chromatography using 4% methanol/DCM as the eluent. Yield: 0.1 g (5%) $^1$H NMR (400 MHz, DMSO-d$_6$): δ 1.04-1.08 (m, 2H), 1.18-1.25 (m, 2H), 8.26 (d, 2H), 9.05 (s, 1H). LCMS: (ES+) m/z=136 (M+H)$^+$

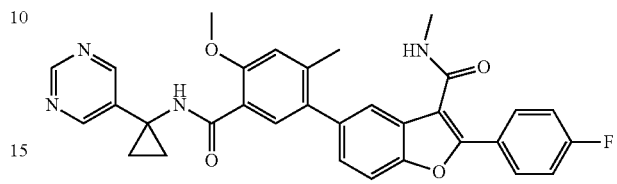

2-(4-Fluorophenyl)-5-(4-methoxy-2-methyl-5-(1-(pyrimidin-5-yl)cyclopropylcarbamoyl)phenyl)-N-methylbenzofuran-3-carboxamide. 5-(2-(4-fluorophenyl)-3-(methylcarbamoyl)benzofuran-5-yl)-2-methoxy-4-methylbenzoic acid (0.2 g, 0.46 mmol, 1 eq), 1-(pyrimidin-5-yl)cyclopropanamine (0.074 g, 0.55 mmol, 1.2 eq), EDCI.HCl (0.076 g, 0.4 mmol, 1.2 eq), HOBT (0.054 g, 0.4 mmol, 2 eq) and TEA (0.14 ml, 1.02 mmol, 3 eq) were dissolved in dichloromethane and the above mixture was stirred at room temperature for 18 h. The mixture was then added with water. The Organic layer was separated, washed with water, concentrated and the crude product was purified by Prep. TLC (20 mm thickness) using 5% methanol/DCM as an eluent. Yield: 50 mg (20%) $^1$HNMR (400 MHz, DMSO-d$_6$): δ 1.33-1.36 (m, 2H), δ 1.42-1.45 (m, 2H), 2.29 (s, 3H), 2.81-2.82 (d, J=4.4 Hz, 3H), 3.96 (s, 3H), 7.14 (s, 1H), 7.33 (dd, J=1.6, 8.4 Hz, 1H), 7.40 (t, J=8.8, 2H), 7.50 (d, J=1.2 Hz, 1H), 7.52 (s, 1H), 7.72 (d, J=8.4 Hz, 1H), 7.97-8.01 (m, 2H), 8.47 (q, J=4.4 Hz, 1H), 8.67 (s, 2H), 8.91 (s, 1H), 9.00 (s, 1H) LCMS: (ES+) m/z=551.2 (M+H)$^+$ LCMS Method: Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.87, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 1 | 10 |
| 12 | 100 |
| 15 | 100 |

Wavelength: 254 nm, RT min: 10.45
Wavelength: 220 nm, RT min: 10.45

Purity: 98.6%
: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.78
Wavelength: 220 nm, RT min: 9.78
Purity: 98.5%

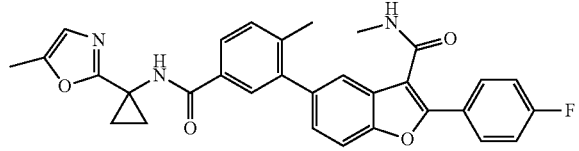

2-(4-Fluorophenyl)-N-methyl-5-(2-methyl-5-(1-(5-methyloxazol-2-yl)cyclopropylcarbamoyl)phenyl)benzofuran-3-carboxamide. 3-(2-(4-fluorophenyl)-3-(methylcarbamoyl)benzofuran-5-yl)-4-methylbenzoic acid (0.2 g, 0.5 mmol, 1 eq), 1-(5-methyloxazol-2-yl)cyclopropanamine (0.082 g, 0.6 mmol, 1.1 eq), EDCI.HCl (0.105 g, 0.54 mmol, 1.1 eq), HOBT (0.067 g, 0.5 mmol, 1.0 eq) and TEA (0.21 ml, 1.5 mmol, 3 eq) were dissolved in dichloromethane and the above mixture was stirred at room temperature for 18 h. The mixture was then added with water. The organic layer was separated, washed with water and concentrated to give the crude product which was purified by Prep. TLC (20 mm thickness) using 5% methanol/DCM as an eluent. Yield: 25 mg (25%) $^1$HNMR (400 MHz, DMSO-$d_6$): δ 1.25-1.28 (m, 2H), 1.40-1.44 (m, 2H), 2.21 (d, J=1.2 Hz, 3H), 2.29 (s, 3H), 2.82 (d, J=4.8, 3H), 6.66 (d, J=1.2 Hz, 1H), 7.38-7.44 (m, 4H), 7.57 (d, J=1.2, 1H), 7.76 (d, J=8.8 Hz, 1H), 7.81-7.83 (s and m, 2H), 7.98-8.01 (m, 2H), 8.47 (q, J=4.8 Hz, 1H), 9.28 (s, 1H). LCMS: (ES+) m/z=524.2 (M+H)$^+$
Method: Column-Ascentis Express C18 (5×2.1 mm-2.7 µm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.953, Wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 17.817
Wavelength: 220 nm, RT min: 17.817
Purity: 99.3%
HPLC COLUMN: XBridge phenyl (4.6×150) mm, 3.5 micron
Buffer: 0.05% TFA in water pH 2.5
Mobile Phase A: Buffer:ACN (95:5)
Mobile Phase B: 0.05% TFA in ACN:Buffer (95:5)
FLOW: 1 ml/min

| Time | B % |
|---|---|
| 0 | 10 |
| 25 | 100 |
| 30 | 100 |

Wavelength: 254 nm, RT min: 16.386
Wavelength: 220 nm, RT min: 16.386
Purity: 99.4%

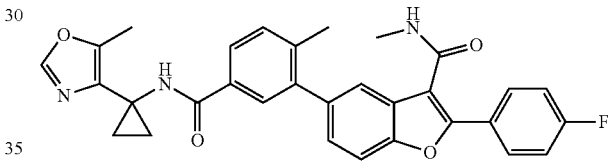

2-(4-Fluorophenyl)-N-methyl-5-(2-methyl-5-(1-(5-methyloxazol-4-yl)cyclopropylcarbamoyl)phenyl)benzofuran-3-carboxamide. 3-(2-(4-fluorophenyl)-3-(methylcarbamoyl)benzofuran-5-yl)-4-methylbenzoic acid (0.2 g, 0.5 mmol, 1 eq), 1-(5-methyloxazol-4-yl)cyclopropanamine (0.103 g, 0.74 mmol, 1.2 eq), EDCI.HCl (0.105 g, 0.54 mmol, 1.1 eq), HOBT (0.067 g, 0.5 mmol, 1.0 eq) and TEA (0.21 ml, 1.5 mmol, 3 eq) were dissolved in dichloromethane and the above mixture was stirred at room temperature for 18 h. The mixture was then added with water. The organic layer was separated, washed with water and concentrated to give the crude product which was purified by Prep. TLC (20 mm thickness) using 5% methanol/DCM as an eluent. Yield: 25 mg (25%) $^1$HNMR (400 MHz, DMSO-$d_6$): δ 1.11 (m, 2H), 1.20-1.22 (m, 2H), 2.28 (s, 3H), 2.29 (s, 3H), 2.82 (d, J=4.4 Hz, 3H), 7.38-7.42 (m, 4H), 7.57 (s, 1H), 7.74-7.81 (m, 3H), 8.04 (s, 1H), 7.97-8.01 (m, 2H), 8.45-8.46 (m, 1H), 9.16 (s, 1H). LCMS: (ES+) m/z=524.2 (M+H)$^+$
Method: Column-Ascentis Express C18 (5×2.1 mm-2.7 µm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.92, Wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 18.085
Wavelength: 220 nm, RT min: 18.085
Purity: 95%
HPLC COLUMN: XBridge phenyl (4.6×150) mm, 3.5 micron
Buffer: 0.05% TFA in water pH 2.5
Mobile Phase A: Buffer:MeCN (95:5)
Mobile Phase B: 0.05% TFA in MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.398
Wavelength: 220 nm, RT min: 16.398
Purity: 95%

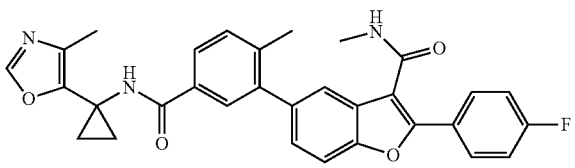

2-(4-Fluorophenyl)-N-methyl-5-(2-methyl-5-(1-(4-methyloxazol-5-yl)cyclopropylcarbamoyl)phenyl)benzofuran-3-carboxamide. 34244-fluorophenyl)-3-(methylcarbamoyl)benzofuran-5-yl)-4-methylbenzoic acid (0.2 g, 0.5 mmol, 1 eq), 1-(4-methyloxazol-5-yl)cyclopropanamine (0.103 g, 0.74 mmol, 1.2 eq), EDCI.HCl (0.105 g, 0.54 mmol, 1.1 eq), HOBT (0.067 g, 0.5 mmol, 1.0 eq) and TEA (0.21 ml, 1.5 mmol, 3 eq) were dissolved in dichloromethane and the above mixture was stirred at room temperature for 18 h. The mixture was then added with water. The organic layer was separated, washed with water and concentrated to give the crude product which was purified by Prep. HPLC. Yield: 25 mg (25%)
$^1$HNMR (400 MHz, DMSO-$d_6$): δ 1.21 (broad s, 4H), 2.17 (s, 3H), 2.28 (s, 3H), 2.83 (d, J=4.8 Hz, 3H), 7.37-7.43 (m, 4H), 7.56 (d, J=1.6 Hz, 1H), 7.74-7.79 (m, 3H), 7.98-8.02 (m, 2H), 8.0 (s, 1H), 8.44-8.45 (m, 1H), 9.20 (s, 1H). LCMS: (ES+) m/z=524.2 (M+H)$^+$
Method: Column-Ascentis Express C18 (5×2.1 mm-2.7 nm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.913, Wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 17.45
Wavelength: 220 nm, RT min: 17.45
Purity: 95%
HPLC COLUMN: XBridge phenyl (4.6×150) mm, 3.5 micron
Buffer: 0.05% TFA in water pH 2.5
Mobile Phase A: Buffer:MeCN (95:5)
Mobile Phase B: 0.05% TFA in MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.01
Wavelength: 220 nm, RT min: 16.01
Purity: 95%
Preparative HPLC Method
Column: Symmetry C18 (19×250×10μ)
Mobile Phase: 0.1% TFA (A), MeCN (B)

| | Gradient: | | |
|---|---|---|---|
| Time | Flow | A | B |
| 0 | 15 ml/min | 70 | 30 |
| 10 | 15 ml/min | 30 | 70 |

RT: 16.9 min.

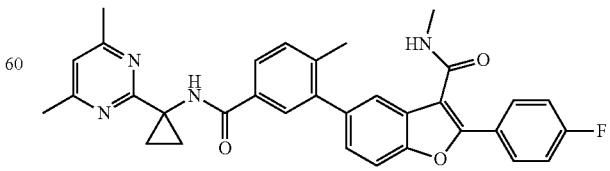

5-(5-(1-(4,6-Dimethylpyrimidin-2-yl)cyclopropylcarbamoyl)-2-methylphenyl)-2-(4-fluorophenyl)-N-methylbenzofuran-3-carboxamide. To a mixture of 3-(2-(4-fluorophenyl)-3-(methylcarbamoyl)benzofuran-5-yl)-4-methylbenzoic acid (0.2 g, 0.5 mmol, 1 eq), 1-(4,6-dimethylpyrimidin-2-yl)cyclopropanamine (0.203 g, 1.2 mmol, 2.5 eq) (60% purity), HOBT (0.068 g, 0.5 mmol, 1.1 eq), EDC.HCl (0.105 g, 0.55 mmol, 1.1 eq) in DCM at ambient temperature under a nitrogen atmosphere was added diisopropylethylamine (0.194 g, 1.5 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and finally purified by preparative HPLC. Yield: 0.15 g (14%). $^1$H NMR (400 MHz, DMSO-$d_6$): δ 1.24-1.27 (m, 2H), 1.53-1.56 (m, 2H), 2.30 (s, 3H), 2.32 (s, 6H), 2.82 (d, J=4.8 Hz, 3H), 7.00 (s, 1H), 7.38-7.44 (m, 4H), 7.59 (d, J=1.2 Hz, 1H), 7.77 (d, J=8.4 Hz, 1H), 7.82-7.84 (s and d, 2H), 7.98-8.02 (m, 2H), 8.47-8.50 (m, 1H), 9.14 (s, 1H). LCMS: (ES+) m/z=549.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |
| 3.6 | 100.0 | 0.0 |

RT min: 1.995, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 4 | 10 |
| 27 | 100 |
| 30 | 100 |

Wavelength: 254 nm, RT min: 10.742
Wavelength: 220 nm, RT min: 10.742
Purity: 99%
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 10.297
Wavelength: 220 nm, RT min: 10.297
Purity: 99%

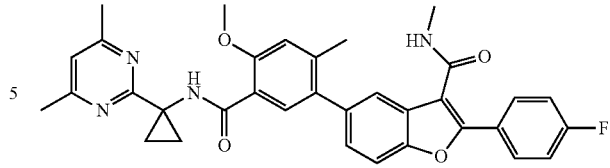

5-(5-(1-(4,6-dimethylpyrimidin-2-yl)cyclopropylcarbamoyl)-4-methoxy-2-methylphenyl)-2-(4-fluorophenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.15 g, 0.34 mmol, 1 eq), 1-(4,6-dimethylpyrimidin-2-yl)cyclopropanamine (0.17 g, 0.1 mmol, 3 eq) (60% purity), HOBT (0.046 g, 0.34 mmol, 1.0 eq), EDC.HCl (0.072 g, 0.37 mmol, 1.1 q) in DCM at ambient temperature under a nitrogen atomsphere was added diisopropylethylamine (0.132 g, 1.0 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was further purified by column chromatography (neutral alumina) using 0.5% Methanol/DCM and finally purified by preparative HPLC. Yield: 0.15 g (14%). $^1$H NMR (400 MHz, DMSO-$d_6$): δ 1.43-1.44 (d, J=3.36 Hz, 2H), 1.51-1.54 (d, J=3.48 Hz, 2H), 2.32-2.34 (d, J=5.8 Hz, 9H), 2.81-2.82 (d, J=4.6 Hz, 3H), 4.0 (s, 3H) 7.0 (s, 1H), 7.15 (s, 1H), 7.34-7.42 (m, 3H), 7.52 (s, 1H), 7.72-7.74 (d, J=8.8 Hz, 2H), 7.97-8.02 (m, 2H), 8.46-8.48 (d, J=4.56 Hz, 1H), 8.91 (s, 1H). LCMS: (ES+) m/z=579.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 2.133, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 5 | 10 |
| 28 | 100 |
| 30 | 100 |

Wavelength: 254 nm, RT min: 18.09
Wavelength: 220 nm, RT min: 18.09
Purity: 99.9%
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 25 | 100 |
| 30 | 100 |

Wavelength: 254 nm, RT min: 16.68
Wavelength: 220 nm, RT min: 16.68
Purity: 99.9%

1-(pyrazin-2-yl)cyclopropanecarbonitrile. A mixture of 2-fluoropyrazine (2.0 g, 20.4 mmol, 1 eq) and cyclopropanecarbonitrile (1.5 ml, 20.4 mmol, 1 eq) In a dry flask under an argon atomsphere were dissolved in dry toluene (50 ml). The solution was cooled to 0° C. and potassium bis(trimethylsilyl) amide (0.5 M in toluene, 40.9 ml, 20.45 mmol, 1 eq) was added slowly over 5 min via syringe. The black, opaque reaction mixture was allowed to warm to room temperature and stirred for 4 h. The reaction was diluted with water (200 ml) and ethyl acetate (200 ml), and the layers were separated. The aqueous layer was back extracted with ethyl acetate (2×100 ml). The combined organic layers were dried over $Na_2SO_4$, filtered and concentrated to give a black oil. The crude was purified by silica gel (60-120) column chromatography using 20% ethyl acetate in hexane as eulent to give 0.25 g of the product as light a yellow oil. Yield: 0.25 g (8.4%). $^1$H NMR (400 MHz, $CD_3OD$): δ 1.84-1.86 (m, 4H), 8.51-8.55 (q, 2H), 8.89 (s, 1H). LCMS: (ES+) m/z=146.2 (M)$^+$ Method: Column: PUROSPHER@star rp-18 (4.6×30) mm, 3 μm
Mphase A: 20 mM $NH_4OAC$ in 90% $H_2O$, 10% MeCN
Mphase B: 20 mM $NH_4OAC$ in 10% $H_2O$, 90% MeCN
Flow: 2.5 ml/min

| Time | % B |
| --- | --- |
| 0.0 | 0.0 |
| 2.0 | 100.0 |
| 2.5 | 100.0 |
| 3.0 | 0.0 |

RT min: 1.063, wavelength: 220 nm 1-(pyrazin-2-yl)cyclopropanecarboxylic acid. 1-(Pyrazin-2-yl)cyclopropanecarbonitrile (0.25 g, 1.72 mmol, 1 eq) was dissolved in MeOH (5 ml) and NaOH solution (20 wt % in water, 2.0 ml) was added via syringe in one portion. The orange mixture was heated to 75° C. for 22 h., cooled to room temperature, and acidified to pH 2-3 with 6N HCl. The mixture was filtered through a pad of celite with MeOH wash and the filtrate was concentrated. The residue was suspended in ethyl acetate, dried with Na2SO4, filtered and concentrated to give the product as an orange solid. Yield: 0.18 g (64%) $^1$H NMR (400 MHz, DMSO-$d_6$): δ 1.42-1.45 (m, 2H), 1.54-1.56 (m, 2H), 8.48-8.53 (m, 2H), 8.86-8.87 (d, 1H, J=1.6 Hz), 12.58 (s, 1H). LCMS: (ES+) m/z=165.2 (M+H)$^+$ Column: PUROSPHER@star rp-18 (4.6×30) mm, 3 μm
Mphase A: 20 mM $NH_4OAC$ in 90% $H_2O$, 10% MeCN
Mphase B: 20 mM $NH_4OAC$ in 10% $H_2O$, 90% MeCN
Flow: 2.5 ml/Min

| Time | % B |
| --- | --- |
| 0.0 | 0.0 |
| 2.0 | 100.0 |
| 2.5 | 100.0 |
| 3.0 | 0.0 |

RT min: 0.206, wavelength: 220 nm allyl 1-(pyrazin-2-yl)cyclopropylcarbamate. To a solution of 1-(pyrazin-2-yl)cyclopropanecarboxylic acid (0.18 g, 1.09 mmol, 1 eq) in dry toluene (5 ml) was added TEA (0.18 ml, 1.3 mmol, 1.2 eq) followed by diphenylphosphoryl azide (0.25 ml, 1.18 mmol, 1.08 eq). The reaction was stirred for 1 h at r.t. Allyl alcohol (0.36 ml, 5.30 mmol, 4.9 eq) was added via syringe and the reaction was heated to 90° C. for 3 h. After cooling to room temperature, the reaction mixture was diluted with water (10 ml) and ethyl acetate (10 ml). The layers were separated and the water layer was extracted with ethyl acetate (2×10 ml). The combined organic layers were dried over $Na_2SO_4$ and concentrated to give a black residue that was purified by silica column chromatography using 20-30% ethyl acetate in hexane. Yield: 0.12 g (50%). $^1$H NMR (400 MHz, $CD_3OD$): δ 1.31-1.38 (m, 2H), 1.60-1.63 (m, 2H), 4.60-4.61 (d, J=5.2 Hz, 2H), 5.23-5.26 (d, J=10.4 Hz, 1H), 5.35-5.39 (d, J=17.2 Hz, 1H,), 5.96-6.03 (m, 1H), 8.36-8.36 (d, J=2.4 Hz, 1H), 8.49-8.508 (q, 1H), 8.63 (s, 1H). LCMS: (ES+) m/z=220.2 (M+H)$^+$ Column: PUROSPHER@star rp-18 (4.6×30) mm, 3 μm
Mphase A: 20 mM $NH_4OAC$ in 90% $H_2O$, 10% MeCN
Mphase B: 20 mM $NH_4OAC$ in 10% $H_2O$, 90% MeCN
Flow: 2.5 ml/Min

| Time | % B |
| --- | --- |
| 0.0 | 0.0 |
| 2.0 | 100.0 |
| 2.5 | 100.0 |
| 3.0 | 0.0 |

RT min: 1.180, wavelength: 220 nm 1-(pyrazin-2-yl)cyclopropanamine. To a solution of allyl 1-(pyrazin-2-yl)cyclopropylcarbamate (0.12 g, 0.547 mmol, 1 eq) and morpholine (0.47 ml, 5.47 mmol, 10 eq) in THF (3 ml) was added Pd(PPh$_3$)$_4$ (0.038 g, 0.033 mmol, 0.06 eq), and the yellow mixture was stirred at 50° C. for 3 h. The solvent was removed under a stream of N2 and the residue was purified by flash chromatography using 4-7% of methanol in dichloromethane to give the compound as a yellow oil. Yield: 0.05 g (68.5%). $^1$H NMR (400 MHz, $CD_3OD$): δ 1.17-1.20 (m, 2H), 1.36-1.38 (m, 2H), 8.36-8.37 (d, J=2.4 Hz, 1H), 8.49-8.50 (q, 1H), 8.85-8.85 (d, J=1.6 Hz, 1H). LCMS: (ES+) m/z=136.2 (M+H)$^+$ Column: PUROSPHER@star rp-18 (4.6×30) mm, 3 μm
Mphase A: 20 mM $NH_4OAC$ in 90% $H_2O$, 10% MeCN
Mphase B: 20 mM $NH_4OAC$ in 10% $H_2O$, 90% MeCN
Flow: 2.5 ml/Min

| Time | % B |
| --- | --- |
| 0.0 | 0.0 |
| 2.0 | 100.0 |
| 2.5 | 100.0 |
| 3.0 | 0.0 |

RT min: 0.408, wavelength: 220 nm.

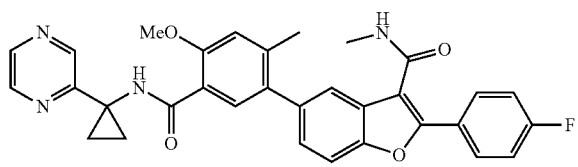

2-(4-Fluorophenyl)-5-(4-methoxy-2-methyl-5-(1-(pyrazin-2-yl)cyclopropylcarbamoyl)phenyl)-N-methylbenzofuran-3-carboxamide. 5-(2-(4-fluorophenyl)-3-(methylcarbamoyl)benzofuran-5-yl)-2-methoxy-4-methylbenzoic acid (0.16 g, 0.369 mmol, 1 eq), 1-(pyrazin-2-yl)cyclopropanamine (0.05 g, 0.369 mmol, 1 eq), EDCI.HCl (0.07 g, 0.369 mmol, 1 eq), HOBT (0.05 g, 0.369 mmol, 1.0 eq) and TEA (0.15 ml, 1.107 mmol, 3 eq) were dissolved in dichloromethane and the above mixture was stirred at room temperature for 18 h. The mixture was then added with water, and organic layer separated and washed with water. The organic layer was dried over $Na_2SO_4$ and concentrated. The crude product obtained was purified by Prep. HPLC. $^1$H NMR (400 MHz, $CD_3OD$): δ 1.43-1.46 (m, 2H), 1.72-1.75 (m, 2H), 2.37 (s, 3H), 2.95 (s, 3H), 4.08 (s, 3H), 7.161 (s, 1H), 7.25-7.30 (m, 2H), 7.35 (dd, J=2, 8.4 Hz, 1H), 7.59 (d, J=1.2 Hz, 1H), 7.64 (d, J=8.4 Hz, 1H), 7.76 (s, 1H), 7.96-7.99 (m, 2H), 8.36 (d, J=2.8 Hz, 1H), 8.520-8.531 (m, 1H), 8.72 (d, J=1.2 Hz, 1H). LCMS: (ES+) m/z=551.2 (M+H)$^+$ Column: ZORBAX SB C18 (4.6×50) mm, 5 μm.
Mphase A: 10% $CH_3OH$-90% $H_2O$-0.1% TFA
Mphase B: 90% $CH_3OH$-10% $H_2O$-0.1% TFA
Flow: 5 ml/Min

| Time | % B |
|---|---|
| 0.0 | 0.0 |
| 2.0 | 100.0 |
| 3.0 | 0.0 |

RT min: 2.039, wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 18.267
Wavelength: 220 nm, RT min: 18.267
Purity: 98.9%
HPLC COLUMN: XBridge phenyl (4.6×150) mm, 3.5 micron
Mobile Phase A: 0.05% TFA in Water:MeCN (95:5)
Mobile Phase B: 0.05% TFA in MeCN:Water (95:5) pH: 2.5
FLOW: 1 ml/min

| Time | B % |
|---|---|
| 0 | 10 |
| 25 | 100 |
| 30 | 100 |

Wavelength: 254 nm, RT min: 16.461
Wavelength: 220 nm, RT min: 16.461
Purity: 99.6%

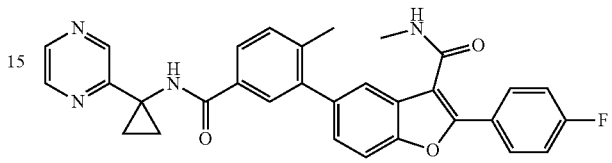

2-(4-Fluorophenyl)-N-methyl-5-(2-methyl-5-(1-(pyrazin-2-yl)cyclopropylcarbamoyl)phenyl)benzofuran-3-carboxamide. 3-(2-(4-fluorophenyl)-3-(methylcarbamoyl)benzofuran-5-yl)-4-methylbenzoic acid (0.149 g, 0.369 mmol, 1 eq), 1-(pyrazin-2-yl)cyclopropanamine (0.05 g, 0.369 mmol, 1 eq), EDCI.HCl (0.07 g, 0.369 mmol, 1 eq), HOBT (0.05 g, 0.369 mmol, 1.0 eq) and TEA (0.15 ml, 1.107 mmol, 3 eq) were dissolved in dichloromethane and the above mixture was stirred at room temperature for 18 h. The mixture was then added with water, and organic layer separated and washed with water. The organic layer was dried over $Na_2SO_4$ and concentrated. The crude product obtained was purified by Prep. HPLC. $^1$H NMR (400 MHz, $CD_3OD$): δ 1.43-1.46 (m, 2H), 1.71-1.74 (m, 2H), 2.37 (s, 3H), 2.95 (s, 3H), 7.25-7.31 (m, 2H), 7.40 (dd, J=2, 8.4 Hz, 1H), 7.47 (d, J=8.4 Hz, 1H), 7.66 (s, 1H), 7.67 (d, J=7.2 Hz, 1H), 7.84-7.87 (m, 2H), 7.95-8.00 (m, 2H), 8.37 (d, J=2.4 Hz, 1H), 8.52 (t, 1H), 8.59 (s, 1H). LCMS: (ES+) m/z=521.2 (M+H)$^+$ Column: Ascentis Express C18 (5×2.1) mm, 2.7 μm.
Mphase A: 2% Acetonitrile-98% Water-10 mM $NH_4COOH$
Mphase B: 98% Acetonitrile-2% Water-10 mM $NH_4COOH$
Flow: 1 ml/Min

| Time | % A | % B |
|---|---|---|
| 0.0 | 100.0 | 0.0 |
| 1.5 | 0.0 | 100.0 |
| 3.2 | 0.0 | 100.0 |

RT min: 1.902, wavelength: 220 nm
HPLC COLUMN: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 10.807
Wavelength: 220 nm, RT min: 10.807
Purity: 99.1%
HPLC COLUMN: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.897
Wavelength: 220 nm, RT min: 9.897
Purity: 99.7%
Preparative HPLC Method
  Column: Xbridge C18 (19×100) mm, 5μ
  Mobile phase: 0.1% TFA in water (A), MeCN (B)
  Flow: 12 ml/min

| Time | % B |
|---|---|
| 0 | 30 |
| 10 | 45 |

RT=18 min.

4-methylpyrimidine-2-carbonitrile. A mixture of 2-chloro-4-methylpyrimidine (725 mg, 5.63 mmol, 1 eq), zinc cyanide (396 mg, 3.38 mmol, 0.6 eq) and tetrakis(triphenylphosphine)palladium(0) (716 mg, 0.562, 0.1 eq) in DMF (10 ml) was heated at 110° C. under nitrogen for 1 hr. The mixture was cooled to r.t., diluted with EtOAc and washed twice with 2N ammonium hydroxide (50 ml). The organic layer was washed with brine (20 ml) dried over sodium sulphate and concentrated in vacuum to provide the crude mixture. The crude product was then purified by column chromatography (30% EtOAc in Hexane) to afford 4-methylpyrimidine-2-carbonitrile Yield: 380 mg (56%). $^1$H NMR (400 MHz, CDCl$_3$): δ 2.61 (s, 3H), 7.36 (d, 1H, J=5.2 Hz), 8.66 (d, 1H, J=5.2 Hz), 1-(4-methylpyrimidin-2-yl)cyclopropanamine. To a solution of 4-methylpyrimidine-2-carbonitrile (200 mg, 1.7 mmol, 1 eq) in dry THF under an argon atmosphere was added titanium isopropoxide (0.58 ml, 2.0 mmol, 1.2 eq) slowly at ambient temperature and the reaction mixture was stirred for 15 min. Ethyl magnesium bromide (1 M solution) in THF (4 ml, 4.0 mmol, 2.4 eq) was added via syringe slowly at ambient temperature (during the addition of EtMgBr, the reaction mixture turned black). Then the reaction mixture was stirred for an hour. BF$_3$.EtO (0.36 ml, 2.6 mmol, 1.5 eq) was added slowly through syringe to the mixture at 0° C. The mixture was allowed to attain ambient temperature and stirred for another one hour. 10 ml of water was added to the reaction mixture, which was then filtered through Celite and the bed washed with water and ethyl acetate. The filtrate was basified with 10% NaOH solution (pH=9) and then extracted with DCM. The organic was washed with brine, dried over sodium sulphate and concentrated to get the crude product which was taken for coupling reaction without further purification. Yield: 120 mg (crude).

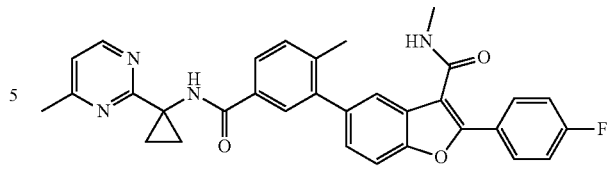

2-(4-Fluorophenyl)-N-methyl-5-(2-methyl-5-(1-(4-methylpyrimidin-2-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.04 g, 0.099 mmol, 1 eq), 1-(4-methylpyrimidin-2-yl)cyclopropanamine (120 mg, crude), Py-Bop (0.067 g, 0.13 mmol, 1.3 eq) in DMF at ambient temperature under nitrogen was added triethylamine (0.026 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 31 mg (58%). $^1$H NMR (400 MHz, CD$_3$OD): δ 8.48 (d, J=5.0 Hz, 1H), 8.02-7.95 (m, 2H), 7.89-7.82 (m, 2H), 7.67 (d, J=5.8 Hz, 2H), 7.48-7.37 (m, 2H), 7.33-7.23 (m, 2H), 7.19-7.13 (m, 1H), 2.96 (s, 3H), 2.48 (s, 3H), 2.36 (s, 3H), 1.82-1.75 (m, 2H), 1.51-1.43 (m, 2H) LCMS: (ES+) m/z=535.2 (M+H)$^+$
  Column-Ascentis Express C18 (5×2.1 mm-2.7 μm)
  Mphase A: 2% MeCN-98% H$_2$O-10 mM NH$_4$COOH
  Mphase B: 98% MeCN-2% H$_2$O-10 mM NH$_4$COOH
  Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.94, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 11.02
Wavelength: 220 nm, RT min: 11.02
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.22
Wavelength: 220 nm, RT min: 10.22

5-methylpyrimidine-2-carbonitrile. To a 10 ml microwave vial was charged with 2-chloro-5-methylpyrimidine (0.97 g, 7.54 mmol, 1 eq), $Pd_2(dba)_3$ (0.274 g, 0.3 mmol, 0.04 eq), DPPF (0.335 g, 0.6 mmol, 0.08 eq), zinc cyanide (0.575 g, 4.9 mmol, 0.65 eq), and zinc dust (0.118 g, 1.81 mmol, 0.24 eq). The flask was evacuated and backfilled with $N_2$ and anhydrous dimethylacetamide. The vial was mounted onto a microwave reactor and heated at 100° C. for 10 hr. The reaction mixture was diluted with EtOAc and then washed with brine thrice, dried over sodium sulphate and concentrated in vacuum to provide the crude mixture. The crude was then purified by column chromatography (30% EtOAc in Hexane) to afford 5-fluoro pyrimidine-2-carbonitrile Yield: 458 mg (51%). $^1$H NMR (400 MHz, $CDCl_3$): δ 2.43 (s, 3H), 8.67 (s, 2H).

1-(5-methylpyrimidin-2-yl)cyclopropanamine. To a solution of 5-methylpyrimidine-2-carbonitrile (200 mg, 1.7 mmol, 1 eq) in dry THF under an argon atmosphere was added titanium isopropoxide (0.58 ml, 2.0 mmol, 1.2 eq) slowly at ambient temperature and the reaction mixture was stirred for 15 mins Ethyl magnesium bromide (1M solution) in THF (4 ml, 4.0 mmol, 2.4 eq) was added via syringe slowly at ambient temperature. Then the reaction mixture was stirred for an hour. $BF_3$.EtO (0.36 ml, 2.6 mmol, 1.5 eq) was added slowly through syringe to the mixture at 0° C. The mixture was allowed to attain ambient temperature and stirred for another one hour. 10 ml of water was added to the reaction mixture which was then filtered through Celite and the bed washed with water and ethyl acetate. The filtrate was basified with 10% NaOH solution (pH=9) then extracted with DCM. The organic was washed with brine solution, dried over sodium sulphate and concentrated to give the crude product which was taken for coupling reaction without further purification. Yield: 125 mg (crude).

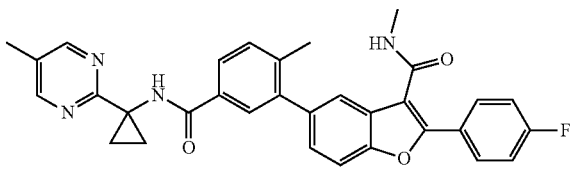

2-(4-Fluorophenyl)-N-methyl-5-(2-methyl-5-(1-(5-methylpyrimidin-2-yl)cyclopropylcarbamoyl)phenyl)benzofuran-3-carboxamide. To a mixture of 3-(2-(4-fluorophenyl)-3-(methylcarbamoyl)benzofuran-5-yl)-4-methylbenzoic acid (0.04 g, 0.099 mmol, 1 eq), 1-(5-methylpyrimidin-2-yl)cyclopropanamine (125 mg, crude), Py-Bop (0.067 g, 0.13 mmol, 1.3 eq) in DMF at ambient temperature under nitrogen was added triethylamine (0.026 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative TLC (Eluent Chloroform:Methanol 9.5:0.5, 200 ml). Yield: 29 mg (54%). $^1$H NMR (400 MHz, $CD_3OD$): δ 8.50 (d, J=0.5 Hz, 2H), 8.03-7.94 (m, 2H), 7.89-7.82 (m, 2H), 7.69-7.64 (m, 2H), 7.47-7.37 (m, 2H), 7.33-7.24 (m, 2H), 2.96 (s, 3H), 2.36 (s, 3H), 2.29 (s, 3H), 1.77-1.70 (m, 2H), 1.47-1.40 (m, 2H) LCMS: (ES+) m/z=535.2 (M+H)$^+$ Column-Ascentis Express C18 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.93, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 6 | 10 |
| 12 | 100 |
| 15 | 100 |

Wavelength: 254 nm, RT min: 11.02
Wavelength: 220 nm, RT min: 11.02
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.19
Wavelength: 220 nm, RT min: 10.19

5-fluoropyrimidine-2-carbonitrile. To a 10 ml microwave vial was charged with 2-chloro-5-fluoropyrimidine (1.0 g, 7.54 mmol, 1 eq), $Pd_2(dda)_3$ (0.274 g, 0.3 mmol, 0.04 eq), DPPF (0.335 g, 0.6 mmol, 0.08 eq), zinc cyanide (0.575 g, 4.9 mmol, 0.65 eq), and zinc dust (0.118 g, 1.81 mmol, 0.24 eq). The flask was evacuated and backfilled with $N_2$ and anhydrous dimethylacetamide. The vial was mounted onto a microwave reactor and heated at 100° C. for 10 hr. The reaction mixture was diluted with EtOAc and then washed with brine thrice, dried over sodium sulphate and concentrated in vacuum to provide the crude mixture. The crude was then purified by column chromatography (30% EtOAc in Hexane) to afford 5-fluoropyrimidine-2-carbonitrile Yield: 468 mg (51%). $^1$H NMR (400 MHz, $CDCl_3$): δ 8.73 (s, 2H).

1-(5-fluoropyrimidin-2-yl)cyclopropanamine. To a solution of 5-fluoropyrimidine-2-carbonitrile (200 mg, 1.6 mmol, 1 eq) in a dry THF under an argon atmosphere was added titanium isopropoxide (0.55 ml, 1.9 mmol, 1.2 eq) at ambient temperature and the reaction mixture was stirred for 15 min. Ethyl magnesium bromide (1M solution) in THF (4 ml, 4.0 mmol, 2.5 eq) was added via syringe slowly at ambient temperature. Then the reaction mixture was stirred for an hour. $BF_3$.EtO (0.34 ml, 2.4 mmol, 1.5 eq) was added slowly through syringe to the mixture at 0° C. The mixture was allowed to attain ambient temperature and stirred for another one hour. 10 ml of water was added to the reaction mixture which was then filtered through Celite and the bed washed with water and ethyl acetate. The filtrate was basified with 10% NaOH solution (pH=9) then extracted with DCM and washed with brine solution, dried over sodium sulphate and concentrated to give the crude product which was taken for coupling reaction without further purification. Yield: 125 mg (crude).

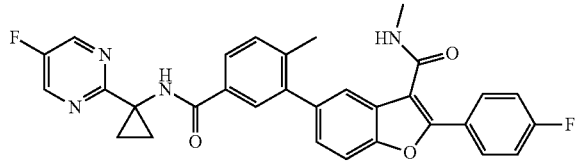

2-(4-Fluorophenyl)-5-(5-(1-(5-fluoropyrimidin-2-yl)-cyclopropylcarbamoyl)-2-methylphenyl)-N-methylbenzofuran-3-carboxamide. To a mixture of 3-(2-(4-fluorophenyl)-3-(methylcarbamoyl)benzofuran-5-yl)-4-methylbenzoic acid (0.04 g, 0.099 mmol, 1 eq), 1-(5-fluoropyrimidin-2-yl)cyclopropanamine (125 mg, crude), Py-Bop (0.067 g, 0.13 mmol, 1.3 eq) in DMF at ambient temperature under nitrogen was added triethylamine (0.026 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative TLC (Eluent Chloroform:Methanol 9.5:0.5 200 ml. Yield: 32 mg (55%). $^1$H NMR (400 MHz, CD$_3$OD): δ 8.58 (d, J=0.5 Hz, 2H), 8.05-7.93 (m, 2H), 7.89-7.79 (m, 2H), 7.68 (s, 2H), 7.49-7.36 (m, 2H), 7.34-7.23 (m, 2H), 2.96 (s, 3H), 2.36 (s, 3H), 1.83-1.68 (m, 2H), 1.55-1.38 (m, 2H). LCMS: (ES+) m/z=539.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.97, wavelength: 220 nm
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.53
Wavelength: 220 nm, RT min: 10.53

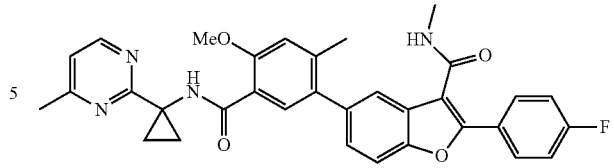

2-(4-Fluorophenyl)-5-(4-methoxy-2-methyl-5-(1-(4-methyl-pyrimidin-2-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.092 mmol, 1 eq), 1-(4-methylpyrimidin-2-yl)cyclopropanamine (130 mg, crude), Py-Bop (0.062 g, 0.12 mmol, 1.3 eq) in DMF at ambient temperature under nitrogen was added triethylamine (0.028 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.028 g (53%). $^1$H NMR (400 MHz, CD$_3$OD): δ 8.49 (d, J=5.3 Hz, 1H), 8.07-7.95 (m, 2H), 7.92 (s, 1H), 7.69-7.51 (m, 2H), 7.39-7.23 (m, 3H), 7.16 (d, J=5.3 Hz, 2H), 4.08 (s, 3H), 2.95 (s, 3 H), 2.49 (s, 3H), 2.37 (s, 3H), 1.87-1.76 (m, 2H), 1.57-1.45 (m, 2H). $^{19}$F NMR (376.47 MHz, CD$_3$OD): δ −78.09 (TFA), −113.44 LCMS: (ES+) m/z=565.2 (M+H)$^+$ Column-Ascentis Express C18 (5×2.1 mm-2.7 μm)

Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.98, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 7 | 10 |
| 12 | 100 |
| 15 | 100 |

Wavelength: 254 nm, RT min: 11.37
Wavelength: 220 nm, RT min: 11.37
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.53
Wavelength: 220 nm, RT min: 10.53

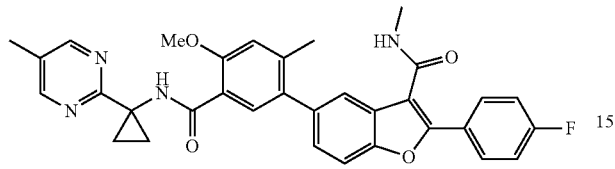

2-(4-Fluorophenyl)-5-(4-methoxy-2-methyl-5-(1-(5-methyl-pyrimidin-2-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.092 mmol, 1 eq), 1-(5-methylpyrimidin-2-yl)cyclopropanamine (130 mg, crude), Py-Bop (0.062 g, 0.12 mmol, 1.3 eq) in DMF at ambient temperature under nitrogen was added triethylamine (0.028 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.025 g (49%). $^1$H NMR (400 MHz, CD$_3$OD): δ 8.50 (d, J=0.8 Hz, 2H), 8.01-7.96 (m, 2H), 7.92 (s, 1H), 7.63 (d, J=8.5 Hz, 1H), 7.59 (d, J=1.3 Hz, 1H), 7.34 (dd, J=1.9, 8.4 Hz, 1H), 7.30-7.25 (m, 2H), 7.15 (s, 1H), 4.08 (s, 3H), 2.96 (s, 3H), 2.37 (s, 3H), 2.29 (s, 3H), 1.80-1.69 (m, 2H), 1.52-1.43 (m, 2H). $^{19}$F NMR (376.47 MHz, CD$_3$OD): δ -113.45 LCMS: (ES+) m/z=565.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.97, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 8 | 10 |
| 12 | 100 |
| 15 | 100 |

Wavelength: 254 nm, RT min: 11.50
Wavelength: 220 nm, RT min: 11.50

HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.57
Wavelength: 220 nm, RT min: 10.57

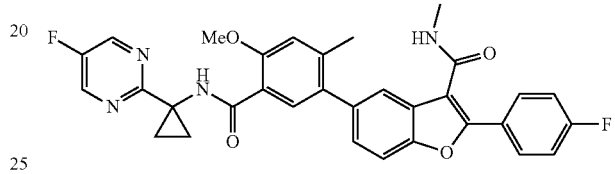

2-(4-Fluorophenyl)-5-(5-(1-(5-fluoropyrimidin-2-yl)cyclo-propylcarbamoyl)-4-methoxy-2-methylphenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.092 mmol, 1 eq), 1-(5-fluoropyrimidin-2-yl)cyclopropanamine (130 mg, crude), Py-Bop (0.062 g, 0.12 mmol, 1.3 eq) in DMF at ambient temperature under nitrogen was added triethylamine (0.028 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.03 g (57%). $^1$H NMR (400 MHz, CD$_3$OD): δ 8.59 (s, 2H), 8.04-7.93 (m, 2H), 7.90 (s, 1H), 7.65 (s, 1H), 7.59 (d, J=1.5 Hz, 1H), 7.34 (dd, J=1.8, 8.5 Hz, 1H), 7.31-7.25 (m, 2H), 7.15 (s, 1 H), 4.07 (s, 3H), 3.00-2.92 (m, 3H), 2.37 (s, 3H), 1.80-1.72 (m, 2H), 1.54-1.43 (m, 2H). $^{19}$F NMR (376.47 MHz, CD$_3$OD): δ -113.44, 146.33 LCMS: (ES+) m/z=569.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.99, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 9 | 10 |
| 12 | 100 |
| 15 | 100 |

Wavelength: 254 nm, RT min: 11.91
Wavelength: 220 nm, RT min: 11.91
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.95
Wavelength: 220 nm, RT min: 10.95

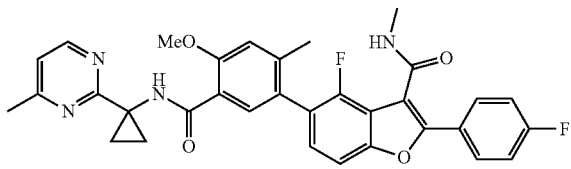

4-Fluoro-2-(4-fluorophenyl)-5-(4-methoxy-2-methyl-5-(1-(4-methylpyrimidin-2-yl)cyclopropylcarbamoyl)phenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (0.04 g, 0.089 mmol, 1 eq), 1-(4-methylpyrimidin-2-yl)cyclopropanamine (130 mg, crude), Py-Bop (0.06 g, 0.11 mmol, 1.3 eq) in DMF at ambient temperature under nitrogen was added triethylamine (0.027 g, 0.26 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.022 g (42%). $^1$H NMR (400 MHz, CD$_3$OD): δ 8.54 (d, J=5.6 Hz, 1H), 7.97-7.94 (m, 2H), 7.90 (s, 1H), 7.51 (d, J=8.4 Hz, 1H), 7.31-7.25 (m, 4H), 7.19 (s, 1H), 4.10 (s, 3H), 2.96 (s, 3H), 2.55 (s, 3H), 2.31 (s, 3H), 1.89-1.86 (m, 2H), 1.59-1.56 (m, 2H). $^{19}$F NMR (376.57 MHz, CD$_3$OD): δ −77.65 (TFA), −112.33, −122.77 LCMS: (ES+) m/z=583.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.96, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 10 | 10 |
| 12 | 100 |
| 15 | 100 |

Wavelength: 254 nm, RT min: 11.27
Wavelength: 220 nm, RT min: 11.27
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.51
Wavelength: 220 nm, RT min: 10.51

4-Fluoro-2-(4-fluorophenyl)-5-(4-methoxy-2-methyl-5-(1-(5-methylpyrimidin-2-yl)cyclopropylcarbamoyl)phenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (0.04 g, 0.089 mmol, 1 eq), 1-(5-methylpyrimidin-2-yl)cyclopropanamine (130 mg, crude), Py-Bop (0.06 g, 0.11 mmol, 1.3 eq) in DMF at ambient temperature under nitrogen was added triethylamine (0.027 g, 0.26 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.025 g (48%). $^1$H NMR (400 MHz, CD$_3$OD): δ 8.58 (d, J=0.8 Hz, 2H), 7.97-7.94 (m, 2H), 7.90 (s, 1H), 7.51 (d, J=8.4 Hz, 1H), 7.31-7.25 (m, 3H), 7.19 (s, 1H), 4.10 (s, 3H), 2.96 (s, 3H), 2.33 (s, 3H), 2.31 (s, 3H), 1.82-1.79 (m, 2H), 1.55-1.52 (m, 2H). $^{19}$F NMR (376.57 MHz, CD$_3$OD) δ −77.67 (TFA), −112.34, −122.75 LCMS: (ES+) m/z=583.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.95, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 11 | 10 |
| 12 | 100 |
| 15 | 100 |

Wavelength: 254 nm, RT min: 11.23
Wavelength: 220 nm, RT min: 11.23
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.46
Wavelength: 220 nm, RT min: 10.46

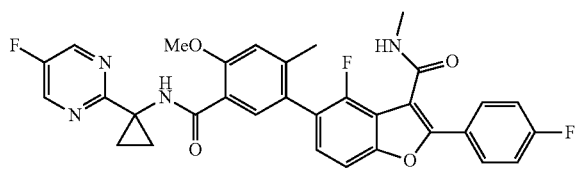

4-Fluoro-2-(4-fluorophenyl)-5-(5-(1-(5-fluoropyrimidin-2-yl)cyclopropyl carbamoyl)-4-methoxy-2-methylphenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (0.04 g, 0.089 mmol, 1 eq), 1-(5-fluoropyrimidin-2-yl)cyclopropanamine (130 mg, crude), Py-Bop (0.06 g, 0.11 mmol, 1.3 eq) in DMF at ambient temperature under nitrogen was added triethylamine (0.027 g, 0.26 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC.

Yield: 0.023 g (44%). $^1$H NMR (400 MHz, CD$_3$OD): δ 8.59 (d, J=0.4 Hz, 2H), 7.98-7.94 (m, 2H), 7.87 (s, 1H), 7.52 (d, J=8.4 Hz, 1H), 7.31-7.25 (m, 3H), 7.18 (s, 1H), 4.09 (s, 3H), 2.96 (s, 3H), 2.30 (s, 3H), 1.79-1.76 (m, 2H), 1.52-1.48 (m, 2H). $^{19}$F NMR (376.57 MHz, CD$_3$OD) δ −77.62 (TFA), −112.36, −122.73, −145.58 LCMS: (ES+) m/z=587.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.97, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 12 | 10 |
| 12 | 100 |
| 15 | 100 |

Wavelength: 254 nm, RT min: 11.51
Wavelength: 220 nm, RT min: 11.51
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.79
Wavelength: 220 nm, RT min: 10.79

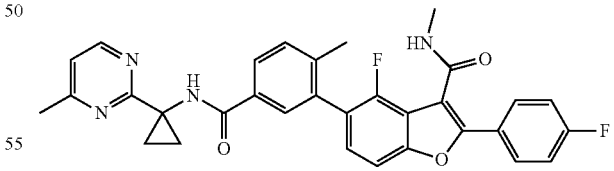

4-Fluoro-2-(4-fluorophenyl)-N-methyl-5-(2-methyl-5-(1-(4-methylpyrimidin-2-yl)cyclopropylcarbamoyl)phenyl)benzofuran-3-carboxamide. To a mixture of 3-(4-fluoro-2-(4-fluorophenyl)-3-(methylcarbamoyl)benzofuran-5-yl)-4-methylbenzoic acid (0.04 g, 0.095 mmol, 1 eq), 1-(4-methylpyrimidin-2-yl)cyclopropanamine (130 mg, crude), Py-Bop (0.064 g, 0.12 mmol, 1.3 eq) in DMF at ambient temperature under nitrogen was added triethylamine (0.029 g, 0.28 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.024 g (46%). $^1$H NMR (400 MHz, CDCl$_3$): δ 8.63 (d, J=6.0 Hz, 1H), 8.39 (bs, 1H), 7.99-7.95 (m, 2H), 7.82 (dd, J=2.0, 8.0 Hz, 1H), 7.73 (d, J=1.6 Hz, 1H), 7.41-7.36 (m, 2H), 7.34 (d, J=5.6 Hz, 1H), 7.21-7.15 (m, 3H), 6.39 (bs, 1H), 3.03 (d, J=4.8 Hz, 3H), 2.71 (s, 3H), 2.24 (s, 3H), 2.06-2.03 (m, 2H), 1.74-1.71 (m, 2H). $^{19}$F NMR (376.47 MHz, CDCl$_3$) δ −75.92 (TFA), −109.79, −119.33. LCMS: (ES+) m/z=553.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.92, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 13 | 10 |
| 12 | 100 |
| 15 | 100 |

Wavelength: 254 nm, RT min: 10.59
Wavelength: 220 nm, RT min: 10.59
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.98
Wavelength: 220 nm, RT min: 9.98

4-Fluoro-2-(4-fluorophenyl)-N-methyl-5-(2-methyl-5-(1-(5-methylpyrimidin-2-yl)cyclopropylcarbamoyl)phenyl)benzofuran-3-carboxamide. To a mixture of 3-(4-fluoro-2-(4-fluorophenyl)-3-(methylcarbamoyl)benzofuran-5-yl)-4-methylbenzoic acid (0.04 g, 0.095 mmol, 1 eq), 1-(5-methylpyrimidin-2-yl)cyclopropanamine (130 mg, crude), Py-Bop (0.064 g, 0.12 mmol, 1.3 eq), in DMF at ambient temperature under nitrogen was added triethylamine (0.029 g, 0.28 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.023 g (44%). $^1$H NMR (400 MHz, CDCl$_3$): δ 8.64 (s, 2H), 8.14 (bs, 1H), 7.99-7.95 (m, 2H), 7.82 (dd, J=2.0, 8.0 Hz, 1H), 7.66 (bs, 1H), 7.42 (d, J=8.4 Hz, 1H), 7.37 (d, J=8.0 Hz, 1H), 7.21-7.15 (m, 3 H), 6.18 (bs, 1H), 3.03 (d, J=4.8 Hz, 3H), 2.35 (s, 3H), 2.24 (s, 3H), 1.92 (m, 2H), 1.67 (m, 2H). $^{19}$F NMR (376.47 MHz, CDCl$_3$) δ −76.71 (TFA), −110.50, −120.06. LCMS: (ES+) m/z=553.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.90, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 14 | 10 |
| 12 | 100 |
| 15 | 100 |

Wavelength: 254 nm, RT min: 17.19
Wavelength: 220 nm, RT min: 17.19
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 15.84
Wavelength: 220 nm, RT min: 15.84

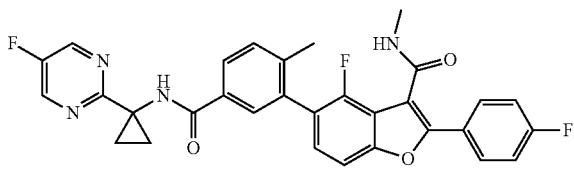

4-Fluoro-2-(4-fluorophenyl)-5-(5-(1-(5-fluoropyrimidin-2-yl)cyclopropyl carbamoyl)-2-methylphenyl)-N-methyl-benzofuran-3-carboxamide. To a mixture of 3-(4-fluoro-2-(4-fluorophenyl)-3-(methylcarbamoyl)benzofuran-5-yl)-4-methylbenzoic acid (0.04 g, 0.095 mmol, 1 eq), 1-(5-fluoropyrimidin-2-yl)cyclopropanamine (130 mg, crude), Py-Bop (0.064 g, 0.12 mmol, 1.3 eq), in DMF at ambient temperature under nitrogen was added triethylamine (0.029 g, 0.28 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.026 g (50%). $^1$H NMR (400 MHz, CDCl$_3$): δ 8.46 (s, 2H), 7.99-7.95 (m, 2H), 7.80 (dd, J=2.0, 8.0 Hz, 1H), 7.74 (d, J=1.6 Hz, 1H), 7.43-7.39 (m, 2H), 7.23-7.15 (m, 3H), 7.07 (bs, 1H), 6.18 (bs, 1H), 3.03 (d, J=4.8 Hz, 3H), 2.27 (s, 3H), 1.81-1.78 (m, 2H), 1.55-1.53 (m, 2H). $^{19}$F NMR (376.47 MHz, CDCl$_3$) δ −75.77 (TFA), −109.62, −119.26, −142.84 LCMS: (ES+) m/z=557.4 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.92, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 15 | 10 |
| 12 | 100 |
| 15 | 100 |

Wavelength: 254 nm, RT min: 10.98
Wavelength: 220 nm, RT min: 10.98
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.33
Wavelength: 220 nm, RT min: 10.33

1-(furan-2-yl)cyclopropanamine. To a solution of 2-furonitrile (5 g, 53.71 mmol, 1.0 eq) in dry THF under an argon atmosphere was added slowly titanium isopropoxide (18.9 ml, 64.4 mmol, 1.2 eq) at r.t. The reaction mixture was stirred for 15 min. A 1M solution of EtMgBr in THF (129 ml, 129 mmol, 2.4 eq) was added slowly via syringe to the mixture at 0° C. After addition, the reaction mixture was allowed to warm to r.t. and stirred at r.t. for 2 hour. BF$_3$.Et$_2$O (10.4 ml) was then added slowly to the mixture at 0° C. After the completion of addition, the reaction mixture was stirred at r.t. for 30 min. The reaction mixture was added with ice, and then with 10% NaOH solution slowly till the reaction mixture becomes basic. The mixture was extracted with EtOAc. The organic was washed with brine, dried over Na$_2$SO$_4$ and concentrated. The crude product was purified by silica gel (60-120) column chromatography using 35% EtOAc/Pet ether as eluent. Yield: 2.5 g (crude).

tert-butyl 1-(furan-2-yl)cyclopropylcarbamate. A solution of 1-(furan-2-yl)cyclopropanamine (2.3 g, 18.69 mmol, 1.0 eq) in THF (25 ml) was added Boc anhydride (4.9 g, 22.47 mmol, 1.2 eq) at 0° C. and then stirred at r.t. overnight. The reaction mixture was concentrated and crude product was purified by silica gel (60-120) column chromatography using 5% EtOAc/Pet ether as eluent. Yield: 2.5 g (60%). $^1$H NMR (400 MHz, CDCl$_3$): δ 1.17 (s, 2H), 1.28 (s, 2H), 1.43 (s, 9H), 5.21 (bs, 1H) 6.09 (d, J=2.8 Hz, 1H), 6.26 (q, J=3.2 Hz 1H), 7.23 (q, J=2.0 Hz, 1H). LCMS (ES+) m/z=123.7 (M)$^+$ tert-butyl 1-(pyridazin-3-yl)cyclopropylcarbamate. A solution of tert-butyl 1-(furan-2-yl)cyclopropylcarbamate (2.15 g, 9.64 mmol, 1.0 eq) in acetone (86 ml) and water (86 ml) was purged N$_2$ and cooled to −20° C. NaHCO$_3$ (1.62 g, 19.28 mmol, 2.0 eq) and N-bromosuccinimide (2.23 g, 12.52 mmol, 1.3 eq) were added to the mixture at −20° C. which was stirred at the same temperature for 2 hr. To the reaction mixture at −20° C. was added THF (4.3 ml) and the temperature raised to 0° C. over 30 min. Acetone was removed from the reaction mixture by a stream of N$_2$ and to the residue at 0° C. was added isopropanol (86 ml) followed by hydrazine hydrate (12.9 ml). The reaction mixture was stirred at r.t. overnight. Product formation was confirmed by LCMS. After removal of the solvent by vacuum, the residue was diluted with water and extracted with EtOAc. The organic was washed with brine, dried over Na$_2$SO$_4$, filtered and concentrated. The crude product was purified by silica gel (60-120) column chromatography using 4% MeOH/CHCl$_3$ as eluent. Yield: 0.8 g (36%). $^1$H NMR (400 MHz, CDCl$_3$): δ 8.95 (d, J=3.6 Hz, 1H), 7.53 (d, J=8 Hz, 1H), 7.39 (m, 1H), 5.45 (bs, 1H), 1.82 (m, 2H), 1.46 (s, 9H) 1.24 (m, 2H). LCMS: (ES+) m/z=236.2 (M+H)$^+$ 1-(pyridazin-3-yl)cyclopropanamine hydrochloride. To a solution of tert-butyl 1-(pyridazin-3-yl)cyclopropylcarbamate (0.3 g) in THF (3 ml) at 0° C. was added HCl in dioxane (5 ml) and the mixture stirred at r.t. for 3 hr. The reaction mixture was concentrated, and the crude product was taken for the next coupling reaction. Yield: 0.21 g 2-(4-Fluorophenyl)-5-(4-methoxy-2-methyl-5-(1-(pyridazin-3-yl)cyclo propylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.092 mmol, 1 eq), 1-(pyridazin-3-yl)cyclopropanamine HCl salt (0.017 g, 0.092 mmol, 1 eq) and Py-Bop (0.062 g, 0.12 mmol, 1.3 eq) in DMF at ambient temperature under nitrogen was added triethylamine (0.028 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by flash column chromatography using 4% MeOH/CHCl$_3$ as eluant. Yield: 0.032 g (63%). $^1$H NMR (400 MHz, CD$_3$OD): δ 9.15 (s, 1H), 9.00 (d, J=3.8 Hz, 1H), 8.53-8.40 (m, 1H), 8.02-7.95 (m, 2H), 7.84 (dd, J=1.5, 8.5 Hz, 1H), 7.79 (s, 1H), 7.70-7.62 (m, 2H), 7.59 (d, J=1.5 Hz, 1H), 7.34 (dd, J=1.8, 8.5 Hz, 1H), 7.31-7.26 (m, 2H), 7.16 (s, 1H), 4.09 (s, 3H), 2.98-2.95 (m, 3H), 2.38 (s, 3H), 1.89-1.87 (m, 2H), 1.57-1.52 (m, 2H). $^{19}$F NMR (376.57 MHz, CD$_3$OD): δ −112.66 LCMS: (ES+) m/z=551.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.88, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 16 | 10 |
| 12 | 100 |
| 15 | 100 |

Wavelength: 254 nm, RT min: 10.35
Wavelength: 220 nm, RT min: 10.35
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.77
Wavelength: 220 nm, RT min: 9.77

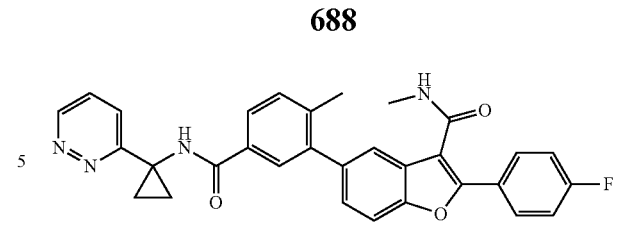

2-(4-Fluorophenyl)-N-methyl-5-(2-methyl-5-(1-(pyridazin-3-yl)cyclopropylcarbamoyl)phenyl)benzofuran 3-carboxamide. To a mixture of 3-(2-(4-fluorophenyl)-3-(methylcarbamoyl)benzofuran-5-yl)-4-methylbenzoic acid (0.04 g, 0.099 mmol, 1 eq), 1-(pyridazin-3-yl)cyclopropanamine HCl salt (0.018, 0.099 mmol, 1 eq) and Py-Bop (0.067 g, 0.13 mmol, 1.3 eq) in DMF at ambient temperature under nitrogen was added triethylamine (0.026 g, 0.3 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.031 mg (60%). $^1$H NMR (400 MHz, CDCl$_3$): δ 9.17 (s, 1H), 7.92-7.96 (m, 3H), 7.77-7.69 (m, 4H), 7.65 (s, 1 H), 7.56 (d, J=8.4 Hz, 1H), 7.38 (d, J=8.0 Hz, 1H), 7.30 (dd, J=1.6, 8.4 Hz, 1H), 7.23-7.19 (m, 2H), 5.94 (bs, 1H), 3.0 (s, 3H), 2.33 (s, 3H), 1.89-1.86 (m, 2H), 1.60-1.57 (m, 2H). $^{19}$F NMR (376.47 MHz, CDCl$_3$): δ −75.82 (TFA), −109.29 LCMS: (ES+) m/z=521.0 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.86, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 17 | 10 |
| 12 | 100 |
| 15 | 100 |

Wavelength: 254 nm, RT min: 9.77
Wavelength: 220 nm, RT min: 9.77
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.33
Wavelength: 220 nm, RT min: 9.33

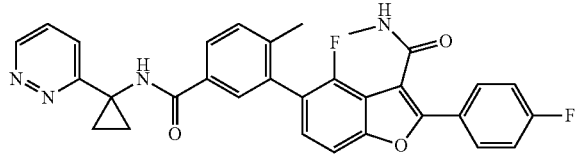

4-Fluoro-2-(4-fluorophenyl)-N-methyl-5-(2-methyl-5-(1-(pyridazin-3-yl)cyclopropylcarbamoyl)phenyl)benzofuran-3-carboxamide. To a mixture 3-(4-fluoro-2-(4-fluorophenyl)-3-(methylcarbamoyl)benzofuran-5-yl)-4-methylbenzoic acid (0.04 g, 0.095 mmol, 1 eq), 1-(pyridazin-3-yl)cyclopropanamine HCl salt (0.017, 0.095 mmol, 1 eq) and Py-Bop (0.064 g, 0.12 mmol, 1.3 eq) in DMF at ambient temperature under nitrogen was added triethylamine (0.029 g, 0.28 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.029 g (57%). $^1$H NMR (400 MHz, CD$_3$OD): δ 9.14 (d, J=3.6 Hz, 1H), 7.97-7.85 (m, 6H), 7.56 (d, J=8.4 Hz, 1H), 7.51 (d, J=8.0 Hz, 1H), 7.34-7.28 (m, 3H), 2.96 (s, 3H), 2.30 (s, 3H), 1.89-1.86 (m, 2H), 1.62-1.59 (m, 2H). $^{19}$F NMR (376.57 MHz, CD$_3$OD): δ −77.63 (TFA), −112.22, −112.77 LCMS: (ES+) m/z=539.2 (M+H)$^+$ Column-Ascentis Express C18 (5×2.1 mm-2.7 µm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.83, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 18 | 10 |
| 12 | 100 |
| 15 | 100 |

Wavelength: 254 nm, RT min: 9.49
Wavelength: 220 nm, RT min: 9.49
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.28
Wavelength: 220 nm, RT min: 9.28

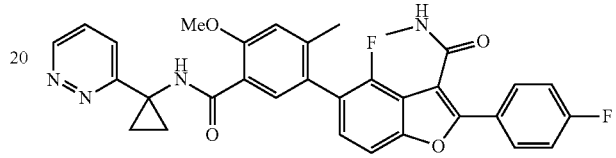

4-Fluoro-2-(4-fluorophenyl)-5-(4-methoxy-2-methyl-5-(1-(pyridazin-3-yl)cyclopropylcarbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.089 mmol, 1 eq), 1-(pyridazin-3-yl)cyclopropanamine HCl salt (0.017 g, 0.089 mmol, 1 eq) and Py-Bop (0.06 g, 0.11 mmol, 1.3 eq) in DMF at ambient temperature under nitrogen was added triethylamine (0.027 g, 0.26 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by flash column chromatography using 4% MeOH/CHCl$_3$ as eluant. Yield: 0.033 g (63%). $^1$H NMR (400 MHz, CD$_3$OD): δ 9.15 (s, 1H), 8.98 (d, 1H), 8.75 (d, J=4.0 Hz, 1H), 7.97-7.93 (m, 2H), 7.82 (dd, J=1.6, 8.8 Hz, 1H), 7.76 (s, 1H), 7.66 (dd, J=5.2, 8.8 Hz, 1H), 7.52 (d, J=8.4 Hz, 1H), 7.31-7.25 (m, 3H), 7.19 (s, 1H), 4.09 (s, 3H), 2.96 (s, 3 H), 2.30 (s, 3H), 1.88 (m, 2H), 1.54 (m, 2H). LCMS: (ES+) m/z=569.2 (M+H)$^+$ Column-Ascentis Express C18 (5×2.1 mm-2.7 µm)
Mphase A: 2% MeCN-98% H$_2$O-10 mM NH$_4$COOH
Mphase B: 98% MeCN-2% H$_2$O-10 mM NH$_4$COOH
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.89, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 19 | 10 |
| 12 | 100 |
| 15 | 100 |

Wavelength: 254 nm, RT min: 15.49
Wavelength: 220 nm, RT min: 15.49
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 15.10
Wavelength: 220 nm, RT min: 15.10

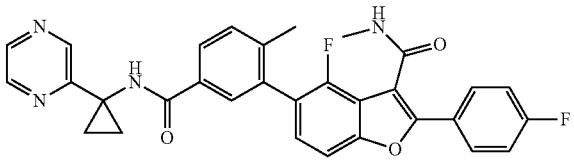

4-Fluoro-2-(4-fluorophenyl)-N-methyl-5-(2-methyl-5-(1-(pyrazin-2-yl)cyclopropylcarbamoyl)phenyl)benzofuran-3-carboxamide. To a mixture of 3-(4-fluoro-2-(4-fluorophenyl)-3-(methylcarbamoyl)benzofuran-5-yl)-4-methylbenzoic acid (0.04 g, 0.095 mmol, 1 eq), 1-(pyrazin-2-yl)cyclopropanamine (0.015 g, 0.011 mmol, 1.2 eq) and Py-Bop (0.064 g, 0.12 mmol, 1.3 eq) in DMF at ambient temperature under nitrogen was added triethylamine (0.029 g, 0.28 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.034 g (66%). $^1$H NMR (400 MHz, $CD_3OD$): δ 8.60 (d, J=1.6 Hz, 1H), 8.52 (m, 1H), 8.37 (d, J=2.4 Hz, 1H), 7.98-7.95 (m, 2H), 7.92 (dd, J=1.6, 7.8 Hz, 1H), 7.85 (d, J=1.6 Hz, 1H), 7.55 (d, J=8.4 Hz, 1H), 7.51 (d, J=8.0 Hz, 1H), 7.36-7.28 (m, 3H), 2.96 (s, 3H), 2.30 (s, 3H), 1.73-1.71 (m, 2H), 1.47-1.43 (m, 2H). $^{19}$F NMR (376.57 MHz, $CD_3OD$) δ -77.68 (TFA), -112.27, -122.72 LCMS: (ES+) m/z=539.2 $(M+H)^+$ Column-Ascentis Express C18 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.87, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 20 | 10 |
| 12 | 100 |
| 15 | 100 |

Wavelength: 254 nm, RT min: 10.40
Wavelength: 220 nm, RT min: 10.40
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 9.83
Wavelength: 220 nm, RT min: 9.83

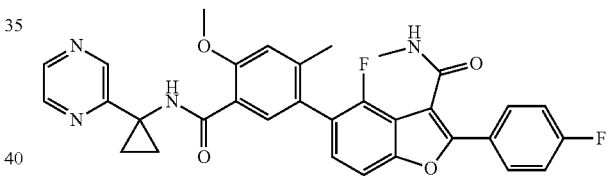

4-Fluoro-2-(4-fluorophenyl)-5-(4-methoxy-2-methyl-5-(1-(pyrazin-2-yl)cyclopropylcarbamoyl)phenyl)-N-methyl-benzofuran-3-carboxamide. To a mixture of 5-(2-(4-fluorophenyl)-3-(methylcarbamoyl)benzofuran-5-yl)-2-methoxy-4-methylbenzoic acid (0.04 g, 0.089 mmol, 1 eq), 1-(pyrazin-2-yl)cyclopropanamine (0.014 g, 0.01 mmol, 1.2 eq) and Py-Bop (0.06 g, 0.11 mmol, 1.3 eq) in DMF at ambient temperature under nitrogen was added triethylamine (0.027 g, 0.26 mmol, 3 eq). The clear mixture was stirred at ambient temperature for 12 h. The mixture was concentrated, diluted with water and extracted with EtOAc. The organic layer was further washed with water, dried over sodium sulphate and concentrated. The product obtained was purified by preparative HPLC. Yield: 0.031 g (62%). $^1$H NMR (400 MHz, $CD_3OD$): δ 8.73 (br. s., 1H), 8.56 (br. s., 1H), 8.47-8.31 (m, 1H), 8.06-7.88 (m, 2H), 7.74 (s, 1H), 7.53 (s, 1H), 7.36-7.26 (m, 3H), 7.19 (s, 1H), 4.10 (s, 3H), 2.96 (s, 3H), 2.31 (s, 3H), 1.84-1.67 (m, 2H), 1.56-1.38 (m, 2H). $^{19}$F NMR (376.57 MHz, $CD_3OD$) δ -77.80 (TFA), -112.34, -122.74 LCMS: (ES+) m/z=569.2 $(M+H)^+$ Column-Ascentis Express C18 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.91, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 21 | 10 |
| 12 | 100 |
| 15 | 100 |

Wavelength: 254 nm, RT min: 10.91
Wavelength: 220 nm, RT min: 10.91
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.17
Wavelength: 220 nm, RT min: 10.17

2-Chloro-4,6-dimethylpyrimidine. To a 50 ml single neck round-bottomed flask was added 4,6-dimethylpyrimidin-2-ol (5.0 g, 0.04 mol) followed by POCl$_3$ (15.0 ml, 0.097 mol). The resulting suspension was heated to reflux overnight. Heating was stopped. After cooling, the mixture was concentrated, poured into crushed ice and extracted with diethyl ether (100 ml×2). The organic layer was washed with 10% NaHCO$_3$ solution, dried over Na$_2$SO$_4$ and evaporated to get a pale yellow solid. Yield: 3.3 g (58%) $^1$H NMR (400 MHz, CDCl$_3$): δ 2.48 (s, 6H), 6.97 (s, 1H). LCMS: (ES+) m/z=143.6 (M+H)$^+$
Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.428, wavelength: 220 nm
4,6-dimethylpyrimidine-2-carbonitrile. 2-Chloro-4,6-dimethylpyrimidine (3.3 g, 0.023 mol) was combined with zinc cyanide (2.7 g, 0.023 mol, 1 eq.) and tetrakis(triphenylphosphine)palladium (0) (2.7 g, 0.0023 mol, 0.1 eq.) in DMF (20 ml), and the slurry was heated at 110° C. under nitrogen for 0.5 h. The mixture was cooled to room temperature, diluted with EtOAc (70 ml) and washed twice with 2N ammonium hydroxide (50 ml). The EtOAc solution was washed with brine (20 ml) and concentrated in vacuum to provide the crude mixture. The crude was then purified by column chromatography (30% EtOAc/hexane) to afford 4,6-dimethylpyrimidine-2-carbonitrile. Yield: 0.8 g (26%). $^1$H NMR (400 MHz, CDCl$_3$): δ 2.48 (s, 6H), 7.21 (s, 1H). LCMS: (ES+) m/z=133.6 (M)$^+$
Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.239, wavelength: 220 nm
1-(4,6-dimethylpyrimidin-2-yl)cyclopropanamine. To a stirred solution of 4,6-dimethylpyrimidine-2-carbonitrile (0.2 g, 1.5 mmol) in anhydrous THF was added Ti(OiPr)$_4$ (0.43 ml, 1.8 mmol, 1.2 eq.). After stirring for 15 min., Ethyl magnesium bromide (3.8 ml, 3.8 mmol, 2.5 eq.) in THF was added dropwise to the mixture at −78° C. (during the addition of EtMgBr the reaction mixture turned black). The reaction mixture was then stirred for an hour at room temperature, and then BF$_3$.Et$_2$O (0.320 ml, 2.2 mmol, 1.5 eq.) was added slowly to the mixture at 0° C. After the addition completed, the reaction was stirred at room temperature for one hour. 50 ml of water was added to the reaction mixture which was then filtered through Celite. The filtrate was basified with 10% NaOH solution (pH=9) and then extracted with DCM (25 ml×2) and washed with brine. The organic layer was concentrated to yield crude product was taken for the next step without purification.

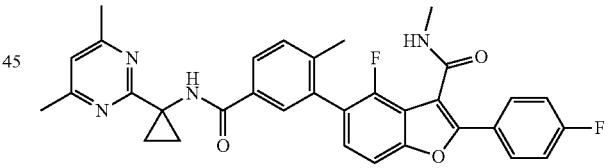

5-(5-(1-(4,6-dimethylpyrimidin-2-yl)cyclopropycarbamoyl)-2-methylphenyl)-4-fluoro-2-(4-fluorophenyl)-N-methylbenzofuran-3-carboxamide. To a mixture of 3-(4-fluoro-2-(4-fluorophenyl)-3-(methylcarbamoyl)benzofuran-5-yl)-4-methylbenzoic acid (50 mg, 0.12 mmol), crude 1-(4,6-dimethylpyrimidin-2-yl)cyclopropanamine (150 mg) in 2 ml DMF at room temperature was added BOP (106 mg, 0.24 mmol, 2.0 eq.) and triethyl amine (0.050 ml, 0.36 mmol, 3.0 eq.), and the mixture stirred overnight under an N$_2$ atmosphere. The mixture was poured into crushed ice, and solid precipitate was filtered and dried. The product obtained was further purified by column chromatography using Silica gel (230-400) and CHCl$_3$-MeOH (95:5) as a mobile phase. Yield: 40 mg (60%). $^1$H NMR (400 MHz, CDCl$_3$): δ 8.00-7.97 (m, 2H), 7.80-7.76 (m, 2H), 7.41-7.37 (m, 3H), 7.21-7.15 (m, 3H), 6.77 (s, 1H), 6.22 (br. s., 1H), 3.01 (d, J=5.0 Hz, 3H), 2.37 (s, 6H), 2.26 (s, 3H), 1.76-1.73 (m, 2H), 1.56-1.54 (m, 2H). $^{19}$F NMR (376.57 MHz, CDCl$_3$): δ −109.83, −119.22
LCMS: (ES+) m/z=567.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.971, wavelength: 220 nm
HPLC Method: SUNFIRE C18 (4.6×150) mm, 3.5 micron
Buffer: 0.05% TFA in water pH 2.5 adjusted with dil NH$_3$
Mobile Phase A: Buffer:MeCN (95:5)
Mobile Phase B: MeCN:Buffer (95:5)
FLOW: 1 ml/min

| Time | B % |
|---|---|
| 22 | 10 |
| 29 | 100 |
| 30 | 100 |

Wavelength: 254 nm, RT min: 16.83
Wavelength: 220 nm, RT min: 16.83
Purity: 95.31%
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.03
Wavelength: 220 nm, RT min: 16.03
Purity: 96.63%

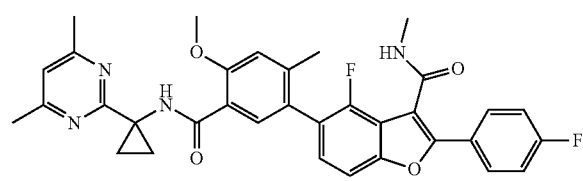

5-(5-(1-(4,6-dimethylpyrimidin-2-yl)cyclopropylcarbamoyl)-4-methoxy-2-methylphenyl)-4-fluoro-2-(4-fluorophenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (50 mg, 0.11 mmol), crude 1-(4,6-dimethylpyrimidin-2-yl)cyclopropanamine (100 mg) in 2 ml DMF at room temperature was added BOP (100 mg, 0.22 M, 2.0 eq.) and triethyl amine (0.046 ml 0.33 M, 3.0 eq.), and the mixture stirred overnight under an N$_2$ atmosphere. The mixture was poured into crushed ice, and the solid precipitate was filtered and dried. The product obtained was further purified by preparative HPLC. Yield: 15 mg (24%) $^1$H NMR (400 MHz, CD$_3$OD): δ 7.97-7.94 (m, 2H), 7.89 (s, 1H), 7.51 (d, J=8.5 Hz, 1H), 7.31-7.25 (m, 3H), 7.19 (s, 1H), 7.14 (s, 1H), 4.11 (s, 3H), 2.96 (s, 3H), 2.48 (s, 6H), 2.31 (s, 3H), 1.86-1.83 (m, 2H), 1.55-1.52 (m, 2H). $^{19}$F NMR (376.57 MHz, CD$_3$OD) δ −77.40 (TFA), −112.33, −122.75 (CFCl$_3$ as reference). LCMS: (ES+) m/z=597.2 (M+H)$^+$ Column-Ascentis Express C18 (5×2.1 mm-2.7 μm)
Mphase A: 2% MeCN-98% H$_2$O-10 mM NH$_4$COOH
Mphase B: 98% MeCN-2% H$_2$O-10 mM NH$_4$COOH
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 2.01, wavelength: 220 nm
HPLC Method: SUNFIRE C18 (4.6×150) mm, 3.5 micron
Buffer: 0.05% TFA in water pH 2.5 adjusted with dil NH$_3$
Mobile Phase A: Buffer:MeCN (95:5)
Mobile Phase B: MeCN:Buffer (95:5)
FLOW: 1 ml/min

| Time | B % |
|---|---|
| 23 | 10 |
| 30 | 100 |
| 30 | 100 |

Wavelength: 254 nm, RT min: 17.97
Wavelength: 220 nm, RT min: 17.97
Purity: 98.65%
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.61
Wavelength: 220 nm, RT min: 16.61
Purity: 98.78%
Preparative HPLC method:
Column: X-bridge C18 (100×4.6×5.0μ)
Mobile Phase A: 0.05% TFA in Water
Mobile Phase B: Acetonitrile

| Gradient: | | | |
|---|---|---|---|
| Time | Flow | A(%) | B(%) |
| 0 | 15 ml/min | 80 | 20 |
| 5 | 15 ml/min | 55 | 45 |

RT: 18 min.

tert-butyl 1(methoxy(methyl)carbamoyl)cyclopropylcarbamate. To a solution of 1-(tert-butoxycarbonylamino)cyclopropanecarboxylic acid (11.00 g, 54.7 mmol, 1.0 eq) in methylene chloride at 0° C. was added N,O-dimethyl hydroxylamine HCl (5.9 g, 60.4 mmol, 1.1 eq), TEA (13.82 g, 13.6 mmol, 2.5 eq) and HATU (22.90 g, 60.2 mmol, 1.1 eq). The resulting reaction mixture was stirred at room temperature under an $N_2$ atmosphere overnight. After TLC showed reaction was completed, the reaction mixture was concentrated, diluted with water and extracted with diethyl ether. The organic layer was washed with brine, dried over $Na_2SO_4$ and concentrated to get the desired product as a white solid. Yield: 13.00 g (97.52%).

tert-butyl 1-propioloylcyclopropylcarbamate. To a stirred solution of tert-butyl 1-(methoxy(methyl)carbamoyl)cyclopropylcarbamate (5.0 g, 20.49 mmol, 1.0 eq) in THF at −78° C. was added (trimethylsilyl)acetylene (6.36 g, 61.15 mmol, 3.0 eq), and the stirring continued at the same temperature for 5 hr. Product formation was confirmed by LCMS. Saturated $NH_4Cl$ solution was added to the reaction mixture, which was then extracted with EtOAC. The organic layer was washed with brine, dried over $Na_2SO_4$ and concentrated. The crude product was purified by column chromatography using silica gel (60-120). The desired compound was eluted with 15% EtOAC in Pet ether. Yield: 1.5 g (35.70%).

(E)-tert-butyl 1-(3-(dimethylamino)acryloyl)cyclopropylcarbamate. A 2M solution of dimethylamine in THF (14.5 ml) and tert-butyl propioloylcyclopropylcarbamate (1.5 g, 7.17 mmol, 1.0 eq) was stirred at 0° C., and then the stirring continued at r.t. for 4 hr. TLC showed completion of the reaction. The reaction mixture was concentrated to yield the crude solid product which was then recrystalised in EtOAC/Pet ether to get the desired product as light yellow solid. Yield: 1.4 g (77.8%). $^1$H NMR (400 MHz, $CDCl_3$): δ 7.59 (d, J=12.4, 1H), 5.52 (d, J=10.8, 1H), 5.37 (d, J=12.4, 1H), 3.07 (bs, 3H), 2.82 (bs, 3H), 1.52 (s, 2H), 1.45 (s, 9H), 1.05 (s, 2H). LCMS: (ES+) m/z=255.2 $(M+H)^+$ Column: Ascentis Express C8 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.57, wavelength: 220 nm tert-butyl 1-(pyrimidin-4-yl)cyclopropylcarbamate. A solution of (E)-tert-butyl 1-(3-(dimethylamino)acryloyl)cyclopropyl carbamate (0.300 g, 1.18 mmol, 1.0 eq), formamidine acetate (0.490 g, 4.724 mmol, 4.0 eq) and sodium methoxide (0.510 g, 9.44 mmol, 8.0 eq) in MeOH in a pressure tube was stirred at 90° C. overnight. TLC and LCMS showed completion of the reaction. The reaction mixture was diluted with water, extracted with EtOAC. The organic was washed with brine, dried over $Na_2SO_4$, filtered and concentrated. The crude product was purified by silica gel (60-120) column chromatography using 30% EtOAC/hexane as eluent. Yield: 0.180 g (65.0%). $^1$H NMR (400 MHz, $CDCl_3$): δ 9.0 (s, 1H), 8.58 (d, J=5.6, 1H), 7.37 (d, J=4.0, 1H), 5.27 (bs, 1H), 1.73 (s, 2H), 1.48 (s, 9H), 1.36 (s, 2H). LCMS: (ES+) m/z=236.2 $(M+H)^+$ Column: purospher@star RP-18 (4×55) mm, 3 μm)
Mphase A: 20 mM $NH_4OAC$ IN 90% $H_2O$, 10% MeCN
Mphase B: 20 mM $NH_4OAC$ IN 10% $H_2O$, 90% MeCN
Flow: 2.5 mL/Min

| Time | % A | % B |
|---|---|---|
| 0.0 | 100.0 | 0 |
| 2 | 0.0 | 100.0 |
| 2.5 | 0.0 | 100.0 |
| 3 | 100.0 | 0.0 |

RT min: 1.33, wavelength: 220 nm 1-(pyrimidin-4-yl)cyclopropanamine HCl salt. A solution of tert-butyl 1-(pyrimidin-4-yl)cyclopropylcarbamate (0.100 g, 0.425 mmol, 1.0 eq), in 4.0 M HCl in 1,4-dioxane (4.0 ml) was stirred at r.t. for 5 hr. The reaction mixture was concentrated completely and the HCl salt was taken to next step.

1-(furan-3-yl)cyclopropanamine. To solution of 3-furonitrile (5 g, 53.71 mmol, 1.0 eq) in dry THF at r.t. under an argon atmosphere was added slowly titanium isopropoxide (18.9 ml, 64.4 mmol, 1.2 eq). The reaction mixture was stirred for 15 min. A solution of 1.0 Methyl magnesium bromide in THF (129 ml, 128 mmol, 2.4 eq) was added via syringe slowly to the mixture at 0° C. After addition, the reaction mixture was stirred at r.t. for 2 hour. $BF_3.Et_2O$ (10.4 ml) was then added slowly to the mixture at 0° C. After completion of the addition, the reaction mixture was stirred at r.t. for 30 min. 10% NaOH solution was added slowly till the reaction mixture becomes basic and then extracted with EtOAC. The organic was washed with brine, dried over $Na_2SO_4$ and concentrated. The crude product was purified by silica gel (60-120) column chromatography using 35% EtOAC/pet ether as eluent. Yield: 2.5 g (38%). $^1$H NMR (400 MHz, $CDCl_3$): δ 7.32 (m, 2H), 6.10 (s, 1H), 0.98-0.95 (m, 2H), 0.83-0.78 (m, 2H). LCMS: (ES+) m/z=123.7 $(M)^+$ Column: ATLANTS T3(2.1×50 mm) 3 micron
Mphase A: 10 mM $NH_4COOH$ IN 98% $H_2O$, 2% MeCN
Mphase B: 10 mM $NH_4COOH$ IN 2% $H_2O$, 98% MeCN
Flow: 0.8 ML/Min

| Time | % A | % B |
|---|---|---|
| 0.0 | 100.0 | 0 |
| 6 | 0.0 | 100.0 |
| 7.0 | 0.0 | 100.0 |

RT min: 1.65, wavelength: 220 nm tert-butyl 1-(furan-3-yl)cyclopropylcarbamate. A solution of Boc anhydride (4.9 g, 22.47 mmol, 1.2 eq) and 1-(furan-3-yl)cyclopropanamine (2.3 g, 18.69 mmol, 1.0 eq) in THF (25 ml) was stirred at 0° C., and the stirring was continued at r.t. overnight. The reaction mixture was concentrated, and the crude product was purified by silica gel (60-120) column chromatography using 5% EtOAC/Pet ether as an eluent. Yield: 2.5 g (60%). $^1$H NMR (400 MHz, $CDCl_3$): δ 7.30 (d, J=3.2, 1H), 7.26 (d, J=3.2, 1H), 6.16 (s, 1H), 5.17 (bs, 1H), 1.44 (s, 9H), 1.16 (s, 2H), 1.03 (s, 2H). LCMS (ES+) m/z=168.2 (M-CMe$_3$+2H)$^+$ Column: purospher@star RP-18 (4×55) mm, 3 μm Mphase A: 20 mM NH$_4$OAc IN 90% H$_2$O, 10% MeCN Mphase B: 20 mM NH$_4$OAc IN 10% H$_2$O, 90% MeCN Flow: 2.5 ML/Min

| Time | % A | % B |
|---|---|---|
| 0.0 | 100.0 | 0 |
| 2 | 0.0 | 100.0 |
| 2.5 | 0.0 | 100.0 |
| 3 | 100.0 | 0.0 |

RT min: 1.75, wavelength: 220 nm tert-butyl 1-(pyridazin-4-yl)cyclopropylcarbamate. A solution of tert-butyl 1-(furan-3-yl)cyclopropylcarbamate (2.15 g, 9.64 mmol, 1.0 eq), in acetone (86 ml) and water (86 ml) at r.t. was purged with N$_2$ and cooled to −20° C. NaHCO$_3$ (1.62 g, 19.28 mmol, 2.0 eq) and N-bromosuccinimide (2.23 g, 12.52 mmol, 1.3 eq) were added to the mixture at −20° C. and the stirring was continued at the same temperature for 2 hr. To the reaction mixture at −20° C. was added THF (4.3 ml) and the temperature raised to 0° C. over 30 min. Acetone was removed from the reaction mixture with a stream of N$_2$, and to the residue at 0° C. was added isopropanol (86 ml) followed by hydrazine hydrate (12.9 ml). The reaction mixture was stirred at r.t. overnight. Product formation was confirmed by LCMS. The solvent was evaporated under reduced pressure, and the residue diluted with water and then extracted with EtOAC. The organic was washed with brine, dried over Na$_2$SO$_4$ and concentrated. The crude product was purified by silica gel (60-120) column chromatography using 4% MeOH/CHCl$_3$ as an eluent. Yield: 1.3 g (57.5%). $^1$H NMR (400 MHz, CDCl$_3$): δ 9.04 (d, J=5.6, 1H), 8.95 (d, J=2.8, 1H), 7.19 (s, 1H), 5.25 (bs, 1H), 1.42 (s, 9H), 1.25 (bs, 4H). LCMS: (ES+) m/z=236.2 (M+H)$^+$ Column: purospher@star RP-18 (4×55) mm, 3 μm Mphase A: 20 mM NH$_4$OAc IN 90% H$_2$O, 10% MeCN Mphase B: 20 mM NH$_4$OAc IN 10% H$_2$O, 90% MeCN Flow: 2.5 mL/Min

| Time | % A | % B |
|---|---|---|
| 0.0 | 100.0 | 0 |
| 2 | 0.0 | 100.0 |
| 2.5 | 0.0 | 100.0 |
| 3 | 100 | 0 |

RT min: 1.18, wavelength: 220 nm 1-(pyridazin-4-yl)cyclopropanamine HCl salt. To a mixture of tert-butyl 1-(pyridazin-4-yl)cyclopropylcarbamate (0.100 g, 0.425 mmol, 1.0 eq) in a solution of 4.0 M HCl in 1,4-dioxane (4.0 ml) was stirred at r.t. for 5 hr. The reaction mixture was concentrated under vacuum and dried HCl salt was taken to next step.

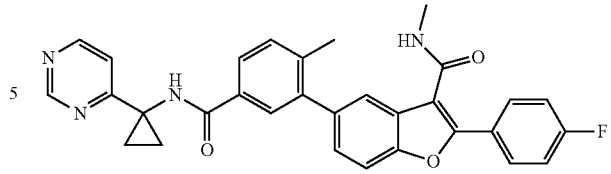

2-(4-Fluorophenyl)-N-methyl-5-(2-methyl-5-(1-(pyrimidin-4-yl)cyclopropyl carbamoyl)phenyl)benzofuran-3-carboxamide. To a mixture of 3-(2-(4-fluorophenyl)-3-(methylcarbamoyl)benzofuran-5-yl)-4-methylbenzoic acid (0.07 g, 0.173 mmol, 1.0 eq) and 1-(pyrimidin-4-yl)cyclopropanamine HCl (0.023 g, 0.173 mmol, 1.0 eq) in DMF at 0° C. was added TEA (0.087 g, 0.861 mmol, 5.0 eq) and BOP reagent (0.114 g, 0.257 mmol, 1.5 eq). The reaction mixture was stirred at r.t. overnight. The reaction mixture was diluted with water and extracted with EtOAc. The organic was dried over Na$_2$SO$_4$, filtered and concentrated. The crude product was purified by silica gel (60-120) column chromatography using 3% MeOH/CHCl$_3$ as eluent and further purified by prep HPLC. Yield: 0.040 g (44.45%). $^1$H NMR (400 MHz, CD$_3$OD): δ 9.03 (d, J=1.0 Hz, 1H), 8.61 (d, J=5.8 Hz, 1H), 8.04-7.94 (m, 2H), 7.91-7.83 (m, 2H), 7.72-7.64 (m, 2H), 7.57-7.45 (m, 2H), 7.43-7.37 (m, 1H), 7.34-7.24 (m, 2H), 2.96 (s, 3H), 2.37 (s, 3H), 1.90-1.81 (m, 2H), 1.57-1.49 (m, 2H). $^{19}$F NMR (376.51 MHz, CD$_3$OD): δ −78.35 (TFA), −113.31. LCMS: (ES+) m/z=521.2 (M+H)$^+$ Column: purospher@star RP-18 (4×55) mm, 3 μm Mphase A: 20 mM NH$_4$OAc IN 90% H$_2$O, 10% MeCN Mphase B: 20 mM NH$_4$OAc IN 10% H$_2$O, 90% MeCN Flow: 2.5 ML/Min

| Time | % A | % B |
|---|---|---|
| 0.0 | 100.0 | 0 |
| 2 | 0.0 | 100.0 |
| 2.5 | 0.0 | 100.0 |
| 3 | 100 | 0 |

RT min: 1.82, wavelength: 220 nm

HPLC Method: SUNFIRE C18 (4.6×150) mm, 3.5 micron

Buffer: 0.05% TFA in water pH 2.5

Mobile Phase A: Buffer:MeCN (95:5)

Mobile Phase B: MeCN:Buffer (95:5)

FLOW: 1 ml/min

| Time | B % |
|---|---|
| 24 | 10 |
| 31 | 100 |
| 30 | 100 |

Wavelength: 254 nm, RT min: 16.43

Wavelength: 220 nm, RT min: 16.43

HPLC Method: XBridge phenyl (4.6×150) mm, 3.5 micron

Buffer: 0.05% TFA in water pH 2.5

Mobile Phase A: 0.05% TFA in water:MeCN (95:5)

Mobile Phase B: 0.05% TFA in MeCN:water (95:5)

FLOW: 1 ml/min

701

| Time | B % |
| --- | --- |
| 0 | 10 |
| 25 | 100 |
| 30 | 100 |

Wavelength: 254 nm, RT min: 15.265

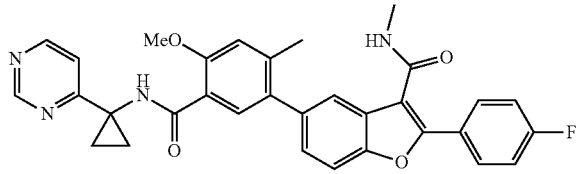

2-(4-Fluorophenyl)-5-(4-methoxy-2-methyl-5-(1-(pyrimidin-4-yl)cyclopropyl carbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.096 g, 0.221 mmol, 1.0 eq), 1-(pyrimidin-4-yl)cyclopropanamine HCl (0.03 g, 0.221 mmol, 1.0 eq) in DMF at 0° C. was added TEA (0.12 g, 1.188 mmol, 5.0 eq) and BOP reagent (0.146 g, 0.330 mmol, 1.5 eq). The reaction mixture was stirred as RT overnight. The reaction mixture was diluted with water, extracted with EtOAc. The organic layer was washed with brine, dried over $Na_2SO_4$, filtered and concentrated. The crude product was purified by silica gel (60-120) column chromatography using 3% $MeOH/CHCl_3$ as eluent. Yield: 0.070 g (57.33%). $^1$H NMR (400 MHz, $CD_3OD$): δ 8.99 (d, J=1.0 Hz, 1H), 8.61 (d, J=5.6 Hz, 1H), 7.99-7.93 (m, 2H), 7.79 (s, 1H), 7.69-7.54 (m, 3H), 7.39-7.23 (m, 3H), 7.16 (s, 1H), 4.08 (s, 3H), 2.96 (s, 3H), 2.34 (s, 3H), 1.85-1.82 (m, 2H), 1.61-1.49 (m, 2H). LCMS: (ES+) m/z=551.2 $(M+H)^+$ Column-Ascentis Express C18 (5×2.1 mm-2.7 µm)
Mphase A: 2% MeCN-98% $H_2O$-10 mM $NH_4COOH$
Mphase B: 98% MeCN-2% $H_2O$-10 mM $NH_4COOH$
Flow: 1 mL/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.91, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 25 | 10 |
| 25 | 100 |
| 30 | 100 |

Wavelength: 254 nm, RT min: 17.55
Wavelength: 220 nm, RT min: 17.55
HPLC Method: XBridge phenyl (4.6×150) mm, 3.5 micron

702

Buffer: 0.05% TFA in water pH 2.5
Mobile Phase A: 0.05% TFA in water:MeCN (95:5)
Mobile Phase B: 0.05% TFA in MeCN:water (95:5)
FLOW: 1 ml/min

| Time | B % |
| --- | --- |
| 0 | 10 |
| 25 | 100 |
| 30 | 100 |

Wavelength: 254 nm, RT min: 16.06
Wavelength: 220 nm, RT min: 16.06

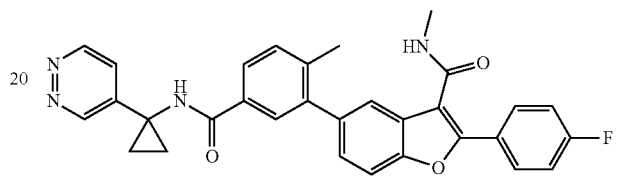

2-(4-Fluorophenyl)-N-methyl-5-(2-methyl-5-(1-(pyridazin-4-yl)cyclopropyl carbamoyl)phenyl)benzofuran-3-carboxamide. To a mixture of 34244-fluorophenyl)-3-(methylcarbamoyl)benzofuran-5-yl)-4-methylbenzoic acid (0.075 g, 0.186 mmol, 1.0 eq), 1-(pyridazin-4-yl)cyclopropanamine HCl (0.025 g, 0.185 mmol, 1.0 eq) in DMF at 0° C. was added TEA (0.094 g, 0.93 mmol, 5.0 eq) and BOP reagent (0.123 g, 0.278 mmol, 1.5 eq). The reaction mixture was stirred at RT overnight. The reaction mixture was diluted with water, extracted with EtOAc. the The organic layer was washed with brine, dried over $Na_2SO_4$, filtered and concentrated. The crude product was purified by silica gel (60-120) column chromatography using 4% $MeOH/CHCl_3$ as eluent, and further purified the product by prep HPLC. Yield: 0.050 g (52.00%). 1H NMR (400 MHz, $CD_3OD$): δ 9.44 (s, 1 H), 9.15 (d, 1H), 9.11 (s, 1H), 8.02-7.94 (m, 2H), 7.86 (dd, J=2.3, 4.3 Hz, 2H), 7.73 (br s, 1H), 7.68 (d, J=8.8 Hz, 1H), 7.66 (d, J=1.2 Hz, 1H), 7.48 (d, J=8.8 Hz, 1H), 7.40 (dd, J=1.8, 8.5 Hz, 1H), 7.29 (t, J=8.9 Hz, 2H), 2.96 (s, 3H), 2.37 (s, 3 H), 1.71 (s, 4H). $^{19}$F NMR (376.51 MHz, $CD_3OD$): δ −78.16 (TFA), −113.29 LCMS: (ES+) m/z=521.2 $(M+H)^+$ Column: purospher@star RP-18 (4×55) mm, 3 µm
Mphase A: 20 mM $NH_4OAc$ IN 90% $H_2O$, 10% MeCN
Mphase B: 20 mM $NH_4OAc$ IN 10% $H_2O$, 90% MeCN
Flow: 2.5 mL/Min

| Time | % A | % B |
| --- | --- | --- |
| 0.0 | 100.0 | 0 |
| 2 | 0.0 | 100.0 |
| 2.5 | 0.0 | 100.0 |
| 3 | 100 | 0 |

RT min: 1.71, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 26 | 10 |
| 25 | 100 |
| 30 | 100 |

Wavelength: 254 nm, RT min: 14.37
Wavelength: 220 nm, RT min: 14.37
HPLC Method: XBridge phenyl (4.6×150) mm, 3.5 micron
Buffer: 0.05% TFA in water pH 2.5
Mobile Phase A: 0.05% TFA in water:MeCN (95:5)
Mobile Phase B: 0.05% TFA in MeCN:water (95:5)
FLOW: 1 ml/min

| Time | B % |
|---|---|
| 0 | 10 |
| 25 | 100 |
| 30 | 100 |

Wavelength: 254 nm, RT min: 14.05
Wavelength: 220 nm, RT min: 14.05

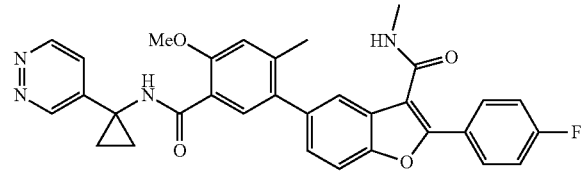

2-(4-Fluorophenyl)-5-(4-methoxy-2-methyl-5-(1-(pyridazin-4-yl)cyclopropyl carbamoyl)phenyl)-N-methylbenzofuran-3-carboxamide. To a mixture of 5-(2-(4-fluorophenyl)-3-(methylcarbamoyl)benzofuran-5-yl)-2-methoxy-4-methylbenzoic acid (0.080 g, 0.184 mmol, 1.0 eq), 1-(pyridazin-4-yl)cyclopropanamine HCl (0.025 g, 0.185 mmol, 1.0 eq) in DMF at 0° C. was added TEA (0.093 g, 0.920 mmol, 5.0 eq) and BOP reagent (0.120 g, 0.271 mmol, 1.5 eq). The reaction mixture was to stirred at RT overnight. The reaction mixture was diluted with water, extracted with EtOAc. The organic layer was washed with brine and dried over $Na_2SO_4$, filtered and concentrated. The crude product was purified by silica gel (60-120) column chromatography using 4% MeOH/$CHCl_3$ as eluent and further purified by prep HPLC. Yield: 0.053 g (52.42%). $^1H$ NMR (400 MHz, $CD_3OD$): δ 9.21-9.16 (m, 2H), 8.01-7.94 (m, 2H), 7.81 (br. s., 1H), 7.77 (s, 1H), 7.66 (s, 1H), 7.60 (s, 1H), 7.34 (dd, J=1.8, 8.5 Hz, 1H), 7.32-7.25 (m, 2H), 7.17 (s, 1H), 4.10 (s, 3H), 2.96 (s, 3H), 2.38 (s, 3H), 1.75 (s, 4H). $^{19}F$ NMR (376.51 MHz, $CD_3OD$): δ −77.43 (TFA), −112.62. LCMS: (ES+) m/z=551.2 $(M+H)^+$ Column-Ascentis Express C18 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.84, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 14.99
Wavelength: 220 nm, RT min: 14.99
HPLC Method: XBridge phenyl (4.6×150) mm, 3.5 micron
Buffer: 0.05% TFA in water pH 2.5
Mobile Phase A: 0.05% TFA in water:MeCN (95:5)
Mobile Phase B: 0.05% TFA in MeCN:water (95:5)
FLOW: 1 ml/min

| Time | B % |
|---|---|
| 0 | 10 |
| 25 | 100 |
| 30 | 100 |

Wavelength: 254 nm, RT min: 14.07
Wavelength: 220 nm, RT min: 14.07

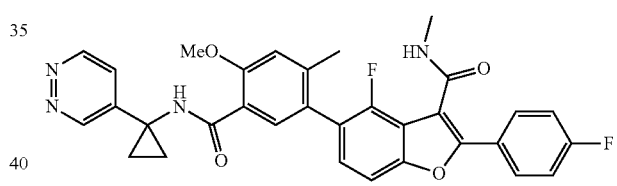

4-Fluoro-2-(4-fluorophenyl)-5-(4-methoxy-2-methyl-5-(1-(pyridazin-4-yl)cyclopropylcarbamoyl)phenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (0.080 g, 0.177 mmol, 1.0 eq), 1-(pyridazin-4-yl)cyclopropanamine HCl (0.024 g, 0.177 mmol, 1.0 eq) in DMF at 0° C. was added TEA (0.090 g, 0.89 mmol, 5.0 eq) and BOP reagent (0.117 g, 0.264 mmol, 1.5 eq). The reaction mixture was stirred at RT overnight. The reaction mixture was diluted with water, extracted with EtOAc. The organic layer was washed with brine, dried over $Na_2SO_4$, filtered and concentrated. The crude product was purified by silica gel (60-120) column chromatography using 4% MeOH/$CHCl_3$ as eluent. Yield: 0.060 g (60.0%). $^1H$ NMR (400 MHz, $CD_3OD$): δ 9.08 (m, 1H), 9.05 (d, J=1.0, 5.8 Hz, 1H), 7.97-7.93 (m, 2H), 7.72 (s., 1H), 7.54 (m, 1H), 7.51 (d, J=8.4 Hz, 1H), 7.31-7.25 (m, 3H), 7.19 (s, 1H), 4.10 (s, 3H), 2.95 (s, 3H), 2.30 (s, 3H), 1.63 (s, 4H). $^{19}F$ NMR (376.57 MHz, $CD_3OD$): δ −112.33, −122.75. LCMS: (ES+) m/z=569.2 $(M+H)^+$ Column: purospher@star RP-18 (4×55) mm, 3 μm
Mphase A: 20 mM $NH_4OAc$ IN 90% $H_2O$, 10% MeCN
Mphase B: 20 mM $NH_4OAc$ IN 10% $H_2O$, 90% MeCN
Flow: 2.5 ML/Min

| Time | % A | % B |
|---|---|---|
| 0.0 | 100.0 | 0 |
| 2 | 0.0 | 100.0 |
| 2.5 | 0.0 | 100.0 |
| 3 | 100 | 0 |

RT min: 1.74, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.33
Wavelength: 220 nm, RT min: 9.33
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 12 | 100 |
| 15 | 100 |

Wavelength: 254 nm, RT min: 9.21
Wavelength: 220 nm, RT min: 9.21

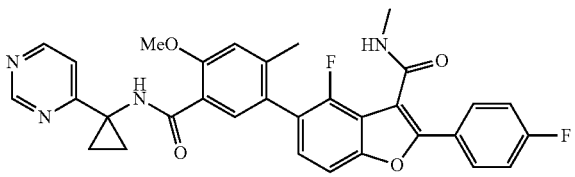

4-Fluoro-2-(4-fluorophenyl)-5-(4-methoxy-2-methyl-5-(1-(pyrimidin-4-yl)cyclopropylcarbamoyl)phenyl)-N-methylbenzofuran-3-carboxamide. To a mixture of 5-(4-fluoro-2-(4-fluorophenyl)-3-(methylcarbamoyl)benzofuran-5-yl)-2-methoxy-4-methylbenzoic acid (0.080 g, 0.185 mmol, 1.0 eq), 1-(pyrimidin-4-yl)cyclopropanamine HCl (0.025 g, 0.185 mmol, 1.0 eq) in DMF and at 0° C. was added TEA (0.094 g, 0.930 mmol, 5.0 eq) and BOP reagent (0.120 g, 0.271 mmol, 1.5 eq). The reaction mixture was warmed to RT, and stirring was continued at RT overnight. The reaction mixture was diluted with water and extracted with EtOAc. The organic layer was washed with brine, dried over $Na_2SO_4$, filtered and concentrated. The crude product was purified by prep HPLC. Yield: 0.058 g (58.0%). $^1$H NMR (400 MHz, $CD_3OD$): δ 9.03 (s, 1H), 8.64 (d, J=1.4 Hz, 1H), 7.97-7.79 (m., 2H), 7.76 (s, 1H), 7.65 (d, J=5.6 Hz, 1H), 7.52 (d, J=8.4 Hz, 1H), 7.31-7.25 (m, 3H), 7.19 (s, 1H), 4.09 (s, 3H), 2.95 (s, 3H), 2.30 (s, 3H), 1.88-1.85 (m, 2H), 1.55-1.52 (m, 2H). $^{19}$F NMR (376.57 MHz, $CD_3OD$): δ −77.58 (TFA), −112.32, −122.76. LCMS: (ES+) m/z=569.2 (M+H)$^+$ Column-Ascentis Express C18 (5×2.1 mm-2.7 μm)
Mphase A: 2% MeCN-98% $H_2O$-10 mM $NH_4COOH$
Mphase B: 98% MeCN-2% $H_2O$-10 mM $NH_4COOH$
Flow: 1 mL/Min

| Time | % A | % B |
|---|---|---|
| 0.0 | 100.0 | 0 |
| 1.5 | 0.0 | 100.0 |
| 3.2 | 0.0 | 100.0 |

RT min: 1.89, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
|---|---|
| 0 | 10 |
| 25 | 100 |
| 30 | 100 |

Wavelength: 254 nm, RT min: 16.78
Wavelength: 220 nm, RT min: 16.78
HPLC Method: XBridge phenyl (4.6×150) mm, 3.5 micron
Buffer: 0.05% TFA in water pH 2.5
Mobile Phase A: 0.05% TFA in water:MeCN (95:5)
Mobile Phase B: 0.05% TFA in MeCN:water (95:5)
FLOW: 1 ml/min

| Time | B % |
|---|---|
| 0 | 10 |
| 25 | 100 |
| 30 | 100 |

Wavelength: 254 nm, RT min: 15.08
Wavelength: 220 nm, RT min: 15.08

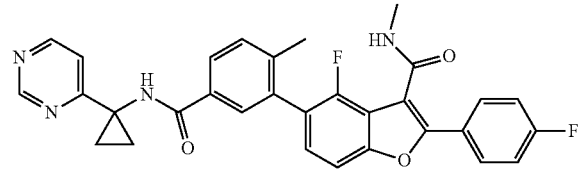

4-Fluoro-2-(4-fluorophenyl)-N-methyl-5-(2-methyl-5-(1-(pyrimidin-4-yl)-cyclopropylcarbamoyl)phenyl)benzofuran-3-carboxamide. To a mixture of 3-(4-fluoro-2-(4-fluorophenyl)-3-(methylcarbamoyl)benzofuran-5-yl)-4-methylbenzoic acid (0.050 g, 0.114 mmol, 1.0 eq), 1-(pyrimidin-4-yl)cyclopropanamine HCl (0.015 g, 0.113 mmol, 1.0 eq) in DMF at 0° C. was added TEA (0.060 g, 0.594 mmol, 5.0 eq) and BOP reagent (0.076 g, 0.172 mmol, 1.5 eq). The reaction mixture was stirred at RT overnight. The reaction mixture was diluted with water and extracted with EtOAc. the organic layer was washed with brine, dried over Na$_2$SO$_4$, filtered and concentrated. The crude product was purified by preparative HPLC. Yield: 0.035 g (57.37%). $^1$H NMR (400 MHz, CD$_3$OD): δ 9.00 (d, J=1.2 Hz, 1H), 8.60 (d, J=5.6 Hz, 1H), 7.98-7.90 (m and dd, 3H), 7.85 (d, J=2.0 Hz, 1H), 7.56 (d, J=8.4 Hz, 1H), 7.51-7.49 (two overlapping d, 2H), 7.35-7.28 (m, 3H), 2.96 (s, 3H), 2.30 (s, 3H), 1.84-1.81 (m, 2H), 1.52-1.49 (m, 2H). $^{19}$F NMR (376.57 MHz, CD$_3$OD): δ −76.94 (TFA), −112.22, −122.76 LCMS: (ES+) m/z=539.2 (M+H)$^+$ Column: purospher@star RP-18 (4×55) mm, 3 μm
Mphase A: 20 mM NH$_4$OAc IN 90% H$_2$O, 10% MeCN
Mphase B: 20 mM NH$_4$OAc IN 10% H$_2$O, 90% MeCN
Flow: 2.5 mL/Min

| Time | % A | % B |
| --- | --- | --- |
| 0.0 | 100.0 | 0 |
| 2 | 0.0 | 100.0 |
| 2.5 | 0.0 | 100.0 |
| 3 | 100 | 0 |

RT min: 1.78, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: meCN:Buffer (95:5)
FLOW: 1 ml/min

| Time | B % |
| --- | --- |
| 0 | 10 |
| 12 | 100 |
| 15 | 100 |

Wavelength: 254 nm, RT min: 10.02
Wavelength: 220 nm, RT min: 10.02
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 12 | 100 |
| 15 | 100 |

Wavelength: 254 nm, RT min: 9.53
Wavelength: 220 nm, RT min: 9.53

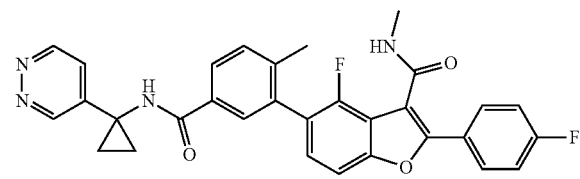

4-Fluoro-2-(4-fluorophenyl)-N-methyl-5-(2-methyl-5-(1-(pyridazin-4-yl)-cyclopropylcarbamoyl)phenyl)benzofuran-3-carboxamide. To a mixture of 3-(4-fluoro-2-(4-fluorophenyl)-3-(methylcarbamoyl)benzofuran-5-yl)-4-methylbenzoic acid (0.050 g, 0.114 mmol, 1.0 eq), 1-(pyridazin-4-yl)cyclopropanamine HCl (0.015 g, 0.113 mmol, 1.0 eq) in DMF at 0° C. was added TEA (0.060 g, 0.594 mmol, 5.0 eq) and BOP reagent (0.076 g, 0.172 mmol, 1.5 eq). The reaction mixture was stirred at RT. overnight. The reaction mixture was diluted with water and extracted with EtOAc. The organic layer was washed with brine, dried over Na$_2$SO$_4$, filtered and concentrated. The crude product was purified by preparative HPLC. Yield: 0.030 g (50.0%). $^1$H NMR (400 MHz, CDCl$_3$): δ 9.03 (d, J=5.6 Hz, 1H), 8.98 (m, 1H), 8.01-7.98 (m., 2H), 7.81-7.78 (dd, J=2.0, 8.0 Hz, 1H), 7.73 (d, J=2 Hz, 1H), 7.44 (d, J=8.4, 2 H), 7.28-7.26 (dd, 1H), 7.23-7.18 (m, 3H), 7.08 (s, 1H), 6.20 (bs, 1H), 3.04 (d, J=5.2 Hz, 3H), 2.29 (s, 3H), 1.61-1.54 (m, 4H). $^{19}$F NMR (376.57 MHz, CDCl$_3$): δ −109.53, −119.52. LCMS: (ES+) m/z=539.2 (M+H)$^+$ Column: purospher@star RP-18 (4×55) mm, 3 μm
Mphase A: 20 mM NH$_4$OAc IN 90% H$_2$O, 10% MeCN
Mphase B: 20 mM NH$_4$OAc IN 10% H$_2$O, 90% MeCN
Flow: 2.5 mL/Min

| Time | % A | % B |
| --- | --- | --- |
| 0.0 | 100.0 | 0 |
| 2 | 0.0 | 100.0 |
| 2.5 | 0.0 | 100.0 |
| 3 | 100 | 0 |

RT min: 1.68, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 12 | 100 |
| 15 | 100 |

Wavelength: 254 nm, RT min: 9.00
Wavelength: 220 nm, RT min: 9.00
HPLC Method: XBridge phenyl (4.6×150) mm, 3.5 micron
Buffer: 0.05% TFA in water pH 2.5
Mobile Phase A: Buffer:MeCN (95:5)
Mobile Phase B: MeCN:Buffer (95:5)
FLOW: 1 ml/min

| Time | B % |
| --- | --- |
| 0 | 10 |
| 12 | 100 |
| 15 | 100 |

Wavelength: 254 nm, RT min: 8.89
Wavelength: 220 nm, RT min: 8.89

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A composition comprising the compound 4-Fluoro-2-(4-fluorophenyl)-N-methyl-5-(2-methyl-5-(1-(pyrimidin-2-yl)cyclopropylcarbamoyl)phenyl)benzofuran-3-carboxamide or a pharmaceutically acceptable salt thereof, an interferon, and a pharmaceutically acceptable carrier.

2. The composition of claim 1 where the interferon is selected from interferon alpha 2B, pegylated interferon alpha, consensus interferon, interferon alpha 2A, and lymphoblastoid interferon tau.

* * * * *